US012760124B2

(12) United States Patent
Yang et al.

(10) Patent No.: US 12,760,124 B2
(45) Date of Patent: *Oct. 13, 2026

(54) TRISPECIFIC AND/OR TRIVALENT BINDING PROTEINS

(71) Applicant: Sanofi, Paris (FR)

(72) Inventors: Zhi-Yong Yang, Cambridge, MA (US); Gary J. Nabel, Cambridge, MA (US); Lan Wu, Cambridge, MA (US); Edward Seung, Cambridge, MA (US); Ronnie Wei, Needham, MA (US); Jochen Beninga, Frankfurt am Main (DE); Ercole Rao, Morfelden-Walldorf (DE); Wulf Dirk Leuschner, Frankfurt am Main (DE); Christian Beil, Frankfurt am Main (DE); Christian Lange, Frankfurt am Main (DE); Carsten Corvey, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/433,295

(22) Filed: Feb. 5, 2024

(65) Prior Publication Data

US 2024/0279362 A1 Aug. 22, 2024

Related U.S. Application Data

(63) Continuation of application No. 17/515,227, filed on Oct. 29, 2021, now Pat. No. 11,932,704, which is a continuation of application No. 17/099,439, filed on Nov. 16, 2020, now Pat. No. 11,192,960, which is a continuation of application No. 15/487,243, filed on Apr. 13, 2017, now Pat. No. 10,882,922.

(60) Provisional application No. 62/412,187, filed on Oct. 24, 2016, provisional application No. 62/331,191, filed on May 3, 2016, provisional application No. 62/322,036, filed on Apr. 13, 2016.

(30) Foreign Application Priority Data

Mar. 17, 2017 (EP) .................................... 17305298

(51) Int. Cl.

| | |
|---|---|
| ***C07K 16/46*** | (2006.01) |
| ***A61K 39/395*** | (2006.01) |
| ***A61K 45/06*** | (2006.01) |
| ***C07K 1/22*** | (2006.01) |
| ***C07K 16/24*** | (2006.01) |
| ***C07K 16/28*** | (2006.01) |
| ***C07K 16/32*** | (2006.01) |
| *A61K 39/00* | (2006.01) |

(52) U.S. Cl.

CPC ........ *C07K 16/468* (2013.01); *A61K 39/3955* (2013.01); *A61K 39/39558* (2013.01); *A61K 45/06* (2013.01); *C07K 1/22* (2013.01); *C07K 16/241* (2013.01); *C07K 16/244* (2013.01); *C07K 16/247* (2013.01); *C07K 16/2803* (2013.01); *C07K 16/2809* (2013.01); *C07K 16/2818* (2013.01); *C07K 16/2887* (2013.01); *C07K 16/2896* (2013.01); *C07K 16/32* (2013.01); *A61K 2039/505* (2013.01); *C07K 2317/31* (2013.01); *C07K 2317/35* (2013.01); *C07K 2317/52* (2013.01); *C07K 2317/526* (2013.01); *C07K 2317/56* (2013.01); *C07K 2317/565* (2013.01); *C07K 2317/64* (2013.01); *C07K 2317/73* (2013.01); *C07K 2317/75* (2013.01); *C07K 2317/76* (2013.01); *C07K 2317/92* (2013.01); *C07K 2317/94* (2013.01); *C07K 2319/00* (2013.01)

(58) Field of Classification Search

CPC .................................................... C07K 16/468
USPC ...................................................... 424/136.1
See application file for complete search history.

(56) References Cited

U.S. PATENT DOCUMENTS

| | | | |
|---|---|---|---|
| 9,181,349 | B2 | 11/2015 | Baurin et al. |
| 9,221,917 | B2 | 12/2015 | Baurin et al. |
| 10,626,169 | B2 | 4/2020 | Beil et al. |
| 10,882,922 | B2 | 1/2021 | Yang et al. |
| 11,129,905 | B2 | 9/2021 | Yang et al. |
| 11,186,649 | B2 | 11/2021 | Wu et al. |
| 11,192,960 | B2 | 12/2021 | Yang et al. |
| 11,365,261 | B2 | 6/2022 | Cameron et al. |

(Continued)

FOREIGN PATENT DOCUMENTS

| | | |
|---|---|---|
| CN | 101684158 A | 3/2010 |
| CN | 103562221 A | 2/2014 |

(Continued)

OTHER PUBLICATIONS

Suzuki et al (Cytokine, 2015, 75: 79-88)).*

(Continued)

*Primary Examiner* — Sean E Aeder
(74) *Attorney, Agent, or Firm* — MORRISON & FOERSTER LLP

(57) ABSTRACT

The disclosure provides trispecific and/or trivalent binding proteins comprising four polypeptide chains that form three antigen binding sites that specifically bind one or more target proteins, wherein a first pair of polypeptides forming the binding protein possess dual variable domains having a cross-over orientation and wherein a second pair of polypeptides forming the binding protein possess a single variable domain. The disclosure also provides methods for making trispecific and/or trivalent binding proteins and uses of such binding proteins.

10 Claims, 51 Drawing Sheets

Specification includes a Sequence Listing.

(56) References Cited

U.S. PATENT DOCUMENTS

| | | | |
|---|---|---|---|
| 11,530,268 | B2 | 12/2022 | Wu et al. |
| 11,779,651 | B2 | 10/2023 | Yang et al. |
| 11,932,704 | B2 | 3/2024 | Yang et al. |
| 2010/0226923 | A1 | 9/2010 | Rao et al. |
| 2012/0076782 | A1 | 3/2012 | Tesar et al. |
| 2012/0201827 | A1 | 8/2012 | Elias et al. |
| 2012/0251541 | A1 | 10/2012 | Baurin et al. |
| 2013/0345404 | A1 | 12/2013 | Baurin et al. |
| 2014/0213772 | A1 | 7/2014 | Ghayur et al. |
| 2014/0322163 | A1 | 10/2014 | Kwong et al. |
| 2014/0322217 | A1 | 10/2014 | Moore et al. |
| 2016/0024147 | A1 | 1/2016 | Tustian et al. |
| 2016/0200811 | A1 | 7/2016 | Baurin et al. |
| 2017/0320967 | A1 | 11/2017 | Yang et al. |
| 2018/0237511 | A1 | 8/2018 | Beil et al. |
| 2019/0054182 | A1 | 2/2019 | Yang et al. |
| 2019/0106504 | A1 | 4/2019 | Wu et al. |
| 2020/0054765 | A1 | 2/2020 | Yang et al. |
| 2020/0140552 | A1 | 5/2020 | Wu et al. |
| 2020/0317761 | A1 | 10/2020 | Beil et al. |
| 2020/0385470 | A1 | 12/2020 | Bacac et al. |
| 2020/0399369 | A1 | 12/2020 | Asokan et al. |
| 2021/0061925 | A1 | 3/2021 | Yang et al. |
| 2022/0041746 | A1 | 2/2022 | Cameron et al. |
| 2022/0119553 | A1 | 4/2022 | Yang et al. |
| 2022/0226495 | A1 | 7/2022 | Yang et al. |
| 2022/0275102 | A1 | 9/2022 | Cameron et al. |
| 2023/0220079 | A1 | 7/2023 | Beil et al. |
| 2023/0357401 | A1 | 11/2023 | Wu et al. |
| 2025/0312475 | A1 | 10/2025 | Yang et al. |

FOREIGN PATENT DOCUMENTS

| | | | |
|---|---|---|---|
| CN | 104968685 | A | 10/2015 |
| CN | 105837688 | A | 8/2016 |
| CN | 109311966 | A | 2/2019 |
| EP | 0308936 | A2 | 3/1989 |
| EP | 1378520 | A1 | 1/2004 |
| EP | 1736484 | A1 | 12/2006 |
| EP | 2014680 | A1 | 1/2009 |
| JP | 2014-511684 | A | 5/2014 |
| JP | 2014-519322 | A | 8/2014 |
| JP | 2015-535828 | A | 12/2015 |
| JP | 2018-521308 | A | 8/2018 |
| JP | 2018-537966 | A | 12/2018 |
| TW | 201437227 | A | 10/2014 |
| TW | I750139 | B | 12/2021 |
| WO | WO-1996/27011 | A1 | 9/1996 |
| WO | WO-1999/051642 | A1 | 10/1999 |
| WO | WO-2002/056910 | A1 | 7/2002 |
| WO | WO-2005/000899 | A2 | 1/2005 |
| WO | WO-2009/149189 | A2 | 12/2009 |
| WO | WO-2011/038290 | A2 | 3/2011 |
| WO | WO-2011/154453 | A1 | 12/2011 |
| WO | WO-2012/065055 | A3 | 7/2012 |
| WO | WO-2012/092612 | A1 | 7/2012 |
| WO | WO-2012/135345 | A1 | 10/2012 |
| WO | WO-2012/154312 | A1 | 11/2012 |
| WO | WO-2012/158818 | A2 | 11/2012 |
| WO | WO-2012/158948 | A1 | 11/2012 |
| WO | WO-2013/070776 | A1 | 5/2013 |
| WO | WO-2013/086533 | A1 | 6/2013 |
| WO | WO-2013/163427 | A1 | 10/2013 |
| WO | WO-2014/047231 | A1 | 3/2014 |
| WO | WO-2014/089152 | A1 | 6/2014 |
| WO | WO-2014/093894 | | 7/2014 |
| WO | WO-2014/116846 | A2 | 7/2014 |
| WO | WO-2014/144299 | A2 | 9/2014 |
| WO | WO-2014/144722 | A2 | 9/2014 |
| WO | WO-2015/017755 | A1 | 2/2015 |
| WO | WO-2015/063339 | A1 | 5/2015 |
| WO | WO-2015/149077 | A1 | 10/2015 |
| WO | WO-2016/033690 | A1 | 3/2016 |
| WO | WO-2016/116626 | A1 | 7/2016 |
| WO | WO-2016/187580 | A1 | 11/2016 |
| WO | WO-2016/196740 | A1 | 12/2016 |
| WO | WO-2017/074878 | A1 | 5/2017 |
| WO | WO-2017/180913 | A2 | 10/2017 |
| WO | WO-2018-120842 | A1 | 7/2018 |
| WO | WO-2018/151841 | A1 | 8/2018 |
| WO | WO-2017/106346 | A2 | 9/2018 |
| WO | WO-2018/183294 | A1 | 10/2018 |
| WO | WO-2017/053556 | A1 | 12/2018 |
| WO | WO-2020/076853 | A1 | 4/2020 |

OTHER PUBLICATIONS

Alegre, M.L. et al. (Jun. 1, 1994). "A Non-Activating "Humanized" Anti-CD3 Monoclonal Antibody Retains Immunosuppressive Properties In Vivo," *Transplantation* 57(11):1537-1543.

Almeida, J. et al. (1999). "High-Sensitive Immunophenotyping and DNA Ploidy Studies for the Investigation of Minimal Residual Disease in Multiple Myeloma," *British J of Haematol*. 107:121-131.

Altschul, S.F. et al. (Sep. 1, 1997). "Gapped BLAST and PSI-BLAST: A New Generation of Protein Database Search Programs," *Nucleic Acids Res*. 25(17):3389-3402.

Atwell, S. et al. (Jul. 4, 1997). "Stable Heterodimers from Remodeling the Domain Interface of a Homodimer Using a Phage Display Library," *J. Mol. Biol*. 270(1):26-35.

Brandsma, A.M. et al. (Oct. 1, 2017; e-pub. Aug. 16, 2017). "Single Nucleotide Polymorphisms of the High Affinity IgG Receptor FcγRI Reduce Immune Complex Binding and Downstream Effector Functions," *The Journal of Immunology* 199(7):2432-2439.

Chai, J.G. et al. (1997). "Immobilized Anti-CD3 mAb Induces Anergy in Murine Naive and Memory $CD4^+$ T Cells," *Int Immunol*. 9(7):935-944.

Chen, H.W. et al. (Apr. 1, 2006). "Ex Vivo Expansion of Dendritic-Cell-Activated Antigenspecific CD41\+ T Cells With Anti-CD3/CD28, Interleukin-? and Interleukin-15: Potential For Adoptive T Cell Immunotherapy," Clinical Immunology 119(1):21-31.

Chothia, C. et al. (Aug. 20, 1987). "Canonical Structures for the Hypervariable Regions of Immunoglobulins," *J. Mol. Biol*. 196(4):901-917.

Chothia, C. et al. (Dec. 21-28, 1989). "Conformations of Immunoglobulin Hypervariable Regions," *Nature* 342(6252): 877-883.

Chu, S.Y. et al. (Dec. 4, 2014). "Immunotherapy with Long-Lived Anti-CD38×Anti-CD3 Bispecific Antibodies Stimulates Potent T Cell-Mediated Killing of Human Myeloma Cell Lines and CD38+ Cells in Monkeys: A Potential Therapy for Multiple Myeloma," *Blood* 124(21): 4727, 6 pages.

Colombian Opposition mailed on Mar. 15, 2019 for CO Application No. NC2018/0012107 filed on Nov. 9, 2018, twenty-one pages. (English Translation).

Deckkert, J. et al. (2014; e-pub. Jul. 1, 2014). "SAR650984, a Novel Humanized CD38-Targeting Antibody, Demonstrates Potent Anti-Tumor Activity in Models of Multiple Myeloma and Other CD38+ Hematologic Malignancies," *Clin. Cancer Res* 20:4574-4583.

Digiammarino, E. et al. (Sep.-Oct. 2011, e-pub. Sep. 1, 2011). "Ligand Association Rates to the Inner-Variable-Domain of a Dual-Variable-Domain Immunoglobulin are Significantly Impacted by Linker Design," *MAbs*. 3(5):487-494.

EBI Accession No. GSP: BAH64671 Sequence (Jan. 13, 2013). "Anti-HIV Human Antibody Variable Light Chain (Vl), VRCO1," one page.

EBI Accession No. GSP: BAO38135 Sequence (Jul. 4, 2013). "Human Germline 10E8 Antibody Heavy Chain Revertant Seq ID No. 149," one page.

Eifler, N. et al. (2014, e-pub. Aug. 6, 2014). "Development of a Novel Affinity Chromatography Resin for Platform Purification of Lambda Fabs," Biotechnology Progress 30(6):1311-1318.

Esensten, J.H. et al. (May 17, 2016). "CD28 Costimulation: From Mechanism to Therapy," *Immunity* 44:973-988.

Findlay, L. et al. (2010; e-pub. Nov. 4, 2009). "Improved In Vitro Methods to Predict the In Vivo Toxicity in Man of Therapeutic Monoclonal Antibodies Including TGN1412," *J Immunol Methods* 352:1-12.

Fournier, P. et al. (Jan. 2010). "Tumor Antigen-Dependent and Tumor Antigen-Independent Activation of Antitumor Activity in

(56) References Cited

OTHER PUBLICATIONS

TCells by a Bispecific Antibody-Modified Tumor Vaccine," *Clinical & Developmental Immunology* 2010(1):Article IDS 423781, 12 pages.
Garfall, A.L. et al. (Nov. 21, 2019). "Three is a Charm for an Antibody to Fight Cancer," Nature 575:450-451.
Gratama, J,W. et al. (Sep. 1, 2001). "Tetramer-Based Quantification of Cytomegalovirus (CMV)-Specific CD81 T Lymphocytes in T-Cell-Depleted Stem Cell Grafts and After Transplantation May Identify Patients at Risk for Progressive CMV Infection," *Blood* 98(5):1358-1364.
Haas, C. et al. (Mar. 31, 2005; e-pub. Nov. 25, 2004). "T-cell Triggering by CD3- and CD28-Binding Molecules Linked to a Human Virus-Modified Tumor Cell Vaccine," *Vaccine* 23(19):2439-2453.
Hahn, R. et al. (2003). "Comparison Of Protein A Affinity Sorbents," Journal of Chromatography B 790(1-2):35-51.
Hartman, W.R. et al. (May 17, 2010). "CD38 Expression, Function, And Gene Resequencing in a Human Lymphoblastoid Cell Line-Based Model System," Leukemia and Lymphoma 51(7):1315-1325.
Hinton, P.R. et al. (Jan. 1, 2006). "An Engineered Human IgG1 Antibody With Longer Serum Half-Life," *J. Immunol.* 176(1):346-356.
Hitoshi, N. et al. (Dec. 15, 1991). "Efficient Selection for High-Expression Transfectants with a Novel Eukaryotic Vector," *Gene* 108(2):193-200.
Hui, E. et al. (Mar. 31, 2017). "T Cell Costimulatory Receptor CD28 is a Primary Target for PD-1-Mediated Inhibition," *Science* 355(6332):1428-1433.
International Search Report mailed on Dec. 17, 2019, for PCT Application No. PCT/US2019/055232, filed on Oct. 8, 2019, seven pages.
International Preliminary Report on Patentability mailed on May 11, 2018 for PCT Application No. PCT/US2016/058540 filed on Oct. 24, 2016, seven pages.
International Preliminary Report on Patentability mailed on Oct. 25, 2018 for PCT Application No. PCT/US2017/027488, filed on Apr. 13, 2017, thirty one pages.
International Search Report and Written Opinion mailed on Jan. 2, 2018 for PCT Application No. PCT/US2017/027488, filed on Apr. 13, 2017, forty four pages.
International Search Report and Written Opinion of the International Searching Authority mailed on Mar. 10, 2017 for PCT Application No. PCT/US2016/058540 filed on Oct. 24, 2016, fifteen pages.
International Search Report and Written Opinion of the International Searching Authority mailed on May 17, 2019, for PCT Application No. PCT/US2018/055084, filed on Oct. 9, 2018, twenty seven pages.
Invitation to Pay Additional Fees and, Where Applicable, Protest Fee mailed on Oct. 16, 2017, for PCT Application No. PCT/US2017/027488, filed on Apr. 13, 2017, twenty eight pages.
Invitation to Pay Additional Fees and, Where Applicable, Protest Fee mailed on Feb. 20, 2019, for PCT Application No. PCT/US2018/055084, filed on Oct. 9, 2018, twenty three pages.
Jakob, C.G. et al. (May 1, 2013, e-pub. Apr. 2, 2013). "Structure Reveals Function of the Dual Variable Domain Immunoglobulin (DVD-Ig™) Molecule," *MAbs*. 5(3):358-363.
Kalim, M. et al. (2017; e-pub. Aug. 2, 2017). "Intracellular Trafficking of New Anticancer Therapeutics: Antibody-Drug Conjugates," *Drug Des. Devel. Ther*. 11:2265-2276.
Kilpatrick, K.E. et al. (Aug. 1997). "Rapid Development of Affinity Matured Monoclonal Antibodies Using RIMMS," *Hybridoma* 16(4):381-389.
Lefranc, M.P. et al. (Jan. 2003). "IMGT Unique Numbering for Immunoglobulin and T Cell Receptor Variable Domains and Ig Superfamily V-Like Domains," *Dev. Comp. Immunol*. 27(1):55-77.
Li, T. et al. (Jun. 2, 2016). "Immuno-Targeting the Multifunctional CD38 Using Nanobody," *Scientific Reports* 6(1):27055, 11 pages.
Liu, Q. et al. (Sep. 2005). "Crystal Structure of Human CD38 Extracellular Domain," *Structure* 13(9):1331-1339.
Maccallum, R.M. et al. (Oct. 11, 1996). "Antibody-Antigen Interactions: Contact Analysis and Binding Site Topography," *J. Mol. Biol*. 262(5): 732-745.
Masui, S. et al. (Mar. 1, 2005). "An Efficient System to Establish Multiple Embryonic Stem Cell Lines Carrying an Inducible Expression Unit," *Nucleic Acids Res*. 33(4):e43, pp. 1-8.
Mateo, G. et al. (May 15, 2005). "Genetic Abnormalities and Patterns of Antigenic Expression in Multiple Myeloma," *Clin. Cancer Res*. 11(10):3661-3667.
Mazor, Y. et al. (Mar. 11, 2015). "Improving target cell specificity using a novel monovalent bispecific IgG design," In MAbs 7(2):377-389.
Mcdermott, S.P. et al. (Jul. 15, 2010, e-published as Apr. 19, 2010). "Comparison of Human Cord Blood Engraftment Between Immunocompromised Mouse Strains," *Blood* 116(2):193-200.
Mckeage, K. (Feb. 2016). "Daratumumab: First Global Approval," *Drugs*. 76(2):275-281.
Merchant, A.M. et al. (Jul. 1998). "An Efficient Route to Human Bispecific IgG," *Nature Biotechnol*. 16(7):677-681.
Moore, G. et al. (Dec. 5, 2015). "1798 Tuning T Cell Affinity Improves Efficacy and Safety of Anti-CD38×Anti-CD3 Bispecific Antibodies in Monkeys—a Potential Therapy for Multiple Myeloma," American Society of Hematology, Poster Abstract presented at $57^{th}$ Annual Meeting & Exposition, Orlando, FL, three pages.
Morphosys. (Nov. 25, 2010). "R&D Day 2010," 102 pages.
Nair, J.R. et al. (2011; e-pub. Jun. 29, 2011). "CD28 Expressed on Malignant Plasma Cells Induces a Prosurvival and Immunosuppressive Microenvironment," *J Immunol*. 187:1243-1253.
Nilson, B. H. et al. (Feb. 5, 1992). "Protein L From Peptostreptococcus Magnus Binds to the Kappa Light Chain Variable Domain," *Journal of Biological Chemistry* 267(4):2234-2239.
Padlan, E.A. et al. (Jan. 1995). "Identification of Specificity-Determining Residues in Antibodies," *FASEB J*. 9(1):133-139.
Parslow, A.C. et al. (2016). "Antibody-Drug Conjugates for Cancer Therapy," *Biomedicines* 4:14, pp. 1-17.
Penaranda, C.I. et al. (Aug. 15, 2011). "Anti-CD3 Therapy Promotes Tolerance by Selectively Depleting Pathogenic Cells While Preserving Regulatory T Cells," *J Immunol*. 187(4):2015-2022, 19 pages.
Peters, B. et al. (Mar. 2005; e-pub. Mar. 15, 2005). "The Immune Epitope Database and Analysis Resource: From Vision to Blueprint," *PLos Biol*. 3(3):e91, pp. 0379-0381.
Ridgway, J.B. et al. (Jul. 1996). "'Knobs-Into-Holes' Engineering of Antibody CH3 Domains for Heavy Chain Heterodimerization," *Protein Eng*. 9(7):617-621.
Robillard, N. et al. (Jun. 1998). "CD28, a Marker Associated with Tumoral Expansion in Multiple Myeloma," *Clin Cancer Res*. 4:1521-1526.
Rodrigo, G. et al. (Sep. 11, 2015). "Antibody Fragments and Their Purification by Protein L Affinity Chromatography," Antibodies 4(3):259-277.
Rudikoff, S. et al. (Mar. 1982). "Single Amino Acid Substitution Altering Antigen-Binding Specificity," Proc. Natl. Acad. Sci. USA 79(6):1979-1983.
Sarzotti-Kelsoe, M. et al. (Jul. 2014; e-published on Dec. 1, 2013). "Optimization and Validation of the TZM-BI Assay for Standardized Assessments of Neutralizing Antibodies Against HIV-1," *J. Immunological Methods* 409:131-146, thirty seven pages.
Sharma, P. et al. (Apr. 3, 2015). "The Future of Immune Checkpoint Therapy," *Science* 348(6230):56-61.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *J. Biol. Chem*. 276(9):6591-6604.
Shultz, L.D. et al. (Jul. 2014). "Human Cancer Growth and Therapy in NOD/SCID/IL2R$\gamma\gamma^{null}$ (NSG) Mice," *Cold Spring Harb. Protoc*. 2014(7):694-708, 24 pages.
Smith, E.J. et al. (Dec. 11, 2015). "A Novel, Native-Format Bispecific Antibody Triggering T-Cell Killing of B-Cells is Robustly Active in Mouse Tumor Models and Cynomolgus Monkeys," *Sci. Rep*. 5:17943, pp. 1-12.

(56) References Cited

OTHER PUBLICATIONS

Song, Li-Ping et al. (Jun. 1, 2003). "A New Model of Trispecific Antibody with Cytotoxicity Against Tumor Cells," *Acta Biochimica Etbiophysica Sinica* 35(6):503-510.
Spiess, C. et al. (2015; e-pub. Jan. 27, 2015). "Alternative Molecular Formats and Therapeutic Applications for Bispecific Antibodies," *Molecular Immunology* 67(2):95-106.
Spiess, C. et al. (Sep. 13, 2013, e-published on Jul. 23, 2013). "Development of a Human IgG4 Bispecific Antibody for Dual Targeting of Interleukin-4 (IL-4) and Interleukin-13 (IL-13) Cytokines," *J. Biol. Chem.* 288:26583-26593.
Stebbings, R. et al. (Sep. 1, 2007). "'Cytokine Storm' In The Phase I Trial of Monoclonal Antibody TGN1412: Better Understanding the Causes to Improve Preclinical Testing of Immunotherapeutics," *J. Immunol.* 179(5):3325-3331.
Steinmetz, A. et al. (Mar. 16, 2016). "CODV-Ig, A Universal Bispecific Tetravalent and Multifunctional Immunoglobulin Format for Medical Applications," *MABS* 8(5):867-878, with Supplementary material, fifty nine pages.
Stevenson, G.T. (Nov.-Dec. 2006). "CD38 as a Therapeutic Target," *Mol. Med.* 12(11-12):345-346.
Suntharalingam, G. et al. (Sep. 7, 2006). "Cytokine Storm in a Phase 1 Trial of the Anti-CD28 Monoclonal Antibody TGN1412," *N Engl J Med* 355(10):1018-1028.
Tabares, P. et al. (Apr. 2014; e-pub. Feb. 1, 2014). "Human Regulatory T Cells are Selectively Activated by Low-Dose Application of the CD28 Superagonist TGN1412/TAB08," *Eur J Immunol.* 44:1225-1236.
Thompson, J.D. (Nov. 11, 1994). "CLUSTAL W: Improving the Sensitivity of Progressive Multiple Sequence Alignment Through Sequence Weighting, Position-Specific Gap Penalties and Weight Matrix Choice," *Nucleic Acids Res.* 22(22):4673-4680.
Tiller, T. et al. (Oct. 2009). "Cloning and Expression of Murine Ig Genes From Single B Cells," *J. Immunol. Methods* 350(1-2):183-193.
U.S. Appl. No. 16/843,792, filed Apr. 8, 2020, for Mangaiarkarasi et al. (not submitted herewith pursuant to the waiver of 37 C.F.R. 1.98(a)(2)(iii) issued by the Office on Sep. 21, 2004).
U.S. Appl. No. 18/054,734, filed Nov. 11, 2022, for Wu et al. (not submitted herewith pursuant to the waiver of 37 C.F.R. 1.98(a)(2)(iii) issued by the Office on Sep. 21, 2004).
U.S. Appl. No. 18/458,060, filed Aug. 29, 2023, for Yang et al. (not submitted herewith pursuant to the waiver of 37 C.F.R. 1.98(a)(2)(iii) issued by the Office on Sep. 21, 2004).
Waibler, Z. et al. (Mar. 5, 2008). "Signaling Signatures and Functional Properties of Anti-Human CD28 Superagonistic Antibodies," *PLoS One* 3(3):e1708, pp. 1-13.
Wang, X. (Apr. 1, 2004). "A New Recombinant Single Chain Trispecific Antibody Recruits T Lymphocytes to Kill CEA (Carcinoma Embryonic Antigen) Positive Tumor Cells In Vitro Efficiently," *Journal of Biochemistry* 135(4):555-565.
Wang, X. et al. (Jan. 2018; e-pub. Oct. 6, 2017). "IgG Fc Engineering to Modulate Antibody Effector Functions," *Protein & Cell* 9(1):63-73.
Wennerberg, A.E. et al. (Oct. 1993). "Hepatocyte Paraffin 1: A Monoclonal Antibody that Reacts with Hepatocytes and can be Used for Differential Diagnosis of Hepatic Tumors," *Am J Pathol.* 143(4):1050-1054.
Willems, A. et al. (Nov. 1, 2005; e-pub. May 13, 2005). "CD3 CD28 Cross-Interacting Bispecific Antibodies Improve Tumor Cell Dependent T-Cell Activation," *Cancer Immunology, Immunotherapy* 54(11):1059-1071.
Written Opinion of the International Searching Authority mailed on Dec. 17, 2019, for PCT Application No. PCT/US2019/055232, filed on Oct. 8, 2019, six pages.
Wu, L. et al. (Nov. 18, 2019). "Trispecific Antibodies Enhance the Therapeutic Efficacy of Tumor-Directed T Cells Through T Cell Receptor Co-Stimulation," Nat Cancer 1:86-98.
Xu, L. et al. (Oct. 6, 2017; e-pub. Sep. 20, 2017). "Trispecific Broadly Neutralizing HIV Antibodies Mediate Potent SHIV Protection in Macaques," *Science* 358(6359):85-90, 17 pages.
Liu, J. et al. (Nov. 2005). "A New Format Of Single Chain Tri-Specific Antibody With Diminished Molecular Size Efficiently Induces Ovarian Tumor Cell Killing," Biotechnol Lett. 27(22): 1821-1827.
U.S. Appl. No. 18/960,890, filed Nov. 26, 2024, for Yang et al. (not submitted herewith pursuant to the waiver of 37 C.F.R. 1.98(a)(2)(iii) issued by the Office on Sep. 21, 2004).

* cited by examiner

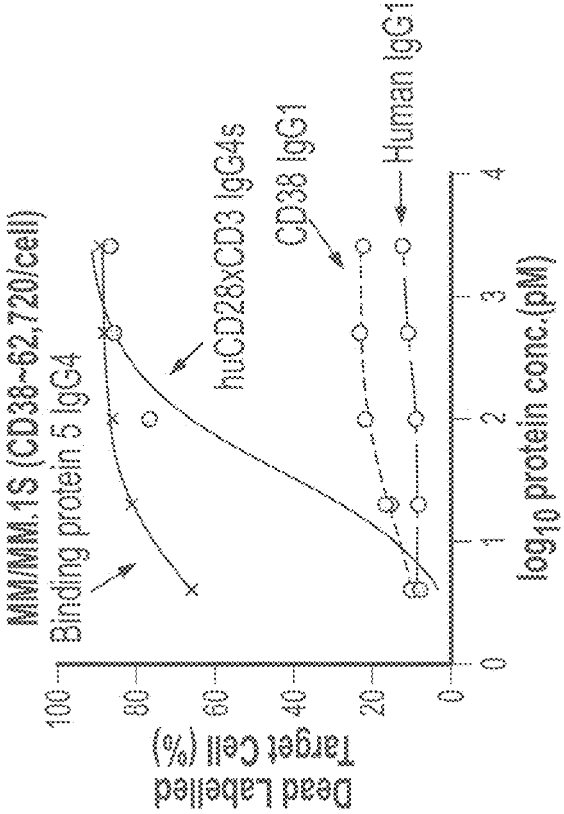
FIG. 12B
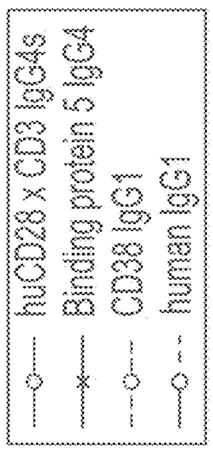
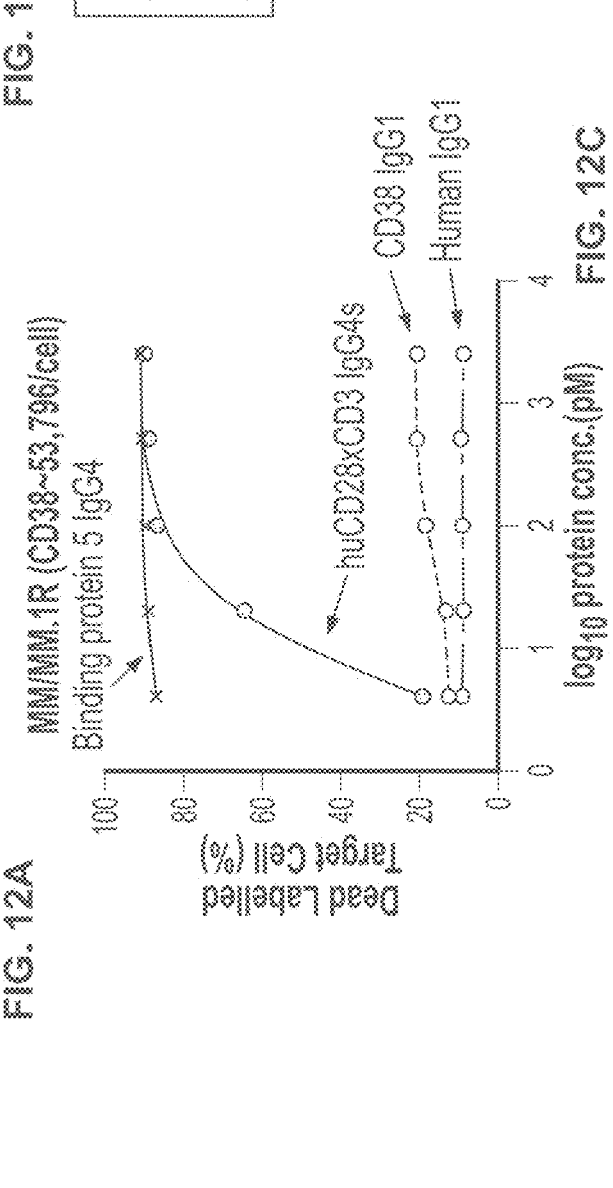
FIG. 12C
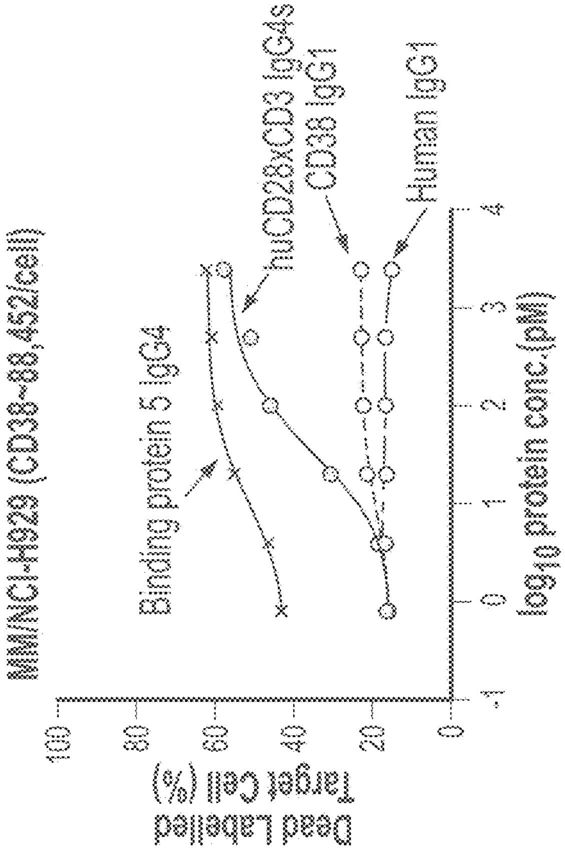
FIG. 12A

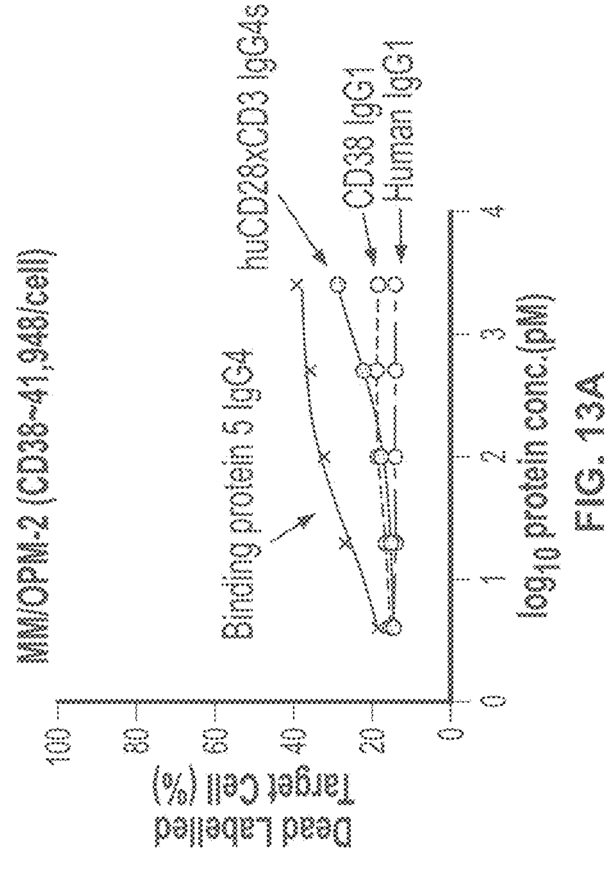
FIG. 13A
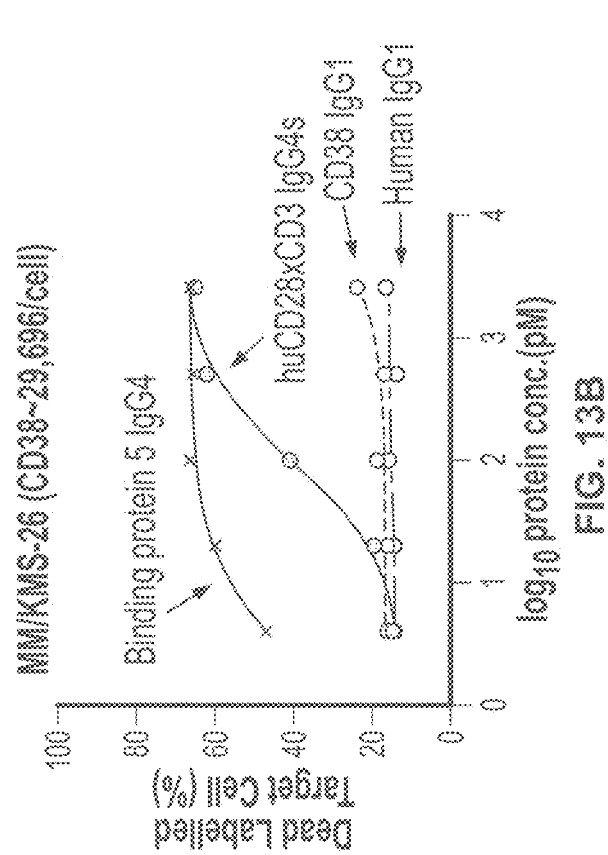
FIG. 13B
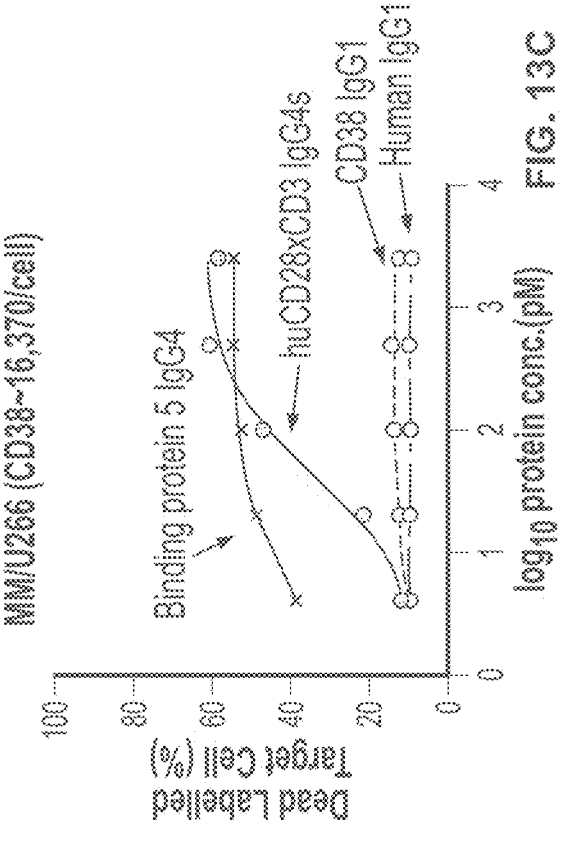
FIG. 13C
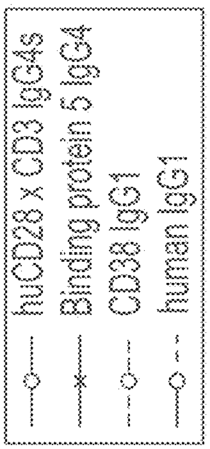

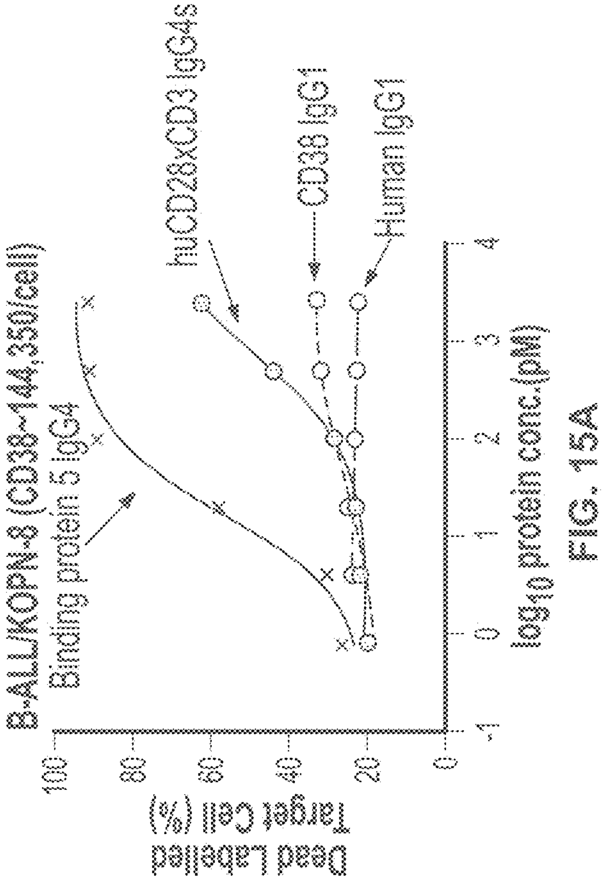
FIG. 15A
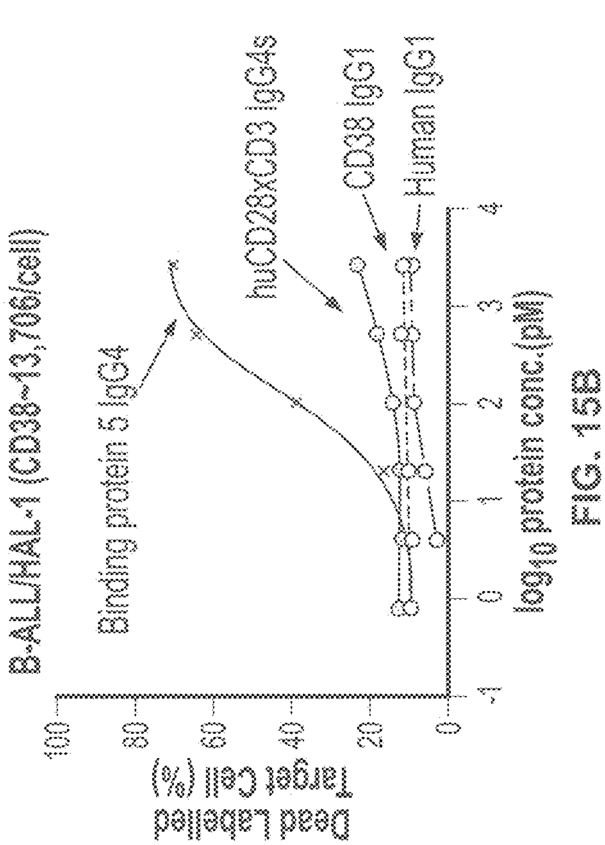
FIG. 15B
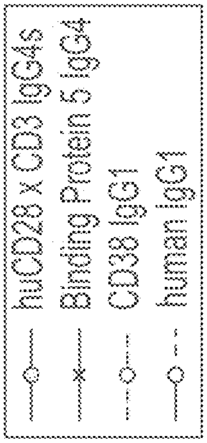
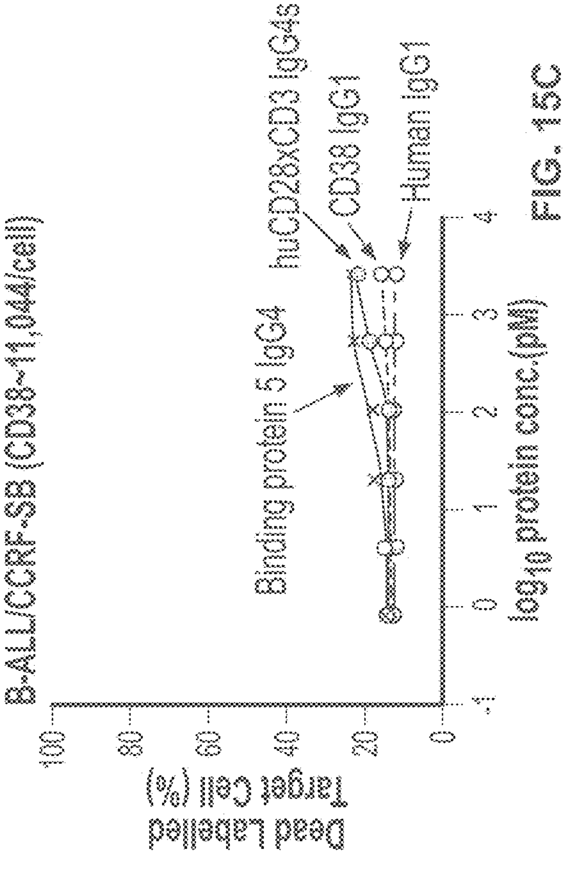
FIG. 15C 5 hr stimulation Anti-hCD8

Anti-hCD4

Binding Protein 12
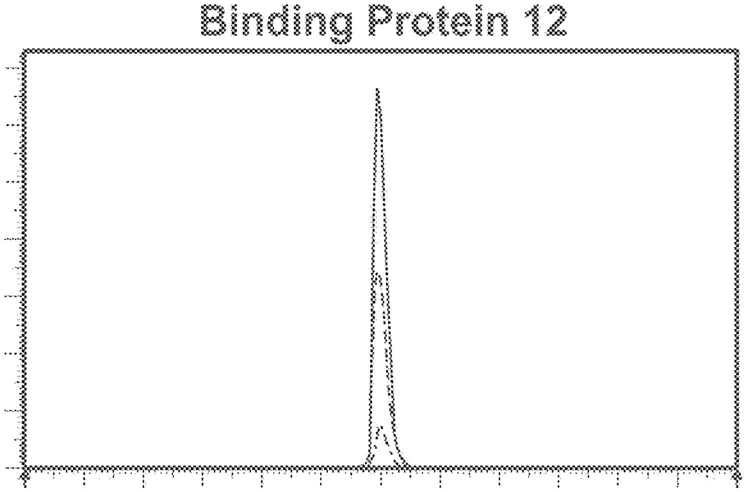
Binding Protein 13
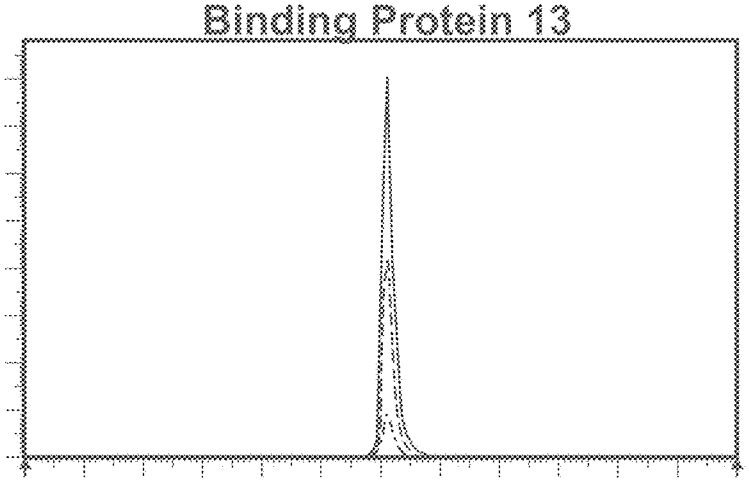
Binding Protein 14
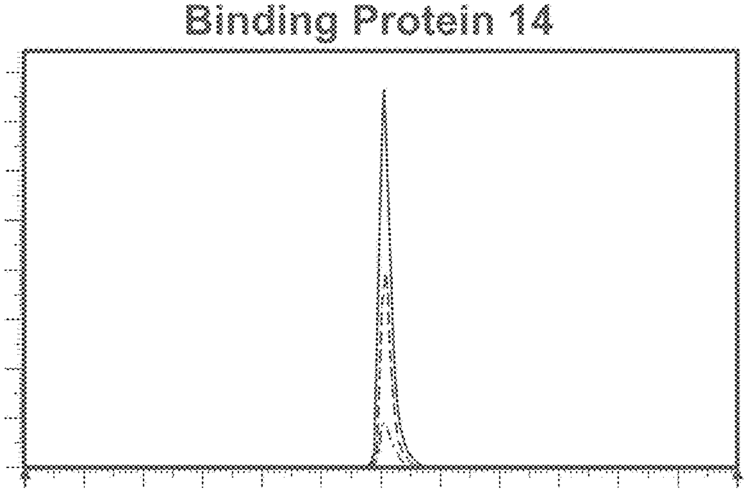
FIG. 27A (Cont.)

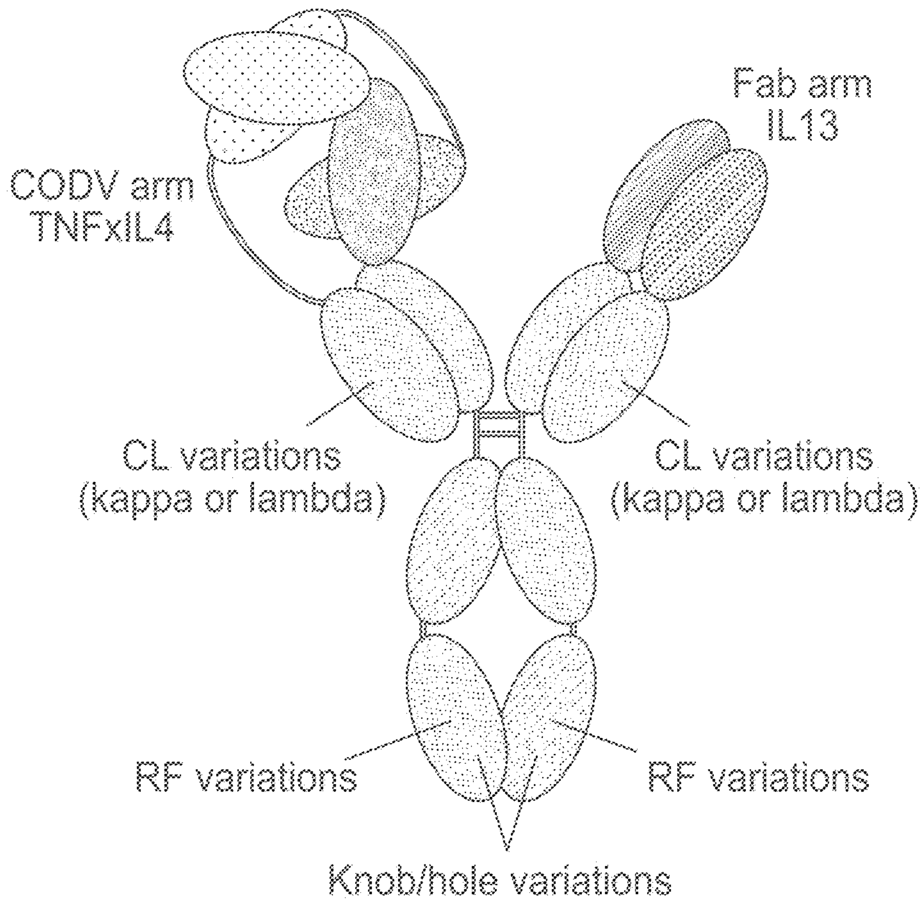

FIG. 28A

| CODV-arm | Fab-arm | CODV-arm | Fab-arm | RF mutation |
|---|---|---|---|---|
| Kappa | Kappa | Hole | Knob | no RF |
| Kappa | Kappa | Hole | Knob | Hole |
| Kappa | Kappa | Hole | Knob | Knob |
| Kappa | lambda | Knob | Hole | no RF |
| Kappa | lambda | Knob | Hole | Hole |
| Kappa | lambda | Knob | Hole | Knob |
| lambda | Kappa | Knob | Hole | no RF |
| lambda | Kappa | Knob | Hole | Hole |
| lambda | Kappa | Knob | Hole | Knob |
| Kappa | Kappa | Knob | Hole | no RF |
| Kappa | Kappa | Knob | Hole | Hole |
| Kappa | Kappa | Knob | Hole | Knob |
| Kappa | lambda | Hole | Knob | no RF |
| Kappa | lambda | Hole | Knob | Hole |
| Kappa | lambda | Hole | Knob | Knob |
| lambda | Kappa | Hole | Knob | no RF |
| lambda | Kappa | Hole | Knob | Hole |
| lambda | Kappa | Hole | Knob | Knob |

FIG. 28B

TRISPECIFIC AND/OR TRIVALENT BINDING PROTEINS

CROSS REFERENCES TO RELATED APPLICATIONS

This application is a continuation of U.S. patent application Ser. No. 17/515,227, filed Oct. 29, 2021, which is a continuation of U.S. patent application Ser. No. 17/099,439 (now U.S. Pat. No. 11,192,960), filed Nov. 16, 2020, which is a continuation of U.S. patent application Ser. No. 15/487,243 (now U.S. Pat. No. 10,882,922), filed Apr. 13, 2017, which claims the priority benefit of U.S. Provisional Application No. 62/322,036, filed Apr. 13, 2016; U.S. Provisional Application No. 62/331,191, filed May 3, 2016; U.S. Provisional Application No. 62/412,187, filed Oct. 24, 2016; and EP Application No. 17305298.6, filed Mar. 17, 2017; all of which are incorporated herein by reference in their entirety.

SUBMISSION OF SEQUENCE LISTING ON ASCII TEXT FILE

REFERENCE TO AN ELECTRONIC SEQUENCE LISTING

The contents of the electronic sequence listing (file name: 183952027104SEQLIST.xml; Size: 274,444 bytes; and Date of Creation: Nov. 30, 2022) are incorporated herein by reference in their entirety.

FIELD OF THE INVENTION

The disclosure relates to trispecific and/or trivalent binding proteins comprising four polypeptide chains that form three antigen binding sites that specifically bind one or more target proteins, wherein a first pair of polypeptides forming the binding protein possess dual variable domains having a cross-over orientation and wherein a second pair of polypeptides forming the binding protein possess a single variable domain. The disclosure also relates to methods for making trispecific and/or trivalent binding proteins and uses of such binding proteins.

BACKGROUND

Monoclonal antibody based biotherapeutics have become an important avenue for new drug development. Monoclonal antibody technology offers specific targeting, precise signaling delivery and/or payload to specific cell population, and provides long lasting biological effect through its Fc functions. Efforts in antibody engineering have allowed developing bispecific antibodies combining the specificities of two monoclonal antibodies for various biological applications, expanding the scope of antibody drug development. Newly discovered neutralizing antibodies with improved breadth and potency may provide more options for developing biotherapeutics to treat complexed diseases such as cancer, arthritis, and/or inflammatory disorders.

BRIEF SUMMARY

Provided herein are multispecific binding proteins (e.g., antibodies) that form three antigen binding sites. These binding proteins can specifically bind one, two, or three antigen targets or target proteins.

In one embodiment, the disclosure provides a binding protein comprising four polypeptide chains that form three antigen binding sites that specifically bind one or more antigen targets or target proteins, wherein a first polypeptide chain has a structure represented by the formula:

$$V_{L2}—L_1—V_{L1}—L_2—C_L \quad [I]$$

and a second polypeptide chain has a structure represented by the formula:

$$V_{H1}—L_3—V_{H2}—L_4—C_{H1} \quad [II]$$

and a third polypeptide chain has a structure represented by the formula:

$$V_{H3}—C_{H1} \quad [III]$$

and a fourth polypeptide chain has a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In some embodiments, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains.

In another embodiment, the disclosure provides a binding protein comprising four polypeptide chains that form three antigen binding sites that specifically bind one or more target proteins, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}-L_4—C_{H1}-\text{hinge}—C_{H2}-C_{H3} \quad [II]$$

and a third polypeptide chain comprises a structure represented by the formula:

$$V_{H3}—C_{H1}-\text{hinge}—C_{H2}-C_{H3} \quad [III]$$

and a fourth polypeptide chain comprises a structure represented by the formula:

$$V_{L3}—C_L \quad [IV]$$

wherein:

- $V_{L1}$ is a first immunoglobulin light chain variable domain;
- $V_{L2}$ is a second immunoglobulin light chain variable domain;
- $V_{L3}$ is a third immunoglobulin light chain variable domain;
- $V_{H1}$ is a first immunoglobulin heavy chain variable domain;
- $V_{H2}$ is a second immunoglobulin heavy chain variable domain;
- $V_{H3}$ is a third immunoglobulin heavy chain variable domain;
- $C_L$ is an immunoglobulin light chain constant domain;
- $C_{H1}$ is an immunoglobulin $C_{H1}$ heavy chain constant domain;
- $C_{H2}$ is an immunoglobulin $C_{H2}$ heavy chain constant domain;
- $C_{H3}$ is an immunoglobulin $C_{H3}$ heavy chain constant domain;
- hinge is an immunoglobulin hinge region connecting the $C_{H1}$ and $C_{H2}$ domains; and
- $L_1$, $L_2$, $L_3$ and $L_4$ are amino acid linkers;
- and wherein the polypeptide of formula I and the polypeptide of formula II form a cross-over light chain-heavy chain pair.

In some embodiments, the binding protein is trispecific and capable of specifically binding three different antigen targets. In some embodiments, the binding protein is trivalent but bispecific and capable of specifically binding three antigen targets, two of them being identical. In some embodiments, the binding protein of the present disclosure is trivalent but monospecific and capable of specifically binding three antigen targets, all of them being identical. In some embodiments, the binding protein is capable of inhibiting the function of one or more target proteins. In some embodiments, the binding protein is trispecific and capable of specifically binding three different antigen targets.

In some embodiments, a binding protein of the present disclosure comprises one, two, or three antigen binding sites that specifically bind a target protein selected from A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets. In some embodiments, the binding protein of the present disclosure is trispecific and capable of specifically binding three different antigen targets selected from the above list. In some embodiments, the binding protein of the present disclosure is trivalent but bispecific and capable of specifically binding three antigen targets selected from the above list, two of them being identical. In some embodiments, the binding protein of the present disclosure is trivalent but monospecific and capable of specifically binding three antigen targets selected from the above list, all of them being identical. In some embodiments, the binding protein specifically binds three target proteins that correspond to two target proteins on T cells and to one tumor target protein. In some embodiments, one of said target proteins on T cells is CD3. In some embodiments, one of said target proteins on T cells is CD28. In some embodiments, said tumor target protein is CD38. In some embodiments, the binding protein specifically binds three target proteins that correspond to two target proteins on T cells and to one target protein selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

In another embodiment, the disclosure provides a binding protein comprising four polypeptide chains that form three antigen binding sites, wherein a first polypeptide chain has a structure represented by the formula:

$$V_{L2}—L_1—V_{L1}-L_2—C_L \quad [I]$$

and a second polypeptide chain has a structure represented by the formula:

$$V_{H1}—L_3—V_{H2}-L_4—C_{H1} \quad [II]$$

and a third polypeptide chain has a structure represented by the formula:

$$V_{H3}—C_{H1} \quad [III]$$

and a fourth polypeptide chain has a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ are each independently a variable domain derived from an amino acid sequence as set forth in any one of SEQ ID NOs: 2, 4, 10, 14, 18, 22, 115;

(b) $V_{L1}$, $V_{L2}$ and $V_{L3}$ each independently comprise light chain complementarity determining regions of a variable domain comprising an amino acid sequence as set forth in any one of SEQ ID NOs: 43-59, 123-125;

(c) $V_{L1}$, $V_{L2}$ and $V_{L3}$ each independently comprise a variable domain sequence as set forth in any one of SEQ ID NOs:151, 153, 155, 157, 159, 161, 163, 165, and 167;

(d) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; or (e) $V_{L1}$, $V_{L2}$ and $V_{L3}$ each independently comprise light chain complementarity determining regions and/or a variable domain sequence shown in Tables 2-5; and wherein:

(a) $V_{H1}$, $V_{H2}$, and $V_{H3}$ are each independently a variable domain derived from an amino acid sequence as set forth in any one of SEQ ID NOs: 1, 3, 9, 13, 17, 21, 114;

(b) $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122;

(c) $V_{H1}$, $V_{H2}$, and $V_{H3}$ each independently comprise a variable domain sequence as set forth in any one of SEQ ID NOs:150, 152, 154, 156, 158, 160, 162, 164, and 166;

(d) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128; or (e) $V_{H1}$, $V_{H2}$ and $V_{H3}$ each independently comprise heavy chain complementarity determining regions and/or a variable domain sequence shown in Tables 2-5.

In some embodiments, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains.

In another embodiment, the disclosure provides a binding protein comprising four polypeptide chains that form three antigen binding sites, wherein a first polypeptide chain comprises a structure represented by the formula:

$$V_{L2}—L_1—V_{L1}-L_2—C_L \quad [I]$$

and a second polypeptide chain comprises a structure represented by the formula:

$$V_{H1}—L_3—V_{H2}-L_4—C_{H1}-\text{hinge}—C_{H2}-C_{H3} \quad [II]$$

and a third polypeptide chain comprises a structure represented by the formula:

$$V_{H3}—C_{H1}-\text{hinge}—C_{H2}-C_{H3} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ are each independently a variable domain derived from an amino acid sequence as set forth in any one of SEQ ID NOs: 2, 4, 10, 14, 18, 22, 115;

(b) $V_{L1}$, $V_{L2}$ and $V_{L3}$ each independently comprise light chain complementarity determining regions of a variable domain comprising an amino acid sequence as set forth in any one of SEQ ID NOs: 43-59, 123-125;

(c) $V_{L1}$, $V_{L2}$ and $V_{L3}$ each independently comprise a variable domain sequence as set forth in any one of SEQ ID NOs:151, 153, 155, 157, 159, 161, 163, 165, and 167;

(d) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; or (e) $V_{L1}$, $V_{L2}$ and $V_{L3}$ each independently comprise light chain complementarity determining regions and/or a variable domain sequence shown in Tables 2-5;

wherein:

(a) $V_{H1}$, $V_{H2}$, and $V_{H3}$ are each independently a variable domain derived from an amino acid sequence as set forth in any one of SEQ ID NOs: 1, 3, 9, 13, 17, 21, 114;

(b) $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122;

(c) $V_{H1}$, $V_{H2}$, and $V_{H3}$ each independently comprise a variable domain sequence as set forth in any one of SEQ ID NOs:150, 152, 154, 156, 158, 160, 162, 164, and 166;

(d) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128; or (e) $V_{H1}$, $V_{H2}$ and $V_{H3}$ each independently comprise heavy chain complementarity determining regions and/or a variable domain sequence shown in Tables 2-5.

In some embodiments, $V_{L1}$, $V_{L2}$ and $V_{L3}$ each independently comprise a variable domain sequence as set forth in any one of SEQ ID NOs:151, 153, 155, 157, 159, 161, 163, 165, and 167; and $V_{H1}$, $V_{H2}$, and $V_{H3}$ each independently comprise a variable domain sequence as set forth in any one of SEQ ID NOs:150, 152, 154, 156, 158, 160, 162, 164, and 166. In some embodiments, $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and (d) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

In some embodiments of any of the binding proteins described herein, (a) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; (b) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ Comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; (c) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57; (d) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ Comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57; (e) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59; (f) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ Comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59; (g) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140; (h) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ Comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140; (i) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125; or (j) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ Comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125. In some embodiments, (a) $V_{H1}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L1}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H2}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; $V_{L2}$ Comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, the binding protein comprises one antigen binding site that specifically binds a T-cell surface protein and another antigen binding site that specifically binds an antigen target, e.g., a tumor target protein. In some embodiments, the binding protein comprises an antigen binding site that specifically binds CD3, an antigen binding site that specifically binds CD28, and an antigen binding site that specifically binds a tumor target protein selected from the group consisting of CD19, CD20, CD38, Her2, and LAMP1. In some embodiments, $V_{H1}$ and $V_{L1}$ form a first antigen binding site that specifically binds human CD3, $V_{H2}$ and $V_{L2}$ form a second antigen binding site that specifically binds human CD28, and $V_{H3}$ and $V_{L3}$ form a third antigen binding site that specifically binds a human tumor target protein. In some embodiments, $V_{H1}$ and $V_{L1}$ form a first antigen binding site that specifically binds human CD28, $V_{H2}$ and $V_{L2}$ form a second antigen binding site that specifically binds human CD3, and $V_{H3}$ and $V_{L3}$ form a third binding site that specifically binds a human tumor target protein. In some embodiments, the antigen binding site specifically binds a human tumor target protein selected from the group consisting of CD19, CD20, CD38, Her2, and LAMP1. In some embodiments, the antigen binding site that specifically binds CD3 comprises: (a) a heavy chain variable domain comprising the amino acid sequence of SEQ ID NO: 152 and a light chain variable domain comprising the amino acid sequence of SEQ ID NO: 153; or (b) a heavy chain variable domain comprising the amino acid sequence of SEQ ID NO: 154 and a light chain variable domain comprising the amino acid sequence of SEQ ID NO: 155. In some embodiments, the antigen binding site that specifically binds CD3 comprises six CDRs, or a heavy chain and a light chain variable domain, shown in Tables 2-5. In some embodiments, the antigen binding site that specifically binds CD28 comprises: (a) a heavy chain variable domain comprising the amino acid sequence of SEQ ID NO: 160 and a light chain variable domain comprising the amino acid sequence of SEQ ID NO: 161; or (b) a heavy chain variable domain comprising the amino acid sequence of SEQ ID NO: 162 and a light chain variable domain comprising the amino acid sequence of SEQ ID NO: 163. In some embodiments, the antigen binding site that specifically binds CD28 comprises six CDRs, or a heavy chain and a light chain variable domain, shown in Tables 2-5. In some embodiments, the antigen binding site that specifically binds a tumor target protein comprises: (a) a heavy chain variable domain comprising the amino acid sequence of SEQ ID NO: 156 and a light chain variable domain comprising the amino acid sequence of SEQ ID NO: 157; (b) a heavy chain variable domain comprising the amino acid sequence of SEQ ID NO: 158 and a light chain variable domain comprising the amino acid sequence of SEQ ID NO: 159; (c) a heavy chain variable domain comprising the amino acid sequence of SEQ ID NO: 164 and a light chain variable domain comprising the amino acid sequence of SEQ ID NO: 165; (d) a heavy chain variable domain comprising the amino acid sequence of SEQ ID NO: 150 and a light chain variable domain comprising the amino acid sequence of SEQ ID NO: 151; or (e) a heavy chain variable domain comprising the amino acid sequence of SEQ ID NO: 166 and a light chain variable domain comprising the amino acid sequence of SEQ ID NO: 167. In some embodiments, the antigen binding site that specifically binds a tumor target protein comprises six CDRs, or a heavy chain and a light chain variable domain, shown in Tables 2-5. In some embodiments, the antigen binding site that specifically binds a tumor target protein comprises six CDRs, or a heavy chain and a light chain variable domain, of an anti-Her2, anti-CD19, anti-CD20, anti-CD38, or anti-LAMP1 binding domain shown in Tables 2-5.

In another embodiment, the disclosure provides a binding protein comprising four polypeptide chains that form three antigen binding sites, wherein a first polypeptide chain has a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ are each independently a variable domain derived from an amino acid sequence as set forth in any one of SEQ ID NOs: 61, 63, 69, 71, 74, 76, 82, 86, 88, 94; or (b) $V_{L1}$, $V_{L2}$ and $V_{L3}$ each independently comprise light chain complementarity determining regions of a variable domain of at least one amino acid sequence set forth in any one of SEQ ID NOs: 61, 63, 69, 71, 74, 76, 82, 86, 88, 94;

(c) $V_{L1}$, $V_{L2}$ and $V_{L3}$ each independently comprise a variable domain sequence as set forth in any one of SEQ ID NOs:169, 171, and 173;

(d) $V_{L1}$, $V_{L2}$ and $V_{L3}$ each independently comprise light chain complementarity determining regions comprising an amino acid sequence selected from the group consisting of SEQ ID NOs: 141-147, 178, and 179; or (e) $V_{L1}$, $V_{L2}$ and $V_{L3}$ each independently comprise light chain complementarity determining regions and/or a variable domain sequence shown in Tables 2-5; and wherein:

(a) $V_{H1}$, $V_{H2}$, and $V_{H3}$ are each independently a variable domain derived from an amino acid sequence as set forth in any one of SEQ ID NOs: 60, 62, 68, 73, 75, 81, 85, 87, 93; or (b) $V_{H1}$, $V_{H2}$, and $V_{H3}$ each independently comprise heavy chain complementarity determining regions of a variable domain of at least one amino acid sequence set forth in any one of in any one of SEQ ID NOs: 60, 62, 68, 73, 75, 81, 85, 87, 93;

(c) $V_{H1}$, $V_{H2}$, and $V_{H3}$ each independently comprise a variable domain sequence as set forth in any one of SEQ ID NOs:168, 170, and 172;

(d) $V_{H1}$, $V_{H2}$ and $V_{H3}$ each independently comprise heavy chain complementarity determining regions comprising an amino acid sequence selected from the group consisting of SEQ ID NOs: 129-137; or (e) $V_{H1}$, $V_{H2}$ and $V_{H3}$ each independently comprise heavy chain complementarity determining regions and/or a variable domain sequence shown in Tables 2-5.

In some embodiments, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains.

In another embodiment, the disclosure provides a binding protein comprising four polypeptide chains that form three antigen binding sites, wherein a first polypeptide chain comprises a structure represented by the formula:

$$V_{L2}\text{—}L_1\text{—}V_{L1}\text{—}L_2\text{—}C_L \quad [I]$$

and a second polypeptide chain comprises a structure represented by the formula:

$$V_{H1}\text{—}L_3\text{—}V_{H2}\text{-}L_4\text{—}C_{H1}\text{-hinge—}C_{H2}\text{-}C_{H3} \quad [II]$$

and a third polypeptide chain comprises a structure represented by the formula:

$$V_{H3}\text{—}C_{H1}\text{—hinge—}C_{H2}\text{—}C_{H3} \quad [III]$$

and a fourth polypeptide chain comprises a structure represented by the formula:

$$V_{L3}\text{—}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ are each independently a variable domain derived from an amino acid sequence as set forth in any one of SEQ ID NOs: 61, 63, 69, 71, 74, 76, 82, 86, 88, 94;

(b) $V_{L1}$, $V_{L2}$ and $V_{L3}$ each independently comprise light chain complementarity determining regions of a variable domain of at least one amino acid sequence set forth in any one of SEQ ID NOs: 61, 63, 69, 71, 74, 76, 82, 86, 88, 94;

(c) $V_{L1}$, $V_{L2}$ and $V_{L3}$ each independently comprise a variable domain sequence as set forth in any one of SEQ ID NOs:169, 171, and 173;

(d) $V_{L1}$, $V_{L2}$ and $V_{L3}$ each independently comprise light chain complementarity determining regions comprising an amino acid sequence selected from the group consisting of SEQ ID NOs: 141-147, 178, and 179; or (e) $V_{L1}$, $V_{L2}$ and $V_{L3}$ each independently comprise light chain complementarity determining regions and/or a variable domain sequence shown in Tables 2-5;

wherein:

(a) $V_{H1}$, $V_{H2}$, and $V_{H3}$ are each independently a variable domain derived from an amino acid sequence as set forth in any one of SEQ ID NOs: 60, 62, 68, 73, 75, 81, 85, 87, 93;

(b) $V_{H1}$, $V_{H2}$, and $V_{H3}$ each independently comprise heavy chain complementarity determining regions of a variable domain of at least one amino acid sequence set forth in any one of in any one of SEQ ID NOs: 60, 62, 68, 73, 75, 81, 85, 87, 93;

(c) $V_{H1}$, $V_{H2}$, and $V_{H3}$ each independently comprise a variable domain sequence as set forth in any one of SEQ ID NOs:168, 170, and 172;

(d) $V_{H1}$, $V_{H2}$ and $V_{H3}$ each independently comprise heavy chain complementarity determining regions comprising an amino acid sequence selected from the group consisting of SEQ ID NOs: 129-137;

(e) $V_{H1}$, $V_{H2}$ and $V_{H3}$ each independently comprise heavy chain complementarity determining regions and/or a variable domain sequence shown in Tables 2-5.

In some embodiments, $V_{L1}$, $V_{L2}$ and $V_{L3}$ each independently comprise a variable domain sequence as set forth in any one of SEQ ID NOs:169, 171, and 173; and $V_{H1}$, $V_{H2}$, and $V_{H3}$ each independently comprise a variable domain sequence as set forth in any one of SEQ ID NOs:168, 170, and 172. In some embodiments, $V_{L1}$, $V_{L2}$ and $V_{L3}$ each independently comprise light chain complementarity determining regions comprising an amino acid sequence selected from the group consisting of SEQ ID NOs: 141-147, 178, and 179; and $V_{H1}$, $V_{H2}$ and $V_{H3}$ each independently comprise heavy chain complementarity determining regions comprising an amino acid sequence selected from the group consisting of SEQ ID NOs: 129-137.

In some embodiments of any of the binding proteins described herein, (a) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; (b) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; (c) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

$V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; (d) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; (e) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; (f) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; (g) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; (h) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; (i) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO: 144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; or (j) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144. In some embodiments, one or more of $V_{H1}$, $V_{L1}$, $V_{H2}$, $V_{L2}$, $V_{H3}$, and $V_{L3}$ comprises one, two, or three CDR sequences of an antibody shown in Tables 2-5.

In some embodiments, the binding protein comprises three antigen binding sites, where one, two, or three of the antigen binding site(s) specifically bind(s) a cytokine target protein selected from the group consisting of IL-4, IL-13 and TNFa. In some embodiments, (a) $V_{H1}$ and $V_{L1}$ form a first antigen binding site that specifically binds human TNFa, $V_{H2}$ and $V_{L2}$ form an antigen binding site that specifically binds human IL13, and $V_{H3}$ and $V_{L3}$ form an antigen binding site that specifically binds human IL4; (b) $V_{H1}$ and $V_{L1}$ form a first antigen binding site that specifically binds human TNFa, $V_{H2}$ and $V_{L2}$ form a second antigen binding site that specifically binds human IL4, and $V_{H3}$ and $V_{L3}$ form a third antigen binding site that specifically binds human IL13; (c) $V_{H1}$ and $V_{L1}$ form a first antigen binding site that specifically binds human IL4, $V_{H2}$ and $V_{L2}$ form a second antigen binding site that specifically binds human TNFa, and $V_{H3}$ and $V_{L3}$ form a third antigen binding site that specifically binds human IL13; (d) $V_{H1}$ and $V_{L1}$ form a first antigen binding site that specifically binds human IL4, $V_{H2}$ and $V_{L2}$ form a second antigen binding site that specifically binds human IL13, and $V_{H3}$ and $V_{L3}$ form a third antigen binding site that specifically binds human TNFa; (e) $V_{H1}$ and $V_{L1}$ form a first antigen binding site that specifically binds human IL13, $V_{H2}$ and $V_{L2}$ form a second antigen binding site that specifically binds human IL4, and $V_{H3}$ and $V_{L3}$ form a third antigen binding site that specifically binds human TNFa; or (f) $V_{H1}$ and $V_{L1}$ form a first antigen binding site that specifically binds human IL13, $V_{H2}$ and $V_{L2}$ form a second antigen binding site that specifically binds human TNFa, and $V_{H3}$ and $V_{L3}$ form a third antigen binding site that specifically binds human IL4. In some embodiments, the antigen binding site that specifically binds human TNFa comprises a heavy chain variable domain comprising the amino acid sequence of SEQ ID NO:168 and a light chain variable domain comprising the amino acid sequence of SEQ ID NO:169. In some embodiments, the antigen binding site that specifically binds human IL4 comprises a heavy chain variable domain comprising the amino acid sequence of SEQ ID NO:170 and a light chain variable domain comprising the amino acid sequence of SEQ ID NO:171. In some embodiments, the antigen binding site that specifically binds human IL13 comprises a heavy chain variable domain comprising the amino acid sequence of SEQ ID NO:172 and a light chain variable domain comprising the amino acid sequence of SEQ ID NO:173.

In some embodiments of any of the binding proteins described herein, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains. In some embodiments, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, the binding protein is trispecific and capable of specifically binding three different antigen targets. In some embodiments, the binding protein is trispecific and capable of specifically binding three different antigen targets. In some embodiments, the binding protein is capable of inhibiting the function of one or more target proteins.

In some embodiments of any of the binding proteins described herein, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, one, two, three, or all four of $L_1$, $L_2$, $L_3$ and $L_4$ are between 0 and 15 amino acids in length. In some embodiments, at least two of $L_1$, $L_2$, $L_3$ and $L_4$ are between 1 and 15 amino acids in length. In some embodiments, (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148). In some embodiments, $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT; $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length; $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

In some embodiments of any of the binding proteins described herein, the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains, and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the $C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W. In some embodiments, the $C_{H3}$ domains of the second and the third polypeptide chains both comprise amino acid substitutions at positions corresponding to positions 428 and 434 of human IgG1 or IgG4 according to EU Index, wherein the amino acid substitutions are M428L and N434S. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, the $C_{H3}$ domains of the second and the third polypeptide chains are human IgG1 $C_{H3}$ domains, and wherein only one of the $C_{H3}$ domains comprises amino acid substitutions at positions corresponding to positions 435 and 436 of human IgG1 or IgG4 according to EU Index, wherein the amino acid substitutions are H435R and Y436F. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, the $C_{H3}$ domains of the second and the third polypeptide chains are human IgG4 $C_{H3}$ domains, and wherein the $C_{H3}$ domains each comprise amino acid substitutions at positions corresponding to positions 228 and 409 of human IgG4 according to EU Index, wherein the amino acid substitutions are S228P and R409K. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions are human IgG4 Fc regions; and wherein the first and the second Fc regions each comprise amino acid substitutions at positions corresponding to positions 234 and 235 of human IgG4 according to EU Index, wherein the amino acid substitutions are F234A and L235A. In some embodiments, the $C_{H3}$ domains of the second and the third polypeptide chains are human IgG4 $C_{H3}$ domains, and wherein the $C_{H3}$ domains each comprise amino acid substitutions at positions corresponding to positions 234 and 235 of human IgG4 according to EU Index, wherein the amino acid substitutions are F234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the $C_{H3}$ domains of the second and the third polypeptide chains are human IgG1 $C_{H3}$ domains, and wherein the $C_{H3}$ domains each comprise amino acid substitutions at positions corresponding to positions 234 and 235 of human IgG1 according to EU Index, wherein the amino acid substitutions are L234A and L235A. In some embodiments, the first and/or second Fc regions are human IgG1 Fc regions. In some embodiments, the first and/or second Fc regions are human IgG4 Fc regions.

In some embodiments of any of the binding proteins described herein, the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain. In some embodiments, the first polypeptide chain comprises a lambda $C_L$ domain; wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and wherein the fourth polypeptide chain comprises a kappa $C_L$ domain. In some embodiments, the first polypeptide chain comprises a lambda $C_L$ domain; wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W; wherein the $C_{H3}$ domain of the second polypeptide chain comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and wherein the fourth polypeptide chain comprises a kappa $C_L$ domain. In some embodiments, the first polypeptide chain comprises a lambda $C_L$ domain; wherein the $C_{H3}$ domain of the second polypeptide chain comprises amino acid substitutions at positions corresponding to positions 354, 366, 435, and 436 of human IgG1 or IgG4 according to EU Index, wherein the amino acid substitutions are S354C, T366W, H435R, and Y436F; wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the fourth polypeptide chain comprises a kappa $C_L$ domain. In some embodiments, the first polypeptide chain comprises a kappa $C_L$ domain; wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and wherein the fourth polypeptide chain comprises a lambda $C_L$ domain. In some embodiments, second and/or third polypeptide chain comprise a human IgG1 or IgG4 Fc region.

In another embodiment, the disclosure provides a binding protein comprising a first polypeptide chain, a second polypeptide chain, a third polypeptide chain and a fourth polypeptide chain wherein:

(a) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(b) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(c) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(d) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(e) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18

(f) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18;

(g) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(h) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(i) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(j) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(k) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 71 or an amino acid sequence that is at least 95% identical to the amino acid sequence of SEQ ID NO: 71; (l) the first polypeptide chain comprises the amino acid sequence of SEQ ID NO: 76 or an amino acid sequence that is at least 95% identical to the amino acid sequence of SEQ ID NO: 76; the second polypeptide chain comprises the amino acid sequence of SEQ ID NO: 75 or an amino acid sequence that is at least 95% identical to the amino acid sequence of SEQ ID NO: 75; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(m) the first polypeptide chain comprises the amino acid sequence of SEQ ID NO: 82 or an amino acid sequence that is at least 95% identical to the amino acid sequence of SEQ ID NO: 82; the second polypeptide chain comprises the amino acid sequence of SEQ ID NO: 81 or an amino acid sequence that is at least 95% identical to the amino acid sequence of SEQ ID NO:81; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(n) the first polypeptide chain comprises the amino acid sequence of SEQ ID NO: 88 or an amino acid sequence that is at least 95% identical to the amino acid sequence of SEQ ID NO:88; the second polypeptide chain comprises the amino acid sequence of SEQ ID NO: 87 or an amino acid sequence that is at least 95% identical to the amino acid sequence of SEQ ID NO: 87; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(o) the first polypeptide chain comprises the amino acid sequence of SEQ ID NO: 94 or an amino acid sequence that is at least 95% identical to the amino acid sequence of SEQ ID NO: 94; the second polypeptide chain comprises the amino acid sequence of SEQ ID NO: 93 or an amino acid sequence that is at least 95% identical to the amino acid sequence of SEQ ID NO: 93; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(p) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(q) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(r) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(s) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(t) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115; or (u) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115.

In another embodiment, the disclosure provides an isolated nucleic acid molecule comprising a nucleotide sequence encoding the binding protein or polypeptide thereof according to any of the above embodiments. In another embodiment, the disclosure provides an expression vector comprising the nucleic acid molecule according to one of the above embodiments. In another embodiment, the disclosure provides an isolated host cell comprising the nucleic acid molecule according to any of the above embodiments. In another embodiment, the disclosure provides an isolated host cell comprising the expression vector according to any of the above embodiments. In some embodiments, the isolated host cell is a mammalian cell or an insect cell. In one embodiment, the disclosure provides a vector system comprising one or more vectors encoding a first, second, third, and fourth polypeptide chain of a binding protein according to any of the above embodiments. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the one or more vectors are expression vectors. In one embodiment, the disclosure provides an isolated host cell comprising the vector system according to any of the above embodiments. In one embodiment, the disclosure provides a method of producing a binding protein, the method comprising: a) culturing a host cell according to any of the above embodiments under conditions such that the host cell expresses the binding protein; and b) isolating the binding protein from the host cell. In one embodiment, the disclosure provides a pharmaceutical composition comprising the binding protein according to any of the above embodiments and a pharmaceutically acceptable carrier.

In another embodiment, the disclosure provides a method of preventing and/or treating cancer in a patient comprising administering to the patient a therapeutically effective amount of at least one binding protein or pharmaceutical composition according to any of the above embodiments. In another embodiment, the disclosure provides a binding protein or pharmaceutical composition according to any of the above embodiments for use in preventing and/or treating cancer in a patient. In another embodiment, the disclosure provides a binding protein according to any of the above embodiments for the manufacture of a medicament for preventing and/or treating cancer in a patient. In some embodiments, the binding protein comprises one antigen binding site that specifically binds a T-cell surface protein and another antigen binding site that specifically binds a tumor target protein. In some embodiments, the binding protein comprises an antigen binding site that specifically binds CD3, an antigen binding site that specifically binds CD28, and an antigen binding site that specifically binds a tumor target protein selected from the group consisting of CD19, CD20, CD38, Her2, and LAMP1. In some embodiments, the at least one binding protein is co-administered with a chemotherapeutic agent. In some embodiments, the patient is a human. In some embodiments, the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

In another embodiment, the disclosure provides a method of preventing and/or treating an inflammatory disease or disorder in a patient comprising administering to the patient a therapeutically effective amount of at least one binding protein or pharmaceutical composition according to any of the above embodiments. In another embodiment, the disclosure provides a binding protein or pharmaceutical composition according to any of the above embodiments for use in preventing and/or treating an inflammatory disease or disorder in a patient. In another embodiment, the disclosure provides a binding protein according to any of the above embodiments for the manufacture of a medicament for preventing and/or treating an inflammatory disease or disorder in a patient. In some embodiments, the binding protein comprises three antigen binding sites that each specifically bind a cytokine target protein selected from the group consisting of IL-4, IL-13 and TNFa. In some embodiments, two of the three binding sites specifically bind a cytokine target protein selected from the group consisting of IL-4, IL-13 and TNFa. In some embodiments, the at least one binding protein is co-administered with an anti-inflammatory agent. In some embodiments, the patient is a human. In some embodiments, the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

In another embodiment, the disclosure provides a method of purifying a binding protein produced by a host cell, comprising:

(a) producing in a host cell a binding protein comprising four polypeptide chains that form three antigen binding sites that specifically bind one or more antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1} \quad [III]$$

and a fourth polypeptide chain comprises a structure represented by the formula:

$$V_{L3}\text{-}C_L \quad [IV]$$

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair; wherein only one of the $C_{H3}$ domain of the second polypeptide chain and the $C_{H3}$ domain of the third polypeptide chain comprises amino acid substitutions at positions corresponding to positions 435 and 436 of human IgG1 or IgG4 according to EU Index, wherein the amino acid substitutions are H435R and Y436F;

(b) contacting the binding protein produced in (a) with Protein A; and (c) eluting the binding protein from Protein A under conditions suitable for isolating the binding protein away from binding proteins comprising either 0 or 2 $C_{H3}$ domains comprising the amino acid substitutions are H435R and Y436F.

In some embodiments, the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises: (d) contacting the binding protein eluted in (c) with a kappa light chain affinity medium; and (e) eluting the binding protein from the kappa light chain affinity medium under conditions suitable for isolating the binding protein away from binding proteins comprising only lambda $C_L$ domains. In some embodiments, the method further comprises, after (e), (f) contacting the binding protein eluted in (e) with a lambda light chain affinity medium; and (g) eluting the binding protein from the lambda light chain affinity medium under conditions suitable for isolating the binding protein away from binding proteins comprising only kappa $C_L$ domains. In some embodiments, the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises: (d) contacting the binding protein eluted in (c) with a lambda light chain affinity medium; and (e) eluting the binding protein from the lambda light chain affinity medium under conditions suitable for isolating the binding protein away from binding proteins comprising only kappa $C_L$ domains. In some embodiments, the method further comprises, after (e), (f) contacting the binding protein eluted in (e) with a kappa light chain affinity medium; and (g) eluting the binding protein from the kappa light chain affinity medium under conditions suitable for isolating the binding protein away from binding proteins comprising only lambda $C_L$ domains. In some embodiments, the first polypeptide chain comprises a lambda $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain. In some embodiments, the binding protein is detected in one or more of (c) and (e) using hydrophobic interaction chromatography (HIC). In some embodiments, the $C_{H3}$ domains and/or Fc regions of the second and the third polypeptide chains are human IgG1 or IgG4 $C_{H3}$ domains and/or Fc regions.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A shows a trispecific binding protein comprising a "knobs-into-holes" mutation, where the knob is on the second pair of polypeptides with a single variable domain. FIG. 1B shows a trispecific binding protein comprising a "knobs-into-holes" mutation, where the knob is on the first pair of polypeptides having the cross-over orientation. FIG. 1C shows the orientation of variable domains on the polypeptide chains, and the knob/hole orientation for the binding proteins shown in Tables 1-3. "Heavy chain A" (e.g., a third polypeptide chain of the present disclosure) indicates the variable domain of heavy chain A. "Light chain A" (e.g., a fourth polypeptide chain of the present disclosure) indicates the variable domain of light chain A. "Heavy chain B" (e.g., a second polypeptide chain of the present disclosure) indicates variable domain 1 and variable domain 2 of heavy chain B. "Light chain B" (e.g., a first polypeptide chain of the present disclosure) indicates variable domain 1 and variable domain 2 of light chain B.

FIG. 3A shows the results of trispecific antibody-mediated specific killing of ZR-75-1 cells. FIG. 3B shows the results of trispecific antibody-mediated specific killing of AU565 cells. FIG. 3C shows the results of FACS analysis determining the cell surface expression of the indicated markers on ZR-75-1 and AU565 cells.

FIG. 4 shows the results of antibody-mediated specific killing of ZR-75-1 cells using human peripheral blood mononuclear cells (PBMCs) from donor KP45926 at E:T=10.

FIG. 5 shows the results of antibody-mediated specific killing of AU565 cells using human PBMCs from donor KP45944 at E:T=10.

FIGS. 4 & 5 confirm similar cell killing results as shown in FIGS. 3A-3C using PBMCs from a different donor.

FIG. 6A shows the activation ($CD69^+$) of human $CD4^+$ T cells from three donors. FIG. 6B shows the activation ($CD69^+$) of human $CD8^+$ T cells from three donors. $CD28_{sup}$: anti-CD28 superagonist antibody. $CD3_{mid}$: anti-CD3 antibody.

FIG. 9A shows the results of antibody-mediated specific killing of OCI-LY19 cells. FIG. 9N shows the results of antibody-mediated specific killing of OCI-Ly3 cells using PBMCs from donor KP48775 at E:T=10.

FIG. 11A shows the results of antibody-mediated specific killing of MOLP-8 cells using human PBMC as effector cells at E:T=10. FIG. 11B shows the results of antibody-mediated specific killing of RPMI-8226 cells using human PBMC as effector cells at E:T=10. FIG. 11C shows the results of antibody-mediated specific killing of KMS-12-BM cells using human PBMC as effector cells at E:T=10. FIG. 11D shows the results of FACS analysis determining the cell surface expression of the indicated markers on MOLP-8, RPMI-8226, and KMS-12-BM cells.

FIGS. 12A-12D show the results of antibody-mediated specific killing of $CD38^+$ human multiple myeloma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10. FIG. 12A shows the results of antibody-mediated specific killing of NCI-H929 cells. FIG. 12B shows the results of antibody-mediated specific killing of MM.1S cells. FIG. 12C shows the results of antibody-mediated specific killing of MM.1R cells. FIG. 12D shows the results of FACS analysis determining the cell surface expression of the indicated markers on NCI-H929, MM.1S, and MM.1R cells.

FIGS. 13A-13D show the results of antibody-mediated specific killing of $CD38^+$ human multiple myeloma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10. FIG. 13A shows the results of antibody-mediated specific killing of OPM-2 cells. FIG. 13B shows the results of antibody-mediated specific killing of KMS-26 cells. FIG. 13C shows the results of antibody-mediated specific killing of U266 cells. FIG. 13D shows the results of FACS analysis determining the cell surface expression of the indicated markers on OPM-2, KMS-26, and U226 cells.

FIG. 14A shows the results of antibody-mediated specific killing of SUDHL-8 cells. FIG. 14B shows the results of antibody-mediated specific killing of OCI-LY19 cells. FIG. 14C shows the results of FACS analysis determining the cell surface expression of the indicated markers on SUDHL-8 and OCI-LY19 cells.

FIGS. 15A-15D show the results of antibody-mediated specific killing of $CD38^+$ ALL cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10. FIG. 15A shows the results of antibody-mediated specific killing of KOPN-8 cells. FIG. 15B shows the results of antibody-mediated specific killing of HAL-1 cells. FIG. 15C shows the results of antibody-mediated specific killing of CCRF-SB cells. FIG. 15D shows the results of FACS analysis determining the cell surface expression of the indicated markers on KOPN-8, HAL-1, and CCRF-SB cells.

FIG. 18A shows the results of circulating $CD4^+$ T cells percentage in each animal, 6 hours post administering the anti-Her2×CD28×CD3 trispecific antibody. FIG. 18B shows the results of circulating $CD8^+$ T cells percentage in each animal, 6 hours post administering the anti-Her2×CD28×CD3 trispecific antibody. FIG. 18C shows the results of the activation ($CD69^+$) of circulating $CD4^+$ T cells 6 hours post dosing. FIG. 18D shows the results of the activation ($CD69^+$) of circulating $CD8^+$ T cells 6 hours post dosing. FIG. 18E shows the inflammatory cytokine release observed 6 hours post administering the anti-Her2×CD28×CD3 trispecific antibody at each dosing.

FIG. 19A shows the change in body weight of mice treated with the indicated concentrations of the anti-Her2×CD28×CD3 trispecific binding protein or PBS control. FIG. 19B shows the change in tumor volume in mice treated with the indicated concentrations of the anti-Her2×CD28×CD3 trispecific binding protein or PBS control.

FIG. 20A shows the effect of administering the indicated concentrations of the anti-Her2×CD28×CD3 trispecific binding protein, the indicated concentrations of Herceptin, or vehicle control, on the body weight of the mice. FIG. 20B shows the dose-dependent anti-tumor activity of the anti-Her2×CD28×CD3 trispecific binding protein, Herceptin or indicated controls, as in individual mice. FIG. 20C shows the average tumor volume in the mice after administration of the indicated concentrations of the anti-Her2×CD28×CD3 trispecific binding protein or PBS control. FIG. 20D shows the average tumor volume in the mice after administration of the indicated concentrations of Herceptin or PBS control. FIG. 20E shows bar graphs of the average tumor volume at day 34 in the mice after administration of the indicated concentrations of the anti-Her2×CD28×CD3 trispecific binding protein, the indicated concentrations of Herceptin, or PBS control. FIG. 20F shows the average tumor weight at day 34 in the mice after administration of the indicated concentrations of the anti-Her2×CD28×CD3 trispecific binding protein, the indicated concentrations of Herceptin, or PBS control. FIG. 20G shows the human CD45+, CD3+, CD4+, CD8+ cells in the blood of the mice at the end of the study. FIG. 20H shows the human CD45+, CD3+, CD4+, CD8+ cells in the spleens of the mice at the end of the study.

FIG. 21A shows T cell activation ($CD69^+$) (line graph) and proliferation (bar graph) of circulating $CD4^+$ T cells after administration of the anti-CD38×CD28×CD3 trispecific antibody. FIG. 21B shows T cell activation ($CD69^+$) (line graph) and proliferation (bar graph) of circulating $CD8^+$ T cells after administration of the anti-CD38×CD28×CD3 trispecific antibody. FIG. 21C shows IL6 release in animals receiving the anti-CD38×CD28×CD3 trispecific antibody 6 hours post each dosing by individual animal. FIG. 21D shows IL10 release in animals receiving the anti-CD38×CD28×CD3 trispecific antibody 6 hours post each dosing by individual animal. FIG. 21E shows TNFa release in animals receiving the anti-CD38×CD28×CD3 trispecific antibody. FIG. 21F shows IFNγ release in animals receiving the anti-CD38×CD28×CD3 trispecific antibody 6 hours post each dosing by individual animal.

FIG. 22A shows the in vivo tumor growth curve in groups of the indicated concentrations of the anti-CD38×CD28×CD3 trispecific binding protein or controls. FIG. 22B shows tumor infiltrating human $CD8^+$ T cells in mice administered the anti-CD38×CD28×CD3 trispecific binding protein or the indicated controls. FIG. 22C shows tumor infiltrating human $CD4^+$ T cells in mice administered the anti-CD38×CD28×CD3 trispecific binding protein or the indicated controls.

FIG. 23A shows the change in body weight of mice treated with the indicated concentrations of the anti-CD38×CD28×CD3 trispecific binding protein or PBS control. FIG. 23B shows the change in tumor volume in mice treated with the indicated concentrations of the anti-CD38×CD28×CD3 trispecific binding protein or PBS control. FIG. 23C shows the tumor volumes in each group at Day 19. The tumor volumes in all treated groups showed marked reduction, which are statistically different form the PBS control group. FIG. 23D shows the serum concentration of inflammatory cytokines IFN-g, TNF, and IL-2 in mice four hours after the first dose of the indicated concentrations of the anti-CD38×CD28×CD3 trispecific binding protein or PBS control.

FIG. 24 shows the in vivo activation of $CD4^+$ T cells.

FIG. 25 shows the in vivo activation of $CD8^+$ T cells.

FIG. 26A shows the serum levels of IL-2. FIG. 26B shows the serum levels of TNF. FIG. 26C shows the serum levels of IFN-γ.

FIG. 27A shows the purification of Binding Proteins 9-15 by size exclusion chromatography. FIG. 27B shows the purification of Binding Proteins 16-19 by size exclusion chromatography.

FIG. 28A depicts the trispecific binding protein used in experiments for optimizing a purification scheme and configuration of optional binding protein features (e.g., kappa/lambda light chains, knob/hole mutations, and H435R/Y436F mutations).

FIG. 28B shows each of the configurations tested.

FIG. 30A) and SDS-PAGE (FIG. 30B).

DETAILED DESCRIPTION

Figure 1B:
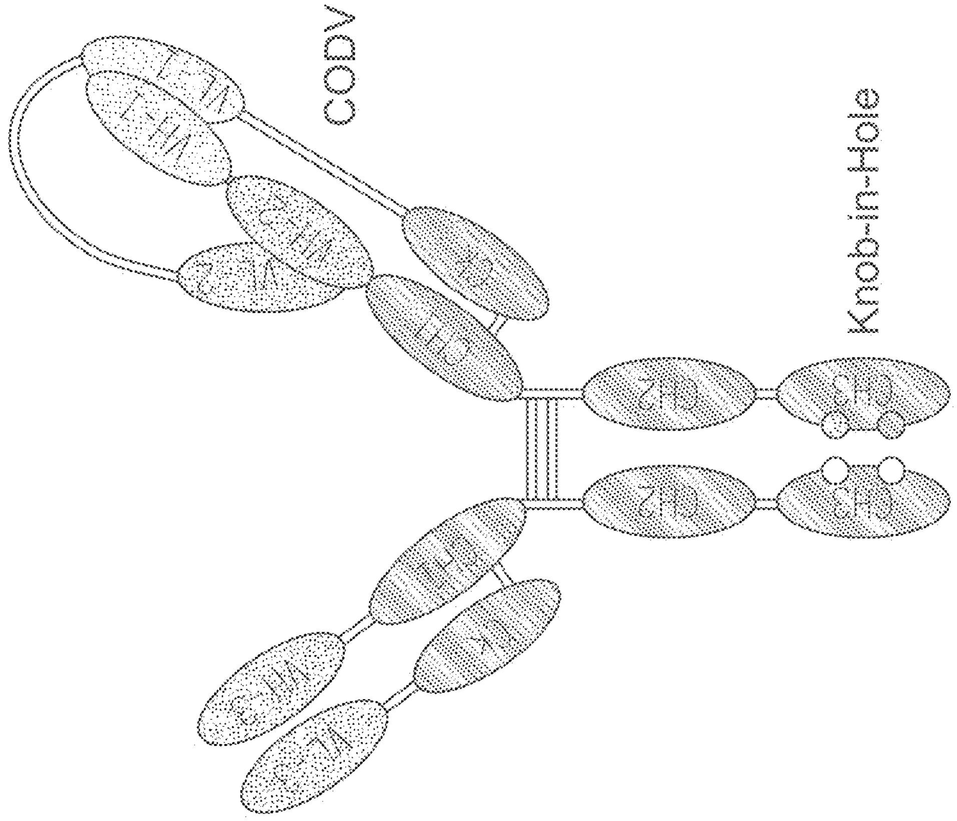
FIGS. 1A-1C show schematic representations of trispecific binding proteins comprising four polypeptide chains that form three antigen binding sites that specifically binds three target proteins, wherein a first pair of polypeptides possess dual variable domains having a cross-over orientation ($V_{H1}$-$V_{H2}$ and $V_{L2}$-$V_{L1}$) forming two antigen binding sites, and wherein a second pair of polypeptides possess a single variable domain ($V_{H3}$ and $V_{L3}$) forming a single antigen binding site.

The disclosure provides trispecific and/or trivalent binding proteins comprising four polypeptide chains that form three antigen binding sites that specifically bind to one or more target proteins, wherein a first pair of polypeptides forming the binding protein possess dual variable domains having a cross-over orientation and wherein a second pair of polypeptides forming the binding protein possess a single variable domain.

General Definitions

As utilized in accordance with the present disclosure, the following terms, unless otherwise indicated, shall be understood to have the following meanings. Unless otherwise required by context, singular terms shall include pluralities and plural terms shall include the singular.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain (VH) and three constant domains ($C_{H1}$, $C_{H2}$, and $C_{H3}$), wherein the VH domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, *J. Mol. Biol.* 196: 901-17; Chothia et al., 1989, *Nature* 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, *FASEB J.* 9: 133-39; MacCallum, 1996, *J. Mol. Biol.* 262(5): 732-45; and Lefranc, 2003, *Dev. Comp. Immunol.* 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," In *Antibody Engineering*, Vol. 2. Kontermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, *Nucleic Acids Res.* 22: 4673-80. Molecular models are conventionally used to correctly delineate framework and CDR regions and thus correct the sequence-based assignments.

The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the $V_H$ and $C_{H1}$ domains of one heavy chain, wherein the $V_H$-$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a $F(ab')_2$ molecule.

The term "binding protein" as used herein refers to a non-naturally occurring (or recombinant or engineered) molecule that specifically binds to at least one target antigen, and which comprises four polypeptide chains that form at least three antigen binding sites, wherein a first polypeptide chain has a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "swapability" as used herein refers to the interchangeability of variable domains within the binding protein format and with retention of folding and ultimate binding affinity. "Full swapability" refers to the ability to swap the order of both $V_{H1}$ and $V_{H2}$ domains, and therefore the order of $V_{L1}$ and $V_{L2}$ domains, in the polypeptide chain of formula I or the polypeptide chain of formula II (i.e., to reverse the order) while maintaining full functionality of the binding protein as evidenced by the retention of binding affinity. Furthermore, it should be noted that the designations $V_H$ and $V_L$ refer only to the domain's location on a particular protein chain in the final format. For example, $V_{H1}$ and $V_{H2}$ could be derived from $V_{L1}$ and $V_{L2}$ domains in parent antibodies and placed into the $V_{H1}$ and $V_{H2}$ positions in the binding protein. Likewise, $V_{L1}$ and $V_{L2}$ could be derived from $V_{H1}$ and $V_{H2}$ domains in parent antibodies and placed in the $V_{H1}$ and $V_{H2}$ positions in the binding protein. Thus, the $V_H$ and $V_L$ designations refer to the present location and not the original location in a parent antibody. $V_H$ and $V_L$ domains are therefore "swappable."

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen. A target antigen may have one or more epitopes. With respect to each target antigen recognized by a binding protein, the binding protein is capable of competing with an intact antibody that recognizes the target antigen.

The term "Her2" refers to human epidermal growth factor receptor 2 which is a member of the epidermal growth factor receptor family.

"CD3" is cluster of differentiation factor 3 polypeptide and is a T-cell surface protein that is typically part of the T cell receptor (TCR) complex.

"CD28" is cluster of differentiation 28 polypeptide and is a T-cell surface protein that provides co-stimulatory signals for T-cell activation and survival.

"CD19" is cluster of differentiation 19 polypeptide and is located on B-cells.

"CD20" is cluster of differentiation 20 polypeptide and is an activated-glycosylated phosphoprotein expressed on the surface of B-cells.

"CD38" is cluster of differentiation 38 polypeptide and is a glycoprotein found on the surface of many immune cells.

"LAMP1" is lysosomal-associated membrane protein 1.

"IL-4" is interleukin 4 and is a cytokine that induces differentiation of naïve helper T cells.

"IL-13" is interleukin 13 and is a cytokine secreted by many cell types such as T-cells.

"TNFa" is tumor necrosis factor alpha and is a cytokine involved in systematic inflammation.

The term "T-cell engager" refers to binding proteins directed to a host's immune system, more specifically the T cells' cytotoxic activity as well as directed to a tumor target protein.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets.

The term "bivalent binding protein" refers to a binding protein that has two binding sites.

The term "trispecific binding protein" refers to a binding protein that specifically binds to three different antigen targets.

The term "trivalent binding protein" refers to a binding protein that has three binding sites. In particular embodiments the trivalent binding protein can bind to one antigen target. In other embodiments, the trivalent binding protein can bind to two antigen targets. In other embodiments, the trivalent binding protein can bind to three antigen targets.

An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

A "neutralizing" binding protein as used herein refers to a molecule that is able to block or substantially reduce an effector function of a target antigen to which it binds. As used herein, "substantially reduce" means at least about 60%, preferably at least about 70%, more preferably at least about 75%, even more preferably at least about 80%, still more preferably at least about 85%, most preferably at least about 90% reduction of an effector function of the target antigen.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, NJ). Surface plasmon analysis can also be performed by immobilizing the analyte (binding protein on a biosensor matrix) and presenting the ligand (target antigen). The term "$K_D$," as used herein refers to the dissociation constant of the interaction between a particular binding protein and a target antigen.

The term "specifically binds" as used herein refers to the ability of a binding protein or an antigen-binding fragment thereof to bind to an antigen containing an epitope with an Kd of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or to bind to an epitope with an affinity that is at least two-fold greater than its affinity for a nonspecific antigen.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers described herein are referred to as $L_1$, which is located on the light chain between the C-terminus of the $V_{L2}$ and the N-terminus of the $V_{L1}$ domain; and $L_2$, which is located on the light chain between the C-terminus of the $V_{L1}$ and the N-terminus of the $C_L$ domain. The heavy chain linkers are known as $L_3$, which is located between the C-terminus of the $V_{H1}$ and the N-terminus of the $V_{H2}$ domain; and $L_4$, which is located between the C-terminus of the $V_{H2}$ and the N-terminus of the $C_{H1}$ domain.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-, α-disubstituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:

(1) hydrophobic: Met, Ala, Val, Leu, Ile, Phe, Trp, Tyr, Pro;
(2) polar hydrophilic: Arg, Asn, Asp, Gln, Glu, His, Lys, Ser, Thr;
(3) aliphatic: Ala, Gly, Ile, Leu, Val, Pro;
(4) aliphatic hydrophobic: Ala, Ile, Leu, Val, Pro;
(5) neutral hydrophilic: Cys, Ser, Thr, Asn, Gln;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects.

The terms "treatment" or "treat" as used herein refer to both therapeutic treatment and prophylactic or preventative measures. Those in need of treatment include those having a disorder as well as those prone to have the disorder or those in which the disorder is to be prevented. In particular embodiments, binding proteins can be used to treat humans with cancer, or humans susceptible to cancer, or ameliorate cancer in a human subject. The binding proteins can also be used to prevent cancer in a human patient. In particular embodiments, the cancer is multiple myeloma, acute lymphoblastic leukemia, chronic lymphocytic leukemia, acute myeloid leukemia, lymphoma, breast cancer such as Her2+ breast cancer, germinal center B-cell lymphoma or B-cell acute lymphoblastic leukemia, In other embodiments, the binding proteins can be used to treat humans with inflammatory disorders, or humans susceptible to inflammatory disorders, or ameliorate inflammatory disorders in a human subject.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding protein.

Trispecific and/or Trivalent Binding Proteins

In one embodiment, the binding protein of the disclosure is a trispecific and/or trivalent binding protein comprising four polypeptide chains that form three antigen binding sites that specifically bind one or more (e.g., three) different antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1} \quad [II]$$

and a third polypeptide chain comprises a structure represented by the formula:

$$V_{H3}\text{-}C_{H1} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In one embodiment, the binding protein of the disclosure is a trispecific and/or trivalent binding protein comprising four polypeptide chains that form three antigen binding sites that specifically bind one or more (e.g., three) antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1} \quad [II]$$

and a third polypeptide chain comprises a structure represented by the formula:

$$V_{H3}\text{-}C_{H1} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In one embodiment, the binding protein of the disclosure is a trispecific and/or trivalent binding protein comprising four polypeptide chains that form three antigen binding sites that specifically bind one or more (e.g., three) different antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In one embodiment, the binding protein of the disclosure is a trispecific and/or trivalent binding protein comprising four polypeptide chains that form three antigen binding sites that specifically bind one or more (e.g., three) antigen targets or target proteins, wherein a first polypeptide chain comprises a structure represented by the formula:

$$V_{L2}\text{-}L_1\text{-}V_{L1}\text{-}L_2\text{-}C_L \quad \text{[I]}$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad \text{[II]}$$

and a third polypeptide chain comprises a structure represented by the formula:

$$V_{H3}\text{-}C_{H1}\text{-hinge-}C_{H2}\text{-}C_{H3} \quad \text{[III]}$$

and a fourth polypeptide chain comprises a structure represented by the formula:

$$V_{L3}\text{-}C_L \quad \text{[IV]}$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In some embodiments, the first polypeptide chain and the second polypeptide chain have a cross-over orientation that forms two distinct antigen binding sites. In some embodiments, the $V_{H1}$ and $V_{L1}$ form a binding pair and form the first antigen binding site. In some embodiments, the $V_{H2}$ and $V_{L2}$ form a binding pair and form the second antigen binding site. In some embodiments, the third polypeptide and the fourth polypeptide form a third antigen binding site. In some embodiments, the $V_{H3}$ and $V_{L3}$ form a binding pair and form the third antigen binding site.

In one embodiment, the binding protein of the disclosure is a trispecific and/or trivalent binding protein comprising four polypeptide chains that form three antigen binding sites that specifically bind one or more (e.g., three) antigen targets or target proteins, wherein a first polypeptide chain comprises a structure represented by the formula:

$$V_{D1}\text{-}L_1\text{-}V_{D2}\text{-}L_2\text{-}C_L \quad \text{[I]}$$

and a second polypeptide chain comprises a structure represented by the formula:

$$V_{D3}\text{-}L_3\text{-}V_{D4}\text{-}L_4\text{-}C_{H1}\text{-hinge-}C_{H2}\text{-}C_{H3} \quad \text{[II]}$$

and a third polypeptide chain comprises a structure represented by the formula:

$$V_{H3}\text{-}C_{H1}\text{-hinge-}C_{H2}\text{-}C_{H3} \quad \text{[III]}$$

and a fourth polypeptide chain comprises a structure represented by the formula:

$$V_{L3}\text{-}C_L \quad \text{[IV]}$$

wherein:

$V_{D1}$ is a variable domain of heavy or light chain of a first immunoglobulin;

$V_{D2}$ is a variable domain of heavy or light chain of a second immunoglobulin;

$V_{D3}$ is a variable domain of heavy or light chain of a third immunoglobulin;

$V_{D4}$ is a variable domain of heavy or light chain of a fourth immunoglobulin;

$V_{H3}$ is an immunoglobulin heavy chain variable domain;

$V_{L3}$ is an immunoglobulin light chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In some embodiments, the binding protein of the disclosure comprises three antigen binding sites that specifically bind one, two, or three antigen targets or target proteins. In some embodiments, the binding protein binds three antigen targets. In some embodiments, the binding protein binds three different antigen targets. In some embodiments, two of the antigen binding sites bind the same antigen target. In those embodiments, the binding protein comprises the same binding domains twice, or different binding domains, and/or specifically binds different antigens or epitopes on the same antigen target. In some embodiments, three of the antigen binding sites bind the same antigen target. In those embodiments, the binding protein comprises the same binding domains three times, or different binding domains, and/or specifically binds different antigens or epitopes on the same antigen target.

In some embodiments, $V_{L1}$, $V_{L2}$ and $V_{L3}$ are each independently a variable domain derived from an amino acid sequence as set forth in any one of SEQ ID NOs: 2, 4, 10, 14, 18, 22 or 115; and $V_{H1}$, $V_{H2}$ and $V_{H3}$, are each independently a variable domain derived from an amino acid sequence as set forth in any one of SEQ ID NOs: 1, 3, 9, 13, 17, 21 or 114. In other embodiments, $V_{L1}$, $V_{L2}$ and $V_{L3}$ are each independently a variable domain derived from an amino acid sequence as set forth in any one of SEQ ID NOs: 61, 63, 69, 71, 74, 76, 82, 86, 88 or 94; and $V_{H1}$, $V_{H2}$ and $V_{H3}$, are each independently a variable domain derived from an amino acid sequence as set forth in any one of SEQ ID NOs: 60, 62, 68, 73, 75, 81, 85, 87 or 93. In other embodiments, $V_{L1}$, $V_{L2}$ and $V_{L3}$ each independently comprise light chain complementarity determining regions of a variable domain comprising an amino acid sequence as set forth in any one of SEQ ID NOs: 43-59, 123-125; and $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122. In other embodiments, $V_{L1}$, $V_{L2}$ and $V_{L3}$ each independently comprise light chain complementarity determining regions of a variable domain comprising an amino acid sequence as set forth in any one of SEQ ID NOs: 61, 63, 69, 71, 74, 76, 82, 86, 88 or 94; and $V_{H1}$, $V_{H2}$ and $V_{H3}$ each independently comprise heavy chain complementarity determining regions of a variable domain comprising an amino acid sequence as set forth in any one of SEQ ID NOs: 60, 62, 68, 73, 75, 81, 85, 87 or 93. In some embodiments, $V_{H1}$, $V_{H2}$ and $V_{H3}$ each independently comprise heavy chain complementarity determining regions and/or a variable domain sequence shown in Tables 2-5.

In some embodiments, $V_{L1}$, $V_{L2}$ and $V_{L3}$ each independently comprise a variable domain sequence as set forth in any one of SEQ ID NOs:169, 171, and 173; and/or $V_{H1}$, $V_{H2}$, and $V_{H3}$ each independently comprise a variable domain sequence as set forth in any one of SEQ ID NOs: 168, 170, and 172. In some embodiments, $V_{L1}$, $V_{L2}$ and $V_{L3}$ each independently comprise light chain complementarity determining regions comprising an amino acid sequence selected from the group consisting of SEQ ID NOs: 141-147, 178, and 179; and/or $V_{H1}$, $V_{H2}$ and $V_{H3}$ each independently comprise heavy chain complementarity determining regions comprising an amino acid sequence selected from the group consisting of SEQ ID NOs: 129-137. In some embodiments, $V_{L1}$, $V_{L2}$ and $V_{L3}$ each independently comprise a variable domain sequence as set forth in any one of SEQ ID NOs:151, 153, 155, 157, 159, 161, 163, 165, and 167; and/or $V_{H1}$, $V_{H2}$, and $V_{H3}$ each independently comprise a variable domain sequence as set forth in any one of SEQ ID NOs:150, 152, 154, 156, 158, 160, 162, 164, and 166. In some embodiments, $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and/or $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122, and 126-128. In some embodiments, $V_{L1}$, $V_{L2}$ and $V_{L3}$ each independently comprise light chain complementarity determining regions and/or a variable domain sequence shown in Tables 2-5.

In particular embodiments, the order of the $V_{H1}$ and $V_{H2}$ domains, and therefore the order of $V_{L1}$ and $V_{L2}$ domains, in the polypeptide chain of formula I or the polypeptide chain of formula II (i.e., to reverse the order) are swapped.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 1 or an amino acid sequence that is at least 95% identical to the amino acid sequence of SEQ ID NO: 1 optionally comprising CDRs that are 100% identical to the CDRs of the polypeptide chain of SEQ ID NO: 1; and the fourth polypeptide chain comprises the amino acid sequence of SEQ ID NO: 2 or an amino acid sequence that is at least 95% identical to the amino acid sequence of SEQ ID NO: 2 optionally comprising CDRs that are 100% identical to the CDRs of the polypeptide chain of SEQ ID NO: 2.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 1 or an amino acid sequence that is at least 95% identical to the amino acid sequence of SEQ ID NO: 1 optionally comprising CDRs that are 100% identical to the CDRs of the polypeptide chain of SEQ ID NO: 1; and the fourth polypeptide chain comprises the amino acid sequence of SEQ ID NO: 2 or an amino acid sequence that is at least 95% identical to the amino acid sequence of SEQ ID NO: 2 optionally comprising CDRs that are 100% identical to the CDRs of the polypeptide chain of SEQ ID NO: 2.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 13 or an amino acid sequence that is at least 95% identical to the amino acid sequence of SEQ ID NO: 13 optionally comprising CDRs that are 100% identical to the CDRs of the polypeptide chain of SEQ ID NO: 13; and the fourth polypeptide chain comprises the amino acid sequence of SEQ ID NO: 14 or an amino acid sequence that is at least 95% identical to the amino acid sequence of SEQ ID NO: 14 optionally comprising CDRs that are 100% identical to the CDRs of the polypeptide chain of SEQ ID NO: 14.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 13 or an amino acid sequence that is at least 95% identical to the amino acid sequence of SEQ ID NO: 13 optionally comprising CDRs that are 100% identical to the CDRs of the polypeptide chain of SEQ ID NO: 13; and the fourth polypeptide chain comprises the amino acid sequence of SEQ ID NO: 14 or an amino acid sequence that is at least 95% identical to the amino acid sequence of SEQ ID NO: 14 optionally comprising CDRs that are 100% identical to the CDRs of the polypeptide chain of SEQ ID NO: 14.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 17 or an amino acid sequence that is at least 95% identical to the amino acid sequence of SEQ ID NO: 17 optionally comprising CDRs that are 100% identical to the CDRs of the polypeptide chain of SEQ ID NO: 17; and the fourth polypeptide chain comprises the amino acid sequence of SEQ ID NO: 18 or an amino acid sequence that is at least 95% identical to the amino acid sequence of SEQ ID NO: 18 optionally comprising CDRs that are 100% identical to the CDRs of the polypeptide chain of SEQ ID NO: 18.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 17 or an amino acid sequence that is at least 95% identical to the amino acid sequence of SEQ ID NO: 17 optionally comprising CDRs that are 100% identical to the CDRs of the polypeptide chain of SEQ ID NO: 17; and the fourth polypeptide chain comprises the amino acid sequence of SEQ ID NO: 18 or an amino acid sequence that is at least 95% identical to the amino acid sequence of SEQ ID NO: 18 optionally comprising CDRs that are 100% identical to the CDRs of the polypeptide chain of SEQ ID NO: 18.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 21 or an amino acid sequence that is at least 95% identical to the amino acid sequence of SEQ ID NO: 21 optionally comprising CDRs that are 100% identical to the CDRs of the polypeptide chain of SEQ ID NO: 21; and the fourth polypeptide chain comprises the amino acid sequence of SEQ ID NO: 22 or an amino acid sequence that is at least 95% identical to the amino acid sequence of SEQ ID NO: 22 optionally comprising CDRs that are 100% identical to the CDRs of the polypeptide chain of SEQ ID NO: 22.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 21 or an amino acid sequence that is at least 95% identical to the amino acid sequence of SEQ ID NO: 21 optionally comprising CDRs that are 100% identical to the CDRs of the polypeptide chain of SEQ ID NO: 21; and the fourth polypeptide chain comprises the amino acid sequence of SEQ ID NO: 22 or an amino acid sequence that is at least 95% identical to the amino acid sequence of SEQ ID NO: 22 optionally comprising CDRs that are 100% identical to the CDRs of the polypeptide chain of SEQ ID NO: 22.

In some embodiments, the first polypeptide chain comprises the amino acid sequence of SEQ ID NO: 63 or an amino acid sequence that is at least 95% identical to the amino acid sequence of SEQ ID NO: 63 optionally comprising CDRs that are 100% identical to the CDRs of the polypeptide chain of SEQ ID NO: 63; the second polypeptide chain comprises the amino acid sequence of SEQ ID NO: 62 or an amino acid sequence that is at least 95% identical to the amino acid sequence of SEQ ID NO: 62 optionally comprising CDRs that are 100% identical to the CDRs of the polypeptide chain of SEQ ID NO: 62; the third polypeptide chain comprises the amino acid sequence of SEQ ID NO: 60 or an amino acid sequence that is at least 95% identical to the amino acid sequence of SEQ ID NO: 60 optionally comprising CDRs that are 100% identical to the CDRs of the polypeptide chain of SEQ ID NO: 60; and the fourth polypeptide chain comprises the amino acid sequence of SEQ ID NO: 61 or an amino acid sequence that is at least 95% identical to the amino acid sequence of SEQ ID NO: 61 optionally comprising CDRs that are 100% identical to the CDRs of the polypeptide chain of SEQ ID NO: 61.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 60 or an amino acid sequence that is at least 95% identical to the amino acid sequence of SEQ ID NO: 60 optionally comprising CDRs that are 100% identical to the CDRs of the polypeptide chain of SEQ ID NO: 60; and the fourth polypeptide chain comprises the amino acid sequence of SEQ ID NO: 61 or an amino acid sequence that is at least 95% identical to the amino acid sequence of SEQ ID NO: 61 optionally comprising CDRs that are 100% identical to the CDRs of the polypeptide chain of SEQ ID NO: 61.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 60 or an amino acid sequence that is at least 95% identical to the amino acid sequence of SEQ ID NO: 60 optionally comprising CDRs that are 100% identical to the CDRs of the polypeptide chain of SEQ ID NO: 60; and the fourth polypeptide chain comprises the amino acid sequence of SEQ ID NO: 71 or an amino acid sequence that is at least 95% identical to the amino acid sequence of SEQ ID NO: 71 optionally comprising CDRs that are 100% identical to the CDRs of the polypeptide chain of SEQ ID NO: 71.

In some embodiments, the first polypeptide chain comprises the amino acid sequence of SEQ ID NO: 76 or an amino acid sequence that is at least 95% identical to the amino acid sequence of SEQ ID NO: 76 optionally comprising CDRs that are 100% identical to the CDRs of the polypeptide chain of SEQ ID NO: 76; the second polypeptide chain comprises the amino acid sequence of SEQ ID NO: 75 or an amino acid sequence that is at least 95% identical to the amino acid sequence of SEQ ID NO: 75 optionally comprising CDRs that are 100% identical to the CDRs of the polypeptide chain of SEQ ID NO: 75; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 82 or an amino acid sequence that is at least 95% identical to the amino acid sequence of SEQ ID NO: 82 optionally comprising CDRs that are 100% identical to the CDRs of the polypeptide chain of SEQ ID NO: 82; the second polypeptide chain comprises the amino acid sequence of SEQ ID NO: 81 or an amino acid sequence that is at least 95% identical to the amino acid sequence of SEQ ID NO:81 optionally comprising CDRs that are 100% identical to the CDRs of the polypeptide chain of SEQ ID NO: 81; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 88 or an amino acid sequence that is at least 95% identical to the amino acid sequence of SEQ ID NO: 88 optionally comprising CDRs that are 100% identical to the CDRs of the polypeptide chain of SEQ ID NO: 88; the second polypeptide chain comprises the amino acid sequence of SEQ ID NO: 87 or an amino acid sequence that is at least 95% identical to the amino acid sequence of SEQ ID NO: 87 optionally comprising CDRs that are 100% identical to the CDRs of the polypeptide chain of SEQ ID NO: 87; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 94 or an amino acid sequence that is at least 95% identical to the amino acid sequence of SEQ ID NO: 94 optionally comprising CDRs that are 100% identical to the CDRs of the polypeptide chain of SEQ ID NO: 94; the second polypeptide chain comprises the amino acid sequence of SEQ ID NO: 93 or an amino acid sequence that is at least 95% identical to the amino acid sequence of SEQ ID NO: 93 optionally comprising CDRs that are 100% identical to the CDRs of the polypeptide chain of SEQ ID NO: 93; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 63 or an amino acid sequence that is at least 95% identical to the amino acid sequence of SEQ ID NO: 63 optionally comprising CDRs that are 100% identical to the CDRs of the polypeptide chain of SEQ ID NO: 63; the second polypeptide chain comprises the amino acid sequence of SEQ ID NO: 62 or an amino acid sequence that is at least 95% identical to the amino acid sequence of SEQ ID NO: 62 optionally comprising CDRs that are 100% identical to the CDRs of the polypeptide chain of SEQ ID NO: 62; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 63 or an amino acid sequence that is at least 95% identical to the amino acid sequence of SEQ ID NO: 63 optionally comprising CDRs that are 100% identical to the CDRs of the polypeptide chain of SEQ ID NO: 63; the second polypeptide chain comprises the amino acid sequence of SEQ ID NO: 62 or an amino acid sequence that is at least 95% identical to the amino acid sequence of SEQ ID NO: 62 optionally comprising CDRs that are 100% identical to the CDRs of the polypeptide chain of SEQ ID NO: 62; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 114 or an amino acid sequence that is at least 95% identical to the amino acid sequence of SEQ ID NO: 114 optionally comprising CDRs that are 100% identical to the CDRs of the polypeptide chain of SEQ ID NO: 114; and the fourth polypeptide chain comprises the amino acid sequence of SEQ ID NO: 115 or an amino acid sequence that is at least 95% identical to the amino acid sequence of SEQ ID NO: 115 optionally comprising CDRs that are 100% identical to the CDRs of the polypeptide chain of SEQ ID NO: 115.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 114 or an amino acid sequence that is at least 95% identical to the amino acid sequence of SEQ ID NO: 114 optionally comprising CDRs that are 100% identical to the CDRs of the polypeptide chain of SEQ ID NO: 114; and the fourth polypeptide chain comprises the amino acid sequence of SEQ ID NO: 115 or an amino acid sequence that is at least 95% identical to the amino acid sequence of SEQ ID NO: 115 optionally comprising CDRs that are 100% identical to the CDRs of the polypeptide chain of SEQ ID NO: 115.

In other embodiments, the binding protein of the disclosure is a trispecific and/or trivalent binding protein comprising four polypeptide chains that form three antigen binding sites that specifically bind one or more (e.g., three) different target proteins, wherein a first polypeptide chain has a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1}\text{-hinge-}C_{H2}\text{-}C_{H3}\text{(hole)} \quad [II]$$

and a third polypeptide chain has a structure represented by the formula:

$$V_{H3}\text{-}C_{H1}\text{-hinge-}C_{H2}\text{-}C_{H3}\text{(knob)} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In other embodiments, the binding protein of the disclosure is a trispecific and/or trivalent binding protein comprising four polypeptide chains that form three antigen binding sites that specifically bind one or more (e.g., three) target proteins, wherein a first polypeptide chain has a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1}\text{-hinge-}C_{H2}\text{-}C_{H3}\text{(hole)} \quad [II]$$

and a third polypeptide chain has a structure represented by the formula:

$$V_{H3}\text{-}C_{H1}\text{-hinge-}C_{H2}\text{-}C_{H3}\text{(knob)} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In some embodiments, the first polypeptide chain and the second polypeptide chain have a cross-over orientation that forms two distinct antigen binding sites. In some embodiments, the VH1 and VL1 form a binding pair and form the first antigen binding site. In some embodiments, the VH2 and VL2 form a binding pair and form the second antigen binding site. In some embodiments, the third polypeptide and the fourth polypeptide form a third antigen binding site. In some embodiments, the VH3 and VL3 form a binding pair and form the third antigen binding site. In some embodiments, the second polypeptide chain and the third polypeptide chain comprise one or more modifications. In some embodiments, the second polypeptide chain and the third polypeptide chain of a binding protein are different, e.g., having different $C_{H1}$, $C_{H2}$, and/or $C_{H3}$ domain(s) (such as those including a modification described herein). In some embodiments, the first polypeptide chain and the fourth polypeptide chain comprise one or more modifications. In some embodiments, the first polypeptide chain and the fourth polypeptide chain of a binding protein are different, e.g., having different $C_L$ domains (such as those including a modification described herein, and/or lambda vs. kapp $C_L$ domains).

In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:150, optionally comprising CDRs that are 100% identical to the CDRs of the polypeptide chain of SEQ ID NO: 150, and/or a light chain variable domain comprising an amino acid sequence that is at least 95%, at least 96%, at least 97%, at least 98%, at least 99%, or 100% identical to SEQ ID NO:151, optionally comprising CDRs that are 100% identical to the CDRs of the polypeptide chain of SEQ ID NO: 151. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:152, optionally comprising CDRs that are 100% identical to the CDRs of the polypeptide chain of SEQ ID NO: 152, and/or a light chain variable domain comprising an amino acid sequence that is at least 95%, at least 96%, at least 97%, at least 98%, at least 99%, or 100% identical to SEQ ID NO:153, optionally comprising CDRs that are 100% identical to the CDRs of the polypeptide chain of SEQ ID NO: 153. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:154, optionally comprising CDRs that are 100% identical to the CDRs of the polypeptide chain of SEQ ID NO: 154, and/or a light chain variable domain comprising an amino acid sequence that is at least 95%, at least 96%, at least 97%, at least 98%, at least 99%, or 100% identical to SEQ ID NO:155, optionally comprising CDRs that are 100% identical to the CDRs of the polypeptide chain of SEQ ID NO: 155. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:156, optionally comprising CDRs that are 100% identical to the CDRs of the polypeptide chain of SEQ ID NO: 156, and/or a light chain variable domain comprising an amino acid sequence that is at least 95%, at least 96%, at least 97%, at least 98%, at least 99%, or 100% identical to SEQ ID NO:157, optionally comprising CDRs that are 100% identical to the CDRs of the polypeptide chain of SEQ ID NO: 157. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:158, optionally comprising CDRs that are 100% identical to the CDRs of the polypeptide chain of SEQ ID NO: 158, and/or a light chain variable domain comprising an amino acid sequence that is at least 95%, at least 96%, at least 97%, at least 98%, at least 99%, or 100% identical to SEQ ID NO:159, optionally comprising CDRs that are 100% identical to the CDRs of the polypeptide chain of SEQ ID NO: 159. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:160, optionally comprising CDRs that are 100% identical to the CDRs of the polypeptide chain of SEQ ID NO: 160, and/or a light chain variable domain comprising an amino acid sequence that is at least 95%, at least 96%, at least 97%, at least 98%, at least 99%, or 100% identical to SEQ ID NO:161, optionally comprising CDRs that are 100% identical to the CDRs of the polypeptide chain of SEQ ID NO: 161. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:162, optionally comprising CDRs that are 100% identical to the CDRs of the polypeptide chain of SEQ ID NO: 162, and/or a light chain variable domain comprising an amino acid sequence that is at least 95%, at least 96%, at least 97%, at least 98%, at least 99%, or 100% identical to SEQ ID NO:163, optionally comprising CDRs that are 100% identical to the CDRs of the polypeptide chain of SEQ ID NO: 163. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:164, optionally comprising CDRs that are 100% identical to the CDRs of the polypeptide chain of SEQ ID NO: 164, and/or a light chain variable domain comprising an amino acid sequence that is at least 95%, at least 96%, at least 97%, at least 98%, at least 99%, or 100% identical to SEQ ID NO:165, optionally comprising CDRs that are 100% identical to the CDRs of the polypeptide chain of SEQ ID NO: 165. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:166, optionally comprising CDRs that are 100% identical to the CDRs of the polypeptide chain of SEQ ID NO: 166, and/or a light chain variable domain comprising an amino acid sequence that is at least 95%, at least 96%, at least 97%, at least 98%, at least 99%, or 100% identical to SEQ ID NO:167, optionally comprising CDRs that are 100% identical to the CDRs of the polypeptide chain of SEQ ID NO: 167. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:168, optionally comprising CDRs that are 100% identical to the CDRs of the polypeptide chain of SEQ ID NO: 168, and/or a light chain variable domain comprising an amino acid sequence that is at least 95%, at least 96%, at least 97%, at least 98%, at least 99%, or 100% identical to SEQ ID NO:169, optionally comprising CDRs that are 100% identical to the CDRs of the polypeptide chain of SEQ ID NO: 169. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:170, optionally comprising CDRs that are 100% identical to the CDRs of the polypeptide chain of SEQ ID NO: 170, and/or a light chain variable domain comprising an amino acid sequence that is at least 95%, at least 96%, at least 97%, at least 98%, at least 99%, or 100% identical to SEQ ID NO:171, optionally comprising CDRs that are 100% identical to the CDRs of the polypeptide chain of SEQ ID NO: 171. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:172, optionally comprising CDRs that are 100% identical to the CDRs of the polypeptide chain of SEQ ID NO: 172, and/or a light chain variable domain comprising an amino acid sequence that is at least 95%, at least 96%, at least 97%, at least 98%, at least 99%, or 100% identical to SEQ ID NO:173, optionally comprising CDRs that are 100% identical to the CDRs of the polypeptide chain of SEQ ID NO: 173.

In some embodiments, a binding protein of the present disclosure binds to one, two, or three antigen targets with an equilibrium dissociation constant ($K_D$) that is less than or equal to 1 μM, 500 nM, 100 nM, 50 nM, 10 nM, 5 nM, or 1 nM. Exemplary assays for determining $K_D$ are known in the art. For example, in some embodiments, $K_D$ is determined by measuring binding kinetics at between 0° C. and 37° C. e.g., at 0° C., 4° C., 25° C., or 37° C.) using the techniques described in Example 1 (e.g., SPR or ELISA).

In some embodiments, a binding protein of the present disclosure activates CD4 and/or CD8 T cells in vitro and/or induces antibody-mediated in vitro cell killing of a cell expressing one or more antigen targets of one or more binding domains of the binding protein. Exemplary in vitro cell killing and T cell activation assays are known in the art. For example, in some embodiments, in vitro cell killing and/or T cell activation is assayed using the techniques described in Example 1.

In some embodiments, a binding protein of the present disclosure specifically binds to, and/or blocks signaling mediated by, one or more cytokines. Exemplary cytokine release assays are known in the art. For example, in some embodiments, cytokine release is assayed using the techniques described in Example 1.

In some embodiments, a binding protein of the present disclosure comprises a first antigen binding site that specifically binds a target protein on T cells, a second antigen binding site that specifically binds a target protein on T cells, and a third antigen binding site that specifically binds an antigen target or target protein. In some embodiments, a binding protein of the present disclosure comprises a first antigen binding site that specifically binds a target protein on T cells, a second antigen binding site that specifically binds a target protein on T cells, and a third antigen binding site that specifically binds a tumor target protein. In some embodiments, a binding protein of the present disclosure comprises a first antigen binding site that specifically binds a target protein on T cells, a second antigen binding site that specifically binds a target protein on T cells, and a third antigen binding site that specifically binds a human tumor target protein. In some embodiments, the first and second antigen binding sites specifically bind a tumor target protein for instance selected from CD3 and CD28, respectively. In some some embodiments, the first and second antigen binding sites specifically bind a tumor target protein for instance selected from CD28 and CD3, respectively. In some embodiments, the third antigen binding site specifically binds CD19, CD20, CD38, Her2, or LAMP1. Further examples of such targets and target proteins are provided infra.

In some embodiments, a binding protein of the present disclosure comprises a first antigen binding site that specifically binds CD3, a second antigen binding site that specifically binds CD28, and a third antigen binding site that specifically binds an antigen target or target protein. In some embodiments, a binding protein of the present disclosure comprises a first antigen binding site that specifically binds CD28, a second antigen binding site that specifically binds CD3, and a third antigen binding site that specifically binds an antigen target or target protein. Further examples of such antigen targets or target proteins are provided infra. In some embodiments, a binding protein of the present disclosure comprises a first antigen binding site that specifically binds CD3, a second antigen binding site that specifically binds CD28, and a third antigen binding site that specifically binds a tumor target protein. In some embodiments, a binding protein of the present disclosure comprises a first antigen binding site that specifically binds human CD3, a second antigen binding site that specifically binds human CD28, and a third antigen binding site that specifically binds a human tumor target protein. In some embodiments, a binding protein of the present disclosure comprises a first antigen binding site that specifically binds CD28, a second antigen binding site that specifically binds CD3, and a third antigen binding site that specifically binds a tumor target protein. In some embodiments, a binding protein of the present disclosure comprises a first antigen binding site that specifically binds human CD28, a second antigen binding site that specifically binds human CD3, and a third antigen binding site that specifically binds a human tumor target protein. In some embodiments, the third antigen binding site specifically binds CD19, CD20, CD38, Her2, or LAMP1. Further examples of such tumor antigen targets or tumor target proteins are provided infra.

In some embodiments, the antigen binding site that specifically binds CD3 comprises a heavy chain variable domain comprising the amino acid sequence of SEQ ID NO: 152 and a light chain variable domain comprising the amino acid sequence of SEQ ID NO: 153; or a heavy chain variable domain comprising the amino acid sequence of SEQ ID NO: 154 and a light chain variable domain comprising the amino acid sequence of SEQ ID NO: 155. Additional VH, VL, and/or CDR sequences of antibodies that specifically bind CD3 suitable for use in any of the binding proteins described herein may be found in International Publication No. WO2016/116626, which is incorporated by reference herein in its entirety. In some embodiments, the antigen binding site that specifically binds CD3 comprises six CDRs, or a heavy chain and a light chain variable domain, shown in Tables 2-5. In some embodiments, the antigen binding site that specifically binds CD3 comprises (i) three heavy chain CDRs of SEQ ID Nos. 34, 35 and 36, respectively, and three light chain CDRs of SEQ ID Nos. 52, 53 and 54, respectively; or (ii) three heavy chain CDRs of SEQ ID Nos. 34, 35 and 36, respectively, and three light chain CDRs of SEQ ID Nos. 149, 53 and 54, respectively. In some embodiments, the antigen binding site that specifically binds CD3 is part of a polypeptide chain comprising the amino acid sequence of SEQ ID NO:3 or an amino acid sequence that is at least 95% identical to the amino acid sequence of SEQ ID NO:3 optionally comprising CDRs that are 100% identical to the CDRs of the polypeptide chain of SEQ ID NO:3. In some embodiments, the antigen binding site that specifically binds CD3 is part of a polypeptide chain comprising the amino acid sequence of SEQ ID NO:4 or an amino acid sequence that is at least 95% identical to the amino acid sequence of SEQ ID NO:4 optionally comprising CDRs that are 100% identical to the CDRs of the polypeptide chain of SEQ ID NO:4.

In some embodiments, the antigen binding site that specifically binds CD28 comprises a heavy chain variable domain comprising the amino acid sequence of SEQ ID NO: 160 and a light chain variable domain comprising the amino acid sequence of SEQ ID NO: 161; or a heavy chain variable domain comprising the amino acid sequence of SEQ ID NO: 162 and a light chain variable domain comprising the amino acid sequence of SEQ ID NO: 163. In some embodiments, the antigen binding site that specifically binds CD28 comprises six CDRs, or a heavy chain and a light chain variable domain, shown in Tables 2-5. In some embodiments, the antigen binding site that specifically binds CD28 comprises (i) three heavy chain CDRs of SEQ ID Nos. 28, 29 and 30, respectively, and three light chain CDRs of SEQ ID Nos. 46, 47 and 48, respectively; or (ii) three heavy chain CDRs of SEQ ID Nos. 31, 32 and 33, respectively, and three light chain CDRs of SEQ ID Nos. 49, 50 and 51, respectively. In some embodiments, the antigen binding site that specifically binds CD28 is part of a polypeptide chain comprising the amino acid sequence of SEQ ID NO:3 or an amino acid sequence that is at least 95% identical to the amino acid sequence of SEQ ID NO:3 optionally comprising CDRs that are 100% identical to the CDRs of the polypeptide chain of SEQ ID NO:3. In some embodiments, the antigen binding site that specifically binds CD28 is part of a polypeptide chain comprising the amino acid sequence of SEQ ID NO:4 or an amino acid sequence that is at least 95% identical to the amino acid sequence of SEQ ID NO:4 optionally comprising CDRs that are 100% identical to the CDRs of the polypeptide chain of SEQ ID NO:4.

In some embodiments, a binding protein of the present disclosure comprises a first antigen binding site that specifically binds CD3, a second antigen binding site that specifically binds CD28, and a third antigen binding site that specifically binds CD38, or a first antigen binding site that specifically binds CD28, a second antigen binding site that specifically binds CD3, and a third antigen binding site that specifically binds CD38, wherein:

the antigen binding site specifically binding CD3 comprises (i) three heavy chain CDRs of SEQ ID Nos. 34, 35 and 36, respectively, and three light chain CDRs of SEQ ID Nos. 52, 53 and 54, respectively; or (ii) three heavy chain CDRs of SEQ ID Nos. 34, 35 and 36, respectively, and three light chain CDRs of SEQ ID Nos. 149, 53 and 54, respectively; and the antigen binding site specifically binding CD28 comprises (i) three heavy chain CDRs of SEQ ID Nos. 28, 29 and 30, respectively, and three light chain CDRs of SEQ ID Nos. 46, 47 and 48, respectively; or (ii) three heavy chain CDRs of SEQ ID Nos. 31, 32 and 33, respectively, and three light chain CDRs of SEQ ID Nos. 49, 50 and 51, respectively; and the antigen binding site specifically binding CD38 comprises (i) three heavy chain CDRs of SEQ ID Nos. 40, 41 and 42, respectively, and three light chain CDRs of SEQ ID Nos. 58, 44 and 59, respectively.

In some embodiments, the antigen binding site that specifically binds a tumor target protein comprises a heavy chain variable domain comprising the amino acid sequence of SEQ ID NO: 156 and a light chain variable domain comprising the amino acid sequence of SEQ ID NO: 157; a heavy chain variable domain comprising the amino acid sequence of SEQ ID NO: 158 and a light chain variable domain comprising the amino acid sequence of SEQ ID NO: 159; a heavy chain variable domain comprising the amino acid sequence of SEQ ID NO: 164 and a light chain variable domain comprising the amino acid sequence of SEQ ID NO: 165; a heavy chain variable domain comprising the amino acid sequence of SEQ ID NO: 150 and a light chain variable domain comprising the amino acid sequence of SEQ ID NO: 151; or a heavy chain variable domain comprising the amino acid sequence of SEQ ID NO: 166 and a light chain variable domain comprising the amino acid sequence of SEQ ID NO: 167. In some embodiments, the antigen binding site that specifically binds a tumor target protein comprises six CDRs, or a heavy chain and a light chain variable domain, shown in Tables 2-5. In some embodiments, the antigen binding site that specifically binds a tumor target protein comprises six CDRs of an anti-Her2, anti-CD19, anti-CD20, anti-CD38, or anti-LAMP1 binding domain shown in Tables 2-5.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise a variable domain sequence as set forth in any one of SEQ ID NOs:169, 171, and 173; and wherein:

$V_{H1}$, $V_{H2}$, and $V_{H3}$ each independently comprise a variable domain sequence as set forth in any one of SEQ ID NOs:168, 170, and 172.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise light chain complementarity determining regions comprising an amino acid sequence selected from the group consisting of SEQ ID NOs: 141-147, 178, and 179; and wherein:

$V_{H1}$, $V_{H2}$ and $V_{H3}$ each independently comprise heavy chain complementarity determining regions comprising an amino acid sequence selected from the group consisting of SEQ ID NOs: 129-137.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise a variable domain sequence as set forth in any one of SEQ ID NOs:151, 153, 155, 157, 159, 161, 163, 165, and 167; and wherein:

$V_{H1}$, $V_{H2}$, and $V_{H3}$ each independently comprise a variable domain sequence as set forth in any one of SEQ ID NOs:150, 152, 154, 156, 158, 160, 162, 164, and 166.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and wherein:

$V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

In some embodiments, a binding protein of the present disclosure comprises an antigen binding site that specifically binds CD3, an antigen binding site that specifically binds CD28, and an antigen binding site that specifically binds an antigen target other than CD3 or CD28. In some embodiments, a binding protein of the present disclosure comprises an antigen binding site that specifically binds human CD3, an antigen binding site that specifically binds human CD28, and an antigen binding site that specifically binds a human antigen target other than CD3 or CD28. In some embodiments, a binding protein of the present disclosure comprises (a) an antigen binding site that specifically binds CD3, wherein the antigen binding site that specifically binds CD3 comprises (i) a heavy chain variable domain comprising the amino acid sequence of SEQ ID NO: 152 and a light chain variable domain comprising the amino acid sequence of SEQ ID NO: 153, (ii) a heavy chain variable domain comprising the amino acid sequence of SEQ ID NO: 154 and a light chain variable domain comprising the amino acid sequence of SEQ ID NO: 155, (iii) a heavy chain variable domain comprising a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36, and a light chain variable domain comprising a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54, or (iv) a heavy chain variable domain comprising a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36, and a light chain variable domain comprising a CDR-L1 comprising the amino acid sequence of SEQ ID NO:149, a CDR-L2 comprising the amino acid sequence of SEQ ID NO:53, and a CDR-L3 comprising the amino acid sequence of SEQ ID NO:54; (b) an antigen binding site that specifically binds CD28, wherein the antigen binding site that specifically binds CD28 comprises (i) a heavy chain variable domain comprising the amino acid sequence of SEQ ID NO: 160 and a light chain variable domain comprising the amino acid sequence of SEQ ID NO: 161, (ii) a heavy chain variable domain comprising the amino acid sequence of SEQ ID NO: 162 and a light chain variable domain comprising the amino acid sequence of SEQ ID NO: 163, (iii) a heavy chain variable domain comprising a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30, and a light chain variable domain comprising a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48, or (iv) a heavy chain variable domain comprising a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33, and a light chain variable domain comprising a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; and (c) an antigen binding site that specifically binds an antigen target other than CD3 or CD28. In some embodiments, a binding protein of the present disclosure comprises a first polypeptide chain comprising the amino acid sequence of SEQ ID NO:4 or 10, a second polypeptide chain comprising the amino acid sequence of SEQ ID NO:3 or 9, and a third and a fourth polypeptide chain, wherein the third and fourth polypeptide chains form an antigen binding domain that specifically binds an antigen target other than CD3 or CD28. In some embodiments, the antigen binding site that specifically binds an antigen target other than CD3 or CD28 binds an antigen target selected from A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD19, CD20, CD23 (also known as FCER2, a receptor for IgE), CD24, CD27, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTP-Dase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1).

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ Comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, $V_{H1}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L1}$ Comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H2}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; $V_{L2}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; $V_{H3}$ Comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ Comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ Comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ Comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ Comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ Comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ Comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ Comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ Comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ Comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ Comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ Comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

Antigen Targets

In some embodiments, a binding protein of the present disclosure binds one or more (e.g., one, two, or three) of the following antigen targets or target proteins: A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In one embodiment, the binding proteins specifically bind to one or more tumor antigen targets (e.g., target proteins). In other embodiments, the binding proteins specifically bind to one or more tumor target protein and one or more target protein on a T-cell including a T cell receptor complex. These T-cell engager binding proteins are capable of recruiting T cells transiently to target cells and, at the same time, activating the cytolytic activity of the T cells. Examples of target proteins on T cells include but are not limited to CD3 and CD28, among others. Further examples of such antigen targets or target proteins are provided supra. In some embodiments, the trispecific binding proteins may be generated by combining the antigen binding domains of two or more monospecific antibodies (parent antibodies) into one antibody. In some embodiments, a binding protein of the present disclosure binds one or more (e.g., one, two, or three) of the following antigen targets: CD3, CD19, CD20, CD28, CD38, Her2, LAMP1, IL-4, IL-13 and TNFa.

In some embodiments of the disclosure, the trivalent binding protein is capable of binding three antigen targets. In some embodiments of the disclosure, the trivalent binding protein is capable of binding three different antigen targets. In one embodiment, the binding protein is trispecific and one light chain-heavy chain pair is capable of binding two different antigen targets or epitopes and one light chain-heavy chain pair is capable of binding one antigen target or epitope. In another embodiment, the binding protein is capable of binding three tumor antigen targets. In another embodiment, the binding protein is capable of binding three different tumor antigen targets. In other embodiments, the binding protein is capable of inhibiting the function of one or more of the antigen targets.

In some embodiments, a binding protein of the present disclosure binds one or more tumor target proteins. In some embodiments, the binding protein is capable of specifically binding three epitopes on a single tumor target protein. In some embodiments, the binding protein is capable of specifically binding three different epitopes on a single tumor target protein. In some embodiments, the binding protein is capable of binding two different epitopes on a first tumor target protein, and one epitope on a second tumor target protein. In some embodiments, the first and second tumor target proteins are different. In some embodiments, the binding protein is capable of specifically binding three different tumor target proteins.

In some embodiments, a binding protein of the present disclosure binds one or more cytokine target proteins. In some embodiments, the binding protein is capable of specifically binding three epitopes on a single cytokine target protein. In some embodiments, the binding protein is capable of specifically binding three different epitopes on a single cytokine target protein. In some embodiments, the binding protein is capable of binding two different epitopes on a first cytokine target protein, and one epitope on a second cytokine target protein. In some embodiments, the first and second cytokine target proteins are different. In some embodiments, the binding protein is capable of specifically binding three different cytokine target proteins. In some embodiments, the one or more cytokine target proteins are one or more of IL-4, IL-13 and/or TNFa. Further examples of cytokine target proteins are provided infra.

In some embodiments, a binding protein of the present disclosure binds one or more tumor target proteins and one or more T cell target proteins. In some embodiments, the binding protein is capable of specifically binding one tumor target protein and two different epitopes on a single T cell target protein. In some embodiments, the binding protein is capable of specifically binding one tumor target protein and two different T cell target proteins (e.g., CD28 and CD3). In some embodiments, the binding protein is capable of specifically binding one T cell target protein and two different epitopes on a single tumor target protein. In some embodiments, the binding protein is capable of specifically binding one T cell target protein and two different tumor target proteins. In some embodiments, the first and second polypeptide chains of the binding protein form two antigen binding sites that specifically target two T cell target proteins, and the third and fourth polypeptide chains of the binding protein form an antigen binding site that specifically binds a tumor target protein. In some embodiments, the first and second polypeptide chains of the binding protein form two antigen binding sites that specifically target two tumor target proteins, and the third and fourth polypeptide chains of the binding protein form an antigen binding site that specifically binds a T cell target protein. In some embodiments, the one or more tumor target proteins are one or more of CD3, CD19, CD20, CD28, CD38, Her2, LAMP1, IL-4, IL-13 and/or TNFa. In some embodiments, the one or more T cell target proteins are one or more of CD3 and CD28. Further examples of tumor target proteins and T cell target proteins are provided supra.

In some embodiments, a binding protein of the present disclosure binds, independently of each other, same or different, one, two or three antigen targets or target proteins, selected from cytokine target proteins, tumor target antigens or tumor target proteins, T cell target proteins, immune checkpoint inhibitors, immune checkpoint modulators, immune checkpoint costimulatory molecules, and/or target molecules on the surface of an immune cell. In some embodiments, a binding protein of the present disclosure is trivalent but bispecific and capable of specifically binding twice to the same antigen targets or target proteins. In some embodiments, a binding protein of the present disclosure is capable of specifically binding two different epitopes on a single cytokine target proteins, tumor target antigens or tumor target proteins, T cell target proteins, immune checkpoint inhibitors, immune checkpoint modulators, immune checkpoint costimulatory molecules, and/or target molecules on the surface of an immune cell. Further examples of such antigen targets or target proteins are provided supra.

The binding proteins of the disclosure may be prepared using domains or sequences obtained or derived from any human or non-human antibody, including, for example, human, murine, or humanized antibodies.

Linkers

In some embodiments, the linkers $L_1$, $L_2$, $L_3$ and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$ and $L_4$ in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues (Gly-Gly-Gly-Gly; SEQ ID NO: 98); a peptide with five glycine residues (Gly-Gly-Gly-Gly-Gly; SEQ ID NO: 99); a peptide with six glycine residues (Gly-Gly-Gly-Gly-Gly-Gly; SEQ ID NO: 100); a peptide with seven glycine residues (Gly-Gly-Gly-Gly-Gly-Gly-Gly; SEQ ID NO: 101); a peptide with eight glycine residues (Gly-Gly-Gly-Gly-Gly-Gly-Gly-Gly; SEQ ID NO: 102). Other combinations of amino acid residues may be used such as the peptide Gly-Gly-Gly-Gly-Ser (SEQ ID NO: 103), the peptide Gly-Gly-Gly-Gly-Ser-Gly-Gly-Gly-Gly-Ser (SEQ ID NO: 104), the peptide Gly-Gly-Gly-Gly-Ser-Gly-Gly-Gly-Gly-Ser-Gly-Gly-Gly-Gly-Ser (SEQ ID NO: 105), and the peptide Gly-Gly-Ser-Gly-Ser-Ser-Gly-Ser-Gly-Gly (SEQ ID NO:148). Other suitable linkers include a single Ser, and Val residue; the dipeptide Arg-Thr, Gln-Pro, Ser-Ser, Thr-Lys, and Ser-Leu; Thr-Lys-Gly-Pro-Ser (SEQ ID NO: 106), Thr-Val-Ala-Ala-Pro (SEQ ID NO: 107), Gln-Pro-Lys-Ala-Ala (SEQ ID NO: 108), Gln-Arg-Ile-Glu-Gly (SEQ ID NO: 109); Ala-Ser-Thr-Lys-Gly-Pro-Ser (SEQ ID NO: 110), Arg-Thr-Val-Ala-Ala-Pro-Ser (SEQ ID NO:111), Gly-Gln-Pro-Lys-Ala-Ala-Pro (SEQ ID NO:112), and His-Ile-Asp-Ser-Pro-Asn-Lys (SEQ ID NO:113). The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In some embodiments, the length of $L_1$ is at least twice the length of $L_3$. In some embodiments, the length of $L_2$ is at least twice the length of $L_4$. In some embodiments, the length of $L_1$ is at least twice the length of $L_3$, and the length of $L_2$ is at least twice the length of $L_4$. In some embodiments, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In some embodiments, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In some embodiments, $L_1$ is 7 amino acid residues in length, $L_2$ is 5 amino acid residues in length, $L_3$ is 1 amino acid residue in length, and $L_4$ is 2 amino acid residues in length. In some embodiments, $L_1$ is 10 amino acid residues in length, $L_2$ is 10 amino acid residues in length, $L_3$ is 0 amino acid residue in length, and $L_4$ is 0 amino acid residues in length. In some embodiments, $L_1$, $L_2$, $L_3$, and $L_4$ each have an independently selected length from 0 to 15 amino acids (e.g., 0, 1, 2, 3, 4, 5, 6, 7, 8, 9, 10, 11, 12, 13, 14, or 15 amino acids), wherein at least two of the linkers have a length of 1 to 15 amino acids (e.g., 1, 2, 3, 4, 5, 6, 7, 8, 9, 10, 11, 12, 13, 14, or 15 amino acids). In some embodiments, $L_1$, $L_2$, $L_3$, and $L_4$ are each 0 amino acids in length.

In some embodiments, $L_1$, $L_2$, $L_3$, and/or $L_4$ comprise the sequence Asp-Lys-Thr-His-Thr (SEQ ID NO: 525). In some embodiments, $L_1$ comprises the sequence Asp-Lys-Thr-His-Thr (SEQ ID NO: 525). In some embodiments, $L_3$ comprises the sequence Asp-Lys-Thr-His-Thr (SEQ ID NO: 525).

In some embodiments, $L_1$, $L_2$, $L_3$, and/or $L_4$ comprise a sequence derived from a naturally occurring sequence at the junction between an antibody variable domain and an antibody constant domain (e.g., as described in WO2012/135345). For example, in some embodiments, the linker comprises a sequence found at the transition between an endogenous $V_H$ and $C_{H1}$ domain, or between an endogenous $V_L$ and $C_L$ domain (e.g., kappa or lambda). In some embodiments, the linker comprises a sequence found at the transition between an endogenous human $V_H$ and $C_{H1}$ domain, or between an endogenous human $V_L$ and $C_L$ domain (e.g., human kappa or lambda).

In some embodiments, $L_1$, $L_2$, $L_3$, and/or $L_4$ comprise the sequence Gly-Gln-Pro-Lys-Ala-Ala-Pro (SEQ ID NO: 175). In some embodiments, $L_1$ comprises the sequence Gly-Gln-Pro-Lys-Ala-Ala-Pro (SEQ ID NO: 175). In some embodiments, $L_1$ comprises the sequence Gly-Gln-Pro-Lys-Ala-Ala-Pro (SEQ ID NO: 175), $L_2$ comprises the sequence Thr-Lys-Gly-Pro-Ser-Arg (SEQ ID NO: 176), $L_3$ comprises the sequence Ser, and $L_4$ comprises the sequence Arg-Thr. In some embodiments, $L_3$ comprises the sequence Gly-Gln-Pro-Lys-Ala-Ala-Pro (SEQ ID NO: 175). In some embodiments, $L_1$ comprises the sequence Ser, $L_2$ comprises the sequence Arg-Thr, $L_3$ comprises the sequence Gly-Gln-Pro-Lys-Ala-Ala-Pro (SEQ ID NO: 175) and $L_4$ comprises the sequence Thr-Lys-Gly-Pro-Ser-Arg (SEQ ID NO: 176).

In some embodiments, $L_1$, $L_2$, $L_3$ and $L_4$ each independently comprise a sequence selected from $(GGGGS)_n$ (wherein n is an integer between 0 and 5; SEQ ID NO:174), GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148). In some embodiments, $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT. In some embodiments, $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length. In some embodiments, $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length. In some embodiments, $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length. In some embodiments, $L_1$ and $L_2$ are zero amino acids in length, and $L_3$ and $L_4$ each comprise an independently selected sequence selected from $(GGGGS)_n$ (wherein n is an integer between 0 and 5; SEQ ID NO:174), GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148). In some embodiments, $L_3$ and $L_4$ are zero amino acids in length, and $L_1$ and $L_2$ each comprise an independently selected sequence selected from $(GGGGS)_n$ (wherein n is an integer between 0 and 5; SEQ ID NO:174), GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Fc Regions and Constant Domains

In some embodiments, a binding protein of the present disclosure comprises a second polypeptide chain further comprising an Fc region linked to CH1, the Fc region comprising an immunoglobulin hinge region and CH2 and CH3 immunoglobulin heavy chain constant domains. In some embodiments, a binding protein of the present disclosure comprises a third polypeptide chain further comprising an Fc region linked to CH1, the Fc region comprising an immunoglobulin hinge region and CH2 and CH3 immunoglobulin heavy chain constant domains. In some embodiments, a binding protein of the present disclosure comprises a second polypeptide chain further comprising an Fc region linked to CH1, the Fc region comprising an immunoglobulin hinge region and CH2 and CH3 immunoglobulin heavy chain constant domains, and a third polypeptide chain further comprising an Fc region linked to CH1, the Fc region comprising an immunoglobulin hinge region and CH2 and CH3 immunoglobulin heavy chain constant domains.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

To improve the yields of the binding proteins, the $C_{H3}$ domains can be altered by the "knob-into-holes" technology which is described in detail with several examples in, for example, International Publication No. WO 96/027011, Ridgway et al., 1996, *Protein Eng.* 9: 617-21; and Merchant et al., 1998, *Nat. Biotechnol.* 16: 677-81. Specifically, the interaction surfaces of the two $C_{H3}$ domains are altered to increase the heterodimerisation of both heavy chains containing these two $C_{H3}$ domains. Each of the two $C_{H3}$ domains (of the two heavy chains) can be the "knob," while the other is the "hole." The introduction of a disulfide bridge further stabilizes the heterodimers (Merchant et al., 1998; Atwell et al., 1997, *J. Mol. Biol.* 270: 26-35) and increases the yield. In particular embodiments, the knob is on the second pair of polypeptides with a single variable domain. In other embodiments, the knob is on the first pair of polypeptides having the cross-over orientation. In yet other embodiments, the $C_{H3}$ domains do not include a knob in hole.

In some embodiments, a binding protein of the present disclosure comprises a "knob" mutation on the second polypeptide chain and a "hole" mutation on the third polypeptide chain. In some embodiments, a binding protein of the present disclosure comprises a "knob" mutation on the third polypeptide chain and a "hole" mutation on the second polypeptide chain. In some embodiments, the "knob" mutation comprises substitution(s) at positions corresponding to positions 354 and/or 366 of human IgG1 or IgG4 according to EU Index. In some embodiments, the amino acid substitutions are S354C, T366W, T366Y, S354C and T366W, or S354C and T366Y. In some embodiments, the "knob" mutation comprises substitutions at positions corresponding to positions 354 and 366 of human IgG1 or IgG4 according to EU Index. In some embodiments, the amino acid substitutions are S354C and T366W. In some embodiments, the "hole" mutation comprises substitution(s) at positions corresponding to positions 407 and, optionally, 349, 366, and/or 368 and of human IgG1 or IgG4 according to EU Index. In some embodiments, the amino acid substitutions are Y407V or Y407T and optionally Y349C, T366S, and/or L368A. In some embodiments, the "hole" mutation comprises substitutions at positions corresponding to positions 349, 366, 368, and 407 of human IgG1 or IgG4 according to EU Index. In some embodiments, the amino acid substitutions are Y349C, T366S, L368A, and Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366 and optionally 354 of human IgG1 or IgG4 according to EU Index, wherein the amino acid substitutions are T366W or T366Y and optionally S354C; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366 and optionally 354 of human IgG1 or IgG4 according to EU Index, wherein the amino acid substitutions are T366W or T366Y and optionally S354C.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution at position corresponding to position 366 of human IgG1 or IgG4 according to EU Index, wherein the amino acid substitution is T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366, 368, and/or 407 and of human IgG1 or IgG4 according to EU Index, wherein the amino acid substitutions are T366S, L368A, and/or Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366, 368, and/or 407 and of human IgG1 or IgG4 according to EU Index, wherein the amino acid substitutions are T366S, L368A, and/or Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution at position corresponding to position 366 of human IgG1 or IgG4 according to EU Index, wherein the amino acid substitution is T366W.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve serum half-life (See e.g., Hinton, P. R. et al. (2006) *J. Immunol.* 176(1):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve stability, e.g., of the hinge region and/or dimer interface of IgG4 (See e.g., Spiess, C. et al. (2013) *J. Biol. Chem.* 288:26583-26593). In some embodiments, the mutation comprises substitutions at positions corresponding to positions 228 and 409 of human IgG4 according to EU Index, wherein the amino acid substitutions are S228P and R409K. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, a binding protein of the present disclosure comprises knob and hole mutations and one or more mutations to improve stability. In some embodiments, the first and/or second Fc regions are human IgG4 Fc regions.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) *Sci. Rep.* 5:17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and hole mutations and one or more mutations to improve purification. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234, 235, 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the mutation comprises substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A. In some embodiments, a binding protein of the present disclosure comprises knob and hole mutations and one or more mutations to reduce effector function. In some embodiments, the first and/or second Fc regions are human IgG1 Fc regions. In some embodiments, the first and/or second Fc regions are human IgG4 Fc regions. For further description of Fc mutations at position 329, see, e.g., Shields, R. L. et al. (2001) *J. Biol. Chem.* 276:6591-6604 and WO1999051642.

In some embodiments, the types of mutations described supra can be combined in any order or combination. For example, a binding protein of the present disclosure can comprise two or more of the “knob” and “hole” mutations, the one or more mutations to improve serum half-life, the one or more mutations to improve IgG4 stability, the one or more mutations to improve purification, and/or the one or more mutations to reduce effector function described supra.

In certain embodiments, a binding protein of the present disclosure comprises: a first polypeptide chain that comprises a lambda $C_L$ domain; a $C_{H3}$ domain of a second polypeptide chain that comprises amino acid substitutions at positions corresponding to positions 354 and 366 of human IgG1 according to EU Index, wherein the amino acid substitutions are S354C and T366W; a $C_{H3}$ domain of a third polypeptide chain that comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and a fourth polypeptide chain that comprises a kappa $C_L$ domain. In some embodiments, the first polypeptide chain comprises a lambda $C_L$ domain; wherein the $C_{H3}$ domain of the third polypeptide chain comprises amino acid substitutions at positions corresponding to positions 354 and 366 of human IgG1 according to EU Index, wherein the amino acid substitutions are S354C and T366W; wherein the $C_{H3}$ domain of the second polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain. In some embodiments, the first polypeptide chain comprises a lambda $C_L$ domain; wherein the $C_{H3}$ domain of the second polypeptide chain comprises amino acid substitutions at positions corresponding to positions 354, 366, 435, and 436 of human IgG1 according to EU Index, wherein the amino acid substitutions are S354C, T366W, H435R, and Y436F; wherein the $C_{H3}$ domain of the third polypeptide chain comprises amino acid substitutions at positions corresponding to positions 349, 366, 368, and 407 of human IgG1 according to EU Index, wherein the amino acid substitutions are Y349C, T366S, L368A, and Y407V; and wherein the fourth polypeptide chain comprises a kappa $C_L$ domain. In some embodiments, the first polypeptide chain comprises a kappa $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a lambda $C_L$ domain.

In some embodiments, a binding protein of the present disclosure is purified by protein A affinity chromatography, kappa light chain affinity chromatography (e.g., using a KappaSelect resin according to manufacturer’s instructions; GE Healthcare), and optionally lambda light chain affinity chromatography (e.g., using a LambdaFabSelect resin according to manufacturer’s instructions; GE Healthcare). In some embodiments, a binding protein of the present disclosure is purified by Protein A affinity chromatography, lambda light chain affinity chromatography (e.g., using a LambdaFabSelect resin according to manufacturer’s instructions; GE Healthcare), and optionally kappa light chain affinity chromatography (e.g., using a KappaSelect resin according to manufacturer’s instructions; GE Healthcare). In some embodiments, the binding protein comprises two Fc regions, each comprising a $C_{H3}$ domain, and only one of the $C_{H3}$ domains comprises amino acid substitutions at positions corresponding to positions 435 and 436 of human IgG1 or IgG4 according to EU Index, wherein the amino acid substitutions are H435R and Y436F. In some embodiments, a binding protein of the present disclosure is purified by protein A affinity chromatography, then kappa light chain affinity chromatography (e.g., using a KappaSelect resin according to manufacturer’s instructions; GE Healthcare), then optionally lambda light chain affinity chromatography (e.g., using a LambdaFabSelect resin according to manufacturer’s instructions; GE Healthcare) in sequence. In some embodiments, a binding protein of the present disclosure is purified by Protein A affinity chromatography, then lambda light chain affinity chromatography (e.g., using a LambdaFabSelect resin according to manufacturer’s instructions; GE Healthcare), then optionally kappa light chain affinity chromatography (e.g., using a KappaSelect resin according to manufacturer’s instructions; GE Healthcare) in sequence. For example, in some embodiments, the binding protein is contacted with Protein A, eluted from Protein A under conditions suitable for isolating the binding protein away from binding proteins comprising either 0 or 2 $C_{H3}$ domains comprising the amino acid substitutions are H435R and Y436F, contacted with a kappa light chain affinity medium (e.g., as used in the KappaSelect resin; GE Healthcare), and eluted from the kappa light chain affinity medium under conditions suitable for isolating the binding protein away from binding proteins comprising only lambda $C_L$ domains (e.g., according to manufacturer's instructions). Conditions suitable for the Protein A elution are known in the art, including without limitation a stepwise elution gradient from pH4.5-2.8. In some embodiments, Protein A or a Protein A variant useful for protein purification is employed. In some embodiments, the Protein A is attached to a substrate or resin, e.g., as part of a chromatography medium. In some embodiments, after elution from the kappa light chain affinity medium, the binding protein is contacted with a lambda light chain affinity medium (e.g., as used in the Lambda-FabSelect resin; GE Healthcare), and eluted from the lambda light chain affinity medium under conditions suitable for isolating the binding protein away from binding proteins comprising only kappa $C_L$ domains (e.g., according to manufacturer's instructions). In some embodiments, a binding protein of the present disclosure is detected using HIC chromatography. In some embodiments, the binding protein comprises: a first polypeptide chain that comprises a lambda $C_L$ domain; a $C_{H3}$ domain of a second polypeptide chain that comprises amino acid substitutions at positions corresponding to positions 354 and 366 of human IgG1 or IgG4 according to EU Index, wherein the amino acid substitutions are S354C and T366W; a $C_{H3}$ domain of a third polypeptide chain that comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and a fourth polypeptide chain that comprises a kappa $C_L$ domain. In some embodiments, the binding protein is produced by a host cell. In some embodiments, the binding protein is purified from a cell culture medium or host cell extract. In some embodiments, the binding proteins are secreted by a host cell or produced and extracted from a host cell (e.g., before being contacted with Protein A). In some embodiments, the binding protein is in a cell culture medium or host cell extract when contacted with Protein A. In some embodiments, the binding protein is purified away from other binding proteins, polypeptides, and/or other cellular components.

In some embodiments, CH1, CH2, CH3 and CL of the trispecific binding proteins described herein may comprise any of CH1, CH2, CH3 and CL sequences of binding proteins 1-53.

Nucleic Acids

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, Molecular Cloning: A Laboratory Manual (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins described herein. In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2):193-9, 1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art, and can be used to transfect any cell of interest.

Other aspects of the present disclosure relate to a vector system comprising one or more vectors encoding a first, second, third, and fourth polypeptide chain of any of the binding proteins described herein. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the vector system comprises a first vector encoding the first and third polypeptide chains of the binding protein, and a second vector encoding the second and fourth polypeptide chains of the binding protein. In some embodiments, the vector system comprises a first vector encoding the first and fourth polypeptide chains of the binding protein, and a second vector encoding the second and third polypeptide chains of the binding protein. In some embodiments, the vector system comprises a first vector encoding the first, second, third, and fourth polypeptide chains of the binding protein. The one or more vectors of the vector system may be any of the vectors described herein. In some embodiments, the one or more vectors are expression vectors.

Isolated Host Cells

Other aspects of the present disclosure relate to an isolated host cell comprising one or more isolated polynucleotides, vectors, and/or vector systems described herein. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frugiperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), Expi293TM cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding protein; and b) isolating the binding protein from the host cell. Methods of culturing host cells under conditions to express a protein are well known to one of ordinary skill in the art. Methods of isolating proteins from cultured host cells are well known to one of ordinary skill in the art, including, for example, by affinity chromatography (e.g., two step affinity chromatography comprising protein A affinity chromatography followed by size exclusion chromatography).

Uses for Binding Proteins

The binding proteins can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

For diagnostic applications, in certain embodiments, binding proteins can be labeled with a detectable moiety. The detectable moiety can be any one that is capable of producing, either directly or indirectly, a detectable signal. For example, the detectable moiety can be a radioisotope, such as $^{3}H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, preferably into the bloodstream, and the presence and location of the labeled antibody in the host assayed. The binding protein can be labeled with any moiety that is detectable in an animal, whether by nuclear magnetic resonance, radiology, or other detection means known in the art.

The binding proteins can also be used for cell activation, tumor targeting, neutralization of cytokine activities, neutralization of viral infection, combination of multiple signaling events, to treat cancer, arthritis, and/or inflammatory disorders. For example, in some embodiments, a binding protein specifically binds one, two, or three antigen targets selected from A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In some embodiments, a binding protein of the present disclosure is adminstered to a patient in need thereof for the treatment or prevention of cancer. For example, in some embodiments, the binding protein comprises one antigen binding site that specifically binds a T-cell surface protein and another antigen binding site that specifically binds a tumor target protein (e.g., two antigen binding sites that specifically bind T-cell surface proteins and one antigen binding site that specifically binds a tumor target protein, or two antigen binding sites that specifically bind tumor target proteins and one antigen binding site that specifically binds a T-cell surface protein). In certain embodiments, the binding protein comprises an antigen binding site that specifically binds CD3, an antigen binding site that specifically binds CD28, and an antigen binding site that specifically binds a tumor target protein selected from CD19, CD20, CD38, Her2, and LAMP1. In some embodiments, the binding protein is co-administered with a chemotherapeutic agent. In some embodiments, the patient is a human.

In some embodiments, a binding protein of the present disclosure is adminstered to a patient in need thereof for the treatment or prevention of an inflammatory disease or disorder. In some embodiments, the binding protein comprises three antigen binding sites that each specifically bind a cytokine target protein selected from IL-4, IL-13 and TNFa. In some embodiments, the binding protein is co-administered with an anti-inflammatory agent. In some embodiments, the patient is a human.

The disclosure also relates to a kit comprising a binding protein and other reagents useful for detecting target antigen levels in biological samples. Such reagents can include a detectable label, blocking serum, positive and negative control samples, and detection reagents. In some embodiments, the kit comprises a composition comprising any binding protein, polynucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper pierceable by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Binding Protein Therapeutic Compositions and Administration Thereof

Therapeutic or pharmaceutical compositions comprising binding proteins are within the scope of the disclosure. Such therapeutic or pharmaceutical compositions can comprise a therapeutically effective amount of a binding protein, or binding protein-drug conjugate, in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., Remington's Pharmaceutical Sciences (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, binding protein compositions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

The pharmaceutical compositions of the disclosure can be selected for parenteral delivery or subcutaneous. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry powder for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes. Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

In some embodiments, the present disclosure relates to a method of preventing and/or treating a proliferative disease or disorder (e.g., cancer). In some embodiments, the method comprises administering to a patient a therapeutically effective amount of at least one of the binding proteins described herein. In some embodiments, the patient is a human. In some embodiments, the at least one binding protein is administered in combination with one or more anti-cancer therapies (e.g., any anti-cancer therapy known in the art). In some embodiments, the at least one binding protein is administered before the one or more anti-cancer therapies. In some embodiments, the at least one binding protein is administered concurrently with the one or more anti-cancer therapies. In some embodiments, the at least one binding protein is administered after the one or more anti-retroviral therapies.

In some embodiments, the present disclosure relates to a method of preventing and/or treating an inflammatory disease or disorder (e.g., cancer). In some embodiments, the method comprises administering to a patient a therapeutically effective amount of at least one of the binding proteins described herein. In some embodiments, the patient is a human. In some embodiments, the at least one binding protein is administered in combination with one or more anti-inflammatory therapies (e.g., any anti-inflammatory therapy known in the art). In some embodiments, the at least one binding protein is administered before the one or more anti-inflammatory therapies. In some embodiments, the at least one binding protein is administered concurrently with the one or more anti-inflammatory therapies. In some embodiments, the at least one binding protein is administered after the one or more anti-inflammatory therapies.

Without limiting the present disclosure, a number of embodiments of the present disclosure are described below for purpose of illustration.

Item 1: A binding protein comprising four polypeptide chains that form three antigen binding sites that specifically bind one or more target proteins, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}—L_4—C_{H1} \quad [II]$$

and a third polypeptide chain comprises a structure represented by the formula:

$$V_{H3}—C_{H1} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

Item 2: A binding protein comprising four polypeptide chains that form three antigen binding sites that specifically bind one or more target proteins, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}—L_4—C_{H1}—\text{hinge}—C_{H2}—C_{H3} \quad [II]$$

and a third polypeptide chain comprises a structure represented by the formula:

$$V_{H3}—C_{H1}—\text{hinge}—C_{H2}—C_{H3} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

Item 3: The binding protein of item 1, wherein the second and/or the third polypeptide chain further comprises an Fc region linked to $C_{H1}$, the Fc region comprising an immunoglobulin hinge region and $C_{H2}$ and $C_{H3}$ immunoglobulin heavy chain constant domains.

Item 4: The binding protein of any one of items 1-3, wherein at least one of $L_1$, $L_2$, $L_3$ or $L_4$ is independently 0 amino acids in length.

Item 5: The binding protein of any one of items 1-3, wherein $L_1$, $L_2$, $L_3$ or $L_4$ are each independently at least one amino acid in length.

Item 6: The binding protein of any one of items 1-3 and 5, wherein (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Item 7: The binding protein of any one of items 1-5, wherein (a) $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

Item 8: The binding protein of any one of items 1-7, wherein the binding protein is trispecific and capable of specifically binding three different antigen targets.

Item 9: The binding protein of any one of items 1-8, wherein the binding protein specifically binds three target proteins that correspond to two target proteins on T cells and to one tumor target protein.

Item 10: The binding protein of item 9, wherein one of said target proteins on T cells is CD3.

Item 11: The binding protein of item 9 or item 10, wherein one of said target proteins on T cells is CD28.

Item 12: The binding protein of any one of items 9-11, wherein said tumor target protein is CD38.

Item 13: The binding protein of any one of items 1-8, wherein the binding protein specifically binds three target proteins that correspond to two target proteins on T cells and to one target protein selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

Item 14: The binding protein of any one of items 1-13, wherein the binding protein is capable of inhibiting the function of one or more target proteins.

Item 15: The binding protein of item 14, wherein the one or more target proteins are selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

Item 16: A binding protein comprising four polypeptide chains that form three antigen binding sites, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}—L_4—C_{H1} \quad [II]$$

and a third polypeptide chain comprises a structure represented by the formula:

$$V_{H3}—C_{H1} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain; and
$L_1$, $L_2$, $L_3$ and $L_4$ are amino acid linkers;
wherein the polypeptide of formula I and the polypeptide of formula II form a cross-over light chain-heavy chain pair;
wherein:
(a) $V_{L1}$, $V_{L2}$ and $V_{L3}$ each independently comprise a variable domain sequence as set forth in any one of SEQ ID NOs:151, 153, 155, 157, 159, 161, 163, 165, and 167; or
(b) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and
wherein:
(a) $V_{H1}$, $V_{H2}$, and $V_{H3}$ each independently comprise a variable domain sequence as set forth in any one of SEQ ID NOs:150, 152, 154, 156, 158, 160, 162, 164, and 166; or
(b) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

Item 17: A binding protein comprising four polypeptide chains that form three antigen binding sites, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}—L_4—C_{H1}—\text{hinge}—C_{H2}—C_{H3} \quad [II]$$

and a third polypeptide chain comprises a structure represented by the formula:

$$V_{H3}—C_{H1}—\text{hinge}—C_{H2}—C_{H3} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;
$V_{L2}$ is a second immunoglobulin light chain variable domain;
$V_{L3}$ is a third immunoglobulin light chain variable domain;
$V_{H1}$ is a first immunoglobulin heavy chain variable domain;
$V_{H2}$ is a second immunoglobulin heavy chain variable domain;
$V_{H3}$ is a third immunoglobulin heavy chain variable domain;
$C_L$ is an immunoglobulin light chain constant domain;
$C_{H1}$ is an immunoglobulin $C_{H1}$ heavy chain constant domain;
$C_{H2}$ is an immunoglobulin $C_{H2}$ heavy chain constant domain;
$C_{H3}$ is an immunoglobulin $C_{H3}$ heavy chain constant domain;
hinge is an immunoglobulin hinge region connecting the CHM and $C_{H2}$ domains; and
$L_1$, $L_2$, $L_3$ and $L_4$ are amino acid linkers;
wherein the polypeptide of formula I and the polypeptide of formula II form a cross-over light chain-heavy chain pair;
wherein:
(a) $V_{L1}$, $V_{L2}$ and $V_{L3}$ each independently comprise a variable domain sequence as set forth in any one of SEQ ID NOs:151, 153, 155, 157, 159, 161, 163, 165, and 167; or
(b) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and
wherein:
(a) $V_{H1}$, $V_{H2}$, and $V_{H3}$ each independently comprise a variable domain sequence as set forth in any one of SEQ ID NOs:150, 152, 154, 156, 158, 160, 162, 164, and 166; or
(b) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

Item 18: The binding protein of item 16, wherein the second and/or the third polypeptide chain further comprises an Fc region linked to $C_{H1}$, the Fc region comprising an immunoglobulin hinge region and $C_{H2}$ and $C_{H3}$ immunoglobulin heavy chain constant domains.

Item 19: The binding protein of any one of items 16-18, wherein at least one of $L_1$, $L_2$, $L_3$ or $L_4$, is independently 0 amino acids in length.

Item 20: The binding protein of any one of items 16-18, wherein $L_1$, $L_2$, $L_3$ or $L_4$ are each independently at least one amino acid in length.

Item 21: The binding protein of any one of items 16-18 and 20, wherein (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Item 22: The binding protein of any one of items 16-20, wherein:

(a) $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

Item 23: The binding protein of any one of items 16-22, wherein:

(a) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45;

(b) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45;

(c) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57;

(d) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57;

(e) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO:179, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ Comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59;

(f) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59;

(g) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140;

(h) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140;

(i) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125; or (j) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51;

$V_{H2}$ Comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36;

$V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54;

$V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

Item 24: A binding protein comprising four polypeptide chains that form three antigen binding sites, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}—L_4—C_{H1} \quad [II]$$

and a third polypeptide chain comprises a structure represented by the formula:

$$V_{H3}—C_{H1} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ each independently comprise a variable domain sequence as set forth in any one of SEQ ID NOs:169, 171, and 173; or (b) $V_{L1}$, $V_{L2}$ and $V_{L3}$ each independently comprise light chain complementarity determining regions comprising an amino acid sequence selected from the group consisting of SEQ ID NOs: 141-147, 178, and 179;

wherein:

(a) $V_{H1}$, $V_{H2}$, and $V_{H3}$ each independently comprise a variable domain sequence as set forth in any one of SEQ ID NOs:168, 170, and 172; or (b) $V_{H1}$, $V_{H2}$ and $V_{H3}$ each independently comprise heavy chain complementarity determining regions comprising an amino acid sequence selected from the group consisting of SEQ ID NOs: 129-137.

Item 25: A binding protein comprising four polypeptide chains that form three antigen binding sites, wherein a first polypeptide chain comprises a structure represented by the formula:

$$V_{L2}—L_1—V_{L1}—L_2—C_L \quad [I]$$

and a second polypeptide chain comprises a structure represented by the formula:

$$V_{H1}—L_3—V_{H2}—L_4—C_{H1}—\text{hinge}—C_{H2}—C_{H3} \quad [II]$$

and a third polypeptide chain comprises a structure represented by the formula:

$$V_{H3}—C_{H1}—\text{hinge}—C_{H2}—C_{H3} \quad [III]$$

and a fourth polypeptide chain comprises a structure represented by the formula:

$$V_{L3}—C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ each independently comprise a variable domain sequence as set forth in any one of SEQ ID NOs:169, 171, and 173; or (b) $V_{L1}$, $V_{L2}$ and $V_{L3}$ each independently comprise light chain complementarity determining regions comprising an amino acid sequence selected from the group consisting of SEQ ID NOs: 141-147, 178, and 179;

wherein:

(a) $V_{H1}$, $V_{H2}$, and $V_{H3}$ each independently comprise a variable domain sequence as set forth in any one of SEQ ID NOs:168, 170, and 172; or (b) $V_{H1}$, $V_{H2}$ and $V_{H3}$ each independently comprise heavy chain complementarity determining regions comprising an amino acid sequence selected from the group consisting of SEQ ID NOs: 129-137.

Item 26: The binding protein of item 24, wherein the second and/or the third polypeptide chain further comprises an Fc region linked to $C_{H1}$, the Fc region comprising an immunoglobulin hinge region and $C_{H2}$ and $C_{H3}$ immunoglobulin heavy chain constant domains.

Item 27: The binding protein of any one of items 24-26, wherein at least one of $L_1$, $L_2$, $L_3$ and $L_4$, is independently 0 amino acids in length.

Item 28: The binding protein of any one of items 24-26, wherein $L_1$, $L_2$, $L_3$ and $L_4$ are each independently at least one amino acid in length.

Item 29: The binding protein of any one of items 24-26 and 28, wherein (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Item 30: The binding protein of any one of items 24-28, wherein:

(a) $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

Item 31: The binding protein of any one of items 24-30, wherein:

(a) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

(b) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:47, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

(c) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(d) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ Comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(e) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(f) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ Comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(g) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(h) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ Comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(i) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ Comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; or (j) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ Comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

Item 32: The binding protein of any one of items 1, 3-16, 18-24, and 26-31, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V.

Item 33: The binding protein of any one of items 1, 3-16, 18-24, and 26-31, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W.

Item 34: The binding protein of any one of items 1, 3-16, 18-24, and 26-33, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains, and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions comprise amino acid substitutions at positions corresponding to positions 428 and 434 of human IgG1 or IgG4 according to EU Index, wherein the amino acid substitutions are M428L and N434S.

Item 35: The binding protein of any one of items 2, 4-15, 17, 19-23, 25, and 27-31, wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V.

Item 36: The binding protein of any one of items 2, 4-15, 17, 19-23, 25, and 27-31, wherein the $C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W.

Item 37: The binding protein of any one of items 2, 4-15, 17, 19-23, 25, 27-31, 35, and 36, wherein the $C_{H3}$ domains of the second and the third polypeptide chains both comprise amino acid substitutions at positions corresponding to positions 428 and 434 of human IgG1 or IgG4 according to EU Index, wherein the amino acid substitutions are M428L and N434S Item 38: The binding protein of any one of items 1, 3-16, 18-24, and 26-34, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 or IgG4 Fc regions; and wherein only one of the first and the second Fc regions comprises amino acid substitutions at positions corresponding to positions 435 and 436 of human IgG1 or IgG4 according to EU Index, wherein the amino acid substitutions are H435R and Y436F.

Item 39: The binding protein of any one of items 2, 4-15, 17, 19-23, 25, 27-31, and 35-37, wherein the $C_{H3}$ domains of the second and the third polypeptide chains are human IgG1 or IgG4 $C_{H3}$ domains, and wherein only one of the $C_{H3}$ domains comprises amino acid substitutions at positions corresponding to positions 435 and 436 of human IgG1 or IgG4 according to EU Index, wherein the amino acid substitutions are H435R and Y436F.

Item 40: The binding protein of any one of items 1, 3-16, 18-24, 26-34, and 38, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K.

Item 41: The binding protein of any one of items 2, 4-15, 17, 19-23, 25, 27-31, 35-37, and 39, wherein the $C_{H3}$ domains of the second and the third polypeptide chains are human IgG4 $C_{H3}$ domains, and wherein the $C_{H3}$ domains each comprise amino acid substitutions at positions corresponding to positions 228 and 409 of human IgG4 according to EU Index, wherein the amino acid substitutions are S228P and R409K.

Item 42: The binding protein of any one of items 1, 3-16, 18-24, 26-34, 38, and 40, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 234 and 235 of human IgG4 according to EU Index, wherein the amino acid substitutions are F234A and L235A.

Item 43: The binding protein of any one of items 2, 4-15, 17, 19-23, 25, 27-31, 35-37, 39, and 41, wherein the $C_{H3}$ domains of the second and the third polypeptide chains are human IgG4 $C_{H3}$ domains, and wherein the $C_{H3}$ domains each comprise amino acid substitutions at positions corresponding to positions 234 and 235 of human IgG4 according to EU Index, wherein the amino acid substitutions are F234A and L235A.

Item 44: The binding protein of any one of items 1, 3-16, 18-24, 26-34, 38, and 40, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG4 according to EU Index, wherein the amino acid substitutions are L234A and L235A.

Item 45: The binding protein of any one of items 2, 4-15, 17, 19-23, 25, 27-31, 35-37, 39, and 41, wherein the $C_{H3}$ domains of the second and the third polypeptide chains are human IgG1 $C_{H3}$ domains, and wherein the $C_{H3}$ domains each comprise amino acid substitutions at positions corresponding to positions 234 and 235 of human IgG4 according to EU Index, wherein the amino acid substitutions are L234A and L235A.

Item 46: The binding protein of any one of items 2, 4-15, 17, 19-23, 25, 27-31, 35-37, 39, 41, 43, and 45, wherein VH1 and VL1 form a first antigen binding site that specifically binds human CD3, wherein VH2 and VL2 form a second antigen binding site that specifically binds human CD28, and wherein VH3 and VL3 form a third antigen binding site that specifically binds a human tumor target protein.

Item 47: The binding protein of any one of items 2, 4-15, 17, 19-23, 25, 27-31, 35-37, 39, 41, 43, and 45, wherein VH1 and VL1 form a first antigen binding site that specifically binds human CD28, wherein VH2 and VL2 form a second antigen binding site that specifically binds human CD3, and wherein VH3 and VL3 form a third antigen binding site that specifically binds a human tumor target protein.

Item 48: The binding protein of item 46 or item 47, wherein the third antigen binding site specifically binds a human tumor target protein selected from the group consisting of CD19, CD20, CD38, Her2, and LAMP1.

Item 49: The binding protein of any one of items 46-48, wherein the antigen binding site that specifically binds CD3 comprises:

(a) a heavy chain variable domain comprising the amino acid sequence of SEQ ID NO: 152 and a light chain variable domain comprising the amino acid sequence of SEQ ID NO: 153; or (b) a heavy chain variable domain comprising the amino acid sequence of SEQ ID NO: 154 and a light chain variable domain comprising the amino acid sequence of SEQ ID NO: 155.

Item 50: The binding protein of any one of items 46-49, wherein the antigen binding site that specifically binds CD28 comprises:

(a) a heavy chain variable domain comprising the amino acid sequence of SEQ ID NO: 160 and a light chain variable domain comprising the amino acid sequence of SEQ ID NO: 161; or (b) a heavy chain variable domain comprising the amino acid sequence of SEQ ID NO: 162 and a light chain variable domain comprising the amino acid sequence of SEQ ID NO: 163.

Item 51: The binding protein of any one of items 46-50, wherein the antigen binding site that specifically binds a tumor target protein comprises:

(a) a heavy chain variable domain comprising the amino acid sequence of SEQ ID NO: 156 and a light chain variable domain comprising the amino acid sequence of SEQ ID NO: 157;

(b) a heavy chain variable domain comprising the amino acid sequence of SEQ ID NO: 158 and a light chain variable domain comprising the amino acid sequence of SEQ ID NO: 159;

(c) a heavy chain variable domain comprising the amino acid sequence of SEQ ID NO: 164 and a light chain variable domain comprising the amino acid sequence of SEQ ID NO: 165;

(d) a heavy chain variable domain comprising the amino acid sequence of SEQ ID NO: 150 and a light chain variable domain comprising the amino acid sequence of SEQ ID NO: 151; or (e) a heavy chain variable domain comprising the amino acid sequence of SEQ ID NO: 166 and a light chain variable domain comprising the amino acid sequence of SEQ ID NO: 167.

Item 52: The binding protein of any one of items 2, 17, 35-37, 39, 41, 43, and 45, wherein:

(a) VH1 and VL1 form a first antigen binding site that specifically binds human TNFa, VH2 and VL2 form a second antigen binding site that specifically binds human IL13, and VH3 and VL3 form a third antigen binding site that specifically binds human IL4;

(b) VH1 and VL1 form a first antigen binding site that specifically binds human TNFa, VH2 and VL2 form a second antigen binding site that specifically binds human IL4, and VH3 and VL3 form a third antigen binding site that specifically binds human IL13;

(c) VH1 and VL1 form a first antigen binding site that specifically binds human IL4, VH2 and VL2 form a second antigen binding site that specifically binds human TNFa, and VH3 and VL3 form a third antigen binding site that specifically binds human IL13;

(d) VH1 and VL1 form a first antigen binding site that specifically binds human IL4, VH2 and VL2 form a second antigen binding site that specifically binds human IL13, and VH3 and VL3 form a third antigen binding site that specifically binds human TNFa;

(e) VH1 and VL1 form a first antigen binding site that specifically binds human IL13, VH2 and VL2 form a second antigen binding site that specifically binds human IL4, and VH3 and VL3 form a third antigen binding site that specifically binds human TNFa; or (f) VH1 and VL1 form a first antigen binding site that specifically binds human IL13, VH2 and VL2 form a second antigen binding site that specifically binds human TNFa, and VH3 and VL3 form a third antigen binding site that specifically binds human IL4.

Item 53: The binding protein of item 52, wherein the antigen binding site that specifically binds human TNFa comprises a heavy chain variable domain comprising the amino acid sequence of SEQ ID NO:168 and a light chain variable domain comprising the amino acid sequence of SEQ ID NO:169.

Item 54: The binding protein of item 52 or item 53, wherein the antigen binding site that specifically binds human IL4 comprises a heavy chain variable domain comprising the amino acid sequence of SEQ ID NO:170 and a light chain variable domain comprising the amino acid sequence of SEQ ID NO:171.

Item 55: The binding protein of any one of items 52-54, wherein the antigen binding site that specifically binds human IL13 comprises a heavy chain variable domain comprising the amino acid sequence of SEQ ID NO:172 and a light chain variable domain comprising the amino acid sequence of SEQ ID NO:173.

Item 56: The binding protein of any one of items 1-55, wherein:

(a) the $C_L$ domain of the first polypeptide chain is a human kappa $C_L$ domain, and the $C_L$ domain of the fourth polypeptide chain is a human lambda $C_L$ domain; or (b) the $C_L$ domain of the first polypeptide chain is a human lambda $C_L$ domain, and the $C_L$ domain of the fourth polypeptide chain is a human kappa $C_L$ domain.

Item 57: The binding protein of any one of items 2, 17, 25, 35-37, 39, 41, and 43-55, wherein the first polypeptide chain comprises a lambda $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain.

Item 58: A binding protein comprising a first polypeptide chain, a second polypeptide chain, a third polypeptide chain and a fourth polypeptide chain wherein:

(a) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(b) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(c) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(d) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(e) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18;

(f) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18;

(g) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(h) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(i) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(j) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(k) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 71 or an amino acid sequence that is at least 95% identical to the amino acid sequence of SEQ ID NO: 71;

(l) the first polypeptide chain comprises the amino acid sequence of SEQ ID NO: 76 or an amino acid sequence that is at least 95% identical to the amino acid sequence of SEQ ID NO: 76; the second polypeptide chain comprises the amino acid sequence of SEQ ID NO: 75 or an amino acid sequence that is at least 95% identical to the amino acid sequence of SEQ ID NO: 75; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(m) the first polypeptide chain comprises the amino acid sequence of SEQ ID NO: 82 or an amino acid sequence that is at least 95% identical to the amino acid sequence of SEQ ID NO: 82; the second polypeptide chain comprises the amino acid sequence of SEQ ID NO: 81 or an amino acid sequence that is at least 95% identical to the amino acid sequence of SEQ ID NO:81; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(n) the first polypeptide chain comprises the amino acid sequence of SEQ ID NO: 88 or an amino acid sequence that is at least 95% identical to the amino acid sequence of SEQ ID NO:88; the second polypeptide chain comprises the amino acid sequence of SEQ ID NO: 87 or an amino acid sequence that is at least 95% identical to the amino acid sequence of SEQ ID NO: 87; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(o) the first polypeptide chain comprises the amino acid sequence of SEQ ID NO: 94 or an amino acid sequence that is at least 95% identical to the amino acid sequence of SEQ ID NO: 94; the second polypeptide chain comprises the amino acid sequence of SEQ ID NO: 93 or an amino acid sequence that is at least 95% identical to the amino acid sequence of SEQ ID NO: 93; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(p) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(q) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(r) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(s) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(t) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115; or (u) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115.

Item 59: An isolated nucleic acid molecule comprising a nucleotide sequence encoding the binding protein of any one of items 1-58.

Item 60: An expression vector comprising the nucleic acid molecule of item 59.

Item 61: An isolated host cell comprising the nucleic acid molecule of item 59.

Item 62: An isolated host cell comprising the expression vector of item 60.

Item 63: The isolated host cell of item 61 or item 62, wherein the host cell is a mammalian cell or an insect cell.

Item 64: A pharmaceutical composition comprising the binding protein of any one of items 1-58 and a pharmaceutically acceptable carrier.

Item 65: A method of preventing and/or treating cancer in a patient comprising administering to the patient a therapeutically effective amount of at least one binding protein of any one of items 1-23 and 32-58 or the pharmaceutical composition of item 64.

Item 66: The method of item 65, wherein the binding protein comprises one antigen binding site that specifically binds a T-cell surface protein and another antigen binding site that specifically binds a tumor target protein.

Item 67: The method of item 66, wherein the binding protein comprises a first antigen binding site that specifically binds CD3, a second antigen binding site that specifically binds CD28, and a third antigen binding site that specifically binds a tumor target protein selected from the group consisting of CD19, CD20, CD38, Her2, and LAMP1.

Item 68: The method of any one of items 65-67, wherein the at least one binding protein is co-administered with a chemotherapeutic agent.

Item 69: A method of preventing and/or treating an inflammatory disease or disorder in a patient comprising administering to the patient a therapeutically effective amount of at least one binding protein of any one of items 1-15, 24-45, and 52-58 or the pharmaceutical composition of item 64.

Item 70: The method of item 69, wherein the binding protein comprises three antigen binding sites that each specifically bind a cytokine target protein selected from the group consisting of IL-4, IL-13 and TNFa.

Item 71: The method of item 69 or item 70, wherein the at least one binding protein is co-administered with an anti-inflammatory agent.

Item 72: The method of any one of items 65-71, wherein the patient is a human.

Item 73: The method of item 65 or item 69, wherein the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, S152, SISP1, SLC, SPG64, ST2, Syk kinase, TACI, TDO, T14, TIGIT, TIM3, TLR, TLR2, TLR4, TLR5, TLR9, TNFa, TNFRSF7, Tp55, TREM1, TSLP, TSLPR, TWEAK, VEGF, VISTA, Vstm3, WUCAM, and XCR1.

Item 74: The binding protein of any one of items 1-23 and 32-58 or the composition of item 64 for use in preventing and/or treating cancer in a patient.

Item 75: The binding protein for use or the composition for use of item 74, wherein the binding protein comprises one antigen binding site that specifically binds a T-cell surface protein and another antigen binding site that specifically binds a tumor target protein.

Item 76: The binding protein for use or the composition for use of item 75, wherein the binding protein comprises a first antigen binding site that specifically binds CD3, a second antigen binding site that specifically binds CD28, and a third antigen binding site that specifically binds a tumor target protein selected from the group consisting of CD19, CD20, CD38, Her2, and LAMP1.

Item 77: The binding protein for use or the composition for use of any one of items 74-76, wherein the binding protein is co-administered with a chemotherapeutic agent.

Item 78: The binding protein of any one of items 1-15, 24-45, and 52-58 or the pharmaceutical composition of item 64 for use in preventing and/or treating an inflammatory disease or disorder in a patient.

Item 79: The binding protein for use or the composition for use of item 78, wherein the binding protein comprises three antigen binding sites that each specifically bind a cytokine target protein selected from the group consisting of IL-4, IL-13 and TNFa.

Item 80: The binding protein for use or the composition for use of item 78 or item 79, wherein the binding protein is co-administered with an anti-inflammatory agent.

Item 81: The binding protein for use or the composition for use of any one of items 74-80, wherein the patient is a human.

Item 82: The binding protein for use or the composition for use of item 74 or item 78, wherein the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

Item 83: A method of purifying a binding protein produced by a host cell, comprising:

(a) producing the binding protein of any one of items 2, 17, 25, 35-37, 41, 43, 45, and 46-55 in a host cell, wherein only one of the $C_{H3}$ domain of the second polypeptide chain and the $C_{H3}$ domain of the third polypeptide chain comprises amino acid substitutions at positions corresponding to positions 435 and 436 of human IgG1 or IgG4 according to EU Index, wherein the amino acid substitutions are H435R and Y436F;

(b) contacting the binding protein produced in (a) with Protein A; and (c) eluting the binding protein from Protein A under conditions suitable for isolating the binding protein away from binding proteins comprising either 0 or 2 $C_{H3}$ domains comprising the amino acid substitutions are H435R and Y436F, thereby purifying the binding protein.

Item 84: The method of item 83, wherein the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises:

(d) contacting the binding protein eluted in (c) with a kappa light chain affinity medium; and (e) eluting the binding protein from the kappa light chain affinity medium under conditions suitable for isolating the binding protein away from binding proteins comprising only lambda $C_L$ domains.

Item 85: The method of item 84, further comprising, after (e):

(f) contacting the binding protein eluted in (e) with a lambda light chain affinity medium; and (g) eluting the binding protein from the lambda light chain affinity medium under conditions suitable for isolating the binding protein away from binding proteins comprising only kappa $C_L$ domains.

Item 86: The method of item 83, wherein the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises:

(d) contacting the binding protein eluted in (c) with a lambda light chain affinity medium; and (e) eluting the binding protein from the lambda light chain affinity medium under conditions suitable for isolating the binding protein away from binding proteins comprising only kappa $C_L$ domains.

Item 87: The method of item 86, further comprising, after (e):

(f) contacting the binding protein eluted in (e) with a kappa light chain affinity medium; and (g) eluting the binding protein from the kappa light chain affinity medium under conditions suitable for isolating the binding protein away from binding proteins comprising only lambda $C_L$ domains.

Item 88: The method of any one of items 83-87, wherein the first polypeptide chain comprises a lambda $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain.

Item 89: The method of any one of items 83-88, wherein the binding protein is detected in one or more of (c) and (e) using hydrophobic interaction chromatography (HIC).

Item 90: The method of any one of items 83-89, wherein the $C_{H3}$ domains of the second and the third polypeptide chains are human IgG1 or IgG4 $C_{H3}$ domains.

EXAMPLES

The Examples that follow are illustrative of specific embodiments of the disclosure, and various uses thereof. They are set forth for explanatory purposes only, and should not be construed as limiting the scope of the invention in any way.

Example 1: Materials and Methods

The following materials and methods were used for the experiments described in Examples 2-5.

Trispecific Antibody Design

Figure 1A:
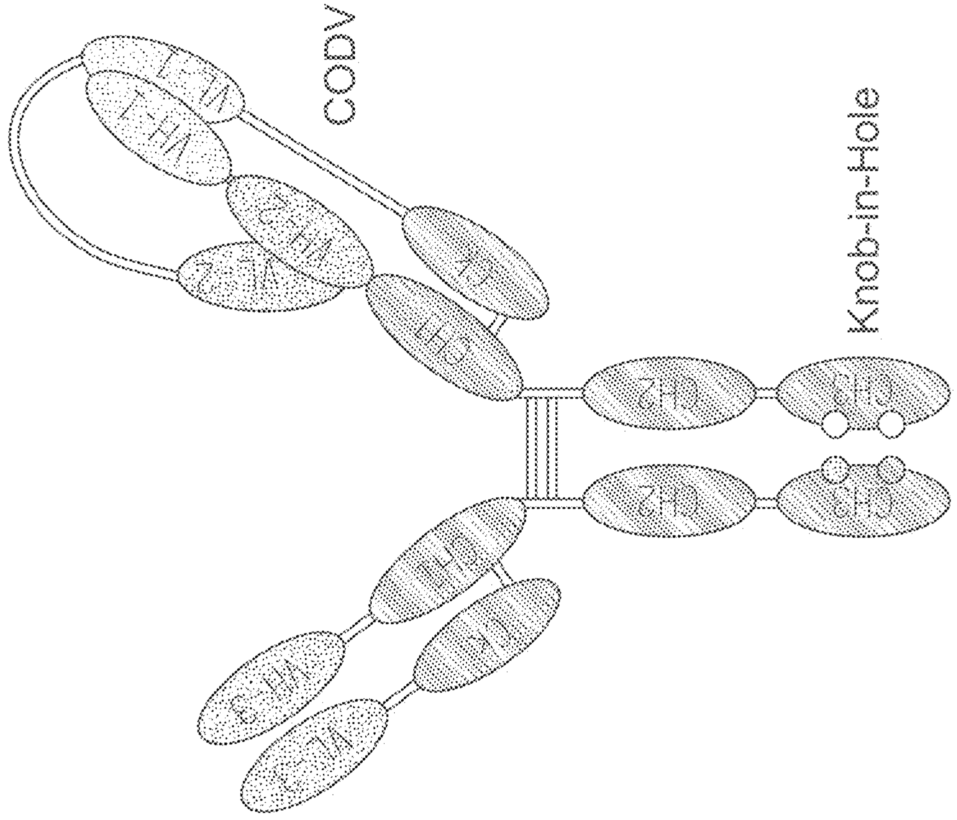
Figure 1C:
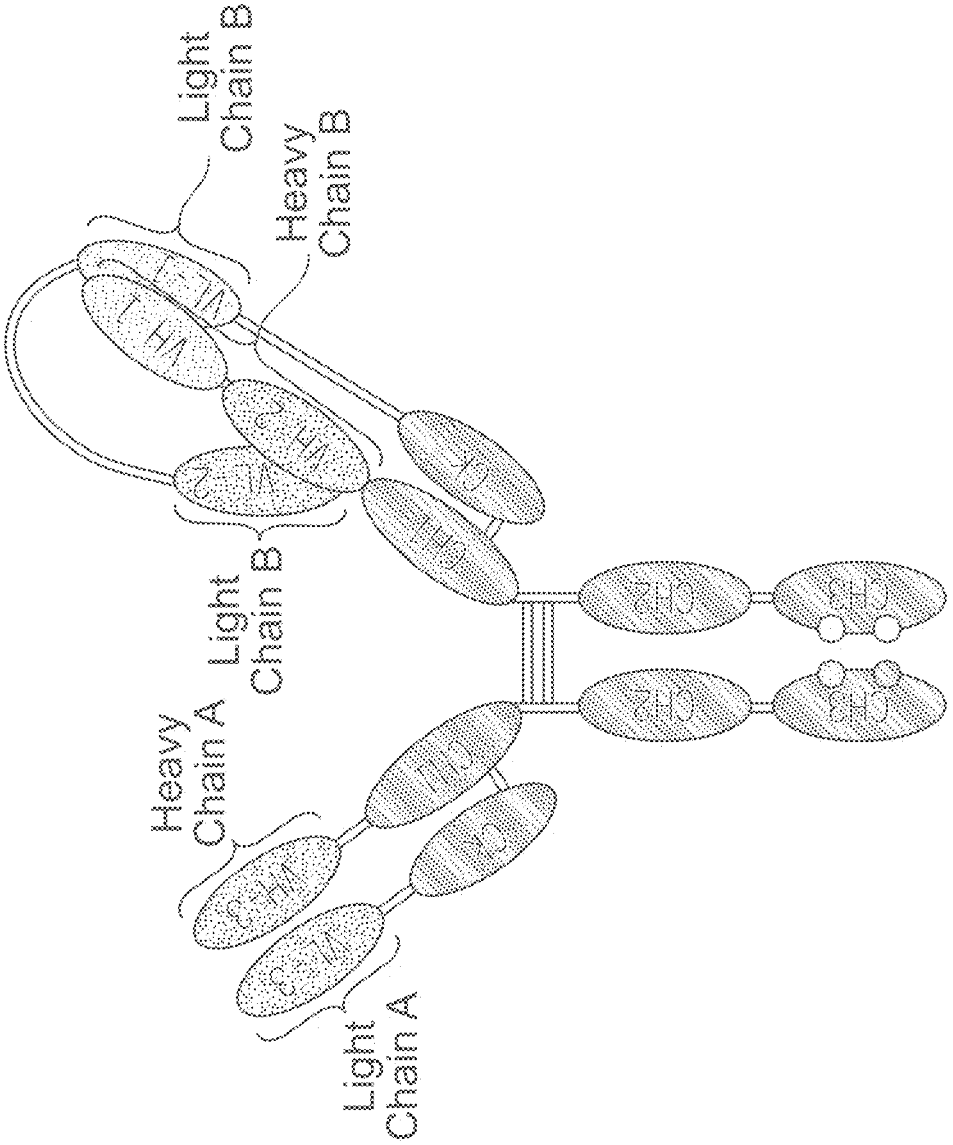

A schematic illustration of the general trispecific antibody design is illustrated in FIGS. 1A-1C. Individual trispecific antibodies were designed based on 5 parameters: 1) Selection of antibody binding sites; 2) Consideration of the position of each binding site; 3) Choice of linkers for the bispecific binding arm (i.e., heavy chain/light chain B in FIG. 1C); 4). "Knob" and "Hole" mutation integration into respective halves of the antibody; 5) Choice of Fc isotype (IgG1 or IgG4). After assembly of the amino acid sequences for each trispecific molecule, four genes for each trispecific Ab were synthesized using human preferred codons (CambrY Applied Biosciences, Cambridge, MA, USA), and cloned into a eukaryotic expression vector.

Production and Purification of Trispecific Antibodies

Trispecific antibodies were produced by transient transfection of 4 expression plasmids into Expi293 cells using ExpiFectamine™ 293 Transfection Kit (Thermo Fisher Scientific) according to manufacturer's protocol. Briefly, 25% (w/w) of each plasmid was diluted into Opti-MEM, mixed with pre-diluted ExpiFectamine reagent for 20-30 minutes at room temperature (RT), and added into Expi293 cells ($2.5\times10^6$ cells/ml). An optimization of transfection to determine the best ratio of plasmids was often used in order to produce the trispecific antibody with good yield and purity.

4-5 days post transfection, the supernatant from transfected cells was collected and filtered through 0.45 μm filter unit (Nalgene). The trispecific antibody in the supernatant was purified using a 3-step procedure. First, protein A affinity purification was used, and the bound Ab was eluted using "IgG Elution Buffer" (Thermo Fisher Scientific). Second, product was dialyzed against PBS (pH7.4) overnight with 2 changes of PBS buffer. Any precipitate was cleared by filtration through 0.45 μm filter unit (Nalgene) before next step. Third, size-exclusion chromatography (SEC) purification (Hiload 16/600 Superdex 200 pg, or Hiload 26/600 Superdex 200 pg, GE Healthcare) was used to remove aggregates and different species in the prep. The fractions were analyzed on reduced and non-reduced SDS-PAGE to identify the fractions that contained the monomeric trispecific antibody before combining them. The purified antibody can be aliquoted and stored at −80° C. long term.

ELISA Assays

The binding properties of the purified antibodies were analyzed either using ELISA or SPR methods. For ELISA, corresponding antigens for each binding site in the trispecific antibody were used to coat a 96-well Immuno Plate (Nunc 439454, Thermo Fisher Scientific) overnight at 4° C. using 2 μg/ml each antigen in PBS (pH7.4). The coated plate was blocked using 5% skim milk+2% BSA in PBS for one hour at RT, followed by washing with PBS+0.25% Tween 20 three times (Aqua Max 400, Molecular Devices). Serial dilution of antibodies (trispecific and control Abs) were prepared and added onto the ELISA plates (100 μl/well in duplicate), incubated at RT for one hour, followed by washing 5 times with PBS+0.25% Tween 20.

After washing, the HRP conjugated secondary anti-human Fab (1:5000, Cat. No. 109-035-097, Jackson ImmunoResearch Inc) was added to each well and incubated at RT for 30 minutes. After washing 5 times with PBS+0.25% Tween 20, 100 μl of TMB Microwell Peroxidase Substrate (KPL, Gaithersburg, MD, USA) was added to each well. The reaction was terminated by adding 50 μl 1M $H_2SO_4$, and $OD_{450}$ was measured using SpectraMax M5 (Molecular Devices) and analyzed using SoftMax Pro6.3 software (Molecular Devices). The final data was transferred to GraphPad Prism software (GraphPad Software, CA, USA), and plotted as shown. EC50 was calculated using the same software.

SPR Assays

Two pairs of heavy and light chains were selected for full kinetic analysis. Kinetic characterization of purified antibodies was performed using surface plasmon resonance (SPR) technology on a BIACORE 3000 (GE Healthcare). A capture assay using a tag specific antibody capture and orientation of the investigated antibodies was used. For capture of Fc containing protein constructs the human antibody capture kit (GE Healthcare) was used, for capture of His tag containing protein constructs the His capture kit (GE Healthcare) was used. The capture antibody was immobilized via primary amine groups (11000 RU) on a research grade CM5 chip (GE Life Sciences) using standard procedures. The analyzed antibody was captured at a flow rate of 10 μL/min with an adjusted RU value that would result in maximal analyte binding signal of typically 30 RU.

For an exemplary assay, recombinant human IL13 (catalog #IL012) and human IL4 (catalog #IL004) were purchased from Millipore, recombinant human TNFa (catalog #H8916) was purchased from Sigma Aldrich. Binding kinetics were measured against recombinant human IL4 and IL13 over a concentration range between 0.1 to 3 nM for IL4 and 0.8 to 25 nM for IL13. For human TNFα a concentration range from 3 to 100 nM was used. As assay buffer HBS EP (10 mM HEPES, pH 7.4, 150 mM NaCl, 3 mM EDTA, and 0.005% Surfactant P20) was used at a flow rate of 30 μl/min. Chip surfaces were regenerated with the regeneration solution of the respective capture kit. Kinetic parameters were analyzed and calculated in the BIAevaluation program package v4.1 using a flow cell without captured antibody as reference and the 1:1 Langmuir binding model with mass transfer. To study simultaneous binding of antigens the trispecific antibodies were captured by an anti-human antibody capture surface. Antigens were used in single concentrations with IL4 at 3 nM, IL13 at 25 nM and TNFα at 100 nM. To show simultaneous binding of all three antigens, a mixture of IL4, IL13 and TNFα was injected. In separate analysis cycles, IL13 was injected alone, followed by either IL4 or TNFα, and followed by a co-inject of either IL4/TNFα or a co-inject of TNFα/IL4. The final response measured in each cycle was compared to show similarity of consecutive binding of either two or three antigens and simultaneous binding of a mixture of all three antigens.

In Vitro T Cell Activation and Proliferation Assays

Human PBMCs were purified from buffy coat purchased from Blood Research Component (Brookline, MA, USA) using Ficoll-Paque Plus method. Briefly, fresh buffy coat was first diluted at 1:3 ratio in PBS (pH7.4), and mixed with Ficoll-Paque Plus solution (Ficoll) thoroughly before use by inverting the bottle several times. 15 mL density gradient medium was added to each Leucosep® tube and spin for 30s at 1000×g, RT. The medium is now located below the porous barrier. 30-40 mL diluted buffy coat then was carefully poured into each Leucosep tube, and centrifuged at 800×g for 15 minutes at room temperature, with the brake off and Max accel at 5. Plasma layer was removed, and the rest of the supernatant, which contains the enriched PBMCs, was transferred into a new tube (Leucosep tube was not held in the inverted position for longer than 2 seconds). Enriched PBMCs were washed with 45 ml PBS, and spun down at 250×g for 10 minutes at room temperature. Wash was repeated, and multiple tubes were combined into one tube. Cells were resuspended in 20 mL PBS and counted using a Bio-Rad TC20.

To set up the in vitro T cell activation assay, purified human PBMCs were resuspended in culture medium (RPMI1640 with 10% FBS and supplemented with glutamine/Streptomycin)(Thermo Fisher Scientific) ($10^6$ cells/ml). Indicated concentrations of different trispecific and control antibodies were added to each well, or used to coat the plate before use as described in Stebbings, R. et al. (2007) *J. Immunol.* 179:3325-3331, and incubated for 16-24 hours in a tissue culture incubator. The cells were spin down, and the supernatant was either collected for measuring cytokine release, or discarded. The cells were stained with florescent labeled antibodies for T cell markers (CD3, CD4, CD8, etc.) and activation markers (CD69, CD62L, etc.), and analyzed by running the samples on an Fortessa flow cytometer (Beckton Dickinson, San Jose, CA), followed by analysis using the Flowjo software (FlowJo v10) and plotted as shown.

To set up the in vitro T cell proliferation assay, purified human PBMCs were resuspended in culture medium (RPMI1640 with 10% FBS and supplemented with glutamine/Streptomycin)(Thermo Fisher Scientific) ($10^6$ cells/ml). Indicated concentrations of different trispecific and control antibodies were added to each well and incubated for 1-7 days in a tissue culture incubator. The cells were spun down, and the supernatant was either collected for measuring cytokine release, or discarded. The cells were stained with florescent labeled antibodies for T cell markers (CD3, CD4, CD8, etc.) and activation markers (CD69, CD62L, etc.), and analyzed by running the samples on an Fortessa flow cytometer (Beckton Dickinson, San Jose, CA), followed by analysis using the Flowjo software (FlowJo v10) and plotted as shown.

In Vitro Cell Killing Assay

Purified human PBMCs were using for in vitro killing assays against various cancer cells using different trispecific antibodies. Briefly, the killing assay was set up in 96-well V-bottom plate. For each plate, 40 ml PBMCs from each donor were plated at 2×10^6 cells/ml, and 30 ml of PKH26 (Sigma #MINI26) labeled target cells at 2.5×10^5 cells/ml (4 μL of dye to stain up to 1×10^7 cells) were prepared. First 20 μL/well test proteins at various concentrations or PMA were added into each well, followed by adding 80 μL/well labeled target cells into each well (2×10^4 cells/well). 100 μL of PBMC were then added to each well, reaching E:T=10:1 well (2×10^5 cells/well), and incubated for 24 hours at 37° C. 5% CO2 incubator. The cells were spin down, and the supernatant was either collected for measuring cytokine release, or discarded. The cells were stained with Vivid LIVE/DEAD™ Fixable Violet Dead Cell Staining buffer (Life Technology #L34955) (staining buffer was prepared by adding 60 μL Vivid reagent into 60 ml PBS). Cells were resuspended into 100 μL staining buffer by incubation for 15 min at RT in the dark. After washing the cells with 1×PBS, the cells were resuspended in 200 μL PBS with 0.5% Paraformaldehyde, and PKH26+Vivid+ cancer cells were collected by Fortessa flow cytometer (Beckton Dickinson, San Jose, CA), followed by analysis using the Flowjo software. The percentage of killing is calculated as "specific killing-spontaneous killing/total cells and plotted as shown.

Cytokine Release Assay

For measuring inflammatory cytokine concentrations in the in vitro activation assays, in vitro killing assays, in vivo activation assays in CD34+ umbilical cord cell humanized NSG mice, and the toxicity study, cell culture supernatant was collected, and serum samples were diluted according to manufacturer's protocol using Milliplex Human High Sensitivity T cell I3-plex Kit (EMD Millipore). These were subsequently analyzed by EMD Millipore MAGPIX® System, and MILLIPLEX® Analyst 5.1 software.

In Vivo Mouse Models and Efficacy Studies

Human CD34+ hematopoietic stem cell-engrafted NSG mice (hu-CD34) were used as an in vivo mouse model. These mice develop multi-lineage human immune cells, and are a validated platform for immuno-oncology efficacy studies (see, e.g., Shultz, L. D. et al. (2014) *Cold Spring Harb. Protoc.* 2014:694-708). Hu-$CD34^+$ NSG mice are produced by injecting $CD34^+$ hematopoietic stem cells, showing effective multi-lineage engraftment of human immune cell populations including T cells, B cells and some other populations (McDermott, S. P. et al. (2010) *Blood* 116:193-200). Multi-lineage hematopoiesis occurs within 12 weeks. Engraftment is stable for over one year without graft-versus-host disease.

For the efficacy study using hu-CD34 NSG mice, mice were purchased from The Jackson Laboratory (Maine, USA), and human cell populations were validated before use. In general, $5\times10^6$ tumor cells mixed in Matrigel (BD Biosciences) (50% v/v) were used for inoculating tumor in each mouse. Once tumor size reached the range of 100-150 $mm^3$, mice were selected and randomized into each group for study. Antibodies were given intravenously at given doses 3 times weekly. Body weight was monitored 1-3 times weekly. Tumor size was measured by caliper tumor measurements 1-3 times/week. All mice were terminated when the tumor size reached 1,500 $mm^3$, or 24 hours after the last dose. Terminal blood samples (0.3 mL) were collected into serum separator tubes, mixed by gently inverting five times, and placed into a tube rack. Terminal tumors were also collected and weighed before being put into fixative for immunohistochemistry analysis.

Human PBMC humanized (hu-PBMC) NSG mice were used as another in vivo mouse model. These mice are produced by injecting purified human PBMC from health donors, which have the fastest engraftment rate using adult peripheral blood mononuclear cells and enable short-term studies requiring a strong effector and memory T cell and NK cell function, and are suitable for short term efficacy study (3-4 weeks) due to graft-versus-host disease.

For the efficacy study using hu-PBMC NSG mice, 8-10 week old NSG mice (Cat. No: 005557, NOD.Cg-Prkdcscid Il2rgtm1Wjl/SzJ) were purchased from The Jackson Laboratory (Maine, USA). Each mouse was innoculated with $5\times10^6$ tumor cells mixed in Matrigel (BD Biosciences) (50% v/v). Once tumor size reached the range of 50-100 $mm^3$, $10\times10^6$ human PBMCs from a healthy donor were reconstituted to each mouse. Human cell reconstitution was validated the next day. Once tumor size reached the range of 100-150 $mm^3$, mice were selected and randomized into each group for study. Antibodies were given intravenously at given doses 3 times weekly. Body weight was monitored 1-3 times weekly. Tumor size was measured by caliper tumor measurements 1-3 times/week. All mice were terminated when the tumor size reached 1,500 $mm^3$ or 24 hours after the last dose. Terminal blood samples (0.3 mL) were collected into serum separator tubes, mixed by gently inverting five times, and placed into a tube rack. Terminal tumors were also collected and weighed before being put into fixative for immunohistochemistry analysis.

NHP Tolerability and Pharmacokinetic Study

All NHP studies were carried out by Covance (Princeton, New Jersey, USA) according to Covance ICUCA protocol. Drug- and protein-naïve or protein-naïve male Cynomolgus Monkeys were used in all studies. Based on study design, monkeys were selected and grouped for each trispecific antibody. Antibody was given by intravenous infusion for 1 hour via saphenous vein. Increasing doses were given on consecutive days for low doses (<10 μg/kg), but with a 1-2 day interval for higher doses (>10 μg/kg) for observation purposes. Blood samples were collected at 0 hour (Day 1 only), 0.5 hour (mid-infusion), 1, and 6 hours from start of infusion for all animals after each dose, as specified. Additional unscheduled blood samples were collected at the discretion of the study director, pathologist, and/or clinical veterinarian. All animals were returned to colony on Day 60. PBMC and serum from the blood samples were prepared using standard methods, and preserved for future analysis.

Luciferase Reporter Assay

GloResponse™ IL2-luc2P Jurkat Cells, Thaw and Use (Promega part #CS187002) and GloResponse™ NFAT-Luc2 Jurkat Cells (Promega Cat #CS176401) were purchased from Promega (WI, USA), and prepared for use according to manufacturer's protocol.

Briefly, the cells were thawed for 2 min in a 37° C. water bath and gently transferred to a 15 mL conical centrifuge tube containing 10 mL pre-warmed R10 media. Tube was centrifuged at 300 g for 5 min at RT. Supernatant was removed, and the cells were resuspended in 20 mL pre-warmed R10 media and transferred to a 75 cm2 culture flask, followed by incubation in 37° C. tissue culture incubator until cells were growing and stable (~3-4 days). The cells were split twice a week to 0.1e6 cells/mL. Cells were maintained in R10+Hygromycin B media for selection. Cells were used for assays ~7 days after thawing.

For antibody stimulation, trispecific or control antibodies were prepared at various concentrations and serially diluted in PBS. 25 μL of antibodies were dispensed per well. For plate-bound Abs, Maxisorp plate was used and incubated at 4° C. overnight. For soluble Abs, a U-bottom plate was used. Reporter cells were resuspended to 0.3-0.5 e6/mL, and 175 uL cells were added to each well, and incubated in 37° C. $CO_2$ incubator for 6 hours. The plate was then taken out of the incubator and allowed to equilibrate to ambient temperature (10-15 min). Then 50 μl of Bio-Glo™ Reagent (Promega Cat #G7941) (ambient temperature) was added to the each well of the assay plate. After incubation for 5 minutes, luminescence activity was measured using Micro- Beta2 LumiJET microplate counter (Perkin Elmer; is read time). Data were plotted using GraphPad Prism software.

Conformational Stability

Thermostability measurements (e.g., melting points, Tm) were determined using differential scanning fluorimetry (DSF). Samples were diluted in D-PBS buffer (Invitrogen) to a final concentration of 0.2 μg/μl including a 4× concentrated solution of SYPRO-Orange dye (Invitrogen, 5000× stock in DMSO) in D-PBS in white semi-skirt 96-well plates (BIORAD). All measurements were done in duplicate using a MyiQ2 real time PCR instrument (BIORAD). Negative first derivative curves (−d(RFU)/dT) of the melting curves were generated in the iQ5 Software v2.1 (BIORAD). Data were then exported into Microsoft Excel for Tm determination and graphical display of the data.

IC50 Measurements

Detection of Antibody Activity Against IL-4 and IL-13 with a Reporter Cell Line

Activities of bispecific antibodies or derivatives against cytokines IL4 and IL13 were determined in commercially available HEK-Blue IL-4/IL-13 reporter cells (InvivoGen). HEK-Blue IL-4/IL-13 cells are designed to monitor the activation of the STAT6 pathway by IL-4 or IL13. Stimulation of the cells with either cytokine results in production of the reporter gene secreted embryonic alkaline phosphatase (SEAP) which can be measured in the culture supernatant with the QUANTI-Blue assay. To test antibody activities against IL4 or IL13, the cytokines were pre-incubated for 1 hour with different concentrations of the antibodies and added to 50.000 HEK-Blue IL-4/IL-13 cells. Cytokine-mediated induction of SEAP was measured after 24 hours incubation in the cell culture supernant with the QUANTI-Blue assay (InvivoGen). Each experiment was performed with n=3 datapoints for each antibody concentration. The half-maximal inhibitory concentration (IC50) for each antibody was calculated via the internal application Biostat-Speed V2.0 (Sanofi).

Detection of Antibody Activity Against TNFα with a Reporter Cell Line

Activities of bispecific antibodies or derivatives against TNFa were determined by using commercially available HEK-Blue TNF-a reporter cells (InvivoGen). HEK-Blue TNF-a cells are designed to detect bioactive TNFa by monitoring the activation of the NFkB pathway via the expression of the reporter gene secreted embryonic alkaline phosphatase (SEAP) which can be measured in the culture supernatant with an QUANTI Blue Assay (InvivoGen). To determine antibody activities against TNFα the cytokines were pre-incubated for 1 hour with different concentrations of the antibodies and added to 50,000 HEK Blue TNF-a cells. Cytokine mediated induction of SEAP was measured after 24 hours in the culture supernatant with the QUANTI-Blue assay (InvivoGen). Each experiment was performed with n=3 datapoints for each antibody concentration. The half maximal inhibitory concentration for each antibody was calculated.

Example 2: Overview of the Trispecific Binding Proteins

A novel strategy was developed for the generation of trispecific binding proteins. The trispecific proteins comprised four polypeptides that formed three target binding sites (FIGS. 1A-C). Each target binding site comprised the $V_H$ and $V_L$ domain from an antibody that targeted a distinct human antigen target (See e.g., Table 1). The trispecific binding proteins contained a first pair of polypeptides that possessed dual variable domains having a cross-over orientation forming two distinct antigen binding sites (called the CODV Ig format), and a second pair of polypeptides, each with a single variable domain that formed a third antigen binding site (FIGS. 1A and 1B).

TABLE 1

Heavy and light chain SEQ ID NOs for binding proteins 1-21, and the target antigens to which the binding proteins are directed.

| Binding Protein # | SEQ ID NOS | Directed to: |
|---|---|---|
| 1 | 1, 2, 3, 4 | Her2 × (CD28 × CD3) |
| 2 | 1, 2, 9, 10 | Her2 × (CD28 × CD3) |
| 3 | 13, 14, 3, 4 | CD19 × (CD28 × CD3) |
| 4 | 13, 14, 9, 10 | CD19 × (CD28 × CD3) |
| 5 | 17, 18, 3, 4 | CD38 × (CD28 × CD3) |
| 6 | 17, 18, 9, 10 | CD38 × (CD28 × CD3) |
| 7 | 21, 22, 3, 4 | LAMP1 × (CD28 × CD3) |
| 8 | 21, 22, 9, 10 | LAMP1 × (CD28 × CD3) |
| 9 | 60, 61, 62, 63 | TNFa × (IL4 × IL13) |
| 10 | 60, 61, 68, 69 | TNFa × (IL13 × IL4) |
| 11 | 60, 71, 68, 69 | TNFa × (IL13 × IL4) |
| 12 | 73, 74, 75, 76 | IL13 × (IL4 × TNFa) |
| 13 | 73, 74, 81, 82 | IL13 × (TNFa × IL4) |
| 14 | 85, 86, 87, 88 | IL4 × (IL13 × TNFa) |
| 15 | 85, 86, 93, 94 | IL4 × (TNFa × IL13) |
| 16 | 73, 74, 68, 69 | IL13 × (IL13 × IL4) |
| 17 | 85, 86, 68, 69 | IL4 × (IL13 × IL4) |
| 18 | 73, 74, 62, 63 | IL13 × (IL4 × IL13) |
| 19 | 85, 86, 62, 63 | IL4 × (IL4 × IL13) |
| 20 | 114, 115, 3, 4 | CD20 × (CD28 × CD3) |
| 21 | 114, 115, 9, 10 | CD20 × (CD28 × CD3) |

The first pair of polypeptides (that possessed the dual variable domains) comprised a first polypeptide having the structure $V_{L2}$-Linker-$V_L$-Linker-Immunoglobulin light chain constant domain, and a second polypeptide having the structure $V_{H1}$-Linker-$V_{H2}$—Linker-Immunoglobulin $C_{H1}$ heavy chain constant domain, resulting in a pair of polypeptides which had a cross over orientation that formed two distinct antigen binding sites: $V_{H1}$-$V_{L1}$ and $V_{H2}$-$V_{L2}$ (FIG. 1C, see light and heavy chains B). Table A provides a summary of the design of the bispecific arm (i.e., the arm comprising heavy and light chains B) of IgG1 and IgG4 variants of representative trispecific binding proteins, including indicating the various combinations of the linkers used in the bispecific arm of the trispecific binding proteins. The second pair of polypeptides (that each possessed a single variable domain) comprised a first polypeptide having the structure $V_{H3}$-Immunoglobulin $C_{H1}$ heavy chain constant domain, and a second polypeptide having the structure $V_{L3}$-Immunoglobulin light chain constant domain, resulting in a pair of polypeptides that formed a third antigen binding site: $V_{H3}$-$V_{L3}$ (FIG. 1C, see light and heavy chains A). Furthermore, the trispecific binding proteins were constructed such that either of the $C_{H3}$ domains could include a knob or a hole modification to facilitate antibody heterodimerization (FIG. 1).

TABLE A summary of the design of the bispecific arm of the trispecific binding proteins as an IgG1 (Hole) or IgG4 (Hole)

| | | CD28 x CD3 | | | CD3 x CD28 | | | CD28 x CD3 | | | CD3 x CD28 | | |
|---|---|---|---|---|---|---|---|---|---|---|---|---|---|
| | | HC-1 | HC-2 | HC-3 | HC-1 | HC-2 | HC-3 | HC-1 | HC-2 | HC-3 | HC-1 | HC-2 | HC-3 |
| CD28 × | LC-1 | X | | | | | | | | | | | |
| CD3 | LC-2 | | X | | | | | | | | | | |
| | LC-3 | | | X | | | | | | | | | |
| CD3 × | LC-1 | | | | X | | | | | | | | |
| CD28 | LC-2 | | | | | X | | | | | | | |
| | LC-3 | | | | | | X | | | | | | |
| CD28 × | LC-1 | | | | | | | X | | | | | |
| CD3 | LC-2 | | | | | | | | X | | | | |
| | LC-3 | | | | | | | | | X | | | |
| CD3 × | LC-1 | | | | | | | | | | X | | |
| CD28 | LC-2 | | | | | | | | | | | X | |
| | LC-3 | | | | | | | | | | | | X |

Linkers:
[L3, L4]/[L1, L2]-[S, RT]/[GQPKAAP (SEQ ID NO: 175), TKGPS (SEQ ID NO: 106)]; [,]/[GGGGSGGGGS (SEQ ID NO: 104), GGGGSGGGGS (SEQ ID NO: 104)]; or [GGGGSGGGGSGGGGS (SEQ ID NO: 105),]/[GGGGSGGGGSGGGGS (SEQ ID NO: 105),]

Example 3: In Vitro Binding Activity and Antibody-Mediated Specific Killing of T Cell Engagers This example describes in vitro assays for characterizing the activities of the T cell engagers.

Using the approach described in Example 2 above for trispecific binding protein design, four trispecific binding proteins (Binding Proteins 1, 3, 5, and 6) were generated. These trispecific binding proteins were created by grafting onto a trispecific binding protein framework the $V_H$ and $V_L$ domains isolated from antibodies targeting distinct human proteins: CD3, CD19, CD28, CD38, or Her2. Binding Protein 1 was constructed such that the first pair of polypeptides (which formed two antigen binding sites) targeted CD28 and CD3, and the second pair of polypeptides (which formed the single antigen binding site) targeted Her2 (Binding Protein 1=Her2×(CD28×CD3)). Binding Protein 3 was constructed such that the first pair of polypeptides (which formed two antigen binding sites) targeted CD28 and CD3, and the second pair of polypeptides (which formed the single antigen binding site) targeted CD19 (Binding Protein 3=CD19×(CD28×CD3)). Binding Protein 5 was constructed such that the first pair of polypeptides (which formed two antigen binding sites) targeted CD28 and CD3, and the second pair of polypeptides (which formed the single antigen binding site) targeted CD38 (Binding Protein 5=CD38×(CD28×CD3)). Binding Protein 6 was constructed such that the first pair of polypeptides (which formed two antigen binding sites) targeted CD28 and CD3, and the second pair of polypeptides (which formed the single antigen binding site) targeted CD38 (Binding Protein 6=CD38×(CD28×CD3)).

In Vitro Assays Using Trispecific Binding Proteins Comprising Anti-Her2

Figure 2:
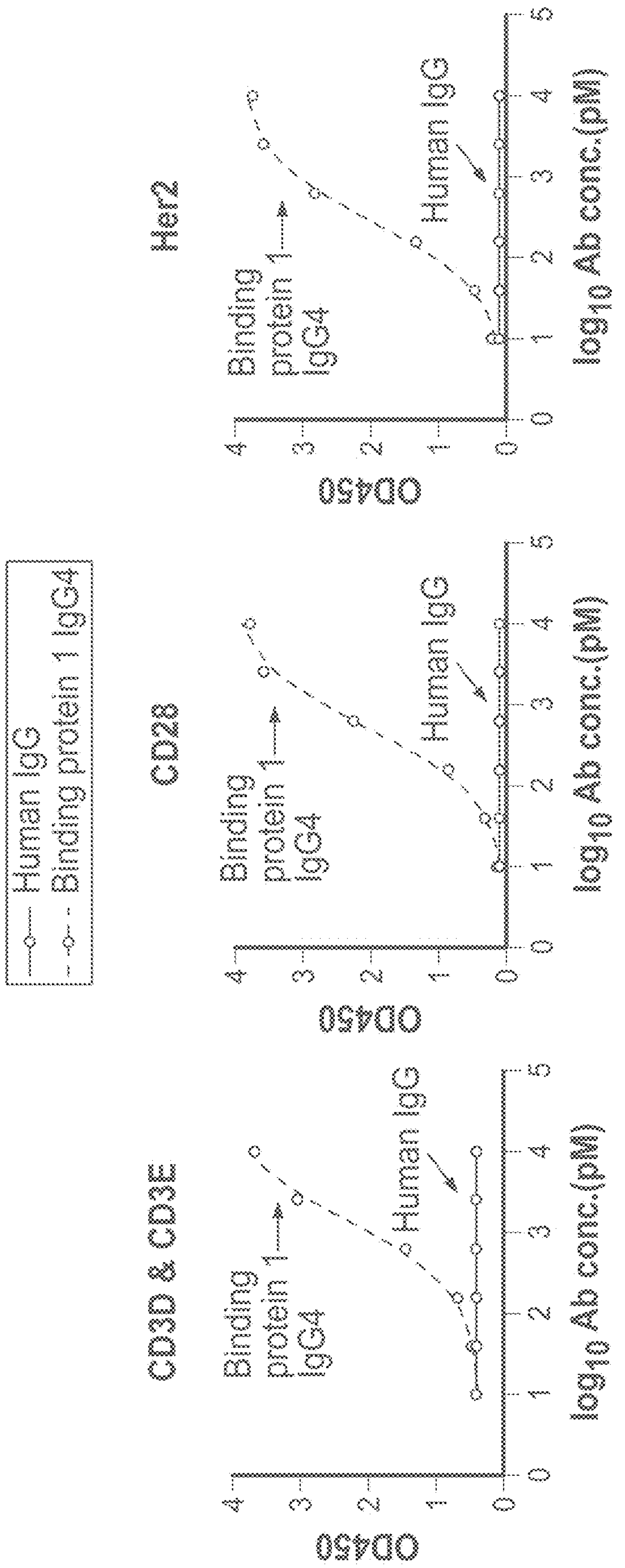
FIG. 2 shows the results of an ELISA assay determining the binding of an anti-Her2×CD28×CD3 IgG4 trispecific antibody (Binding Protein 1), or isotype control antibody, to human CD3, CD28 and Her2. The bound antibodies were detected using a horseradish peroxidase (HRP)-conjugated anti-Fab secondary antibody.

To test the ability of the trispecific binding proteins to target and bind three different human antigens, the specificity of Binding Protein 1 for its targets was first examined by ELISA assay. Binding Protein 1 was capable of binding all three of its target proteins—CD3, CD28, and Her2 (FIG. 2)—indicating that each binding domain in the trispecific format retained its function.

ZR-75-1, AU565 (Her2$^+$), ARH-77 (CD19$^+$), MOLP-8, RPMI-8226, KMS-12_BM, NCI-H929, MM.1.S, MM.1., R OPM-2, KMS-26, and U266 cells (CD38$^+$) were labeled with the membrane dye PKH-26 (Sigma) and used as target cells in a cytotoxicity assay. These labeled cell lines were co-cultured at an E:T ratio of 10:1 with enriched human Pan T cells in the presence of increasing concentrations of a trispecific antibody, bispecific antibody, or control proteins for 24 hours. The extent of cell lysis in the target cells was determined by staining with a live/dead cell marker (Life Technologies) and measuring the number of dead cells in the labeled target cell population by running the samples on a Fortessa flow cytometer (Beckton Dickinson, San Jose, CA) followed by analysis using the Flowjo software (FlowJo v10).

Her2+, CD19+, CD38+ tumor cell lines were stained with fluorescently conjugated antibodies against human CD3, CD28, CD19, CD38, LAMP1, and/or Her2 (Biolegend). Staining with respective isotype-matched control antibodies was also included. The cells were then acquired on the Fortessa (Beckton Dickinson, San Jose, CA) instrument. Flow analysis was performed on FlowJo v10. The mediated killing results of various binding proteins are shown in FIGS. 3A-5, 9A, 9B, & 11A-16.

Figure 3B:
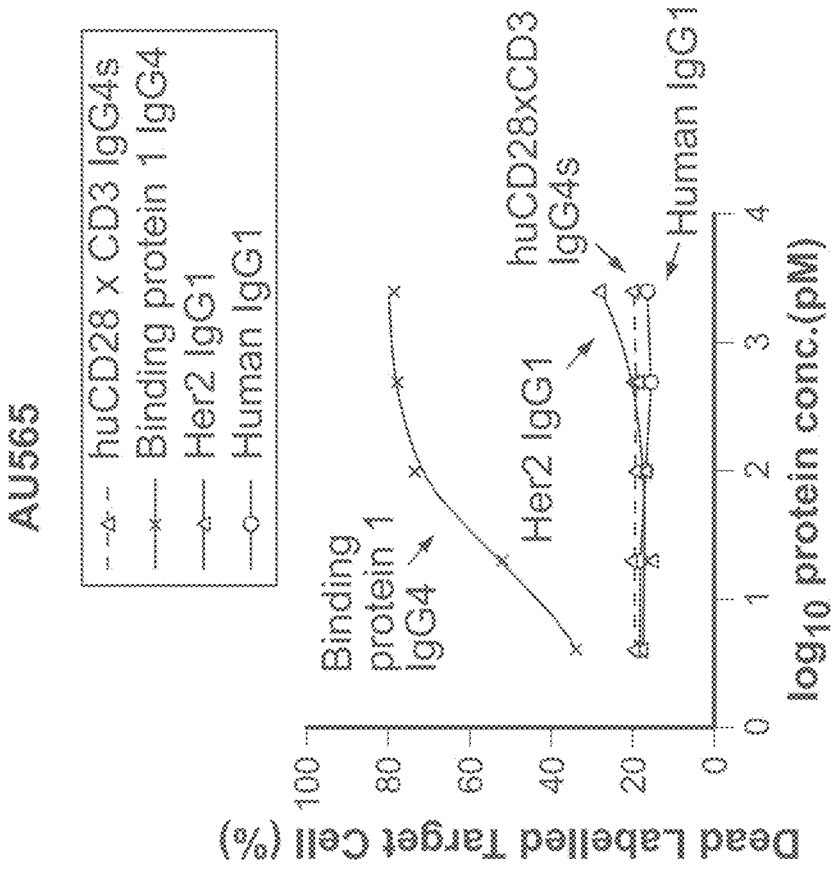
FIGS. 3A-3C show the results of antibody-mediated specific killing of $Her2^+$ breast cancer cells using an anti-Her2×CD28×CD3 IgG4 trispecific antibody (referred to herein as "Binding protein 1"), an anti-CD28×CD3 IgG4 bispecific antibody (huCD28×CD3), an anti-Her2 IgG1 antibody, or a control antibody (human-IgG1), using human PBMC at the E:T=10.
Figure 3A:
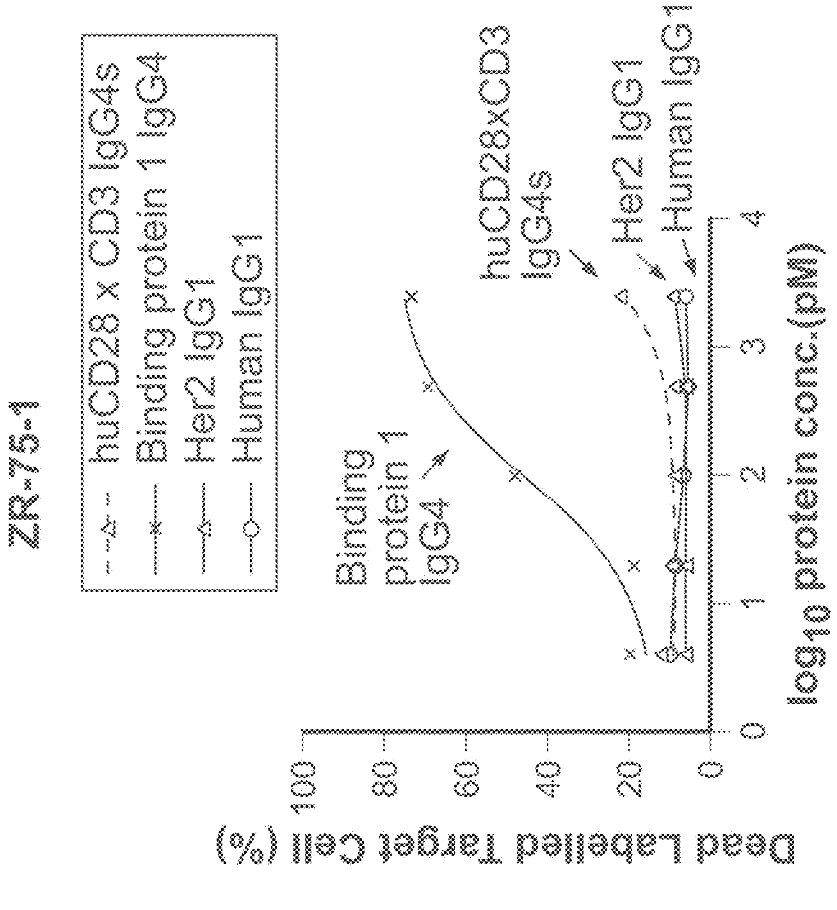
Figure 3C:
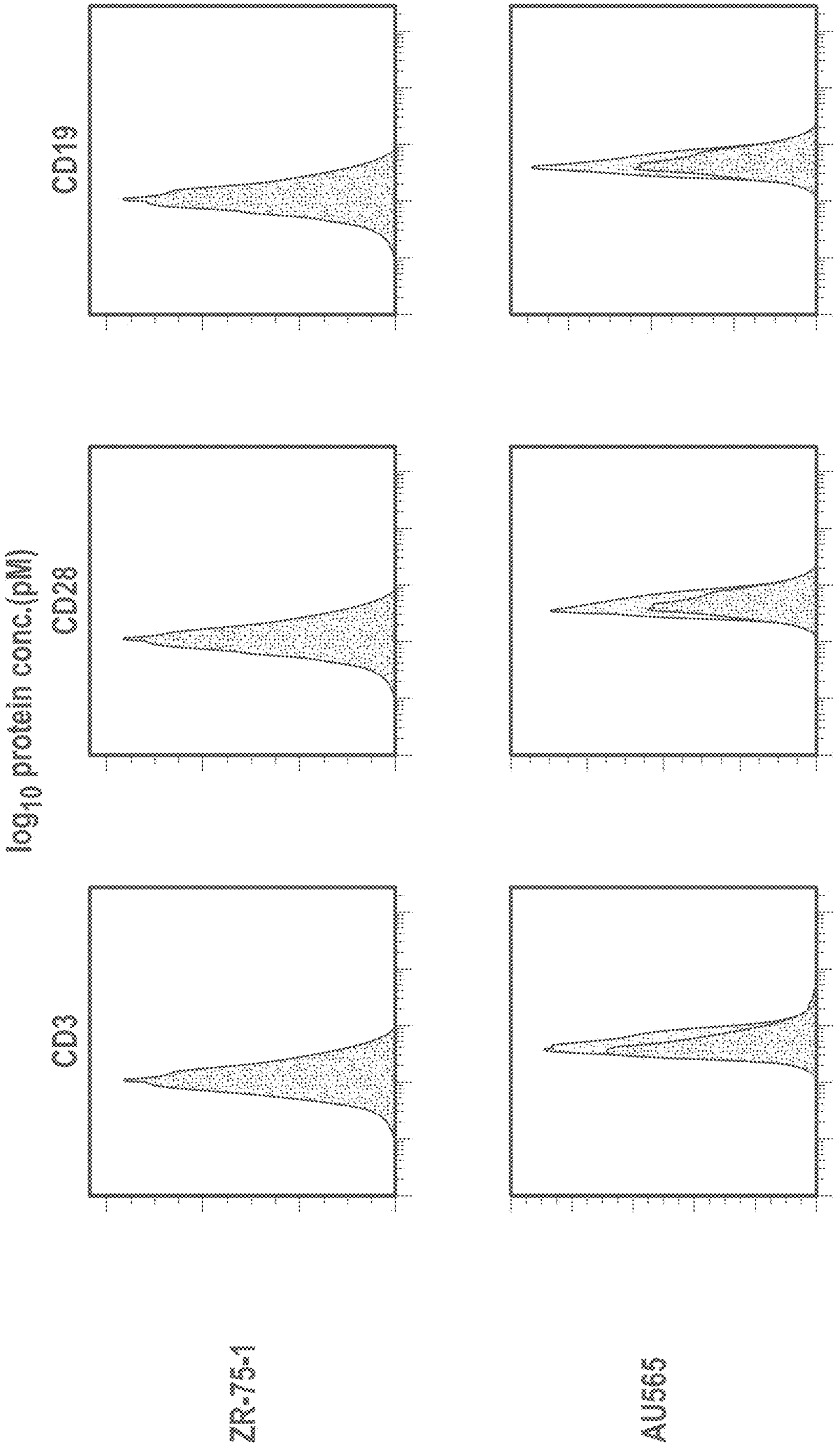
Figure 3C:
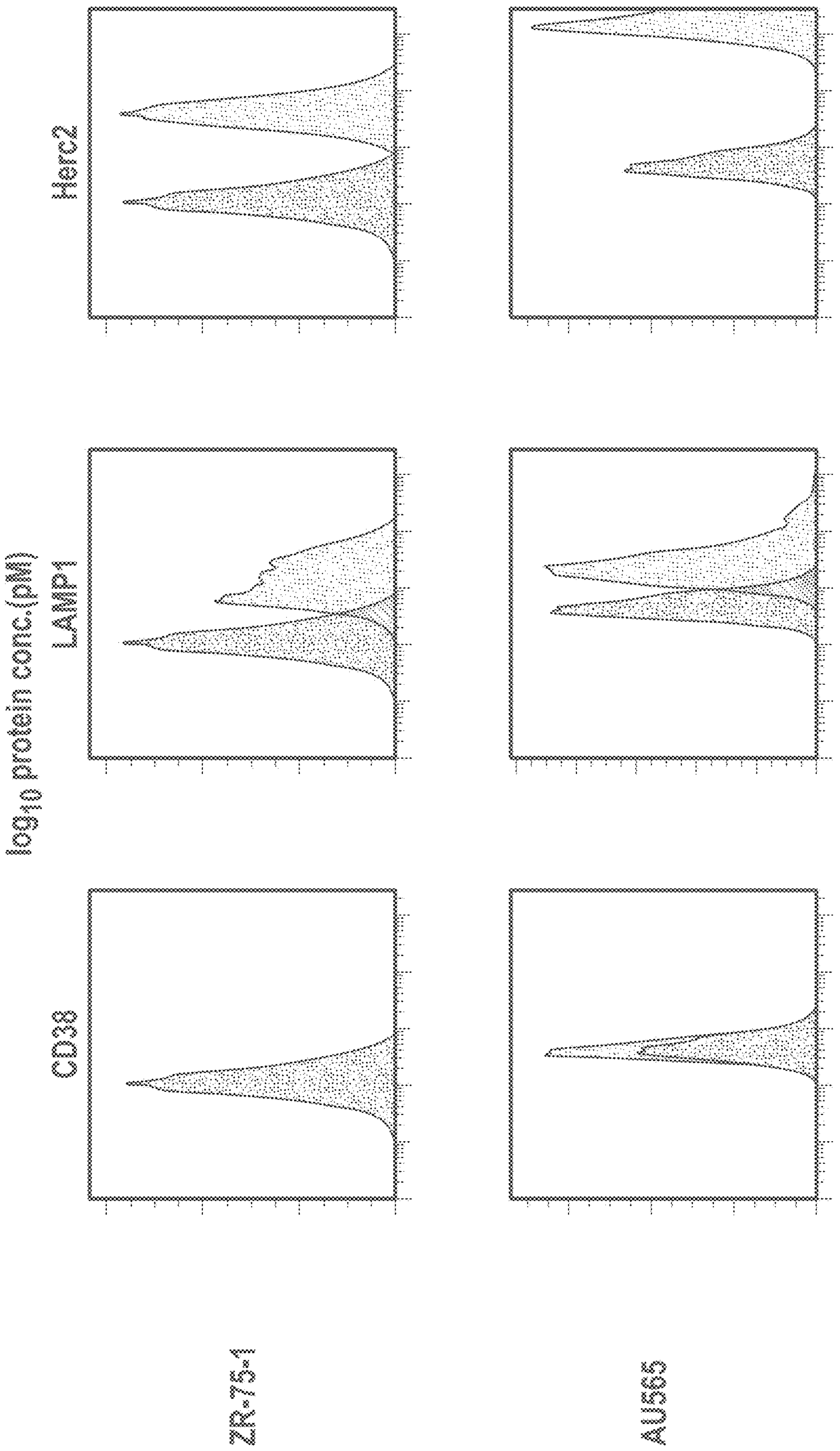
Figure 4:
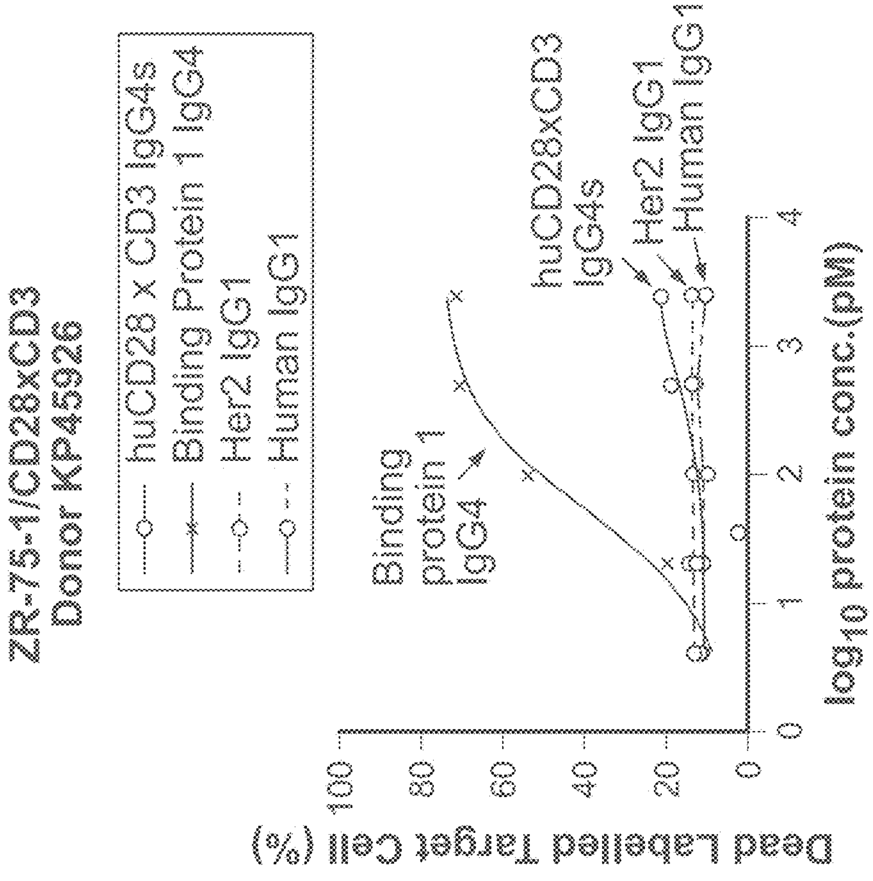
FIGS. 4 & 5 show the results of antibody-mediated specific killing of $Her2^+$ breast cancer cells using an anti-Her2×CD28×CD3 IgG4 trispecific antibody (Binding protein 1), an anti-CD28×CD3 IgG4 bispecific antibody (huCD28×CD3), an anti-Her2 IgG1 antibody, or a control antibody (human-IgG1).
Figure 5:
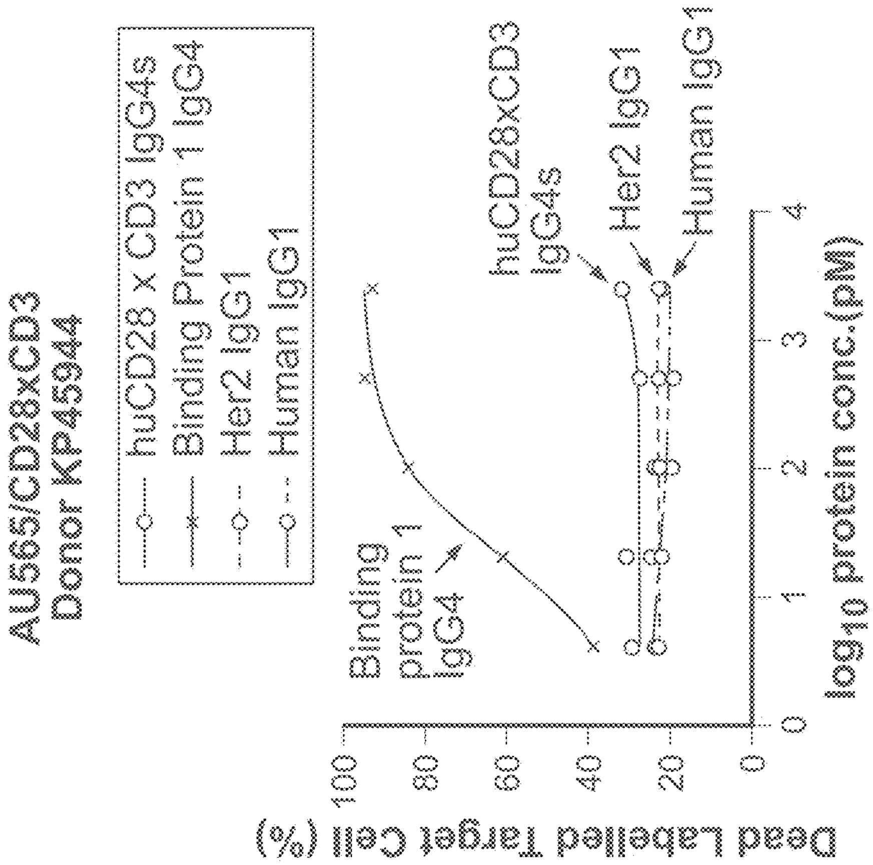

The ability of Binding Protein 1 to induce antibody-mediated cell killing of tumor cells expressing HER2 proteins on their surface was tested. Not only was Binding Protein 1 capable of binding to all three of its target proteins, but it was also able to induce antibody-mediated cell killing of Her2$^+$ cell lines (FIGS. 3A-4). Binding Protein 1 exhibited potent antibody-mediated cell killing activities, while anti-CD3/CD28 bispecific Ab and anti-Her2 antibodies showed minimal killing activities. (FIGS. 3A, 3B, 4, & 5), demonstrating the effectiveness of using the trispecific Ab to engage tumor cells with T cells through a tumor antigen (HER2) and T cell markers (CD3 and CD28). Anti-CD3/CD28 is not only important for T cell recruitment, but it also provides more effective T cell activation and survival signaling, potentially improving the efficacy.

Figure 6A:
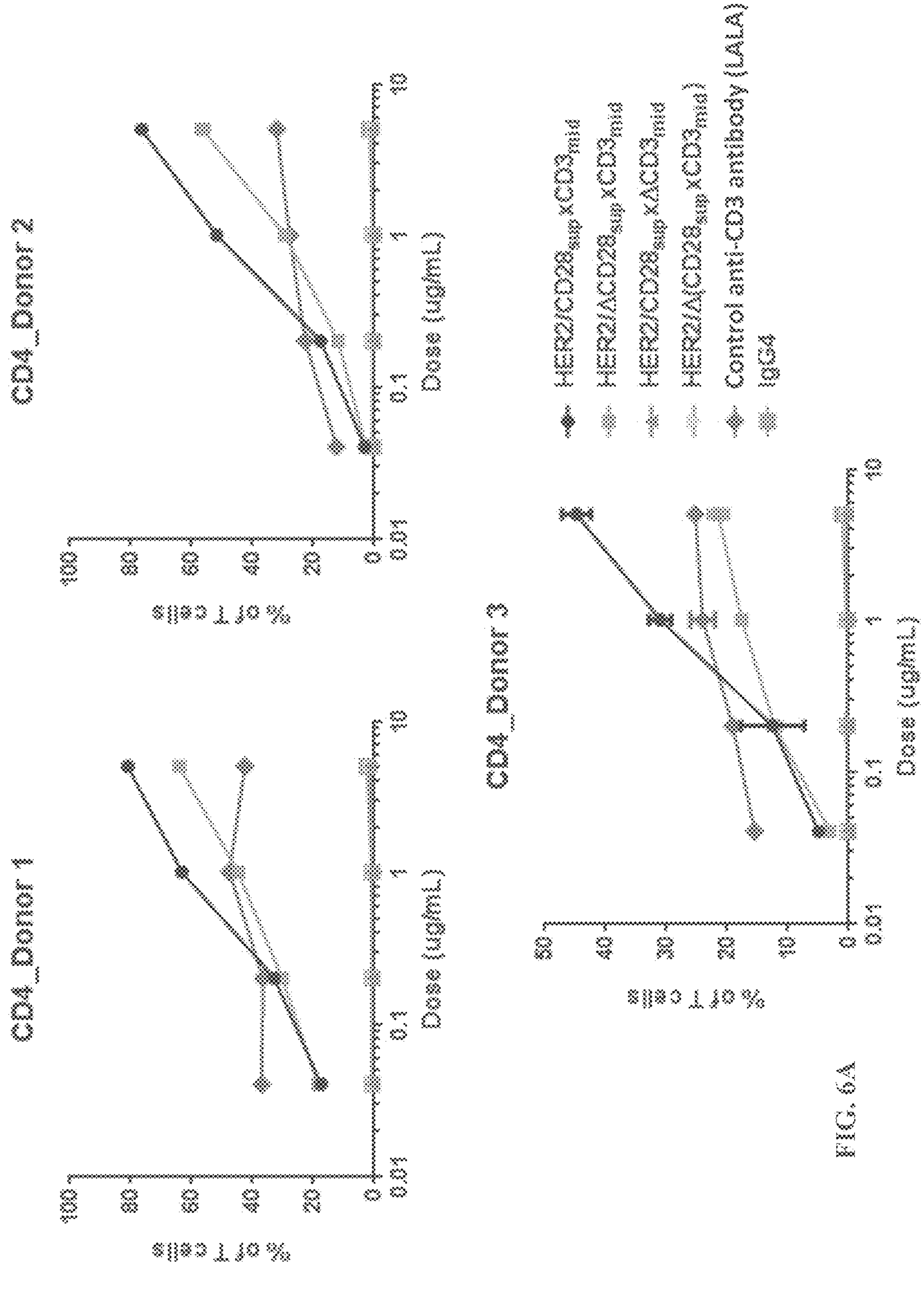
FIGS. 6A & 6B show the activation (CD69+) and proliferation of human T cells treated with anti-Her2×CD28×CD3 IgG4 trispecific binding protein (HER2/$CD28_{sup}$×$CD3_{mid}$; referred to herein as "Binding Protein 1"), anti-Her2×CD28×CD3 IgG4 trispecific binding protein lacking the anti-CD28 binding domain (HER2/Δ$CD28_{sup}$×$CD3_{mid}$), anti-Her2×CD28×CD3 IgG4 trispecific binding protein lacking the anti-CD3 binding domain (HER2/$CD28_{sup}$×Δ$CD3_{mid}$), anti-Her2×CD28×CD3 IgG4 trispecific binding protein lacking both anti-CD28 and anti-CD3 binding domains (HER2/Δ($CD28_{sup}$×Δ$CD3_{mid}$)), control anti-CD3 monoclonal antibody, or control IgG4 antibody.
Figure 6B:
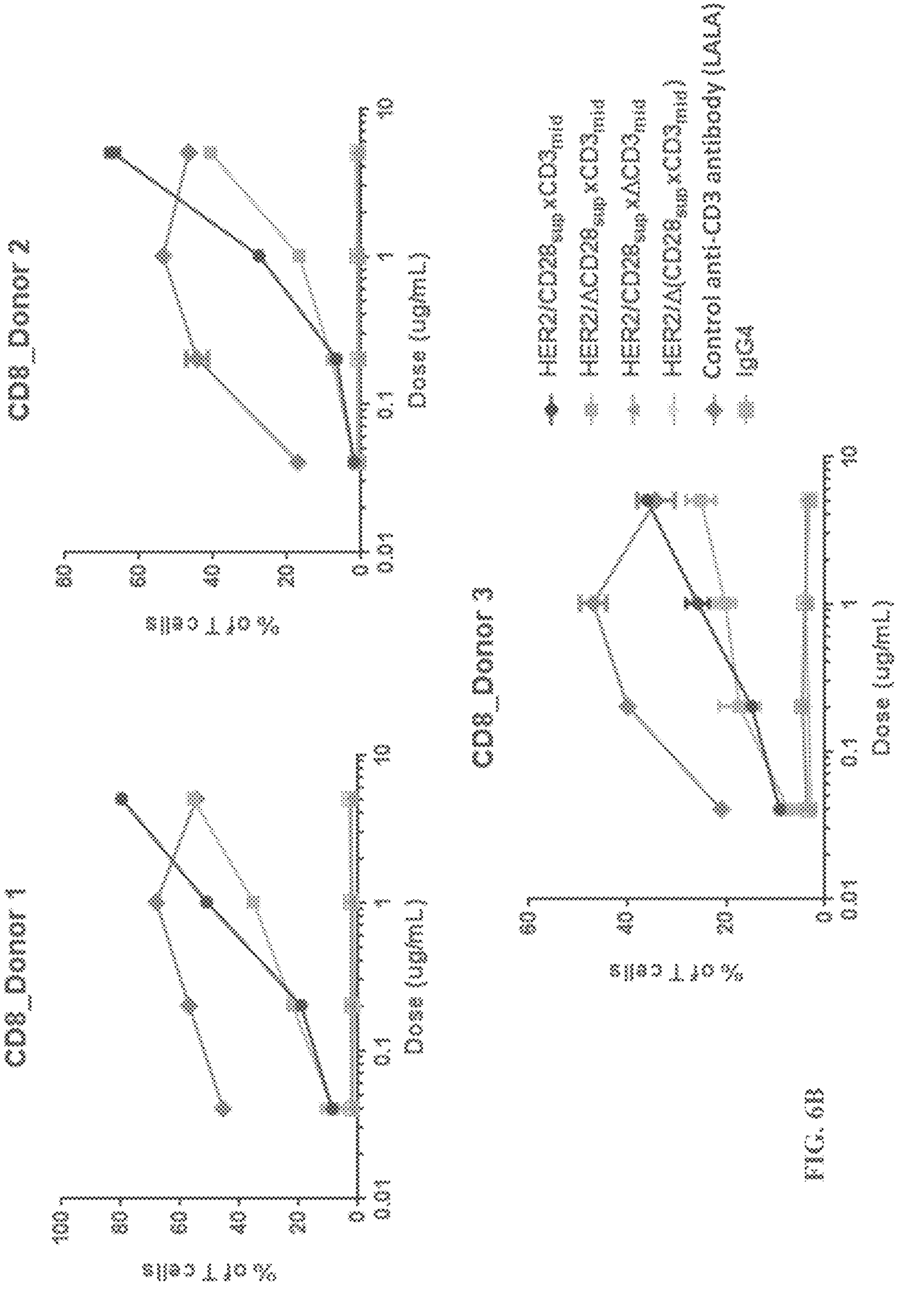
Figure 7B:
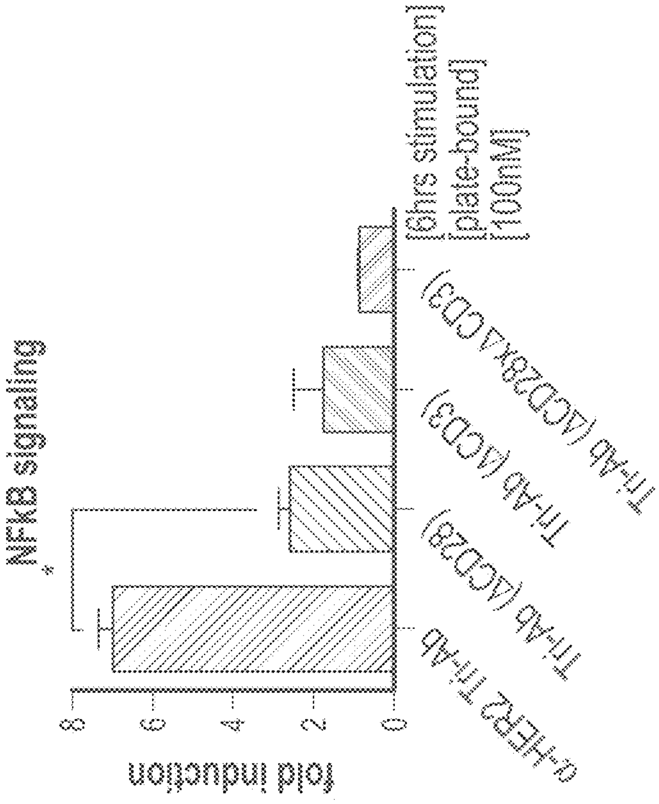
FIGS. 7A-C show IL-2, NFκB, and nuclear factor of activated T-cells (NFAT) pathway activation via anti-CD3 and anti-CD28 signaling, as measured by luciferase assay using human Jurkat T cells with an IL-2 promoter-luciferase construct (FIG. 7A), an NFκB promoter-luciferase construct (FIG. 7B), or an NFAT promoter-luciferase construct (FIG. 7C). Antibodies tested were those described above in reference to FIGS. 6A-6D.
Figure 7A:
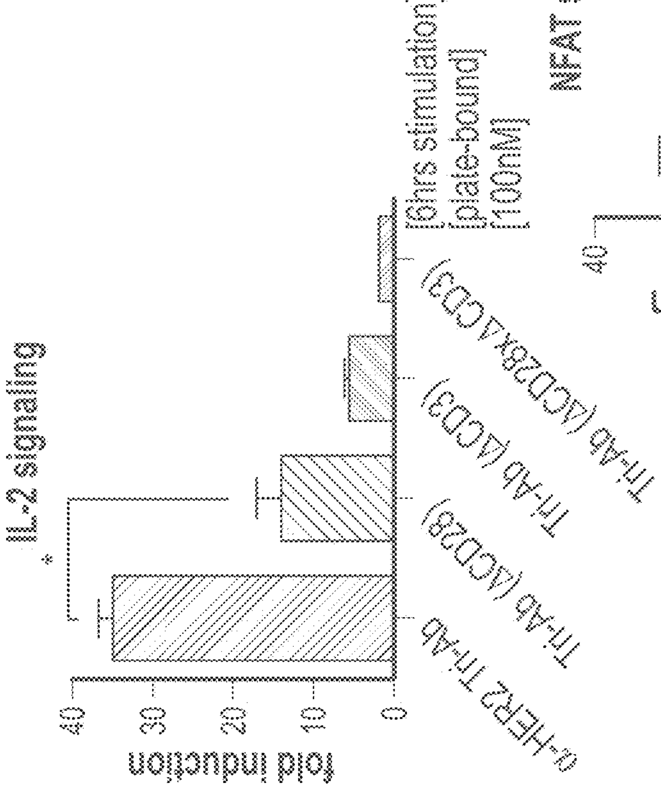
Figure 7C:
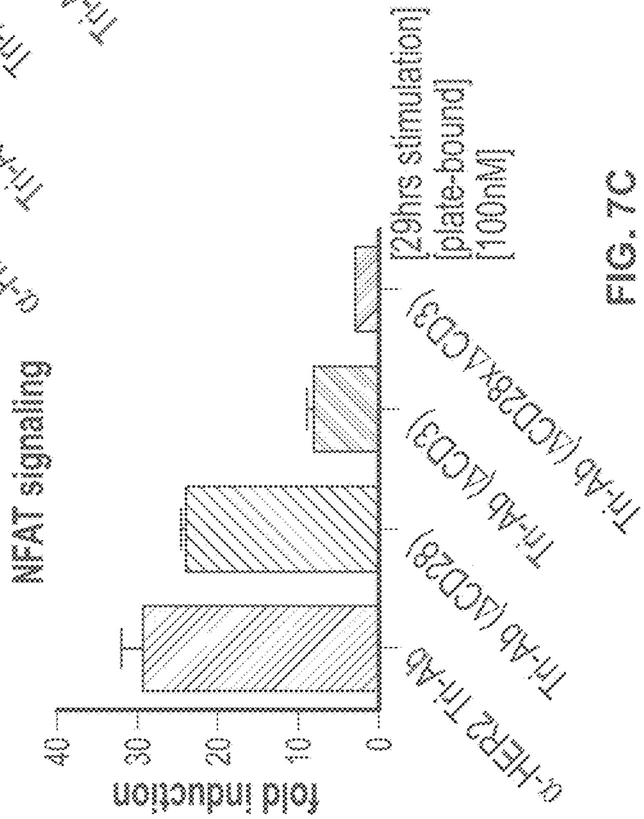

Additionally, studies were carried out on in vitro T cell activation and proliferation, as well as cytokine production, using the anti-Her2×CD28×CD3 trispecific antibody (Binding Protein 1). Binding protein 1 and control variants having one or two binding domains inactivated by site-directed mutagenesis (ΔCD28: anti-CD28 inactivated; ΔCD3: anti-CD3 inactivated; Δ(CD3×CD28): both anti-CD3 and anti-CD28 inactivated) were used in human PBMC in vitro activation assay as described in Example 1. The results showed that Binding protein 1 activated both human primary CD4 T cells and CD8 T cells effectively in vitro. Inactivation of anti-CD28 reduced the activation potency, indicating the importance of anti-CD28 co-signaling pathway. Inactivation of anti-CD3 binding site rendered Binding protein 1 to minimal activity, suggesting that the anti-CD3 provided the primary T cell activation signaling (FIGS. 6A & 6B). Similar results were obtained using IL2 and NFAT reporter human T cell lines (Jurkat-IL2 and Jurkat-NFAT) (FIGS. 7A-7C).

In Vitro Assays Using Trispecific Binding Proteins Comprising Anti-CD19

Figure 8:
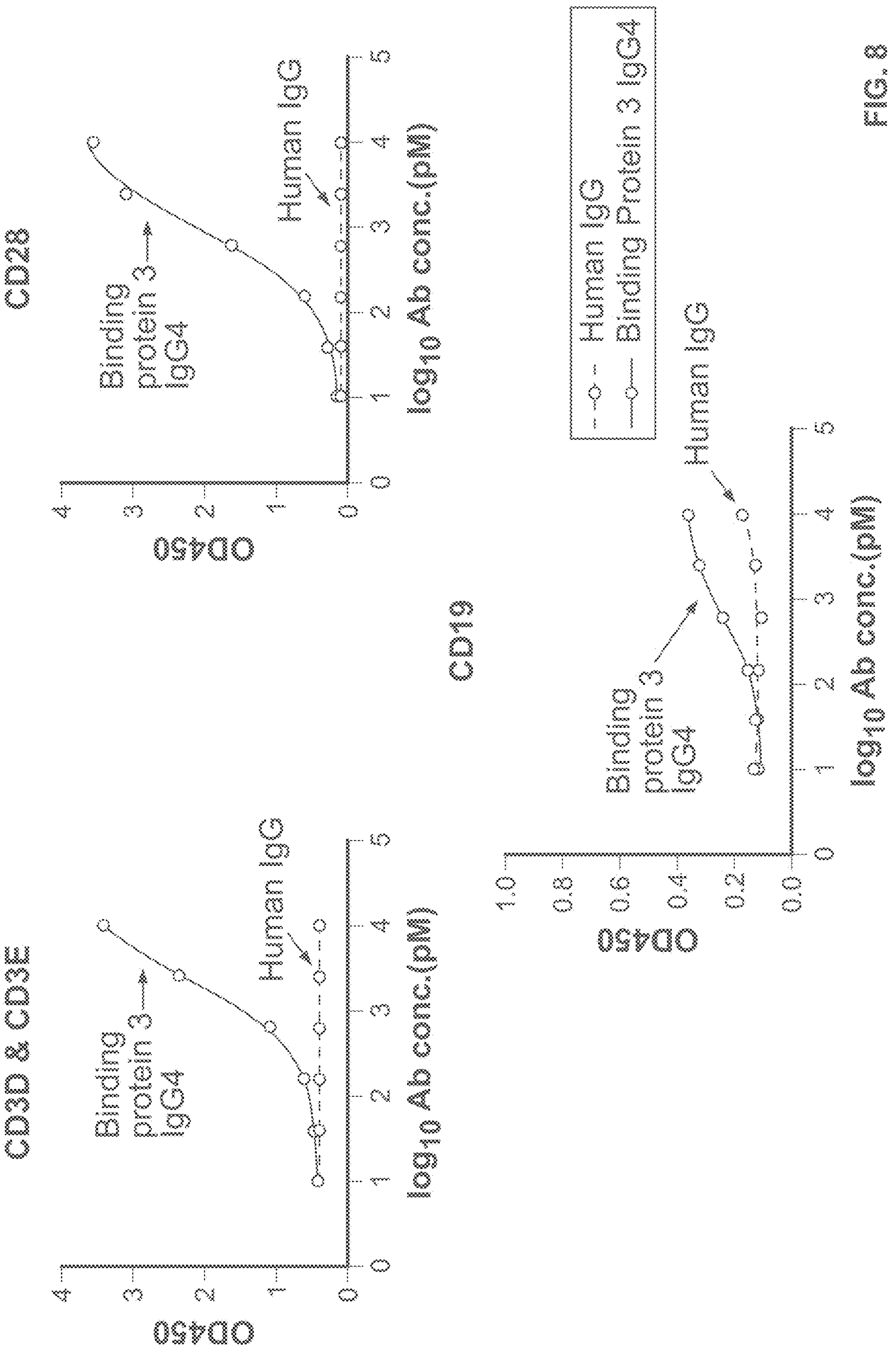
FIG. 8 shows the results of an ELISA assay determining binding of an anti-CD19×CD28×CD3 IgG4 trispecific antibody (referred to herein as "Binding Protein 3"), or isotype control antibody, to CD3, CD28, and CD19. The bound antibodies were detected using a horseradish peroxidase (HRP)-conjugated anti-Fab secondary antibody.

The anti-CD19×CD28×CD3 trispecific binding protein was capable of binding its target antigens (FIG. 8), indicating that each binding domain in the trispecific format retained its function.

Figure 9A:
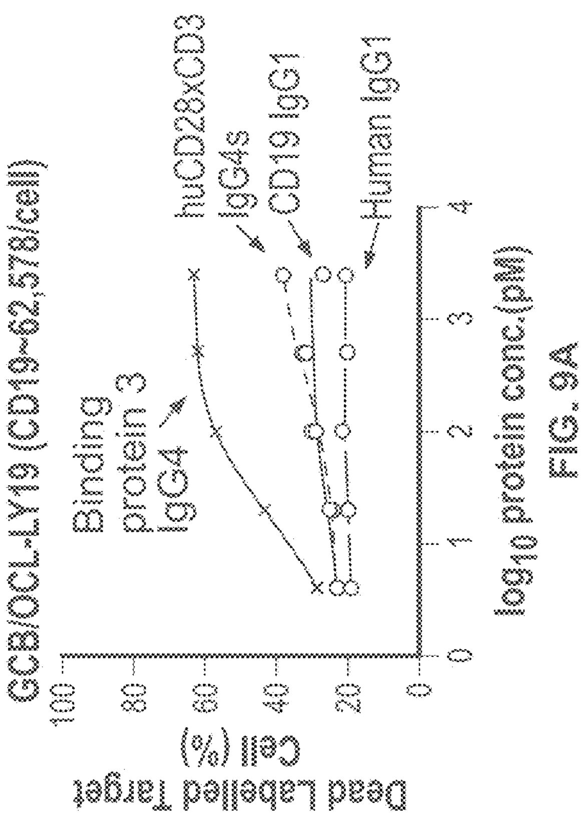
FIGS. 9A-9N show the results of antibody-mediated specific killing of $CD19^+$ human GCB lymphoma cells using an anti-CD19×CD28×CD3 IgG4 trispecific antibody (referred to herein as "Binding Protein 3"), or the indicated controls, using human PBMC as effector cells at E:T=10.
Figure 9B:
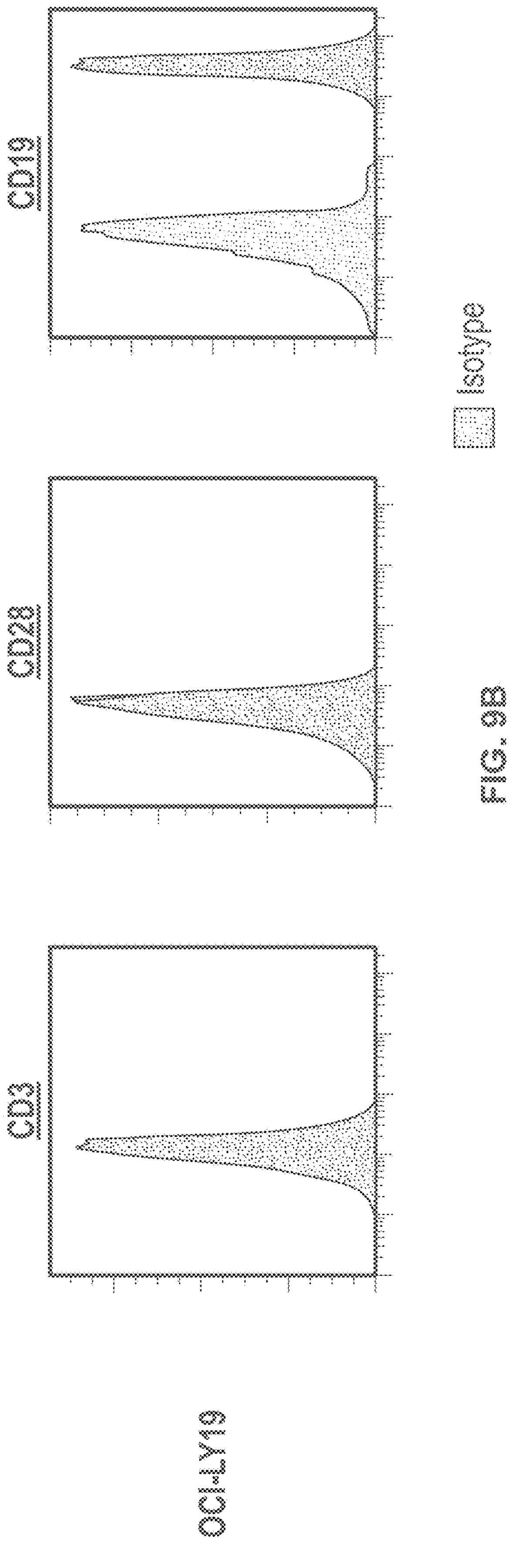
FIG. 9B shows the results of FACS analysis determining the cell surface expression of the indicated markers on OCI-LY19 cells.
Figure 9C:
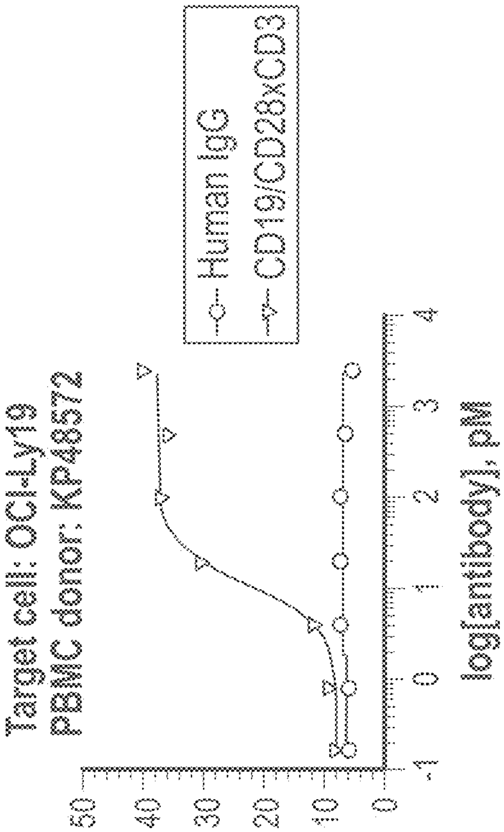
FIG. 9C shows the results of antibody-mediated specific killing of OCI-LY19 cells using PBMCs from donor KP48572 at E:T=10.
Figure 9D:
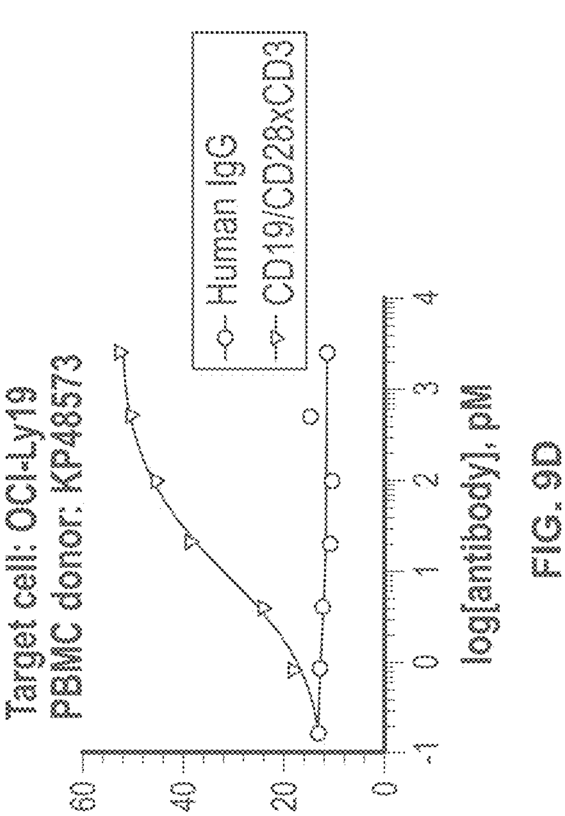
FIG. 9D shows the results of antibody-mediated specific killing of OCI-LY19 cells using PBMCs from donor KP48573 at E:T=10.
Figure 9E:
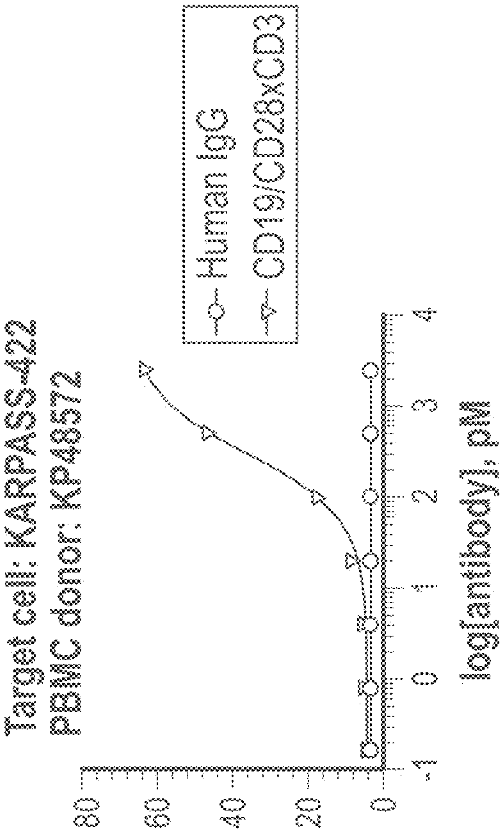
FIG. 9E shows the results of antibody-mediated specific killing of human lymphoma KARPASS-422 cells using PBMCs from donor KP48572 at E:T=10.
Figure 9F:
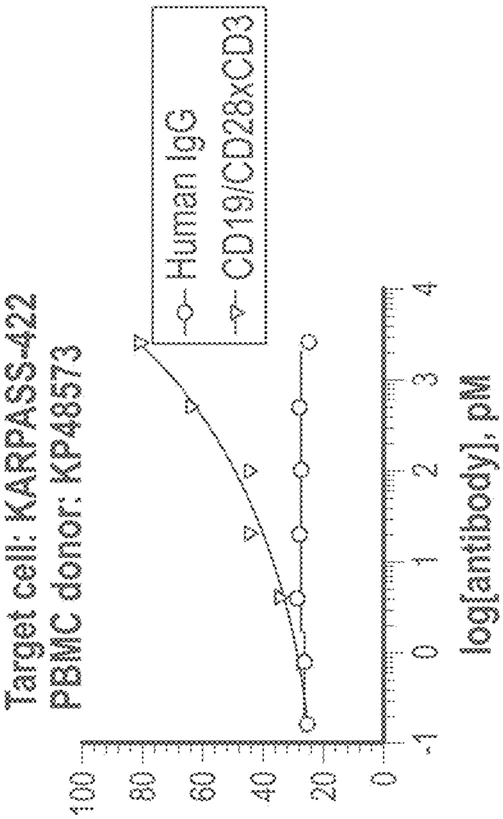
FIG. 9F shows the results of antibody-mediated specific killing of KARPASS-422 cells using PBMCs from donor KP48573 at E:T=10.
Figure 9G:
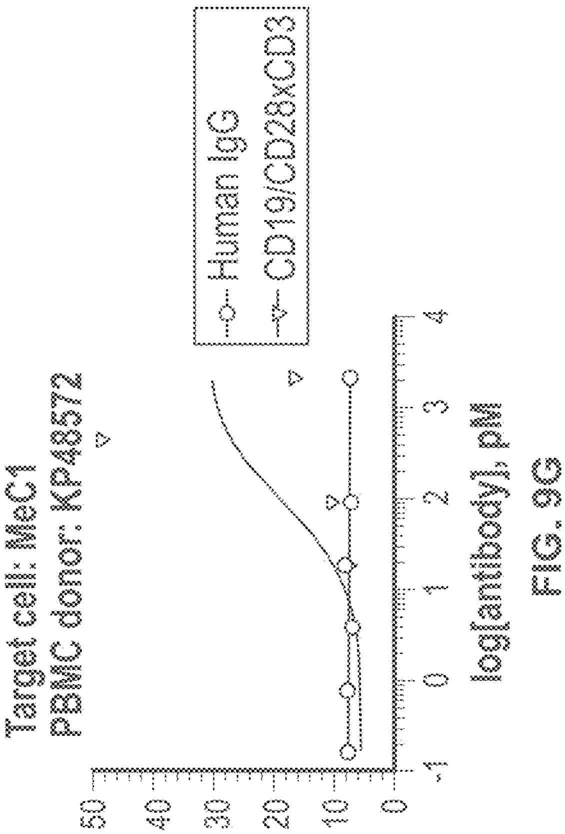
FIG. 9G shows the results of antibody-mediated specific killing of human chronic B cell leukemia MeC1 cells using PBMCs from donor KP48572 at E:T=10.
Figure 9H:
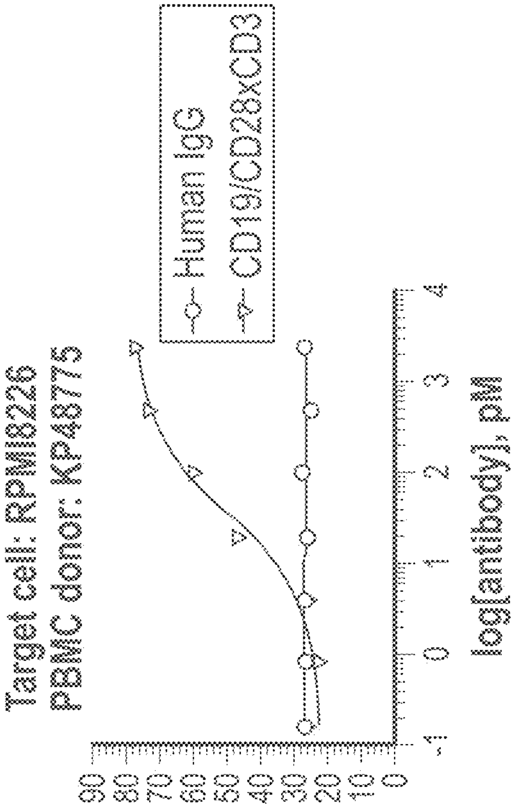
FIG. 9H shows the results of antibody-mediated specific killing of human multiple myeloma RPMI8226 cells using PBMCs from donor KP48775 at E:T=10.
Figure 9I:
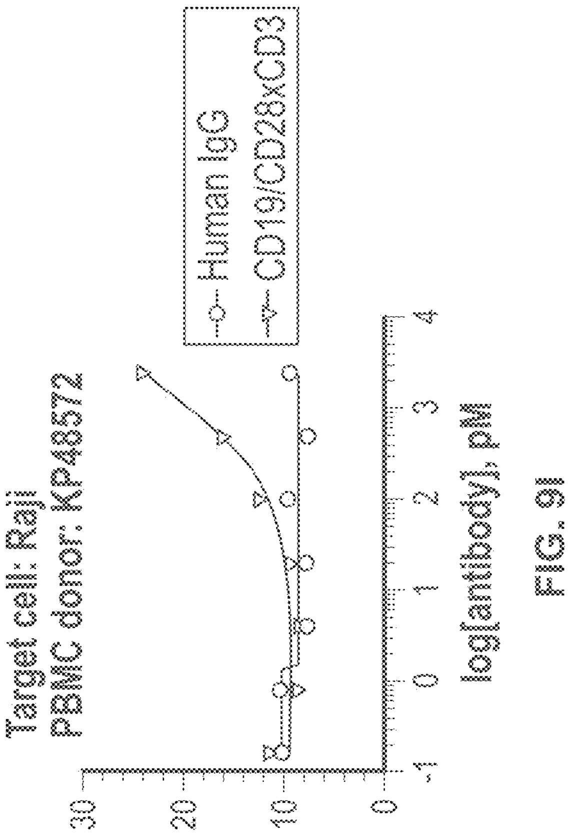
FIG. 9I shows the results of antibody-mediated specific killing of human Burkitt's lymphoma Raji cells using PBMCs from donor KP48572 at E:T=10.
Figure 9J:
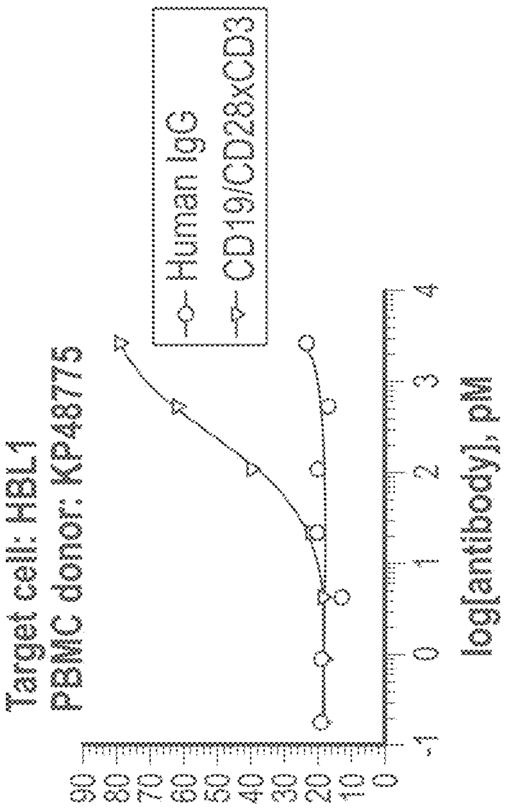
FIG. 9J shows the results of antibody-mediated specific killing of Human diffuse large B-cell lymphoma HBL1 cells using PBMCs from donor KP48775 at E:T=10.
Figure 9K:
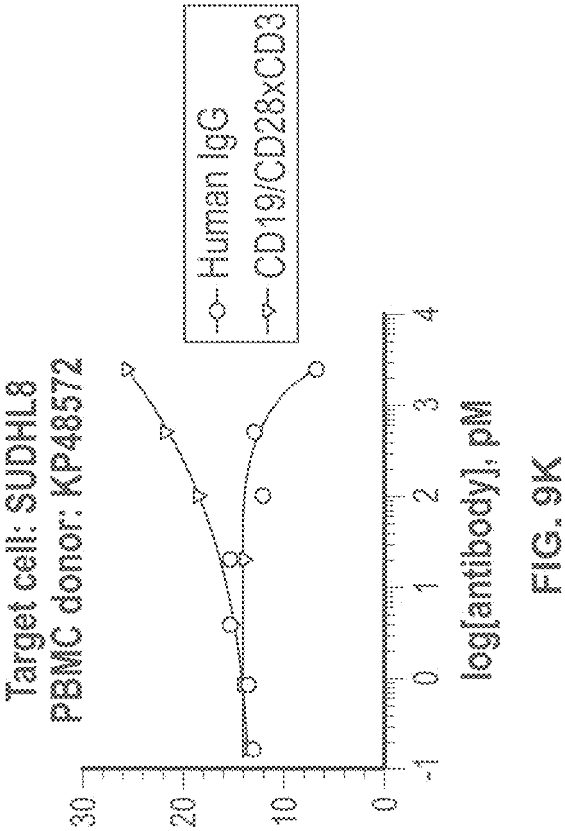
FIG. 9K shows the results of antibody-mediated specific killing of Large cell lymphoma SUDHL8 cells using PBMCs from donor KP48572 at E:T=10.
Figure 9L:
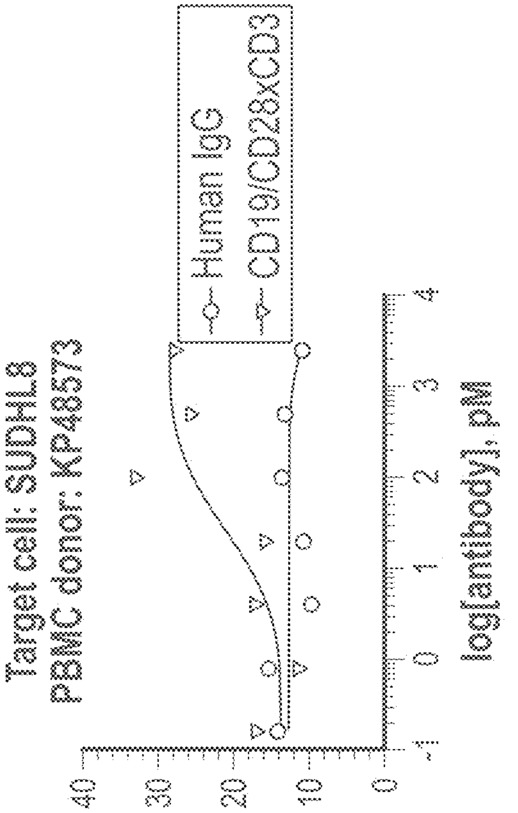
FIG. 9L shows the results of antibody-mediated specific killing of SUDHL8 cells using PBMCs from donor KP48573 at E:T=10.
Figure 9M:
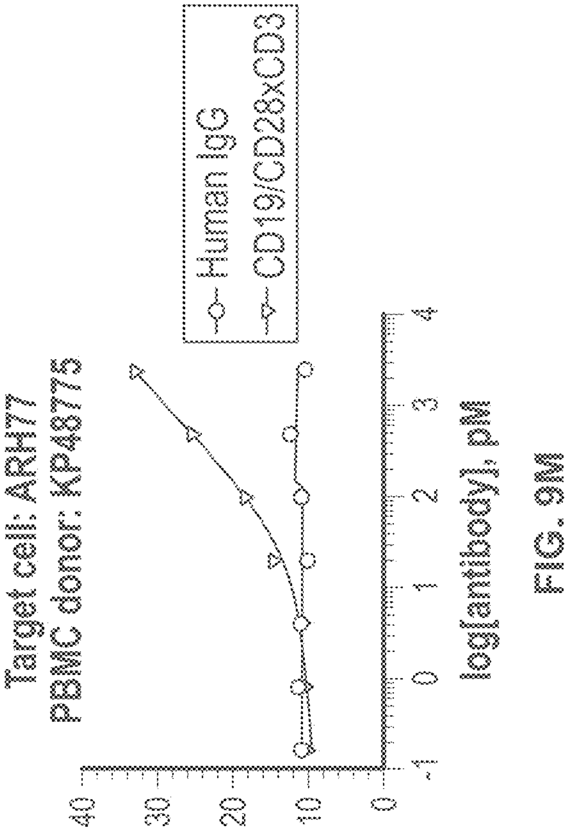
FIG. 9M shows the results of antibody-mediated specific killing of human B cell lymphoma ARH77 cells using PBMCs from donor KP48775 at E:T=10.
Figure 9N:
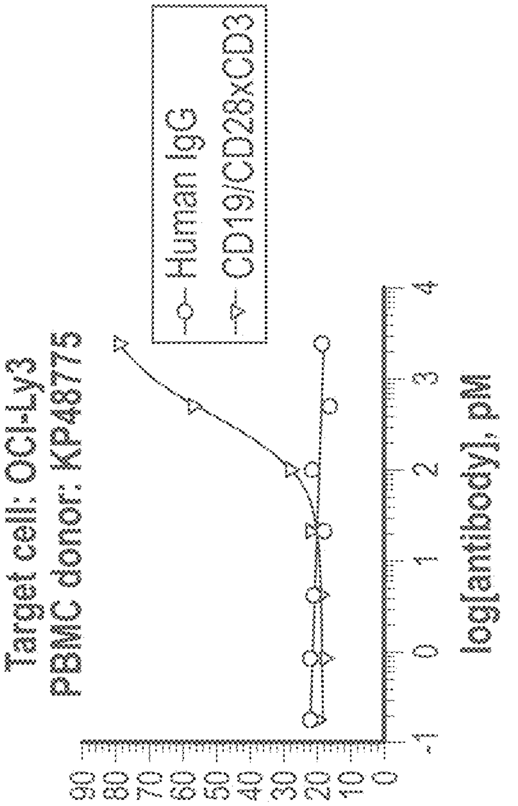

The anti-CD19×CD28×CD3 trispecific binding protein was also capable of inducing antibody-mediated cell killing of CD19+ cells (FIGS. 9A-9N). Similarly, anti-CD19×CD28×CD3 trispecific binding protein exhibited potent killing activity against human lymphoma cells, while both the anti-CD3/CD28, anti-CD19, and isotype control antibodies showed minimal killing activities, demonstrating the effectiveness of using the trispecific Ab to engage tumor cells with T cells through a tumor antigen (CD19) and T cell markers (CD3 and CD28).

In Vitro Assays Using Trispecific Binding Proteins Comprising Anti-CD38

Figure 10:
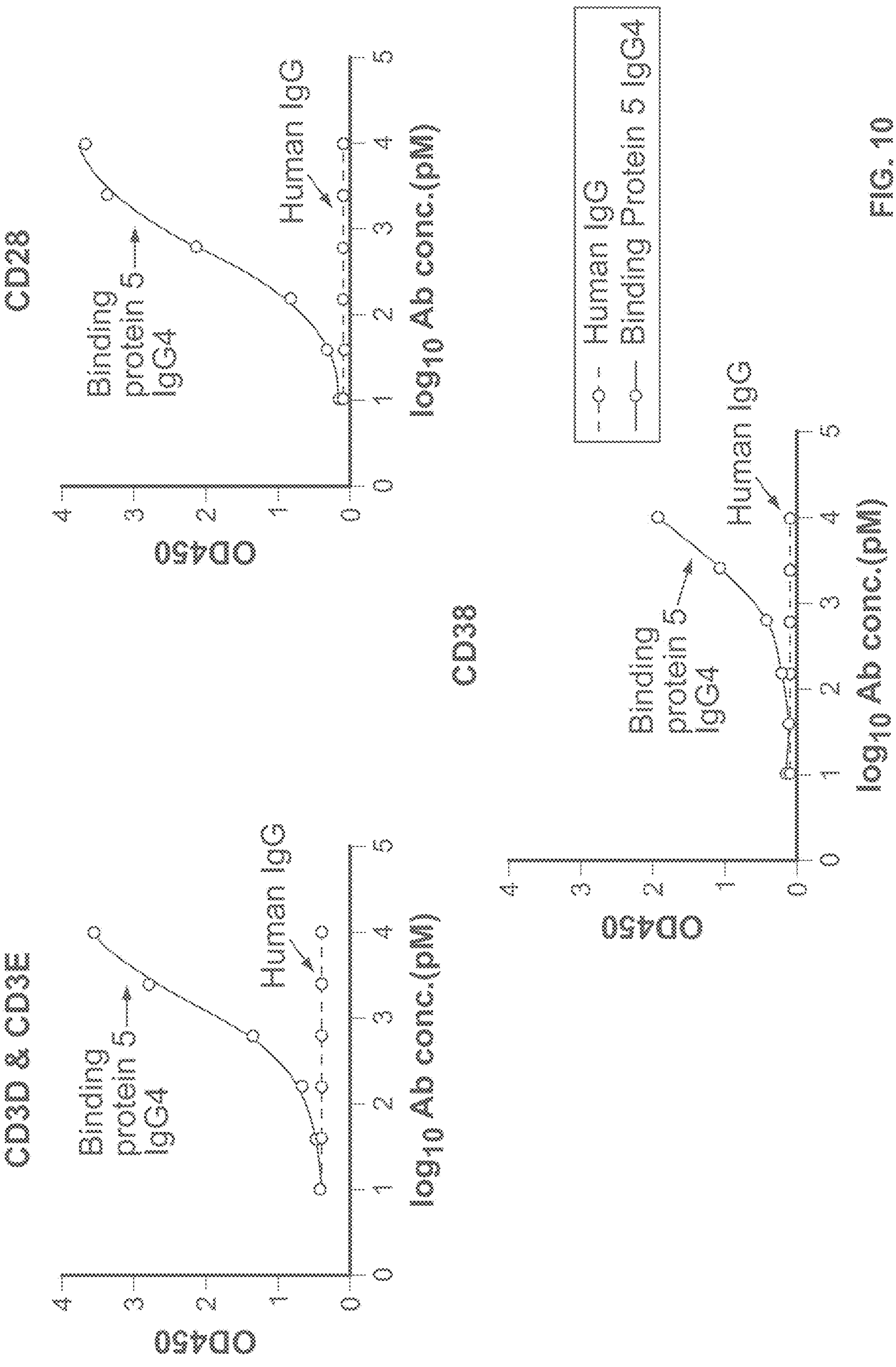
FIG. 10 shows the results of an ELISA assay determining binding of an anti-CD38×CD28×CD3 IgG4 trispecific antibody (Binding Protein 5), or isotype control antibody, to CD3, CD28 and CD38. The bound antibodies were detected using a horseradish peroxidase (HRP)-conjugated anti-Fab secondary antibody.

As observed with Binding Proteins 1 and 3, Binding Protein 5 was able to bind all three of its target proteins (CD3, CD28, and CD38), as assessed by ELISA assay (FIG. 10), indicating that each binding domain in the trispecific format retained its function.

Figures 11A, 11B, 11C:
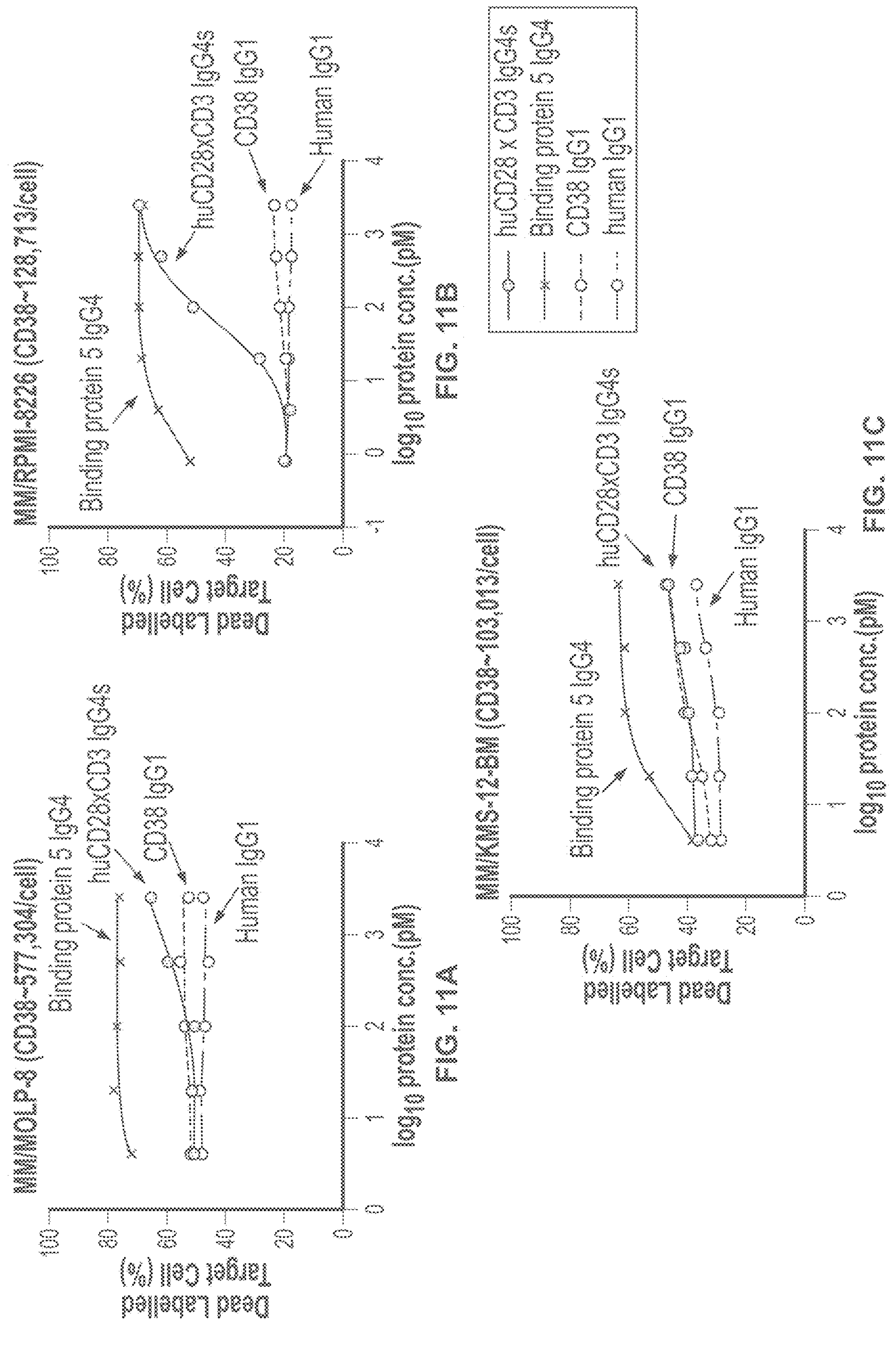
FIGS. 11A-11D show the results of antibody-mediated specific killing of $CD38^+$ human multiple myeloma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1).
Figure 11D:
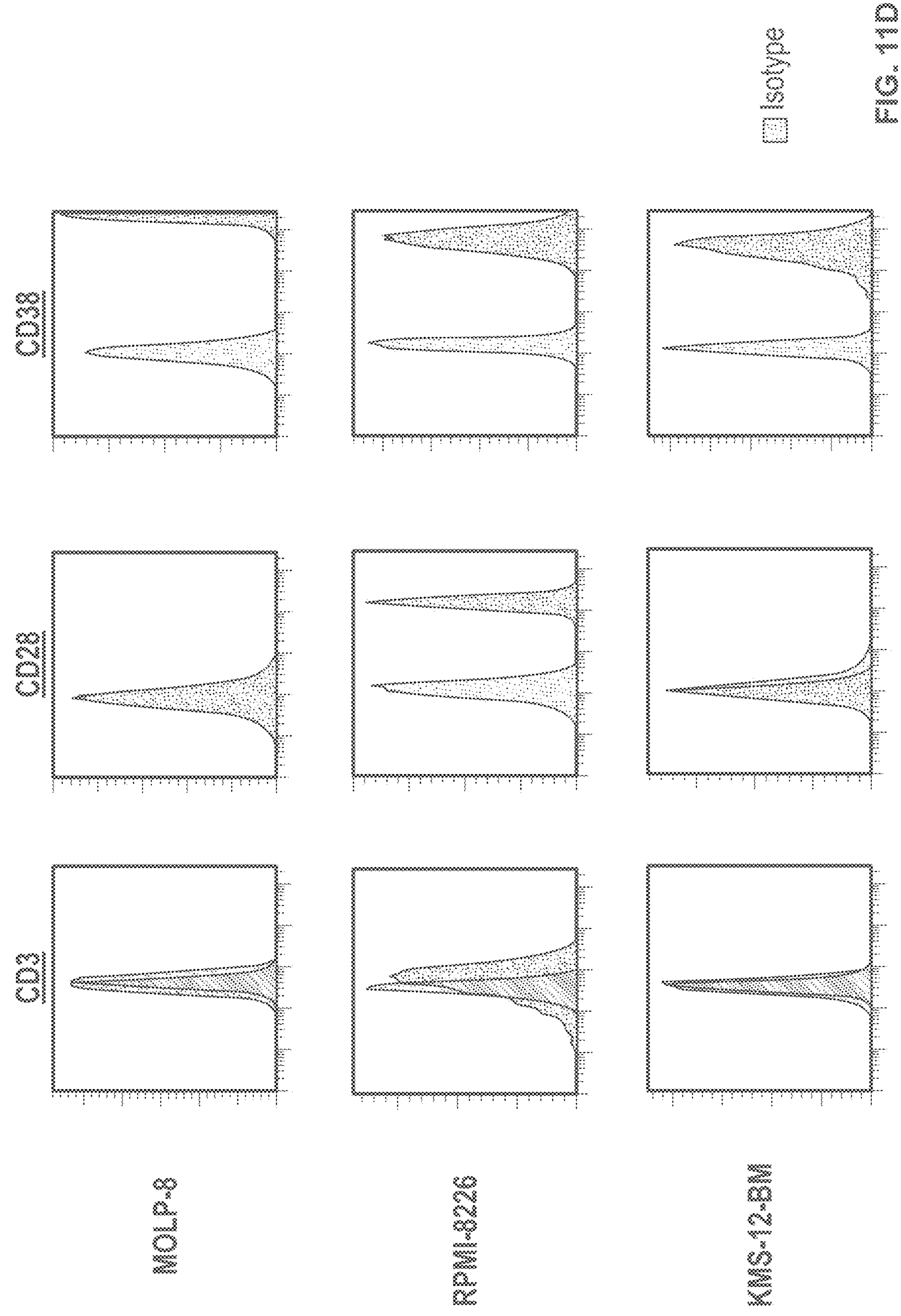
Figure 12D:
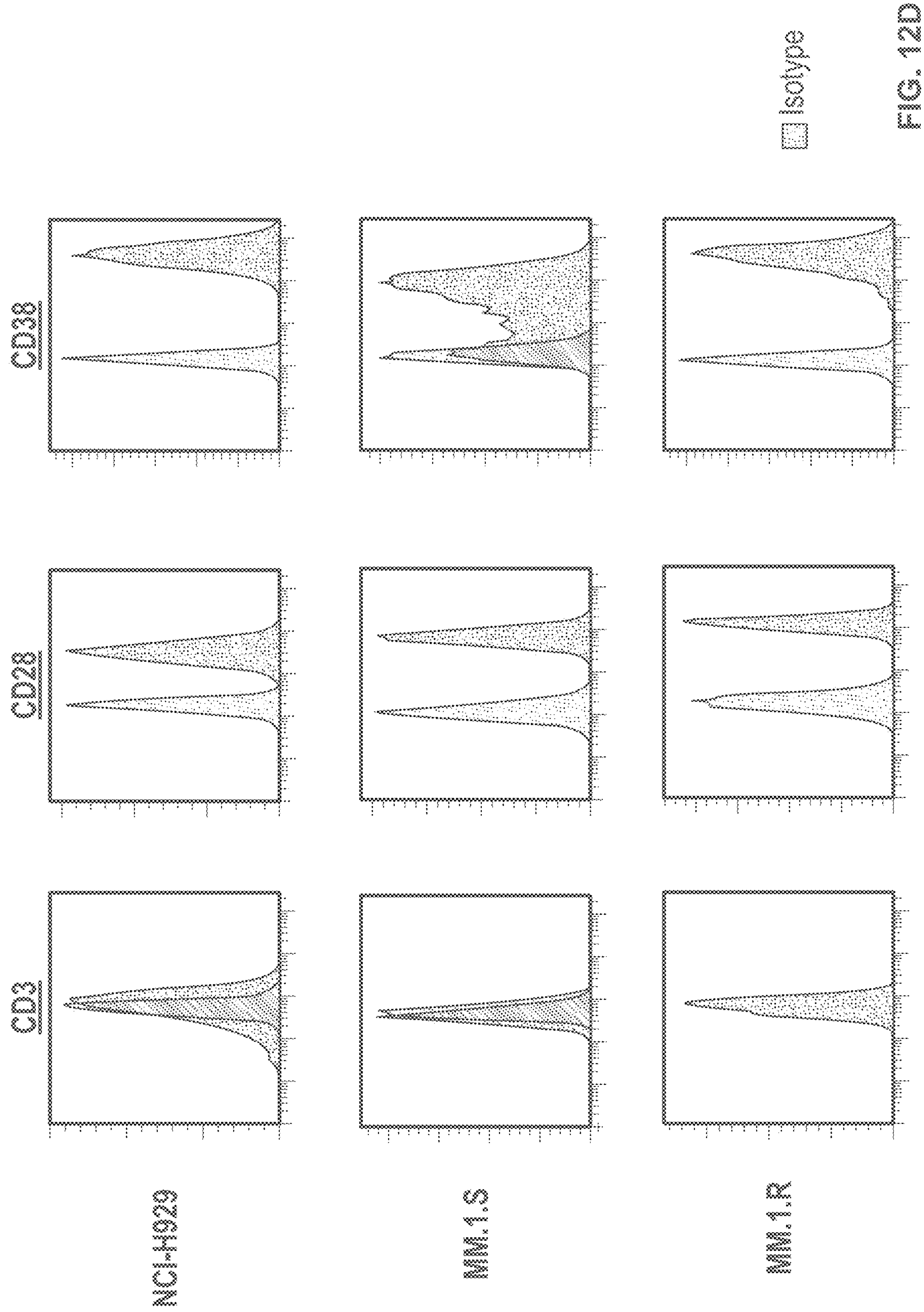
Figure 13D:
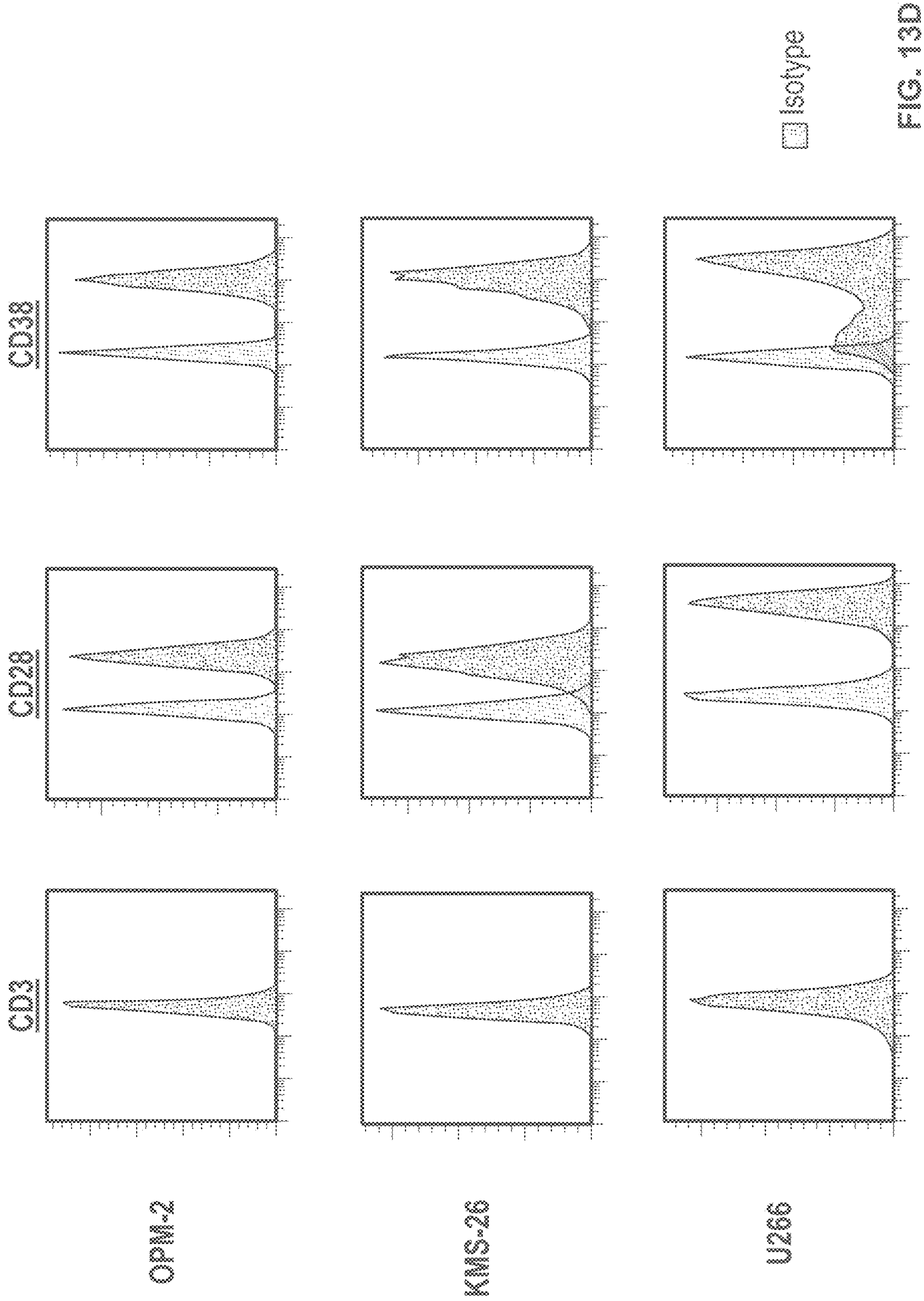
Figure 14B:
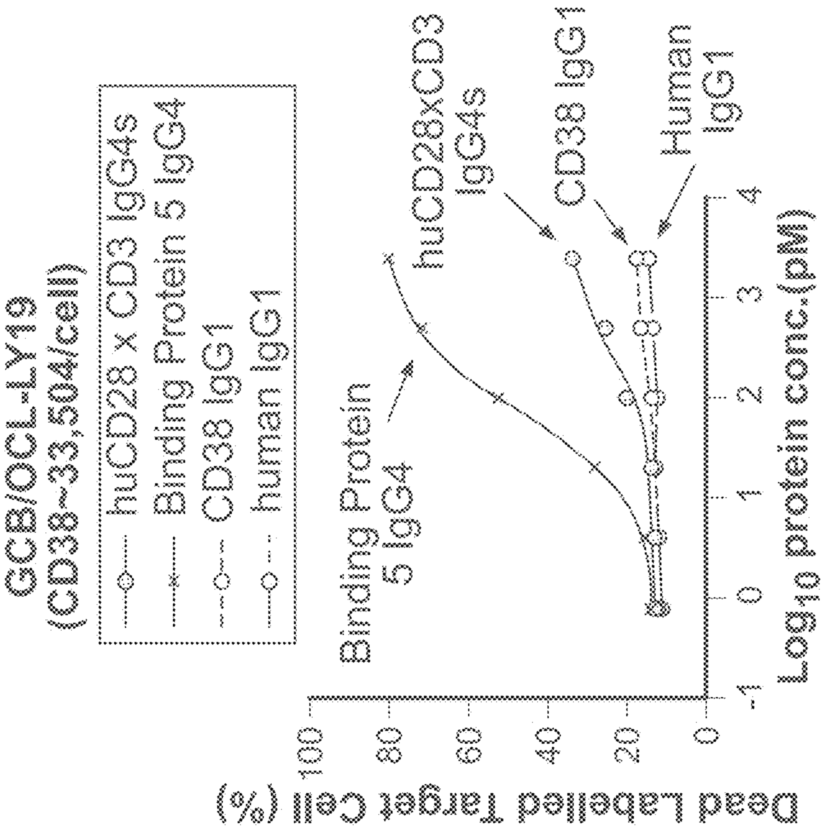
FIGS. 14A-14C show the results of antibody-mediated specific killing of $CD38^+$ human lymphoma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10.
Figure 14A:
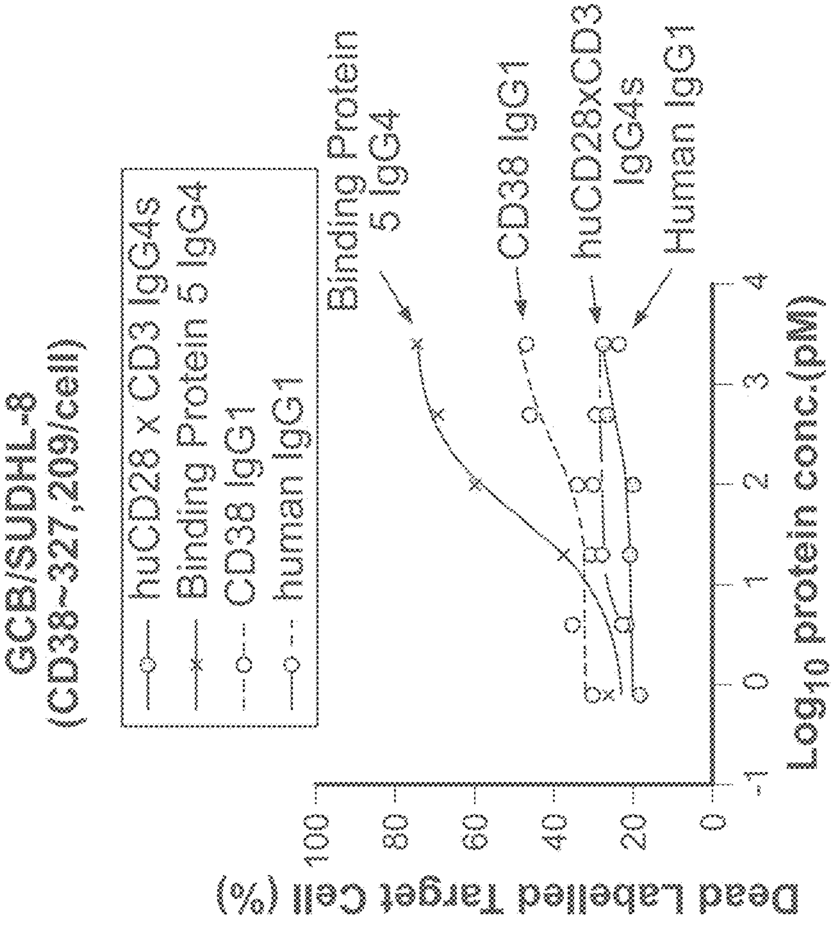
Figure 14C:
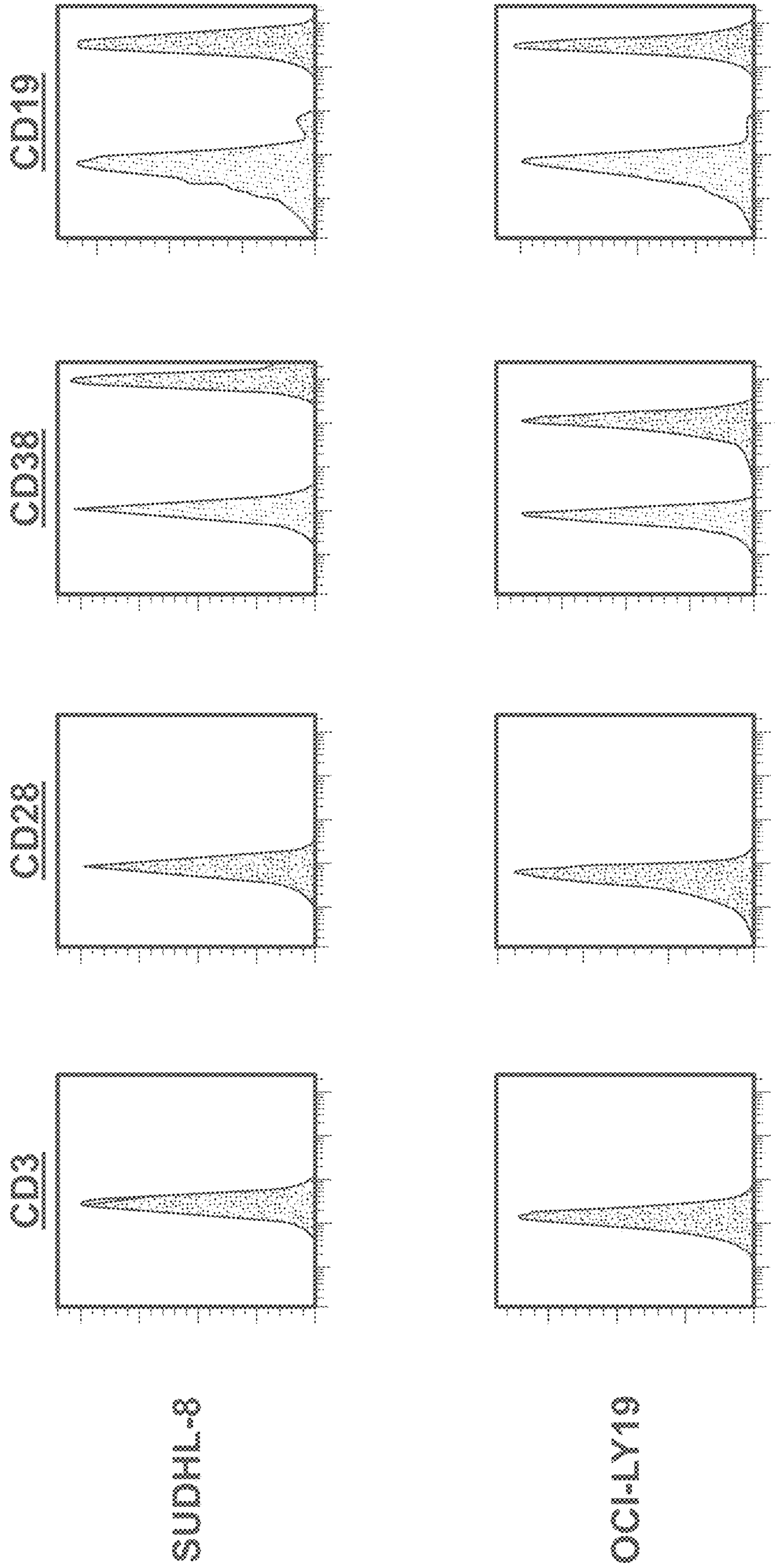
Figure 15D:
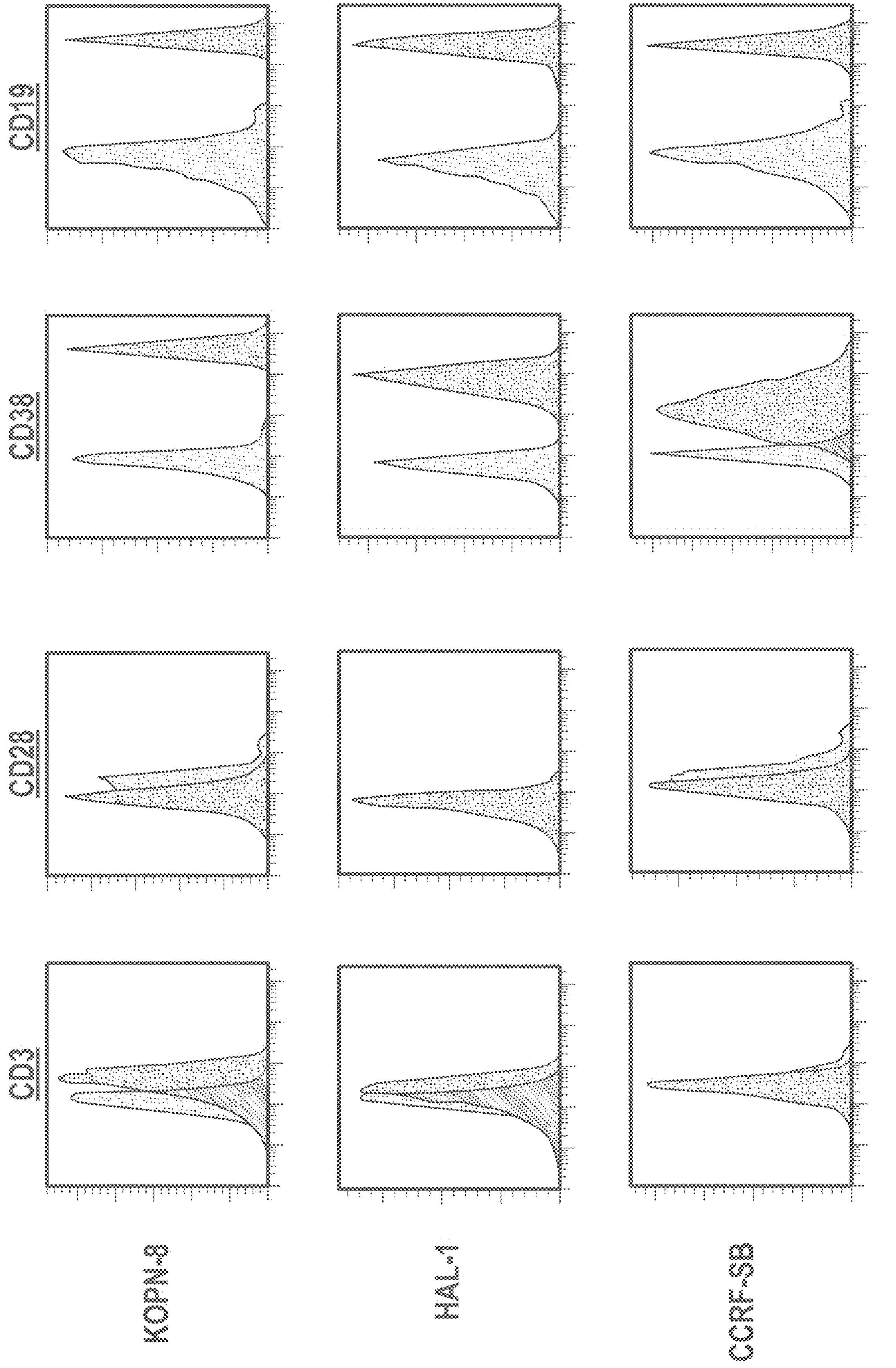

Binding Protein 5 was also found to induce antibody-mediated cell killing of cells (FIGS. 11A-15D) against 9 human multiple myeloma cells with various levels of CD38 and CD28 expression (see FIGS. 11D, 12D, & 13D). Similarly, trispecific Binding protein 5 exhibited potent killing activity against human multiple myeloma cells, while both the anti-CD38 and isotype control antibodies showed minimal killing activities, demonstrating the effectiveness of using the trispecific Ab to engage tumor cells with T cells through tumor antigens (CD38 and CD28) and T cell markers (CD3 and CD28). Bispecific anti-CD3/CD28 control antibody also showed marginal killing activity against CD28+MM cells see FIGS. 11B, 12A-C, & 13A-C).

These results demonstrate that the trispecific antibody platform described herein provides the possibility of integrating binding sites for two tumor markers, or two binding sites for T cell markers, allowing flexibility for scientific designs and various applications. Binding Protein 5 was also effective against 5 CD38+ human lymphoma cell lines (FIGS. 14C & 15D), showing potent killing activities (FIGS. 14A-B & 15A-C).

Figure 16:
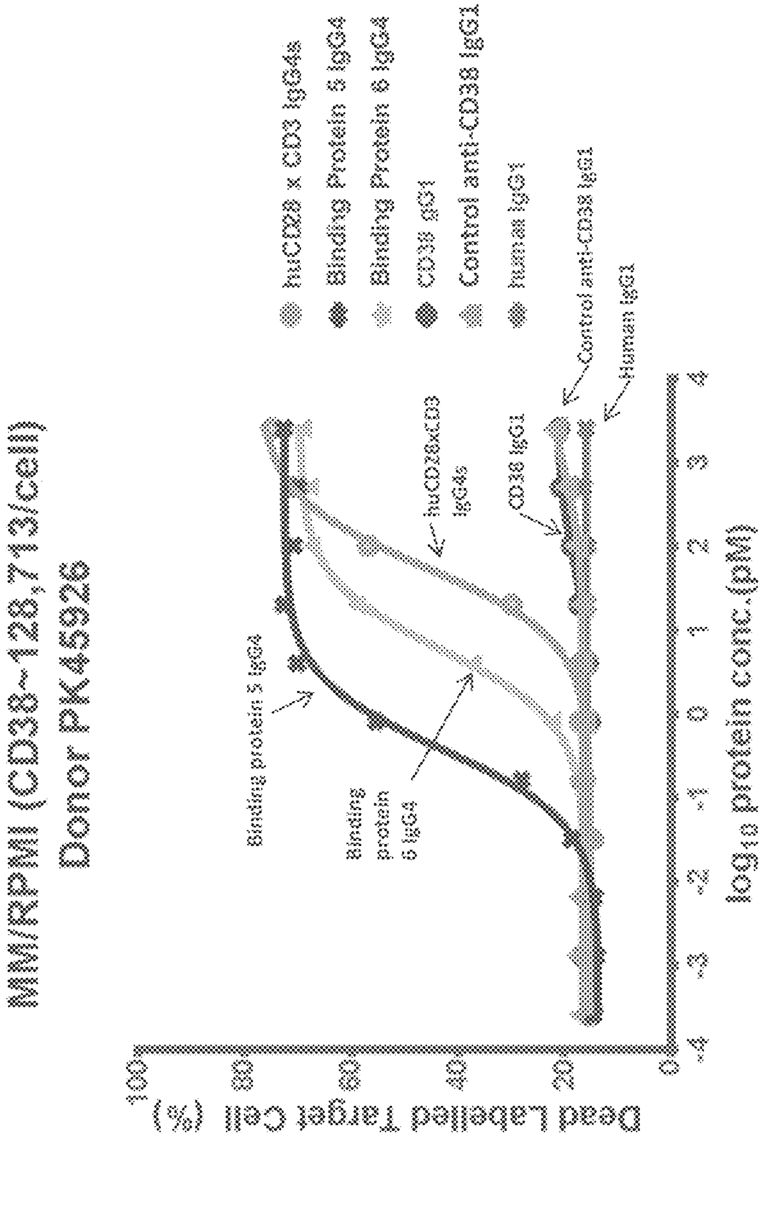
FIG. 16 shows the results of antibody-mediated specific killing of $CD38^+$ myeloma cancer cells using anti-CD38×CD28×CD3 IgG4 trispecific antibodies (referred to herein as "Binding protein 5" and "Binding Protein 6," depending on the specific anti-CD28 binding domain used), an anti-CD28×CD3 IgG4 bispecific antibody (huCD28×CD3), an anti-CD38 IgG1 antibody, a control anti-CD38 IgG1 antibody, or a control antibody (human-IgG1), using PBMCs from donor PK45926 at E:T=10.

The antibody-mediated cell killing against multiple myeloma cell line RPMI8226 using Binding Proteins 5 and 6 were tested, and their $EC_{50}$s were calculated and compared to that of a CODV format bispecific antibody targeting CD28 and CD3 (FIG. 16 and Table B). Binding proteins 5 and 6 differ only in anti-CD28 binding domain; Binding protein 5 contains an anti-CD28 superagonist, while Binding protein 6 contains a conventional anti-CD28. Binding protein 5 showed more potent killing activity.

TABLE B

| $EC_{50}$ values calculated for bispecific and trispecific binding proteins | |
|---|---|
| | $EC_{50}$ (pM) |
| huCD28 × CD3 IgG4 | 56.16 |
| Binding Protein 5 IgG4 | 0.3787 |
| Binding Protein 6 IgG4 | 5.709 |

Figure 17B:
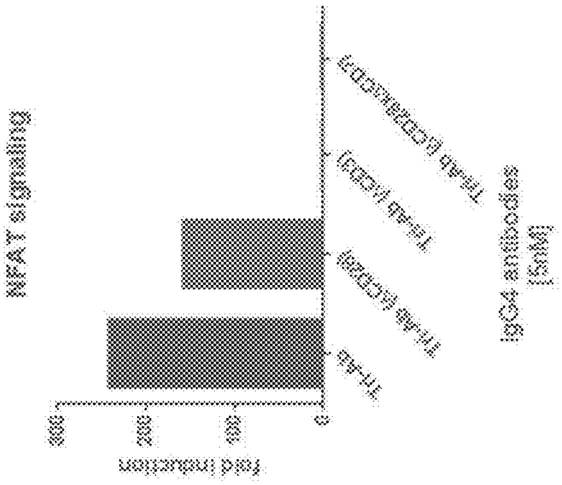
FIGS. 17A & 17B show IL-2, NFκB, and nuclear factor of activated T-cells (NFAT) pathway activation via anti-CD3 and anti-CD28 signaling, as measured by luciferase assay using human Jurkat T cells with an IL-2 promoter-luciferase construct (FIG. 17A) or an NFAT promoter-luciferase construct (FIG. 17B). Antibodies tested were anti-CD38×CD28×CD3 IgG4 trispecific IgG4 antibody (Binding Protein 5, labeled as "Tri-Ab"), anti-CD38×CD28×CD3 IgG4 trispecific IgG4 antibody lacking the CD28 binding domain (labeled as "Tri-Ab (ΔCD28)), anti-CD38×CD28×CD3 IgG4 trispecific IgG4 antibody lacking the CD3 binding domain (labeled as "Tri-Ab (ΔCD3)), and anti-CD38×CD28×CD3 IgG4 trispecific IgG4 antibody lacking the CD3 and CD28 binding domains (labeled as "Tri-Ab (ΔCD28×ΔCD3)). Luciferase assays were performed in duplicate for each of the indicated Tri-Abs.
Figure 17A:
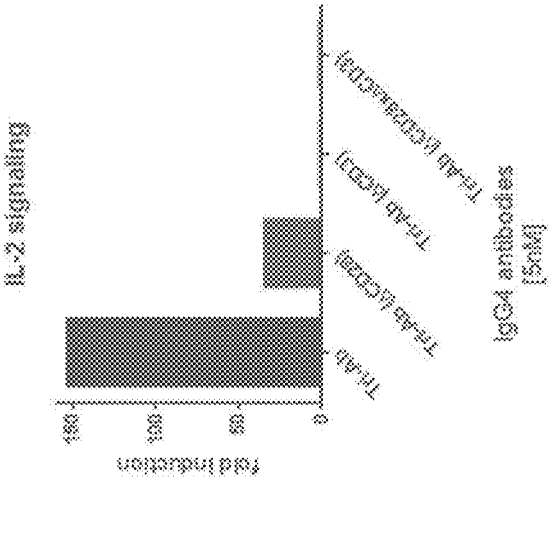

The activity of the anti-CD38×CD28×CD3 trispecific binding protein 5 and control variants having one or two binding domains inactivated by site-directed mutagenesis (ΔCD28: anti-CD28 inactivated; ΔCD3: anti-CD3 inactivated; Δ(CD3×CD28): both anti-CD3 and anti-CD28 inactivated) were tested using IL2 and NFAT reporter human T cell lines (Jurkat-IL2 and Jurkat-NFAT) in the in vitro activation assay as described in Example 1. The results showed that Binding protein 5 activated both human IL2 and NFAT promoters effectively in vitro (FIGS. 17A & 17B). Inactivation of anti-CD28 reduced the activation potency, which was more prominent for IL2 reporter, indicating the importance of anti-CD28 co-signaling pathway. Inactivation of anti-CD3 binding site rendered Binding protein 5 to minimal activity, suggesting that the anti-CD3 provided the primary T cell activation signaling.

Example 4: In Vivo Activity of the T Cell Engagers

This example describes experiments characterizing the properties and activities of the anti-Her2 or anti-CD38 containing T cell engagers in vivo.

In Vivo Assays Using Trispecific Binding Proteins Comprising Anti-Her2

Figures 18A, 18B, 18C, 18D:
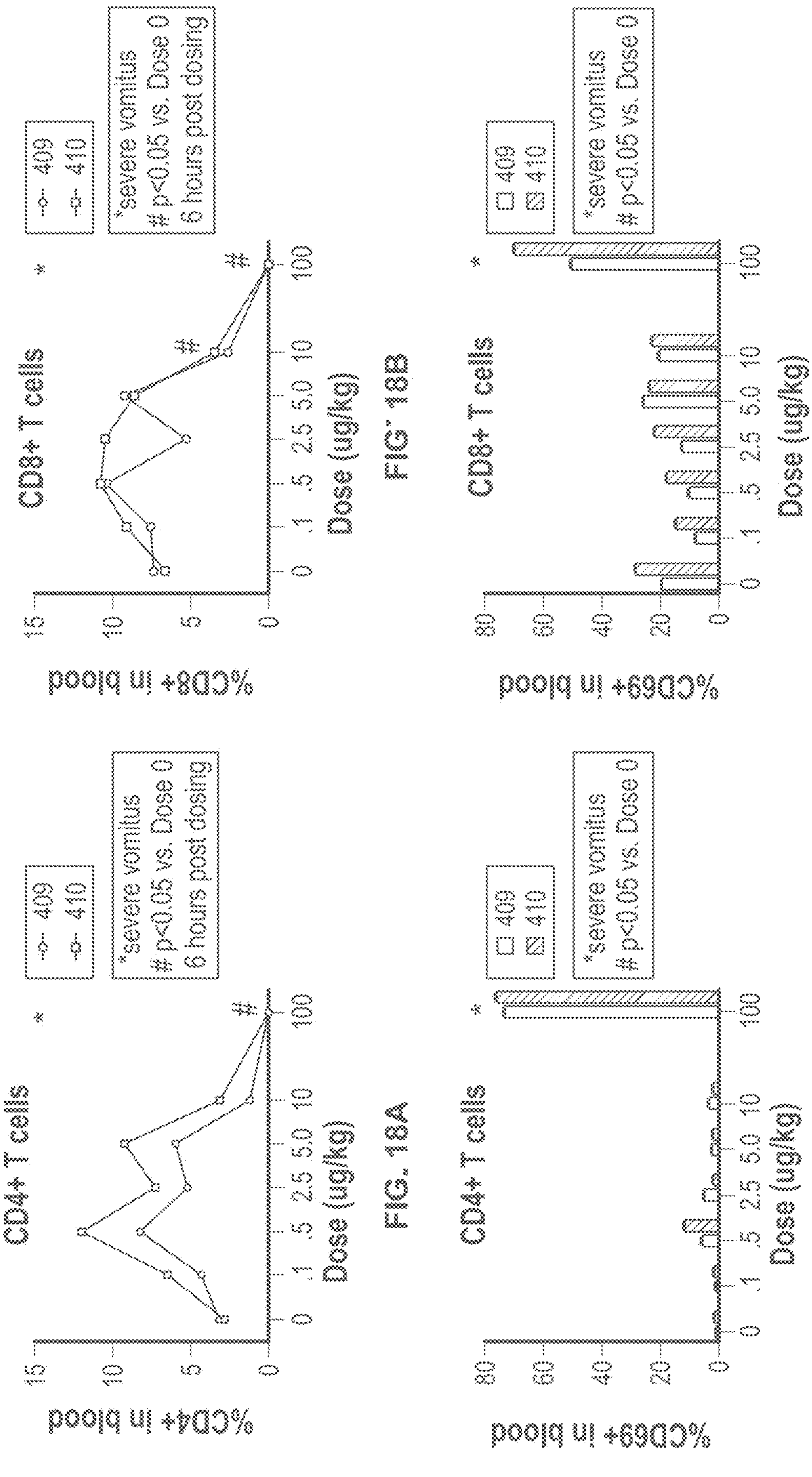
FIGS. 18A-18E show the results of a dose escalation toxicity study using the anti-Her2×CD28×CD3 IgG4 trispecific antibody (referred to herein as "Binding protein 1") in non-human primates (dose escalating from 0.1, 0.5, 2.5, 5, 10, to 100 μg/kg; animals labeled as "409" and "410").
Figure 18E:
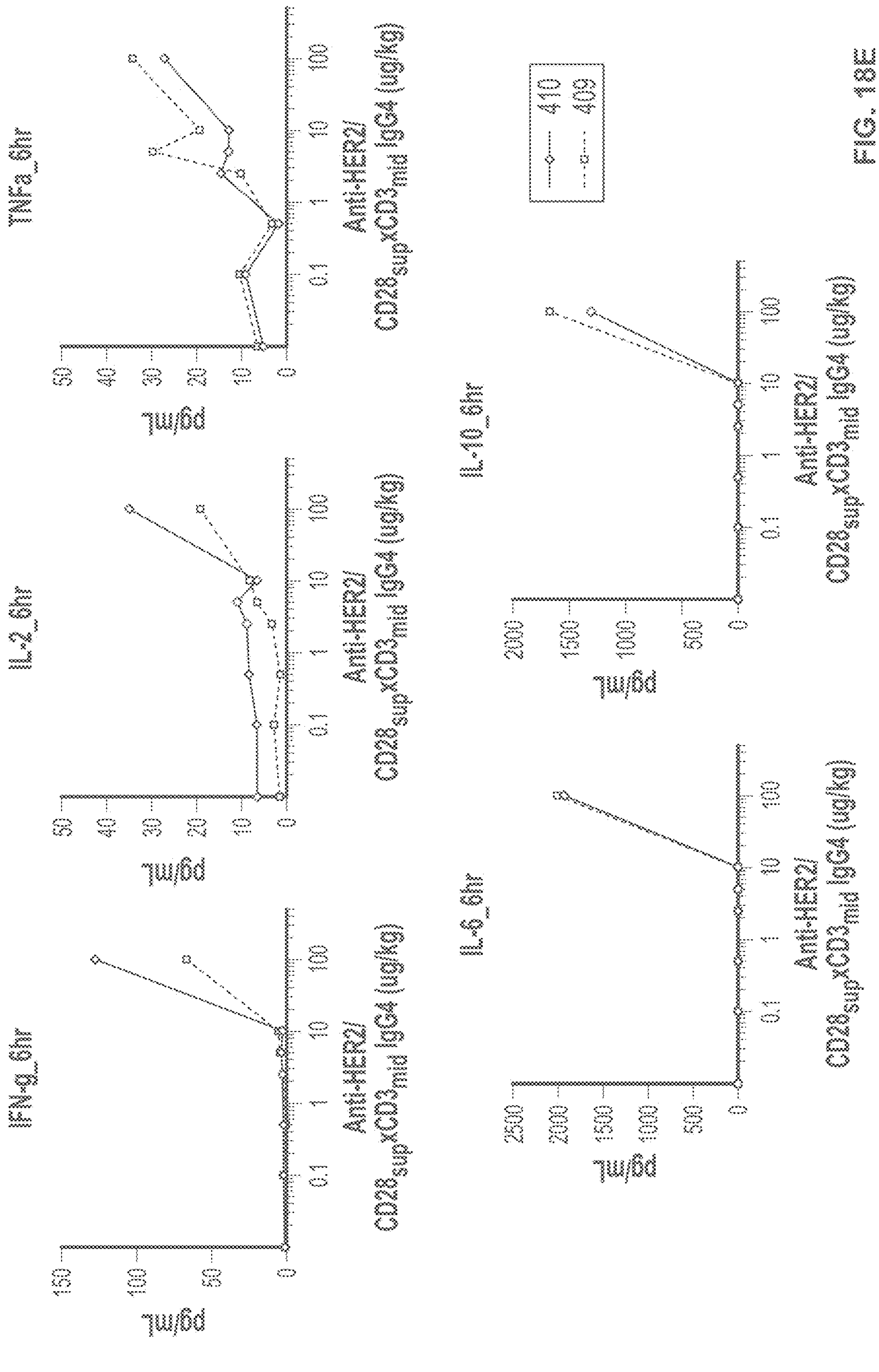

A dose escalation study using the Her2×CD28×CD3 trispecific antibody was carried out in non-human primates (FIGS. 18A-18E) as described in Example 1. All three binding domains in Binding protein 1 are cross-reactive with monkey CD3/CD28/HER2. A dose escalation toxicity study was devised to assess the potential toxicity profile of the molecular. Blood samples were collected for serum and PBMC isolations. Circulating T cell populations were investigated after each dosing (FIGS. 18A & 18B), along with T cell subpopulation activation (CD69+) (FIGS. 18C & 18D). Percentage of CD4 and CD8 T-cells in circulation were increased at low dose escalation, but eventually decreased at high dose escalation. Significant CD4 and CD8 T cell activation were only prominent at 100 μg/kg dose, suggesting rather a relative high tolerable dose. Serum level of several cytokines were also measured. Significant cytokine release was only observed at the highest dose (100 μg/kg; FIG. 18E).

Figure 19A:
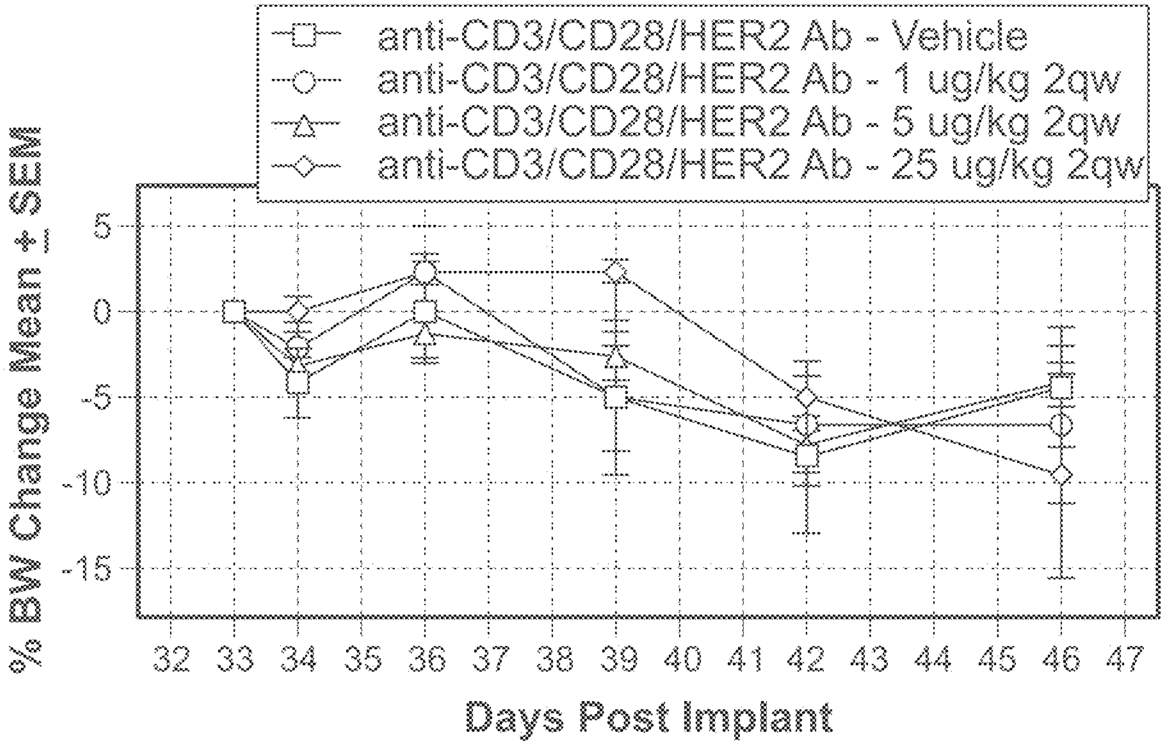
FIGS. 19A-B show the in vivo anti-tumor activity of the anti-Her2×CD28×CD3 IgG4 trispecific antibody (referred to herein as "Binding protein 1") in the $CD34^+$ umbilical cord blood cell humanized NSG mouse model implanted with BT474 cells.
Figure 19B:
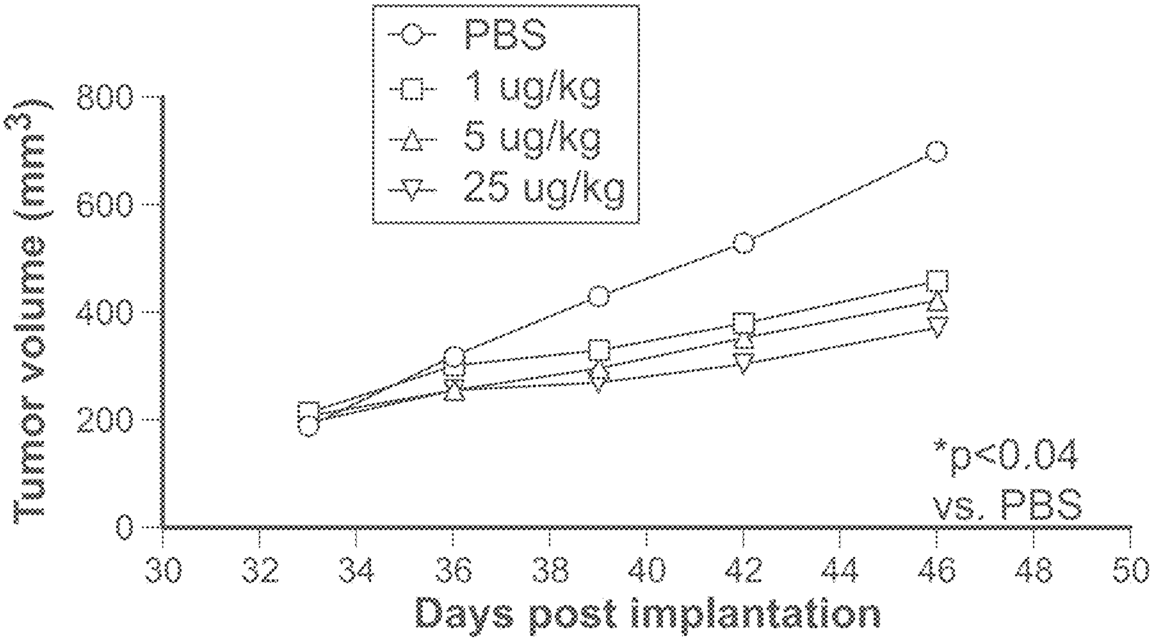
Figure 20A:
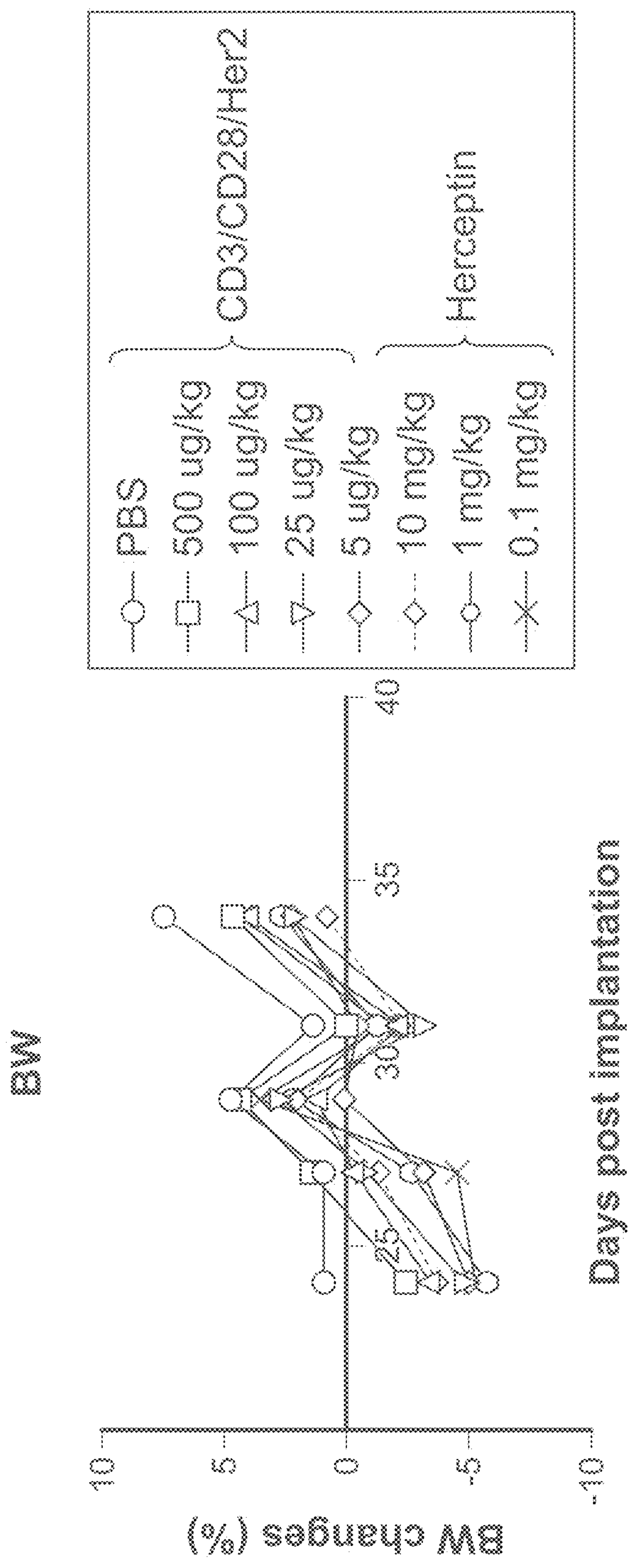
FIGS. 20A-20H show the in vivo anti-tumor activity of the anti-Her2×CD28×CD3 IgG4 trispecific antibody (referred to herein as "Binding protein 1") in the human PBMCs humanized NSG mouse model implanted with BT474 cells.
Figure 20B:
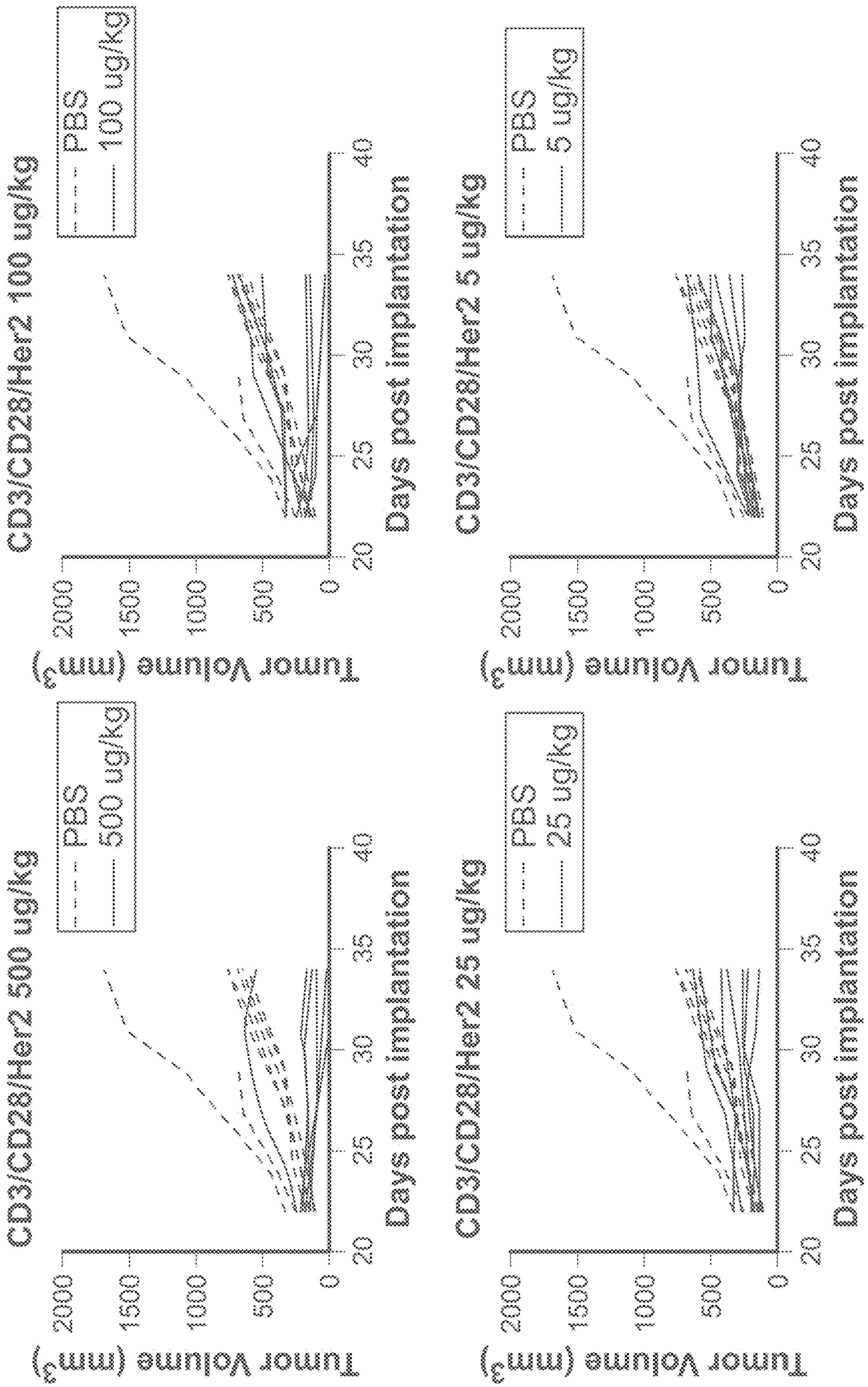
Figure 20B:
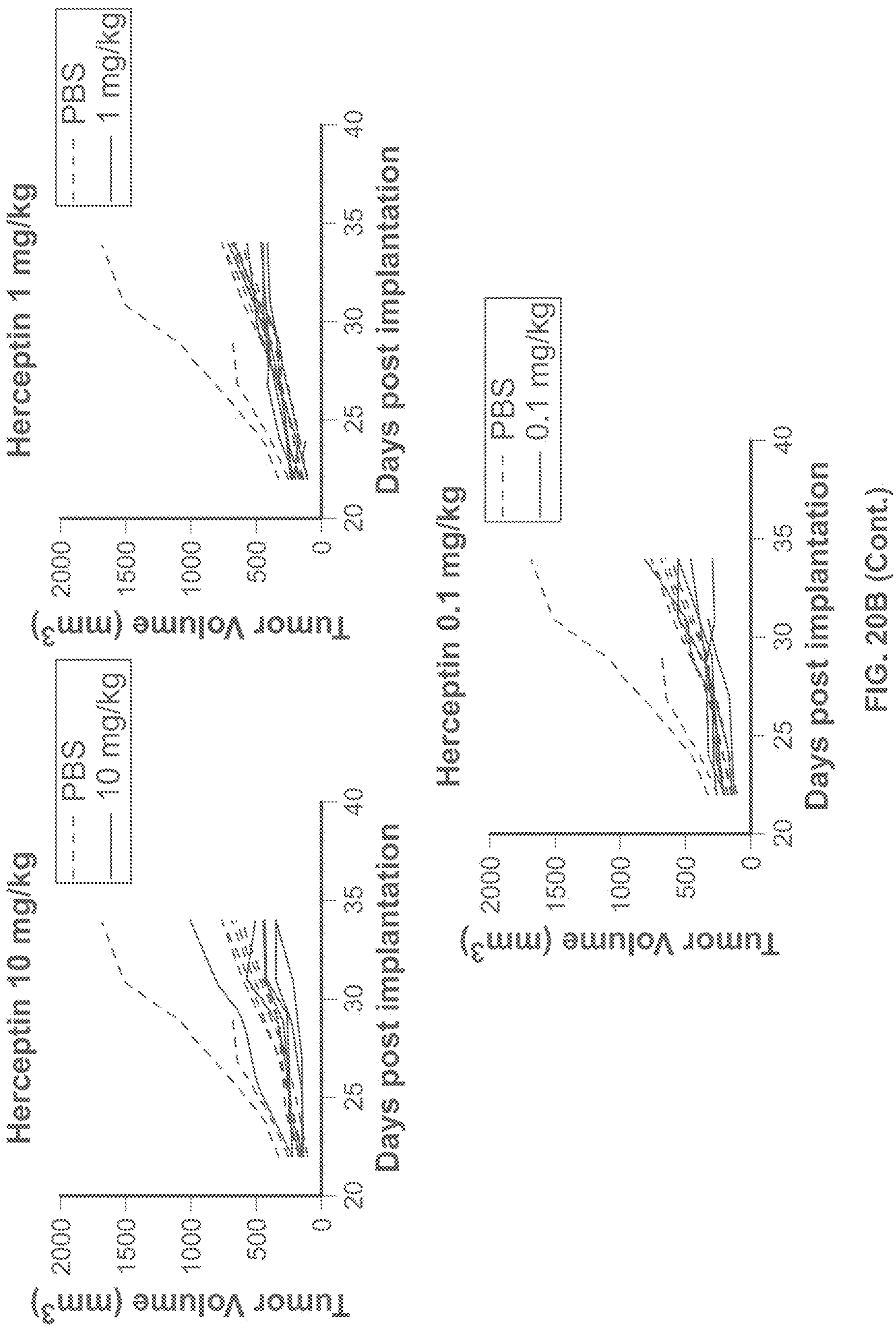
Figure 20C:
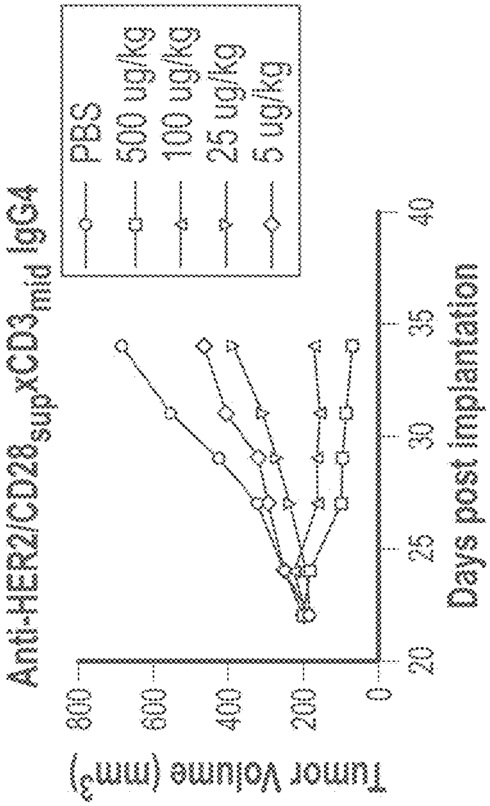
Figure 20D:
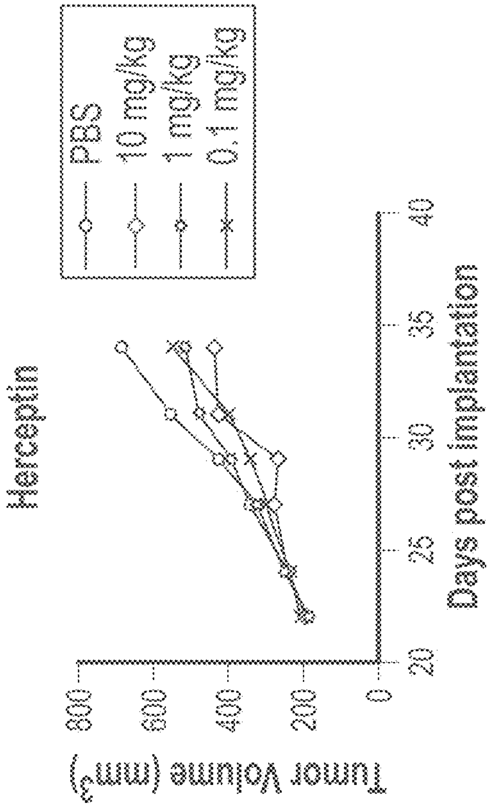
Figure 20E:
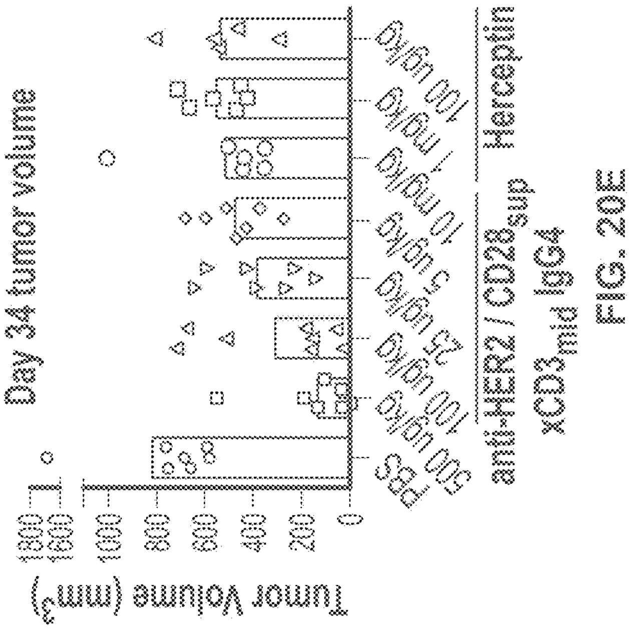
Figure 20F:
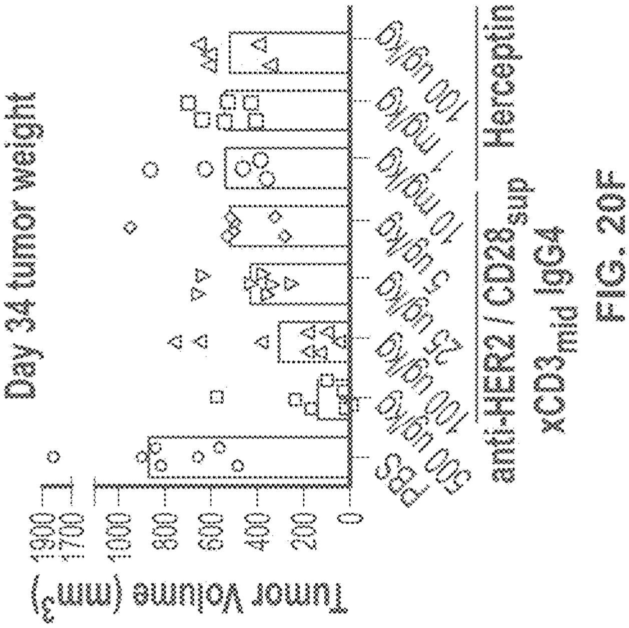
Figure 20G:
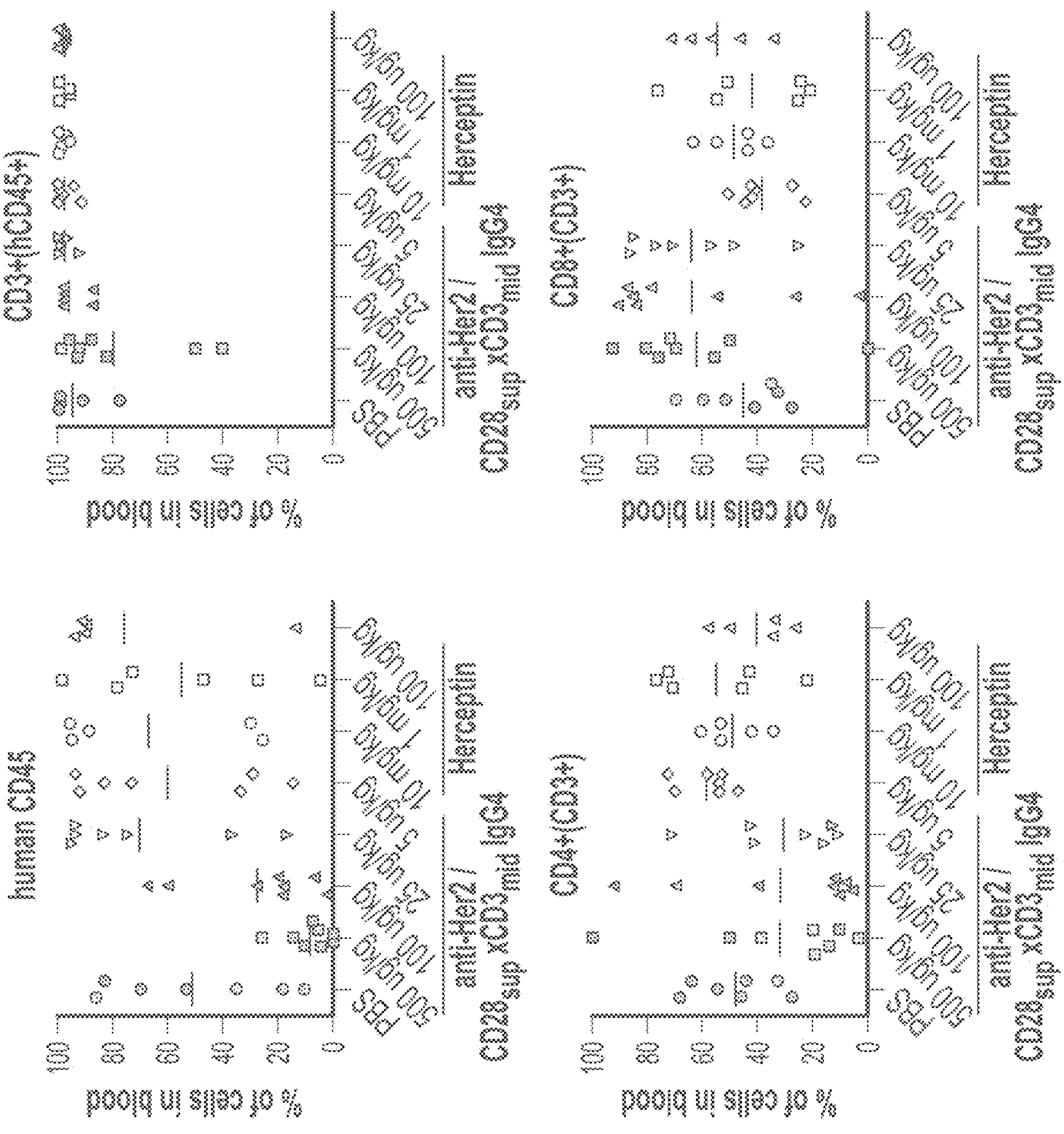
Figure 20H:
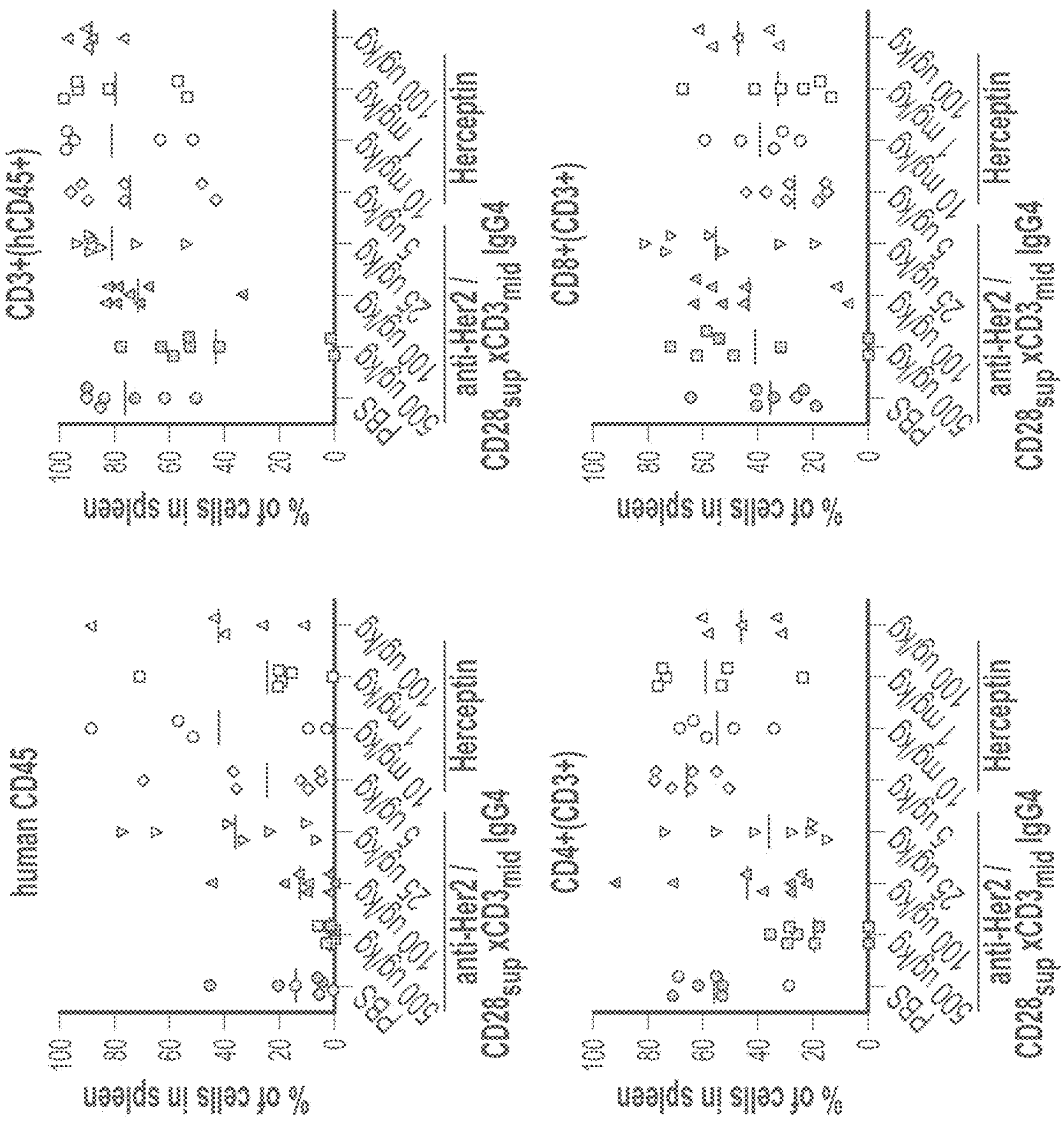

Next, the effect of the trispecific anti-Her2×CD28×CD3 Binding protein 1 antibody on tumor growth in humanized mouse models was examined as described in Example 1 (FIGS. 19A-20H). FIGS. 19A & 19B summarize the results obtained using the human CD34+ hematopoietic stem cell-engrafted NSG mice (hu-CD34) model inoculated with human HER2+ breast cancer line BT474. Significant anti-tumor activities were evident within all dose groups. The anti-tumor activity was dose dependent, which is statistically different compared to the control group at 25 μg/kg. No significant body weight loss in any treated groups observed.

A $2^{nd}$ in vivo study using human PBMC reconstituted NSG mice model inoculated with human HER2+ breast cancer line BT474 was also done (FIGS. 20A-20H). Significant anti-tumor activities were observed within high dose groups (100 and 500 μg/kg). Tumor shrinkage was seen in 40% of the mice in 500 μg/kg group. The anti-tumor activity was dose dependent. The anti-tumor activity in groups treated with 100 and 500 μg/kg doses were significantly better than anti-HER2-treated groups (0.1 to 10 mg/kg), indicating superior anti-tumor activity from Binding protein 1. No significant body weight loss in any treated groups observed.

In Vivo Assays Using Trispecific Binding Proteins Comprising Anti-CD38

Figures 21A, 21B, 21C, 21D:
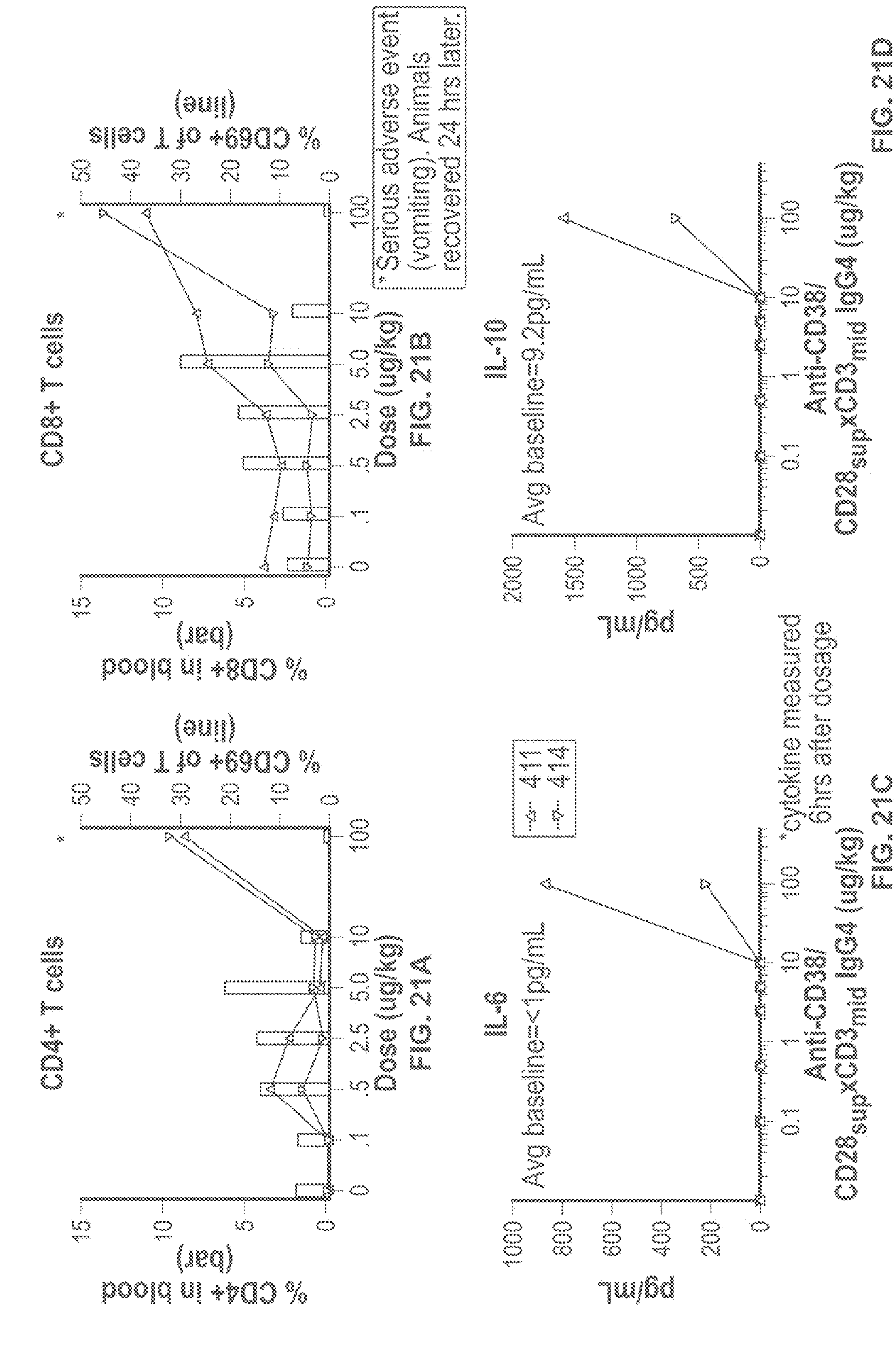
FIGS. 21A-F show the results of a dose escalation toxicity study using the anti-CD38×CD28×CD3 IgG4 trispecific antibody (Binding protein 5) in non-human primates (dose escalating from 0.1, 0.5, 2.5, 5, 10, to 100 μg/kg).
Figure 21F:
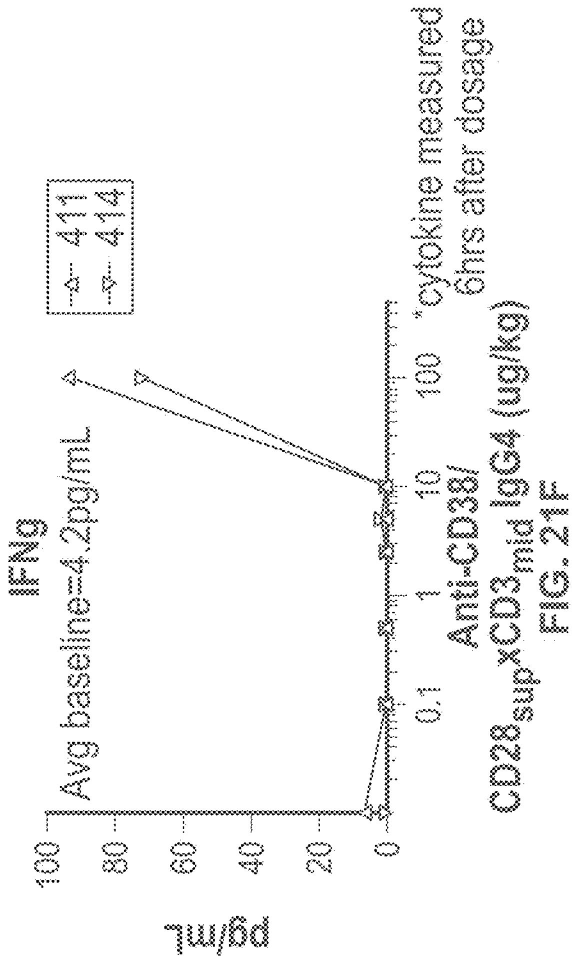
Figure 21E:
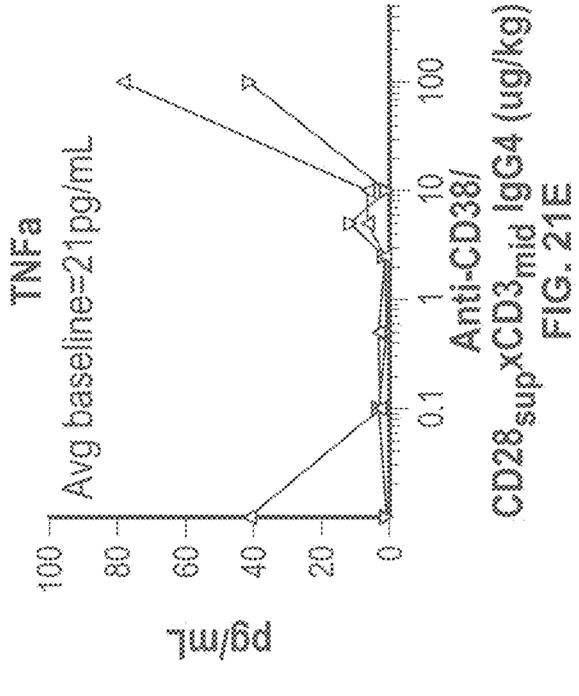

A dose escalation study was conducted in non-human primates using the trispecific anti-CD38×CD28×CD3 antibody (Binding protein 5) as described in Example 1 (FIGS. 21A-21F). Two of the three binding domains in Binding protein 5 are cross-reactive with monkey CD3 and CD28. A dose escalation toxicity study was devised to assess the potential toxicity profile of the molecule. Blood samples were collected for serum and PBMC isolations. Circulating T cell populations were investigated after each dosing (FIGS. 21A & 21B, bar graphs), along with T cell subpopulation activation (CD69+) (FIGS. 21A & 21B, line graphs). Percentage of CD4 and CD8 T-cells in circulation increased at low dose escalation, but eventually decreased at high dose escalation. Significant CD4 and CD8 T cell activation were only prominent at 100 μg/kg dose, suggesting rather a relative high tolerable dose. Serum level of several cytokines was also measured. Significant cytokine release was only observed at the highest dose (100 μg/kg; FIGS. 21C-21F).

Figure 22A:
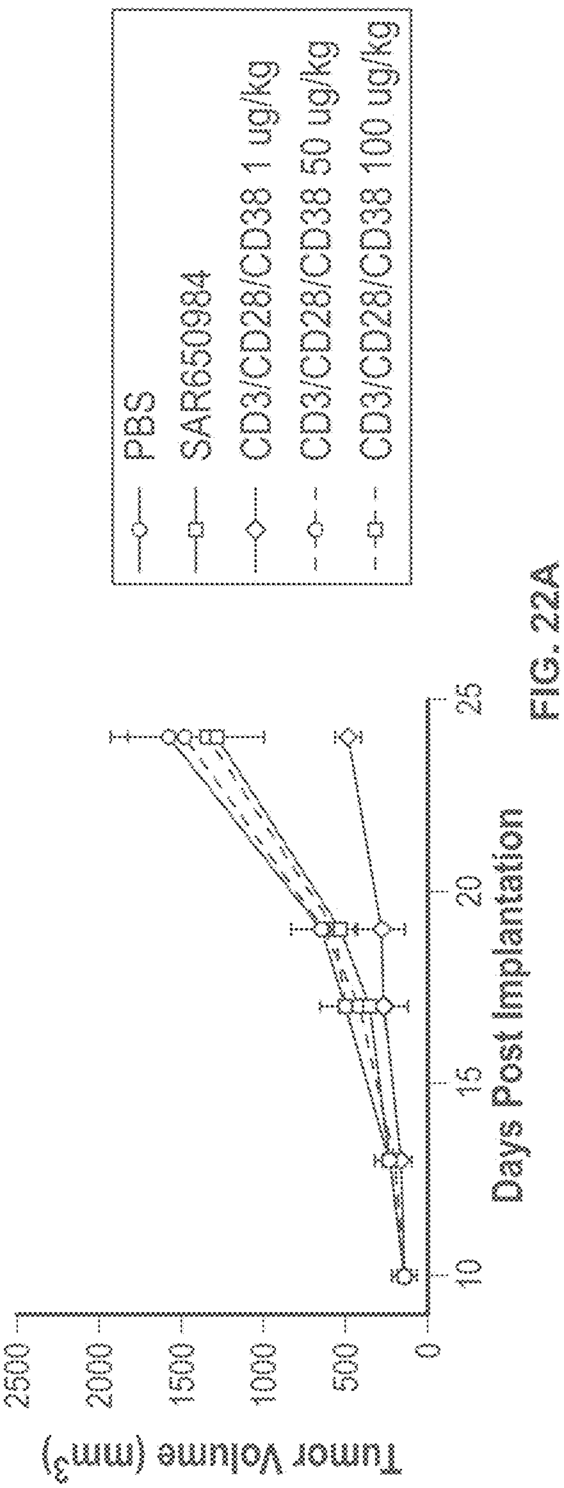
FIGS. 22A-22C show the in vivo anti-tumor activity of the anti-CD38×CD28×CD3 IgG4 trispecific antibody (Binding protein 5) in the CD34+ umbilical cord blood cells humanized NSG mouse model implanted with RPMI-8226 multiple myeloma cells transduced with CD38 and PD-$L_1$. As a pilot study, this experiment determined the working dose range for the Binding protein 5.
Figure 22B:
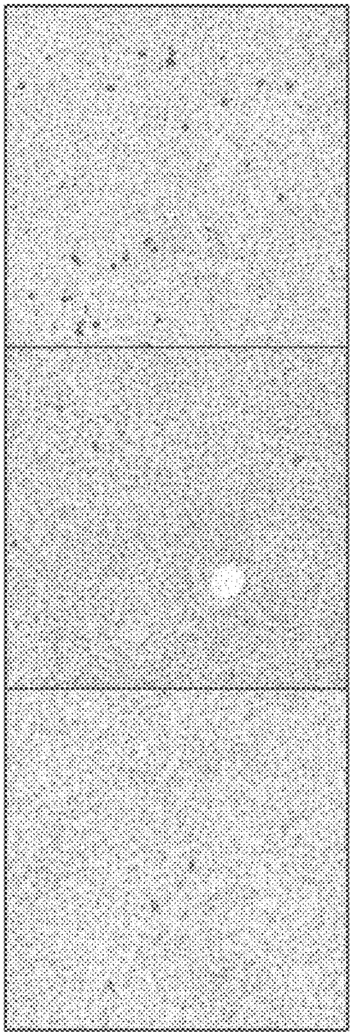
Figure 22C:
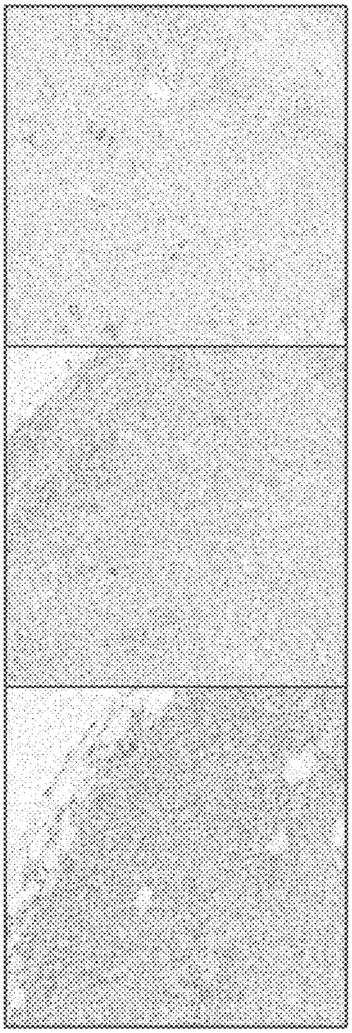

The in vivo activity of the anti-CD38×CD28×CD3 trispecific antibody was next tested in humanized mice (FIGS. 22A-23D) as described in Example 1. FIGS. 22A-22C summarized the result from a dose determining pilot study using the human CD34+ hematopoietic stem cell-engrafted NSG mice (hu-CD34) model implanted with human MM cell line RPMI-8226 transduced with CD38 and PD-L1, treated with Binding protein 5 at doses 5, 50 and 100 μg/kg. Significant anti-tumor activity was only evident in group treated with 5 μg/kg (FIG. 22A). CD8 T cell infiltration was observed in Binding protein 5 treated mice (5 μg/kg) (FIGS. 22B & 22C).

Figure 23A:
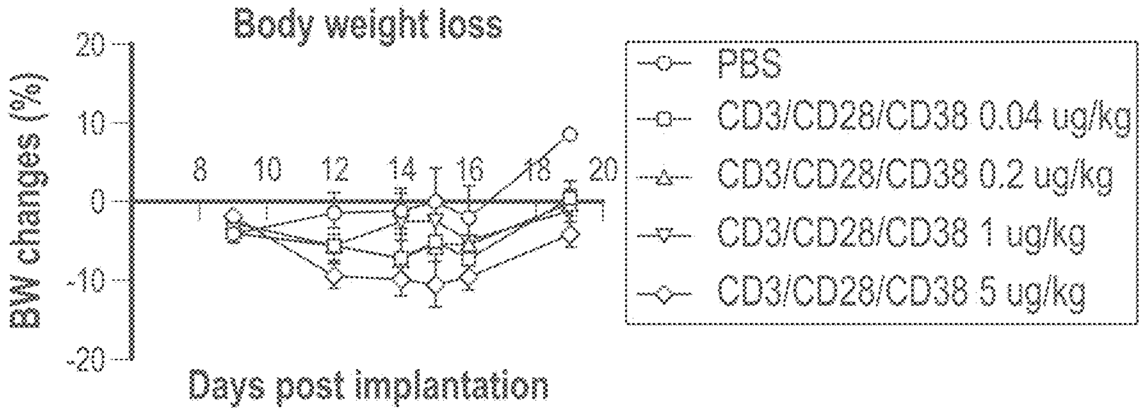
FIGS. 23A-23D show the in vivo activity of the anti-CD38×CD28×CD3 IgG4 trispecific antibody (Binding protein 5) in the $CD34^+$ umbilical cord blood cells humanized NSG mouse model implanted with RPMI-8226 cells transduced with CD38 and PD-L1.
Figure 23B:
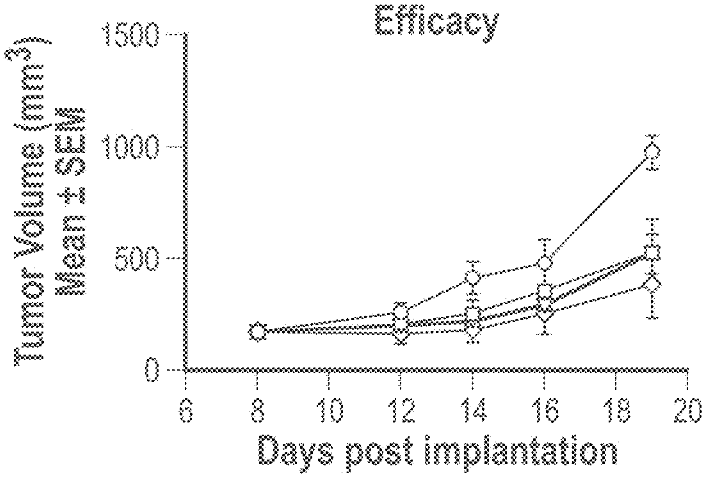
Figure 23C:
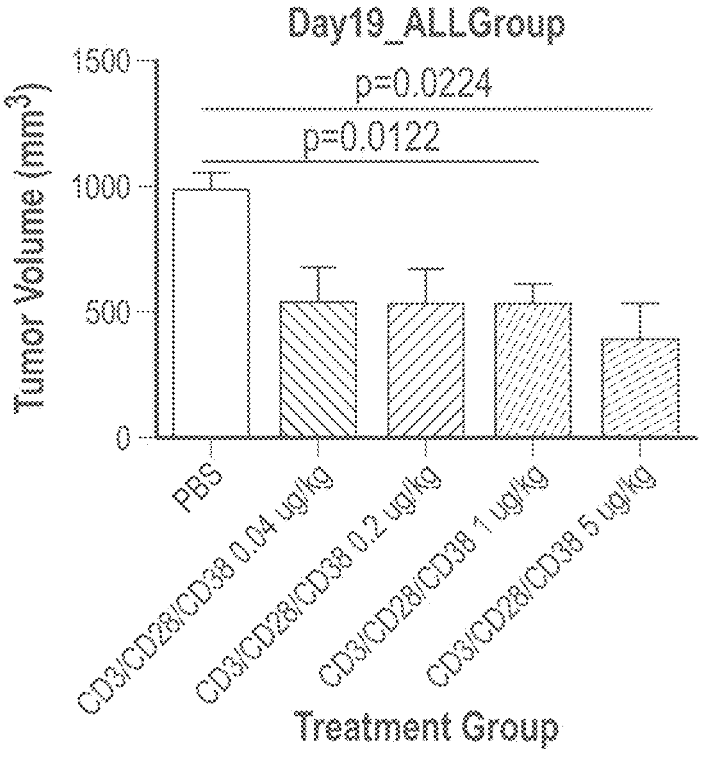
Figure 23D:
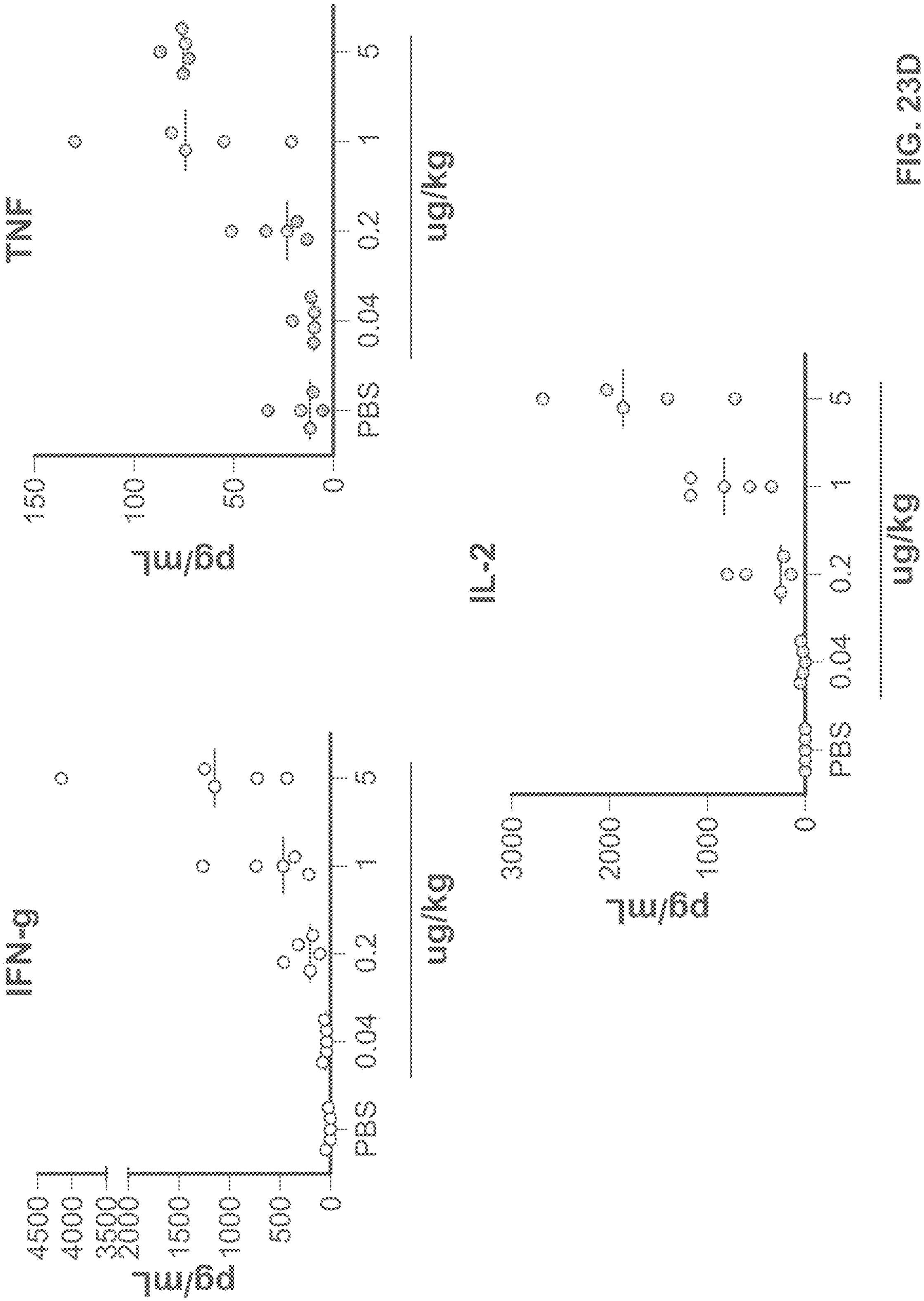

A follow up study in the same model was performed using Binding protein 5 at dosing from 0.04-5 μg/kg (FIGS. 23A-23D). Significant anti-tumor activity was shown in all group treated with Binding protein 5 (FIG. 23B), which were statistically different from the control at the end of study (FIG. 23C). No significant body weight loss was observed in any treated groups (FIG. 23A). Dose dependent induction of serum inflammatory cytokines IFN-7, TNF-α and IL-2 four hours after the first dose was observed in mice treated with indicated concentrations of the Binding protein 5 or PBS control (FIG. 23D), indicating effective T cell activation by trispecific Binding protein 5 in vivo.

Humanized CD34+ NSG mice (n=3) were injected i.v. with 100 mcg/kg of Trispecific Ab (triangel), Bi-specific Ab (square), or single-specific Ab (circle). Activation of CD4+ or CD8+ T cells was measured at 0 (pre-injection), 1, 24, and 72 hours after Ab injection by determining mean increase in % of CD69, decrease % of CD62L and/or concentration of inflammatory cytokines in plasma at each time points by Luminex's xMAP multiplexing technology. The T cell activation results of various trispecific antibodies are shown in FIGS. 24-26C.

Figure 24:
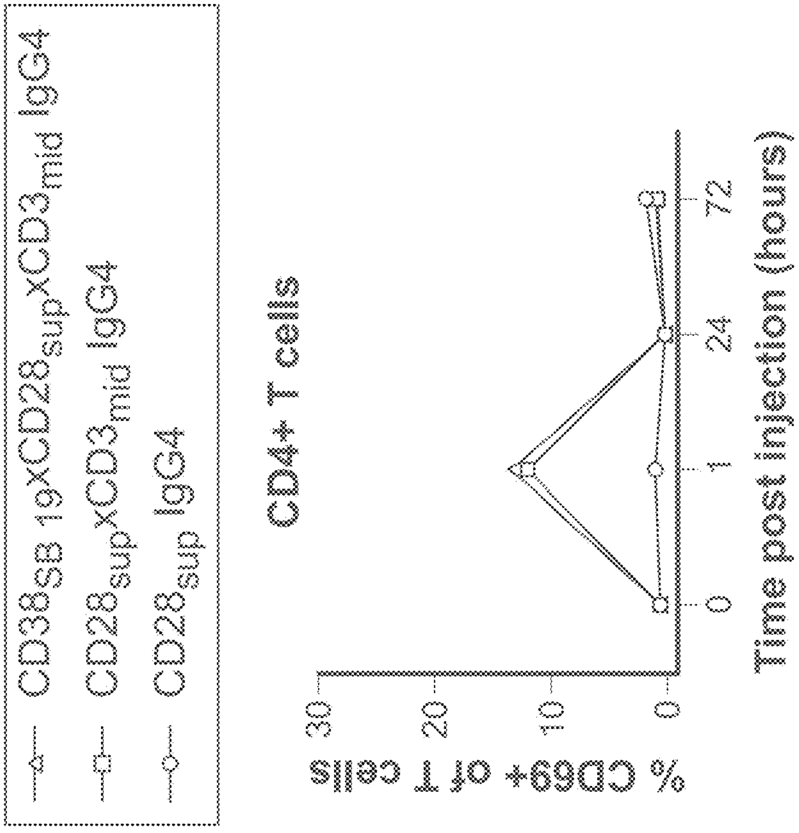
FIGS. 24 & 25 show the in vivo activation of T cells in the CD34+ umbilical cord blood cells humanized NSG mouse model by administering an anti-CD38×CD28×CD3 IgG4 trispecific antibody (Binding protein 5; triangles), an anti-CD28×CD3 IgG4 bispecific antibody (squares), or an anti-CD28 IgG4 antibody (circles) by determining the increase in the percentage of $CD69^+$ T cells.
Figure 25:
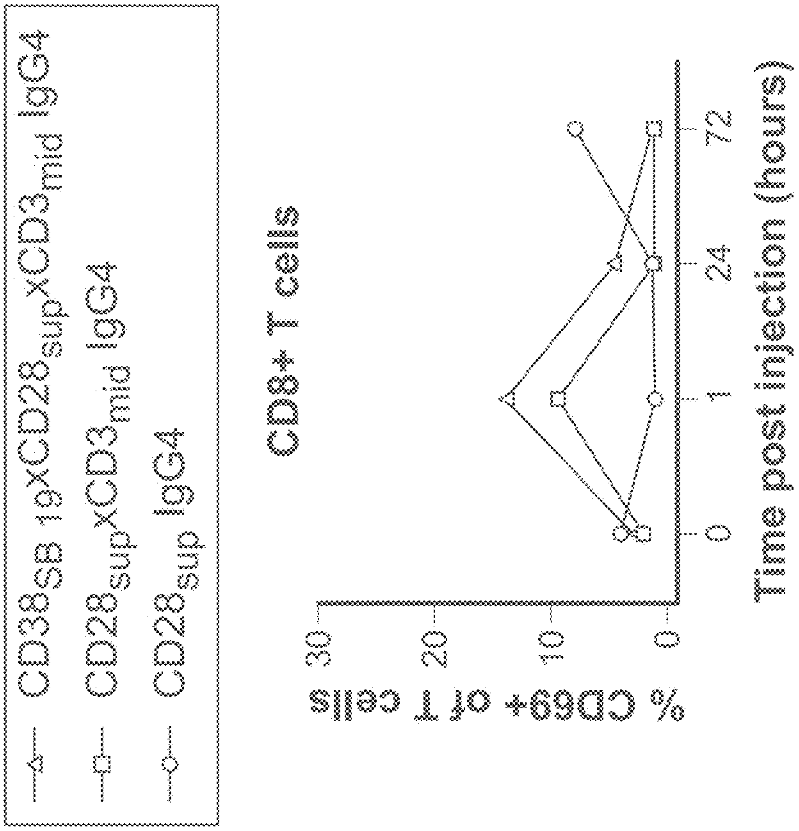
Figures 26A, 26B, 26C:
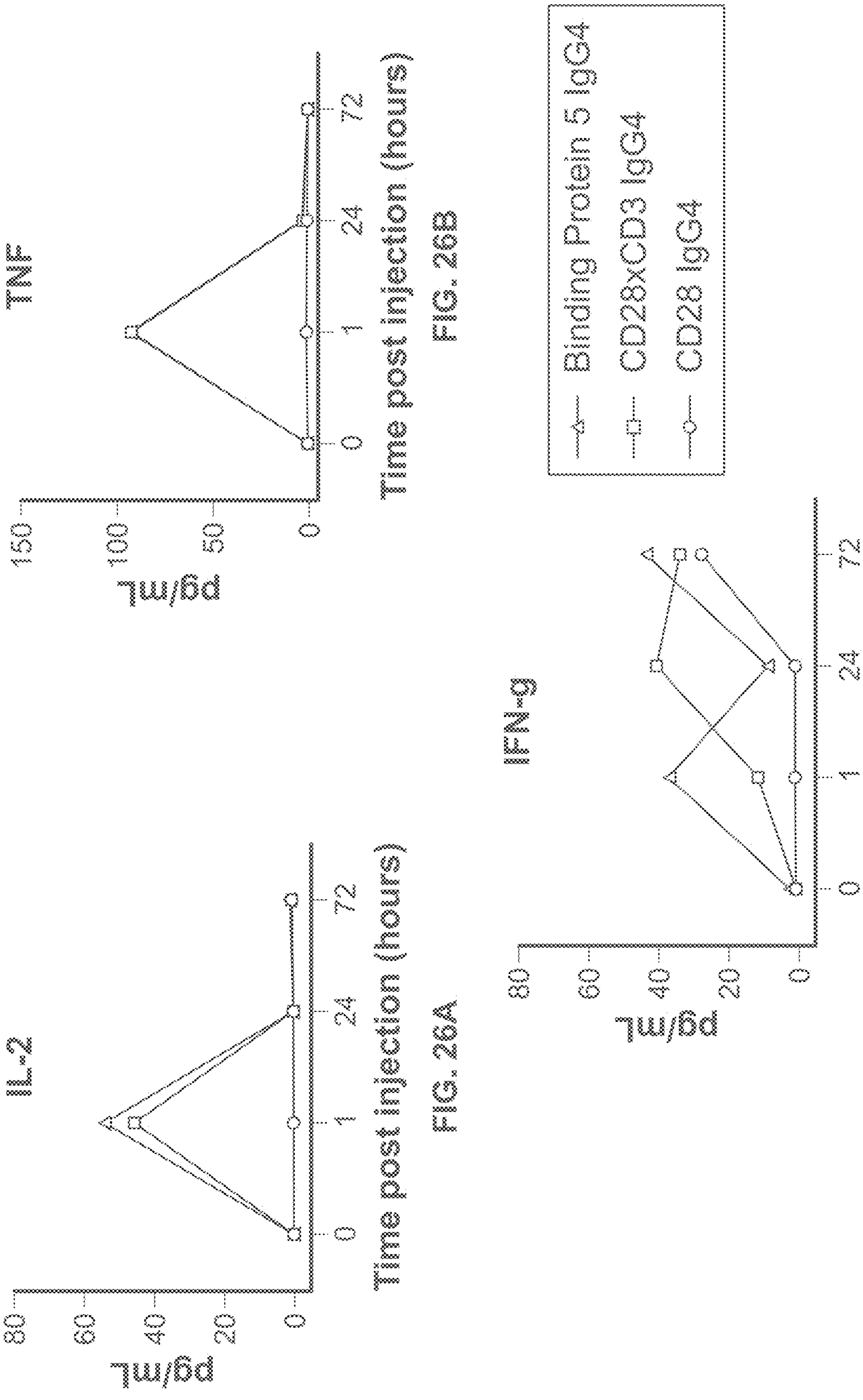
FIGS. 26A-26C show the in vivo activation of T cells in the CD34+ umbilical cord blood cells humanized NSG mouse model by administering an anti-CD38×CD28×CD3 IgG4 trispecific antibody (Binding protein 5; triangles), an anti-CD28×CD3 IgG4 bispecific antibody (squares), or an anti-CD28 IgG4 antibody (circles) by determining the serum levels of inflammatory cytokines.

Systemic in vivo T cell activation was studied in human CD34+ hematopoietic stem cell-engrafted NSG mice (hu-CD34) model after administration of Binding protein 5, anti-CD3/CD28_IgG4 bispecific antibody and anti-CD28 IgG4 antibody controls (FIG. 24). 100 μg/kg of the Binding protein 5 and control antibodies were administered into 3 mice/group. Blood samples were collected at pre, 1 hour, 24 hours and 72 hours post administration. Mouse sera and human T cells were isolated from blood, and preserved for T cell activation analysis and for measurement of serum cytokine level. FIGS. 24 & 25 show that both human CD4 and CD8 T cell were activated 1 hour post antibody infusion, which returned to baseline at 72 hours. FIGS. 26A-26C shows the elevation of serum IFN-7, TNF-α and IL-2 release in the same mice, which was observed 1 hour post infusion, and returned to baseline 24 hours later. These results demonstrated both Binding protein 5 and anti-CD3/CD28 IgG4 bispecific antibody are effective in activating T cell in the given animal model, making it suitable for in vivo efficacy study.

Example 5: Characterization of Cytokine-Directed Trispecific and Bispecific-Trivalent Binding Proteins The follow example describes experiments characterizing the stability, binding properties, and activities of novel trispecific and bispecific-trivalent binding proteins that target human cytokines.

Trispecific binding proteins (e.g., that bind three different target proteins; Binding Proteins 9-15), as well as bispecific-trivalent binding proteins (e.g., that bind one antigen bivalently on one antigen monovalently; Binding Proteins 16-19), were designed (Table C). With the exception of Binding Protein 11 where a kappa constant domain was used on both the CODV-LC and the Fab-arm-LC, all other Binding Proteins (9-10 and 12-19) were produced with a kappa constant domain on the CODV-LC and a lambda constant domain on the Fab-arm-LC. As Fc-backbone the IgG1 sequence was used. Whereas the CODV-HC harbors the knob-RF mutations (S354C, T366W; H435R and Y436F) the Fab-arm-HC contains the hole mutations (Y349C, T366S, L368A, Y407V).

TABLE C summary of the trispecific/trivalent binding proteins directed to anti-IL-4/IL-13/TNFα

| Antibody | Specificity | Construct | Format |
|---|---|---|---|
| Binding Protein 9 | (anti-IL4 × anti-IL13) × anti-TNFα | (CODV-Fab) × Fab-IgG1 Fc | Trispecific |
| Binding Protein 10 | (anti-IL13 × anti-IL4) × anti-TNFα | (CODV-Fab) × Fab-IgG1 Fc | Trispecific |
| Binding Protein 11 | (anti-IL13 × anti-IL4) × anti-TNFα | (CODV-Fab) × Fab-IgG1 Fc | Trispecific |
| Binding Protein 12 | (anti-IL4 × anti-TNFα) × anti-IL13 | (CODV-Fab) × Fab-IgG1 Fc | Trispecific |
| Binding Protein 13 | (anti-TNFα × anti-IL4) × anti-IL13 | (CODV-Fab) × Fab-IgG1 Fc | Trispecific |
| Binding Protein 14 | (anti-IL13 × anti-TNFα) × anti-IL4 | (CODV-Fab) × Fab-IgG1 Fc | Trispecific |
| Binding Protein 15 | (anti-TNFα × anti-IL13) × anti-IL4 | (CODV-Fab) × Fab-IgG1 Fc | Trispecific |
| Binding Protein 16 | (anti-IL13 × anti-IL4) × anti-IL13 | (CODV-Fab) × Fab-IgG1 Fc | Bispecific Trivalent |
| Binding Protein 17 | (anti-IL13 × anti-IL4) × anti-IL4 | (CODV-Fab) × Fab-IgG1 Fc | Bispecific Trivalent |
| Binding Protein 18 | (anti-IL4 × anti-IL13) × anti-IL13 | (CODV-Fab) × Fab-IgG1 Fc | Bispecific Trivalent |

TABLE C-continued

| summary of the trispecific/trivalent binding proteins directed to anti-IL-4/IL-13/TNFα | | | |
|---|---|---|---|
| Antibody | Specificity | Construct | Format |
| Binding Protein 19 | (anti-IL4 × anti-IL13) × anti-IL4 | (CODV-Fab) × Fab-IgG1 Fc | Bispecific Trivalent |

Figure 27A:
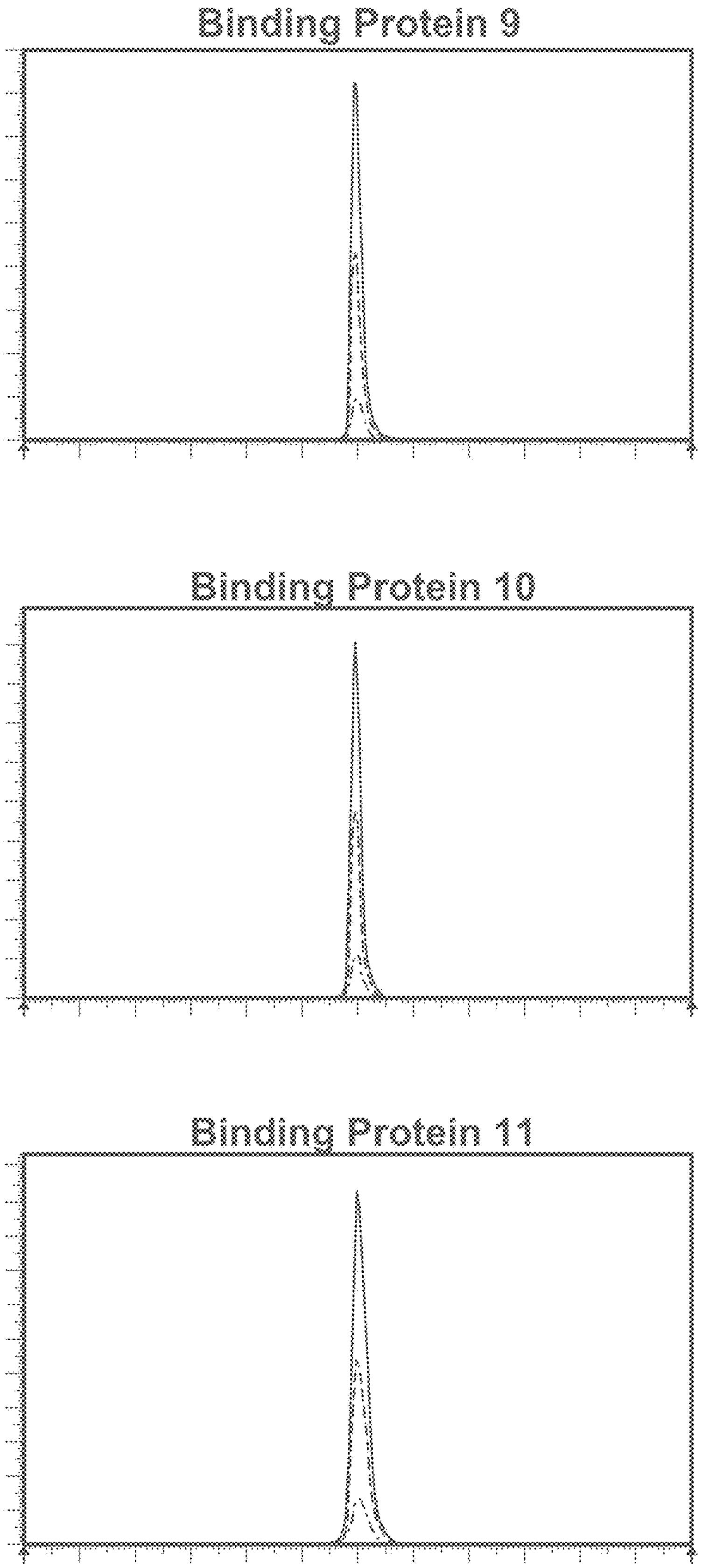
FIGS. 27A & 27B show the purification of the indicated proteins by size exclusion chromatography.
Figure 27A:
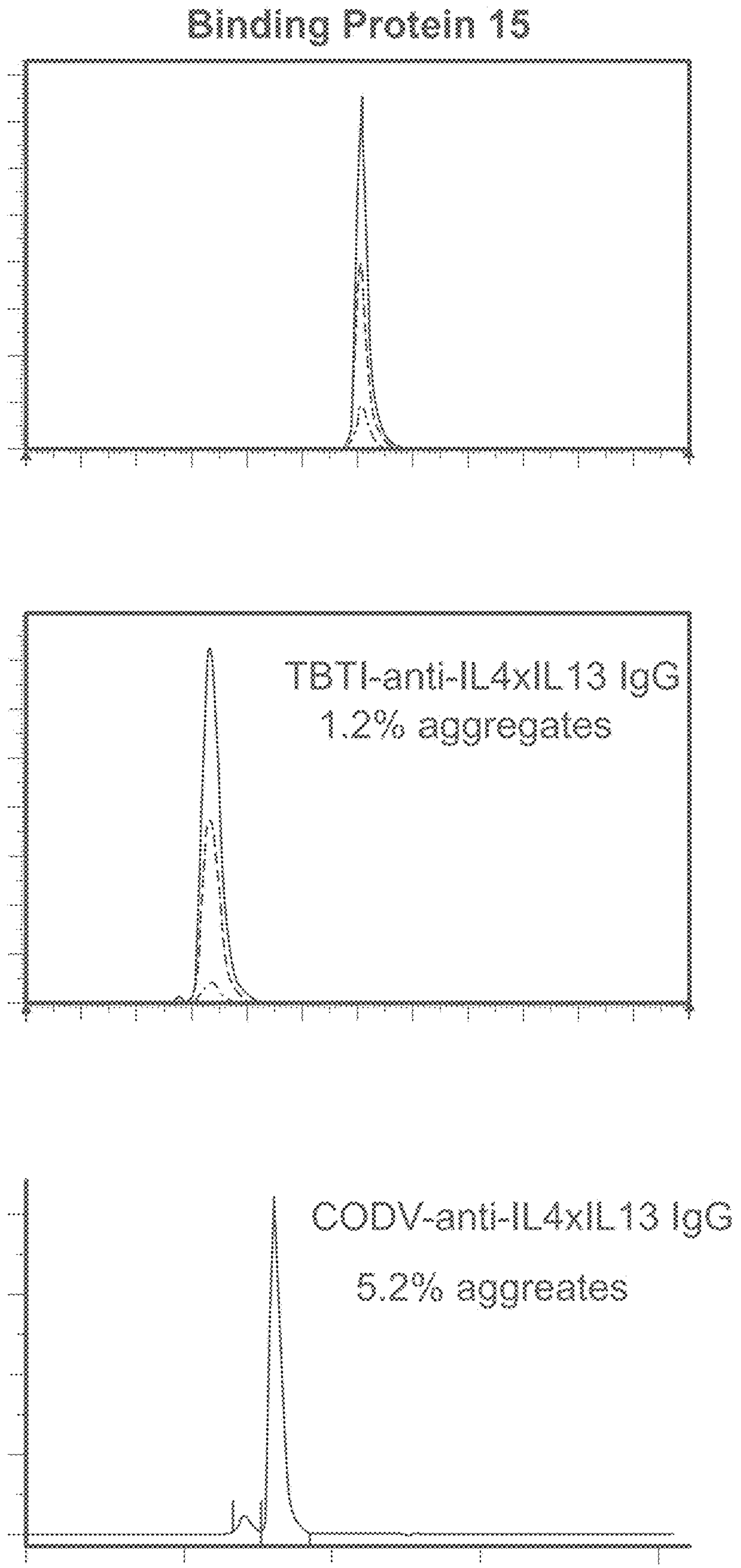
Figure 27B:
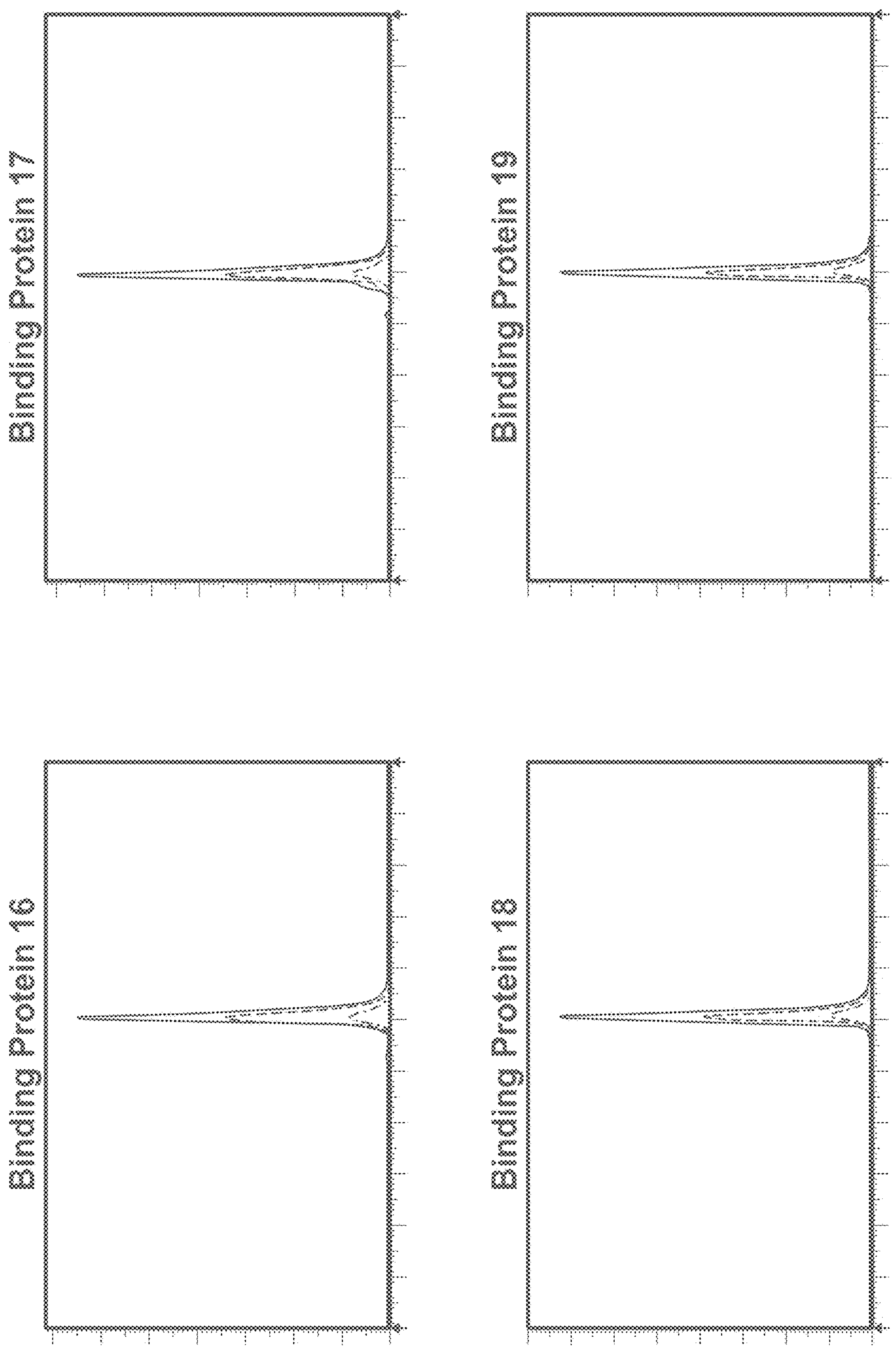

The trispecific and bispecific-trivalent binding proteins were produced and purified as described above (FIG. 27).

TABLE D

SEC purification of Binding Proteins 16-19

| Construct | Reten-tion (mL) | Peak Height (mAU) | Area (mAU * mL) | Aggregation (%) | MW by SEC (kDa) | MW Calc. (kDa) |
|---|---|---|---|---|---|---|
| Binding Protein 16 | 3.02 | 64.8 | 8.1 | 1.5 | 211 | 11 |
| Binding Protein 17 | 2.99 | 65.9 | 8.9 | 2.1 | 225 | 172 |
| Binding Protein 18 | 3.01 | 72.9 | 8.8 | 0.0 | 214 | 171 |
| Binding Protein 19 | 2.98 | 73.2 | 8.8 | 0.9 | 228 | 171 |

In order to assess the stability of the trispecific binding proteins, their melting point was assessed by DSF and compared with the thermostability of the parental antibodies (Table E).

TABLE E summary of the thermostability by DSF and percent monomers from preparative size exclusion chromatography for various trispecific binding proteins

| Construct | Tm (° C.) | | Prep SEC Monomer (%) |
|---|---|---|---|
| IL4 | 70 | 81 | 100 |
| IL13 | 67 | 78 | 92.5 |
| TNFα | 70 | — | nd |
| Binding Protein 9 | 63 | — | 92.2 |
| Binding Protein 10 | 62 | — | 85.7 |
| Binding Protein 11 | 63 | 70 | 65.7 |
| Binding Protein 12 | 59 | 70 | 87.3 |
| Binding Protein 13 | 59 | 70 | 94.5 |
| Binding Protein 14 | 56 | 69 | 92.4 |
| Binding Protein 15 | 58 | 66 | 92.2 |
| IL13 × IL4 | 63 | 75 | 88.0 |
| IL4 × IL13 | 64 | — | nd |

nd = not determined

To assess the binding affinity of every single antibody binding domain within the trispecific format, SPR analysis for each single antigen was performed as described previously. The results were benchmarked against the affinities of the parental antibodies (Tables F, G, and H).

TABLE F summary of surface plasmon resonance results for IL-4 for various trispecific binding proteins

| Construct | $K_a$ [1/M * s] | $K_d$ [1/s] | $K_D$ [M] | Rmax | Chi^2 |
|---|---|---|---|---|---|
| IL4 IL13 TNFα | 8.70E+07 | 1.57E−04 | 1.81E−12 | 24 | 0.24 |
| Binding Protein 9 | 7.86E+07 | 3.80E−04 | 4.83E−12 | 26 | 0.309 |
| Binding Protein 10 | 1.88E+07 | 8.41E−05 | 4.47E−12 | 23 | 0.763 |
| Binding Protein 11 | 5.92E+07 | 2.39E−04 | 4.04E−12 | 20 | 0.198 |
| Binding Protein 12 | 6.02E+07 | 2.39E−04 | 3.97E−12 | 35 | 0.406 |
| Binding Protein 13 | 3.57E+07 | 1.81E−04 | 5.07E−12 | 30 | 0.257 |
| Binding Protein 14 | 8.96E+07 | 1.52E−04 | 1.69E−12 | 33 | 0.254 |
| Binding Protein 15 | 7.35E+07 | 1.23E−04 | 1.67E−12 | 31 | 0.547 |

TABLE G summary of surface plasmon resonance results for IL-13 for various trispecific binding proteins

| Construct | $K_a$ [1/M * s] | $K_d$ [1/s] | $K_D$ [M] | Rmax | Chi^2 |
|---|---|---|---|---|---|
| IL4 IL13 TNFα | 2.44E+05 | 2.50E−05 | 1.03E−10 | 33 | 0.938 |
| Binding Protein 9 | 6.25E+05 | 9.27E−06 | 1.48E−11 | 22 | 0.176 |
| Binding Protein 10 | 7.16E+05 | 3.76E−05 | 5.25E−11 | 25 | 0.145 |
| Binding Protein 11 | 2.95E+05 | 4.28E−05 | 1.45E−10 | 16 | 0.372 |
| Binding Protein 12 | 4.17E+05 | 5.06E−05 | 1.21E−10 | 28 | 0.338 |
| Binding Protein 13 | 6.15E+05 | 7.58E−05 | 1.23E−10 | 23 | 0.186 |
| Binding Protein 14 | 6.93E+05 | 1.19E−04 | 1.72E−10 | 22 | 0.232 |
| Binding Protein 15 | 2.50E+05 | 5.61E−05 | 2.24E−10 | 30 | 0.631 |

TABLE H summary of surface plasmon resonance results for TNFα for various trispecific binding proteins

| Construct | Ka [1/M * s] | $K_d$ [1/s] | $K_D$ [M] | Rmax | Chi^2 |
|---|---|---|---|---|---|
| IL4 IL13 TNFα | 1.78E+05 | 1.64E−04 | 9.22E−10 | 33 | 0.745 |
| Binding Protein 9 | 1.32E+05 | 3.20E−04 | 2.42E−9 | 23 | 0.213 |
| Binding Protein 10 | 1.40E+05 | 2.90E−04 | 2.07E−9 | 27 | 0.241 |
| Binding Protein 11 | 3.36E+05 | 1.82E−04 | 5.41E−10 | 28 | 0.539 |
| Binding Protein 12 | 4.49E+05 | 1.80E−04 | 4.00E−10 | 28 | 0.647 |
| Binding Protein 13 | 5.84E+05 | 1.96E−04 | 3.35E−10 | 27 | 0.529 |

TABLE H-continued

| summary of surface plasmon resonance results for TNFα for various trispecific binding proteins | | | | | |
|---|---|---|---|---|---|
| Construct | Ka [1/M * s] | $K_d$ [1/s] | $K_D$ [M] | Rmax | Chi^2 |
| Binding Protein 14 | 5.29E+05 | 1.86E−04 | 3.52E−10 | 25 | 0.485 |
| Binding Protein 15 | 5.59E+05 | 1.84E−04 | 3.28E−10 | 27 | 0.409 |

In order to assess the neutralization activity of the trispecific binding proteins, a cellular assay was performed using different HEK Blue kits (Invivogen). Cytokines were pre-incubated with different concentrations of anti-cytokine antibodies for 30 minutes at room temperatures in a 96 well plate. Controls included use of only the cytokine or only the antibody. 50,000 HEK Blue Cells (HEK Blue TNFα/IL1β cells (InvivoGen, Cat. #hkb-tnfil1; HEK Blue STAT-6 cells (InvivoGen, Cat. #Hkb.stat6) were added to the cytokine/antibody mixture and incubated for 23 hours at 37° C., 5% CO2 in an incubator. QuantiBlue Reagent was added to each culture well and incubated for 2 hours at 37° C. The OD was measured at 620 nm and the IC50 was calculated using BioStat Speed 2.0. The HEK Blue Reporter Cell Assay results of various trispecific antibodies are shown in Tables I and M.

Next, $IC_{50}$ values were calculated for Binding Proteins 9-15 and benchmarked against the single parental antibodies (Table I).

TABLE I

| summary of HEK Blue Reporter Assays ($IC_{50}$ Data) for various trispecific binding proteins | | | |
|---|---|---|---|
| Construct | IL4 $IC_{50}$ (ng/mL) | IL13 $IC_{50}$ (ng/mL) | TNFα $IC_{50}$ (ng/mL) |
| IL4 | 2.14E+00<br>1.85E+00<br>1.82E+01 | — | — |
| IL13 | — | 1.10E+02<br>8.83E+01<br>1.42E+01 | — |

TABLE I-continued

| summary of HEK Blue Reporter Assays ($IC_{50}$ Data) for various trispecific binding proteins | | | |
|---|---|---|---|
| Construct | IL4 $IC_{50}$ (ng/mL) | IL13 $IC_{50}$ (ng/mL) | TNFα $IC_{50}$ (ng/mL) |
| TNFα | — | — | 3.63E+00<br>5.78E+00<br>2.41E+00 |
| Binding Protein 9 | 4.51E+00 | 1.77E+02 | 3.95E+01 |
| Binding Protein 10 | 5.93E+00 | 4.68E+02 | 4.76E+01 |
| Binding Protein 11 | 6.96E+00 | 4.89E+02 | 2.65E+01 |
| Binding Protein 12 | 5.03E+00 | 1.83E+02 | 2.17E+01 |
| Binding Protein 13 | 1.38E+01 | 7.54E+01 | 2.26E+01 |
| Binding Protein 14 | 1.02E+01 | 1.20E+02 | 6.26E+00 |
| Binding Protein 15 | 1.30E+01 | 1.07E+02 | 2.38E+01 |

The thermostability of the bispecific-trivalent binding proteins was measured by differential scanning fluorimetry (DSF; Table J).

TABLE J

| summary of the thermostability by DSF for various trivalent binding proteins | | |
|---|---|---|
| Construct | Tm1 (° C.) | Tm2 (° C.) |
| IL4 | 70 | 81 |
| IL13 | 67 | 78 |
| Binding Protein 16 | 63 | — |
| Binding Protein 17 | 63 | — |
| Binding Protein 18 | 65 | — |
| Binding Protein 19 | 55 | — |

The binding affinity and number of target proteins bound by each of the bispecific-trivalent binding proteins was measured for human IL-4 (Table K) and IL-13 (Tables K and L).

TABLE K

| summary of surface plasmon resonance results for IL-4 for various trivalent binding proteins | | | | | | | | | |
|---|---|---|---|---|---|---|---|---|---|
| Construct | RU Capture | Analyte | Ka (1/Ms) | Kd (1/s) | Rmax (RU) | KD (M) | Chi2 | kDa Bound | No. of ILs Bound |
| IL4 | 116 | IL4 | 8.70E+07 | 1.57E−04 | 24 | 1.81E−12 | 0.240 | 15 | 1 |
| Binding Protein 16 | 218 | IL4 | 4.77E+07 | 2.80E−04 | 20 | 5.88E−12 | 0.172 | 17 | 1 |
| Binding Protein 17 | 218 | IL4 | 3.16E+08 | 7.60E−04 | 43 | 2.40E−12 | 0.278 | 35 | 2 |
| Binding Protein 18 | 215 | IL4 | 3.52E+07 | 3.59E−04 | 22 | 1.02E−12 | 0.408 | 18 | 1 |
| Binding Protein 19 | 226 | IL4 | 8.27E+07 | 3.85E−04 | 43 | 4.65E−12 | 0.486 | 34 | 2 |

TABLE L summary of surface plasmon resonance results for IL-13 for various trivalent binding proteins

| Construct | RU Capture | Analyte | Ka (1/Ms) | Kd (1/s) | Rmax (RU) | KD (M) | Chi2 | kDa Bound | No. of ILs Bound |
|---|---|---|---|---|---|---|---|---|---|
| IL13 | 201 | IL13 | 8.95E+05 | 5.47E−05 | 37 | 6.11E−11 | 0.211 | 14 | 1 |
| Binding Protein 16 | 226 | IL13 | 7.17E+05 | 4.54E−05 | 35 | 6.34E−11 | 0.132 | 26 | 2 |
| Binding Protein 17 | 235 | IL13 | 5.92E+05 | 5.70E−05 | 15 | 9.64E−11 | 0.128 | 11 | 1 |
| Binding Protein 18 | 231 | IL13 | 1.00E+06 | 3.54E−05 | 35 | 3.53E−11 | 0.166 | 28 | 2 |
| Binding Protein 19 | 282 | IL13 | 1.91E+06 | 3.81E−05 | 18 | 2.00E−11 | 0.265 | 14 | 1 |

Finally, $IC_{50}$ values were calculated for Binding Proteins 16-19 (Table M).

TABLE M summary of HEK Blue Reporter Assays ($IC_{50}$ Data) for various trivalent binding proteins

| Construct | IL4 $IC_{50}$ (ng/mL) | IL13 $IC_{50}$ (ng/mL) |
|---|---|---|
| IL4 | 6.07E+00 | — |
| IL13 | — | 1.12E+03 |
| Binding Protein 16 | 1.30E+01 | 1.24E+03 |
| Binding Protein 17 | 8.62E+00 | 9.30E+03 |
| Binding Protein 18 | 1.46E+01 | 1.10E+03 |
| Binding Protein 19 | 5.73E+00 | 6.93E+03 |

Example 6: Trispecific Binding Protein Format Optimization

A problem with many existing heterodimeric binding protein formats (e.g., bispecific antibodies and variants thereof) is that it can be difficult to purify only the desired heterodimeric species without also including either homodimeric species. Thus, a process for efficient purification of the desired, heterodimeric binding protein is of great interest, e.g., for industrial-scale production.

As described herein, binding proteins of the present disclosure can include several optional features, including without limitation knob and hole mutations (e.g., to promote proper heterodimer formation) and mutations to improve purification. In addition, these binding proteins include two light chains, leading to four potential configurations: two kappa light chains, two lambda light chains, a kappa light chain on the arm with dual variable domains (the "CODV arm") and a lambda light chain on the traditional antibody arm (the "Fab arm"), and a lambda light chain on the CODV arm and a kappa light chain on the Fab arm.

Therefore, experiments were undertaken to identify a process that allows for efficient purification of the desired binding protein of interest. Binding protein variants were also tested for their efficiency of purification.

FIG. 28A shows a diagram of an exemplary binding protein of the present disclosure, indicating variations that lead to unique configurations. These experiments tested the effect of the placement of: kappa and lambda light chains (e.g., two kappa, two lambda, kappa on CODV arm and lambda on Fab arm, and lambda on CODV arm and kappa on Fab arm), knob and hole mutations (e.g., knob mutations on CODV arm and hole mutations on Fab arm, or hole mutations on CODV arm and knob mutations on Fab arm), and H435R/Y436F mutations ("RF mutations," e.g., RF mutations on CODV or Fab arm, or no RF mutations). A total of 18 different variants were tested, as shown in FIG. 28B. For these experiments, the CODV arm had antigen binding sites specific for TNFa (i.e., VH and VL sequences of SEQ ID NOs:168 and 169, respectively) and IL4 (i.e., VH and VL sequences of SEQ ID NOs:170 and 171, respectively), whereas the Fab arm had an antigen binding site specific for IL13 (i.e., VH and VL sequences of SEQ ID NOs:172 and 173, respectively). S354C and T366W were used for the knob mutations, and Y349C, T366S, L368A, and Y407V were used for the hole mutations.

Figure 29:
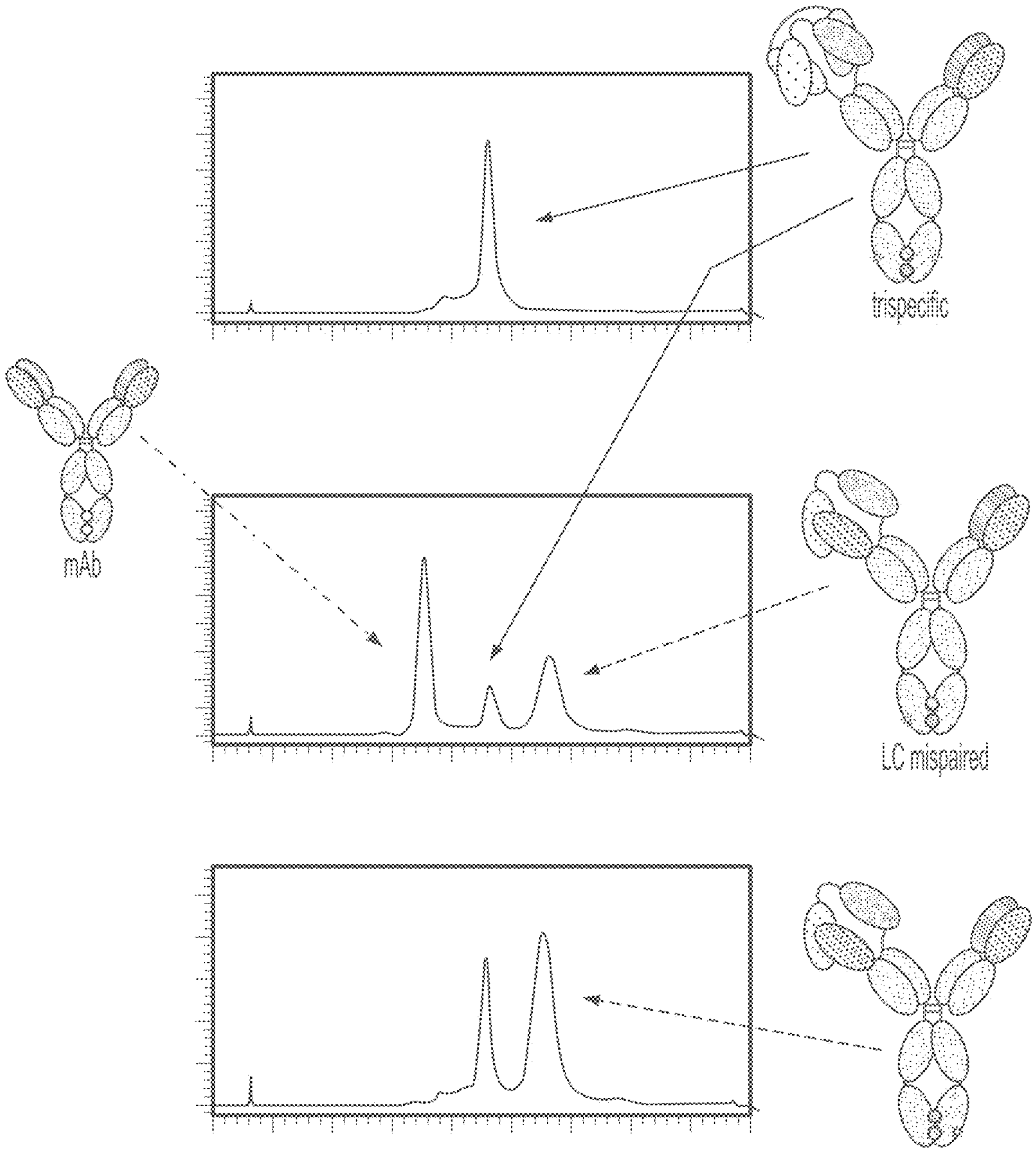
FIG. 29 shows representative chromatograms from analytical hydrophobic interaction chromatography (HIC), demonstrating that trispecific binding proteins were distinguishable from mispaired species.

Various processing steps were tested for the ability to monitor correct pairing of CODV and Fab arms (e.g., as opposed to CODV or Fab homodimers), as well as correct heavy chain-light chain pairing (e.g., as opposed to pairing between Fab arm light chain and CODV arm heavy chain, or between Fab arm heavy chain and CODV arm light chain). Analytical size exclusion chromatography (SEC) was found to be ineffective at distinguishing correct heavy chain and light chain pairing; binding proteins with Fab arm light chain mispaired with CODV heavy chain and homodimeric binding proteins with two Fab arms were found to co-elute with the desired trispecific binding proteins. However, analytical hydrophobic interaction chromatography (HIC) was found to resolve the desired trispecific binding proteins from binding proteins with Fab arm light chain mispaired with CODV heavy chain and homodimeric binding proteins with two Fab arms (FIG. 29).

Figure 30A:
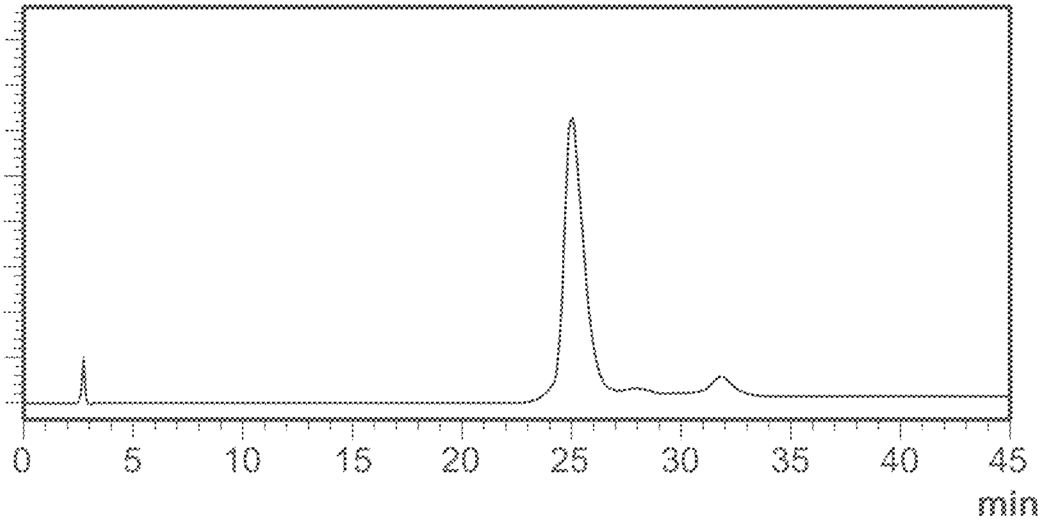
FIGS. 30A & 30B show the successful purification of a binding protein with lambda light chain for CODV arm, kappa light chain for Fab arm, knob mutations on CODV arm, hole mutations on Fab arm, and RF mutations on Fab arm by Protein A followed by KappaSelect (GE Healthcare) purification steps. Successful purification of binding protein from mispaired species was demonstrated by hydrophobic interaction chromatography (HIC.
Figure 30B:
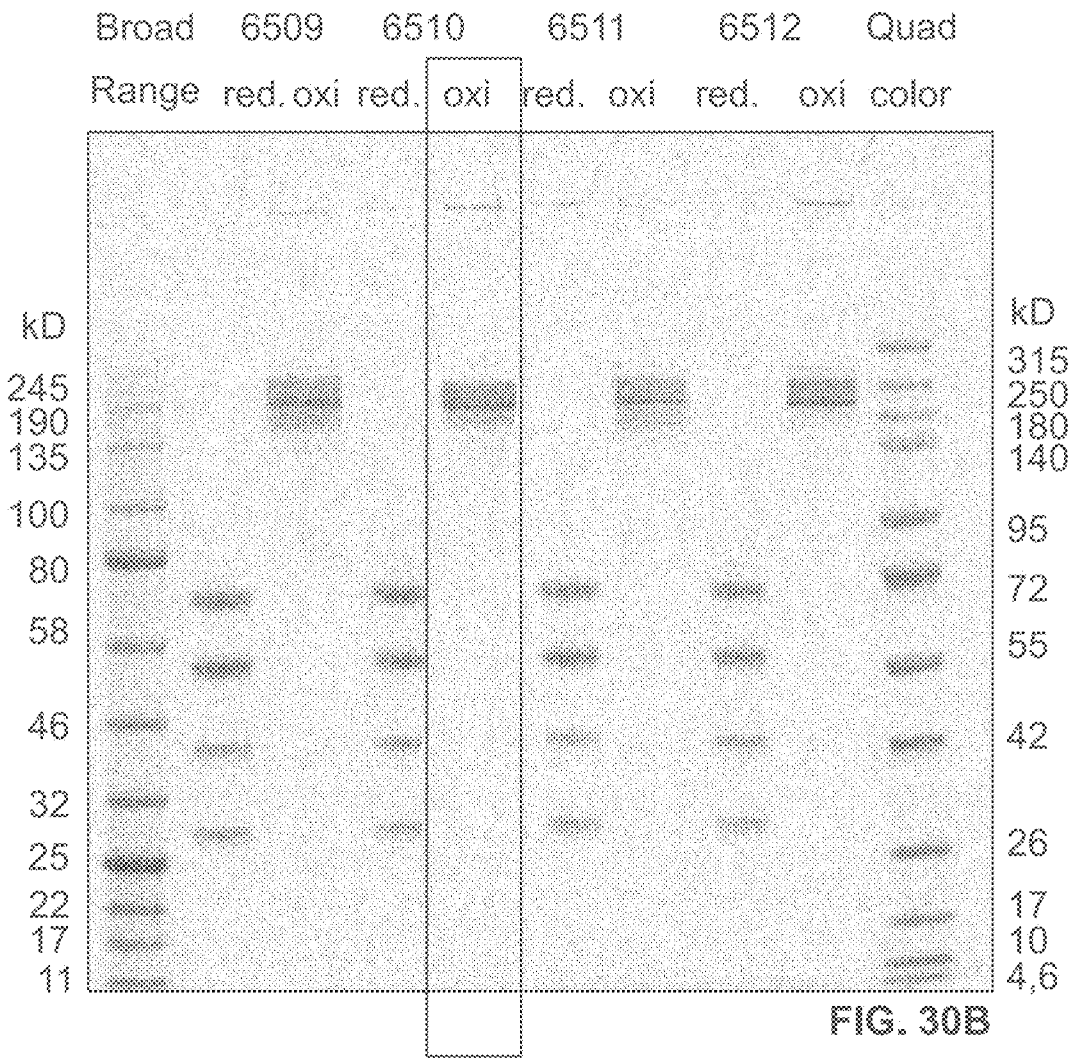

The 18 binding protein configurations shown in FIG. 28B were purified by Protein A affinity chromatography, then KappaSelect (GE Healthcare) purification. Species were monitored by HIC chromatography. One binding protein configuration was purified efficiently without inclusion of mispaired species: lambda light chain for CODV arm, kappa light chain for Fab arm, knob mutations on CODV arm, hole mutations on Fab arm, and RF mutations on Fab arm. HIC chromatography (FIG. 30A), SDS-PAGE (FIG. 30B), and intact mass analysis demonstrated that a single species corresponding to the desired trispecific binding protein was purified.

These results identify a binding protein configuration that allows for more efficient purification of binding proteins of interest away from mispaired species. Moreover, the purification process of Protein A followed by KappaSelect purification steps was shown to provide effective separation of binding proteins of interest away from mispaired species.

While the disclosure includes various embodiments, it is understood that variations and modifications will occur to those skilled in the art. Therefore, it is intended that the appended claims cover all such equivalent variations that come within the scope of the disclosure. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

SEQUENCES

TABLE 1

Heavy and light chain SEQ ID NOs for binding proteins 1-21 and the target antigens to which the binding proteins are directed.

| Binding Protein # | SEQ ID NOs Included | Directed to: |
|---|---|---|
| 1 | 1, 2, 3, 4 | Her2 × (CD28 × CD3) |
| 2 | 1, 2, 9, 10 | Her2 × (CD28 × CD3) |
| 3 | 13, 14, 3, 4 | CD19 × (CD28 × CD3) |
| 4 | 13, 14, 9, 10 | CD19 × (CD28 × CD3) |
| 5 | 17, 18, 3, 4 | CD38 × (CD28 × CD3) |
| 6 | 17, 18, 9, 10 | CD38 × (CD28 × CD3) |
| 7 | 21, 22, 3, 4 | LAMP1 × (CD28 × CD3) |
| 8 | 21, 22, 9, 10 | LAMP1 × (CD28 × CD3) |
| 9 | 60, 61, 62, 63 | TNFa × (IL4 × IL13) |
| 10 | 60, 61, 68, 69 | TNFa × (IL13 × IL4) |
| 11 | 60, 71, 68, 69 | TNFa × (IL13 × IL4) |
| 12 | 73, 74, 75, 76 | IL13 × (IL4 × TNFa) |
| 13 | 73, 74, 81, 82 | IL13 × (TNFa × IL4) |
| 14 | 85, 86, 87, 88 | IL4 × (IL13 × TNFa) |
| 15 | 85, 86, 93, 94 | IL4 × (TNFa × IL13) |
| 16 | 73, 74, 68, 69 | IL13 × (IL13 × IL4) |
| 17 | 85, 86, 68, 69 | IL4 × (IL13 × IL4) |
| 18 | 73, 74, 62, 63 | IL13 × (IL4 × IL13) |
| 19 | 85, 86, 62, 63 | IL4 × (IL4 × IL13) |
| 20 | 114, 115, 3, 4 | CD20 × (CD28 × CD3) |
| 21 | 114, 115, 9, 10 | CD20 × (CD28 × CD3) |

TABLE 2

Heavy and light chain sequences of binding proteins specifically directed to Her2, CD3, CD28, CD19 and/or CD20. CDR sequences are bolded and italicized.

Binding Protein 1 Amino Acid Sequences

| | | |
|---|---|---|
| Heavy chain A (Anti-Her2-H_knob) | Anti-Her2-H_Knob:<br>Evqlvesggglvqpggsldscaas***gfnikdty***ihwvrqapgkglewvar***iyptngyt***<br>ryadsvkgrftisadtskntaylqlmnslraedtavyyc***rwggdgfyamdy***wgqgtl<br>vtvssastkgpsvfplapcsrstsestaalgclvkdyfpepvtvswnsgaltsgvhtfpa<br>vlqssglyslssvvtvpssslgtktytcnvdhkpsntkvdkrveskygppcppcpape<br>flggpsvflfppkpkdtlmisrtpevtcvvvdvsqedpevqfnwyvdgvevhnakt<br>kpreeqfnstyrvvsvltvlhqdwlngkeykckvsnkglpssiektiskakgqprepq<br>vytlppcqeemtknqvslwclvkgfypsdiavewesngqpennykttppvldsdgs<br>fflyskltvdksrwqegnvfscsvmhealhnhytqkslslslgk | SEQ ID NO: 1 |
| Light chain A (Anti-Her2-L) | Anti-Her2-L:<br>Diqmtqspsslsasvgdrvtitcras***qdvnta***vawyqqkpgkapklliy***sas***flysgv<br>psrfsgsrsgtdfdtisslqpedfatyy***qqhyttppt***fgqgtkveikrtvaapsyfifpp<br>sdeqlksgtasvvcllnnfypreakyqwkvdnalqsgnsqesvteqdskdstyslsstl<br>tlskadyekhkvyacevthqglsspvtksfnrgec | SEQ ID NO: 2 |
| Heavy chain B (Anti-CD28 × Anti-CD3-H_Hole) | Anti-CD28 × Anti-CD3-H_Hole:<br>Qvqlvqsgaevvkpgasvkvsckas***gytftsyy***ihwvrqapgqglewigs***i***<br>***ypgnvnt***nyaqkfqgratltvdtsistaymelsrlrsddtavyyc***trshygldw***<br>***nfdv***wgkgttvtvsssqvqlvesgggvvqpgrslrlscaas***gftftkaw***mhw<br>vrqapgkqlewvaq***ikdksns***yatyyadsvkgrftisrddskntlylqmnslr<br>aedtavyyc***rgvyyalspfdy***wgqgtlvtvssrtastkgpsvfplapcsrstses<br>taalgclvkdyfpepvtvswnsgaltsgvhtfpavlqssglyslssvvtvpsssl<br>gtktytcnvdhkpsntkvdkrveskygppcppcpapeflggpsvflfppkpk<br>dtlmisrtpevtcvvvdvsqedpevqfnwyvdgvevhnaktkpreeqfnst<br>yrvvsvltvlhqdwlngkeykckvsnkglpssiektiskakgqprepqvctlp<br>psqeemtknqvslscavkgfypsdiavewesngqpennykttppvldsdgs<br>fflvskltvdksrwqegnvfscsvmhealhnhytqkslslslgk | SEQ ID NO: 3 |
| Light chain B (Anti-CD3 × Anti-CD28-L) | Anti-CD3 × Anti-CD28-L:<br>Diymtqtplslsvtpgqpasisckss***qslvhnnanty***lswylqkpgqspqsliy kvs n<br>rfsgvpdrfsgsgsgtdftlkisrveaedygyyyc***gqgtqyp***ftfgsgtkveikgqpka<br>apdiqmtqspsslsasygdrvtitcqas***qniyvw***lnwyqqkpgkapklliy***kas***nlht<br>gvpsrfsgsgsgtdftltisslqpediatyyc***qqgqtypyt***fgqgtkleiktkgpsrtvaa | SEQ ID NO: 4 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | psvfifppsdeqlksgtasvvcllnnfypreakyqwkydnalqsgnsqesvteqdsk<br>dstyslsstltlskadyekhkvyacevthqglsspytksfnrgec | |
| | Binding Protein 1 Nucleotide Sequences | |
| Heavy chain A (Anti-Her2-H_Knob:) | Anti-Her2-H_Knob:<br>gaagtgcagctggtggaatctggcggcggactggtgcagcctggcggatctctgagact<br>gagctgtgccgccagcggcttcaacatcaaggacacctacatccactgggtgcgccag<br>gcccctggcaagggactggaatgggtggccagaatctaccccaccaacggctacacca<br>gatacgccgacagcgtgaagggccggttcaccatcagcgccgacaccagcaagaaca<br>ccgcctacctgcagatgaacagcctgcgggccgaggacaccgccgtgtactactgtagt<br>agatggggaggcgacggcttctacgccatggactattggggccagggcaccctcgtga<br>ccgtgtctagtgcgtcgaccaagggcccatcggtgttccctctggccccttgcagcagaa<br>gcaccagcgaatctacagccgccctgggctgcctcgtgaaggactactttcccgagccc<br>gtgaccgtgtcctggaactctggcgctctgacaagcggcgtgcacacctttccagccgtg<br>ctccagagcagcggcctgtactctctgagcagcgtcgtgacagtgcccagcagcagcct<br>gggcaccaagacctacacctgtaacgtggaccacaagcccagcaacaccaaggtgga<br>caagcgggtggaatctaagtacggccctccctgccctccttgcccagcccctgaatttctg<br>ggcggaccctccgtgttcctgttcccccaaagcccaaggacaccctgatgatcagccg<br>gacccccgaagtgacctgcgtggtggtggatgtgtcccaggaagatcccgaggtgcagt<br>tcaattggtacgtggacggcgtggaagtgcacaacgccaagaccaagcccagagagg<br>aacagttcaacagcacctaccgggtggtgtccgtgctgaccgtgctgcaccaggactgg<br>ctgaacggcaaagagtacaagtgcaaggtgtccaacaagggcctgcccagctccatcg<br>agaaaaccatcagcaaggccaagggccagccccgcgagcctcaagtgtataccctgcc<br>cccttgccaggaagagatgaccaagaaccaggtgtccctgtggtgtctcgtgaaaggctt<br>ctaccccagcgacattgccgtggaatgggagagcaacggccagcccgagaacaacta<br>caagaccacccccccctgtgctggacagcgacggctcattcttcctgtactccaagctgac<br>cgtggacaagagccggtggcaggaaggcaacgtgttcagctgctccgtgatgcacgag<br>gccctgcacaaccactacacccagaagtccctgtctctgtccctgggcaag | SEQ ID NO: 5 |
| Light chain A (Anti-Her2-L:) | Anti-Her2-L:<br>gacatccagatgacccagagccccagcagcctgtctgccagcgtgggcgacagagtga<br>ccatcacctgtagagccagccaggacgtgaacaccgccgtggcctggtatcagcagaa<br>gcctggcaaggcccccaagctgctgatctacagcgccagcttcctgtacagcggcgtgc<br>ccagcagattcagcggaagcagaagcggcaccgacttcaccctgaccatcagctccct<br>gcagcccgaggacttcgccacctactactgccagcagcactacaccacccccccacat<br>ttggccagggcaccaaggtggaaatcaagcgtacggtggccgctcccagcgtgttcatc<br>ttcccacctagcgacgagcagctgaagtccggcacagcctctgtcgtgtgcctgctgaac<br>aacttctacccccgcgaggccaaagtgcagtggaaggtggacaacgccctgcagagcg<br>gcaacagccaggaaagcgtgaccgagcaggacagcaaggactccacctacagcctga<br>gcagcaccctgacactgagcaaggccgactacgagaagcacaaggtgtacgcctgcg<br>aagtgacccaccagggcctgtctagccccgtgaccaagagcttcaaccggggcgagtg<br>t | SEQ ID NO: 6 |
| Heavy chain B (Anti-CD28 × Anti-CD3-H_Hole:) | Anti-CD28 × Anti-CD3-H_Hole:<br>caggtgcagctggtgcagtctggcgccgaggtcgtgaaacctggcgcctctgtgaaggt<br>gtcctgcaaggccagcggctacacctaaccagctactacatccactgggtgcgccagg<br>cccctggacagggactggaatggatcggcagcatctaccccggcaacgtgaacaccaa<br>ctacgcccagaagaccagggcagagccaccctgaccgtggacaccagcatcagcacc<br>gcctacatggaactgagccggctgagaagcgacgacaccgccgtgtactactgcaccc<br>ggtcccactacggcctggattggaacttcgacgtgtggggcaagggcaccaccgtgac<br>agtgtctagcagccaggtgcagctggtggaatctggcggcggagtggtgcagcctggc<br>agaagcctgagactgagctgtgccgccagcggcttcaccttcaccaaggcctggatgca<br>ctgggtgcgccaggcccctggaaagcagctggaatgggtggcccagatcaaggacaa<br>gagcaacagctacgccacctactacgccgacagcgtgaagggccggttcaccatcagc<br>cgggacgacagcaagaacaccctgtacctgcagatgaacagcctgcgggccgaggac<br>accgccgtgtactactgtcggggcgtgtactatgccctgagccccttcgattactggggcc<br>agggaaccctcgtgaccgtgtctagtcggaccgccagcacaaagggcccatcggtgttc<br>cctctggccccttgcagcagaagcaccagcgaatctacagccgccctgggctgcctcgt<br>gaaggactactttcccgagcccgtgaccgtgtcctggaactctggcgctctgacaagcg<br>gcgtgcacacctttccagccgtgctccagagcagcggcctgtactctctgagcagcgtcg<br>tgacagtgcccagcagcagcctgggcaccaagacctacacctgtaacgtggaccacaa<br>gcccagcaacaccaaggtggacaagcgggtggaatctaagtacggccctccctgccct<br>ccttgcccagcccctgaatactgggcggaccctccgtgacctgacccccccaaagccca<br>aggacaccctgatgatcagccggacccccgaagtgacctgcgtggtggtggatgtgtcc<br>caggaagatcccgaggtgcagttcaattggtacgtggacggcgtggaagtgcacaacg<br>ccaagaccaagcccagagaggaacagttcaacagcacctaccgggtggtgtccgtgct<br>gaccgtgctgcaccaggactggctgaacggcaaagagtacaagtgcaaggtgtccaac<br>aagggcctgcccagctccatcgagaaaaccatcagcaaggccaagggccagccccgc<br>gagcctcaagtgtgtaccctgccccctagccaggaagagatgaccaagaaccaggtgtc<br>cctgagctgtgccgtgaaaggcttctaccccagcgacattgccgtggaatgggagagca<br>acggccagcccgagaacaactacaagaccacccccccctgtgctggacagcgacggct<br>cattcttcctggtgtccaagctgaccgtggacaagagccggtggcaggaaggcaacgtg<br>ttcagctgctccgtgatgcacgaggccctgcacaaccactacacccagaagtccctgtct<br>ctgtccctgggcaag | SEQ ID NO: 7 |

TABLE 2-continued

| Heavy and light chain sequences of binding proteins specifically directed to Her2, CD3, CD28, CD19 and/or CD20. CDR sequences are bolded and italicized. | | |
|---|---|---|
| Light chain B (Anti-CD3 × Anti-CD28-L:) | Anti-CD3 × Anti-CD28-L:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagcccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatccagatgacccagagccccagcagcctgtctgccagcgtgggcga<br>cagagtgaccatcacctgtcaggccagccagaacatctacgtgtggctgaactggtatca<br>gcagaagcccggcaaggcccccaagctgctgatctacaaggccagcaacctgcacac<br>cggcgtgcccagcagattttctggcagcggctccggcaccgacttcaccctgacaatca<br>gctccctgcagcccgaggacattgccacctactactgccagcagggccagacctacccc<br>tacacctttggccagggcaccaagctggaaatcaagaccaagggccccagccgtacgg<br>tggccgctcccagcgtgttcatcttcccacctagcgacgagcagctgaagtccggcaca<br>gcctctgtcgtgtgcctgctgaacaacttctacccccgcgaggccaaagtgcagtggaag<br>gtggacaacgccctgcagagcggcaacagccaggaaagcgtgaccgagcaggacag<br>caaggactccacctacagcctgagcagcaccctgacactgagcaaggccgactacgag<br>aagcacaaggtgtacgcctgcgaagtgacccaccagggcctgtctagccccgtgacca<br>agagcttcaaccggggcgagtgt | SEQ ID NO: 8 |
| | Binding Protein 2 Amino Acid Sequences | |
| Heavy chain A (Anti-Her2-H_knob) | Anti-Her2-H_Knob:<br>Evqlvesggglvqpggsldscaas***gfnikdty***ihwvrqapgkglewvar***iyptngyt***<br>ryadsvkgrftisadtskntaylqlmnslraedtavyyc***rwggdgfyamdy***wgqgtl<br>vtvssastkgpsvfplapcsrstsestaalgclvkdyfpepvtvswnsgaltsgvhtfpa<br>vlqssglyslssvvtvpssslgtktytcnvdhkpsntkvdkrveskygppcppcpape<br>flggpsvflfppkpkdtlmisrtpevtcvvvdvsqedpevqfnwyvdgvevhnakt<br>kpreeqfnstyrvvsvltvlhqdwlngkeykckvsnkglpssiektiskakgqprepq<br>vytlppcqeemtknqvslwclvkgfypsdiavewesngqpennykttppvldsdgs<br>fflyskltvdksrwqegnvfscsvmhealhnhytqkslslslgk | SEQ ID NO: 1 |
| Light chain A (Anti-Her2-L) | Anti-Her2-L:<br>Diqmtqspsslsasvgdrvtitcras***qdvnta***vawyqqkpgkapklliy***sas***flysgv<br>psrfsgsrsgtdfdtisslqpedfatyy***qqhyttppt***fgqgtkveikrtvaapsyfifpp<br>sdeqlksgtasvvcllnnfypreakyqwkvdnalqsgnsqesvteqdskdstyslsstl<br>tlskadyekhkvyacevthqglsspvtksfnrgec | SEQ ID NO: 2 |
| Heavy chain B (Anti-CD28 × Anti-CD3-H_Hole) | Anti-CD28 × Anti-CD3-H_Hole<br>Qvqlqesgpglvkpsqtlsltctvsgfslsdygvhwvrqppgkglewlgviw<br>agggtnynpslksrktiskdtsknqvslklssvtaadtavyycardkgysyyys<br>mdywgqgttvtvsssqvqlvesgggvvqpgrslrlscaasgftftkawmhw<br>vrqapgkqlewvaqikdksnsyatyyadsvkgrftisrddskntlylqmnslr<br>aedtavyycrgvyyalspfdywgqgtlvtvssrtastkgpsvfplapcsrstses<br>taalgclvkdyfpepvtvswnsgaltsgvhtfpavlqssglyslssvvtvpsssl<br>gtktytcnvdhkpsntkvdkrveskygppcppcpapeflggpsvflfppkpk<br>dtlmisrtpevtcvvvdvsqedpevqfnwyvdgvevhnaktkpreeqfnst<br>yrvvsvltvlhqdwlngkeykckvsnkglpssiektiskakgqprepqvctlp<br>psqeemtknqvslscavkgfypsdiavewesngqpennykttppvldsdgs<br>fflvskltvdksrwqegnvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslyhnnantylswylqkpgqspqsliykvsn<br>rfsgvpdrfsgsgsgtdftlkisrveaedvgvyycgqgtqypftfgsgtkveikgqpka<br>apdivltqspaslavspgqratitcrasesveyyvtslmqwyqqkpgqppkllifaasn<br>vesgvparfsgsgsgtdftltinpveandvanyycqqsrkvpytfgqgtkleiktkgps<br>rtvaapsvfifppsdeqlksgtasyycllnnfypreakvqwkvdnalqsgnsqesvte<br>qdskdstyslsstltlskadyekhkvyacevthqglsspvtksfnrgec | SEQ ID NO: 10 |
| | Binding Protein 2 Nucleotide Sequences | |
| Heavy chain A (Anti-Her2-H_Knob:) | Anti-Her2-H_Knob:<br>gaagtgcagctggtggaatctggcggcggactggtgcagcctggcggatctctgagact<br>gagctgtgccgccagcggcttcaacatcaaggacacctacatccactgggtgcgccagg<br>cccctggcaagggactggaatgggtggccagaatctaccccaccaacggctacaccag<br>atacgccgacagcgtgaagggccggttcaccatcagcgccgacaccagcaagaacac<br>cgcctacctgcagatgaacagcctgcgggccgaggacaccgccgtgtactactgtagta<br>gatggggaggcgacggcttctacgccatggactattggggccagggcaccctcgtgac<br>cgtgtctagtgcgtcgaccaagggcccatcggtgttccctctggccccttgcagcagaag<br>caccagcgaatctacagccgccctgggctgcctcgtgaaggactactttcccgagcccgt<br>gaccgtgtcctggaactctggcgctctgacaagcggcgtgcacacctttccagccgtgct<br>ccagagcagcggcctgtactctctgagcagcgtcgtgacagtgcccagcagcagcctg<br>ggcaccaagacctacacctgtaacgtggaccacaagcccagcaacaccaaggtggaca<br>agcgggtggaatctaagtacggccctccctgccctccttgcccagcccctgaatttctggg<br>cggaccctccgtgttcctgttccccccaaagcccaaggacaccctgatgatcagccggac<br>cccgaagtgacctgcgtggtggtggatgtgtcccaggaagatcccgaggtgcagttca | SEQ ID NO: 5 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | attggtacgtggacggcgtggaagtgcacaacgccaagaccaagcccagagaggaac<br>agttcaacagcacctaccgggtggtgtccgtgctgaccgtgctgcaccaggactggctga<br>acggcaaagagtacaagtgcaaggtgtccaacaagggcctgcccagctccatcgagaa<br>aaccatcagcaaggccaagggccagccccgcgagcctcaagtgtataccctgccccctt<br>gccaggaagagatgaccaagaaccaggtgtccctgtggtgtctcgtgaaaggcnctacc<br>ccagcgacattgccgtggaatgggagagcaacggccagcccgagaacaactacaaga<br>ccaccccccctgtgctggacagcgacggctcattcttcctgtactccaagctgaccgtgga<br>caagagccggtggcaggaaggcaacgtgttcagctgctccgtgatgcacgaggccctg<br>cacaaccactacacccagaagtccctgtctctgtccctgggcaag | |
| Light chain A (Anti-Her2-L:) | Anti-Her2-L:<br>gacatccagatgacccagagccccagcagcctgtctgccagcgtgggcgacagagtga<br>ccatcacctgtagagccagccaggacgtgaacaccgccgtggcctggtatcagcagaa<br>gcctggcaaggcccccaagctgctgatctacagcgccagcttcctgtacagcggcgtgc<br>ccagcagattcagcggaagcagaagcggcaccgacttcaccctgaccatcagctccctg<br>cagcccgaggacttcgccacctactactgccagcagcactacaccacccccccacattt<br>ggccagggcaccaaggtggaaatcaagcgtacggtggccgctcccagcgtgttcatctt<br>cccacctagcgacgagcagctgaagtccggcacagcctctgtcgtgtgcctgctgaaca<br>acttctacccccgcgaggccaaagtgcagtggaaggtggacaacgccctgcagagcgg<br>caacagccaggaaagcgtgaccgagcaggacagcaaggactccacctacagcctgag<br>cagcaccctgacactgagcaaggccgactacgagaagcacaaggtgtacgcctgcgaa<br>gtgacccaccagggcctgtctagccccgtgaccaagagcttcaaccggggcgagtgt | SEQ ID NO: 6 |
| Heavy chain B (Anti-CD28 × Anti-CD3-H_Hole:) | Anti-CD28 × Anti-CD3_Hole:<br>caggtgcagctgcaggaatctggccctggcctcgtgaagcctagccagaccctgagcct<br>gacctgtaccgtgtccggcttcagcctgagcgactacggcgtgcactgggtgcgccagc<br>cacctggaaaaggcctggaatggctgggcgtgatctgggctggcggaggcaccaacta<br>caaccccagcctgaagtccagaaagaccatcagcaaggacaccagcaagaaccaggt<br>gtccctgaagctgagcagcgtgacagccgccgataccgccgtgtactactgcgccagag<br>acaagggctacagctactactacagcatggactactggggccagggcaccaccgtgac<br>cgtgtcatcctctcaggtgcagctggtggaatctggcggcggagtggtgcagcctggca<br>gaagcctgagactgagctgtgccgccagcggcttcaccttcaccaaggcctggatgcac<br>tgggtgcgccaggcccctggaaagcagctggaatgggtggcccagatcaaggacaag<br>agcaacagctacgccacctactacgccgacagcgtgaagggccggttcaccatcagcc<br>gggacgacagcaagaacaccctgtacctgcagatgaacagcctgcgggccgaggaca<br>ccgccgtgtactactgtcggggcgtgtactatgccctgagccccttcgattactggggcca<br>gggaaccctcgtgaccgtgtctagtcggaccgcttcgaccaagggcccatcggtgttccc<br>tctggccccttgcagcagaagcaccagcgaatctacagccgccctgggctgcctcgtga<br>aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagcccctgaatttctgggcggaccctccgtgttcctgttccccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgcccccctagccaggaagagatgaccaagaaccaggtgtccctg<br>agctgtgccgtgaaaggcttctaccccagcgacattgccgtggaatgggagagcaacgg<br>ccagcccgagaacaactacaagaccaccccccctgtgctggacagcgacggctcattct<br>tcctggtgtccaagctgaccgtggacaagagccggtggcaggaaggcaacgtgttcagc<br>tgctccgtgatgcacgaggccctgcacaaccactacacccagaagtccctgtctctgtcc<br>ctgggcaag | SEQ ID NO: 11 |
| Light chain B (Anti-CD3 × Anti-CD28-L | Anti-CD3 × Anti-CD28-L:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagcccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatcgtgctgacacagagccctgctagcctggccgtgtctcctggacaga<br>gggccaccatcacctgtagagccagcgagagcgtggaatattacgtgaccagcctgatg<br>cagtggtatcagcagaagcccggccagcccccaagctgctgattttcgccgccagcaa<br>cgtggaaagcggcgtgccagccagattttccggcagcggctctggcaccgacttcaccc<br>tgaccatcaaccccgtggaagccaacgacgtggccaactactactgccagcagagccg<br>gaaggtgccctacacctttggccagggcaccaagctggaaatcaagaccaagggcccc<br>agccgtacggtggccgctcccagcgtgttcatcttcccacctagcgacgagcagctgaa<br>gtccggcacagcctctgtcgtgtgcctgctgaacaacttctacccccgcgaggccaaagt<br>gcagtggaaggtggacaacgccctgcagagcggcaacagccaggaaagcgtgaccg<br>agcaggacagcaaggactccacctacagcctgagcagcaccctgacactgagcaagg<br>ccgactacgagaagcacaaggtgtacgcctgcgaagtgacccaccagggcctgtctag<br>ccccgtgaccaagagcttcaaccggggcgagtgt | SEQ ID NO: 12 |

TABLE 2-continued

Heavy and light chain sequences of binding proteins specifically directed to Her2, CD3, CD28, CD19 and/or CD20. CDR sequences are bolded and italicized.

Binding Protein 3 Amino Acid Sequences

| | | |
|---|---|---|
| Heavy chain A (Anti-CD19(B34)-H_knob) | Anti-CD19(B34)-H_Knob:<br>Qvqlvqsgaevkkpgssvkvsckasgyafssywmnwyrqapgqglewigqiwp<br>gdgdtnynqkfkgratltadeststaymelsslrsedtavyycarretttvgryyyamdy<br>wgqgttvtvssastkgpsvfplapcsrstsestaalgclvkdyfpepvtvswnsgaltsg<br>vhtfpavlqssglyslssvvtvpssslgtktytcnvdhkpsntkvdkrveskygppcpp<br>cpapeflggpsvflfppkpkdtlmisrtpevtcvvvdvsqedpevqfnwyvdgvev<br>hnaktkpreeqfnstyrvvsvltvlhqdwlngkeykckvsnkglpssiektiskakgq<br>prepqvytlppcqeemtknqvslwclvkgfypsdiavewesngqpennykttppvl<br>dsdgsfflyskltvdksrwqegnvfscsvmhealhnhytqkslslslgk | SEQ ID NO: 13 |
| Light chain A (Anti-CD19(B34)-L) | Anti-CD19(B34)-L:<br>Dlvltqspaslavspgqratitckasqsvdydgdsylnwyqqkpgqppklliydasnl<br>vsgvparfsgsgsgtdftltinpveandtanyycqqstedpwtfgqgtkleikrtvaaps<br>vfifppsdeqlksgtasvvcllnnfypreakvqwkvdnalqsgnsqesvteqdskdst<br>yslsstltlskadyekhkvyacevthqglsspvtksfnrgec | SEQ ID NO: 14 |
| Heavy chain B (Anti-CD28 × Anti-CD3-H_Hole) | Anti-CD28 × Anti-CD3-H_Hole:<br>Qvqlvqsgaevvkpgasvkvsckas***gytftsyy***ihwvrqapgqglewigs***iy***<br>***pgnvnt***nyaqkfqgratltvdtsistaymelsrlrsddtavyyc***trshygldwnf***<br>***dv***wgkgttvtvsssqvqlvesgggvvqpgrslrlscaas***gftftkaw***mhwvr<br>qapgkqlewvaq***ikdksn***yatyyadsvkgrftisrddskntlylqmnslrae<br>dtavyyc***rgvyyalspfdy***wgqgtlvtvssrtastkgpsvfplapcsrstsestaa<br>lgclvkdyfpepvtvswnsgaltsgvhtfpavlqssglyslssvvtvpssslgtkt<br>ytcnvdhkpsntkvdkrveskygppcppcpapeflggpsvflfppkpkdtl<br>misrtpevtcvvvdvsqedpevqfnwyvdgvevhnaktkpreeqfnstyrv<br>vsvltvlhqdwlngkeykckvsnkglpssiektiskakgqprepqvctlppsq<br>eemtknqvslscavkgfypsdiavewesngqpennykttppvldsdgsfflv<br>skltvdksrwqegnvfscsvmhealhnhytqkslslslgk | SEQ ID NO: 3 |
| Light chain B (Anti-CD3 × Anti-CD28-L) | Anti-CD3 × Anti-CD28-L:<br>Divmtqtplslsvtpgqpasisckss***qslvhnnanty***lswylqkpgqspqsliy***kv***sn<br>rfsgvpdrfsgsgsgtdftlkisrveaedvgvyyc***gqgtqyp***ftfgsgtkveikgqpka<br>apdiqmtqspsslsasvgdrvtitcqas***qniyvw***lnwyqqkpgkapklliy***kas***nlht<br>gvpsrfsgsgsgtdftltisslqpediatyyc***qqgqtypyt***fgqgtkleiktkgpsrtvaap<br>svfifppsdeqlksgtasvvcllnnfypreakvqwkvdnalqsgnsqesvteqdskds<br>tyslsstltlskadyekhkvyacevthqglsspvtksfnrgec | SEQ ID NO: 4 |

Binding Protein 3 Nucleotide Sequences

| | | |
|---|---|---|
| Heavy chain A (Anti-CD19(B34)-H_Knob) | Anti-CD19(B34)-H_Knob:<br>caggtgcagctggtgcagagcggcgccgaagtgaagaagcctggcagcagcgtgaag<br>gtgagctgcaaggccagcggctatgccttcagcagctactggatgaactgggtgaggca<br>ggcacctggccagggcctggagtggataggccaaatatggcctggcgatggcgacacc<br>aactacaaccagaagttcaagggcagagcgaccttgaccgccgacgagagcaccagc<br>accgcgtacatggagctgagcagcctgaggagcgaggacaccgccgtgtactattgcg<br>ccagaagggagaccaccaccgtgggcaggtactactacgccatggactactggggcca<br>gggaaccaccgtgaccgtgagcagcgcctcgaccaagggcccatcggtgttccctctg<br>gccccttgcagcagaagcaccagcgaatctacagccgccctgggctgcctcgtgaagg<br>actactttcccgagcccgtgaccgtgtcctggaactctggcgctctgacaagcggcgtgc<br>acacctttccagccgtgctccagagcagcggcctgtactctctgagcagcgtcgtgacag<br>tgcccagcagcagcctgggcaccaagacctacacctgtaacgtggaccacaagcccag<br>caacaccaaggtggacaagcgggtggaatctaagtacggccctccctgccctccttgcc<br>cagcccctgaatttctgggcggaccctccgtgttcctgttccccccaaagcccaaggaca<br>ccctgatgatcagccggacccccgaagtgacctgcgtggtggtggatgtgtcccaggaa<br>gatcccgaggtgcagttcaattggtacgtggacggcgtggaagtgcacaacgccaagac<br>caagcccagagaggaacagttcaacagcacctaccgggtggtgtccgtgctgaccgtgc<br>tgcaccaggactggctgaacggcaaagagtacaagtgcaaggtgtccaacaagggcct<br>gcccagctccatcgagaaaaccatcagcaaggccaagggccagccccgcgagcctca<br>agtgtataccctgcccccttgccaggaagagatgaccaagaaccaggtgtccctgtggtg<br>tctcgtgaaaggcttctaccccagcgacattgccgtggaatgggagagcaacggccagc<br>ccgagaacaactacaagaccacccccccctgtgctggacagcgacggctcattcttcctgt<br>actccaagctgaccgtggacaagagccggtggcaggaaggcaacgtgttcagctgctc<br>cgtgatgcacgaggccctgcacaaccactacacccagaagtccctgtctctgtccctggg<br>caag | SEQ ID NO: 15 |
| Light chain A (Anti-CD19(B34)-L) | Anti-CD19(B34)-L:<br>gacctcgtgctgacccagagccctgcgagcctggctgtgagccctggccagagagcca<br>ccatcacctgcaaagccagccagagcgtggactacgacggcgacagctacctcaactg<br>gtaccagcagaagcctggccagcccccaagctgctgatttacgatgccagcaacctgg<br>tgagcggcgtgcctgctagattcagcggctccggcagcggcaccgacttcaccctgacc<br>atcaaccccgtggaggccaacgacaccgccaactactactgccagcagagcacggag<br>gacccctggaccttcggccagggcacaaagctggagatcaagcgtacggtggccgctc<br>ccagcgtgttcatcacccacctagcgacgagcagctgaagtccggcacagcctctgtcg<br>tgtgcctgctgaacaacttctacccccgcgaggccaaagtgcagtggaaggtggacaac | SEQ ID NO: 16 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | gccctgcagagcggcaacagccaggaaagcgtgaccgagcaggacagcaaggactc<br>cacctacagcctgagcagcaccctgacactgagcaaggccgactacgagaagcacaag<br>gtgtacgcctgcgaagtgacccaccagggcctgtctagccccgtgaccaagagcttcaa<br>ccggggcgagtgt | |
| Heavy chain B (Anti-CD28 × Anti-CD3-H_Hole) | Anti-CD28 × Anti-CD3-H_Hole:<br>caggtgcagctggtgcagtctggcgccgaggtcgtgaaacctggcgcctctgtgaaggt<br>gtcctgcaaggccagcggctacacctaaccagctactacatccactgggtgcgccaggc<br>ccctggacagggactggaatggatcggcagcatctaccccggcaacgtgaacaccaac<br>tacgcccagaagttccagggcagagccaccctgaccgtggacaccagcatcagcaccg<br>cctacatggaactgagccggctgagaagcgacgacaccgccgtgtactactgcacccg<br>gtcccactacggcctggattggaacttcgacgtgtggggcaagggcaccaccgtgacag<br>tgtctagcagccaggtgcagctggtggaatctggcggcggagtggtgcagcctggcag<br>aagcctgagactgagctgtgccgccagcggcttcaccttcaccaaggcctggatgcact<br>gggtgcgccaggcccctggaaagcagctggaatgggtggcccagatcaaggacaaga<br>gcaacagctacgccacctactacgccgacagcgtgaagggccggttcaccatcagccg<br>ggacgacagcaagaacaccctgtacctgcagatgaacagcctgcgggccgaggacac<br>cgccgtgtactactgtcggggcgtgtactatgccctgagccccttcgattactggggccag<br>ggaaccctcgtgaccgtgtctagtcggaccgccagcacaaagggcccatcggtgaccc<br>tctggccccttgcagcagaagcaccagcgaatctacagccgccctgggctgcctcgtga<br>aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagcccctgaatttctgggcggaccctccgtgacctgacccccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgcccccctagccaggaagagatgaccaagaaccaggtgtccctg<br>agctgtgccgtgaaaggcttctaccccagcgacattgccgtggaatgggagagcaacgg<br>ccagcccgagaacaactacaagaccaccccccctgtgctggacagcgacggctcattct<br>tcctggtgtccaagctgaccgtggacaagagccggtggcaggaaggcaacgtgttcagc<br>tgctccgtgatgcacgaggccctgcacaaccactacacccagaagtccctgtctctgtcc<br>ctgggcaag | SEQ ID NO: 7 |
| Light chain B (Anti-CD3 × Anti-CD28-L:) | Anti-CD3 × Anti-CD28-L:<br>gacatcgtgatgacccagaccccccctgagcctgagcgtgacacctggacagcctgcca<br>gcatcagctgcaagagcagccagagcctggtgcacaacaacgccaacacctacctgag<br>ctggtatctgcagaagcccggccagagcccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatccagatgacccagagccccagcagcctgtctgccagcgtgggcgac<br>agagtgaccatcacctgtcaggccagccagaacatctacgtgtggctgaactggtatcag<br>cagaagcccggcaaggcccccaagctgctgatctacaaggccagcaacctgcacaccg<br>gcgtgcccagcagattttctggcagcggctccggcaccgacttcaccctgacaatcagct<br>ccctgcagcccgaggacattgccacctactactgccagcagggccagacctacccctac<br>acctttggccagggcaccaagctggaaatcaagaccaagggccccagccgtacggtgg<br>ccgctcccagcgtgttcatcttcccacctagcgacgagcagctgaagtccggcacagcct<br>ctgtcgtgtgcctgctgaacaacttctacccccgcgaggccaaagtgcagtggaaggtgg<br>acaacgccctgcagagcggcaacagccaggaaagcgtgaccgagcaggacagcaag<br>gactccacctacagcctgagcagcaccctgacactgagcaaggccgactacgagaagc<br>acaaggtgtacgcctgcgaagtgacccaccagggcctgtctagccccgtgaccaagag<br>cttcaaccggggcgagtgt | SEQ ID NO: 8 |
| | **Binding Protein 4 Amino Acid Sequences** | |
| Heavy chain A (Anti-CD19(B34)-H_knob) | Anti-CD19(B34)-H_Knob:<br>Qvqlvqsgaevkkpgssvkvsckasgyafssywmnwyrqapgqglewigqiwp<br>gdgdtnynqkfkgratltadeststaymelsslrsedtavyycarretttvgryyyamdy<br>wgqgttvtvssastkgpsvfplapcsrstsestaalgclvkdyfpepvtvswnsgaltsg<br>yhtfpavlqssglyslssvvtvpssslgtktytcnvdhkpsntkvdkrveskygppcpp<br>cpapeflggpsvflfppkpkdtlmisrtpevtcvvvdvsqedpevqfnwyvdgvev<br>hnaktkpreeqfnstyrvvsvltvlhqdwlngkeykckvsnkglpssiektiskakgq<br>prepqvytlppcqeemtknqvslwclvkgfypsdiavewesngqpennykttppvl<br>dsdgsfflyskltvdksrwqegnvfscsvmhealhnhytqkslslslgk | SEQ ID NO: 13 |
| Light chain A (Anti-CD19(B34)-L) | Anti-CD19(B34)-L:<br>Dlvltqspaslavspgqratitckasqsvdydgdsylnwyqqkpgqppklliydasnl<br>vsgvparfsgsgsgtdftltinpveandtanyycqqstedpwtfgqgtkleikrtvaaps<br>vfifppsdeqlksgtasvvcllnnfypreakvqwkvdnalqsgnsqesvteqdskdst<br>yslsstltlskadyekhkvyacevthqglsspvtksfnrgec | SEQ ID NO: 14 |

TABLE 2-continued

| Heavy and light chain sequences of binding proteins specifically directed to Her2, CD3, CD28, CD19 and/or CD20. CDR sequences are bolded and italicized. | | |
|---|---|---|
| Heavy chain B (Anti-CD28 × Anti-CD3-H_Hole) | Anti-CD28 × Anti-CD3-H_Hole:<br>Qvqlqesgpglvkpsqtlsltctvsgfslsdygvhwvrqppgkglewlgviw<br>agggtnynpslksrktiskdtsknqvslklssvtaadtavyycardkgysyyys<br>mdywgqgttvtvsssqvqlvesgggvvqpgrslrlscaasgftftkawmhw<br>vrqapgkqlewvaqikdksnsyatyyadsvkgrftisrddskntlylqmnslr<br>aedtavyycrgvyyalspfdywgqgtlvtvssrtastkgpsvfplapcsrstses<br>taalgclvkdyfpepvtvswnsgaltsgvhtfpavlqssglyslssvvtvpsssl<br>gtktytcnvdhkpsntkvdkrveskygppcppcpapeflggpsvflfppkpk<br>dtlmisrtpevtcvvvdvsqedpevqfnwyvdgvevhnaktkpreeqfnsty<br>rvvsvltvlhqdwlngkeykckvsnkglpssiektiskakgqprepqvctlpp<br>sqeemtknqvslscavkgfypsdiavewesngqpennykttppvldsdgsff<br>lvskltvdksrwqegnvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsn<br>rfsgvpdrfsgsgsgtdftlkisrveaedvgvyycgqgtqypftfgsgtkveikgqpka<br>apdivltqspaslavspgqratitcrasesveyyvtslmqwyqqkpgqppkllifaasn<br>vesgvparfsgsgsgtdftltinpveandvanyycqqsrkvpytfgqgtkleiktkgps<br>rtvaapsvfifppsdeqlksgtasyycllnnfypreakvqwkvdnalqsgnsqesvte<br>qdskdstyslsstltlskadyekhkvyacevthqglsspvtksfnrgec | SEQ ID NO: 10 |
| Binding Protein 4 Nucleotide Sequences | | |
| Heavy chain A (Anti-CD19(B34)-H_Knob) | Anti-CD19(B34)-H_Knob:<br>caggtgcagctggtgcagagcggcgccgaagtgaagaagcctggcagcagcgtgaag<br>gtgagctgcaaggccagcggctatgccttcagcagctactggatgaactgggtgaggca<br>ggcacctggccagggcctggagtggataggccaaatatggcctggcgatggcgacacc<br>aactacaaccagaagttcaagggcagagcgaccttgaccgccgacgagagcaccagc<br>accgcgtacatggagctgagcagcctgaggagcgaggacaccgccgtgtactattgcg<br>ccagaagggagaccaccaccgtgggcaggtactactacgccatggactactggggcca<br>gggaaccaccgtgaccgtgagcagcgcctcgaccaagggcccatcggtgaccctctg<br>gccccttgcagcagaagcaccagcgaatctacagccgccctgggctgcctcgtgaagg<br>actactttcccgagcccgtgaccgtgtcctggaactctggcgctctgacaagcggcgtgc<br>acacctttccagccgtgctccagagcagcggcctgtactctctgagcagcgtcgtgacag<br>tgcccagcagcagcctgggcaccaagacctacacctgtaacgtggaccacaagcccag<br>caacaccaaggtggacaagcgggtggaatctaagtacggccctccctgccctccttgcc<br>cagcccctgaatttctgggcggaccctccgtgacctgacccccccaaagcccaaggaca<br>ccctgatgatcagccggacccccgaagtgacctgcgtggtggtggatgtgtcccaggaa<br>gatcccgaggtgcagttcaattggtacgtggacggcgtggaagtgcacaacgccaagac<br>caagcccagagaggaacagttcaacagcacctaccgggtggtgtccgtgctgaccgtgc<br>tgcaccaggactggctgaacggcaaagagtacaagtgcaaggtgtccaacaagggcct<br>gcccagctccatcgagaaaaccatcagcaaggccaagggccagccccgcgagcctca<br>agtgtataccctgccccccttgccaggaagagatgaccaagaaccaggtgtccctgtggtg<br>tctcgtgaaaggcttctaccccagcgacattgccgtggaatgggagagcaacggccagc<br>ccgagaacaactacaagaccaccccccctgtgctggacagcgacggctcattcttcctgt<br>actccaagctgaccgtggacaagagccggtggcaggaaggcaacgtgttcagctgctc<br>cgtgatgcacgaggccctgcacaaccactacacccagaagtccctgtctctgtccctggg<br>caag | SEQ ID NO: 15 |
| Light chain A (Anti-CD19(B34)-L) | Anti-CD19(B34)-L:<br>gacctcgtgctgacccagagccctgcgagcctggctgtgagccctggccagagagcca<br>ccatcacctgcaaagccagccagagcgtggactacgacggcgacagctacctcaactg<br>gtaccagcagaagcctggccagcccccaagctgctgatttacgatgccagcaacctgg<br>tgagcggcgtgcctgctagattcagcggctccggcagcggcaccgacttcaccctgacc<br>atcaaccccgtggaggccaacgacaccgccaactactactgccagcagagcacggag<br>gacccctggaccttcggccagggcacaaagctggagatcaagcgtacggtggccgctc<br>ccagcgtgttcatcttcccacctagcgacgagcagctgaagtccggcacagcctctgtcg<br>tgtgcctgctgaacaacttctacccccgcgaggccaaagtgcagtggaaggtggacaac<br>gccctgcagagcggcaacagccaggaaagcgtgaccgagcaggacagcaaggactc<br>cacctacagcctgagcagcaccctgacactgagcaaggccgactacgagaagcacaag<br>gtgtacgcctgcgaagtgacccaccagggcctgtctagccccgtgaccaagagcttcaa<br>ccggggcgagtgt | SEQ ID NO: 16 |
| Heavy chain B (Anti-CD28 × Anti-CD3-H_Hole:) | Anti-CD28 × Anti-CD3-H_Hole:<br>caggtgcagctgcaggaatctggccctggcctcgtgaagcctagccagaccctgagcct<br>gacctgtaccgtgtccggcttcagcctgagcgactacggcgtgcactgggtgcgccagc<br>cacctggaaaaggcctggaatggctgggcgtgatctgggctggcggaggcaccaacta<br>caaccccagcctgaagtccagaaagaccatcagcaaggacaccagcaagaaccaggt<br>gtccctgaagctgagcagcgtgacagccgccgataccgccgtgtactactgcgccagag<br>acaagggctacagctactactacagcatggactactggggccagggcaccaccgtgac<br>cgtgtcatcctctcaggtgcagctggtggaatctggcggcggagtggtgcagcctggca<br>gaagcctgagactgagctgtgccgccagcggcttcaccttcaccaaggcctggatgcac<br>tgggtgcgccaggcccctggaaagcagctggaatgggtggcccagatcaaggacaag<br>agcaacagctacgccacctactacgccgacagcgtgaaggccggttcaccatcagcc<br>gggacgacagcaagaacaccctgtacctgcagatgaacagcctgcgggccgaggaca<br>ccgccgtgtactactgtcggggcgtgtactatgccctgagccccttcgattactggggcca | |

TABLE 2-continued

| Heavy and light chain sequences of binding proteins specifically directed to Her2, CD3, CD28, CD19 and/or CD20. CDR sequences are bolded and italicized. | | |
|---|---|---|
| | gggaaccctcgtgaccgtgtctagtcggaccgcttcgaccaagggcccatcggtgttccc<br>tctggccccttgcagcagaagcaccagcgaatctacagccgccctgggctgcctcgtga<br>aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagcccctgaatttctgggcggaccctccgtgttcctgttccccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgcccccctagccaggaagagatgaccaagaaccaggtgtccctg<br>agctgtgccgtgaaaggcttctaccccagcgacattgccgtggaatgggagagcaacgg<br>ccagcccgagaacaactacaagaccacccccccctgtgctggacagcgacggctcattct<br>tcctggtgtccaagctgaccgtggacaagagccggtggcaggaaggcaacgtgttcagc<br>tgctccgtgatgcacgaggccctgcacaaccactacacccagaagtccctgtctctgtcc<br>ctgggcaag | |
| Light chain B (Anti-CD3 × Anti-CD28-L:) | Anti-CD3 × Anti-CD28-L:<br>gacatcgtgatgacccagaccccccctgagcctgagcgtgacacctggacagcctgcca<br>gcatcagctgcaagagcagccagagcctggtgcacaacaacgccaacacctacctgag<br>ctggtatctgcagaagcccggccagagccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatcgtgctgacacagagccctgctagcctggccgtgtctcctggacaga<br>gggccaccatcacctgtagagccagcgagagcgtggaatattacgtgaccagcctgatg<br>cagtggtatcagcagaagcccggccagccccccaagctgctgattttcgccgccagcaa<br>cgtggaaagcggcgtgccagccagattttccggcagcggctctggcaccgacttcaccc<br>tgaccatcaaccccgtggaagccaacgacgtggccaactactactgccagcagagccg<br>gaaggtgccctacacctttggccagggcaccaagctggaaatcaagaccaagggcccc<br>agccgtacggtggccgctcccagcgtgttcatcttcccacctagcgacgagcagctgaa<br>gtccggcacagcctctgtcgtgtgcctgctgaacaacttctacccccgcgaggccaaagt<br>gcagtggaaggtggacaacgccctgcagagcggcaacagccaggaaagcgtgaccg<br>agcaggacagcaaggactccacctacagcctgagcagcaccctgacactgagcaagg<br>ccgactacgagaagcacaaggtgtacgcctgcgaagtgacccaccagggcctgtctag<br>ccccgtgaccaagagcttcaaccggggcgagtgt | SEQ ID NO: 12 |
| Binding Protein 5 Amino Acid Sequences | | |
| Heavy chain A (Anti-CD38-H_knob) | Anti-CD38-H_Knob:<br>Qvqlvqsgaevakpgtsvklsckasgytftdywmqwykqrpgqglewigtiypgd<br>gdtgyaqkfqgkatltadkssktvymhlsslasedsavyycargdyygsnsldywgq<br>gtsvtvssastkgpsvfplapcsrstsestaalgclvkdyfpepvtvswnsgaltsgvhtf<br>pavlqssglyslssvvtvpssslgtktytcnvdhkpsntkvdkrveskygppcppcpa<br>peflggpsvflfppkpkdtlmisrtpevtcvvvdvsqedpevqfnwyvdgvevhna<br>ktkpreeqfnstyrvvsvltvlhqdwlngkeykckvsnkglpssiektiskakgqpre<br>pqvytlppcqeemtknqvslwclvkgfypsdiavewesngqpennykttppvldsd<br>gsfflyskltvdksrwqegnvfscsvmhealhnhytqkslslslgk | SEQ ID NO: 17 |
| Light chain A (Anti-CD38-L) | Anti-CD38-L:<br>Divmtqshlsmstslgdpvsitckasqdvstvvawyqqkpgqsprrliysasyryig<br>vpdrftgsgagtdftftissvqaedlavyycqqhysppytfgggtkleikrtvaapsyfif<br>ppsdeqlksgtasvvcllnnfypreakyqwkvdnalqsgnsqesvteqdskdstysls<br>stltlskadyekhkvyacevthqglsspvtksfnrgec | SEQ ID NO: 18 |
| Heavy chain B (Anti-CD28 × Anti-CD3-H_Hole) | Anti-CD28 × Anti-CD3-H_Hole<br>Qvqlvqsgaevvkpgasvkvsckas***gytftsyy***ihwvrqapgqglewigs***iy***<br>***pgnvnt***nyaqkfqgratltvdtsistaymelsrlrsddtavyyc***trshygldwn***<br>***fdv***wgkgttvtvsssqvqlvesgggvvqpgrslrlscaas***gftftkaw***mhwv<br>rqapgkqlewvaq***ikdksn***yatyyadsvkgrftisrddskntlylqmnslra<br>edtavyyc***rgvyyalspfdy***wgqgtlvtvssrtastkgpsvfplapcsrstsest<br>aalgclvkdyfpepvtvswnsgaltsgvhtfpavlqssglyslssvvtvpssslg<br>tktytcnvdhkpsntkvdkrveskygppcppcpapeflggpsvflfppkpkd<br>tlmisrtpevtcvvvdvsqedpevqfnwyvdgvevhnaktkpreeqfnstyr<br>vvsvltvlhqdwlngkeykckvsnkglpssiektiskakgqprepqvctlpps<br>qeemtknqvslscavkgfypsdiavewesngqpennykttppvldsdgsffl<br>vskltvdksrwqegnvfscsvmhealhnhytqkslslslgk | SEQ ID NO: 3 |
| Light chain B (Anti-CD3 × Anti-CD28-L) | Anti-CD3 × Anti-CD28-L:<br>Divmtqtplslsvtpgqpasisckss***qslvhnnanty***lswylqkpgqspqsliy***kvs***n<br>rfsgvpdrfsgsgsgtdftlkisrveaedvgvyyc***gqgtqyp***ftfgsgtkveikgqpka<br>apdiqmtqspsslsasvgdrvtitcqas***qniyvw***lnwyqqkpgkapklliy***kas***nlht<br>gvpsrfsgsgsgtdftltisslqpediatyyc***qqgqtypyt***fgqgtkleiktkgpsrtvaap<br>svfifppsdeqlksgtasvvcllnnfypreakvqwkvdnalqsgnsqesvteqdskds<br>tyslsstltlskadyekhkvyacevthqglsspvtksfnrgec | SEQ ID NO: 4 |

TABLE 2-continued

Heavy and light chain sequences of binding proteins specifically directed to Her2, CD3, CD28, CD19 and/or CD20. CDR sequences are bolded and italicized.

| Binding Protein 5 Nucleotide Sequences | | |
|---|---|---|
| Heavy chain A (Anti-CD38-H_Knob) | Anti-CD38-H_Knob:<br>caggtgcagctggtgcagtctggcgccgaagtggccaagcctggcacaagcgtgaagc<br>tgagctgcaaggccagcggctacaccttcaccgactactggatgcagtgggtcaagcag<br>aggccaggccagggcctggaatggatcggcacaatctatcccggcgacggcgatacc<br>ggctacgcccagaagtttcagggcaaggccaccctgaccgccgacaagagcagcaag<br>accgtgtacatgcacctgagcagcctggccagcgaggacagcgccgtgtactattgcgc<br>cagaggcgactactacggcagcaacagcctggactattggggccagggcaccagcgt<br>gacagtgtctagtgcgtcgaccaagggcccatcggtgttccctctggccccttgcagcag<br>aagcaccagcgaatctacagccgccctgggctgcctcgtgaaggactactttcccgagc<br>ccgtgaccgtgtcctggaactctggcgctctgacaagcggcgtgcacacctttccagccg<br>tgctccagagcagcggcctgtactctctgagcagcgtcgtgacagtgcccagcagcagc<br>ctgggcaccaagacctacacctgtaacgtggaccacaagcccagcaacaccaaggtgg<br>acaagcgggtggaatctaagtacggccctccctgccctccttgcccagcccctgaatttct<br>gggcggaccctccgtgttcctgttccccccaaagcccaaggacaccctgatgatcagcc<br>ggacccccgaagtgacctgcgtggtggtggatgtgtcccaggaagatcccgaggtgca<br>gttcaattggtacgtggacggcgtggaagtgcacaacgccaagaccaagcccagagag<br>gaacagttcaacagcacctaccgggtggtgtccgtgctgaccgtgctgcaccaggactg<br>gctgaacggcaaagagtacaagtgcaaggtgtccaacaagggcctgcccagctccatc<br>gagaaaaccatcagcaaggccaagggccagccccgcgagcctcaagtgtataccctgc<br>cccccttgccaggaagagatgaccaagaaccaggtgtccctgtggtgtctcgtgaaaggct<br>tctaccccagcgacattgccgtggaatgggagagcaacggccagcccgagaacaacta<br>caagaccaccccccctgtgctggacagcgacggctcattcttcctgtactccaagctgac<br>cgtggacaagagccggtggcaggaaggcaacgtgttcagctgctccgtgatgcacgag<br>gccctgcacaaccactacacccagaagtccctgtctctgtccctgggcaag | SEQ ID NO: 19 |
| Light chain A (Anti-CD38-L) | Anti-CD38-L:<br>gacatcgtgatgacccagagccacctgagcatgagcaccagcctgggcgaccccgtgt<br>ccatcacctgtaaagccagccaggacgtgtccaccgtggtggcctggtatcagcagaag<br>cctggccagagccccagacggctgatctacagcgccagctatcggtacatcggcgtgcc<br>cgacagattcaccggaagcggagccggcaccgacttcaccttcaccatcagctctgtgc<br>aggccgaggacctggccgtgtactactgccagcagcactacagccccccctacaccttt<br>ggcggaggcaccaagctggaaatcaagcgtacggtggccgctcccagcgtgttcatctt<br>cccacctagcgacgagcagctgaagtccggcacagcctctgtcgtgtgcctgctgaaca<br>acttctacccccgcgaggccaaagtgcagtggaaggtggacaacgccctgcagagcgg<br>caacagccaggaaagcgtgaccgagcaggacagcaaggactccacctacagcctgag<br>cagcaccctgacactgagcaaggccgactacgagaagcacaaggtgtacgcctgcgaa<br>gtgacccaccagggcctgtctagccccgtgaccaagagcttcaaccggggcgagtgt | SEQ ID NO: 20 |
| Heavy chain B (Anti-CD28 × Anti-CD3-H_Hole) | Anti-CD28 × Anti-CD3-H_Hole:<br>caggtgcagctggtgcagtctggcgccgaggtcgtgaaacctggcgcctctgtgaaggt<br>gtcctgcaaggccagcggctacacctttaccagctactacatccactgggtgcgccaggc<br>ccctggacagggactggaatggatcggcagcatctaccccggcaacgtgaacaccaac<br>tacgcccagaagttccagggcagagccaccctgaccgtggacaccagcatcagcaccg<br>cctacatggaactgagccggctgagaagcgacgacaccgccgtgtactactgcacccg<br>gtcccactacggcctggattggaacttcgacgtgtggggcaagggcaccaccgtgacag<br>tgtctagcagccaggtgcagctggtggaatctggcggcggagtggtgcagcctggcag<br>aagcctgagactgagctgtgccgccagcggcttcaccttcaccaaggcctggatgcact<br>gggtgcgccaggcccctggaaagcagctggaatgggtggcccagatcaaggacaaga<br>gcaacagctacgccacctactacgccgacagcgtgaagggccggttcaccatcagccg<br>ggacgacagcaagaacaccctgtacctgcagatgaacagcctgcgggccgaggacac<br>cgccgtgtactactgtcggggcgtgtactatgccctgagccccttcgattactggggccag<br>ggaaccctcgtgaccgtgtctagtcggaccgccagcacaaagggcccatcggtgaccc<br>tctggccccttgcagcagaagcaccagcgaatctacagccgccctgggctgcctcgtga<br>aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagcccctgaatttctgggcggaccctccgtgacctgaccccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgccccctagccaggaagagatgaccaagaaccaggtgtccctg<br>agctgtgccgtgaaaggcttctaccccagcgacattgccgtggaatgggagagcaacgg<br>ccagcccgagaacaactacaagaccaccccccctgtgctggacagcgacggctcattct<br>tcctggtgtccaagctgaccgtggacaagagccggtggcaggaaggcaacgtgttcag<br>ctgctccgtgatgcacgaggccctgcacaaccactacacccagaagtccctgtctctgtc<br>cctgggcaag | SEQ ID NO: 7 |

TABLE 2-continued

| Heavy and light chain sequences of binding proteins specifically directed to Her2, CD3, CD28, CD19 and/or CD20. CDR sequences are bolded and italicized. | | |
|---|---|---|
| Light chain B (Anti-CD3 × Anti-CD28-L:) | Anti-CD3 × Anti-CD28-L:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagcccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatccagatgacccagagccccagcagcctgtctgccagcgtgggcgac<br>agagtgaccatcacctgtcaggccagccagaacatctacgtgtggctgaactggtatcag<br>cagaagcccggcaaggcccccaagctgctgatctacaaggccagcaacctgcacacc<br>ggcgtgcccagcagattttctggcagcggctccggcaccgacttcaccctgacaatcag<br>ctccctgcagcccgaggacattgccacctactactgccagcagggccagacctacccct<br>acacctttggccagggcaccaagctggaaatcaagaccaagggccccagccgtacggt<br>ggccgctcccagcgtgttcatcttcccacctagcgacgagcagctgaagtccggcacag<br>cctctgtcgtgtgcctgctgaacaacttctacccccgcgaggccaaagtgcagtggaagg<br>tggacaacgccctgcagagcggcaacagccaggaaagcgtgaccgagcaggacagc<br>aaggactccacctacagcctgagcagcaccctgacactgagcaaggccgactacgaga<br>agcacaaggtgtacgcctgcgaagtgacccaccagggcctgtctagccccgtgaccaa<br>gagcttcaaccggggcgagtgt | SEQ ID NO: 8 |
| | Binding Protein 6 Amino Acid Sequences | |
| Heavy chain A (Anti-CD38-H_knob) | Anti-CD38-H_Knob:<br>qvqlvqsgaevakpgtsvklsckasgytftdywmqwykqrpgqglewigtiypgd<br>gdtgyaqkfqgkatltadkssktvymhlsslasedsavyycargdyygsnsldywgq<br>gtsvtvssastkgpsvfplapcsrstsestaalgclvkdyfpepvtvswnsgaltsgvhtf<br>pavlqssglyslssvvtvpssslgtktytcnvdhkpsntkvdkrveskygppcppcpa<br>peflggpsvflfppkpkdtlmisrtpevtcvvvdvsqedpevqfnwyvdgvevhna<br>ktkpreeqfnstyrvvsvltvlhqdwlngkeykckvsnkglpssiektiskakgqpre<br>pqyytlppcqeemtknqvslwclvkgfypsdiavewesngqpennykttppvldsd<br>gsfflyskltvdksrwqegnvfscsvmhealhnhytqkslslslgk | SEQ ID NO: 17 |
| Light chain A (Anti-CD38-L) | Anti-CD38-L:<br>Divmtqshlsmstslgdpvsitckasqdvstvvawyqqkpgqsprrliysasyryig<br>vpdrftgsgagtdftftissvqaedlavyycqqhysppytfgggtkleikrtvaapsyfif<br>ppsdeqlksgtasvvcllnnfypreakyqwkvdnalqsgnsqesvteqdskdstysls<br>stltlskadyekhkvyacevthqglsspvtksfnrgec | SEQ ID NO: 18 |
| Heavy chain B (Anti-CD28 × Anti-CD3-H_Hole) | Anti-CD28 × Anti-CD3-H_Hole<br>Qvqlqesgpglvkpsqtlsltctvsgfslsdygvhwvrqppgkglewlgviw<br>agggtnynpslksrktiskdtsknqvslklssvtaadtavyycardkgysyyys<br>mdywgqgttvtvsssqvqlvesgggvvqpgrslrlscaasgftftkawmhw<br>vrqapgkqlewvaqikdksnsyatyyadsvkgrftisrddskntlylqmnslr<br>aedtavyycrgvyyalspfdywgqgtlvtvssrtastkgpsvfplapcsrstses<br>taalgclvkdyfpepvtvswnsgaltsgvhtfpavlqssglyslssvvtvpsssl<br>gtktytcnvdhkpsntkvdkrveskygppcppcpapeflggpsvflfppkpk<br>dtlmisrtpevtcvvvdvsqedpevqfnwyvdgvevhnaktkpreeqfnsty<br>rvvsvltvlhqdwlngkeykckvsnkglpssiektiskakgqprepqvctlpp<br>sqeemtknqvslscavkgfypsdiavewesngqpennykttppvldsdgsff<br>lvskltvdksrwqegnvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsn<br>rfsgvpdrfsgsgsgtdftlkisrveaedvgvyycgqgtqypftfgsgtkveikgqpka<br>apdivltqspaslavspgqratitcrasesveyyvtslmqwyqqkpgqppkllifaasn<br>vesgvparfsgsgsgtdftltinpveandvanyycqqsrkvpytfgqgtkleiktkgps<br>rtvaapsvfifppsdeqlksgtasyycllnnfypreakvqwkvdnalqsgnsqesvte<br>qdskdstyslsstltlskadyekhkvyacevthqglsspvtksfnrgec | SEQ ID NO: 10 |
| | Binding Protein 6 Nucleotide Sequences | |
| Heavy chain A (Anti-CD38-H_Knob) | Anti-CD38-H_Knob:<br>caggtgcagctggtgcagtctggcgccgaagtggccaagcctggcacaagcgtgaagc<br>tgagctgcaaggccagcggctacaccttcaccgactactggatgcagtgggtcaagcag<br>aggccaggccagggcctggaatggatcggcacaatctatcccggcgacggcgatacc<br>ggctacgcccagaagtttcagggcaaggccaccctgaccgccgacaagagcagcaag<br>accgtgtacatgcacctgagcagcctggccagcgaggacagcgccgtgtactattgcgc<br>cagaggcgactactacggcagcaacagcctggactattggggccagggcaccagcgt<br>gacagtgtctagtgcgtcgaccaagggcccatcggtgttccctctggccccttgcagcag<br>aagcaccagcgaatctacagccgccctgggctgcctcgtgaaggactactttcccgagc<br>ccgtgaccgtgtcctggaactctggcgctctgacaagcggcgtgcacacctttccagccg<br>tgctccagagcagcggcctgtactctctgagcagcgtcgtgacagtgcccagcagcagc<br>ctgggcaccaagacctacacctgtaacgtggaccacaagcccagcaacaccaaggtgg<br>acaagcgggtggaatctaagtacggccctccctgccctccttgcccagcccctgaatttct<br>gggcggaccctccgtgttcctgttccccccaaagcccaaggacaccctgatgatcagcc<br>ggacccccgaagtgacctgcgtggtggtggatgtgtcccaggaagatcccgaggtgca | SEQ ID NO: 19 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | gttcaattggtacgtggacggcgtggaagtgcacaacgccaagaccaagcccagagag<br>gaacagttcaacagcacctaccgggtggtgtccgtgctgaccgtgctgcaccaggactg<br>gctgaacggcaaagagtacaagtgcaaggtgtccaacaagggcctgcccagctccatc<br>gagaaaaccatcagcaaggccaagggccagccccgcgagcctcaagtgtataccctgc<br>cccccttgccaggaagagatgaccaagaaccaggtgtccctgtggtgtctcgtgaaaggct<br>tctaccccagcgacattgccgtggaatgggagagcaacggccagcccgagaacaacta<br>caagaccaccccccctgtgctggacagcgacggctcattcttcctgtactccaagctgac<br>cgtggacaagagccggtggcaggaaggcaacgtgttcagctgctccgtgatgcacgag<br>gccctgcacaaccactacacccagaagtccctgtctctgtccctgggcaag | |
| Light chain A (Anti-CD38-L) | Anti-CD38-L:<br>gacatcgtgatgacccagagccacctgagcatgagcaccagcctgggcgaccccgtgt<br>ccatcacctgtaaagccagccaggacgtgtccaccgtggtggcctggtatcagcagaag<br>cctggccagagccccagacggctgatctacagcgccagctatcggtacatcggcgtgcc<br>cgacagattcaccggaagcggagccggcaccgacttcaccttcaccatcagctctgtgc<br>aggccgaggacctggccgtgtactactgccagcagcactacagcccccccctacacctttt<br>ggcggaggcaccaagctggaaatcaagcgtacggtggccgctcccagcgtgttcatctt<br>cccacctagcgacgagcagctgaagtccggcacagcctctgtcgtgtgcctgctgaaca<br>acttctacccccgcgaggccaaagtgcagtggaaggtggacaacgccctgcagagcgg<br>caacagccaggaaagcgtgaccgagcaggacagcaaggactccacctacagcctgag<br>cagcaccctgacactgagcaaggccgactacgagaagcacaaggtgtacgcctgcgaa<br>gtgacccaccagggcctgtctagccccgtgaccaagagcttcaaccggggcgagtgt | SEQ ID NO: 20 |
| Heavy chain B (Anti-CD28 × Anti-CD3-H_Hole:) | Anti-CD28 × Anti-CD3_Hole:<br>caggtgcagctgcaggaatctggccctggcctcgtgaagcctagccagaccctgagcct<br>gacctgtaccgtgtccggatcagcctgagcgactacggcgtgcactgggtgcgccagc<br>cacctggaaaaggcctggaatggctgggcgtgatctgggctggcggaggcaccaacta<br>caaccccagcctgaagtccagaaagaccatcagcaaggacaccagcaagaaccaggt<br>gtccctgaagctgagcagcgtgacagccgccgataccgccgtgtactactgcgccaga<br>gacaagggctacagctactactacagcatggactactggggccagggcaccaccgtga<br>ccgtgtcatcctctcaggtgcagctggtggaatctggcggcggagtggtgcagcctggc<br>agaagcctgagactgagctgtgccgccagcggcttcaccttcaccaaggcctggatgca<br>ctgggtgcgccaggcccctggaaagcagctggaatgggtggcccagatcaaggacaa<br>gagcaacagctacgccacctactacgccgacagcgtgaagggccggttcaccatcagc<br>cgggacgacagcaagaacaccctgtacctgcagatgaacagcctgcgggccgaggac<br>accgccgtgtactactgtcggggcgtgtactatgccctgagccccttcgattactggggcc<br>agggaaccctcgtgaccgtgtctagtcggaccgcttcgaccaagggcccatcggtgttcc<br>ctctggccccttgcagcagaagcaccagcgaatctacagccgccctgggctgcctcgtg<br>aaggactactttcccgagcccgtgaccgtgtcctggaactctggcgctctgacaagcggc<br>gtgcacacctttccagccgtgctccagagcagcggcctgtactctctgagcagcgtcgtg<br>acagtgcccagcagcagcctgggcaccaagacctacacctgtaacgtggaccacaagc<br>ccagcaacaccaaggtggacaagcgggtggaatctaagtacggccctccctgccctcct<br>tgcccagcccctgaatttctgggcggaccctccgtgttcctgttccccccaaagcccaag<br>gacaccctgatgatcagccggacccccgaagtgacctgcgtggtggtggatgtgtccca<br>ggaagatcccgaggtgcagttcaattggtacgtggacggcgtggaagtgcacaacgcc<br>aagaccaagcccagagaggaacagttcaacagcacctaccgggtggtgtccgtgctga<br>ccgtgctgcaccaggactggctgaacggcaaagagtacaagtgcaaggtgtccaacaa<br>gggcctgcccagctccatcgagaaaaccatcagcaaggccaagggccagccccgcga<br>gcctcaagtgtgtaccctgcccccctagccaggaagagatgaccaagaaccaggtgtccc<br>tgagctgtgccgtgaaaggcttctaccccagcgacattgccgtggaatgggagagcaac<br>ggccagcccgagaacaactacaagaccaccccccctgtgctggacagcgacggctcat<br>tcttcctggtgtccaagctgaccgtggacaagagccggtggcaggaaggcaacgtgttc<br>agctgctccgtgatgcacgaggccctgcacaaccactacacccagaagtccctgtctctg<br>tccctgggcaag | SEQ ID NO: 11 |
| Light chain B (Anti-CD3 × Anti-CD28-L | Anti-CD3 × Anti-CD28-L:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagcccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatcgtgctgacacagagccctgctagcctggccgtgtctcctggacaga<br>gggccaccatcacctgtagagccagcgagagcgtggaatattacgtgaccagcctgatg<br>cagtggtatcagcagaagcccggccagccccccaagctgctgattttcgccgccagcaa<br>cgtggaaagcggcgtgccagccagattttccggcagcggctctggcaccgacttcaccc<br>tgaccatcaaccccgtggaagccaacgacgtggccaactactactgccagcagagccg<br>gaaggtgccctacacctttggccagggcaccaagctggaaatcaagaccaagggcccc<br>agccgtacggtggccgctcccagcgtgttcatcttcccacctagcgacgagcagctgaa<br>gtccggcacagcctctgtcgtgtgcctgctgaacaacttctacccccgcgaggccaaagt<br>gcagtggaaggtggacaacgccctgcagagcggcaacagccaggaaagcgtgaccg<br>agcaggacagcaaggactccacctacagcctgagcagcaccctgacactgagcaagg<br>ccgactacgagaagcacaaggtgtacgcctgcgaagtgacccaccagggcctgtctag<br>ccccgtgaccaagagcttcaaccggggcgagtgt | SEQ ID NO: 12 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | Binding Protein 7 Amino Acid Sequences: | |
| Heavy chain A (Anti-LAMP1-H_knob) | Anti-LAMP1-H_Knob:<br>qvqlvqsgaevkkpgssvkvsckas***gyiftnynih***wvkkspgqglewig***aiypgn***<br>***gdap***ysqkfqgkatltadtststtymelsslrsedtavyycvr***anwdvafay***wgqgtl<br>vtvssastkgpsvfplapcsrstsestaalgclvkdyfpepvtvswnsgaltsgvhtfpa<br>vlqssglyslssvvtvpssslgtktytcnvdhkpsntkvdkrveskygppcppcpapef<br>lggpsvflfppkpkdtlmisrtpevtcvvvdvsqedpevqfnwyvdgvevhnaktk<br>preeqfnstyrvvsvltvlhqdwlngkeykckvsnkglpssiektiskakgqprepqv<br>ytlppcqeemtknqvslwclvkgfypsdiavewesngqpennykttppvldsdgsff<br>lyskltvdksrwqegnvfscsvmhealhnhytqksls1slgk | SEQ ID NO: 21 |
| Light chain A (Anti-LAMP1-L) | Anti-LAMP1-L:<br>Diqmtqspsslsasvgdrvtitc***kasqdidryma***wyqdkpgkaprllih***dtstlqs***gv<br>psrfsgsgsgrdytltisnlepedfatyyc***lqydnlwt***fgggtkveikrtvaapsvfifpp<br>sdeqlksgtasvvcllnnfypreakvqwkvdnalqsgnsqesvteqdskdstyslsstl<br>tlskadyekhkvyacevthqglsspvtksfnrgec | SEQ ID NO: 22 |
| Heavy chain B (Anti-CD28 × Anti-CD3-H_Hole) | Anti-CD28 × Anti-CD3-H_Hole<br>Qvqlvqsgaevvkpgasvkvsckas***gytftsyy***ihwvrqapgqglewigs***iy***<br>***pgnvnt***nyaqkfqgratltvdtsistaymelsrlrsddtavyyc***trshygldwnf***<br>***dv***wgkgttvtvsssqvqlvesgggvvqpgrslrlscaas***gftftkaw***mhwvr<br>qapgkqlewvaq***ikdksns***yatyyadsvkgrftisrddskntlylqmnslrae<br>dtavyyc***rgvyyalspfdy***wgqgtlvtvssrtastkgpsvfplapcsrstsestaa<br>lgclvkdyfpepvtvswnsgaltsgvhtfpavlqssglyslssvvtvpssslgtkt<br>ytcnvdhkpsntkvdkrveskygppcppcpapeflggpsvflfppkpkdtl<br>misrtpevtcvvvdvsqedpevqfnwyvdgvevhnaktkpreeqfnstyrv<br>vsvltvlhqdwlngkeykckvsnkglpssiektiskakgqprepqvctlppsq<br>eemtknqvslscavkgfypsdiavewesngqpennykttppvldsdgsfflv<br>skltvdksrwqegnvfscsvmhealhnhytqkslslslgk | SEQ ID NO: 3 |
| Light chain B (Anti-CD3 × Anti-CD28L) | Anti-CD3 × Anti-CD28-L:<br>Divmtqtplslsvtpgqpasisckss***qslvhnnanty***lswylqkpgqspqsliy***kvs***n<br>rfsgvpdrfsgsgsgtdftlkisrveaedvgvyyc***gqgtqyp***ftfgsgtkveikgqpka<br>apdiqmtqspsslsasvgdrvtitcqas***qniyvw***lnwyqqkpgkapklliy***kas***nlht<br>gvpsrfsgsgsgtdftltisslqpediatyyc***qqgqtypyt***fgqgtkleiktkgpsrtvaap<br>svfifppsdeqlksgtasvvcllnnfypreakvqwkvdnalqsgnsqesvteqdskds<br>tyslsstltlskadyekhkvyacevthqglsspvtksfnrgec | SEQ ID NO: 4 |
| | Binding Protein 7 Nucleotide Sequences | |
| Heavy chain A (Anti-LAMP1-H_Knob) | Anti-LAMP1-H_Knob:<br>caggtgcagctggtgcagtctggcgccgaagtgaagaaacccggcagcagcgtgaag<br>gtgtcctgcaaggccagcggctacatcttcaccaactacaacatccactgggtcaagaag<br>tccccaggccagggcctggaatggatcggcgccatctatcccggaaacggcgacgccc<br>cttacagccagaagttccagggcaaggccaccctgaccgccgataccagcacctccacc<br>acctacatggaactgagcagcctgcggagcgaggacaccgccgtgtactattgcgtgcg<br>ggccaactgggatgtggccttcgcctattggggccagggcacactcgtgaccgtgtcctc<br>tgcgtcgaccaagggcccatcggtgttccctctggccccttgcagcagaagcaccagcg<br>aatctacagccgccctgggctgcctcgtgaaggactactttcccgagcccgtgaccgtgt<br>cctggaactctggcgctctgacaagcggcgtgcacacctttccagccgtgctccagagca<br>gcggcctgtactctctgagcagcgtcgtgacagtgcccagcagcagcctgggcaccaa<br>gacctacacctgtaacgtggaccacaagcccagcaacaccaaggtggacaagcgggtg<br>gaatctaagtacggccctccctgccctccttgcccagcccctgaatttctgggcggaccct<br>ccgtgttcctgttccccccaaagcccaaggacaccctgatgatcagccggacccccgaa<br>gtgacctgcgtggtggtggatgtgtcccaggaagatcccgaggtgcagttcaattggtac<br>gtggacggcgtggaagtgcacaacgccaagaccaagcccagagaggaacagttcaac<br>agcacctaccgggtggtgtccgtgctgaccgtgctgcaccaggactggctgaacggcaa<br>agagtacaagtgcaaggtgtccaacaagggcctgcccagctccatcgagaaaaccatca<br>gcaaggccaagggccagccccgcgagcctcaagtgtataccctgcccccttgccagga<br>agagatgaccaagaaccaggtgtccctgtggtgtctcgtgaaaggcttctaccccagcga<br>cattgccgtggaatgggagagcaacggccagcccgagaacaactacaagaccacccc<br>ccctgtgctggacagcgacggctcattcttcctgtactccaagctgaccgtggacaagag<br>ccggtggcaggaaggcaacgtgttcagctgctccgtgatgcacgaggccctgcacaac<br>cactacacccagaagtccctgtctctgtccctgggcaag | SEQ ID NO: 23 |
| Light chain A (Anti-LAMP1-L) | Anti-LAMP1-L:<br>gacatccagatgacccagagccccagcagcctgtctgccagcgtgggcgacagagtga<br>ccatcacatgcaaggccagccaggacatcgatcggtacatggcctggtatcaggacaag<br>cccggcaaggcccccagactgctgatccacgataccagcacactgcagagcggcgtgc<br>ccagcagattttccggctctggcagcggcagagactacaccctgaccatcagcaacctg<br>gaacccgaggacttcgccacctactactgcctgcagtacgacaacctgtggaccttcggc<br>ggaggcaccaaggtggaaatcaagcgtacggtggccgctcccagcgtgttcatcttccc<br>acctagcgacgagcagctgaagtccggcacagcctctgtcgtgtgcctgctgaacaactt<br>ctacccccgcgaggccaaagtgcagtggaaggtggacaacgccctgcagagcggcaa<br>cagccaggaaagcgtgaccgagcaggacagcaaggactccacctacagcctgagcag | SEQ ID NO: 24 |

TABLE 2-continued

| Heavy and light chain sequences of binding proteins specifically directed to Her2, CD3, CD28, CD19 and/or CD20. CDR sequences are bolded and italicized. | | |
|---|---|---|
| | caccctgacactgagcaaggccgactacgagaagcacaaggtgtacgcctgcgaagtg<br>acccaccagggcctgtctagccccgtgaccaagagcttcaaccggggcgagtgt | |
| Heavy chain B(Anti-CD28 × Anti-CD3-H_Hole) | Anti-CD28 × Anti-CD3-H_Hole:<br>caggtgcagctggtgcagtctggcgccgaggtcgtgaaacctggcgcctctgtgaaggt<br>gtcctgcaaggccagcggctacacctttaccagctactacatccactgggtgcgccaggc<br>ccctggacagggactggaatggatcggcagcatctaccccggcaacgtgaacaccaac<br>tacgcccagaagaccagggcagagccaccctgaccgtggacaccagcatcagcaccg<br>cctacatggaactgagccggctgagaagcgacgacaccgccgtgtactactgcacccg<br>gtcccactacggcctggattggaacttcgacgtgtggggcaagggcaccaccgtgacag<br>tgtctagcagccaggtgcagctggtggaatctggcggcggagtggtgcagcctggcag<br>aagcctgagactgagctgtgccgccagcggcttcaccttcaccaaggcctggatgcact<br>gggtgcgccaggcccctggaaagcagctggaatgggtggcccagatcaaggacaaga<br>gcaacagctacgccacctactacgccgacagcgtgaagggccggttcaccatcagccg<br>ggacgacagcaagaacaccctgtacctgcagatgaacagcctgcgggccgaggacac<br>cgccgtgtactactgtcggggcgtgtactatgccctgagccccttcgattactggggccag<br>ggaaccctcgtgaccgtgtctagtcggaccgccagcacaaagggcccatcggtgttccc<br>tctggccccttgcagcagaagcaccagcgaatctacagccgccctgggctgcctcgtga<br>aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagccccctgaatttctgggcggaccctccgtgacctgacccccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgccccctagccaggaagagatgaccaagaaccaggtgtccctg<br>agctgtgccgtgaaaggcttctaccccagcgacattgccgtggaatgggagagcaacgg<br>ccagcccgagaacaactacaagaccaccccccctgtgctggacagcgacggctcattct<br>tcctggtgtccaagctgaccgtggacaagagccggtggcaggaaggcaacgtgttcagc<br>tgctccgtgatgcacgaggccctgcacaaccactacacccagaagtccctgtctctgtcc<br>ctgggcaag | SEQ ID NO: 7 |
| Light chain B (Anti-CD3 × Anti-CD28-L | Anti-CD3 × Anti-CD28-L:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatccagatgacccagagccccagcagcctgtctgccagcgtgggcgac<br>agagtgaccatcacctgtcaggccagccagaacatctacgtgtggctgaactggtatcag<br>cagaagcccggcaaggcccccaagctgctgatctacaaggccagcaacctgcacaccg<br>gcgtgcccagcagattttctggcagcggctccggcaccgacttcaccctgacaatcagct<br>ccctgcagcccgaggacattgccacctactactgccagcagggccagacctacccctac<br>acctttggccagggcaccaagctggaaatcaagaccaagggccccagccgtacggtgg<br>ccgctcccagcgtgttcatcttcccacctagcgacgagcagctgaagtccggcacagcct<br>ctgtcgtgtgcctgctgaacaacttctacccccgcgaggccaaagtgcagtggaaggtgg<br>acaacgccctgcagagcggcaacagccaggaaagcgtgaccgagcaggacagcaag<br>gactccacctacagcctgagcagcaccctgacactgagcaaggccgactacgagaagc<br>acaaggtgtacgcctgcgaagtgacccaccagggcctgtctagccccgtgaccaagag<br>cttcaaccggggcgagtgt | SEQ ID NO: 8 |
| | Binding Protein 8 Amino Acid Sequences | |
| Heavy chain A (Anti-LAMP1-H_knob) | Anti-LAMP1-H_Knob:<br>qvqlvqsgaevkkpgssvkvsckas***gyiftnynih***wvkkspgqglewig***aiypgn***<br>***gdap***ysqkfqgkatltadtststtymelsslrsedtavyycvr***anwdvafay***wgqgtl<br>vtvssastkgpsvfplapcsrstsestaalgclvkdyfpepvtvswnsgaltsgvhtfpa<br>vlqssglyslssvvtvpssslgtktytcnvdhkpsntkvdkrveskygppcppcpapef<br>lggpsvflfppkpkdtlmisrtpevtcvvvdvsqedpevqfnwyvdgvevhnaktk<br>preeqfnstyrvvsvltvlhqdwlngkeykckvsnkglpssiektiskakgqprepqv<br>ytlppcqeemtknqvslwclvkgfypsdiavewesngqpennykttppvldsdgsff<br>lyskltvdksrwqegnvfscsvmhealhnhytqksls1slgk | SEQ ID NO: 21 |
| Light chain A (Anti-LAMP1-L) | Anti-LAMP1-L:<br>Diqmtqspsslsasvgdrvtitc***kasqdidryma***wyqdkpgkaprllih***dtstlqs***gv<br>psrfsgsgsgrdytltisnlepedfatyyc***lqydnlwt***fgggtkveikrtvaapsvfifpp<br>sdeqlksgtasvvcllnnfypreakvqwkvdnalqsgnsqesvteqdskdstyslsstl<br>tlskadyekhkvyacevthqglsspvtksfnrgec | SEQ ID NO: 22 |

TABLE 2-continued

| Heavy and light chain sequences of binding proteins specifically directed to Her2, CD3, CD28, CD19 and/or CD20. CDR sequences are bolded and italicized. | | |
|---|---|---|
| Heavy chain B (Anti-CD28 × Anti-CD3-H_Hole) | Anti-CD28 × Anti-CD3-H_Hole<br>Qvqlqesgpglvkpsqtlsltctvsgfslsdygvhwvrqppgkglewlgviw<br>agggtnynpslksrktiskdtsknqvslklssvtaadtavyycardkgysyyys<br>mdywgqgttvtvsssqvqlvesgggvvqpgrslrlscaasgftftkawmhw<br>vrqapgkqlewvaqikdksnsyatyyadsvkgrftisrddskntlylqmnslr<br>aedtavyycrgvyyalspfdywgqgtlvtvssrtastkgpsvfplapcsrstses<br>taalgclvkdyfpepvtvswnsgaltsgvhtfpavlqssglyslssvvtvpsssl<br>gtktytcnvdhkpsntkvdkrveskygppcppcpapeflggpsvflfppkpk<br>dtlmisrtpevtcvvvdvsqedpevqfnwyvdgvevhnaktkpreeqfnsty<br>rvvsvltvlhqdwlngkeykckvsnkglpssiektiskakgqprepqvctlpp<br>sqeemtknqvslscavkgfypsdiavewesngqpennykttppvldsdgsff<br>lvskltvdksrwqegnvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsn<br>rfsgvpdrfsgsgsgtdftlkisrveaedvgvyycgqgtqypftfgsgtkveikgqpka<br>apdivltqspaslavspgqratitcrasesveyyvtslmqwyqqkpgqppkllifaasn<br>vesgvparfsgsgsgtdftltinpveandvanyycqqsrkvpytfgqgtkleiktkgpsr<br>tvaapsvfifppsdeqlksgtasyycllnnfypreakvqwkvdnalqsgnsqesvteq<br>dskdstyslsstltlskadyekhkvyacevthqglsspvtksfnrgec | SEQ ID NO: 10 |
| Binding Protein 8 Nucleotide Sequences | | |
| Heavy chain A (Anti-LAMP1-H_Knob) | Anti-LAMP1-H_Knob:<br>caggtgcagctggtgcagtctggcgccgaagtgaagaaacccggcagcagcgtgaag<br>gtgtcctgcaaggccagcggctacatcttcaccaactacaacatccactgggtcaagaag<br>tccccaggccagggcctggaatggatcggcgccatctatcccggaaacggcgacgccc<br>cttacagccagaagttccagggcaaggccaccctgaccgccgataccagcacctccacc<br>acctacatggaactgagcagcctgcggagcgaggacaccgccgtgtactattgcgtgcg<br>ggccaactgggatgtggccttcgcctattggggccagggcacactcgtgaccgtgtcctc<br>tgcgtcgaccaagggcccatcggtgttccctctggccccttgcagcagaagcaccagcg<br>aatctacagccgccctgggctgcctcgtgaaggactactttcccgagcccgtgaccgtgt<br>cctggaactctggcgctctgacaagcggcgtgcacacctttccagccgtgctccagagca<br>gcggcctgtactctctgagcagcgtcgtgacagtgcccagcagcagcctgggcaccaa<br>gacctacacctgtaacgtggaccacaagcccagcaacaccaaggtggacaagcgggtg<br>gaatctaagtacggccctccctgccctccttgcccagcccctgaatttctgggcggaccct<br>ccgtgttcctgttcccccaaagcccaaggacaccctgatgatcagccggacccccgaa<br>gtgacctgcgtggtggtggatgtgtcccaggaagatcccgaggtgcagttcaattggtac<br>gtggacggcgtggaagtgcacaacgccaagaccaagcccagagaggaacagttcaac<br>agcacctaccgggtggtgtccgtgctgaccgtgctgcaccaggactggctgaacggcaa<br>agagtacaagtgcaaggtgtccaacaagggcctgcccagctccatcgagaaaaccatca<br>gcaaggccaagggccagccccgcgagcctcaagtgtataccctgcccccttgccagga<br>agagatgaccaagaaccaggtgtccctgtggtgtctcgtgaaaggcttctaccccagcga<br>cattgccgtggaatgggagagcaacggccagcccgagaacaactacaagaccacccc<br>ccctgtgctggacagcgacggctcattcttcctgtactccaagctgaccgtggacaagag<br>ccggtggcaggaaggcaacgtgttcagctgctccgtgatgcacgaggccctgcacaac<br>cactacacccagaagtccctgtctctgtccctgggcaag | SEQ ID NO: 23 |
| Light chain A (Anti-LAMP1-L) | Anti-LAMP1-L:<br>gacatccagatgacccagagccccagcagcctgtctgccagcgtgggcgacagagtga<br>ccatcacatgcaaggccagccaggacatcgatcggtacatggcctggtatcaggacaag<br>cccggcaaggcccccagactgctgatccacgataccagcacactgcagagcggcgtgc<br>ccagcagattttccggctctggcagcggcagagactacaccctgaccatcagcaacctg<br>gaacccgaggacttcgccacctactactgcctgcagtacgacaacctgtggaccttcggc<br>ggaggcaccaaggtggaaatcaagcgtacggtggccgctcccagcgtgttcatcttccc<br>acctagcgacgagcagctgaagtccggcacagcctctgtcgtgtgcctgctgaacaactt<br>ctacccccgcgaggccaaagtgcagtggaaggtggacaacgccctgcagagcggcaa<br>cagccaggaaagcgtgaccgagcaggacagcaaggactccacctacagcctgagcag<br>caccctgacactgagcaaggccgactacgagaagcacaaggtgtacgcctgcgaagtg<br>acccaccagggcctgtctagccccgtgaccaagagcttcaaccggggcgagtgt | SEQ ID NO: 24 |
| Heavy chain B (Anti-CD28 × Anti-CD3-H_Hole:) | Anti-CD28 × Anti-CD3-H_Hole:<br>caggtgcagctgcaggaatctggccctggcctcgtgaagcctagccagaccctgagcct<br>gacctgtaccgtgtccggcttcagcctgagcgactacggcgtgcactgggtgcgccagc<br>cacctggaaaaggcctggaatggctgggcgtgatctgggctggcggaggcaccaacta<br>caaccccagcctgaagtccagaaagaccatcagcaaggacaccagcaagaaccaggt<br>gtccctgaagctgagcagcgtgacagccgccgataccgccgtgtactactgcgccagag<br>acaagggctacagctactactacagcatggactactggggccagggcaccaccgtgac<br>cgtgtcatcctctcaggtgcagctggtggaatctggcggcggagtggtgcagcctggca<br>gaagcctgagactgagctgtgccgccagcggcttcaccttcaccaaggcctggatgcac<br>tgggtgcgccaggcccctggaaagcagctggaatgggtggcccagatcaaggacaag<br>agcaacagctacgccacctactacgccgacagcgtgaagggccggttcaccatcagcc<br>gggacgacagcaagaacaccctgtacctgcagatgaacagcctgcgggccgaggaca<br>ccgccgtgtactactgtcggggcgtgtactatgccctgagccccttcgattactggggcca<br>gggaaccctcgtgaccgtgtctagtcggaccgcttcgaccaagggcccatcggtgttccc<br>tctggccccttgcagcagaagcaccagcgaatctacagccgccctgggctgcctcgtga | SEQ ID NO: 11 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagcccctgaatttctgggcggaccctccgtgttcctgttcccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgcccccctagccaggaagagatgaccaagaaccaggtgtccctg<br>agctgtgccgtgaaaggcttctaccccagcgacattgccgtggaatgggagagcaacgg<br>ccagcccgagaacaactacaagaccaccccccctgtgctggacagcgacggctcattct<br>tcctggtgtccaagctgaccgtggacaagagccggtggcaggaaggcaacgtgttcagc<br>tgctccgtgatgcacgaggccctgcacaaccactacacccagaagtccctgtctctgtcc<br>ctgggcaag | |
| Light chain B (Anti-CD3 × Anti-CD28-L:) | Anti-CD3 × Anti-CD28-L:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctaggcagcggcaccaaggtggaaatcaagggccagcccaaggc<br>cgcccccgacatcgtgctgacacagagccctgctagcctggccgtgtctcctggacaga<br>gggccaccatcacctgtagagccagcgagagcgtggaatattacgtgaccagcctgatg<br>cagtggtatcagcagaagcccggccagcccccccaagctgctgatttcgccgccagcaa<br>cgtggaaagcggcgtgccagccagattttccggcagcggctctggcaccgacttcaccc<br>tgaccatcaaccccgtggaagccaacgacgtggccaactactactgccagcagagccg<br>gaaggtgccctacacctttggccagggcaccaagctggaaatcaagaccaagggcccc<br>agccgtacggtggccgctcccagcgtgttcatcttcccacctagcgacgagcagctgaa<br>gtccggcacagcctctgtcgtgtgcctgctgaacaacttctacccccgcgaggccaaagt<br>gcagtggaaggtggacaacgccctgcagagcggcaacagccaggaaagcgtgaccg<br>agcaggacagcaaggactccacctacagcctgagcagcaccctgacactgagcaagg<br>ccgactacgagaagcacaaggtgtacgcctgcgaagtgacccaccagggcctgtctag<br>ccccgtgaccaagagcttcaaccggggcgagtgt | SEQ ID NO: 12 |
| | Binding Protein 20 Amino Acid Sequences | |
| Heavy chain A (Anti-CD20-H_knob) | Anti-CD20-H_Knob:<br>Qvqlqqpgaelvkpgasvkmsckas***gytftsyn***mhwvkqtpgrglewiga***iypg<br>ngdt***synqkfkgkatltadkssstaymqlssltsedsavyyc***arstyyggdwyfnv***w<br>gagttvtvsaastkgpsvfplapcsrstsestaalgclvkdyfpepvtvswnsgaltsgv<br>htfpavlqssglyslssvvtvpssslgtktytcnvdhkpsntkvdkrveskygppcppc<br>papeflggpsvflfppkpkdtlmisrtpevtcvvvdvsqedpevqfnwyvdgvevh<br>naktkpreeqfnstyrvvsyltvlhqdwlngkeykckvsnkglpssiektiskakgqp<br>repqvytlppcqeemtknqvslwclvkgfypsdiavewesngqpennykttppvld<br>sdgsfflyskltvdksrwqegnvfscsvmhealhnhytqkslslslgk | SEQ ID NO: 114 |
| Light chain A (Anti-CD20-L) | Anti-CD20-L:<br>Qivlsqspailsaspgekvtmtcras***ssvsy***ihwfqqkpgsspkpwiy***ats***nlasgvp<br>vrfsgsgsgtsysltisrveaedaatyyc***qqwtsnp***ptfgggtkleikrtvaapsvfifpp<br>sdeqlksgtasvvcllnnfypreakvqwkvdnalqsgnsqesvteqdskdstyslsstl<br>tlskadyekhkvyacevthqglsspvtksfnrgec | SEQ ID NO: 115 |
| Heavy chain B (CD28 × CD3-H_Hole) | CD28 × CD3-H_Hole:<br>Qvqlvqsgaevvkpgasvkvsckas***gytftsyy***ihwvrqapgqglewigs***iy<br>pgnvnt***nyaqkfqgratltvdtsistaymelsrlrsddtavyyc***trshygldwn<br>fdv***wgkgttvtvsssqvqlvesgggvvqpgrslrlscaas***gftftkaw***mhwv<br>rqapgkqlewvaq***ikdksns***yatyyadsvkgrftisrddskntlylqmnslra<br>edtavyyc***rgvyyalspfdy***wgqgtlvtvssrtastkgpsvfplapcsrstsest<br>aalgclvkdyfpepvtvswnsgaltsgvhtfpavlqssglyslssvvtvpssslg<br>tktytcnvdhkpsntkvdkrveskygppcppcpapeflggpsvflfppkpkd<br>tlmisrtpevtcvvvdvsqedpevqfnwyvdgvevhnaktkpreeqfnstyr<br>vvsvltvlhqdwlngkeykckvsnkglpssiektiskakgqprepqvctlpps<br>qeemtknqvslscavkgfypsdiavewesngqpennykttppvldsdgsffl<br>vskltvdksrwqegnvfscsvmhealhnhytqkslslslgk | SEQ ID NO: 3 |
| Light chain B (CD3 × CD28-L) | CD3 × CD28-L:<br>Divmtqtplslsvtpgqpasiscks***sgslvhnnanty***lswylqkpgqspqsliy***kvs***n<br>rfsgvpdrfsgsgsgtdftlkisrveaedvgvyyc***gqgtqyp***ftfgsgtkveikgqpka<br>apdiqmtqspsslsasvgdrvtitcqas***qniyvw***lnwyqqkpgkapklliy***kas***nlht<br>gvpsrfsgsgsgtdftltisslqpediatyyc***qqgqtypyt***fgqgtkleiktkgpsrtvaap<br>svfifppsdeqlksgtasvvcllnnfypreakvqwkvdnalqsgnsqesvteqdskds<br>tyslsstltlskadyekhkvyacevthqglsspvtksfnrgec | SEQ ID NO: 4 |

TABLE 2-continued

Heavy and light chain sequences of binding proteins specifically directed to Her2, CD3, CD28, CD19 and/or CD20. CDR sequences are bolded and italicized.

Binding Protein 20 Nucleotide Sequences

| | | |
|---|---|---|
| Heavy chain A (Anti-CD20-H_Knob:) | Anti-CD20-H_Knob:<br>caggtgcagctgcagcagcctggcgccgaactcgtgaaacctggcgcctccgtgaaga<br>tgagctgcaaggccagcggctacaccttcaccagctacaacatgcactgggtcaagcag<br>acccccggcagaggcctggaatggatcggcgccatctaccccggcaacggcgacacc<br>tcctacaaccagaagttcaagggcaaggccaccctgaccgccgacaagagcagcagc<br>acagcctacatgcagctgtccagcctgaccagcgaggacagcgccgtgtactactgcgc<br>cagaagcacctactacggcggcgactggtacttcaacgtgtggggagccggcaccacc<br>gtgacagtgtctgctgcttcgaccaagggcccatcggtgttccctctggccccttgcagca<br>gaagcaccagcgaatctacagccgccctgggctgcctcgtgaaggactactttcccgag<br>cccgtgaccgtgtcctggaactctggcgctctgacaagcggcgtgcacacctttccagcc<br>gtgctccagagcagcggcctgtactctctgagcagcgtcgtgacagtgcccagcagcag<br>cctgggcaccaagacctacacctgtaacgtggaccacaagcccagcaacaccaaggtg<br>gacaagcgggtggaatctaagtacggccctccctgccctccttgcccagcccctgaattt<br>ctgggcggaccctccgtgttcctgttccccccaaagcccaaggacaccctgatgatcagc<br>cggacccccgaagtgacctgcgtggtggtggatgtgtcccaggaagatcccgaggtgc<br>agttcaattggtacgtggacggcgtggaagtgcacaacgccaagaccaagcccagaga<br>ggaacagttcaacagcacctaccgggtggtgtccgtgctgaccgtgctgcaccaggact<br>ggctgaacggcaaagagtacaagtgcaaggtgtccaacaagggcctgcccagctccat<br>cgagaaaaccatcagcaaggccaagggccagccccgcgagcctcaagtgtataccctg<br>ccccccttgccaggaagagatgaccaagaaccaggtgtccctgtggtgtctcgtgaaagg<br>cttctaccccagcgacattgccgtggaatgggagagcaacggccagcccgagaacaac<br>tacaagaccacccccccctgtgctggacagcgacggctcattcttcctgtactccaagctga<br>ccgtggacaagagccggtggcaggaaggcaacgtgttcagctgctccgtgatgcacga<br>ggccctgcacaaccactacacccagaagtccctgtctctgtccctgggcaag | SEQ ID NO: 116 |
| Light chain A (Anti-CD20-L) | Anti-CD20-L:<br>cagatcgtgctgagccagagccctgccatcctgagcgcttccccaggcgagaaagtgac<br>catgacctgcagagccagcagcagcgtgtcctacatccactggttccagcagaagcccg<br>gcagcagccccaagccttggatctacgccaccagcaatctggccagcggagtgcctgtg<br>cggtttagcggctctggcagcggcacaagctacagcctgaccatcagccgggtggaag<br>ccgaagatgccgccacctactactgccagcagtggaccagcaacccccccacatttggc<br>ggaggcaccaagctggaaatcaagcgtacggtggccgctcccagcgtgttcatcttccc<br>acctagcgacgagcagctgaagtccggcacagcctctgtcgtgtgcctgctgaacaactt<br>ctaccccgcgaggccaaagtgcagtggaaggtggacaacgccctgcagagcggcaa<br>cagccaggaaagcgtgaccgagcaggacagcaaggactccacctacagcctgagcag<br>caccctgacactgagcaaggccgactacgagaagcacaaggtgtacgcctgcgaagtg<br>acccaccagggcctgtctagccccgtgaccaagagcttcaaccggggcgagtgt | SEQ ID NO: 117 |
| Heavy chain B (CD28 × CD3-H_Hole:) | CD28 × CD3-H_Hole:<br>caggtgcagctggtgcagtctggcgccgaggtcgtgaaacctggcgcctctgtgaaggt<br>gtcctgcaaggccagcggctacacctttaccagctactacatccactgggtgcgccaggc<br>ccctggacagggactggaatggatcggcagcatctaccccggcaacgtgaacaccaac<br>tacgcccagaagttccagggcagagccaccctgaccgtggacaccagcatcagcaccg<br>cctacatggaactgagccggctgagaagcgacgacaccgccgtgtactactgcacccg<br>gtcccactacggcctggattggaacttcgacgtgtggggcaagggcaccaccgtgacag<br>tgtctagcagccaggtgcagctggtggaatctggcggcggagtggtgcagcctggcag<br>aagcctgagactgagctgtgccgccagcggcttcaccttcaccaaggcctggatgcact<br>gggtgcgccaggcccctggaaagcagctggaatgggtggcccagatcaaggacaaga<br>gcaacagctacgccacctactacgccgacagcgtgaagggccggttcaccatcagccg<br>ggacgacagcaagaacaccctgtacctgcagatgaacagcctgcgggccgaggacac<br>cgccgtgtactactgtcggggcgtgtactatgccctgagccccttcgattactggggccag<br>ggaaccctcgtgaccgtgtctagtcggaccgccagcacaaagggcccatcggtgttccc<br>tctggccccttgcagcagaagcaccagcgaatctacagccgccctgggctgcctcgtga<br>aggactactttcccgagcccgtgaccgtgtcctggaactctggcgctctgacaagcggcg<br>tgcacacctttccagccgtgctccagagcagcggcctgtactctctgagcagcgtcgtga<br>cagtgcccagcagcagcctgggcaccaagacctacacctgtaacgtggaccacaagcc<br>cagcaacaccaaggtggacaagcgggtggaatctaagtacggccctccctgccctcctt<br>gcccagcccctgaatttctgggcggaccctccgtgttcctgttccccccaaagcccaagg<br>acaccctgatgatcagccggacccccgaagtgacctgcgtggtggtggatgtgtcccag<br>gaagatcccgaggtgcagttcaattggtacgtggacggcgtggaagtgcacaacgccaa<br>gaccaagcccagagaggaacagttcaacagcacctaccgggtggtgtccgtgctgacc<br>gtgctgcaccaggactggctgaacggcaaagagtacaagtgcaaggtgtccaacaagg<br>gcctgcccagctccatcgagaaaaccatcagcaaggccaagggccagccccgcgagc<br>ctcaagtgtgtaccctgcccccctagccaggaagagatgaccaagaaccaggtgtccctg<br>agctgtgccgtgaaaggcttctaccccagcgacattgccgtggaatgggagagcaacgg<br>ccagcccgagaacaactacaagaccacccccccctgtgctggacagcgacggctcattct<br>tcctggtgtccaagctgaccgtggacaagagccggtggcaggaaggcaacgtgttcag<br>ctgctccgtgatgcacgaggccctgcacaaccactacacccagaagtccctgtctctgtc<br>cctgggcaag | SEQ ID NO: 7 |

TABLE 2-continued

Heavy and light chain sequences of binding proteins specifically directed to Her2, CD3, CD28, CD19 and/or CD20. CDR sequences are bolded and italicized.

| | | |
|---|---|---|
| Light chain B (CD3 × CD28-L_Hole) | CD3 × CD28-L_Hole:<br>gacatcgtgatgacccagacccccctgagcctgagcgtgacacctggacagcctgcca<br>gcatcagctgcaagagcagccagagcctggtgcacaacaacgccaacacctacctgag<br>ctggtatctgcagaagcccggccagagcccccagtccctgatctacaaggtgtccaaca<br>gattcagcggcgtgcccgacagattctccggcagcggctctggcaccgacttcaccctg<br>aagatcagccgggtggaagccgaggacgtgggcgtgtactattgtggccagggcaccc<br>agtaccccttcacctttggcagcggcaccaaggtggaaatcaagggccagcccaaggc<br>cgcccccgacatccagatgacccagagccccagcagcctgtctgccagcgtgggcgac<br>agagtgaccatcacctgtcaggccagccagaacatctacgtgtggctgaactggtatcag<br>cagaagcccggcaaggcccccaagctgctgatctacaaggccagcaacctgcacacc<br>ggcgtgcccagcagattttctggcagcggctccggcaccgacttcaccctgacaatcag<br>ctccctgcagcccgaggacattgccacctactactgccagcagggccagacctacccct<br>acacctttggccagggcaccaagctggaaatcaagaccaagggccccagccgtacggt<br>ggccgctcccagcgtgttcatcttcccacctagcgacgagcagctgaagtccggcacag<br>cctctgtcgtgtgcctgctgaacaacttctacccccgcgaggccaaagtgcagtggaagg<br>tggacaacgccctgcagagcggcaacagccaggaaagcgtgaccgagcaggacagc<br>aaggactccacctacagcctgagcagcaccctgacactgagcaaggccgactacgaga<br>agcacaaggtgtacgcctgcgaagtgacccaccagggcctgtctagccccgtgaccaa<br>gagcttcaaccggggcgagtgt | SEQ ID NO: 8 |
| | Binding Protein 21 Amino Acid Sequences | |
| Heavy chain A (Anti-CD20-H_knob) | Anti-CD20-H_Knob:<br>qvqlqqpgaelvkpgasykmsckas***gytftsyn***mhwvkqtpgrglewiga***iypgngdt***synqkfk<br>gkatltadkssstaymqlssltsedsavyyc***arstyyggdwyfn***wgagttvtvsaastkgpsvfplap<br>csrstsestaalgclvkdyfpepvtvswnsgaltsgvhtfpavlqssglyslssvvtvpssslgtktytcnv<br>dhkpsntkvdkrveskygppcppcpapeflggpsvflfppkpkdtlmisrtpevtcvvvdvsqedp<br>evqfnwyvdgvevhnaktkpreeqfnstyrvvsvltvlhqdwlngkeykckvsnkglpssiektisk<br>akgqprepqvyttppcqeemtknqvslwchkgfypsdiavewesngqpennykttppvldsdgs<br>fflyskltvdksrwqegnyfscsvmhealhnhytqkslslslgk | SEQ ID NO: 114 |
| Light chain A (Anti-CD20-L) | Anti-CD20-L:<br>qivlsqspailsaspgekytmtcras ssvsy ihwfqqkpgsspkpwiy***ats***nlasgvpvrfsgsgsgts<br>ysltisrveaedaatyyc***qqwtsnp***ptfgggtkleikrtvaapsyfifppsdeqlksgtasvvcllnnfyp<br>reakvqwkvdnalqsgnsqesvteqdskdstyslsstltlskadyekhkvyacevthqglsspvtksfn<br>rgec | SEQ ID NO: 115 |
| Heavy chain B (CD28 × CD3-H_Hole) | CD28 × CD3-H_Hole:<br>qvqlqesgpglvkpsqtlsltctvsgfslsdygvhwvrqppgkglewlgviwagggtnynp<br>slksrktiskdtsknqvslklssvtaadtavyycardkgysyyysmdywgqgttvtvsssqv<br>qlvesgggvvqpgrslrlscaasgftftkawmhwvrqapgkqlewvaqikdksnsyatyy<br>adsvkgrftisrddskntlylqmnslraedtavyycrgvyyalspfdywgqgtlvtvssrtast<br>kgpsvfplapcsrstsestaalgclvkdyfpepvtvswnsgaltsgvhtfpavlqssglyslssv<br>vtvpssslgtktytcnvdhkpsntkvdkrveskygppcppcpapeflggpsvflfppkpkdt<br>lmisrtpevtcvvvdvsqedpevqfnwyvdgvevhnaktkpreeqfnstyrvvsvltvlhq<br>dwlngkeykckvsnkglpssiektiskakgqprepqvctlppsqeemtknqvslscavkgf<br>ypsdiavewesngqpennykttppvldsdgsfflvskltvdksrwqegnvfscsmhealh<br>nhytqkslslslgk | SEQ ID NO: 9 |
| Light chain B (CD3 × CD28-L) | CD3 × CD28-L<br>divmtqtplslsvtpgqpasisckssqslyhnnantylswylqkpgqspqsliykvsnrfsgvpdrfsg<br>sgsgtdftlkisrveaedvgvyycgqgtqypftfgsgtkveikgqpkaapdivltqspaslavspgqrat<br>itcrasesveyyvtslmqwyqqkpgqppkilifaasnvesgyparfsgsgsgtdftltinpveandvan<br>yycqqsrkvpytfgqgtkleiktkgpsrtvaapsvfifppsdeqlksgtasvvcllnnfypreakvqwk<br>vdnalqsgnsqesvteqdskdstyslssddskadyekhkvyacevthqglsspvtksfnrgec | SEQ ID NO: 10 |
| | Binding Protein 21 Nucleotide Sequences | |
| Heavy chain A (Anti-CD20-H_Knob:) | Anti-CD20-H_Knob:<br>caggtgcagctgcagcagcctggcgccgaactcgtgaaacctggcgcctccgtgaagatgagctgca<br>aggccagcggctacaccttcaccagctacaacatgcactgggtcaagcagacccccggcagaggcct<br>ggaatggatcggcgccatctaccccggcaacggcgacacctcctacaaccagaagttcaagggcaag<br>gccaccctgaccgccgacaagagcagcagcacagcctacatgcagctgtccagcctgaccagcgag<br>gacagcgccgtgtactactgcgccagaagcacctactacggcggcgactggtacttcaacgtgtgggg<br>agccggcaccaccgtgacagtgtctgctgcttcgaccaagggcccatcggtgttccctctggccccttgc<br>agcagaagcaccagcgaatctacagccgccctgggctgcctcgtgaaggactactacccgagcccgt<br>gaccgtgtcctggaactctggcgctctgacaagcggcgtgcacacctaccagccgtgctccagagcag<br>cggcctgtactctctgagcagcgtcgtgacagtgcccagcagcagcctgggcaccaagacctacacct<br>gtaacgtggaccacaagcccagcaacaccaaggtggacaagcgggtggaatctaagtacggccctcc<br>ctgccctccttgcccagcccctgaatttctgggcggaccctccgtgacctgacccccccaaagcccaag<br>gacaccctgatgatcagccggacccccgaagtgacctgcgtggtggtggatgtgtcccaggaagatcc<br>cgaggtgcagttcaattggtacgtggacggcgtggaagtgcacaacgccaagaccaagcccagagag<br>gaacagttcaacagcacctaccgggtggtgtccgtgctgaccgtgctgcaccaggactggctgaacgg<br>caaagagtacaagtgcaaggtgtccaacaagggcctgcccagctccatcgagaaaaccatcagcaag<br>gccaagggccagccccgcgagcctcaagtgtataccctgcccccttgccaggaagagatgaccaaga<br>accaggtgtccctgtggtgtctcgtgaaaggcttctaccccagcgacattgccgtggaatgggagagca | SEQ ID NO: 116 |

TABLE 2-continued

| Heavy and light chain sequences of binding proteins specifically directed to Her2, CD3, CD28, CD19 and/or CD20. CDR sequences are bolded and italicized. | | |
|---|---|---|
| | acggccagcccgagaacaactacaagaccacccccctgtgctggacagcgacggctcattcacctgt<br>actccaagctgaccgtggacaagagccggtggcaggaaggcaacgtgttcagctgctccgtgatgcac<br>gaggccctgcacaaccactacacccagaagtccctgtctctgtccctgggcaag | |
| Light chain A (Anti-CD20-L:) | Anti-CD20-L:<br>cagatcgtgctgagccagagccctgccatcctgagcgcttccccaggcgagaaagtgaccatgacctg<br>cagagccagcagcagcgtgtcctacatccactggttccagcagaagcccggcagcagccccaagcctt<br>ggatctacgccaccagcaatctggccagcggagtgcctgtgcggtttagcggctctggcagcggcaca<br>agctacagcctgaccatcagccgggtggaagccgaagatgccgccacctactactgccagcagtgga<br>ccagcaacccccccacatttggcggaggcaccaagctggaaatcaagcgtacggtggccgctcccag<br>cgtgttcatcttcccacctagcgacgagcagctgaagtccggcacagcctctgtcgtgtgcctgctgaac<br>aacttctaccccgcgaggccaaagtgcagtggaaggtggacaacgccctgcagagcggcaacagc<br>caggaaagcgtgaccgagcaggacagcaaggactccacctacagcctgagcagcaccctgacactg<br>agcaaggccgactacgagaagcacaaggtgtacgcctgcgaagtgacccaccagggcctgtctagcc<br>ccgtgaccaagagcttcaaccggggcgagtgt | SEQ ID NO: 117 |
| Heavy chain B (CD28 × CD3-H_Hole: | CD28 × CD3-H_Hole:<br>caggtgcagctgcaggaatctggccctggcctcgtgaagcctagccagaccctgagcctgacctgtac<br>cgtgtccggcttcagcctgagcgactacggcgtgcactgggtgcgccagccacctggaaaaggcctg<br>gaatggctgggcgtgatctgggctggcggaggcaccaactacaaccccagcctgaagtccagaaaga<br>ccatcagcaaggacaccagcaagaaccaggtgtccctgaagctgagcagcgtgacagccgccgatac<br>cgccgtgtactactgcgccagagacaagggctacagctactactacagcatggactactggggccagg<br>gcaccaccgtgaccgtgtcatcctctcaggtgcagctggtggaatctggcggcggagtggtgcagcct<br>ggcagaagcctgagactgagctgtgccgccagcggcttcaccttcaccaaggcctggatgcactgggt<br>gcgccaggcccctggaaagcagctggaatgggtggcccagatcaaggacaagagcaacagctacgc<br>cacctactacgccgacagcgtgaagggccggttcaccatcagccgggacgacagcaagaacaccctg<br>tacctgcagatgaacagcctgcgggccgaggacaccgccgtgtactactgtcggggcgtgtactatgc<br>cctgagccccttcgattactggggccagggaaccctcgtgaccgtgtctagtcggaccgcttcgaccaa<br>gggcccatcggtgttccctctggccccttgcagcagaagcaccagcgaatctacagccgccctgggct<br>gcctcgtgaaggactactttcccgagcccgtgaccgtgtcctggaactctggcgctctgacaagcggcg<br>tgcacacctttccagccgtgctccagagcagcggcctgtactctctgagcagcgtcgtgacagtgccca<br>gcagcagcctgggcaccaagacctacacctgtaacgtggaccacaagcccagcaacaccaaggtgg<br>acaagcgggtggaatctaagtacggccctccctgccctccttgcccagcccctgaatttctgggcggac<br>cctccgtgttcctgttccccccaaagcccaaggacaccctgatgatcagccggacccccgaagtgacct<br>gcgtggtggtggatgtgtcccaggaagatcccgaggtgcagttcaattggtacgtggacggcgtggaa<br>gtgcacaacgccaagaccaagcccagagaggaacagttcaacagcacctaccgggtggtgtccgtgc<br>tgaccgtgctgcaccaggactggctgaacggcaaagagtacaagtgcaaggtgtccaacaagggcct<br>gcccagctccatcgagaaaaccatcagcaaggccaagggccagccccgcgagcctcaagtgtgtacc<br>ctgccccctagccaggaagagatgaccaagaaccaggtgtccctgagctgtgccgtgaaaggcttcta<br>ccccagcgacattgccgtggaatgggagagcaacggccagcccgagaacaactacaagaccacccc<br>ccctgtgctggacagcgacggctcattcttcctggtgtccaagctgaccgtggacaagagccggtggca<br>ggaaggcaacgtgttcagctgctccgtgatgcacgaggccctgcacaaccactacacccagaagtccc<br>tgtctctgtccctgggcaag | SEQ ID NO: 118 |
| Light chain B (CD3_CD28-L:) | (CD3_CD28-L::<br>gacatcgtgatgacccagacccccctgagcctgagcgtgacacctggacagcctgccagcatcagctg<br>caagagcagccagagcctggtgcacaacaacgccaacacctacctgagctggtatctgcagaagccc<br>ggccagagcccccagtccctgatctacaaggtgtccaacagattcagcggcgtgcccgacagattctcc<br>ggcagcggctctggcaccgacttcaccctgaagatcagccgggtggaagccgaggacgtgggcgtgt<br>actattgtggccagggcacccagtaccccttcacctttggcagcggcaccaaggtggaaatcaagggc<br>cagcccaaggccgcccccgacatcgtgctgacacagagccctgctagcctggccgtgtctcctggaca<br>gagggccaccatcacctgtagagccagcgagagcgtggaatattacgtgaccagcctgatgcagtggt<br>atcagcagaagcccggccagcccccccaagctgctgattttcgccgccagcaacgtggaaagcggcgt<br>gccagccagattttccggcagcggctctggcaccgacttcaccctgaccatcaaccccgtggaagcca<br>acgacgtggccaactactactgccagcagagccggaaggtgccctacacctttggccagggcaccaa<br>gctggaaatcaagaccaagggccccagccgtacggtggccgctcccagcgtgttcatcttcccacctag<br>cgacgagcagctgaagtccggcacagcctctgtcgtgtgcctgctgaacaacttctaccccgcgagg<br>ccaaagtgcagtggaaggtggacaacgccctgcagagcggcaacagccaggaaagcgtgaccgag<br>caggacagcaaggactccacctacagcctgagcagcaccctgacactgagcaaggccgactacgag<br>aagcacaaggtgtacgcctgcgaagtgacccaccagggcctgtctagccccgtgaccaagagcttcaa<br>ccggggcgagtgt | SEQ ID NO: 119 |

TABLE 3

| Heavy and light chain sequences of binding proteins specifically directed to IL-4, IL-13 and/or TNFa. | | |
|---|---|---|
| Binding Protein 9 Amino Acid Sequences | | |
| Heavy chain A | HC:<br>EVQLVESGGGLVQPGRSLRLSCAASG***FTFDDYAMH***WVRQAPG<br>KGLEWVS***AITWNSGHID***YADSVEGRFTISRDNAKNSLYLQMN<br>SLRAEDTAVYYCAK***VSYLSTASSLDY***WGQGTLVTVSSASTKG<br>PSVFPLAPSSKSTSGGTAALGCLVKDYFPEPVTVSWNSGALT | SEQ ID NO: 60 |

TABLE 3-continued

| Heavy and light chain sequences of binding proteins specifically directed to IL-4, IL-13 and/or TNFa. | | |
|---|---|---|
| | SGVHTFPAVLQSSGLYSLSSVVTVPSSSLGTQTYICNVNHKP<br>SNTKVDKKVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPI<br>EKTISKAKGQPREPQVCTLPPSRDELTKNQVSLSCAVKGFYP<br>SDIAVEWESNGQPENNYKTTPPVLDSDGSFFLVSKLTVDKSR<br>WQQGNVFSCSVMHEALHNHYTQKSLSLSPG | |
| Light chain A | LC:<br>DIQMTQSPSSLSASVGDRVTITC***RASQGIRNYLA***WYQQKPGK<br>APKLLIY***AASTLQS***GVPSRFSGSGSGTDFTLTISSLQPEDVA<br>TYYC***QRYNRAPYT***FGQGTKVEIKGQPKAAPSVTLFPPSSEEL<br>QANKATLVCLISDFYPGAVTVAWKADSSPVKAGVETTTPSKQ<br>SNNKYAASSYLSLTPEQWKSHRSYSCQVTHEGSTVEKTVAPT<br>ECS | SEQ ID NO: 61 |
| Heavy chain B | HC:<br>QVQLQQSGPELVKPGASVKISCKAS***GYSFTSYWIH***WIKQRPG<br>QGLEWIG***MIDPSDGET***RLNQRFQGRATLTVDESTSTAYMQLR<br>SPTSEDSAVYYCTR***LKEYGNYDSFYFDV***WGAGTLVTVSSEVQ<br>LKESGPGLVAPGGSLSITCTVS***GFSLTDSSIN***WVRQPPGKGL<br>EWLG***MIWGDGRID***YADALKSRLSISKDSSKSQVFLEMTSLRT<br>DDTATYYCAR***DGYFPYAMDF***WGQGTSVTVSSASTKGPSVFPL<br>APSSKSTSGGTAALGCLVKDYFPEPVTVSWNSGALTSGVHTF<br>PAVLQSSGLYSLSSVVTVPSSSLGTQTYICNVNHKPSNTKVD<br>KKVEPKSCDKTHTCPPCPAPELLGGPSVFLFPPKPKDTLMIS<br>RTPEVTCVVVDVSHEDPEVKFNWYVDGVEVHNAKTKPREEQY<br>NSTYRVVSVLTVLHQDWLNGKEYKCKVSNKALPAPIEKTISK<br>AKGQPREPQVYTLPPCRDELTKNQVSLWCLVKGFYPSDIAVE<br>WESNGQPENNYKTTPPVLDSDGSFFLYSKLTVDKSRWQQGNV<br>FSCSVMHEALHNRFTQKSLSLSPG | SEQ ID NO: 62 |
| Light chain B | LC:<br>DIVLTQSPASLAVSLGQRATISC***RASESVDSYGQSYMH***WYQQ<br>KAGQPPKLLIY***LASNLES***GVPARFSGSGSRTDFTLTIDPVQA<br>EDAATYYC***QQNAEDSRT***FGGGTKLEIKGGSGSSGSGGDIQMT<br>QSPASLSVSVGDTITLTC***HASQNIDVWLS***WFQQKPGNIPKLL<br>IY***KASNLHT***GVPSRFSGSGSGTGFTLTISSLQPEDIATYYC<br>***QQAHSYPFT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 63 |
| Binding Protein 9 Nucleotide Sequences | | |
| Heavy chain A | HC:<br>gaggtgcagctggtggaaagcggcggaggactggtgcagccc<br>ggcagaagcctgagactgagctgcgccgccagcggcttcacc<br>ttcgacgactacgccatgcactgggtccgccaggcccctggc<br>aagggcctggaatgggtgtccgccatcacctggaacagcggc<br>cacatcgactacgccgacagcgtggaaggccggttcaccatc<br>agccgggacaacgccaagaacagcctgtacctgcagatgaac<br>agcctgcgggccgaggacaccgccgtgtactactgcgccaag<br>gtgtcctacctgagcaccgccagcagcctggactactggggc<br>cagggcaccctggtgacagtgtccagcgcttccaccaagggc<br>cccagcgtgttccccctggcccctagcagcaagagcacatct<br>ggcggcacagccgccctgggctgcctggtcaaggactacttc<br>cccgagcccgtgacagtgtcctggaactctggcgccctgacc<br>agcggagtgcataccttccctgccgtgctgcagtccagcggc<br>ctgtacagcctgagcagcgtggtcacagtgcccagcagcagc<br>ctgggcacccagacctacatctgcaacgtgaaccacaagccc<br>agcaacaccaaggtggacaagaaggtggaacccaagagctgc<br>gacaagacccacacctgtccccctgccctgcccctgaactg<br>ctgggcggaccctccgtgttcctgttccccccaaagcccaag<br>gacaccctgatgatcagccggacccccgaagtgacctgcgtg<br>gtggtggacgtgtcccacgaggaccctgaagtgaagttcaat<br>tggtacgtggacggcgtggaagtgcataacgccaagaccaag<br>cccagagaggaacagtacaacagcacctaccgggtggtgtcc<br>gtgctgaccgtgctgcaccaggactggctgaacggcaaagag<br>tacaagtgcaaggtgtccaacaaggccctgcctgcccccatc<br>gagaaaaccatcagcaaggccaagggccagcctagagagccc<br>caagtctgcaccctgcccccagcagagatgagctgaccaag<br>aaccaggtgtccctgagctgcgccgtgaagggcttctacccc<br>agcgatatcgccgtggaatgggagagcaacggccagcccgag<br>aacaactacaagaccacccccccctgtgctggacagcgacggc<br>tcattcttcctggtgtccaagctgacagtggacaagagccgg<br>tggcagcagggcaacgtgttcagctgcagcgtgatgcacgag | SEQ ID NO: 64 |

TABLE 3-continued

| Heavy and light chain sequences of binding proteins specifically directed to IL-4, IL-13 and/or TNFa. | | |
|---|---|---|
| | gccctgcacaaccattacacccagaagtccctgagcctgagc<br>cccggc | |
| Light chain A | LC:<br>gacatccagatgacccagagccccagcagcctgagcgccagc<br>gtgggcgacagagtgaccatcacctgtcgggccagccagggc<br>atccggaactacctggcctggtatcagcagaagcccggcaag<br>gcccccaagctgctgatctacgccgccagcacactgcagagc<br>ggcgtgcccagcagattcagcggcagcggctccggcaccgac<br>ttcaccctgaccatcagcagcctgcagcccgaggacgtggcc<br>acctactactgccagcggtacaacagagcccctacaccttc<br>ggccagggcaccaaggtggaaatcaagggacagcccaaggct<br>gccccctcggtcaccctgttcccccccaagcagcgaggaactg<br>caggccaacaaggccaccctcgtgtgcctgatcagcgacttc<br>taccctggcgccgtgaccgtggcctggaaggccgatagctct<br>cccgtgaaggccggcgtggaaaccaccaccccccagcaagcag<br>agcaacaacaaatacgccgcctccagctacctgagcctgacc<br>cccgagcagtggaagtcccaccggtcctacagctgccaggtc<br>acacacgagggcagcaccgtggaaaagaccgtggcccccacc<br>gagtgcagc | SEQ ID NO: 65 |
| Heavy chain B | HC:<br>caggtgcagctgcagcagagcggccctgagctggtcaagcct<br>ggcgccagcgtgaagatcagctgcaaggccagcggctacagc<br>ttcaccagctactggatccactggatcaagcagcggcctggc<br>cagggcctggaatggatcggcatgatcgaccccagcgacggc<br>gagacacggctgaaccagagattccagggcagagccaccctg<br>accgtggacgagagcaccagcaccgcctacatgcagctgcgg<br>agccccaccagcgaggacagcgccgtgtactactgcacccgg<br>ctgaaagagtacggcaactacgacagatctacttcgacgtgt<br>ggggagccggcaccctggtcaccgtgtccagcgaagtgcagc<br>tgaaagaaagcggccctggcctggtggcccctggcggcagcc<br>tgagcatcacctgtaccgtgtccggcttcagcctgaccgaca<br>gcagcatcaactgggtccgacagccccctggcaagggcctcg<br>agtggctgggaatgatctggggcgacggccggatcgactacg<br>ccgacgccctgaagtcccggctgagcatcagcaaggacagca<br>gcaagagccaggtgttcctggaaatgaccagcctgcggaccg<br>acgacaccgccacctactactgcgccagggacggctacttcc<br>cctacgccatggatnctggggccagggcaccagcgtgaccgt<br>gtcctctgcttccaccaagggccccagcgtgttccctctggc<br>ccctagcagcaagagcacatctggcggaacagccgccctggg<br>ctgcctggtcaaggactactttcccgagcccgtgaccgtgtc<br>ctggaactctggtgccctgacaagcggagtgcataccttccc<br>tgccgtgctgcagagcagcggcctgtactctctgagcagcgt<br>ggtcaccgtgccaagcagcagcctgggcacccagacctacat<br>ctgcaacgtgaaccacaagccctccaacaccaaggtggacaa<br>gaaggtggaacccaagagctgcgacaagacccacacctgtcc<br>tccctgtcctgcccctgaactgctgggcggaccctccgtgtt<br>cctgttccctccaaagcccaaggataccctgatgatcagccg<br>gacccctgaagtgacctgcgtggtggtggacgtgtcccacga<br>ggatcccgaagtgaagttcaattggtacgtggacggcgtgga<br>agtgcataacgccaagaccaagcccagagaggaacagtacaa<br>cagcacctaccgggtggtgtccgtgctgacagtgctgcacca<br>ggactggctgaacggcaaagagtacaagtgcaaggtgtccaa<br>caaggccctgccagcccctatcgagaaaaccatcagcaaggc<br>caagggccagccccgcgagcctcaggtgtacacactgcctcc<br>atgccgggacgagctgaccaagaaccaggtgtccctgtggtg<br>cctcgtgaagggcttctacccctccgatatcgccgtggaatg<br>ggagagcaacggccagcccgagaacaactacaagaccacccc<br>tcccgtgctggacagcgacggctcattcttcctgtacagcaa<br>gctgaccgtggacaagtcccggtggcagcagggcaacgtgtt<br>cagctgctctgtgatgcacgaggccctgcacaaccggttcac<br>ccagaagtccctgagcctgagccctggc | SEQ ID NO: 66 |
| Light chain B | LC:<br>Gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaagggc<br>ggctccggcagcagcggctctggcggcgatatccagatgacc<br>cagtcccccgcctccctgagcgtgtccgtgggcgacaccatc<br>accctgacatgccacgccagccagaacatcgacgtgtggctg<br>agctggttccagcagaagcctggcaacatccctaagctgctc | SEQ ID NO: 67 |

TABLE 3-continued

| Heavy and light chain sequences of binding proteins specifically directed to IL-4, IL-13 and/or TNFa. | | |
|---|---|---|
| | atctataaggcctccaacctgcacaccggcgtgcccagcagg<br>ttttccggctctggcagcggcaccggctttaccctgacaatc<br>agcagcctgcagcccgaggatatcgccacatattactgtcag<br>caggcccacagctaccccttcacctttggcggcggaacaaag<br>ctcgagattaagggcggcagcggaagctccggctccggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | |
| | Binding Protein 10 Amino Acid Sequences | |
| Heavy chain A | HC:<br>EVQLVESGGGLVQPGRSLRLSCAAS***GFTFDDYAMH***WVRQAPG<br>KGLEWVS***AITWNSGHID***YADSVEGRFTISRDNAKNSLYLQMN<br>SLRAEDTAVYYCAK***VSYLSTASSLDY***WGQGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKKVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPI<br>EKTISKAKGQPREPQVCTLPPSRDELTKNQVSLSCAVKGFYP<br>SDIAVEWESNGQPENNYKTTPPVLDSDGSFFLVSKLTVDKSR<br>WQQGNVFSCSVMHEALHNHYTQKSLSLSPG | SEQ ID NO: 60 |
| Light chain A | LC:<br>DIQMTQSPSSLSASVGDRVTITC***RASQGIRNYLA***WYQQKPGK<br>APKLLIY***AASTLQS***GVPSRFSGSGSGTDFTLTISSLQPEDVA<br>TYYCQ***RYNRAPYT***FGQGTKVEIKGQPKAAPSVTLFPPSSEEL<br>QANKATLVCLISDFYPGAVTVAWKADSSPVKAGVETTTPSKQ<br>SNNKYAASSYLSLTPEQWKSHRSYSCQVTHEGSTVEKTVAPT<br>ECS | SEQ ID NO: 61 |
| Heavy chain B | HC:<br>EVQLKESGPGLVAPGGSLSITCTVS***GFSLTDSSIN***WVRQPPG<br>KGLEWLG***MIWGDGRID***YADALKSRLSISKDSSKSQVFLEMTS<br>LRTDDTATYYCAR***DGYFPYAMDF***WGQGTSVTVSSQVQLQQSG<br>PELVKPGASVKISCKAS***GYSFTSYWIH***WIKQRPGQGLEWIG<br>***MIDPSDGET***RLNQRFQGRATLTVDESTSTAYMQLRSPTSEDS<br>AVYYCTR***LKEYGNYDSFYFDV***WGAGTLVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHTCPPCPAPELLGGPSVFLFPPKPKDTLMI<br>SRTPEVTCVVVDVSHEDPEVKFNWYVDGVEVHNAKTKPREEQ<br>YNSTYRVVSVLTVLHQDWLNGKEYKCKVSNKALPAPIEKTIS<br>KAKGQPREPQVYTLPPCRDELTKNQVSLWCLVKGFYPSDIAV<br>EWESNGQPENNYKTTPPVLDSDGSFFLYSKLTVDKSRWQQGN<br>VFSCSVMHEALHNRFTQKSLSLSPG | SEQ ID NO: 68 |
| Light chain B | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGGSGSSGSGGDIVLTQSPA<br>SLAVSLGQRATISC***RASESVDSYGQSYMH***WYQQKAGQPPKLLIY<br>***LASNLES***GVPARFSGSGSRTDFTLTIDPVQAEDAATYYC<br>***QQNAEDSRT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 69 |
| | Binding Protein_10 Nucleotide Sequences | |
| Heavy chain A | HC:<br>gaggtgcagctggtggaaagcggcggaggactggtgcagccc<br>ggcagaagcctgagactgagctgcgccgccagcggcttcacc<br>ttcgacgactacgccatgcactgggtccgccaggcccctggc<br>aagggcctggaatgggtgtccgccatcacctggaacagcggc<br>cacatcgactacgccgacagcgtggaaggccggttcaccatc<br>agccgggacaacgccaagaacagcctgtacctgcagatgaac<br>agcctgcgggccgaggacaccgccgtgtactactgcgccaag<br>gtgtcctacctgagcaccgccagcagcctggactactggggc<br>cagggcaccctggtgacagtgtccagcgcttccaccaagggc<br>cccagcgtgttccccctggcccctagcagcaagagcacatct | SEQ ID NO: 64 |

TABLE 3-continued

Heavy and light chain sequences of binding proteins specifically directed to IL-4, IL-13 and/or TNFa.

| | | |
|---|---|---|
| | ggcggcacagccgccctgggctgcctggtcaaggactacttc<br>cccgagcccgtgacagtgtcctggaactctggcgccctgacc<br>agcggagtgcataccttccctgccgtgctgcagtccagcggc<br>ctgtacagcctgagcagcgtggtcacagtgcccagcagcagc<br>ctgggcacccagacctacatctgcaacgtgaaccacaagccc<br>agcaacaccaaggtggacaagaaggtggaacccaagagctgc<br>gacaagacccacacctgtccccccctgccctgcccctgaactg<br>ctgggcggaccctccgtgttcctgttcccccccaaagcccaag<br>gacaccctgatgatcagccggacccccgaagtgacctgcgtg<br>gtggtggacgtgtcccacgaggaccctgaagtgaagttcaat<br>tggtacgtggacggcgtggaagtgcataacgccaagaccaag<br>cccagagaggaacagtacaacagcacctaccgggtggtgtcc<br>gtgctgaccgtgctgcaccaggactggctgaacggcaaagag<br>tacaagtgcaaggtgtccaacaaggccctgcctgcccccatc<br>gagaaaaccatcagcaaggccaagggccagcctagagagccc<br>caagtctgcaccctgcccccccagcagagatgagctgaccaag<br>aaccaggtgtccctgagctgcgccgtgaagggcttctacccc<br>agcgatatcgccgtggaatgggagagcaacggccagcccgag<br>aacaactacaagaccaccccccctgtgctggacagcgacggc<br>tcattcttcctggtgtccaagctgacagtggacaagagccgg<br>tggcagcagggcaacgtgttcagctgcagcgtgatgcacgag<br>gccctgcacaaccattacacccagaagtccctgagcctgagc<br>cccggc | |
| Light chain A | LC:<br>gacatccagatgacccagagccccagcagcctgagcgccagc<br>gtgggcgacagagtgaccatcacctgtcgggccagccagggc<br>atccggaactacctggcctggtatcagcagaagcccggcaag<br>gcccccaagctgctgatctacgccgccagcacactgcagagc<br>ggcgtgcccagcagattcagcggcagcggctccggcaccgac<br>ttcaccctgaccatcagcagcctgcagcccgaggacgtggcc<br>acctactactgccagcggtacaacagagccccctacaccttc<br>ggccagggcaccaaggtggaaatcaagggacagcccaaggct<br>gcccccctcggtcaccctgttcccccccaagcagcgaggaactg<br>caggccaacaaggccaccctcgtgtgcctgatcagcgacttc<br>taccctggcgccgtgaccgtggcctggaaggccgatagctct<br>cccgtgaaggccggcgtggaaaccaccacccccagcaagcag<br>agcaacaacaaatacgccgcctccagctacctgagcctgacc<br>cccgagcagtggaagtcccaccggtcctacagctgccaggtc<br>acacacgagggcagcaccgtggaaaagaccgtggcccccacc<br>gagtgcagc | SEQ ID NO: 65 |
| Heavy chain B | HC:<br>gaggtgcagctgaaagagtccggccctggactggtggcccct<br>ggcggcagcctgagcatcacctgtaccgtgtccggcttcagc<br>ctgaccgacagcagcatcaactgggtccgacagccccctggc<br>aagggcctggaatggctgggcatgatctggggcgacggccgg<br>atcgactacgccgacgccctgaagtcccggctgagcatcagc<br>aaggacagcagcaagagccaggtgttcctggaaatgaccagc<br>ctgcggaccgacgacaccgccacctactactgcgccagggac<br>ggctacttcccctacgccatggatttctggggccagggcacc<br>agcgtgaccgtgtccagtcaggtccagctgcagcagagcggc<br>cctgagctggtcaagcctggcgccagcgtgaagatcagctgc<br>aaggccagcggctacagcttcaccagctactggatccactgg<br>atcaagcagcggcctggccagggcctcgagtggatcggaatg<br>atcgaccccagcgacggcgagacacggctgaaccagagattc<br>cagggcagagccaccctgaccgtggacgagagcaccagcacc<br>gcctacatgcagctgcggagccccaccagcgaggacagcgcc<br>gtgtactactgcacccggctgaaagaatacggcaactacgac<br>agcttctacttcgacgtgtggggagccggcaccctggtcacc<br>gtgtctagcgcttccaccaagggccccagcgtgttccctctg<br>gcccctagcagcaagagcacatctggcggaacagccgccctg<br>ggctgcctggtcaaggactactttcccgagcccgtgaccgtg<br>tcctggaactctggtgccctgacaagcggagtgcataccttc<br>cctgccgtgctgcagagcagcggcctgtactctctgagcagc<br>gtggtcaccgtgccaagcagcagcctgggcacccagacctac<br>atctgcaacgtgaaccacaagccctccaacaccaaggtggac<br>aagaaggtggaacccaagagctgcgacaagacccacacctgt<br>cctccctgtcctgcccctgaactgctgggcggaccctccgtg<br>ttcctgttccctccaaagcccaaggataccctgatgatcagc<br>cggacccctgaagtgacctgcgtggtggtggacgtgtcccac<br>gaggatcccgaagtgaagttcaattggtacgtggacggcgtg<br>gaagtgcataacgccaagaccaagcccagagaggaacagtac<br>aacagcacctaccgggtggtgtccgtgctgacagtgctgcac<br>caggactggctgaacggcaaagagtacaagtgcaaggtgtcc<br>aacaaggccctgccagcccctatcgagaaaaccatcagcaag<br>gccaagggccagccccgcgagcctcaggtgtacacactgcct | SEQ ID NO: 97 |

TABLE 3-continued

| Heavy and light chain sequences of binding proteins specifically directed to IL-4, IL-13 and/or TNFa. | | |
|---|---|---|
| | ccatgccgggacgagctgaccaagaaccaggtgtccctgtgg<br>tgcctcgtgaagggcttctaccccctccgatatcgccgtggaa<br>tgggagagcaacggccagcccgagaacaactacaagaccacc<br>cctcccgtgctggacagcgacggctcattcttcctgtacagc<br>aagctgaccgtggacaagtcccggtggcagcagggcaacgtg<br>ttcagctgctctgtgatgcacgaggccctgcacaaccggttc<br>acccagaagtccctgagcctgagccctggc | |
| Light chain B | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggcggcagcggcagc<br>tccggctctggcggcgatatcgtgctgacccagtctcccgcc<br>tccctggccgtgtctctgggccagagagccaccatcagctgc<br>cgggccagcgagagcgtggacagctacggccagagctacatg<br>cactggtatcagcagaaggccggacagccccctaaactgctc<br>atctacctggcctccaacctggaaagcggcgtgcccgccagg<br>ttttccggcagcggctccagaaccgacttcaccctgacaatc<br>gaccccgtgcaggccgaggacgccgccacatattactgtcag<br>cagaacgccgaggacagcagaacctttggcggcggaacaaag<br>ctcgagattaagggcggctccggctccagcggatctggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | SEQ ID NO: 70 |
| Binding Protein 11 Amino Acid Sequences | | |
| Heavy chain A | HC:<br>EVQLVESGGGLVQPGRSLRLSCAAS***GFTFDDYAMH***WVRQAPG<br>KGLEWVS***AITWNSGHID***YADSVEGRFTISRDNAKNSLYLQMN<br>SLRAEDTAVYYCA***KVSYLSTASSLDY***WGQGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKKVEPKSCDKTHTCPPCPAPELLGGPSVFLFPPKPK<br>DTLMISRTPEVTCVVVDVSHEDPEVKFNWYVDGVEVHNAKTK<br>PREEQYNSTYRVVSVLTVLHQDWLNGKEYKCKVSNKALPAPI<br>EKTISKAKGQPREPQVCTLPPSRDELTKNQVSLSCAVKGFYP<br>SDIAVEWESNGQPENNYKTTPPVLDSDGSFFLVSKLTVDKSR<br>WQQGNVFSCSVMHEALHNHYTQKSLSLSPG | SEQ ID NO: 60 |
| Light chain A | LC:<br>DIQMTQSPSSLSASVGDRVTITC***RASQGIRNYLA***WYQQKPGK<br>APKLLIY***AASTLQS***GVPSRFSGSGSGTDFTLTISSLQPEDVA<br>TYYCQQ***RYNRAPYT***FGQGTKVEIKRTVAAPSVFIFPPSDEQLK<br>SGTASVVCLLNNFYPREAKVQWKVDNALQSGNSQESVTEQDS<br>KDSTYSLSSTLTLSKADYEKHKVYACEVTHQGLSSPVTKSFN<br>RGEC | SEQ ID NO: 71 |
| Heavy chain B | HC:<br>EVQLKESGPGLVAPGGSLSITCTVS***GFSLTDSSIN***WVRQPPG<br>KGLEWLG***MIWGDGRID***YADALKSRLSISKDSSKSQVFLEMTSL<br>RTDDTATYYCAR***DGYFPYAMDF***WGQGTSVTVSSQVQLQQSGP<br>ELVKPGASVKISCKAS***GYSFTSYWIH***WIKQRPGQGLEWIG<br>***MIDPSDGET***RLNQRFQGRATLTVDESTSTAYMQLRSPTSEDS<br>AVYYCTR***LKEYGNYDSFYFDV***WGAGTLVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHTCPPCPAPELLGGPSVFLFPPKPKDTLMI<br>SRTPEVTCVVVDVSHEDPEVKFNWYVDGVEVHNAKTKPREEQ<br>YNSTYRVVSVLTVLHQDWLNGKEYKCKVSNKALPAPIEKTIS<br>KAKGQPREPQVYTLPPCRDELTKNQVSLWCLVKGFYPSDIAV<br>EWESNGQPENNYKTTPPVLDSDGSFFLYSKLTVDKSRWQQGN<br>VFSCSVMHEALHNRFTQKSLSLSPG | SEQ ID NO: 68 |

TABLE 3-continued

| Heavy and light chain sequences of binding proteins specifically directed to IL-4, IL-13 and/or TNFa. | | |
|---|---|---|
| Light chain B | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGGSGSSGSGGDIVLTQSPA<br>SLAVSLGQRATISC***RASESVDSYGQSYMH***WYQQKAGQPPKLL<br>IY***LASNLES***GVPARFSGSGSRTDFTLTIDPVQAEDAATYYC<br>***QQNAEDSRT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 69 |
| Binding Protein 11_Nucleotide Sequences | | |
| Heavy chain A | HC:<br>gaggtgcagctggtggaaagcggcggaggactggtgcagccc<br>ggcagaagcctgagactgagctgcgccgccagcggcttcacc<br>ttcgacgactacgccatgcactgggtccgccaggcccctggc<br>aagggcctggaatgggtgtccgccatcacctggaacagcggc<br>cacatcgactacgccgacagcgtggaaggccggttcaccatc<br>agccgggacaacgccaagaacagcctgtacctgcagatgaac<br>agcctgcgggccgaggacaccgccgtgtactactgcgccaag<br>gtgtcctacctgagcaccgccagcagcctggactactggggc<br>cagggcaccctggtgacagtgtccagcgcttccaccaagggc<br>cccagcgtgttccccctggcccctagcagcaagagcacatct<br>ggcggcacagccgccctgggctgcctggtcaaggactacttc<br>cccgagcccgtgacagtgtcctggaactctggcgccctgacc<br>agcggagtgcataccttccctgccgtgctgcagtccagcggc<br>ctgtacagcctgagcagcgtggtcacagtgcccagcagcagc<br>ctgggcacccagacctacatctgcaacgtgaaccacaagccc<br>agcaacaccaaggtggacaagaaggtggaacccaagagctgc<br>gacaagacccacacctgtcccccctgccctgcccctgaactg<br>ctgggcggaccctccgtgttcctgttccccccaaagcccaag<br>gacaccctgatgatcagccggacccccgaagtgacctgcgtg<br>gtggtggacgtgtcccacgaggaccctgaagtgaagttcaat<br>tggtacgtggacggcgtggaagtgcataacgccaagaccaag<br>cccagagaggaacagtacaacagcacctaccgggtggtgtcc<br>gtgctgaccgtgctgcaccaggactggctgaacggcaaagag<br>tacaagtgcaaggtgtccaacaaggccctgcctgcccccatc<br>gagaaaaccatcagcaaggccaagggccagcctagagagccc<br>caagtctgcaccctgcccccagcagagatgagctgaccaag<br>aaccaggtgtccctgagctgcgccgtgaagggcttctacccc<br>agcgatatcgccgtggaatgggagagcaacggccagcccgag<br>aacaactacaagaccacccccccctgtgctggacagcgacggc<br>tcattcttcctggtgtccaagctgacagtggacaagagccgg<br>tggcagcagggcaacgtgttcagctgcagcgtgatgcacgag<br>gccctgcacaaccattacacccagaagtccctgagcctgagc<br>cccggc | SEQ ID NO: 64 |
| Light chain A | LC:<br>gacatccagatgacccagagccccagcagcctgagcgccagc<br>gtgggcgacagagtgaccatcacctgtcgggccagccagggc<br>atccggaactacctggcctggtatcagcagaagcccggcaag<br>gcccccaagctgctgatctacgccgccagcacactgcagagc<br>ggcgtgcccagcagattcagcggcagcggctccggcaccgac<br>ttcaccctgaccatcagcagcctgcagcccgaggacgtggcc<br>acctactactgccagcggtacaacagagccccctacaccttc<br>ggccagggcaccaaggtggaaatcaagcgtacggtggccgct<br>ccttccgtgttcatcttccctccctccgacgagcagctgaag<br>tccggcaccgcctccgtggtgtgtctgctgaacaacttctac<br>cctcgggaggccaaggtgcagtggaaggtggacaacgccctg<br>cagtccggcaactcccaggagtccgtcaccgagcaggactcc<br>aaggacagcacctactccctgtcctccaccctgaccctgtcc<br>aaggccgactacgagaagcacaaggtgtacgcctgtgaggtg<br>acccaccagggcctgtccagccctgtgaccaagtccttcaac<br>cggggcgagtgc | SEQ ID NO: 72 |
| Heavy chain B | HC:<br>gaggtgcagctgaaagagtccggccctggactggtggcccct<br>ggcggcagcctgagcatcacctgtaccgtgtccggcttcagc<br>ctgaccgacagcagcatcaactgggtccgacagcccccctggc<br>aagggcctggaatggctgggcatgatctggggcgacggccgg<br>atcgactacgccgacgccctgaagtcccggctgagcatcagc<br>aaggacagcagcaagagccaggtgttcctggaaatgaccagc<br>ctgcggaccgacgacaccgccacctactactgcgccagggac<br>ggctacttcccctacgccatggatttctggggccagggcacc<br>agcgtgaccgtgtccagtcaggtccagctgcagcagagcggc | SEQ ID NO: 97 |

TABLE 3-continued

| Heavy and light chain sequences of binding proteins specifically directed to IL-4, IL-13 and/or TNFa. | | |
|---|---|---|
| | cctgagctggtcaagcctggcgccagcgtgaagatcagctgc<br>aaggccagcggctacagcttcaccagctactggatccactgg<br>atcaagcagcggcctggccagggcctcgagtggatcggaatg<br>atcgaccccagcgacggcgagacacggctgaaccagagattc<br>cagggcagagccaccctgaccgtggacgagagcaccagcacc<br>gcctacatgcagctgcggagccccaccagcgaggacagcgcc<br>gtgtactactgcacccggctgaaagaatacggcaactacgac<br>agcttctacttcgacgtgtggggagccggcaccctggtcacc<br>gtgtctagcgcttccaccaagggccccagcgtgttccctctg<br>gcccctagcagcaagagcacatctggcggaacagccgccctg<br>ggctgcctggtcaaggactactacccgagcccgtgaccgtgt<br>cctggaactctggtgccctgacaagcggagtgcataccttcc<br>ctgccgtgctgcagagcagcggcctgtactctctgagcagcg<br>tggtcaccgtgccaagcagcagcctgggcacccagacctaca<br>tctgcaacgtgaaccacaagccctccaacaccaaggtggaca<br>agaaggtggaacccaagagctgcgacaagacccacacctgtc<br>ctccctgtcctgcccctgaactgctgggcggaccctccgtgt<br>tcctgttccctccaaagcccaaggataccctgatgatcagcc<br>ggacccctgaagtgacctgcgtggtggtggacgtgtcccacg<br>aggatcccgaagtgaagttcaattggtacgtggacggcgtgg<br>aagtgcataacgccaagaccaagcccagagaggaacagtaca<br>acagcacctaccgggtggtgtccgtgctgacagtgctgcacc<br>aggactggctgaacggcaaagagtacaagtgcaaggtgtcca<br>acaaggccctgccagcccctatcgagaaaaccatcagcaagg<br>ccaagggccagccccgcgagcctcaggtgtacacactgcctc<br>catgccgggacgagctgaccaagaaccaggtgtccctgtggt<br>gcctcgtgaagggcttctacccctccgatatcgccgtggaat<br>gggagagcaacggccagcccgagaacaactacaagaccaccc<br>ctcccgtgctggacagcgacggctcattcttcctgtacagca<br>agctgaccgtggacaagtcccggtggcagcagggcaacgtgt<br>tcagctgctctgtgatgcacgaggccctgcacaaccggttca<br>cccagaagtccctgagcctgagccctggc | |
| Light chain B | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggcggcagcggcagc<br>tccggctctggcggcgatatcgtgctgacccagtctcccgcc<br>tccctggccgtgtctctgggccagagagccaccatcagctgc<br>cgggccagcgagagcgtggacagctacggccagagctacatg<br>cactggtatcagcagaaggccggacagccccctaaactgctc<br>atctacctggcctccaacctggaaagcggcgtgcccgccagg<br>ttttccggcagcggctccagaaccgacttcaccctgacaatc<br>gaccccgtgcaggccgaggacgccgccacatattactgtcag<br>cagaacgccgaggacagcagaacctttggcggcggaacaaag<br>ctcgagattaagggcggctccggctccagcggatctggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | SEQ ID NO: 70 |
| | Binding Protein 12 Amino Acid Sequences | |
| Heavy chain A | HC:<br>EVQLKESGPGLVAPGGSLSITCTVS***GFSLTDSSIN***WVRQPPG<br>KGLEWLG***MIWGDGRID***YADALKSRLSISKDSSKSQVFLEMTSL<br>RTDDTATYYCAR***DGYFPYAMDF***WGQGTSVTVSSASTKGPSVF<br>PLAPSSKSTSGGTAALGCLVKDYFPEPVTVSWNSGALTSGVH<br>TFPAVLQSSGLYSLSSVVTVPSSSLGTQTYICNVNHKPSNTK<br>VDKKVEPKSCDKTHTCPPCPAPELLGGPSVFLFPPKPKDTLM<br>ISRTPEVTCVVVDVSHEDPEVKFNWYVDGVEVHNAKTKPREE<br>QYNSTYRVVSVLTVLHQDWLNGKEYKCKVSNKALPAPIEKTI<br>SKAKGQPREPQVCTLPPSRDELTKNQVSLSCAVKGFYPSDIA<br>VEWESNGQPENNYKTTPPVLDSDGSFFLVSKLTVDKSRWQQG<br>NVFSCSVMHEALHNHYTQKSLSLSPG | SEQ ID NO: 73 |

TABLE 3-continued

| Heavy and light chain sequences of binding proteins specifically directed to IL-4, IL-13 and/or TNFa. | | |
|---|---|---|
| Light chain A | LC:<br>DIVLTQSPASLAVSLGQRATISC***RASESVDSYGQSYMH***WYQQ<br>KAGQPPKLLIY***LASNLES***GVPARFSGSGSRTDFTLTIDPVQA<br>EDAATYYC***QQNAEDSRT***FGGGTKLEIKGQPKAAPSVTLFPPS<br>SEELQANKATLVCLISDFYPGAVTVAWKADSSPVKAGVETTT<br>PSKQSNNKYAASSYLSLTPEQWKSHRSYSCQVTHEGSTVEKT<br>VAPTECS | SEQ ID NO: 74 |
| Heavy chain B | HC:<br>QVQLQQSGPELVKPGASVKISCKAS***GYSFTSYWIH***WIKQRPG<br>QGLEWIG***MIDPSDGET***RLNQUQGRATLTVDESTSTAYMQLRS<br>PTSEDSAVYYCTR***LKEYGNYDSFYFDV***WGAGTLVTVSSEVQL<br>VESGGGLVQPGRSLRLSCAA***SGFTFDDYAMH***WVRQAPGKGLE<br>WVS***AITWNSGHID***YADSVEGRFTISRDNAKNSLYLQMNSLRA<br>EDTAVYYCAK***VSYLSTASSLDY***WGQGTLVTVSSASTKGPSVF<br>PLAPSSKSTSGGTAALGCLVKDYFPEPVTVSWNSGALTSGVH<br>TFPAVLQSSGLYSLSSVVTVPSSSLGTQTYICNVNHKPSNTK<br>VDKKVEPKSCDKTHTCPPCPAPELLGGPSVFLFPPKPKDTLM<br>ISRTPEVTCVVVDVSHEDPEVKFNWYVDGVEVHNAKTKPREE<br>QYNSTYRVVSVLTVLHQDWLNGKEYKCKVSNKALPAPIEKTI<br>SKAKGQPREPQVYTLPPCRDELTKNQVSLWCLVKGFYPSDIA<br>VEWESNGQPENNYKTTPPVLDSDGSFFLYSKLTVDKSRWQQG<br>NVFSCSVMHEALHNRFTQKSLSLSPG | SEQ ID NO: 75 |
| Light chain B | LC:<br>DIQMTQSPSSLSASVGDRVTITC***RASQGIRNYLA***WYQQKPGK<br>APKLLIY***AASTLQS***GVPSRFSGSGSGTDFTLTISSLQPEDVA<br>TYYC***QRYNRAPYT***FGQGTKVEIKGGSGSSGSGGDIQMTQSPA<br>SLSVSVGDTITLTC***HASQNIDVWLS***WFQQKPGNIPKLLIY<br>***KASNLHT***GVPSRFSGSGSGTGFTLTISSLQPEDIATYYC<br>***QQAHSYPFT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 76 |

Binding Protein 12 Nucleotide Sequences

| | | |
|---|---|---|
| Heavy chain A | HC:<br>gaggtgcagctgaaggagagcggccccggcctggtggccccc<br>ggcggcagcctgagcatcacctgcaccgtgagcggcttcagc<br>ctgaccgacagcagcatcaactgggtgcgccagccccccggc<br>aagggcctggagtggctgggcatgatctggggcgacggccgc<br>atcgactacgccgacgccctgaagagccgcctgagcatcagc<br>aaggacagcagcaagagccaggtgttcctggagatgaccagc<br>ctgcgcaccgacgacaccgccacctactactgcgcccgcgac<br>ggctacttcccctacgccatggacttctggggccagggcacc<br>agcgtgaccgtgagcagcgccagcaccaagggccccagcgtg<br>ttccccctggcccctagcagcaagagcacatctggcggcaca<br>gccgccctgggctgcctggtcaaggactacttccccgagccc<br>gtgacagtgtcctggaactctggcgccctgaccagcggagtg<br>catacctt ccctgccgtgctgcagtccagcggcctgtacagc<br>ctgagcagcgtggtcacagtgcccagcagcagcctgggcacc<br>cagacctacatctgcaacgtgaaccacaagcccagcaacacc<br>aaggtggacaagaaggtggaacccaagagctgcgacaagacc<br>cacacctgtccccccctgccctgccccctgaactgctgggcgga<br>ccctccgtgttcctgttcccccccaaagcccaaggacaccctg<br>atgatcagccggacccccgaagtgacctgcgtggtggtggac<br>gtgtcccacgaggaccctgaagtgaagttcaattggtacgtg<br>gacggcgtggaagtgcataacgccaagaccaagcccagagag<br>gaacagtacaacagcacctaccgggtggtgtccgtgctgacc<br>gtgctgcaccaggactggctgaacggcaaagagtacaagtgc<br>aaggtgtccaacaaggccctgcctgcccccatcgagaaaacc<br>atcagcaaggccaagggccagcctagagagccccaagtctgc<br>accctgccccccagcagagatgagctgaccaagaaccaggtg<br>tccctgagctgcgccgtgaagggcttctaccccagcgatatc<br>gccgtggaatgggagagcaacggccagcccgagaacaactac<br>aagaccacccccccctgtgctggacagcgacggctcattcttc<br>ctggtgtccaagctgacagtggacaagagccggtggcagcag<br>ggcaacgtgttcagctgcagcgtgatgcacgaggccctgcac<br>aaccattacacccagaagtccctgagcctgagccccggc | SEQ ID NO: 77 |
| Light chain A | LC:<br>gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccccaagctgctgatctacctggccagc | SEQ ID NO: 78 |

TABLE 3-continued

| Heavy and light chain sequences of binding proteins specifically directed to IL-4, IL-13 and/or TNFa. | | |
|---|---|---|
| | aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaaggga<br>cagcccaaggctgccccctcggtcaccctgttcccccccaagc<br>agcgaggaactgcaggccaacaaggccaccctcgtgtgcctg<br>atcagcgacttctaccctggcgccgtgaccgtggcctggaag<br>gccgatagctctcccgtgaaggccggcgtggaaaccaccacc<br>cccagcaagcagagcaacaacaaatacgccgccagcagctac<br>ctgagcctgacccccgagcagtggaagtcccaccggtcctac<br>agctgccaggtcacacacgagggcagcaccgtggaaaagacc<br>gtggcccccaccgagtgcagc | |
| Heavy chain B | HC:<br>caggtgcagctgcagcagagcggccctgagctggtcaagcct<br>ggcgccagcgtgaagatcagctgcaaggccagcggctacagc<br>ttcaccagctactggatccactggatcaagcagcggcctggc<br>cagggcctggaatggatcggcatgatcgaccccagcgacggc<br>gagacacggctgaaccagagattccagggcagagccaccctg<br>accgtggacgagagcaccagcaccgcctacatgcagctgcgg<br>agccccaccagcgaggacagcgccgtgtactactgcacccgg<br>ctgaaagagtacggcaactacgacagatctacttcgacgtgt<br>ggggagccggcaccctggtcaccgtgtccagcgaagtgcagc<br>tggtggaaagcggcggaggcctggtgcagcccggcagaagcc<br>tgagactgagctgcgccgccagcggcttcaccttcgacgact<br>acgccatgcactgggtccgacaggcccctggcaaaggactgg<br>aatgggtgtccgccatcacctggaacagcggccacatcgact<br>acgccgacagcgtggaaggccggttcaccatcagccgggaca<br>acgccaagaacagcctgtacctgcagatgaacagcctgcggg<br>ccgaggataccgccgtgtattattgcgccaaggtgtcctacc<br>tgagcaccgccagcagcctggactactggggccagggcaccc<br>tcgtgacagtgtcctccgcttccaccaagggccccagcgtgt<br>tccctctggcccctagcagcaagagcacatctggcggaacag<br>ccgccctgggctgcctggtcaaggactactttcccgagcccg<br>tgaccgtgtcctggaactctggtgccctgacaagcggagtgc<br>ataccttccctgccgtgctgcagagcagcggcctgtactctc<br>tgagcagcgtggtcaccgtgccaagcagcagcctgggcaccc<br>agacctacatctgcaacgtgaaccacaagccctccaacacca<br>aggtggacaagaaggtggaacccaagagctgcgacaagaccc<br>acacctgtcctccctgtcctgcccctgaactgctgggcggac<br>cctccgtgttcctgttccctccaaagcccaaggataccctga<br>tgatcagccggacccctgaagtgacctgcgtggtggtggacg<br>tgtcccacgaggatcccgaagtgaagttcaattggtacgtgg<br>acggcgtggaagtgcataacgccaagaccaagcccagagagg<br>aacagtacaacagcacctaccgggtggtgtccgtgctgacag<br>tgctgcaccaggactggctgaacggcaaagagtacaagtgca<br>aggtgtccaacaaggccctgccagcccctatcgagaaaacca<br>tcagcaaggccaagggccagccccgcgagcctcaggtgtaca<br>cactgcctccatgccgggacgagctgaccaagaaccaggtgt<br>ccctgtggtgcctcgtgaagggatctacccctccgatatcgc<br>cgtggaatgggagagcaacggccagcccgagaacaactacaa<br>gaccacccctcccgtgctggacagcgacggctcattcttcct<br>gtacagcaagctgaccgtggacaagtcccggtggcagcaggg<br>caacgtgttcagctgctctgtgatgcacgaggccctgcacaa<br>ccggttcacccagaagtccctgagcctgagccctggc | SEQ ID NO: 79 |
| Light chain B | LC:<br>gacatccagatgacccagagccccagcagcctgagcgccagc<br>gtgggcgacagagtgaccatcacctgtcgggccagccagggc<br>atccggaactacctggcctggtatcagcagaagcccggcaag<br>gcccccaagctgctgatctacgccgccagcacactgcagagc<br>ggcgtgcccagcagattcagcggcagcggctccggcaccgac<br>ttcaccctgaccatcagcagcctgcagcccgaggacgtggcc<br>acctactactgccagcggtacaacagagccccctacaccttc<br>ggccagggcaccaaggtggaaatcaagggcggctctggcagc<br>tccggcagcggcggagacattcagatgacacagtcccccgcc<br>agcctgtccgtgtccgtgggcgataccatcaccctgacatgc<br>cacgccagccagaacatcgacgtgtggctgagctggttccag<br>cagaaacctggcaacatccctaagctgctcatctataaggcc<br>agcaacctgcacacaggcgtgccctccagattctccggctct<br>ggctctggcaccggctttacactgacaatcagttctctgcag<br>cctgaggatatcgccacatattactgtcagcaggcccacagc<br>taccctttcaccttcggaggcggcaccaagctcgagattaag<br>ggcggaagcggctcctccggctccggcggacgtacggtggcc<br>gctccttccgtgttcatcttccctccctccgacgagcagctg<br>aagtccggcaccgcctccgtggtgtgtctgctgaacaacttc<br>taccctcgggaggccaaggtgcagtggaaggtggacaacgcc | SEQ ID NO: 80 |

TABLE 3-continued

| Heavy and light chain sequences of binding proteins specifically directed to IL-4, IL-13 and/or TNFa. | | |
|---|---|---|
| | ctgcagtccggcaactcccaggagtccgtcaccgagcaggac<br>tccaaggacagcacctactccctgtcctccaccctgaccctg<br>tccaaggccgactacgagaagcacaaggtgtacgcctgtgag<br>gtgacccaccagggcctgtccagccctgtgaccaagtccttc<br>aaccggggcgagtgc | |
| | Binding Protein 13 Amino Acid Sequences | |
| Heavy chain A | HC:<br>EVQLKESGPGLVAPGGSLSITCTVS***GFSLTDSSIN***WVRQPP<br>GKGLEWLG***MIWGDGRID***YADALKSRLSISKDSSKSQVFLEMT<br>SLRTDDTATYYCAR***DGYFPYAMDF***WGQGTSVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSN<br>TKVDKKVEPKSCDKTHTCPPCPAPELLGGPSVFLFPPKPKDT<br>LMISRTPEVTCVVVDVSHEDPEVKFNWYVDGVEVHNAKTKPR<br>EEQYNSTYRVVSVLTVLHQDWLNGKEYKCKVSNKALPAPIEK<br>TISKAKGQPREPQVCTLPPSRDELTKNQVSLSCAVKGFYPSD<br>IAVEWESNGQPENNYKTTPPVLDSDGSFFLVSKLTVDKSRWQ<br>QGNVFSCSVMHEALHNHYTQKSLSLSPG | SEQ ID NO: 73 |
| Light chain A | LC:<br>DIVLTQSPASLAVSLGQRATISC***RASESVDSYGQSYMH***WYQQ<br>KAGQPPKLLIY***LASNLES***GVPARFSGSGSRTDFTLTIDPVQA<br>EDAATYYC***QQNAEDSRT***FGGGTKLEIKGQPKAAPSVTLFPPS<br>SEELQANKATLVCLISDFYPGAVTVAWKADSSPVKAGVETTT<br>PSKQSNNKYAASSYLSLTPEQWKSHRSYSCQVTHEGSTVEKT<br>VAPTECS | SEQ ID NO: 74 |
| Heavy chain B | HC:<br>EVQLVESGGGLVQPGRSLRLSCAAS***GFTFDDYAMH***WVRQAPG<br>KGLEWVS***AITWNSGHID***YADSVEGRFTISRDNAKNSLYLQMN<br>SLRAEDTAVYYCAK***VSYLSTASSLDY***WGQGTLVTVSSQVQLQ<br>QSGPELVKPGASVKISCKAS***GYSFTSYWIH***WIKQRPGQGLEW<br>IG***MIDPSDGET***RLNQRFQGRATLTVDESTSTAYMQLRSPTSE<br>DSAVYYCTR***LKEYGNYDSFYFDV***WGAGTLVTVSSASTKGPSV<br>FPLAPSSKSTSGGTAALGCLVKDYFPEPVTVSWNSGALTSGV<br>HTFPAVLQSSGLYSLSSVVTVPSSSLGTQTYICNVNHKPSNT<br>KVDKKVEPKSCDKTHTCPPCPAPELLGGPSVFLFPPKPKDTL<br>MISRTPEVTCVVVDVSHEDPEVKFNWYVDGVEVHNAKTKPRE<br>EQYNSTYRVVSVLTVLHQDWLNGKEYKCKVSNKALPAPIEKT<br>ISKAKGQPREPQVYTLPPCRDELTKNQVSLWCLVKGFYPSDI<br>AVEWESNGQPENNYKTTPPVLDSDGSFFLYSKLTVDKSRWQQ<br>GNVFSCSVMHEALHNRFTQKSLSLSPG | SEQ ID NO: 81 |
| Light chain B | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGGSGSSGSGGDIQMTQSPS<br>SLSASVGDRVTITC***RASQGIRNYLA***WYQQKPGKAPKLLIY<br>***AASTLQS***GVPSRFSGSGSGTDFTLTISSLQPEDVATYYC<br>***QRYNRAPYT***FGQGTKVEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 82 |
| | Binding Protein 13_Nucleotide Sequences | |
| Heavy chain A | HC:<br>gaggtgcagctgaaggagagcggccccggcctggtggccccc<br>ggcggcagcctgagcatcacctgcaccgtgagcggcttcagc<br>ctgaccgacagcagcatcaactgggtgcgccagcccccggc<br>aagggcctggagtggctgggcatgatctggggcgacggccgc<br>atcgactacgccgacgccctgaagagccgcctgagcatcagc<br>aaggacagcagcaagagccaggtgttcctggagatgaccagc<br>ctgcgcaccgacgacaccgccacctactactgcgcccgcgac<br>ggctacttcccctacgccatggacttctggggccagggcacc<br>agcgtgaccgtgagcagcgccagcaccaagggccccagcgtg<br>ttccccctggcccctagcagcaagagcacatctggcggcaca<br>gccgccctgggctgcctggtcaaggactacttccccgagccc<br>gtgacagtgtcctggaactctggcgccctgaccagcggagtg<br>catacctttcctgccgtgctgcagtccagcggcctgtacagc<br>ctgagcagcgtggtcacagtgcccagcagcagcctgggcacc<br>cagacctacatctgcaacgtgaaccacaagcccagcaacacc<br>aaggtggacaagaaggtggaacccaagagctgcgacaagacc<br>cacacctgtccccctgccctgcccctgaactgctgggcgga<br>ccctccgtgttcctgttcccccaaagcccaaggacaccctg | SEQ ID NO: 77 |

TABLE 3-continued

| Heavy and light chain sequences of binding proteins specifically directed to IL-4, IL-13 and/or TNFa. | | |
|---|---|---|
| | atgatcagccggacccccgaagtgacctgcgtggtggtggac<br>gtgtcccacgaggaccctgaagtgaagttcaattggtacgtg<br>gacggcgtggaagtgcataacgccaagaccaagcccagagag<br>gaacagtacaacagcacctaccgggtggtgtccgtgctgacc<br>gtgctgcaccaggactggctgaacggcaaagagtacaagtgc<br>aaggtgtccaacaaggccctgcctgcccccatcgagaaaacc<br>atcagcaaggccaagggccagcctagagagccccaagtctgc<br>accctgcccccccagcagagatgagctgaccaagaaccaggtg<br>tccctgagctgcgccgtgaagggcttctaccccagcgatatc<br>gccgtggaatgggagagcaacggccagcccgagaacaactac<br>aagaccacccccccctgtgctggacagcgacggctcattcttc<br>ctggtgtccaagctgacagtggacaagagccggtggcagcag<br>ggcaacgtgttcagctgcagcgtgatgcacgaggccctgcac<br>aaccattacacccagaagtccctgagcctgagccccggc | |
| Light chain A | LC:<br>gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaaggga<br>cagcccaaggctgcccccctcggtcaccctgttcccccccaagc<br>agcgaggaactgcaggccaacaaggccaccctcgtgtgcctg<br>atcagcgacttctaccctggcgccgtgaccgtggcctggaag<br>gccgatagctctcccgtgaaggccggcgtggaaaccaccacc<br>cccagcaagcagagcaacaacaaatacgccgccagcagctac<br>ctgagcctgacccccgagcagtggaagtcccaccggtcctac<br>agctgccaggtcacacacgagggcagcaccgtggaaaagacc<br>gtggcccccaccgagtgcagc | SEQ ID NO: 78 |
| Heavy chain B | HC:<br>gaggtgcagctggtggaaagcggcggaggactggtgcagccc<br>ggcagaagcctgagactgagctgcgccgccagcggcttcacc<br>ttcgacgactacgccatgcactgggtccgacaggcccctggc<br>aagggcctggaatgggtgtccgccatcacctggaacagcggc<br>cacatcgactacgccgacagcgtggaaggccggttcaccatc<br>agccgggacaacgccaagaacagcctgtacctgcagatgaac<br>agcctgcgggccgaggacaccgccgtgtactactgcgccaag<br>gtgtcctacctgagcaccgccagcagcctggactactggggc<br>cagggcaccctggtcaccgtgtccagtcaggtccagctgcag<br>cagagcggccctgagctggtcaagcctggcgccagcgtgaag<br>atcagctgcaaggccagcggctacagcttcaccagctactgg<br>atccactggatcaagcagcggcctggccagggcctcgagtgg<br>atcggcatgatcgaccccagcgacggcgagacacggctgaac<br>cagagattccagggcagagccaccctgaccgtggacgagagc<br>accagcaccgcctacatgcagctgcggagccccaccagcgag<br>gatagcgccgtgtattattgcacccggctgaaagagtacggc<br>aactacgacagcttctacttcgacgtgtggggagccggcacc<br>ctcgtgacagtgtcctccgcttccaccaagggccccagcgtg<br>ttccctctggcccctagcagcaagagcacatctggcggaaca<br>gccgccctgggctgcctggtcaaggactactucccgagcccg<br>tgaccgtgtcctggaactctggtgccctgacaagcggagtgc<br>ataccttccctgccgtgctgcagagcagcggcctgtactctc<br>tgagcagcgtggtcaccgtgccaagcagcagcctgggcaccc<br>agacctacatctgcaacgtgaaccacaagccctccaacacca<br>aggtggacaagaaggtggaacccaagagctgcgacaagaccc<br>acacctgtcctccctgtcctgcccctgaactgctgggcggac<br>cctccgtgttcctgttccctccaaagcccaaggataccctga<br>tgatcagccggacccctgaagtgacctgcgtggtggtggacg<br>tgtcccacgaggatcccgaagtgaagttcaattggtacgtgg<br>acggcgtggaagtgcataacgccaagaccaagcccagagagg<br>aacagtacaacagcacctaccgggtggtgtccgtgctgacag<br>tgctgcaccaggactggctgaacggcaaagagtacaagtgca<br>aggtgtccaacaaggccctgccagcccctatcgagaaaacca<br>tcagcaaggccaagggccagccccgcgagcctcaggtgtaca<br>cactgcctccatgccgggacgagctgaccaagaaccaggtgt<br>ccctgtggtgcctcgtgaagggcttctacccctccgatatcg<br>ccgtggaatgggagagcaacggccagcccgagaacaactaca<br>agaccacccctcccgtgctggacagcgacggctcattcttcc<br>tgtacagcaagctgaccgtggacaagtcccggtggcagcagg<br>gcaacgtgttcagctgctctgtgatgcacgaggccctgcaca<br>accggttcacccagaagtccctgagcctgagccctggc | SEQ ID NO: 83 |

TABLE 3-continued

| Heavy and light chain sequences of binding proteins specifically directed to IL-4, IL-13 and/or TNFa. | | |
|---|---|---|
| Light chain B | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggcggcagcggcagc<br>tccggcagcggcggagacattcagatgacacagtcccccagc<br>agcctgtccgccagcgtgggcgacagagtgaccatcacctgt<br>cgggccagccagggcatccggaactacctggcctggtatcag<br>cagaaacctggcaaggcccctaaactgctcatctacgccgcc<br>agcacactgcagtctggcgtgccctccagattctccggaagc<br>ggctccggcaccgatttcaccctgacaatctcatctctgcag<br>cctgaggacgtggccacatattactgccagagatacaacaga<br>gccccctacacctttggccagggcaccaaggtcgagattaag<br>ggcggatccggctccagcggcagcggaggacgtacggtggcc<br>gctccttccgtgttcatcttccctccctccgacgagcagctg<br>aagtccggcaccgcctccgtggtgtgtctgctgaacaacttc<br>taccctcgggaggccaaggtgcagtggaaggtggacaacgcc<br>ctgcagtccggcaactcccaggagtccgtcaccgagcaggac<br>tccaaggacagcacctactccctgtcctccaccctgaccctg<br>tccaaggccgactacgagaagcacaaggtgtacgcctgtgag<br>gtgacccaccagggcctgtccagccctgtgaccaagtccttc<br>aaccggggcgagtgc | SEQ ID NO: 84 |
| Binding Protein 14 Amino Acid Sequences | | |
| Heavy chain A | HC:<br>QVQLQQSGPELVKPGASVKISCKAS***GYSFTSYWIH***WIKQRPG<br>QGLEWIG***MIDPSDGET***RLNQRFQGRATLTVDESTSTAYMQLR<br>SPTSEDSAVYYCTR***LKEYGNYDSFYFDV***WGAGTLVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNH<br>KPSNTKVDKKVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVCTLPPSRDELTKNQVSLSCAVKGF<br>YPSDIAVEWESNGQPENNYKTTPPVLDSDGSFFLVSKLTVDK<br>SRWQQGNVFSCSVMHEALHNHYTQKSLSLSPG | SEQ ID NO: 85 |
| Light chain A | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGQPKAAPSVTLFPPSSEEL<br>QANKATLVCLISDFYPGAVTVAWKADSSPVKAGVETTTPSKQ<br>SNNKYAASSYLSLTPEQWKSHRSYSCQVTHEGSTVEKTVAPT<br>ECS | SEQ ID NO: 86 |
| Heavy chain B | HC:<br>EVQLKESGPGLVAPGGSLSITCTVS***GFSLTDSSIN***WVRQPP<br>GKGLEWLG***MIWGDGRID***YADALKSRLSISKDSSKSQVFLEMT<br>SLRTDDTATYYCAR***DGYFPYAMDF***WGQGTSVTVSSEVQLVESG<br>GGLVQPGRSLRLSCAAS***GFTFDDYAMH***WVRQAPGKGLEWVS<br>***AITWNSGHID***YADSVEGRFTISRDNAKNSLYLQMNSLRAEDTA<br>VYYCAK***VSYLSTASSLDY***WGQGTLVTVSSASTKGPSVFPLAP<br>SSKSTSGGTAALGCLVKDYFPEPVTVSWNSGALTSGVHTFPA<br>VLQSSGLYSLSSVVTVPSSSLGTQTYICNVNHKPSNTKVDKK<br>VEPKSCDKTHTCPPCPAPELLGGPSVFLFPPKPKDTLMISRT<br>PEVTCVVVDVSHEDPEVKFNWYVDGVEVHNAKTKPREEQYNS<br>TYRVVSVLTVLHQDWLNGKEYKCKVSNKALPAPIEKTISKAK<br>GQPREPQVYTLPPCRDELTKNQVSLWCLVKGFYPSDIAVEWE<br>SNGQPENNYKTTPPVLDSDGSFFLYSKLTVDKSRWQQGNVFS<br>CSVMHEALHNRFTQKSLSLSPG | SEQ ID NO: 87 |
| Light chain B | LC:<br>IQMTQSPSSLSASVGDRVTITC***RASQGIRNYLA***WYQQKPGKA<br>PKLLIY***AASTLQS***GVPSRFSGSGSGTDFTLTISSLQPEDVAT<br>YYC***QRYNRAPYT***FGQGTKVEIKGGSGSSGSGGDIVLTQSPAS<br>LAVSLGQRATISC***RASESVDSYGQSYMH***WYQQKAGQPPKLLIY<br>***LASNLES***GVPARFSGSGSRTDFTLTIDPVQAEDAATYYC<br>***QQNAEDSRT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 88 |

TABLE 3-continued

Heavy and light chain sequences of binding proteins specifically directed to IL-4, IL-13 and/or TNFa.

Binding Protein 14_Nucleotide Sequences

| | | |
|---|---|---|
| Heavy chain A | HC:<br>caggtgcagctgcagcagagcggccccgagctggtgaagccc<br>ggcgccagcgtgaagatcagctgcaaggccagcggctacagc<br>ttcaccagctactggattcactggatcaagcagcgccccggc<br>cagggcctggagtggatcggcatgatcgaccccagcgacggc<br>gagacccgcctgaaccagcgcttccagggccgcgccaccctg<br>accgtggacgagagcaccagcaccgcctacatgcagctgcgc<br>agccccaccagcgaggacagcgccgtgtactactgcacccgc<br>ctgaaggagtacggcaactacgacagcttctacttcgacgtg<br>tggggcgccggcaccctggtgaccgtgagcagcgccagcacc<br>aagggccccagcgtgttccccctggcccctagcagcaagagc<br>acatctggcggcacagccgccctgggctgcctggtcaaggac<br>tacttccccgagcccgtgacagtgtcctggaactctggcgcc<br>ctgaccagcggagtgcataccttccctgccgtgctgcagtcc<br>agcggcctgtacagcctgagcagcgtggtcacagtgcccagc<br>agcagcctgggcacccagacctacatctgcaacgtgaaccac<br>aagcccagcaacaccaaggtggacaagaaggtggaacccaag<br>agctgcgacaagacccacacctgtccccctgccctgcccct<br>gaactgctgggcggaccctccgtgttcctgttccccccaaag<br>cccaaggacaccctgatgatcagccggacccccgaagtgacc<br>tgcgtggtggtggacgtgtcccacgaggaccctgaagtgaag<br>ttcaattggtacgtggacggcgtggaagtgcataacgccaag<br>accaagcccagagaggaacagtacaacagcacctaccgggtg<br>gtgtccgtgctgaccgtgctgcaccaggactggctgaacggc<br>aaagagtacaagtgcaaggtgtccaacaaggccctgcctgcc<br>cccatcgagaaaaccatcagcaaggccaagggccagcctaga<br>gagccccaagtctgcaccctgcccccccagcagagatgagctg<br>accaagaaccaggtgtccctgagctgcgccgtgaagggcttc<br>taccccagcgatatcgccgtggaatgggagagcaacggccag<br>cccgagaacaactacaagaccaccccccctgtgctggacagc<br>gacggctcattcttcctggtgtccaagctgacagtggacaag<br>agccggtggcagcagggcaacgtgttcagctgcagcgtgatg<br>cacgaggccctgcacaaccattacacccagaagtccctgagc<br>ctgagccccggc | SEQ ID NO: 89 |
| Light chain A | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggacagcccaaggct<br>gccccctcggtcaccctgttccccccaagctctgaggaactg<br>caggccaacaaggccaccctcgtgtgcctgatcagcgacttc<br>taccctggcgccgtgaccgtggcctggaaggccgatagctct<br>cccgtgaaggccggcgtggaaaccaccacccccagcaagcag<br>agcaacaacaaatacgccgccagcagctacctgagcctgacc<br>cccgagcagtggaagtcccaccggtcctacagctgccaggtc<br>acacacgagggcagcaccgtggaaaagaccgtggcccccacc<br>gagtgcagc | SEQ ID NO: 90 |
| Heavy chain B | HC:<br>gaggtgcagctgaaagagtccggccctggactggtggcccct<br>ggcggcagcctgagcatcacctgtaccgtgtccggcttcagc<br>ctgaccgacagcagcatcaactgggtccgacagccccctggc<br>aagggcctggaatggctgggcatgatctggggcgacggccgg<br>atcgactacgccgacgccctgaagtcccggctgagcatcagc<br>aaggacagcagcaagagccaggtgttcctggaaatgaccagc<br>ctgcggaccgacgacaccgccacctactactgcgccagggac<br>ggctacttcccctacgccatggatttctggggccagggcacc<br>agcgtgaccgtgtcctccgaagtgcagctggtggaaagcggc<br>ggaggcctggtgcagcccggcagaagcctgagactgagctgc<br>gccgccagcggcttcaccttcgacgactacgccatgcactgg<br>gtccgccaggctcccggaaagggactcgagtgggtgtccgcc<br>atcacctggaacagcggccacatcgattacgccgatagcgtg<br>gaaggccggttcaccatcagccgggacaacgccaagaacagc<br>ctgtacctgcagatgaacagcctgagagccgaggataccgcc<br>gtgtactactgtgccaaggtgtcctacctgagcaccgccagc<br>agcctggactactggggacagggaaccctggtcaccgtgtcc<br>agcgcttccaccaagggccccagcgtgttccctctggcccct<br>agcagcaagagcacatctggcggaacagccgccctgggctgc<br>ctggtcaaggactactttcccgagcccgtgaccgtgtcctgg | SEQ ID NO: 91 |

TABLE 3-continued

| Heavy and light chain sequences of binding proteins specifically directed to IL-4, IL-13 and/or TNFa. | | |
|---|---|---|
| | aactctggtgccctgacaagcggagtgcataccttccctgcc<br>gtgctgcagagcagcggcctgtactctctgagcagcgtggtc<br>accgtgccaagcagcagcctgggcacccagacctacatctgc<br>aacgtgaaccacaagccctccaacaccaaggtggacaagaag<br>gtggaacccaagagctgcgacaagacccacacctgtcctccc<br>tgtcctgccccctgaactgctgggcggaccctccgtgttcctg<br>ttccctccaaagcccaaggataccctgatgatcagccggacc<br>cctgaagtgacctgcgtggtggtggacgtgtcccacgaggat<br>cccgaagtgaagttcaattggtacgtggacggcgtggaagtg<br>cataacgccaagaccaagcccagagaggaacagtacaacagc<br>acctaccgggtggtgtccgtgctgacagtgctgcaccaggac<br>tggctgaacggcaaagagtacaagtgcaaggtgtccaacaag<br>gccctgccagcccctatcgagaaaaccatcagcaaggccaag<br>ggccagccccgcgagcctcaggtgtacacactgcctccatgc<br>cgggacgagctgaccaagaaccaggtgtccctgtggtgcctc<br>gtgaagggcttctacccctccgatatcgccgtggaatgggag<br>agcaacggccagcccgagaacaactacaagaccacccctccc<br>gtgctggacagcgacggctcattcttcctgtacagcaagctg<br>accgtggacaagtcccggtggcagcagggcaacgtgttcagc<br>tgctctgtgatgcacgaggccctgcacaaccggttcacccag<br>aagtccctgagcctgagccctggc | |
| Light chain B | LC:<br>gacatccagatgacccagagccccagcagcctgagcgccagc<br>gtgggcgacagagtgaccatcacctgtcgggccagccagggc<br>atccggaactacctggcctggtatcagcagaagcccggcaag<br>gcccccaagctgctgatctacgccgccagcacactgcagagc<br>ggcgtgcccagcagattcagcggcagcggctccggcaccgac<br>ttcaccctgaccatcagcagcctgcagcccgaggacgtggcc<br>acctactactgccagcggtacaacagagccccctacaccttc<br>ggccagggcaccaaggtggaaatcaagggcggctctggcagc<br>tccggctctggcggcgatatcgtgctgacccagtctcccgcc<br>agcctggccgtgtctctgggccagagagccaccatcagctgc<br>agagccagcgagagcgtggacagctacggccagagctacatg<br>cattggtatcagcagaaagccggccagcctcctaaactgctc<br>atctacctggccagcaacctggaatccggcgtgcccgccagg<br>ttttccggcagcggcagcagaaccgatttcacactgacaatc<br>gaccccgtgcaggccgaggatgccgccacatattactgtcag<br>cagaacgccgaggacagccggaccttcggcggaggcaccaag<br>ctcgagattaagggcggaagcggctccagcggcagtggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | SEQ ID NO: 92 |
| | Binding Protein 15 Amino Acid Sequences | |
| Heavy chain A | HC:<br>QVQLQQSGPELVKPGASVKISCKAS***GYSFTSYWIH***WIKQRPG<br>QGLEWIG***MIDPSDGET***RLNQRFQGRATLTVDESTSTAYMQLR<br>SPTSEDSAVYYCTR***LKEYGNYDSFYFDV***WGAGTLVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNH<br>KPSNTKVDKKVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVCTLPPSRDELTKNQVSLSCAVKGF<br>YPSDIAVEWESNGQPENNYKTTPPVLDSDGSFFLVSKLTVDK<br>SRWQQGNVFSCSVMHEALHNHYTQKSLSLSPG | SEQ ID NO: 85 |
| Light chain A | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGQPKAAPSVTLFPPSSEEL<br>QANKATLVCLISDFYPGAVTVAWKADSSPVKAGVETTTPSKQ<br>SNNKYAASSYLSLTPEQWKSHRSYSCQVTHEGSTVEKTVAPT<br>ECS | SEQ ID NO: 86 |
| Heavy chain B | HC:<br>EVQLVESGGGLVQPGRSLRLSCAAS***GFTFDDYAMH***WVRQAPG<br>KGLEWVS***AITWNSGHID***YADSVEGRFTISRDNAKNSLYLQMN<br>SLRAEDTAVYYCAK***VSYLSTASSLDY***WGQGTLVTVSSEVQLK<br>ESGPGLVAPGGSLSITCTVS***GFSLTDSSIN***WVRQPPGKGLEW | SEQ ID NO: 93 |

TABLE 3-continued

| Heavy and light chain sequences of binding proteins specifically directed to IL-4, IL-13 and/or TNFa. | | |
|---|---|---|
| | LG***MIWGDGRID***YADALKSRLSISKDSSKSQVFLEMTSLRTDD<br>TATYYCAR***DGYFPYAMDF***WGQGTSVTVSSASTKGPSVFPLAPS<br>SKSTSGGTAALGCLVKDYFPEPVTVSWNSGALTSGVHTFPAV<br>LQSSGLYSLSSVVTVPSSSLGTQTYICNVNHKPSNTKVDKKV<br>EPKSCDKTHTCPPCPAPELLGGPSVFLFPPKPKDTLMISRTP<br>EVTCVVVDVSHEDPEVKFNWYVDGVEVHNAKTKPREEQYNST<br>YRVVSVLTVLHQDWLNGKEYKCKVSNKALPAPIEKTISKAKG<br>QPREPQVYTLPPCRDELTKNQVSLWCLVKGFYPSDIAVEWES<br>NGQPENNYKTTPPVLDSDGSFFLYSKLTVDKSRWQQGNVFSC<br>SVMHEALHNRFTQKSLSLSPG | |
| Light chain B | LC:<br>DIVLTQSPASLAVSLGQRATISC***RASESVDSYGQSYMH***WYQQ<br>KAGQPPKLLIY***LASNLES***GVPARFSGSGSRTDFTLTIDPVQA<br>EDAATYYC***QQNAEDSRT***FGGGTKLEIKGGSGSSGSGGDIQMT<br>QSPSSLSASVGDRVTITC***RASQGIRNYLA***WYQQKPGKAPKLL<br>IY***AASTLQS***GVPSRFSGSGSGTDFTLTISSLQPEDVATYYC<br>***QRYNRAPYT***FGQGTKVEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 94 |
| Binding Protein 15 Nucleotide Sequences | | |
| Heavy chain A | HC:<br>caggtgcagctgcagcagagcggccccgagctggtgaagccc<br>ggcgccagcgtgaagatcagctgcaaggccagcggctacagc<br>ttcaccagctactggattcactggatcaagcagcgccccggc<br>cagggcctggagtggatcggcatgatcgaccccagcgacggc<br>gagacccgcctgaaccagcgcttccagggccgcgccaccctg<br>accgtggacgagagcaccagcaccgcctacatgcagctgcgc<br>agccccaccagcgaggacagcgccgtgtactactgcacccgc<br>ctgaaggagtacggcaactacgacagcttctacttcgacgtg<br>tggggcgccggcaccctggtgaccgtgagcagcgccagcacc<br>aagggccccagcgtgttccccctggcccctagcagcaagagc<br>acatctggcggcacagccgccctgggctgcctggtcaaggac<br>tacttccccgagcccgtgacagtgtcctggaactctggcgcc<br>ctgaccagcggagtgcataccttccctgccgtgctgcagtcc<br>agcggcctgtacagcctgagcagcgtggtcacagtgcccagc<br>agcagcctgggcacccagacctacatctgcaacgtgaaccac<br>aagcccagcaacaccaaggtggacaagaaggtggaacccaag<br>agctgcgacaagacccacacctgtccccctgccctgcccct<br>gaactgctgggcggaccctccgtgttcctgttccccccaaag<br>cccaaggacaccctgatgatcagccggacccccgaagtgacc<br>tgcgtggtggtggacgtgtcccacgaggaccctgaagtgaag<br>ttcaattggtacgtggacggcgtggaagtgcataacgccaag<br>accaagcccagagaggaacagtacaacagcacctaccgggtg<br>gtgtccgtgctgaccgtgctgcaccaggactggctgaacggc<br>aaagagtacaagtgcaaggtgtccaacaaggccctgcctgcc<br>cccatcgagaaaaccatcagcaaggccaagggccagcctaga<br>gagccccaagtctgcaccctgcccccagcagagatgagctg<br>accaagaaccaggtgtccctgagctgcgccgtgaagggcttc<br>taccccagcgatatcgccgtggaatgggagagcaacggccag<br>cccgagaacaactacaagaccaccccccctgtgctggacagc<br>gacggctcattcttcctggtgtccaagctgacagtggacaag<br>agccggtggcagcagggcaacgtgttcagctgcagcgtgatg<br>cacgaggccctgcacaaccattacacccagaagtccctgagc<br>ctgagccccggc | SEQ ID NO: 89 |
| Light chain A | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggacagcccaaggct<br>gccccctcggtcaccctgttcccccaagctctgaggaactg<br>caggccaacaaggccaccctcgtgtgcctgatcagcgacttc<br>taccctggcgccgtgaccgtggcctggaaggccgatagctct<br>cccgtgaaggccggcgtggaaaccaccacccccagcaagcag<br>agcaacaacaaatacgccgccagcagctacctgagcctgacc<br>cccgagcagtggaagtcccaccggtcctacagctgccaggtc<br>acacacgagggcagcaccgtggaaaagaccgtggcccccacc<br>gagtgcagc | SEQ ID NO: 90 |

TABLE 3-continued

Heavy and light chain sequences of binding proteins specifically directed to IL-4, IL-13 and/or TNFa.

| | | |
|---|---|---|
| Heavy chain B | HC:<br>gaggtgcagctggtggaaagcggcggaggactggtgcagccc<br>ggcagaagcctgagactgagctgcgccgccagcggcttcacc<br>ttcgacgactacgccatgcactgggtccgacaggcccctggc<br>aagggcctggaatgggtgtccgccatcacctggaacagcggc<br>cacatcgactacgccgacagcgtggaaggccggttcaccatc<br>agccgggacaacgccaagaacagcctgtacctgcagatgaac<br>agcctgcgggccgaggacaccgccgtgtactactgcgccaag<br>gtgtcctacctgagcaccgccagcagcctggactactggggc<br>cagggcaccctggtcaccgtgtcctccgaagtgcagctgaaa<br>gagtccggccctggcctggtggcccctggcggcagcctgagc<br>atcacctgtaccgtgtccggcttcagcctgaccgacagcagc<br>atcaactgggtccgccagcctcccggaaagggactcgagtgg<br>ctgggcatgatctggggcgacggccggatcgattacgccgat<br>gccctgaagtcccggctgagcatcagcaaggacagcagcaag<br>agccaggtgttcctggaaatgaccagcctgagaaccgacgac<br>accgccacctactactgtgcccgggacggctacttcccctac<br>gccatggatttctggggacagggaaccagcgtgaccgtgtcc<br>agcgcttccaccaagggccccagcgtgttccctctggcccct<br>agcagcaagagcacatctggcggaacagccgccctgggctgc<br>ctggtcaaggactactttcccgagcccgtgaccgtgtcctgg<br>aactctggtgccctgacaagcggagtgcataccttccctgcc<br>gtgctgcagagcagcggcctgtactctctgagcagcgtggtc<br>accgtgccaagcagcagcctgggcacccagacctacatctgc<br>aacgtgaaccacaagccctccaacaccaaggtggacaagaag<br>gtggaacccaagagctgcgacaagacccacacctgtcctccc<br>tgtcctgcccctgaactgctgggcggaccctccgtgttcctg<br>ttccctccaaagcccaaggataccctgatgatcagccggacc<br>cctgaagtgacctgcgtggtggtggacgtgtcccacgaggat<br>cccgaagtgaagttcaattggtacgtggacggcgtggaagtg<br>cataacgccaagaccaagcccagagaggaacagtacaacagc<br>acctaccgggtggtgtccgtgctgacagtgctgcaccaggac<br>tggctgaacggcaaagagtacaagtgcaaggtgtccaacaag<br>gccctgccagcccctatcgagaaaaccatcagcaaggccaag<br>ggccagccccgcgagcctcaggtgtacacactgcctccatgc<br>cgggacgagctgaccaagaaccaggtgtccctgtggtgcctc<br>gtgaagggcttctacccctccgatatcgccgtggaatgggag<br>agcaacggccagcccgagaacaactacaagaccacccctccc<br>gtgctggacagcgacggctcattcttcctgtacagcaagctg<br>accgtggacaagtcccggtggcagcagggcaacgtgttcagc<br>tgctctgtgatgcacgaggccctgcacaaccggttcacccag<br>aagtccctgagcctgagccctggc | SEQ ID NO: 95 |
| Light chain B | LC:<br>gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaagggc<br>ggctccggcagcagcggctctggcggcgatatccagatgacc<br>cagtcccccagcagcctgagcgccagcgtgggcgacagagtg<br>accatcacctgtagagccagccagggcatccggaactacctg<br>gcttggtatcagcagaaacccggaaaggcccctaaactgctc<br>atctacgccgccagcaccctgcagtccggcgtgccaagcaga<br>ttctccggctctggcagcggcaccgatttcacactgacaatc<br>agcagcctgcagcccgaggatgtggccacctattattgccag<br>agatacaacagagccccctacaccttcggccagggcaccaag<br>gtcgagattaagggcggaagcggcagctccggctccggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | SEQ ID NO: 96 |
| | Binding Protein 16 Amino Acid Sequences | |
| Heavy chain A | HC:<br>EVQLKESGPGLVAPGGSLSITCTVS***GFSLTDSSIN***WVRQPPG<br>KGLEWLG***MIWGDGRID***YADALKSRLSISKDSSKSQVFLEMTS<br>LRTDDTATYYCAR***DGYFPYAMDF***WGQGTSVTVSSASTKGPSV<br>FPLAPSSKSTSGGTAALGCLVKDYFPEPVTVSWNSGALTSGV | SEQ ID NO: 73 |

TABLE 3-continued

| Heavy and light chain sequences of binding proteins specifically directed to IL-4, IL-13 and/or TNFa. | | |
|---|---|---|
| | HTFPAVLQSSGLYSLSSVVTVPSSSLGTQTYICNVNHKPSNT<br>KVDKKVEPKSCDKTHTCPPCPAPELLGGPSVFLFPPKPKDTL<br>MISRTPEVTCVVVDVSHEDPEVKFNWYVDGVEVHNAKTKPRE<br>EQYNSTYRVVSVLTVLHQDWLNGKEYKCKVSNKALPAPIEKT<br>ISKAKGQPREPQVCTLPPSRDELTKNQVSLSCAVKGFYPSDI<br>AVEWESNGQPENNYKTTPPVLDSDGSFFLVSKLTVDKSRWQQ<br>GNVFSCSVMHEALHNHYTQKSLSLSPG | |
| Light chain A | LC:<br>DIVLTQSPASLAVSLGQRATISC***RASESVDSYGQSYMH***WYQQ<br>KAGQPPKLLIY***LASNLES***GVPARFSGSGSRTDFTLTIDPVQA<br>EDAATYYC***QQNAEDSRT***FGGGTKLEIKGQPKAAPSVTLFPPS<br>SEELQANKATLVCLISDFYPGAVTVAWKADSSPVKAGVETTT<br>PSKQSNNKYAASSYLSLTPEQWKSHRSYSCQVTHEGSTVEKT<br>VAPTECS | SEQ ID NO: 74 |
| Heavy chain B | HC:<br>EVQLKESGPGLVAPGGSLSITCTV***SGFSLTDSSIN***WVRQPPG<br>KGLEWLG***MIWGDGRID***YADALKSRLSISKDSSKSQVFLEMTS<br>LRTDDTATYYCAR***DGYFPYAMDF***WGQGTSVTVSSQVQLQQSG<br>PELVKPGASVKISCKAS***GYSFTSYWIH***WIKQRPGQGLEWIG<br>***MIDPSDGET***RLNQRFQGRATLTVDESTSTAYMQLRSPTSEDS<br>AVYYCTR***LKEYGNYDSFYFDV***WGAGTLVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHTCPPCPAPELLGGPSVFLFPPKPKDTLMI<br>SRTPEVTCVVVDVSHEDPEVKFNWYVDGVEVHNAKTKPREEQ<br>YNSTYRVVSVLTVLHQDWLNGKEYKCKVSNKALPAPIEKTIS<br>KAKGQPREPQVYTLPPCRDELTKNQVSLWCLVKGFYPSDIAV<br>EWESNGQPENNYKTTPPVLDSDGSFFLYSKLTVDKSRWQQGN<br>VFSCSVMHEALHNRFTQKSLSLSPG | SEQ ID NO: 68 |
| Light chain B | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGGSGSSGSGGDIVLTQSPA<br>SLAVSLGQRATISC***RASESVDSYGQSYMH***WYQQKAGQPPKLL<br>IY***LASNLES***GVPARFSGSGSRTDFTLTIDPVQAEDAATYYC<br>***QQNAEDSRT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 69 |
| Binding Protein 16_Nucleotide Sequences | | |
| Heavy chain A | HC:<br>gaggtgcagctgaaggagagcggccccggcctggtggccccc<br>ggcggcagcctgagcatcacctgcaccgtgagcggcttcagc<br>ctgaccgacagcagcatcaactgggtgcgccagcccccccggc<br>aagggcctggagtggctgggcatgatctggggcgacggccgc<br>atcgactacgccgacgccctgaagagccgcctgagcatcagc<br>aaggacagcagcaagagccaggtgttcctggagatgaccagc<br>ctgcgcaccgacgacaccgccacctactactgcgcccgcgac<br>ggctacttcccctacgccatggacttctggggccagggcacc<br>agcgtgaccgtgagcagcgccagcaccaagggccccagcgtg<br>ttccccctggcccctagcagcaagagcacatctggcggcaca<br>gccgccctgggctgcctggtcaaggactacttccccgagccc<br>gtgacagtgtcctggaactctggcgccctgaccagcggagtg<br>catacctttcctgccgtgctgcagtccagcggcctgtacagc<br>ctgagcagcgtggtcacagtgcccagcagcagcctgggcacc<br>cagacctacatctgcaacgtgaaccacaagcccagcaacacc<br>aaggtggacaagaaggtggaacccaagagctgcgacaagacc<br>cacacctgtccccccctgccctgcccctgaactgctgggcgga<br>ccctccgtgttcctgttcccccccaaagcccaaggacaccctg<br>atgatcagccggacccccgaagtgacctgcgtggtggtggac<br>gtgtcccacgaggaccctgaagtgaagttcaattggtacgtg<br>gacggcgtggaagtgcataacgccaagaccaagcccagagag<br>gaacagtacaacagcacctaccgggtggtgtccgtgctgacc<br>gtgctgcaccaggactggctgaacggcaaagagtacaagtgc<br>aaggtgtccaacaaggccctgcctgcccccatcgagaaaacc<br>atcagcaaggccaagggccagcctagagagccccaagtctgc<br>accctgcccccccagcagagatgagctgaccaagaaccaggtg<br>tccctgagctgcgccgtgaagggcttctaccccagcgatatc<br>gccgtggaatgggagagcaacggccagcccgagaacaactac<br>aagaccacccccccctgtgctggacagcgacggctcattcttc | SEQ ID NO: 77 |

TABLE 3-continued

| Heavy and light chain sequences of binding proteins specifically directed to IL-4, IL-13 and/or TNFa. | | |
|---|---|---|
| | ctggtgtccaagctgacagtggacaagagccggtggcagcag<br>ggcaacgtgttcagctgcagcgtgatgcacgaggccctgcac<br>aaccattacacccagaagtccctgagcctgagccccggc | |
| Light chain A | LC:<br>gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagccccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaaggga<br>cagcccaaggctgcccccctcggtcaccctgttcccccccaagc<br>agcgaggaactgcaggccaacaaggccaccctcgtgtgcctg<br>atcagcgacttctaccctggcgccgtgaccgtggcctggaag<br>gccgatagctctcccgtgaaggccggcgtggaaaccaccacc<br>cccagcaagcagagcaacaacaaatacgccgccagcagctac<br>ctgagcctgacccccgagcagtggaagtcccaccggtcctac<br>agctgccaggtcacacacgagggcagcaccgtggaaaagacc<br>gtggcccccaccgagtgcagc | SEQ ID NO: 78 |
| Heavy chain B | HC:<br>gaggtgcagctgaaagagtccggccctggactggtggcccct<br>ggcggcagcctgagcatcacctgtaccgtgtccggcttcagc<br>ctgaccgacagcagcatcaactgggtccgacagcccccctggc<br>aagggcctggaatggctgggcatgatctggggcgacggccgg<br>atcgactacgccgacgccctgaagtcccggctgagcatcagc<br>aaggacagcagcaagagccaggtgttcctggaaatgaccagc<br>ctgcggaccgacgacaccgccacctactactgcgccagggac<br>ggctacttcccctacgccatggatttctggggccagggcacc<br>agcgtgaccgtgtccagtcaggtccagctgcagcagagcggc<br>cctgagctggtcaagcctggcgccagcgtgaagatcagctgc<br>aaggccagcggctacagcttcaccagctactggatccactgg<br>atcaagcagcggcctggccagggcctcgagtggatcggaatg<br>atcgaccccagcgacggcgagacacggctgaaccagagattc<br>cagggcagagccaccctgaccgtggacgagagcaccagcacc<br>gcctacatgcagctgcggagccccaccagcgaggacagcgcc<br>gtgtactactgcacccggctgaaagaatacggcaactacgac<br>agcttctacttcgacgtgtggggagccggcaccctggtcacc<br>gtgtctagcgcttccaccaagggccccagcgtgttccctctg<br>gcccctagcagcaagagcacatctggcggaacagccgccctg<br>ggctgcctggtcaaggactactttcccgagcccgtgaccgtg<br>tcctggaactctggtgccctgacaagcggagtgcataccttc<br>cctgccgtgctgcagagcagcggcctgtactctctgagcagc<br>gtggtcaccgtgccaagcagcagcctgggcacccagacctac<br>atctgcaacgtgaaccacaagccctccaacaccaaggtggac<br>aagaaggtggaacccaagagctgcgacaagacccacacctgt<br>cctccctgtcctgcccctgaactgctgggcggaccctccgtg<br>ttcctgttccctccaaagcccaaggataccctgatgatcagc<br>cggacccctgaagtgacctgcgtggtggtggacgtgtcccac<br>gaggatcccgaagtgaagttcaattggtacgtggacggcgtg<br>gaagtgcataacgccaagaccaagcccagagaggaacagtac<br>aacagcacctaccgggtggtgtccgtgctgacagtgctgcac<br>caggactggctgaacggcaaagagtacaagtgcaaggtgtcc<br>aacaaggccctgccagcccctatcgagaaaaccatcagcaag<br>gccaagggccagccccgcgagcctcaggtgtacacactgcct<br>ccatgccgggacgagctgaccaagaaccaggtgtccctgtgg<br>tgcctcgtgaagggcttctacccctccgatatcgccgtggaa<br>tgggagagcaacggccagcccgagaacaactacaagaccacc<br>cctcccgtgctggacagcgacggctcattcttcctgtacagc<br>aagctgaccgtggacaagtcccggtggcagcagggcaacgtg<br>ttcagctgctctgtgatgcacgaggccctgcacaaccggttc<br>acccagaagtccctgagcctgagccctggc | SEQ ID NO: 97 |
| Light chain B | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggcggcagcggcagc<br>tccggctctggcggcgatatcgtgctgacccagtctcccgcc<br>tccctggccgtgtctctgggccagagagccaccatcagctgc<br>cgggccagcgagagcgtggacagctacggccagagctacatg | SEQ ID NO: 70 |

TABLE 3-continued

| Heavy and light chain sequences of binding proteins specifically directed to IL-4, IL-13 and/or TNFa. | | |
|---|---|---|
| | cactggtatcagcagaaggccggacagccccctaaactgctc<br>atctacctggcctccaacctggaaagcggcgtgcccgccagg<br>ttttccggcagcggctccagaaccgacttcaccctgacaatc<br>gaccccgtgcaggccgaggacgccgccacatattactgtcag<br>cagaacgccgaggacagcagaacctttggcggcggaacaaag<br>ctcgagattaagggcggctccggctccagcggatctggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | |
| **Binding Protein 17 Amino Acid Sequences** | | |
| Heavy chain A | HC:<br>QVQLQQSGPELVKPGASVKISCKAS***GYSFTSYWIH***WIKQRPG<br>QGLEWIG***MIDPSDGET***RLNQRFQGRATLTVDESTSTAYMQLR<br>SPTSEDSAVYYCTR***LKEYGNYDSFYFDV***WGAGTLVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNH<br>KPSNTKVDKKVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVCTLPPSRDELTKNQVSLSCAVKGF<br>YPSDIAVEWESNGQPENNYKTTPPVLDSDGSFFLVSKLTVDK<br>SRWQQGNVFSCSVMHEALHNHYTQKSLSLSPG | SEQ ID NO: 85 |
| Light chain A | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGQPKAAPSVTLFPPSSEEL<br>QANKATLVCLISDFYPGAVTVAWKADSSPVKAGVETTTPSKQ<br>SNNKYAASSYLSLTPEQWKSHRSYSCQVTHEGSTVEKTVAPT<br>ECS | SEQ ID NO: 86 |
| Heavy chain B | HC:<br>EVQLKESGPGLVAPGGSLSITCTVS***GFSLTDSSIN***WVRQPP<br>GKGLEWLG***MIWGDGRID***YADALKSRLSISKDSSKSQVFLEMT<br>SLRTDDTATYYCAR***DGYFPYAMDF***WGQGTSVTVSSQVQLQQS<br>GPELVKPGASVKISCKAS***GYSFTSYWIH***WIKQRPGQGLEWIG<br>***MIDPSDGET***RLNQRFQGRATLTVDESTSTAYMQLRSPTSEDS<br>AVYYCTR***LKEYGNYDSFYFDV***WGAGTLVTVSSASTKGPSVFP<br>LAPSSKSTSGGTAALGCLVKDYFPEPVTVSWNSGALTSGVHT<br>FPAVLQSSGLYSLSSVVTVPSSSLGTQTYICNVNHKPSNTKV<br>DKKVEPKSCDKTHTCPPCPAPELLGGPSVFLFPPKPKDTLMI<br>SRTPEVTCVVVDVSHEDPEVKFNWYVDGVEVHNAKTKPREEQ<br>YNSTYRVVSVLTVLHQDWLNGKEYKCKVSNKALPAPIEKTIS<br>KAKGQPREPQVYTLPPCRDELTKNQVSLWCLVKGFYPSDIAV<br>EWESNGQPENNYKTTPPVLDSDGSFFLYSKLTVDKSRWQQGN<br>VFSCSVMHEALHNRFTQKSLSLSPG | SEQ ID NO: 68 |
| Light chain B | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA<br>TYYC***QQAHSYPFT***FGGGTKLEIKGGSGSSGSGGDIVLTQSPA<br>SLAVSLGQRATISC***RASESVDSYGQSYMH***WYQQKAGQPPKLLIY<br>***LASNLES***GVPARFSGSGSRTDFTLTIDPVQAEDAATYYC<br>***QQNAEDSRT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 69 |
| **Binding Protein 17_Nucleotide Sequences** | | |
| Heavy chain A | HC:<br>caggtgcagctgcagcagagcggccccgagctggtgaagccc<br>ggcgccagcgtgaagatcagctgcaaggccagcggctacagc<br>ttcaccagctactggattcactggatcaagcagcgccccggc<br>cagggcctggagtggatcggcatgatcgaccccagcgacggc<br>gagacccgcctgaaccagcgcttccagggccgcgccaccctg<br>accgtggacgagagcaccagcaccgcctacatgcagctgcgc<br>agccccaccagcgaggacagcgccgtgtactactgcacccgc<br>ctgaaggagtacggcaactacgacagcttctacttcgacgtg<br>tggggcgccggcaccctggtgaccgtgagcagcgccagcacc | SEQ ID NO: 89 |

TABLE 3-continued

| Heavy and light chain sequences of binding proteins specifically directed to IL-4, IL-13 and/or TNFa. | | |
|---|---|---|
| | aagggccccagcgtgttcccctggcccctagcagcaagagc<br>acatctggcggcacagccgccctgggctgcctggtcaaggac<br>tacttccccgagcccgtgacagtgtcctggaactctggcgcc<br>ctgaccagcggagtgcataccttccctgccgtgctgcagtcc<br>agcggcctgtacagcctgagcagcgtggtcacagtgcccagc<br>agcagcctgggcacccagacctacatctgcaacgtgaaccac<br>aagcccagcaacaccaaggtggacaagaaggtggaacccaag<br>agctgcgacaagacccacacctgtccccctgccctgcccct<br>gaactgctgggcggaccctccgtgttcctgttcccccaaag<br>cccaaggacaccctgatgatcagccggacccccgaagtgacc<br>tgcgtggtggtggacgtgtcccacgaggaccctgaagtgaag<br>ttcaattggtacgtggacggcgtggaagtgcataacgccaag<br>accaagcccagagaggaacagtacaacagcacctaccgggtg<br>gtgtccgtgctgaccgtgctgcaccaggactggctgaacggc<br>aaagagtacaagtgcaaggtgtccaacaaggccctgcctgcc<br>cccatcgagaaaaccatcagcaaggccaagggccagcctaga<br>gagccccaagtctgcaccctgcccccccagcagagatgagctg<br>accaagaaccaggtgtccctgagctgcgccgtgaagggcttc<br>taccccagcgatatcgccgtggaatgggagagcaacggccag<br>cccgagaacaactacaagaccacccccccctgtgctggacagc<br>gacggctcattcttcctggtgtccaagctgacagtggacaag<br>agccggtggcagcagggcaacgtgttcagctgcagcgtgatg<br>cacgaggccctgcacaaccattacacccagaagtccctgagc<br>ctgagccccggc | |
| Light chain A | LC:<br>Gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc<br>ggcggaggcaccaagctggaaatcaagggacagcccaaggct<br>gccccctcggtcaccctgttcccccaagctctgaggaactg<br>caggccaacaaggccaccctcgtgtgcctgatcagcgacttc<br>taccctggcgccgtgaccgtggcctggaaggccgatagctct<br>cccgtgaaggccggcgtggaaaccaccacccccagcaagcag<br>agcaacaacaaatacgccgccagcagctacctgagcctgacc<br>cccgagcagtggaagtcccaccggtcctacagctgccaggtc<br>acacacgagggcagcaccgtggaaaagaccgtggcccccacc<br>gagtgcagc | SEQ ID NO: 90 |
| Heavy chain B | HC:<br>gaggtgcagctgaaagagtccggccctggactggtggcccct<br>ggcggcagcctgagcatcacctgtaccgtgtccggcttcagc<br>ctgaccgacagcagcatcaactgggtccgacagccccctggc<br>aagggcctggaatggctgggcatgatctggggcgacggccgg<br>atcgactacgccgacgccctgaagtcccggctgagcatcagc<br>aaggacagcagcaagagccaggtgttcctggaaatgaccagc<br>ctgcggaccgacgacaccgccacctactactgcgccagggac<br>ggctacttcccctacgccatggatttctggggccagggcacc<br>agcgtgaccgtgtccagtcaggtccagctgcagcagagcggc<br>cctgagctggtcaagcctggcgccagcgtgaagatcagctgc<br>aaggccagcggctacagcttcaccagctactggatccactgg<br>atcaagcagcggcctggccagggcctcgagtggatcggaatg<br>atcgaccccagcgacggcgagacacggctgaaccagagattc<br>cagggcagagccaccctgaccgtggacgagagcaccagcacc<br>gcctacatgcagctgcggagccccaccagcgaggacagcgcc<br>gtgtactactgcacccggctgaaagaatacggcaactacgac<br>agcttctacttcgacgtgtggggagccggcaccctggtcacc<br>gtgtctagcgcttccaccaagggccccagcgtgttccctctg<br>gcccctagcagcaagagcacatctggcggaacagccgccctg<br>ggctgcctggtcaaggactactttcccgagcccgtgaccgtg<br>tcctggaactctggtgccctgacaagcggagtgcataccttc<br>cctgccgtgctgcagagcagcggcctgtactctctgagcagc<br>gtggtcaccgtgccaagcagcagcctgggcacccagacctac<br>atctgcaacgtgaaccacaagccctccaacaccaaggtggac<br>aagaaggtggaacccaagagctgcgacaagacccacacctgt<br>cctccctgtcctgcccctgaactgctgggcggaccctccgtg<br>ttcctgttccctccaaagcccaaggataccctgatgatcagc<br>cggacccctgaagtgacctgcgtggtggtggacgtgtcccac<br>gaggatcccgaagtgaagttcaattggtacgtggacggcgtg<br>gaagtgcataacgccaagaccaagcccagagaggaacagtac<br>aacagcacctaccgggtggtgtccgtgctgacagtgctgcac<br>caggactggctgaacggcaaagagtacaagtgcaaggtgtcc<br>aacaaggccctgccagcccctatcgagaaaaccatcagcaag | SEQ ID NO: 97 |

TABLE 3-continued

| Heavy and light chain sequences of binding proteins specifically directed to IL-4, IL-13 and/or TNFa. | | |
|---|---|---|
| | gccaagggccagccccgcgagcctcaggtgtacacactgcct ccatgccgggacgagctgaccaagaaccaggtgtccctgtgg tgcctcgtgaagggcttctaccccctccgatatcgccgtggaa tgggagagcaacggccagcccgagaacaactacaagaccacc cctcccgtgctggacagcgacggctcattcttcctgtacagc aagctgaccgtggacaagtcccggtggcagcagggcaacgtg ttcagctgctctgtgatgcacgaggccctgcacaaccggttc acccagaagtccctgagcctgagccctggc | |
| Light chain B | LC: gacatccagatgacccagagccccgccagcctgagcgtgtcc gtgggcgataccatcaccctgacctgccacgccagccagaac atcgacgtgtggctgagctggttccagcagaagcccggcaac atccccaagctgctgatctacaaggccagcaacctgcacacc ggcgtgcccagcagattcagcggctctggcagcggcaccggc tttaccctgaccatcagcagcctgcagcccgaggatatcgcc acctactactgccagcaggcccacagctaccccttcaccttc ggcggaggcaccaagctggaaatcaagggcggcagcggcagc tccggctctggcggcgatatcgtgctgacccagtctcccgcc tccctggccgtgtctctgggccagagagccaccatcagctgc cgggccagcgagagcgtggacagctacggccagagctacatg cactggtatcagcagaaggccggacagccccccctaaactgctc atctacctggcctccaacctggaaagcggcgtgcccgccagg ttttccggcagcggctccagaaccgacttcaccctgacaatc gaccccgtgcaggccgaggacgccgccacatattactgtcag cagaacgccgaggacagcagaacctttggcggcggaacaaag ctcgagattaagggcggctccggctccagcggatctggcgga cgtacggtggccgctccttccgtgttcatcttccctccctcc gacgagcagctgaagtccggcaccgcctccgtggtgtgtctg ctgaacaacttctaccctcgggaggccaaggtgcagtggaag gtggacaacgccctgcagtccggcaactcccaggagtccgtc accgagcaggactccaaggacagcacctactccctgtcctcc accctgaccctgtccaaggccgactacgagaagcacaaggtg tacgcctgtgaggtgacccaccagggcctgtccagccctgtg accaagtccttcaaccggggcgagtgc | SEQ ID NO: 70 |
| Binding Protein 18 Amino Acid Sequences | | |
| Heavy chain A | HC: EVQLKESGPGLVAPGGSLSITCTVS***GFSLTDSSIN***WVRQPPG KGLEWLG***MIWGDGRID***YADALKSRLSISKDSSKSQVFLEMTS LRTDDTATYYCAR***DGYFPYAMDF***WGQGTSVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNT KVDKKVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKT ISKAKGQPREPQVCTLPPSRDELTKNQVSLSCAVKGFYPSDI AVEWESNGQPENNYKTTPPVLDSDGSFFLVSKLTVDKSRWQQ GNVFSCSVMHEALHNHYTQKSLSLSPG | SEQ ID NO: 73 |
| Light chain A | LC: DIVLTQSPASLAVSLGQRATISC***RASESVDSYGQSYMH***WYQQ KAGQPPKLLIY***LASNLES***GVPARFSGSGSRTDFTLTIDPVQA EDAATYYC ***QQNAEDSRT***FGGGTKLEIKGQPKAAPSVTLFPPS SEELQANKATLVCLISDFYPGAVTVAWKADSSPVKAGVETTT PSKQSNNKYAASSYLSLTPEQWKSHRSYSCQVTHEGSTVEKT VAPTECS | SEQ ID NO: 74 |
| Heavy chain B | HC: QVQLQQSGPELVKPGASVKISCKAS***GYSFTSYWIH***WIKQRPG QGLEWIG***MIDPSDGET***RLNQRFQGRATLTVDESTSTAYMQLR SPTSEDSAVYYCTR***LKEYGNYDSFYFDV***WGAGTLVTVSSEVQ LKESGPGLVAPGGSLSITCTVS***GFSLTDSSIN***NWVRQPPGKGL EWLG***MIWGDGRID***YADALKSRLSISKDSSKSQVFLEMTSLRT DDTATYYCAR***DGYFPYAMDF***WGQGTSVTVSSASTKGPSVFPL APSSKSTSGGTAALGCLVKDYFPEPVTVSWNSGALTSGVHTF PAVLQSSGLYSLSSVVTVPSSSLGTQTYICNVNHKPSNTKVD KKVEPKSCDKTHTCPPCPAPELLGGPSVFLFPPKPKDTLMIS RTPEVTCVVVDVSHEDPEVKFNWYVDGVEVHNAKTKPREEQY NSTYRVVSVLTVLHQDWLNGKEYKCKVSNKALPAPIEKTISK AKGQPREPQVYTLPPCRDELTKNQVSLWCLVKGFYPSDIAVE WESNGQPENNYKTTPPVLDSDGSFFLYSKLTVDKSRWQQGNV FSCSVMHEALHNRFTQKSLSLSPG | SEQ ID NO: 62 |

TABLE 3-continued

| Heavy and light chain sequences of binding proteins specifically directed to IL-4, IL-13 and/or TNFa. | | |
|---|---|---|
| Light<br>chain B | LC:<br>DIVLTQSPASLAVSLGQRATISC***RASESVDSYGQSYMH***WYQQ<br>KAGQPPKLLIY***LASNLES***GVPARFSGSGSRTDFTLTIDPVQA<br>EDAATYYC***QQNAEDSRT***FGGGTKLEIKGGSGSSGSGGDIQMT<br>QSPASLSVSVGDTITLTC***HASQNIDVWLS***WFQQKPGNIPKLL<br>IY***KASNLHT***GVPSRFSGSGSGTGFTLTISSLQPEDIATYYC<br>***QQAHSYPFT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 63 |
| Binding Protein 18 Nucleotide Sequences | | |
| Heavy<br>chain A | HC:<br>gaggtgcagctgaaggagagcggccccggcctggtggccccc<br>ggcggcagcctgagcatcacctgcaccgtgagcggcttcagc<br>ctgaccgacagcagcatcaactgggtgcgccagcccccggc<br>aagggcctggagtggctgggcatgatctggggcgacggccgc<br>atcgactacgccgacgccctgaagagccgcctgagcatcagc<br>aaggacagcagcaagagccaggtgttcctggagatgaccagc<br>ctgcgcaccgacgacaccgccacctactactgcgcccgcgac<br>ggctacttcccctacgccatggacttctggggccagggcacc<br>agcgtgaccgtgagcagcgccagcaccaagggccccagcgtg<br>ttccccctggcccctagcagcaagagcacatctggcggcaca<br>gccgccctgggctgcctggtcaaggactacttccccgagccc<br>gtgacagtgtcctggaactctggcgccctgaccagcggagtg<br>catacettccctgccgtgctgcagtccagcggcctgtacagc<br>ctgagcagcgtggtcacagtgcccagcagcagcctgggcacc<br>cagacctacatctgcaacgtgaaccacaagcccagcaacacc<br>aaggtggacaagaaggtggaacccaagagctgcgacaagacc<br>cacacctgtccccctgccctgcccctgaactgctgggcgga<br>ccctccgtgttcctgttcccccaaagcccaaggacaccctg<br>atgatcagccggacccccgaagtgacctgcgtggtggtggac<br>gtgtcccacgaggaccctgaagtgaagttcaattggtacgtg<br>gacggcgtggaagtgcataacgccaagaccaagcccagagag<br>gaacagtacaacagcacctaccgggtggtgtccgtgctgacc<br>gtgctgcaccaggactggctgaacggcaaagagtacaagtgc<br>aaggtgtccaacaaggccctgcctgcccccatcgagaaaacc<br>atcagcaaggccaagggccagcctagagagccccaagtctgc<br>accctgcccccagcagagatgagctgaccaagaaccaggtg<br>tccctgagctgcgccgtgaagggcttctaccccagcgatatc<br>gccgtggaatgggagagcaacggccagcccgagaacaactac<br>aagaccacccccctgtgctggacagcgacggctcattcttc<br>ctggtgtccaagctgacagtggacaagagccggtggcagcag<br>ggcaacgtgttcagctgcagcgtgatgcacgaggccctgcac<br>aaccattacacccagaagtccctgagcctgagccccggc | SEQ ID NO: 77 |
| Light<br>chain A | LC:<br>gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaaggga<br>cagcccaaggctgccccctcggtcaccctgttcccccaagc<br>agcgaggaactgcaggccaacaaggccaccctcgtgtgcctg<br>atcagcgacttctaccctggcgccgtgaccgtggcctggaag<br>gccgatagctctcccgtgaaggccggcgtggaaaccaccacc<br>cccagcaagcagagcaacaacaaatacgccgccagcagctac<br>ctgagcctgacccccgagcagtggaagtcccaccggtcctac<br>agctgccaggtcacacacgagggcagcaccgtggaaaagacc<br>gtggcccccaccgagtgcagc | SEQ ID NO: 78 |
| Heavy<br>chain B | HC:<br>caggtgcagctgcagcagagcggccctgagctggtcaagcct<br>ggcgccagcgtgaagatcagctgcaaggccagcggctacagc<br>ttcaccagctactggatccactggatcaagcagcggcctggc<br>cagggcctggaatggatcggcatgatcgaccccagcgacggc<br>gagacacggctgaaccagagattccagggcagagccaccctg<br>accgtggacgagagcaccagcaccgcctacatgcagctgcgg<br>agccccaccagcgaggacagcgccgtgtactactgcacccgg<br>ctgaaagagtacggcaactacgacagatctacttcgacgtgt<br>ggggagccggcaccctggtcaccgtgtccagcgaagtgcagc<br>tgaaagaaagcggccctggcctggtggcccctggcggcagcc | SEQ ID NO: 66 |

TABLE 3-continued

| Heavy and light chain sequences of binding proteins specifically directed to IL-4, IL-13 and/or TNFa. | | |
|---|---|---|
| | tgagcatcacctgtaccgtgtccggcttcagcctgaccgaca<br>gcagcatcaactgggtccgacagcccccctggcaagggcctcg<br>agtggctgggaatgatctggggcgacggccggatcgactacg<br>ccgacgccctgaagtcccggctgagcatcagcaaggacagca<br>gcaagagccaggtgttcctggaaatgaccagcctgcggaccg<br>acgacaccgccacctactactgcgccagggacggctacttcc<br>cctacgccatggatttctggggccagggcaccagcgtgaccg<br>tgtcctctgcttccaccaagggccccagcgtgttccctctgg<br>cccctagcagcaagagcacatctggcggaacagccgccctgg<br>gctgcctggtcaaggactactttcccgagcccgtgaccgtgt<br>cctggaactctggtgccctgacaagcggagtgcataccttcc<br>ctgccgtgctgcagagcagcggcctgtactctctgagcagcg<br>tggtcaccgtgccaagcagcagcctgggcacccagacctaca<br>tctgcaacgtgaaccacaagccctccaacaccaaggtggaca<br>agaaggtggaacccaagagctgcgacaagacccacacctgtc<br>ctccctgtcctgcccctgaactgctgggcggaccctccgtgt<br>tcctgttccctccaaagcccaaggataccctgatgatcagcc<br>ggacccctgaagtgacctgcgtggtggtggacgtgtcccacg<br>aggatcccgaagtgaagttcaattggtacgtggacggcgtgg<br>aagtgcataacgccaagaccaagcccagagaggaacagtaca<br>acagcacctaccgggtggtgtccgtgctgacagtgctgcacc<br>aggactggctgaacggcaaagagtacaagtgcaaggtgtcca<br>acaaggccctgccagcccctatcgagaaaaccatcagcaagg<br>ccaagggccagccccgcgagcctcaggtgtacacactgcctc<br>catgccgggacgagctgaccaagaaccaggtgtccctgtggt<br>gcctcgtgaagggcttctacccctccgatatcgccgtggaat<br>gggagagcaacggccagcccgagaacaactacaagaccaccc<br>ctcccgtgctggacagcgacggctcattcttcctgtacagca<br>agctgaccgtggacaagtcccggtggcagcagggcaacgtgt<br>tcagctgctctgtgatgcacgaggccctgcacaaccggttca<br>cccagaagtccctgagcctgagccctggc | |
| Light chain B | LC:<br>Gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaagggc<br>ggctccggcagcagcggctctggcggcgatatccagatgacc<br>cagtcccccgcctccctgagcgtgtccgtgggcgacaccatc<br>accctgacatgccacgccagccagaacatcgacgtgtggctg<br>agctggttccagcagaagcctggcaacatccctaagctgctc<br>atctataaggcctccaacctgcacaccggcgtgcccagcagg<br>ttttccggctctggcagcggcaccggctttaccctgacaatc<br>agcagcctgcagcccgaggatatcgccacatattactgtcag<br>caggcccacagctaccccttcacctttggcggcggaacaaag<br>ctcgagattaagggcggcagcggaagctccggctccggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg<br>tacgcctgtgaggtgacccaccagggcctgtccagccctgtg<br>accaagtccttcaaccggggcgagtgc | SEQ ID NO: 67 |
| | Binding Protein 19 Amino Acid Sequences | |
| Heavy chain A | HC:<br>QVQLQQSGPELVKPGASVKISCKAS***GYSFTSYWIH***WIKQRPG<br>QGLEWIG***MIDPSDGET***RLNQRFQGRATLTVDESTSTAYMQLR<br>SPTSEDSAVYYCTR***LKEYGNYDSFYFDV***WGAGTLVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNH<br>KPSNTKVDKKVEPKSCDKTHTCPPCPAPELLGGPSVFLFPPK<br>PKDTLMISRTPEVTCVVVDVSHEDPEVKFNWYVDGVEVHNAK<br>TKPREEQYNSTYRVVSVLTVLHQDWLNGKEYKCKVSNKALPA<br>PIEKTISKAKGQPREPQVCTLPPSRDELTKNQVSLSCAVKGF<br>YPSDIAVEWESNGQPENNYKTTPPVLDSDGSFFLVSKLTVDK<br>SRWQQGNVFSCSVMHEALHNHYTQKSLSLSPG | SEQ ID NO: 85 |
| Light chain A | LC:<br>DIQMTQSPASLSVSVGDTITLTC***HASQNIDVWLS***WFQQKPGN<br>IPKLLIY***KASNLHT***GVPSRFSGSGSGTGFTLTISSLQPEDIA | SEQ ID NO: 86 |

TABLE 3-continued

| Heavy and light chain sequences of binding proteins specifically directed to IL-4, IL-13 and/or TNFa. | | |
|---|---|---|
| | TYYC***QQAHSYPFT***FGGGTKLEIKGQPKAAPSVTLFPPSSEEL<br>QANKATLVCLISDFYPGAVTVAWKADSSPVKAGVETTTPSKQ<br>SNNKYAASSYLSLTPEQWKSHRSYSCQVTHEGSTVEKTVAPT<br>ECS | |
| Heavy chain B | HC:<br>QVQLQQSGPELVKPGASVKISCKAS***GYSFTSYWIH***WIKQRPG<br>QGLEWIG***MIDPSDGET***RLNQRFQGRATLTVDESTSTAYMQLR<br>SPTSEDSAVYYCTR***LKEYGNYDSFYFDV***WGAGTLVTVSSEVQ<br>LKESGPGLVAPGGSLSITCTVS***GFSLTDSSIN***WVRQPPGKGL<br>EWLG***MIWGDGRID***YADALKSRLSISKDSSKSQVFLEMTSLRT<br>DDTATYYCAR***DGYFPYAMDF***WGQGTSVTVSSASTKGPSVFPL<br>APSSKSTSGGTAALGCLVKDYFPEPVTVSWNSGALTSGVHTF<br>PAVLQSSGLYSLSSVVTVPSSSLGTQTYICNVNHKPSNTKVD<br>KKVEPKSCDKTHTCPPCPAPELLGGPSVFLFPPKPKDTLMIS<br>RTPEVTCVVVDVSHEDPEVKFNWYVDGVEVHNAKTKPREEQY<br>NSTYRVVSVLTVLHQDWLNGKEYKCKVSNKALPAPIEKTISK<br>AKGQPREPQVYTLPPCRDELTKNQVSLWCLVKGFYPSDIAVE<br>WESNGQPENNYKTTPPVLDSDGSFFLYSKLTVDKSRWQQGNV<br>FSCSVMHEALHNRFTQKSLSLSPG | SEQ ID NO: 62 |
| Light chain B | LC:<br>DIVLTQSPASLAVSLGQRATISC***RASESVDSYGQSYMH***WYQQ<br>KAGQPPKLLIYY***LASNLES***GVPARFSGSGSRTDFTLTIDPVQAED<br>AATYYC***QQNAEDSRT***FGGGTKLEIKGGSGSSGSGGDIQMTQS<br>PASLSVSVGDTITLTC***HASQNIDVWLS***WFQQKPGNIPKLLIY<br>***KASNLHT***GVPSRFSGSGSGTGFTLTISSLQPEDIATYYC<br>***QQAHSYPFT***FGGGTKLEIKGGSGSSGSGGRTVAAPSVFIFPP<br>SDEQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC | SEQ ID NO: 63 |
| Binding Protein 19 Nucleotide Sequences | | |
| Heavy chain A | HC:<br>caggtgcagctgcagcagagcggccccgagctggtgaagccc<br>ggcgccagcgtgaagatcagctgcaaggccagcggctacagc<br>ttcaccagctactggattcactggatcaagcagcgccccggc<br>cagggcctggagtggatcggcatgatcgaccccagcgacggc<br>gagacccgcctgaaccagcgcttccagggccgcgccaccctg<br>accgtggacgagagcaccagcaccgcctacatgcagctgcgc<br>agccccaccagcgaggacagcgccgtgtactactgcacccgc<br>ctgaaggagtacggcaactacgacagcttctacttcgacgtg<br>tggggcgccggcaccctggtgaccgtgagcagcgccagcacc<br>aagggccccagcgtgttccccctggcccctagcagcaagagc<br>acatctggcggcacagccgccctgggctgcctggtcaaggac<br>tacttccccgagcccgtgacagtgtcctggaactctggcgcc<br>ctgaccagcggagtgcataccttccctgccgtgctgcagtcc<br>agcggcctgtacagcctgagcagcgtggtcacagtgcccagc<br>agcagcctgggcacccagacctacatctgcaacgtgaaccac<br>aagcccagcaacaccaaggtggacaagaaggtggaacccaag<br>agctgcgacaagacccacacctgtccccctgccctgcccct<br>gaactgctgggcggaccctccgtgttcctgttccccccaaag<br>cccaaggacaccctgatgatcagccggacccccgaagtgacc<br>tgcgtggtggtggacgtgtcccacgaggaccctgaagtgaag<br>ttcaattggtacgtggacggcgtggaagtgcataacgccaag<br>accaagcccagagaggaacagtacaacagcacctaccgggtg<br>gtgtccgtgctgaccgtgctgcaccaggactggctgaacggc<br>aaagagtacaagtgcaaggtgtccaacaaggccctgcctgcc<br>cccatcgagaaaaccatcagcaaggccaagggccagcctaga<br>gagccccaagtctgcaccctgcccccccagcagagatgagctg<br>accaagaaccaggtgtccctgagctgcgccgtgaagggcttc<br>taccccagcgatatcgccgtggaatgggagagcaacggccag<br>cccgagaacaactacaagaccacccccccctgtgctggacagc<br>gacggctcattcttcctggtgtccaagctgacagtggacaag<br>agccggtggcagcagggcaacgtgttcagctgcagcgtgatg<br>cacgaggccctgcacaaccattacacccagaagtccctgagc<br>ctgagccccggc | SEQ ID NO: 89 |
| Light chain A | LC:<br>gacatccagatgacccagagccccgccagcctgagcgtgtcc<br>gtgggcgataccatcaccctgacctgccacgccagccagaac<br>atcgacgtgtggctgagctggttccagcagaagcccggcaac<br>atccccaagctgctgatctacaaggccagcaacctgcacacc<br>ggcgtgcccagcagattcagcggctctggcagcggcaccggc<br>tttaccctgaccatcagcagcctgcagcccgaggatatcgcc<br>acctactactgccagcaggcccacagctaccccttcaccttc | SEQ ID NO: 90 |

TABLE 3-continued

| Heavy and light chain sequences of binding proteins specifically directed to IL-4, IL-13 and/or TNFa. | | |
|---|---|---|
| | ggcggaggcaccaagctggaaatcaagggacagcccaaggct<br>gccccctcggtcaccctgttcccccaagctctgaggaactg<br>caggccaacaaggccaccctcgtgtgcctgatcagcgacttc<br>taccctggcgccgtgaccgtggcctggaaggccgatagctct<br>cccgtgaaggccggcgtggaaaccaccacccccagcaagcag<br>agcaacaacaaatacgccgccagcagctacctgagcctgacc<br>cccgagcagtggaagtcccaccggtcctacagctgccaggtc<br>acacacgagggcagcaccgtggaaaagaccgtggcccccacc<br>gagtgcagc | |
| Heavy chain B | HC:<br>caggtgcagctgcagcagagcggccctgagctggtcaagcct<br>ggcgccagcgtgaagatcagctgcaaggccagcggctacagc<br>ttcaccagctactggatccactggatcaagcagcggcctggc<br>cagggcctggaatggatcggcatgatcgaccccagcgacggc<br>gagacacggctgaaccagagattccagggcagagccaccctg<br>accgtggacgagagcaccagcaccgcctacatgcagctgcgg<br>agccccaccagcgaggacagcgccgtgtactactgcacccgg<br>ctgaaagagtacggcaactacgacagatctacttcgacgtgt<br>ggggagccggcaccctggtcaccgtgtccagcgaagtgcagc<br>tgaaagaaagcggccctggcctggtggcccctggcggcagcc<br>tgagcatcacctgtaccgtgtccggcttcagcctgaccgaca<br>gcagcatcaactgggtccgacagccccctggcaagggcctcg<br>agtggctgggaatgatctggggcgacggccggatcgactacg<br>ccgacgccctgaagtcccggctgagcatcagcaaggacagca<br>gcaagagccaggtgttcctggaaatgaccagcctgcggaccg<br>acgacaccgccacctactactgcgccagggacggctacttcc<br>cctacgccatggatttctggggccagggcaccagcgtgaccg<br>tgtcctctgcttccaccaagggccccagcgtgttccctctgg<br>cccctagcagcaagagcacatctggcggaacagccgccctgg<br>gctgcctggtcaaggactactttcccgagcccgtgaccgtgt<br>cctggaactctggtgccctgacaagcggagtgcataccttcc<br>ctgccgtgctgcagagcagcggcctgtactctctgagcagcg<br>tggtcaccgtgccaagcagcagcctgggcacccagacctaca<br>tctgcaacgtgaaccacaagccctccaacaccaaggtggaca<br>agaaggtggaacccaagagctgcgacaagacccacacctgtc<br>ctccctgtcctgcccctgaactgctgggcggaccctccgtgt<br>tcctgttccctccaaagcccaaggataccctgatgatcagcc<br>ggacccctgaagtgacctgcgtggtggtggacgtgtcccacg<br>aggatcccgaagtgaagttcaattggtacgtggacggcgtgg<br>aagtgcataacgccaagaccaagcccagagaggaacagtaca<br>acagcacctaccgggtggtgtccgtgctgacagtgctgcacc<br>aggactggctgaacggcaaagagtacaagtgcaaggtgtcca<br>acaaggccctgccagcccctatcgagaaaaccatcagcaagg<br>ccaagggccagccccgcgagcctcaggtgtacacactgcctc<br>catgccgggacgagctgaccaagaaccaggtgtccctgtggt<br>gcctcgtgaagggcttctacccctccgatatcgccgtggaat<br>gggagagcaacggccagcccgagaacaactacaagaccaccc<br>ctcccgtgctggacagcgacggctcattcttcctgtacagca<br>agctgaccgtggacaagtcccggtggcagcagggcaacgtgt<br>tcagctgctctgtgatgcacgaggccctgcacaaccggttca<br>cccagaagtccctgagcctgagccctggc | SEQ ID NO: 66 |
| Light chain B | LC:<br>gacatcgtgctgacccagagccctgccagcctggccgtgtct<br>ctgggccagagagccaccatcagctgccgggccagcgagagc<br>gtggacagctacggccagagctacatgcactggtatcagcag<br>aaggccggccagcccccccaagctgctgatctacctggccagc<br>aacctggaaagcggcgtgcccgccagattcagcggcagcggc<br>agcagaaccgacttcaccctgaccatcgaccccgtgcaggcc<br>gaggacgccgccacctactactgccagcagaacgccgaggac<br>agccggaccttcggcggaggcaccaagctggaaatcaagggc<br>ggctccggcagcagcggctctggcggcgatatccagatgacc<br>cagtccccgcctccctgagcgtgtccgtgggcgacaccatc<br>accctgacatgccacgccagccagaacatcgacgtgtggctg<br>agctggttccagcagaagcctggcaacatccctaagctgctc<br>atctataaggcctccaacctgcacaccggcgtgcccagcagg<br>ttttccggctctggcagcggcaccggctttaccctgacaatc<br>agcagcctgcagcccgaggatatcgccacatattactgtcag<br>caggcccacagctaccccttcacctttggcggcggaacaaag<br>ctcgagattaagggcggcagcggaagctccggctccggcgga<br>cgtacggtggccgctccttccgtgttcatcttccctccctcc<br>gacgagcagctgaagtccggcaccgcctccgtggtgtgtctg<br>ctgaacaacttctaccctcgggaggccaaggtgcagtggaag<br>gtggacaacgccctgcagtccggcaactcccaggagtccgtc<br>accgagcaggactccaaggacagcacctactccctgtcctcc<br>accctgaccctgtccaaggccgactacgagaagcacaaggtg | SEQ ID NO: 67 |

TABLE 3-continued

| Heavy and light chain sequences of binding proteins specifically directed to IL-4, IL-13 and/or TNFa. |
|---|
| tacgcctgtgaggtgacccaccagggcctgtccagccctgtg accaagtccttcaaccggggcgagtgc |

TABLE 4

| CDR sequences of binding proteins | | | | | | |
|---|---|---|---|---|---|---|
| Ab | CDR_H1 | CDR_H2 | CDR_H3 | CDR_L1 | CDR_L2 | CDR_L3 |
| Anti-Her2 | GFNIKDTY (SEQ ID NO: 25) | IYPTNGYT (SEQ ID NO: 26) | SRWGGDGFYAMDY (SEQ ID NO: 27) | QDVNTA (SEQ ID NO: 43) | SAS (SEQ ID NO: 44) | QQHYTTPPT (SEQ ID NO: 45) |
| Anti-CD3 | GFTFTKAW (SEQ ID NO: 34) | IKDKSNS (SEQ ID NO: 35) | RGVYYALSPFDY (SEQ ID NO: 36) | QSLVHNNANTY (SEQ ID NO: 52) | KVS (SEQ ID NO: 53) | GQGTQYP (SEQ ID NO: 54) |
| Anti-CD3-2 | GFTFTKAW (SEQ ID NO: 34) | IKDKSNS (SEQ ID NO: 35) | RGVYYALSPFDY (SEQ ID NO: 36) | QSLVHNNGNTY (SEQ ID NO: 149) | KVS (SEQ ID NO: 53) | GQGTQYP (SEQ ID NO: 54) |
| Anti-CD19 | GYAFSSYW (SEQ ID NO: 37) | IWPGDGDT (SEQ ID NO: 38) | ARRETTTVGRYYYAMD (SEQ ID NO: 39) | QSVDYDGDSY (SEQ ID NO: 55) | DAS (SEQ ID NO: 56) | QQSIEDPWT (SEQ ID NO: 57) |
| Anti-CD20 | GYTFTSYN (SEQ ID NO: 120) | IYPGNGDT (SEQ ID NO: 121) | ARSTYYGGDWYFNV (SEQ ID NO: 122) | SSVSY (SEQ ID NO: 123) | ATS (SEQ ID NO: 124) | QQWTSNP (SEQ ID NO: 125) |
| Anti-CD28-1 | GYTFTSYY (SEQ ID NO: 28) | IYPGNVNT (SEQ ID NO: 29) | TRSHYGLDWNFDV (SEQ ID NO: 30) | QNIYVW (SEQ ID NO: 46) | KAS (SEQ ID NO: 47) | QQGQTYPYT (SEQ ID NO: 48) |
| Anti-CD28-2 | GFSLSDYG (SEQ ID NO: 31) | IWAGGGT (SEQ ID NO: 32) | ARDKGYSYYYSMD (SEQ ID NO: 33) | ESVEYYVTSL (SEQ ID NO: 49) | AAS (SEQ ID NO: 50) | QQSRKVPYT (SEQ ID NO: 51) |
| Anti-CD38 | GYTFTDYW (SEQ ID NO: 40) | IYPGDGDT (SEQ ID NO: 41) | ARGDYYGSNSLDY (SEQ ID NO: 42) | QDVSTV (SEQ ID NO: 58) | SAS (SEQ ID NO: 44) | QQHYSPPYT (SEQ ID NO: 59) |
| Anti-LAMP1 | GYIFTNYNIH (SEQ ID NO: 126) | AIYPGNGDAP (SEQ ID NO: 127) | ANWDVAFAY (SEQ ID NO: 128) | KASQDIDRYMA (SEQ ID NO: 138) | DTSTLQS (SEQ ID NO: 139) | LQYDNLWT (SEQ ID NO: 140) |
| Anti-TNFα | GFTFDDYAMH (SEQ ID NO: 129) | AITWNSGHID (SEQ ID NO: 130) | VSYLSTASSLDY (SEQ ID NO: 131) | RASQGIRNYLA (SEQ ID NO: 141) | AASTLQS (SEQ ID NO: 178) | QRYNRAPYT (SEQ ID NO: 142) |
| Anti-IL4 | GYSFTSYWIH (SEQ ID NO: 132) | MIDPSDGET (SEQ ID NO: 133) | LKEYGNYDSFYFDV (SEQ ID NO: 134) | HASQNIDVWLS (SEQ ID NO: 143) | KASNLHT (SEQ ID NO: 179) | QQAHSYPFT (SEQ ID NO: 144) |
| Anti-IL13 | GFSLTDSSIN (SEQ ID NO: 135) | MIWGDGRID (SEQ ID NO: 136) | DGYFPYAMDF (SEQ ID NO: 137) | RASESVDSYGQSYMH (SEQ ID NO: 145) | LASNLES (SEQ ID NO: 146) | QQNAEDSRT (SEQ ID NO: 147) |

TABLE 5

| VH/VL sequences of binding proteins | | |
|---|---|---|
| Ab | VH (protein) | VL (protein) |
| Anti-Her2 | EVQLVESGGGLVQPGGSLRLSCAAS***GFNIKDTY***IHWVRQAPGKGLEWVAR***IYPTNGYT***RYADSVKGRFTISADTSKNTAYLQMNSLRAEDTAVYYC***SRWGGDGFYAMDY***WGQGTLVTVSS (SEQ ID NO: 150) | DIQMTQSPSSLSASVGDRVTITCRAS***QDVNTA***VAWYQQKPGKAPKLLIY***SAS***FLYSGVPSRFSGSRSGTDFTLTISSLQPEDFATYYC***QQHYTTPPT***FGQGTKVEIK (SEQ ID NO: 151) |

TABLE 5-continued

VH/VL sequences of binding proteins

| Ab | VH (protein) | VL (protein) |
|---|---|---|
| Anti-CD3 | QVQLVESGGGVVQPGRSLRLSCAAS***GFTFTKAW***MHWVRQAPGKQLEWVAQ***IKDKSNS***YATYYADSVKGRFTISRDDSKNTLYLQMNSLRAEDTAVYYC***RGVYYALSPFDY***WGQGTLVTVSS (SEQ ID NO: 152) | DIVMTQTPLSLSVTPGQPASISCKSS***QSLVHNNANTY***LSWYLQKPGQSPQSLIY***KVS***NRFSGVPDRFSGSGSGTDFTLKISRVEAEDVGVYYC***GQGTQYP***FTFGSGTKVEIK (SEQ ID NO: 153) |
| Anti-CD3-2 | QVQLVESGGGVVQPGRSLRLSCAAS***GFTFTKAW***MHVRQAPGKGLEWVAQ***IKDKSNS***YATYYADSVKGRFTISRDNSKNTLYLQMNSLRAEDTAVYYC***RGVYYALSPFDY***WGQGTLVTVSS (SEQ ID NO: 154) | DIVMTQTPLSLSVTPGQPASISCKSS***QSLVHNNGNTY***LSWYLQKPGQSPQLLIY***KV***SNRFSGVPDRFSGSGSGTDFTLKISRVEAEDVGVYYC***GQGTQYP***FTFGGGTKVEIK (SEQ ID NO: 155) |
| Anti-CD19 | QVQLVQSGAEVKKPGSSVKVSCKAS***GYAFSSYW***MNWVRQAPGQGLEWIGQ***IWPGDGDT***NYNQKFKGRATLTADESTSTAYMELSSLRSEDTAVYYC***ARRETTTVGRYYYAMD***YWGQGTTVTVSS (SEQ ID NO: 156) | DLVLTQSPASLAVSPGQRATITCKAS***QSVDYDGDSY***LNWYQQKPGQPPKLLIY***DAS***NLVSGVPARFSGSGSGTDFTLTINPVEANDTANYYC***QQSTEDPWT***FGQGTKLEIK (SEQ ID NO: 157) |
| Anti-CD20 | QVQLQQPGAELVKPGASVKMSCKAS***GYTFTSYN***MHWVKQTPGRGLEWIGA***IYPGNGDT***SYNQKFKGKATLTADKSSSTAYMQLSSLTSEDSAVYYC***ARSTYYGGDWYFNV***WGAGTTVTVSA (SEQ ID NO: 158) | QIVLSQSPAILSASPGEKVTMTCRAS***SSVSY***IHWFQQKPGSSPKPWIY***ATS***NLASGVPVRFSGSGSGTSYSLTISRVEAEDAATYYC ***OOWTSNP***PTFGGGTKLEIK (SEQ ID NO: 159) |
| Anti-CD28-1 | QVQLVQSGAEVVKPGASVKVSCKAS***GYTFTSYY***IHWVRQAPGQGLEWIGS***IYPGNVNT***NYAQKFQGRATLTVDTSISTAYMELSRLRSDDTAVYYC***TRSHYGLDWNFDV***WGKGTTVTVSS (SEQ ID NO: 160) | DIQMTQSPSSLSASVGDRVTITCQAS***QNIYVW***LNWYQQKPGKAPKLLIY***KAS***NLHTGVPSRFSGSGSGTDFTLTISSLQPEDIATYYC***QQGQTYPYT***FGQGTKLEIK (SEQ ID NO: 161) |
| Anti-CD28-2 | QVQLQESGPGLVKPSQTLSLTCTVS***GFSLSDYG***VHWVRQPPGKGLEWLGV***IWAGGGT***NYNPSLKSRKTISKDTSKNQVSLKLSSVTAADTAVYYC***ARDKGYSYYYSMD***YWGQGTTVTVSS (SEQ ID NO: 162) | DIVLTQSPASLAVSPGQRATITCRAS***ESVEYYVTSI***MQWYQQKPGQPPKLLIF***AAS***NVESGVPARFSGSGSGTDFTLTINPVEANDVANYYC***QQSRKVPYT***FGQGTKLEIK (SEQ ID NO: 163) |
| Anti-CD38 | QVQLVQSGAEVAKPGTSVKLSCKAS***GYTFTDYW***MQWVKQRPGQGLEWIGT***IYPGDGDT***GYAQKFQGKATLTADKSSKTVYMHLSSLASEDSAVYYC***ARGDYYGSNSLDY***WGQGTSVTVSS (SEQ ID NO: 164) | DIVMTQSHLSMSTSLGDPVSITCKAS***QDVSTV***VAWYQQKPGQSPRRLIY***SAS***YRYIGVPDRFTGSGAGTDFTFTISSVQAEDLAVYYC***QQHYSPPYT***FGGGTKLEIK (SEQ ID NO: 165) |
| Anti-LAMP 1 | QVQLVQSGAEVKKPGSSVKVSCKAS***GYIFTNYNIH***WVKKSPGQGLEWIG***AIYPGNGDAP***YSQKFQGKATLTADTSTSTTYMELSSLRSEDTAVYYCVR***ANWDVAFAY***WGQGTLVTVSS (SEQ ID NO: 166) | DIQMTQSPSSLSASVGDRVTITC***KASQDIDRYMA***WYQDKPGKAPRLLIH***TSTLQS***GVPSRFSGSGSGRDYTLTISNLEPEDFATYYC***LQYDNLWT***FGGGTKVEIK (SEQ ID NO: 167) |
| Anti-TNFα | EVQLVESGGGLVQPGRSLRLSCAAS***GFTFDDYAMH***WVRQAPGKGLEWVS***AITWNSGHID***YADSVEGRFTISRDNAKNSLYLQMNSLRAEDTAVYYCAK***VSYLSTASSLDY***WGQGTLVTVSS (SEQ ID NO: 168) | DIQMTQSPSSLSASVGDRVTITC***RASQGIRNYLA***WYQQKPGKAPKLLIY***AASTLQS***GVPSRFSGSGSGTDFTLTISSLQPEDVATYYC***QRYNRAPYT***FGQGTKVEIK (SEQ ID NO: 169) |
| Anti-IL4 | QVQLQQSGPELVKPGASVKISCKAS***GYSFTSYWIH***WIKQRPGQGLEWI***MIDPSDGET***RLNQRFQGRATLTVDESTSTAYMQLRSPTSEDSAVYYCTR***LKEYGNYDSFYFDV***WGAGTLVTVSS (SEQ ID NO: 170) | DIQMTQSPASLSVSVGDTITLTC***HASQNIDVWLS***WFQQKPGNIPKLLIY***KASNLHT***GVPSRFSGSGSGTGFTLTISSLQPEDIATYYC***QQAHSYPFT***FGGGTKLEIK (SEQ ID NO: 171) |
| Anti-IL13 | EVQLKESGPGLVAPGGSLSITCTVS***GFSLTDSSIN***WVRQPPGKGLEWLG***MIWGDGRID***YADALKSRLSISKDSSKSQVFLEMTSLRTDDTATYYCAR***DGYFPYAMDF***WGQGTSVTVSS (SEQ ID NO: 172) | DIVLTQSPASLAVSLGQRATISC***RASESVDSYGQSYMH***WYQQKAGQPPKLLIY***LASNLES***GVPARFSGSGSRTDFTLTIDPVQAEDAATYYC***QQNAEDSRT***FGGGTKLEIK (SEQ ID NO: 173) |

Note:
CDR sequences are bolded and italicized in amino acid sequences above.

SEQUENCE LISTING

```
Sequence total quantity: 179
SEQ ID NO: 1            moltype = AA  length = 447
FEATURE                 Location/Qualifiers
REGION                  1..447
                        note = Synthetic Construct
source                  1..447
                        mol_type = protein
                        organism = synthetic construct
SEQUENCE: 1
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPCQEEMTK  360
NQVSLWCLVK GFYPSDIAVE WESNGQPENN YKTTPPVLDS DGSFFLYSKL TVDKSRWQEG  420
NVFSCSVMHE ALHNHYTQKS LSLSLGK                                     447

SEQ ID NO: 2            moltype = AA  length = 214
FEATURE                 Location/Qualifiers
REGION                  1..214
                        note = Synthetic Construct
source                  1..214
                        mol_type = protein
                        organism = synthetic construct
SEQUENCE: 2
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 3            moltype = AA  length = 571
FEATURE                 Location/Qualifiers
REGION                  1..571
                        note = Synthetic Construct
source                  1..571
                        mol_type = protein
                        organism = synthetic construct
SEQUENCE: 3
QVQLVQSGAE VVKPGASVKV SCKASGYTFT SYYIHWVRQA PGQGLEWIGS IYPGNVNTNY  60
AQKFQGRATL TVDTSISTAY MELSRLRSDD TAVYYCTRSH YGLDWNFDVW GKGTTVTVSS  120
SQVQLVESGG GVVQPGRSLR LSCAASGFTF TKAWMHWVRQ APGKQLEWVA QIKDKSNSYA  180
TYYADSVKGR FTISRDDSKN TLYLQMNSLR AEDTAVYYCR GVYYALSPFD YWGQGTLVTV  240
SSRTASTKGP SVFPLAPCSR STSESTAALG CLVKDYFPEP VTVSWNSGAL TSGVHTFPAV  300
LQSSGLYSLS SVVTVPSSSL GTKTYTCNVD HKPSNTKVDK RVESKYGPPC PPCPAPEFLG  360
GPSVFLFPPK PKDTLMISRT PEVTCVVVDV SQEDPEVQFN WYVDGVEVHN AKTKPREEQF  420
NSTYRVVSVL TVLHQDWLNG KEYKCKVSNK GLPSSIEKTI SKAKGQPREP QVCTLPPSQE  480
EMTKNQVSLS CAVKGFYPSD IAVEWESNGQ PENNYKTTPP VLDSDGSFFL VSKLTVDKSR  540
WQEGNVFSCS VMHEALHNHY TQKSLSLSLG K                                 571

SEQ ID NO: 4            moltype = AA  length = 338
FEATURE                 Location/Qualifiers
REGION                  1..338
                        note = Synthetic Construct
source                  1..338
                        mol_type = protein
                        organism = synthetic construct
SEQUENCE: 4
DIVMTQTPLS LSVTPGQPAS ISCKSSQSLV HNNANTYLSW YLQKPGQSPQ SLIYKVSNRF  60
SGVPDRFSGS GSGTDFTLKI SRVEAEDVGV YYCGQGTQYP FTFGSGTKVE IKGQPKAAPD  120
IQMTQSPSSL SASVGDRVTI TCQASQNIYV WLNWYQQKPG KAPKLLIYKA SNLHTGVPSR  180
FSGSGSGTDF TLTISSLQPE DIATYYCQQG QTYPYTFGQG TKLEIKTKGP SRTVAAPSVF  240
IFPPSDEQLK SGTASVVCLL NNFYPREAKV QWKVDNALQS GNSQESVTEQ DSKDSTYSLS  300
STLTLSKADY EKHKVYACEV THQGLSSPVT KSFNRGEC                          338

SEQ ID NO: 5            moltype = DNA  length = 1341
FEATURE                 Location/Qualifiers
misc_feature            1..1341
                        note = Synthetic Construct
source                  1..1341
                        mol_type = other DNA
                        organism = synthetic construct
SEQUENCE: 5
gaagtgcagc tggtggaatc tggcggcgga ctggtgcagc ctggcggatc tctgagactg  60
agctgtgccg ccagcggctt caacatcaag gacacctaca tccactgggt gcgccaggcc  120
cctggcaagg gactggaatg ggtggccaga atctacccca ccaacggcta caccagatac  180
gccgacagcg tgaagggccg gttcaccatc agcgccgaca ccagcaagaa caccgcctac  240
ctgcagatga acagcctgcg ggccgaggac accgccgtgt actactgtag tagatgggga  300
```

-continued

```
ggcgacggct tctacgccat ggactattgg ggccagggca ccctcgtgac cgtgtctagt  360
gcgtcgacca agggcccatc ggtgttccct ctggcccctt gcagcagaag caccagcgaa  420
tctacagccg ccctgggctg cctcgtgaag gactactttc ccgagcccgt gaccgtgtcc  480
tggaactctg gcgctctgac aagcggcgtg cacacctttc cagccgtgct ccagagcagc  540
ggcctgtact ctctgagcag cgtcgtgaca gtgcccagca gcagcctggg caccaagacc  600
tacacctgta acgtggacca caagcccagc aacaccaagg tggacaagcg ggtggaatct  660
aagtacggcc ctccctgccc tccttgccca gcccctgaat ttctgggcgg accctccgtg  720
ttcctgttcc ccccaaagcc caaggacacc ctgatgatca gccggacccc cgaagtgacc  780
tgcgtggtgg tggatgtgtc ccaggaagat cccgaggtgc agttcaattg gtacgtggac  840
ggcgtggaag tgcacaacgc caagaccaag cccagagagg aacagttcaa cagcacctac  900
cgggtggtgt ccgtgctgac cgtgctgcac caggactggc tgaacggcaa agagtacaag  960
tgcaaggtgt ccaacaaggg cctgcccagc tccatcgaga aaaccatcag caaggccaag  1020
ggccagcccc gcgagcctca agtgtatacc ctgcccccct gccaggaaga gatgaccaag  1080
aaccaggtgt ccctgtggtg tctcgtgaaa ggcttctacc ccagcgacat tgccgtggaa  1140
tgggagagca acggccagcc cgagaacaac tacaagacca ccccccctgt gctggacagc  1200
gacggctcat tcttcctgta ctccaagctg accgtggaca agagccggtg gcaggaaggc  1260
aacgtgttca gctgctccgt gatgcacgag gccctgcaca accactacac ccagaagtcc  1320
ctgtctctgt ccctgggcaa g                                          1341

SEQ ID NO: 6           moltype = DNA  length = 642
FEATURE                Location/Qualifiers
misc_feature           1..642
                       note = Synthetic Construct
source                 1..642
                       mol_type = other DNA
                       organism = synthetic construct
SEQUENCE: 6
gacatccaga tgacccagag ccccagcagc ctgtctgcca gcgtgggcga cagagtgacc  60
atcacctgta gagccagcca ggacgtgaac accgccgtgg cctggtatca gcagaagcct  120
ggcaaggccc ccaagctgct gatctacagc gccagcttcc tgtacagcgg cgtgcccagc  180
agattcagcg gaagcagaag cggcaccgac ttcaccctga ccatcagctc cctgcagccc  240
gaggacttcg ccacctacta ctgccagcag cactacacca cccccccac atttggccag  300
ggcaccaagg tggaaatcaa gcgtacggtg gccgctccca gcgtgttcat cttcccacct  360
agcgacgagc agctgaagtc cggcacagcc tctgtcgtgt gcctgctgaa caacttctac  420
cccgcgagg ccaaagtgca gtggaaggtg gacaacgccc tgcagagcgg caacagccag  480
gaaagcgtga ccgagcagga cagcaaggac tccacctaca gcctgagcag caccctgaca  540
ctgagcaagg ccgactacga gaagcacaag gtgtacgcct gcgaagtgac ccaccagggc  600
ctgtctagcc ccgtgaccaa gagcttcaac cggggcgagt gt                    642

SEQ ID NO: 7           moltype = DNA  length = 1713
FEATURE                Location/Qualifiers
misc_feature           1..1713
                       note = Synthetic Construct
source                 1..1713
                       mol_type = other DNA
                       organism = synthetic construct
SEQUENCE: 7
caggtgcagc tggtgcagtc tggcgccgag gtcgtgaaac ctggcgcctc tgtgaaggtg  60
tcctgcaagg ccagcggcta cacctttacc agctactaca tccactgggt gcgccaggcc  120
cctggacagg gactggaatg gatcggcagc atctaccccg gcaacgtgaa caccaactac  180
gcccagaagt tccagggcag agccaccctg accgtggaca ccagcatcag caccgcctac  240
atggaactga gccggctgag aagcgacgac accgccgtgt actactgcac ccggtcccac  300
tacggcctgg attggaactt cgacgtgtgg ggcaagggca ccaccgtgac agtgtctagc  360
agccaggtgc agctggtgga atctggcggc ggagtggtgc agcctggcag aagcctgaga  420
ctgagctgtg ccgccagcgg cttcaccttc accaaggcct ggatgcactg ggtgcgccag  480
gcccctggaa agcagctgga atgggtggcc cagatcaagg acaagagcaa cagctacgcc  540
acctactacg ccgacagcgt gaagggccgg ttcaccatca gccgggacga cagcaagaac  600
accctgtacc tgcagatgaa cagcctgcgg gccgaggaca ccgccgtgta ctactgtcgg  660
ggcgtgtact atgccctgag cccctcgat tactggggcc agggaaccct cgtgaccgtg  720
tctagtcgga ccgccagcac aaagggccca tcggtgttcc ctctggcccc ttgcagcaga  780
agcaccagcg aatctacagc cgccctgggc tgcctcgtga aggactactt tcccgagccc  840
gtgaccgtgt cctggaactc tggcgctctg acaagcggcg tgcacacctt tccagccgtg  900
ctccagagca gcggcctgta ctctctgagc agcgtcgtga cagtgcccag cagcagcctg  960
ggcaccaaga cctacacctg taacgtggac cacaagccca gcaacaccaa ggtggacaag  1020
cgggtggaat ctaagtacgg ccctccctgc cctccttgcc cagcccctga atttctgggc  1080
ggaccctccg tgttcctgtt ccccccaaag cccaaggaca ccctgatgat cagccggacc  1140
cccgaagtga cctgcgtggt ggtggatgtg tcccaggaag atcccgaggt gcagttcaat  1200
tggtacgtgg acggcgtgga agtgcacaac gccaagacca agcccagaga ggaacagttc  1260
aacagcacct accgggtggt gtccgtgctg accgtgctgc accaggactg gctgaacggc  1320
aaagagtaca agtgcaaggt gtccaacaag ggcctgccca gctccatcga gaaaaccatc  1380
agcaaggcca agggccagcc ccgcgagcct caagtgtgta ccctgccccc tagccaggaa  1440
gagatgacca agaaccaggt gtccctgagc tgtgccgtga aaggcttcta ccccagcgac  1500
attgccgtgg aatgggagag caacggccag cccgagaaca actacaagac cacccccct  1560
gtgctggaca gcgacggctc attcttcctg gtgtccaagc tgaccgtgga caagagccgg  1620
tggcaggaag gcaacgtgtt cagctgctcc gtgatgcacg aggccctgca caaccactac  1680
acccagaagt ccctgtctct gtccctgggc aag                              1713

SEQ ID NO: 8           moltype = DNA  length = 1014
FEATURE                Location/Qualifiers
```

-continued

```
misc_feature            1..1014
                        note = Synthetic Construct
source                  1..1014
                        mol_type = other DNA
                        organism = synthetic construct
SEQUENCE: 8
gacatcgtga tgacccagac cccccctgagc ctgagcgtga cacctggaca gcctgccagc  60
atcagctgca agagcagcca gagcctggtg cacaacaacg ccaacaccta cctgagctgg  120
tatctgcaga agcccggcca gagcccccag tccctgatct acaaggtgtc caacagattc  180
agcggcgtgc ccgacagatt ctccggcagc ggctctggca ccgacttcac cctgaagatc  240
agccgggtgg aagccgagga cgtgggcgtg tactattgtg gccagggcac ccagtacccc  300
ttcacctttg gcagcggcac caaggtggaa atcaagggcc agcccaaggc cgcccccgac  360
atccagatga cccagagccc cagcagcctg tctgccagcg tgggcgacag agtgaccatc  420
acctgtcagg ccagccagaa catctacgtg tggctgaact ggtatcagca gaagcccggc  480
aaggccccca agctgctgat ctacaaggcc agcaacctgc acaccggcgt gcccagcaga  540
ttttctggca gcggctccgg caccgacttc accctgacaa tcagctccct gcagcccgag  600
gacattgcca cctactactg ccagcagggc cagacctacc cctacacctt tggccagggc  660
accaagctgg aaatcaagac caagggcccc agccgtacgg tggccgctcc cagcgtgttc  720
atcttcccac ctagcgacga gcagctgaag tccggcacag cctctgtcgt gtgcctgctg  780
aacaacttct acccccgcga ggccaaagtg cagtggaagg tggacaacgc cctgcagagc  840
ggcaacagcc aggaaagcgt gaccgagcag gacagcaagg actccaccta cagcctgagc  900
agcaccctga cactgagcaa ggccgactac gagaagcaca aggtgtacgc ctgcgaagtg  960
acccaccagg gcctgtctag ccccgtgacc aagagcttca accggggcga gtgt         1014

SEQ ID NO: 9            moltype = AA  length = 571
FEATURE                 Location/Qualifiers
REGION                  1..571
                        note = Synthetic Construct
source                  1..571
                        mol_type = protein
                        organism = synthetic construct
SEQUENCE: 9
QVQLQESGPG LVKPSQTLSL TCTVSGFSLS DYGVHWVRQP PGKGLEWLGV IWAGGGTNYN  60
PSLKSRKTIS KDTSKNQVSL KLSSVTAADT AVYYCARDKG YSYYYSMDYW GQGTTVTVSS  120
SQVQLVESGG GVVQPGRSLR LSCAASGFTF TKAWMHWVRQ APGKQLEWVA QIKDKSNSYA  180
TYYADSVKGR FTISRDDSKN TLYLQMNSLR AEDTAVYYCR GVYYALSPFD YWGQGTLVTV  240
SSRTASTKGP SVFPLAPCSR STSESTAALG CLVKDYFPEP VTVSWNSGAL TSGVHTFPAV  300
LQSSGLYSLS SVVTVPSSSL GTKTYTCNVD HKPSNTKVDK RVESKYGPPC PPCPAPEFLG  360
GPSVFLFPPK PKDTLMISRT PEVTCVVVDV SQEDPEVQFN WYVDGVEVHN AKTKPREEQF  420
NSTYRVVSVL TVLHQDWLNG KEYKCKVSNK GLPSSIEKTI SKAKGQPREP QVCTLPPSQE  480
EMTKNQVSLS CAVKGFYPSD IAVEWESNGQ PENNYKTTPP VLDSDGSFFL VSKLTVDKSR  540
WQEGNVFSCS VMHEALHNHY TQKSLSLSLG K                                  571

SEQ ID NO: 10           moltype = AA  length = 342
FEATURE                 Location/Qualifiers
REGION                  1..342
                        note = Synthetic Construct
source                  1..342
                        mol_type = protein
                        organism = synthetic construct
SEQUENCE: 10
DIVMTQTPLS LSVTPGQPAS ISCKSSQSLV HNNANTYLSW YLQKPGQSPQ SLIYKVSNRF  60
SGVPDRFSGS GSGTDFTLKI SRVEAEDVGV YYCGQGTQYP FTFGSGTKVE IKGQPKAAPD  120
IVLTQSPASL AVSPGQRATI TCRASESVEY YVTSLMQWYQ QKPGQPPKLL IFAASNVESG  180
VPARFSGSGS GTDFTLTINP VEANDVANYY CQQSRKVPYT FGQGTKLEIK TKGPSRTVAA  240
PSVFIFPPSD EQLKSGTASV VCLLNNFYPR EAKVQWKVDN ALQSGNSQES VTEQDSKDST  300
YSLSSTLTLS KADYEKHKVY ACEVTHQGLS SPVTKSFNRG EC                      342

SEQ ID NO: 11           moltype = DNA  length = 1713
FEATURE                 Location/Qualifiers
misc_feature            1..1713
                        note = Synthetic Construct
source                  1..1713
                        mol_type = other DNA
                        organism = synthetic construct
SEQUENCE: 11
caggtgcagc tgcaggaatc tggccctggc ctcgtgaagc ctagccagac cctgagcctg  60
acctgtaccg tgtccggctt cagcctgagc gactacggcg tgcactgggt gcgccagcca  120
cctggaaaag gcctggaatg gctgggcgtg atctgggctg gcggaggcac caactacaac  180
cccagcctga agtccagaaa gaccatcagc aaggacacca gcaagaacca ggtgtccctg  240
aagctgagca gcgtgacagc cgccgatacc gccgtgtact actgcgccag agacaagggc  300
tacagctact actacagcat ggactactgg ggccagggca ccaccgtgac cgtgtcatcc  360
tctcaggtgc agctggtgga atctggcggc ggagtggtgc agcctggcag aagcctgaga  420
ctgagctgtg ccgccagcgg cttcaccttc accaaggcct ggatgcactg ggtgcgccag  480
gcccctggaa agcagctgga atgggtggcc cagatcaagg acaagagcaa cagctacgcc  540
acctactacg ccgacagcgt gaagggccgg ttcaccatca gccgggacga cagcaagaac  600
accctgtacc tgcagatgaa cagcctgcgg gccgaggaca ccgccgtgta ctactgtcgg  660
ggcgtgtact atgccctgag ccccttcgat tactggggcc agggaaccct cgtgaccgtg  720
tctagtcgga ccgcttcgac caagggccca tcggtgttcc ctctggcccc ttgcagcaga  780
```

```
agcaccagcg aatctacagc cgccctgggc tgcctcgtga aggactactt tcccgagccc  840
gtgaccgtgt cctggaactc tggcgctctg acaagcggcg tgcacacctt tccagccgtg  900
ctccagagca gcggcctgta ctctctgagc agcgtcgtga cagtgcccag cagcagcctg  960
ggcaccaaga cctacacctg taacgtggac cacaagccca gcaacaccaa ggtggacaag  1020
cgggtggaat ctaagtacgg ccctccctgc cctccttgcc cagcccctga atttctgggc  1080
ggaccctccg tgttcctgtt ccccccaaag cccaaggaca ccctgatgat cagccggacc  1140
cccgaagtga cctgcgtggt ggtggatgtg tcccaggaag atcccgaggt gcagttcaat  1200
tggtacgtgg acggcgtgga agtgcacaac gccaagacca agcccagaga ggaacagttc  1260
aacagcacct accgggtggt gtccgtgctg accgtgctgc accaggactg gctgaacggc  1320
aaagagtaca agtgcaaggt gtccaacaag ggcctgccca gctccatcga gaaaaccatc  1380
agcaaggcca agggccagcc ccgcgagcct caagtgtgta ccctgccccc tagccaggaa  1440
gagatgacca agaaccaggt gtccctgagc tgtgccgtga aaggcttcta ccccagcgac  1500
attgccgtgg aatgggagag caacggccag cccgagaaca actacaagac caccccccct  1560
gtgctggaca gcgacggctc attcttcctg gtgtccaagc tgaccgtgga caagagccgg  1620
tggcaggaag gcaacgtgtt cagctgctcc gtgatgcacg aggccctgca caaccactac  1680
acccagaagt ccctgtctct gtccctgggc aag                              1713

SEQ ID NO: 12           moltype = DNA  length = 1026
FEATURE                 Location/Qualifiers
misc_feature            1..1026
                        note = Synthetic Construct
source                  1..1026
                        mol_type = other DNA
                        organism = synthetic construct
SEQUENCE: 12
gacatcgtga tgacccagac cccccctgagc ctgagcgtga cacctggaca gcctgccagc  60
atcagctgca agagcagcca gagcctggtg cacaacaacg ccaacaccta cctgagctgg  120
tatctgcaga agcccggcca gagcccccag tccctgatct acaaggtgtc caacagattc  180
agcggcgtgc ccgacagatt ctccggcagc ggctctggca ccgacttcac cctgaagatc  240
agccgggtgg aagccgagga cgtgggcgtg tactattgtg gccagggcac ccagtacccc  300
ttcacctttg gcagcggcac caaggtggaa atcaagggcc agcccaaggc cgcccccgac  360
atcgtgctga cacagagccc tgctagcctg gccgtgtctc ctggacagag ggccaccatc  420
acctgtagag ccagcgagag cgtggaatat tacgtgacca gcctgatgca gtggtatcag  480
cagaagcccg gccagccccc caagctgctg attttcgccg ccagcaacgt ggaaagcggc  540
gtgccagcca gattttccgg cagcggctct ggcaccgact tcaccctgac catcaacccc  600
gtggaagcca acgacgtggc caactactac tgccagcaga gccggaaggt gccctacacc  660
tttggccagg gcaccaagct ggaaatcaag accaagggcc ccagccgtac ggtggccgct  720
cccagcgtgt tcatcttccc acctagcgac gagcagctga agtccggcac agcctctgtc  780
gtgtgcctgc tgaacaactt ctacccccgc gaggccaaag tgcagtggaa ggtggacaac  840
gccctgcaga gcggcaacag ccaggaaagc gtgaccgagc aggacagcaa ggactccacc  900
tacagcctga gcagcaccct gacactgagc aaggccgact acgagaagca caaggtgtac  960
gcctgcgaag tgacccacca gggcctgtct agccccgtga ccaagagctt caaccggggc  1020
gagtgt                                                            1026

SEQ ID NO: 13           moltype = AA  length = 451
FEATURE                 Location/Qualifiers
REGION                  1..451
                        note = Synthetic Construct
source                  1..451
                        mol_type = protein
                        organism = synthetic construct
SEQUENCE: 13
QVQLVQSGAE VKKPGSSVKV SCKASGYAFS SYWMNWVRQA PGQGLEWIGQ IWPGDGDTNY  60
NQKFKGRATL TADESTSTAY MELSSLRSED TAVYYCARRE TTTVGRYYYA MDYWGQGTTV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPEFLG  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPCQE  360
EMTKNQVSLW CLVKGFYPSD IAVEWESNGQ PENNYKTTPP VLDSDGSFFL YSKLTVDKSR  420
WQEGNVFSCS VMHEALHNHY TQKSLSLSLG K                                451

SEQ ID NO: 14           moltype = AA  length = 218
FEATURE                 Location/Qualifiers
REGION                  1..218
                        note = Synthetic Construct
source                  1..218
                        mol_type = protein
                        organism = synthetic construct
SEQUENCE: 14
DLVLTQSPAS LAVSPGQRAT ITCKASQSVD YDGDSYLNWY QQKPGQPPKL LIYDASNLVS  60
GVPARFSGSG SGTDFTLTIN PVEANDTANY YCQQSTEDPW TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 15           moltype = DNA  length = 1353
FEATURE                 Location/Qualifiers
misc_feature            1..1353
                        note = Synthetic Construct
source                  1..1353
```

```
                        mol_type = other DNA
                        organism = synthetic construct
SEQUENCE: 15
caggtgcagc tggtgcagag cggcgccgaa gtgaagaagc ctggcagcag cgtgaaggtg  60
agctgcaagg ccagcggcta tgccttcagc agctactgga tgaactgggt gaggcaggca  120
cctggccagg gcctggagtg gataggccaa atatggcctg gcgatggcga caccaactac  180
aaccagaagt tcaagggcag agcgaccttg accgccgacg agagcaccag caccgcgtac  240
atggagctga gcagcctgag gagcgaggac accgccgtgt actattgcgc cagaagggag  300
accaccaccg tgggcaggta ctactacgcc atggactact ggggccaggg aaccaccgtg  360
accgtgagca gcgcctcgac caagggccca tcggtgttcc ctctggcccc ttgcagcaga  420
agcaccagcg aatctacagc cgccctgggc tgcctcgtga aggactactt tcccgagccc  480
gtgaccgtgt cctggaactc tggcgctctg acaagcggcg tgcacacctt tccagccgtg  540
ctccagagca gcggcctgta ctctctgagc agcgtcgtga cagtgcccag cagcagcctg  600
ggcaccaaga cctacacctg taacgtggac cacaagccca gcaacaccaa ggtggacaag  660
cgggtggaat ctaagtacgg ccctccctgc cctccttgcc cagcccctga atttctgggc  720
ggaccctccg tgttcctgtt ccccccaaag cccaaggaca ccctgatgat cagccggacc  780
cccgaagtga cctgcgtggt ggtggatgtg tcccaggaag atcccgaggt gcagttcaat  840
tggtacgtgg acggcgtgga agtgcacaac gccaagacca agcccagaga ggaacagttc  900
aacagcacct accgggtggt gtccgtgctg accgtgctgc accaggactg gctgaacggc  960
aaagagtaca agtgcaaggt gtccaacaag ggcctgccca gctccatcga gaaaaccatc  1020
agcaaggcca agggccagcc ccgcgagcct caagtgtata ccctgccccc ttgccaggaa  1080
gagatgacca agaaccaggt gtccctgtgg tgtctcgtga aaggcttcta ccccagcgac  1140
attgccgtgg aatgggagag caacggccag cccgagaaca actacaagac cacccccccct  1200
gtgctggaca gcgacggctc attcttcctg tactccaagc tgaccgtgga caagagccgg  1260
tggcaggaag gcaacgtgtt cagctgctcc gtgatgcacg aggccctgca caaccactac  1320
acccagaagt ccctgtctct gtccctgggc aag                               1353

SEQ ID NO: 16           moltype = DNA  length = 654
FEATURE                 Location/Qualifiers
misc_feature            1..654
                        note = Synthetic Construct
source                  1..654
                        mol_type = other DNA
                        organism = synthetic construct
SEQUENCE: 16
gacctcgtgc tgacccagag ccctgcgagc ctggctgtga gccctggcca gagagccacc  60
atcacctgca aagccagcca gagcgtggac tacgacggcg acagctacct caactggtac  120
cagcagaagc ctggccagcc ccccaagctg ctgatttacg atgccagcaa cctggtgagc  180
ggcgtgcctg ctagattcag cggctccggc agcggcaccg acttcaccct gaccatcaac  240
cccgtggagg ccaacgacac cgccaactac tactgccagc agagcacgga ggacccctgg  300
accttcggcc agggcacaaa gctggagatc aagcgtacgg tggccgctcc cagcgtgttc  360
atcttcccac ctagcgacga gcagctgaag tccggcacag cctctgtcgt gtgcctgctg  420
aacaacttct acccccgcga ggccaaagtg cagtggaagg tggacaacgc cctgcagagc  480
ggcaacagcc aggaaagcgt gaccgagcag gacagcaagg actccaccta cagcctgagc  540
agcaccctga cactgagcaa ggccgactac gagaagcaca aggtgtacgc ctgcgaagtg  600
acccaccagg gcctgtctag ccccgtgacc aagagcttca accggggcga gtgt        654

SEQ ID NO: 17           moltype = AA  length = 447
FEATURE                 Location/Qualifiers
REGION                  1..447
                        note = Synthetic Construct
source                  1..447
                        mol_type = protein
                        organism = synthetic construct
SEQUENCE: 17
QVQLVQSGAE VAKPGTSVKL SCKASGYTFT DYWMQWVKQR PGQGLEWIGT IYPGDGDTGY  60
AQKFQGKATL TADKSSKTVY MHLSSLASED SAVYYCARGD YYGSNSLDYW GQGTSVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPCQEEMTK  360
NQVSLWCLVK GFYPSDIAVE WESNGQPENN YKTTPPVLDS DGSFFLYSKL TVDKSRWQEG  420
NVFSCSVMHE ALHNHYTQKS LSLSLGK                                     447

SEQ ID NO: 18           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 18
DIVMTQSHLS MSTSLGDPVS ITCKASQDVS TVVAWYQQKP GQSPRRLIYS ASYRYIGVPD  60
RFTGSGAGTD FTFTISSVQA EDLAVYYCQQ HYSPPYTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 19           moltype = DNA  length = 1341
FEATURE                 Location/Qualifiers
```

-continued

```
misc_feature         1..1341
                     note = Synthetic Construct
source               1..1341
                     mol_type = other DNA
                     organism = synthetic construct
SEQUENCE: 19
caggtgcagc tggtgcagtc tggcgccgaa gtggccaagc ctggcacaag cgtgaagctg  60
agctgcaagg ccagcggcta caccttcacc gactactgga tgcagtgggt caagcagagg  120
ccaggccagg gcctggaatg gatcggcaca atctatcccg gcgacggcga taccggctac  180
gcccagaagt ttcagggcaa ggccaccctg accgccgaca agagcagcaa gaccgtgtac  240
atgcacctga gcagcctggc cagcgaggac agcgccgtgt actattgcgc cagaggcgac  300
tactacggca gcaacagcct ggactattgg ggccagggca ccagcgtgac agtgtctagt  360
gcgtcgacca agggcccatc ggtgttccct ctggcccctt gcagcagaag caccagcgaa  420
tctacagccg ccctgggctg cctcgtgaag gactactttc ccgagcccgt gaccgtgtcc  480
tggaactctg gcgctctgac aagcggcgtg cacacctttc cagccgtgct ccagagcagc  540
ggcctgtact ctctgagcag cgtcgtgaca gtgcccagca gcagcctggg caccaagacc  600
tacacctgta acgtggacca caagcccagc aacaccaagg tggacaagcg ggtggaatct  660
aagtacggcc ctccctgccc tccttgccca gcccctgaat ttctgggcgg accctccgtg  720
ttcctgttcc ccccaaagcc caaggacacc ctgatgatca gccggacccc cgaagtgacc  780
tgcgtggtgg tggatgtgtc ccaggaagat cccgaggtgc agttcaattg gtacgtggac  840
ggcgtggaag tgcacaacgc caagaccaag cccagagagg aacagttcaa cagcacctac  900
cgggtggtgt ccgtgctgac cgtgctgcac caggactggc tgaacggcaa agagtacaag  960
tgcaaggtgt ccaacaaggg cctgcccagc tccatcgaga aaaccatcag caaggccaag  1020
ggccagcccc gcgagcctca agtgtatacc ctgccccctt gccaggaaga gatgaccaag  1080
aaccaggtgt ccctgtggtg tctcgtgaaa ggcttctacc ccagcgacat tgccgtggaa  1140
tgggagagca acggccagcc cgagaacaac tacaagacca ccccccctgt gctggacagc  1200
gacggctcat tcttcctgta ctccaagctg accgtggaca agagccggtg gcaggaaggc  1260
aacgtgttca gctgctccgt gatgcacgag gccctgcaca accactacac ccagaagtcc  1320
ctgtctctgt ccctgggcaa g                                            1341

SEQ ID NO: 20        moltype = DNA  length = 642
FEATURE              Location/Qualifiers
misc_feature         1..642
                     note = Synthetic Construct
source               1..642
                     mol_type = other DNA
                     organism = synthetic construct
SEQUENCE: 20
gacatcgtga tgacccagag ccacctgagc atgagcacca gcctgggcga ccccgtgtcc  60
atcacctgta aagccagcca ggacgtgtcc accgtggtgg cctggtatca gcagaagcct  120
ggccagagcc ccagacggct gatctacagc gccagctatc ggtacatcgg cgtgcccgac  180
agattcaccg gaagcggagc cggcaccgac ttcaccttca ccatcagctc tgtgcaggcc  240
gaggacctgg ccgtgtacta ctgccagcag cactacagcc ccccctacac ctttggcgga  300
ggcaccaagc tggaaatcaa gcgtacggtg gccgctccca gcgtgttcat cttcccacct  360
agcgacgagc agctgaagtc cggcacagcc tctgtcgtgt gcctgctgaa caacttctac  420
cccgcgagg ccaaagtgca gtggaaggtg gacaacgccc tgcagagcgg caacagccag  480
gaaagcgtga ccgagcagga cagcaaggac tccacctaca gcctgagcag caccctgaca  540
ctgagcaagg ccgactacga gaagcacaag gtgtacgcct gcgaagtgac ccaccagggc  600
ctgtctagcc ccgtgaccaa gagcttcaac cggggcgagt gt                     642

SEQ ID NO: 21        moltype = AA  length = 445
FEATURE              Location/Qualifiers
REGION               1..445
                     note = Synthetic Construct
source               1..445
                     mol_type = protein
                     organism = synthetic construct
SEQUENCE: 21
QVQLVQSGAE VKKPGSSVKV SCKASGYIFT NYNIHWVKKS PGQGLEWIGA IYPGNGDAPY  60
SQKFQGKATL TADTSTSTTY MELSSLRSED TAVYYCVRAN WDVAFAYWGQ GTLVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EFLGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVYTLP PCQEEMTKNQ  360
VSLWCLVKGF YPSDIAVEWE SNGQPENNYK TTPPVLDSDG SFFLYSKLTV DKSRWQEGNV  420
FSCSVMHEAL HNHYTQKSLS LSLGK                                        445

SEQ ID NO: 22        moltype = AA  length = 213
FEATURE              Location/Qualifiers
REGION               1..213
                     note = Synthetic Construct
source               1..213
                     mol_type = protein
                     organism = synthetic construct
SEQUENCE: 22
DIQMTQSPSS LSASVGDRVT ITCKASQDID RYMAWYQDKP GKAPRLLIHD TSTLQSGVPS  60
RFSGSGSGRD YTLTISNLEP EDFATYYCLQ YDNLWTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213
```

```
SEQ ID NO: 23          moltype = DNA  length = 1335
FEATURE                Location/Qualifiers
misc_feature           1..1335
                       note = Synthetic Construct
source                 1..1335
                       mol_type = other DNA
                       organism = synthetic construct
SEQUENCE: 23
caggtgcagc tggtgcagtc tggcgccgaa gtgaagaaac ccggcagcag cgtgaaggtg  60
tcctgcaagg ccagcggcta catcttcacc aactacaaca tccactgggt caagaagtcc  120
ccaggccagg gcctggaatg gatcggcgcc atctatcccg gaaacggcga cgccccttac  180
agccagaagt tccagggcaa ggccaccctg accgccgata ccagcacctc caccacctac  240
atggaactga gcagcctgcg gagcgaggac accgccgtgt actattgcgt gcgggccaac  300
tgggatgtgg ccttcgccta ttggggccag ggcacactcg tgaccgtgtc ctctgcgtcg  360
accaagggcc catcggtgtt ccctctggcc ccttgcagca gaagcaccag cgaatctaca  420
gccgccctgg gctgcctcgt gaaggactac tttcccgagc ccgtgaccgt gtcctggaac  480
tctggcgctc tgacaagcgg cgtgcacacc tttccagccg tgctccagag cagcggcctg  540
tactctctga gcagcgtcgt gacagtgccc agcagcagcc tgggcaccaa gacctacacc  600
tgtaacgtgg accacaagcc cagcaacacc aaggtggaca agcgggtgga atctaagtac  660
ggccctccct gccctccttg cccagcccct gaatttctgg gcggaccctc cgtgttcctg  720
ttccccccaa agcccaagga caccctgatg atcagccgga cccccgaagt gacctgcgtg  780
gtggtggatg tgtcccagga agatcccgag gtgcagttca attggtacgt ggacggcgtg  840
gaagtgcaca acgccaagac caagcccaga gaggaacagt tcaacagcac ctaccgggtg  900
gtgtccgtgc tgaccgtgct gcaccaggac tggctgaacg gcaaagagta caagtgcaag  960
gtgtccaaca agggcctgcc cagctccatc gagaaaacca tcagcaaggc caagggccag  1020
ccccgcgagc ctcaagtgta taccctgccc ccttgccagg aagagatgac caagaaccag  1080
gtgtccctgt ggtgtctcgt gaaaggcttc taccccagcg acattgccgt ggaatgggag  1140
agcaacggcc agcccgagaa caactacaag accacccccc ctgtgctgga cagcgacggc  1200
tcattcttcc tgtactccaa gctgaccgtg gacaagagcc ggtggcagga aggcaacgtg  1260
ttcagctgct ccgtgatgca cgaggccctg cacaaccact acacccagaa gtccctgtct  1320
ctgtccctgg gcaag                                                  1335

SEQ ID NO: 24          moltype = DNA  length = 639
FEATURE                Location/Qualifiers
misc_feature           1..639
                       note = Synthetic Construct
source                 1..639
                       mol_type = other DNA
                       organism = synthetic construct
SEQUENCE: 24
gacatccaga tgacccagag ccccagcagc ctgtctgcca gcgtgggcga cagagtgacc  60
atcacatgca aggccagcca ggacatcgat cggtacatgg cctggtatca ggacaagccc  120
ggcaaggccc ccagactgct gatccacgat accagcacac tgcagagcgg cgtgcccagc  180
agattttccg gctctggcag cggcagagac tacaccctga ccatcagcaa cctggaaccc  240
gaggacttcg ccacctacta ctgcctgcag tacgacaacc tgtggacctt cggcggaggc  300
accaaggtgg aaatcaagcg tacggtggcc gctcccagcg tgttcatctt cccacctagc  360
gacgagcagc tgaagtccgg cacagcctct gtcgtgtgcc tgctgaacaa cttctacccc  420
cgcgaggcca aagtgcagtg gaaggtggac aacgccctgc agagcggcaa cagccaggaa  480
agcgtgaccg agcaggacag caaggactcc acctacagcc tgagcagcac cctgacactg  540
agcaaggccg actacgagaa gcacaaggtg tacgcctgcg aagtgaccca ccagggcctg  600
tctagccccg tgaccaagag cttcaaccgg ggcgagtgt                        639

SEQ ID NO: 25          moltype = AA  length = 8
FEATURE                Location/Qualifiers
REGION                 1..8
                       note = Synthetic Construct
source                 1..8
                       mol_type = protein
                       organism = synthetic construct
SEQUENCE: 25
GFNIKDTY                                                          8

SEQ ID NO: 26          moltype = AA  length = 8
FEATURE                Location/Qualifiers
REGION                 1..8
                       note = Synthetic Construct
source                 1..8
                       mol_type = protein
                       organism = synthetic construct
SEQUENCE: 26
IYPTNGYT                                                          8

SEQ ID NO: 27          moltype = AA  length = 13
FEATURE                Location/Qualifiers
REGION                 1..13
                       note = Synthetic Construct
source                 1..13
                       mol_type = protein
```

```
                        organism = synthetic construct
SEQUENCE: 27
SRWGGDGFYA MDY                                                    13

SEQ ID NO: 28           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 28
GYTFTSYY                                                          8

SEQ ID NO: 29           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 29
IYPGNVNT                                                          8

SEQ ID NO: 30           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 30
TRSHYGLDWN FDV                                                    13

SEQ ID NO: 31           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 31
GFSLSDYG                                                          8

SEQ ID NO: 32           moltype = AA  length = 7
FEATURE                 Location/Qualifiers
REGION                  1..7
                        note = Synthetic Construct
source                  1..7
                        mol_type = protein
                        organism = synthetic construct
SEQUENCE: 32
IWAGGGT                                                           7

SEQ ID NO: 33           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 33
ARDKGYSYYY SMD                                                    13

SEQ ID NO: 34           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 34
GFTFTKAW                                                          8

SEQ ID NO: 35           moltype = AA  length = 7
FEATURE                 Location/Qualifiers
REGION                  1..7
                        note = Synthetic Construct
source                  1..7
```

```
                        mol_type = protein
                        organism = synthetic construct
SEQUENCE: 35
IKDKSNS                                                                    7

SEQ ID NO: 36           moltype = AA  length = 12
FEATURE                 Location/Qualifiers
REGION                  1..12
                        note = Synthetic Construct
source                  1..12
                        mol_type = protein
                        organism = synthetic construct
SEQUENCE: 36
RGVYYALSPF DY                                                              12

SEQ ID NO: 37           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 37
GYAFSSYW                                                                   8

SEQ ID NO: 38           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 38
IWPGDGDT                                                                   8

SEQ ID NO: 39           moltype = AA  length = 16
FEATURE                 Location/Qualifiers
REGION                  1..16
                        note = Synthetic Construct
source                  1..16
                        mol_type = protein
                        organism = synthetic construct
SEQUENCE: 39
ARRETTTVGR YYYAMD                                                          16

SEQ ID NO: 40           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 40
GYTFTDYW                                                                   8

SEQ ID NO: 41           moltype = AA  length = 8
FEATURE                 Location/Qualifiers
REGION                  1..8
                        note = Synthetic Construct
source                  1..8
                        mol_type = protein
                        organism = synthetic construct
SEQUENCE: 41
IYPGDGDT                                                                   8

SEQ ID NO: 42           moltype = AA  length = 13
FEATURE                 Location/Qualifiers
REGION                  1..13
                        note = Synthetic Construct
source                  1..13
                        mol_type = protein
                        organism = synthetic construct
SEQUENCE: 42
ARGDYYGSNS LDY                                                             13

SEQ ID NO: 43           moltype = AA  length = 6
FEATURE                 Location/Qualifiers
REGION                  1..6
                        note = Synthetic Construct
```

```
source                 1..6
                       mol_type = protein
                       organism = synthetic construct
SEQUENCE: 43
QDVNTA                                                                     6

SEQ ID NO: 44          moltype =   length =
SEQUENCE: 44
000

SEQ ID NO: 45          moltype = AA  length = 9
FEATURE                Location/Qualifiers
REGION                 1..9
                       note = Synthetic Construct
source                 1..9
                       mol_type = protein
                       organism = synthetic construct
SEQUENCE: 45
QQHYTTPPT                                                                  9

SEQ ID NO: 46          moltype = AA  length = 6
FEATURE                Location/Qualifiers
REGION                 1..6
                       note = Synthetic Construct
source                 1..6
                       mol_type = protein
                       organism = synthetic construct
SEQUENCE: 46
QNIYVW                                                                     6

SEQ ID NO: 47          moltype =   length =
SEQUENCE: 47
000

SEQ ID NO: 48          moltype = AA  length = 9
FEATURE                Location/Qualifiers
REGION                 1..9
                       note = Synthetic Construct
source                 1..9
                       mol_type = protein
                       organism = synthetic construct
SEQUENCE: 48
QQGQTYPYT                                                                  9

SEQ ID NO: 49          moltype = AA  length = 10
FEATURE                Location/Qualifiers
REGION                 1..10
                       note = Synthetic Construct
source                 1..10
                       mol_type = protein
                       organism = synthetic construct
SEQUENCE: 49
ESVEYYVTSL                                                                 10

SEQ ID NO: 50          moltype =   length =
SEQUENCE: 50
000

SEQ ID NO: 51          moltype = AA  length = 9
FEATURE                Location/Qualifiers
REGION                 1..9
                       note = Synthetic Construct
source                 1..9
                       mol_type = protein
                       organism = synthetic construct
SEQUENCE: 51
QQSRKVPYT                                                                  9

SEQ ID NO: 52          moltype = AA  length = 11
FEATURE                Location/Qualifiers
REGION                 1..11
                       note = Synthetic Construct
source                 1..11
                       mol_type = protein
                       organism = synthetic construct
SEQUENCE: 52
QSLVHNNANT Y                                                               11

SEQ ID NO: 53          moltype =   length =
```

-continued

```
SEQUENCE: 53
000

SEQ ID NO: 54          moltype = AA  length = 7
FEATURE                Location/Qualifiers
REGION                 1..7
                       note = Synthetic Construct
source                 1..7
                       mol_type = protein
                       organism = synthetic construct
SEQUENCE: 54
GQGTQYP                                                    7

SEQ ID NO: 55          moltype = AA  length = 10
FEATURE                Location/Qualifiers
REGION                 1..10
                       note = Synthetic Construct
source                 1..10
                       mol_type = protein
                       organism = synthetic construct
SEQUENCE: 55
QSVDYDGDSY                                                 10

SEQ ID NO: 56          moltype =   length =
SEQUENCE: 56
000

SEQ ID NO: 57          moltype = AA  length = 9
FEATURE                Location/Qualifiers
REGION                 1..9
                       note = Synthetic Construct
source                 1..9
                       mol_type = protein
                       organism = synthetic construct
SEQUENCE: 57
QQSTEDPWT                                                  9

SEQ ID NO: 58          moltype = AA  length = 6
FEATURE                Location/Qualifiers
REGION                 1..6
                       note = Synthetic Construct
source                 1..6
                       mol_type = protein
                       organism = synthetic construct
SEQUENCE: 58
QDVSTV                                                     6

SEQ ID NO: 59          moltype = AA  length = 9
FEATURE                Location/Qualifiers
REGION                 1..9
                       note = Synthetic Construct
source                 1..9
                       mol_type = protein
                       organism = synthetic construct
SEQUENCE: 59
QQHYSPPYT                                                  9

SEQ ID NO: 60          moltype = AA  length = 450
FEATURE                Location/Qualifiers
REGION                 1..450
                       note = Synthetic Construct
source                 1..450
                       mol_type = protein
                       organism = synthetic construct
SEQUENCE: 60
EVQLVESGGG LVQPGRSLRL SCAASGFTFD DYAMHWVRQA PGKGLEWVSA ITWNSGHIDY  60
ADSVEGRFTI SRDNAKNSLY LQMNSLRAED TAVYYCAKVS YLSTASSLDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVCTLPPSRD  360
ELTKNQVSLS CAVKGFYPSD IAVEWESNGQ PENNYKTTPP VLDSDGSFFL VSKLTVDKSR  420
WQQGNVFSCS VMHEALHNHY TQKSLSLSPG                                  450

SEQ ID NO: 61          moltype = AA  length = 213
FEATURE                Location/Qualifiers
REGION                 1..213
                       note = Synthetic Construct
source                 1..213
```

```
                         mol_type = protein
                         organism = synthetic construct
SEQUENCE: 61
DIQMTQSPSS LSASVGDRVT ITCRASQGIR NYLAWYQQKP GKAPKLLIYA ASTLQSGVPS  60
RFSGSGSGTD FTLTISSLQP EDVATYYCQR YNRAPYTFGQ GTKVEIKGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                              213

SEQ ID NO: 62            moltype = AA  length = 570
FEATURE                  Location/Qualifiers
REGION                   1..570
                         note = Synthetic Construct
source                   1..570
                         mol_type = protein
                         organism = synthetic construct
SEQUENCE: 62
QVQLQQSGPE LVKPGASVKI SCKASGYSFT SYWIHWIKQR PGQGLEWIGM IDPSDGETRL  60
NQRFQGRATL TVDESTSTAY MQLRSPTSED SAVYYCTRLK EYGNYDSFYF DVWGAGTLVT  120
VSSEVQLKES GPGLVAPGGS LSITCTVSGF SLTDSSINWV RQPPGKGLEW LGMIWGDGRI  180
DYADALKSRL SISKDSSKSQ VFLEMTSLRT DDTATYYCAR DGYFPYAMDF WGQGTSVTVS  240
SASTKGPSVF PLAPSSKSTS GGTAALGCLV KDYFPEPVTV SWNSGALTSG VHTFPAVLQS  300
SGLYSLSSVV TVPSSSLGTQ TYICNVNHKP SNTKVDKKVE PKSCDKTHTC PPCPAPELLG  360
GPSVFLFPPK PKDTLMISRT PEVTCVVVDV SHEDPEVKFN WYVDGVEVHN AKTKPREEQY  420
NSTYRVVSVL TVLHQDWLNG KEYKCKVSNK ALPAPIEKTI SKAKGQPREP QVYTLPPCRD  480
ELTKNQVSLW CLVKGFYPSD IAVEWESNGQ PENNYKTTPP VLDSDGSFFL YSKLTVDKSR  540
WQQGNVFSCS VMHEALHNRF TQKSLSLSPG                                  570

SEQ ID NO: 63            moltype = AA  length = 345
FEATURE                  Location/Qualifiers
REGION                   1..345
                         note = Synthetic Construct
source                   1..345
                         mol_type = protein
                         organism = synthetic construct
SEQUENCE: 63
DIVLTQSPAS LAVSLGQRAT ISCRASESVD SYGQSYMHWY QQKAGQPPKL LIYLASNLES  60
GVPARFSGSG SRTDFTLTID PVQAEDAATY YCQQNAEDSR TFGGGTKLEI KGGSGSSGSG  120
GDIQMTQSPA SLSVSVGDTI TLTCHASQNI DVWLSWFQQK PGNIPKLLIY KASNLHTGVP  180
SRFSGSGSGT GFTLTISSLQ PEDIATYYCQ QAHSYPFTFG GGTKLEIKGG SGSSGSGGRT  240
VAAPSVFIFP PSDEQLKSGT ASVVCLLNNF YPREAKVQWK VDNALQSGNS QESVTEQDSK  300
DSTYSLSSTL TLSKADYEKH KVYACEVTHQ GLSSPVTKSF NRGEC                 345

SEQ ID NO: 64            moltype = DNA  length = 1350
FEATURE                  Location/Qualifiers
misc_feature             1..1350
                         note = Synthetic Construct
source                   1..1350
                         mol_type = other DNA
                         organism = synthetic construct
SEQUENCE: 64
gaggtgcagc tggtggaaag cggcggagga ctggtgcagc ccggcagaag cctgagactg  60
agctgcgccg ccagcggctt caccttcgac gactacgcca tgcactgggt ccgccaggcc  120
cctggcaagg gcctggaatg ggtgtccgcc atcacctgga acagcggcca catcgactac  180
gccgacagcg tggaaggccg gttcaccatc agccgggaca acgccaagaa cagcctgtac  240
ctgcagatga acagcctgcg ggccgaggac accgccgtgt actactgcgc caaggtgtcc  300
tacctgagca ccgccagcag cctggactac tggggccagg gcaccctggt gacagtgtcc  360
agcgcttcca ccaagggccc cagcgtgttc cccctggccc ctagcagcaa gagcacatct  420
ggcggcacag ccgccctggg ctgcctggtc aaggactact tccccgagcc cgtgacagtg  480
tcctggaact ctggcgccct gaccagcgga gtgcataccct tccctgccgt gctgcagtcc  540
agcggcctgt acagcctgag cagcgtggtc acagtgccca gcagcagcct gggcacccag  600
acctacatct gcaacgtgaa ccacaagccc agcaacacca aggtggacaa gaaggtggaa  660
cccaagagct gcgacaagac ccacacctgt ccccccctgcc ctgcccctga actgctgggc  720
ggaccctccg tgttcctgtt ccccccaaag cccaaggaca ccctgatgat cagccggacc  780
cccgaagtga cctgcgtggt ggtggacgtg tcccacgagg accctgaagt gaagttcaat  840
tggtacgtgg acggcgtgga agtgcataac gccaagacca agcccagaga ggaacagtac  900
aacagcacct accgggtggt gtccgtgctg accgtgctgc accaggactg gctgaacggc  960
aaagagtaca agtgcaaggt gtccaacaag gccctgcctg cccccatcga gaaaaccatc  1020
agcaaggcca agggccagcc tagagagccc caagtctgca ccctgccccc cagcagagat  1080
gagctgacca agaaccaggt gtccctgagc tgcgccgtga agggcttcta ccccagcgat  1140
atcgccgtgg aatgggagag caacggccag cccgagaaca actacaagac caccccccct  1200
gtgctggaca gcgacggctc attcttcctg gtgtccaagc tgacagtgga caagagccgg  1260
tggcagcagg gcaacgtgtt cagctgcagc gtgatgcacg aggccctgca caaccattac  1320
acccagaagt ccctgagcct gagccccggc                                  1350

SEQ ID NO: 65            moltype = DNA  length = 639
FEATURE                  Location/Qualifiers
misc_feature             1..639
                         note = Synthetic Construct
source                   1..639
```

```
                        mol_type = other DNA
                        organism = synthetic construct
SEQUENCE: 65
gacatccaga tgacccagag ccccagcagc ctgagcgcca gcgtgggcga cagagtgacc  60
atcacctgtc gggccagcca gggcatccgg aactacctgg cctggtatca gcagaagccc  120
ggcaaggccc ccaagctgct gatctacgcc gccagcacac tgcagagcgg cgtgcccagc  180
agattcagcg gcagcggctc cggcaccgac ttcaccctga ccatcagcag cctgcagccc  240
gaggacgtgg ccacctacta ctgccagcgg tacaacagag ccccctacac cttcggccag  300
ggcaccaagg tggaaatcaa gggacagccc aaggctgccc cctcggtcac cctgttcccc  360
ccaagcagcg aggaactgca ggccaacaag gccaccctcg tgtgcctgat cagcgacttc  420
taccctggcg ccgtgaccgt ggcctggaag gccgatagct ctcccgtgaa ggccggcgtg  480
gaaaccacca cccccagcaa gcagagcaac aacaaatacg ccgcctccag ctacctgagc  540
ctgacccccg agcagtggaa gtcccaccgg tcctacagct gccaggtcac acacgagggc  600
agcaccgtgg aaaagaccgt ggcccccacc gagtgcagc                         639

SEQ ID NO: 66           moltype = DNA  length = 1710
FEATURE                 Location/Qualifiers
misc_feature            1..1710
                        note = Synthetic Construct
source                  1..1710
                        mol_type = other DNA
                        organism = synthetic construct
SEQUENCE: 66
caggtgcagc tgcagcagag cggccctgag ctggtcaagc ctggcgccag cgtgaagatc  60
agctgcaagg ccagcggcta cagcttcacc agctactgga tccactggat caagcagcgg  120
cctggccagg gcctggaatg gatcggcatg atcgacccca gcgacggcga gacacggctg  180
aaccagagat tccagggcag agccaccctg accgtggacg agagcaccag caccgcctac  240
atgcagctgc ggagccccac cagcgaggac agcgccgtgt actactgcac ccggctgaaa  300
gagtacggca actacgacag cttctacttc gacgtgtggg gagccggcac cctggtcacc  360
gtgtccagcg aagtgcagct gaaagaaagc ggccctggcc tggtggcccc tggcggcagc  420
ctgagcatca cctgtaccgt gtccggcttc agcctgaccg acagcagcat caactgggtc  480
cgacagcccc ctggcaaggg cctcgagtgg ctgggaatga tctggggcga cggccggatc  540
gactacgccg acgccctgaa gtcccggctg agcatcagca aggacagcag caagagccag  600
gtgttcctgg aaatgaccag cctgcggacc gacgacaccg ccacctacta ctgcgccagg  660
gacggctact tcccctacgc catggatttc tggggccagg gcaccagcgt gaccgtgtcc  720
tctgcttcca ccaagggccc cagcgtgttc cctctggccc ctagcagcaa gagcacatct  780
ggcggaacag ccgccctggg ctgcctggtc aaggactact tcccgagcc cgtgaccgtg  840
tcctggaact ctggtgccct gacaagcgga gtgcatacct tccctgccgt gctgcagagc  900
agcggcctgt actctctgag cagcgtggtc accgtgccaa gcagcagcct gggcacccag  960
acctacatct gcaacgtgaa ccacaagccc tccaacacca aggtggacaa gaaggtggaa  1020
cccaagagct gcgacaagac ccacacctgt cctccctgtc ctgcccctga actgctgggc  1080
ggaccctccg tgttcctgtt ccctccaaag cccaaggata ccctgatgat cagccggacc  1140
cctgaagtga cctgcgtggt ggtggacgtg tcccacgagg atcccgaagt gaagttcaat  1200
tggtacgtgg acggcgtgga agtgcataac gccaagacca agcccagaga ggaacagtac  1260
aacagcacct accgggtggt gtccgtgctg acagtgctgc accaggactg gctgaacggc  1320
aaagagtaca agtgcaaggt gtccaacaag gccctgccag cccctatcga gaaaaccatc  1380
agcaaggcca agggccagcc ccgcgagcct caggtgtaca cactgcctcc atgccgggac  1440
gagctgacca agaaccaggt gtccctgtgg tgcctcgtga agggcttcta cccctccgat  1500
atcgccgtgg aatgggagag caacggccag cccgagaaca actacaagac cacccctccc  1560
gtgctggaca gcgacggctc attcttcctg tacagcaagc tgaccgtgga caagtcccgg  1620
tggcagcagg gcaacgtgtt cagctgctct gtgatgcacg aggccctgca caaccggttc  1680
acccagaagt ccctgagcct gagccctggc                                   1710

SEQ ID NO: 67           moltype = DNA  length = 1035
FEATURE                 Location/Qualifiers
misc_feature            1..1035
                        note = Synthetic Construct
source                  1..1035
                        mol_type = other DNA
                        organism = synthetic construct
SEQUENCE: 67
gacatcgtgc tgacccagag ccctgccagc ctggccgtgt ctctgggcca gagagccacc  60
atcagctgcc gggccagcga gagcgtggac agctacggcc agagctacat gcactggtat  120
cagcagaagg ccggccagcc ccccaagctg ctgatctacc tggccagcaa cctggaaagc  180
ggcgtgcccg ccagattcag cggcagcggc agcagaaccg acttcaccct gaccatcgac  240
cccgtgcagg ccgaggacgc cgccacctac tactgccagc agaacgccga ggacagccgg  300
accttcggcg gaggcaccaa gctggaaatc aagggcggct ccggcagcag cggctctggc  360
ggcgatatcc agatgaccca gtcccccgcc tccctgagcg tgtccgtggg cgacaccatc  420
accctgacat gccacgccag ccagaacatc gacgtgtggc tgagctggtt ccagcagaag  480
cctggcaaca tccctaagct gctcatctat aaggcctcca acctgcacac cggcgtgccc  540
agcaggtttt ccggctctgg cagcggcacc ggctttaccc tgacaatcag cagcctgcag  600
cccgaggata tcgccacata ttactgtcag caggcccaca gctacccctt cacctttggc  660
ggcggaacaa agctcgagat taagggcggc agcggaagct ccggctccgg cggacgtacg  720
gtggccgctc cttccgtgtt catcttccct ccctccgacg agcagctgaa gtccggcacc  780
gcctccgtgg tgtgtctgct gaacaacttc taccctcggg aggccaaggt gcagtggaag  840
gtggacaacg ccctgcagtc cggcaactcc caggagtccg tcaccgagca ggactccaag  900
gacagcacct actccctgtc ctccaccctg accctgtcca aggccgacta cgagaagcac  960
aaggtgtacg cctgtgaggt gacccaccag ggcctgtcca gccctgtgac caagtccttc  1020
aaccggggcg agtgc                                                   1035
```

```
SEQ ID NO: 68           moltype = AA  length = 570
FEATURE                 Location/Qualifiers
REGION                  1..570
                        note = Synthetic Construct
source                  1..570
                        mol_type = protein
                        organism = synthetic construct
SEQUENCE: 68
EVQLKESGPG LVAPGGSLSI TCTVSGFSLT DSSINWVRQP PGKGLEWLGM IWGDGRIDYA  60
DALKSRLSIS KDSSKSQVFL EMTSLRTDDT ATYYCARDGY FPYAMDFWGQ GTSVTVSSQV  120
QLQQSGPELV KPGASVKISC KASGYSFTSY WIHWIKQRPG QGLEWIGMID PSDGETRLNQ  180
RFQGRATLTV DESTSTAYMQ LRSPTSEDSA VYYCTRLKEY GNYDSFYFDV WGAGTLVTVS  240
SASTKGPSVF PLAPSSKSTS GGTAALGCLV KDYFPEPVTV SWNSGALTSG VHTFPAVLQS  300
SGLYSLSSVV TVPSSSLGTQ TYICNVNHKP SNTKVDKKVE PKSCDKTHTC PPCPAPELLG  360
GPSVFLFPPK PKDTLMISRT PEVTCVVVDV SHEDPEVKFN WYVDGVEVHN AKTKPREEQY  420
NSTYRVVSVL TVLHQDWLNG KEYKCKVSNK ALPAPIEKTI SKAKGQPREP QVYTLPPCRD  480
ELTKNQVSLW CLVKGFYPSD IAVEWESNGQ PENNYKTTPP VLDSDGSFFL YSKLTVDKSR  540
WQQGNVFSCS VMHEALHNRF TQKSLSLSPG                                  570

SEQ ID NO: 69           moltype = AA  length = 345
FEATURE                 Location/Qualifiers
REGION                  1..345
                        note = Synthetic Construct
source                  1..345
                        mol_type = protein
                        organism = synthetic construct
SEQUENCE: 69
DIQMTQSPAS LSVSVGDTIT LTCHASQNID VWLSWFQQKP GNIPKLLIYK ASNLHTGVPS  60
RFSGSGSGTG FTLTISSLQP EDIATYYCQQ AHSYPFTFGG GTKLEIKGGS GSSGSGGDIV  120
LTQSPASLAV SLGQRATISC RASESVDSYG QSYMHWYQQK AGQPPKLLIY LASNLESGVP  180
ARFSGSGSRT DFTLTIDPVQ AEDAATYYCQ QNAEDSRTFG GGTKLEIKGG SGSSGSGGRT  240
VAAPSVFIFP PSDEQLKSGT ASVVCLLNNF YPREAKVQWK VDNALQSGNS QESVTEQDSK  300
DSTYSLSSTL TLSKADYEKH KVYACEVTHQ GLSSPVTKSF NRGEC                 345

SEQ ID NO: 70           moltype = DNA  length = 1035
FEATURE                 Location/Qualifiers
misc_feature            1..1035
                        note = Synthetic Construct
source                  1..1035
                        mol_type = other DNA
                        organism = synthetic construct
SEQUENCE: 70
gacatccaga tgacccagag ccccgccagc ctgagcgtgt ccgtgggcga taccatcacc  60
ctgacctgcc acgccagcca gaacatcgac gtgtggctga gctggttcca gcagaagccc  120
ggcaacatcc ccaagctgct gatctacaag gccagcaacc tgcacaccgg cgtgcccagc  180
agattcagcg gctctggcag cggcaccggc tttaccctga ccatcagcag cctgcagccc  240
gaggatatcg ccacctacta ctgccagcag gcccacagct accccttcac cttcggcgga  300
ggcaccaagc tggaaatcaa gggcggcagc ggcagctccg gctctggcgg cgatatcgtg  360
ctgacccagt ctcccgcctc cctggccgtg tctctgggcc agagagccac catcagctgc  420
cgggccagcg agagcgtgga cagctacggc cagagctaca tgcactggta tcagcagaag  480
gccggacagc cccctaaact gctcatctac ctggcctcca acctggaaag cggcgtgccc  540
gccaggtttt ccggcagcgg ctccagaacc gacttcaccc tgacaatcga ccccgtgcag  600
gccgaggacg ccgccacata ttactgtcag cagaacgccg aggacagcag aacctttggc  660
ggcggaacaa agctcgagat taagggcggc tccggctcca gcggatctgg cggacgtacg  720
gtggccgctc cttccgtgtt catcttccct ccctccgacg agcagctgaa gtccggcacc  780
gcctccgtgg tgtgtctgct gaacaacttc taccctcggg aggccaaggt gcagtggaag  840
gtggacaacg ccctgcagtc cggcaactcc caggagtccg tcaccgagca ggactccaag  900
gacagcacct actccctgtc ctccaccctg accctgtcca aggccgacta cgagaagcac  960
aaggtgtacg cctgtgaggt gacccaccag ggcctgtcca gccctgtgac caagtccttc  1020
aaccggggcg agtgc                                                  1035

SEQ ID NO: 71           moltype = AA  length = 214
FEATURE                 Location/Qualifiers
REGION                  1..214
                        note = Synthetic Construct
source                  1..214
                        mol_type = protein
                        organism = synthetic construct
SEQUENCE: 71
DIQMTQSPSS LSASVGDRVT ITCRASQGIR NYLAWYQQKP GKAPKLLIYA ASTLQSGVPS  60
RFSGSGSGTD FTLTISSLQP EDVATYYCQR YNRAPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 72           moltype = DNA  length = 642
FEATURE                 Location/Qualifiers
misc_feature            1..642
                        note = Synthetic Construct
```

-continued

```
source                  1..642
                        mol_type = other DNA
                        organism = synthetic construct
SEQUENCE: 72
gacatccaga tgacccagag ccccagcagc ctgagcgcca gcgtgggcga cagagtgacc  60
atcacctgtc gggccagcca gggcatccgg aactacctgg cctggtatca gcagaagccc  120
ggcaaggccc ccaagctgct gatctacgcc gccagcacac tgcagagcgg cgtgcccagc  180
agattcagcg gcagcggctc cggcaccgac ttcaccctga ccatcagcag cctgcagccc  240
gaggacgtgg ccacctacta ctgccagcgg tacaacagag ccccctacac cttcggccag  300
ggcaccaagg tggaaatcaa gcgtacggtg gccgctcctt ccgtgttcat cttccctccc  360
tccgacgagc agctgaagtc cggcaccgcc tccgtggtgt gtctgctgaa caacttctac  420
cctcgggagg ccaaggtgca gtggaaggtg gacaacgccc tgcagtccgg caactcccag  480
gagtccgtca ccgagcagga ctccaaggac agcacctact ccctgtcctc caccctgacc  540
ctgtccaagg ccgactacga gaagcacaag gtgtacgcct gtgaggtgac ccaccagggc  600
ctgtccagcc ctgtgaccaa gtccttcaac cggggcgagt gc                    642

SEQ ID NO: 73           moltype = AA  length = 447
FEATURE                 Location/Qualifiers
REGION                  1..447
                        note = Synthetic Construct
source                  1..447
                        mol_type = protein
                        organism = synthetic construct
SEQUENCE: 73
EVQLKESGPG LVAPGGSLSI TCTVSGFSLT DSSINWVRQP PGKGLEWLGM IWGDGRIDYA  60
DALKSRLSIS KDSSKSQVFL EMTSLRTDDT ATYYCARDGY FPYAMDFWGQ GTSVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVC TLPPSRDELT  360
KNQVSLSCAV KGFYPSDIAV EWESNGQPEN NYKTTPPVLD SDGSFFLVSK LTVDKSRWQQ  420
GNVFSCSVMH EALHNHYTQK SLSLSPG                                     447

SEQ ID NO: 74           moltype = AA  length = 217
FEATURE                 Location/Qualifiers
REGION                  1..217
                        note = Synthetic Construct
source                  1..217
                        mol_type = protein
                        organism = synthetic construct
SEQUENCE: 74
DIVLTQSPAS LAVSLGQRAT ISCRASESVD SYGQSYMHWY QQKAGQPPKL LIYLASNLES  60
GVPARFSGSG SRTDFTLTID PVQAEDAATY YCQQNAEDSR TFGGGTKLEI KGQPKAAPSV  120
TLFPPSSEEL QANKATLVCL ISDFYPGAVT VAWKADSSPV KAGVETTTPS KQSNNKYAAS  180
SYLSLTPEQW KSHRSYSCQV THEGSTVEKT VAPTECS                          217

SEQ ID NO: 75           moltype = AA  length = 573
FEATURE                 Location/Qualifiers
REGION                  1..573
                        note = Synthetic Construct
source                  1..573
                        mol_type = protein
                        organism = synthetic construct
SEQUENCE: 75
QVQLQQSGPE LVKPGASVKI SCKASGYSFT SYWIHWIKQR PGQGLEWIGM IDPSDGETRL  60
NQRFQGRATL TVDESTSTAY MQLRSPTSED SAVYYCTRLK EYGNYDSFYF DVWGAGTLVT  120
VSSEVQLVES GGGLVQPGRS LRLSCAASGF TFDDYAMHWV RQAPGKGLEW VSAITWNSGH  180
IDYADSVEGR FTISRDNAKN SLYLQMNSLR AEDTAVYYCA KVSYLSTASS LDYWGQGTLV  240
TVSSASTKGP SVFPLAPSSK STSGGTAALG CLVKDYFPEP VTVSWNSGAL TSGVHTFPAV  300
LQSSGLYSLS SVVTVPSSSL GTQTYICNVN HKPSNTKVDK KVEPKSCDKT HTCPPCPAPE  360
LLGGPSVFLF PPKPKDTLMI SRTPEVTCVV VDVSHEDPEV KFNWYVDGVE VHNAKTKPRE  420
EQYNSTYRVV SVLTVLHQDW LNGKEYKCKV SNKALPAPIE KTISKAKGQP REPQVYTLPP  480
CRDELTKNQV SLWCLVKGFY PSDIAVEWES NGQPENNYKT TPPVLDSDGS FFLYSKLTVD  540
KSRWQQGNVF SCSVMHEALH NRFTQKSLSL SPG                              573

SEQ ID NO: 76           moltype = AA  length = 341
FEATURE                 Location/Qualifiers
REGION                  1..341
                        note = Synthetic Construct
source                  1..341
                        mol_type = protein
                        organism = synthetic construct
SEQUENCE: 76
DIQMTQSPSS LSASVGDRVT ITCRASQGIR NYLAWYQQKP GKAPKLLIYA ASTLQSGVPS  60
RFSGSGSGTD FTLTISSLQP EDVATYYCQR YNRAPYTFGQ GTKVEIKGGS GSSGSGGDIQ  120
MTQSPASLSV SVGDTITLTC HASQNIDVWL SWFQQKPGNI PKLLIYKASN LHTGVPSRFS  180
GSGSGTGFTL TISSLQPEDI ATYYCQQAHS YPFTFGGGTK LEIKGGSGSS GSGGRTVAAP  240
SVFIFPPSDE QLKSGTASVV CLLNNFYPRE AKVQWKVDNA LQSGNSQESV TEQDSKDSTY  300
SLSSTLTLSK ADYEKHKVYA CEVTHQGLSS PVTKSFNRGE C                      341
```

```
SEQ ID NO: 77          moltype = DNA  length = 1341
FEATURE                Location/Qualifiers
misc_feature           1..1341
                       note = Synthetic Construct
source                 1..1341
                       mol_type = other DNA
                       organism = synthetic construct
SEQUENCE: 77
gaggtgcagc tgaaggagag cggccccggc ctggtggccc ccggcggcag cctgagcatc  60
acctgcaccg tgagcggctt cagcctgacc gacagcagca tcaactgggt gcgccagccc  120
cccggcaagg gcctggagtg gctgggcatg atctggggcg acggccgcat cgactacgcc  180
gacgccctga agagccgcct gagcatcagc aaggacagca gcaagagcca ggtgttcctg  240
gagatgacca gcctgcgcac cgacgacacc gccacctact actgcgcccg cgacggctac  300
ttcccctacg ccatggactt ctggggccag ggcaccagcg tgaccgtgag cagcgccagc  360
accaagggcc ccagcgtgtt cccccctggcc cctagcagca agagcacatc tggcggcaca  420
gccgccctgg gctgcctggt caaggactac ttccccgagc ccgtgacagt gtcctggaac  480
tctggcgccc tgaccagcgg agtgcatacc ttccctgccg tgctgcagtc cagcggcctg  540
tacagcctga gcagcgtggt cacagtgccc agcagcagcc tgggcaccca gacctacatc  600
tgcaacgtga accacaagcc cagcaacacc aaggtggaca agaaggtgga acccaagagc  660
tgcgacaaga cccacacctg tcccccctgc cctgcccctg aactgctggg cggaccctcc  720
gtgttcctgt tcccccccaaa gcccaaggac accctgatga tcagccggac ccccgaagtg  780
acctgcgtgg tggtggacgt gtcccacgag gaccctgaag tgaagttcaa ttggtacgtg  840
gacggcgtgg aagtgcataa cgccaagacc aagcccagag aggaacagta caacagcacc  900
taccgggtgg tgtccgtgct gaccgtgctg caccaggact ggctgaacgg caaagagtac  960
aagtgcaagg tgtccaacaa ggccctgcct gcccccatcg agaaaaccat cagcaaggcc  1020
aagggccagc ctagagagcc ccaagtctgc accctgcccc ccagcagaga tgagctgacc  1080
aagaaccagg tgtccctgag ctgcgccgtg aagggcttct accccagcga tatcgccgtg  1140
gaatgggaga gcaacggcca gcccgagaac aactacaaga ccaccccccc tgtgctggac  1200
agcgacggct cattcttcct ggtgtccaag ctgacagtgg acaagagccg gtggcagcag  1260
ggcaacgtgt tcagctgcag cgtgatgcac gaggccctgc acaaccatta cacccagaag  1320
tccctgagcc tgagccccgg c                                            1341

SEQ ID NO: 78          moltype = DNA  length = 651
FEATURE                Location/Qualifiers
misc_feature           1..651
                       note = Synthetic Construct
source                 1..651
                       mol_type = other DNA
                       organism = synthetic construct
SEQUENCE: 78
gacatcgtgc tgacccagag ccctgccagc ctggccgtgt ctctgggcca gagagccacc  60
atcagctgcc gggccagcga gagcgtggac agctacggcc agagctacat gcactggtat  120
cagcagaagg ccggccagcc ccccaagctg ctgatctacc tggccagcaa cctggaaagc  180
ggcgtgcccg ccagattcag cggcagcggc agcagaaccg acttcaccct gaccatcgac  240
cccgtgcagg ccgaggacgc cgccacctac tactgccagc agaacgccga ggacagccgg  300
accttcggcg gaggcaccaa gctggaaatc aagggacagc ccaaggctgc cccctcggtc  360
accctgttcc ccccaagcag cgaggaactg caggccaaca aggccaccct cgtgtgcctg  420
atcagcgact tctaccctgg cgccgtgacc gtggcctgga aggccgatag ctctcccgtg  480
aaggccggcg tggaaaccac cacccccagc aagcagagca acaacaaata cgccgccagc  540
agctacctga gcctgacccc cgagcagtgg aagtcccacc ggtcctacag ctgccaggtc  600
acacacgagg gcagcaccgt ggaaaagacc gtggccccca ccgagtgcag c           651

SEQ ID NO: 79          moltype = DNA  length = 1719
FEATURE                Location/Qualifiers
misc_feature           1..1719
                       note = Synthetic Construct
source                 1..1719
                       mol_type = other DNA
                       organism = synthetic construct
SEQUENCE: 79
caggtgcagc tgcagcagag cggccctgag ctggtcaagc ctggcgccag cgtgaagatc  60
agctgcaagg ccagcggcta cagcttcacc agctactgga tccactggat caagcagcgg  120
cctggccagg gcctggaatg gatcggcatg atcgacccca gcgacggcga gacacggctg  180
aaccagagat tccagggcag agccaccctg accgtggacg agagcaccag caccgcctac  240
atgcagctgc ggagccccac cagcgaggac agcgccgtgt actactgcac ccggctgaaa  300
gagtacggca actacgacag cttctacttc gacgtgtggg gagccggcac cctggtcacc  360
gtgtccagcg aagtgcagct ggtggaaagc ggcggaggcc tggtgcagcc cggcagaagc  420
ctgagactga gctgcgccgc cagcggcttc accttcgacg actacgccat gcactgggtc  480
cgacaggccc ctggcaaagg actggaatgg gtgtccgcca tcacctggaa cagcggccac  540
atcgactacg ccgacagcgt ggaaggccgg ttcaccatca gccgggacaa cgccaagaac  600
agcctgtacc tgcagatgaa cagcctgcgg gccgaggata ccgccgtgta ttattgcgcc  660
aaggtgtcct acctgagcac cgccagcagc ctggactact ggggccaggg caccctcgtg  720
acagtgtcct ccgcttccac caagggcccc agcgtgttcc ctctggcccc tagcagcaag  780
agcacatctg gcggaacagc cgccctgggc tgcctggtca aggactactt tcccgagccc  840
gtgaccgtgt cctggaactc tggtgccctg acaagcggag tgcatacctt ccctgccgtg  900
ctgcagagca gcggcctgta ctctctgagc agcgtggtca ccgtgccaag cagcagcctg  960
ggcacccaga cctacatctg caacgtgaac cacaagccct ccaacaccaa ggtggacaag  1020
aaggtggaac ccaagagctg cgacaagacc cacacctgtc ctccctgtcc tgcccctgaa  1080
```

```
ctgctgggcg gaccctccgt gttcctgttc cctccaaagc ccaaggatac cctgatgatc  1140
agccggaccc ctgaagtgac ctgcgtggtg gtggacgtgt cccacgagga tcccgaagtg  1200
aagttcaatt ggtacgtgga cggcgtggaa gtgcataacg ccaagaccaa gcccagagag  1260
gaacagtaca acagcaccta ccgggtggtg tccgtgctga cagtgctgca ccaggactgg  1320
ctgaacggca aagagtacaa gtgcaaggtg tccaacaagg ccctgccagc ccctatcgag  1380
aaaaccatca gcaaggccaa gggccagccc cgcgagcctc aggtgtacac actgcctcca  1440
tgccgggacg agctgaccaa gaaccaggtg tccctgtggt gcctcgtgaa gggcttctac  1500
ccctccgata tcgccgtgga atgggagagc aacggccagc ccgagaacaa ctacaagacc  1560
acccctcccg tgctggacag cgacggctca ttcttcctgt acagcaagct gaccgtggac  1620
aagtcccggt ggcagcaggg caacgtgttc agctgctctg tgatgcacga ggccctgcac  1680
aaccggttca cccagaagtc cctgagcctg agccctggc                         1719

SEQ ID NO: 80           moltype = DNA  length = 1023
FEATURE                 Location/Qualifiers
misc_feature            1..1023
                        note = Synthetic Construct
source                  1..1023
                        mol_type = other DNA
                        organism = synthetic construct
SEQUENCE: 80
gacatccaga tgacccagag ccccagcagc ctgagcgcca gcgtgggcga cagagtgacc  60
atcacctgtc gggccagcca gggcatccgg aactacctgg cctggtatca gcagaagccc  120
ggcaaggccc ccaagctgct gatctacgcc gccagcacac tgcagagcgg cgtgcccagc  180
agattcagcg gcagcggctc cggcaccgac ttcaccctga ccatcagcag cctgcagccc  240
gaggacgtgg ccacctacta ctgccagcgg tacaacagag ccccctacac cttcggccag  300
ggcaccaagg tggaaatcaa gggcggctct ggcagctccg gcagcggcgg agacattcag  360
atgacacagt cccccgccag cctgtccgtg tccgtgggcg ataccatcac cctgacatgc  420
cacgccagcc agaacatcga cgtgtggctg agctggttcc agcagaaacc tggcaacatc  480
cctaagctgc tcatctataa ggccagcaac ctgcacacag gcgtgccctc cagattctcc  540
ggctctggct ctggcaccgg ctttacactg acaatcagtt ctctgcagcc tgaggatatc  600
gccacatatt actgtcagca ggcccacagc taccctttca ccttcggagg cggcaccaag  660
ctcgagatta agggcggaag cggctcctcc ggctccggcg gacgtacggt ggccgctcct  720
tccgtgttca tcttccctcc ctccgacgag cagctgaagt ccggcaccgc ctccgtggtg  780
tgtctgctga acaacttcta ccctcgggag gccaaggtgc agtggaaggt ggacaacgcc  840
ctgcagtccg gcaactccca ggagtccgtc accgagcagg actccaagga cagcacctac  900
tccctgtcct ccaccctgac cctgtccaag gccgactacg agaagcacaa ggtgtacgcc  960
tgtgaggtga cccaccaggg cctgtccagc cctgtgacca agtccttcaa ccggggcgag  1020
tgc                                                                1023

SEQ ID NO: 81           moltype = AA  length = 573
FEATURE                 Location/Qualifiers
REGION                  1..573
                        note = Synthetic Construct
source                  1..573
                        mol_type = protein
                        organism = synthetic construct
SEQUENCE: 81
EVQLVESGGG LVQPGRSLRL SCAASGFTFD DYAMHWVRQA PGKGLEWVSA ITWNSGHIDY  60
ADSVEGRFTI SRDNAKNSLY LQMNSLRAED TAVYYCAKVS YLSTASSLDY WGQGTLVTVS  120
SQVQLQQSGP ELVKPGASVK ISCKASGYSF TSYWIHWIKQ RPGQGLEWIG MIDPSDGETR  180
LNQRFQGRAT LTVDESTSTA YMQLRSPTSE DSAVYYCTRL KEYGNYDSFY FDVWGAGTLV  240
TVSSASTKGP SVFPLAPSSK STSGGTAALG CLVKDYFPEP VTVSWNSGAL TSGVHTFPAV  300
LQSSGLYSLS SVVTVPSSSL GTQTYICNVN HKPSNTKVDK KVEPKSCDKT HTCPPCPAPE  360
LLGGPSVFLF PPKPKDTLMI SRTPEVTCVV VDVSHEDPEV KFNWYVDGVE VHNAKTKPRE  420
EQYNSTYRVV SVLTVLHQDW LNGKEYKCKV SNKALPAPIE KTISKAKGQP REPQVYTLPP  480
CRDELTKNQV SLWCLVKGFY PSDIAVEWES NGQPENNYKT TPPVLDSDGS FFLYSKLTVD  540
KSRWQQGNVF SCSVMHEALH NRFTQKSLSL SPG                                573

SEQ ID NO: 82           moltype = AA  length = 341
FEATURE                 Location/Qualifiers
REGION                  1..341
                        note = Synthetic Construct
source                  1..341
                        mol_type = protein
                        organism = synthetic construct
SEQUENCE: 82
DIQMTQSPAS LSVSVGDTIT LTCHASQNID VWLSWFQQKP GNIPKLLIYK ASNLHTGVPS  60
RFSGSGSGTG FTLTISSLQP EDIATYYCQQ AHSYPFTFGG GTKLEIKGGS GSSGSGGDIQ  120
MTQSPSSLSA SVGDRVTITC RASQGIRNYL AWYQQKPGKA PKLLIYAAST LQSGVPSRFS  180
GSGSGTDFTL TISSLQPEDV ATYYCQRYNR APYTFGQGTK VEIKGGSGSS GSGGRTVAAP  240
SVFIFPPSDE QLKSGTASVV CLLNNFYPRE AKVQWKVDNA LQSGNSQESV TEQDSKDSTY  300
SLSSTLTLSK ADYEKHKVYA CEVTHQGLSS PVTKSFNRGE C                       341

SEQ ID NO: 83           moltype = DNA  length = 1719
FEATURE                 Location/Qualifiers
misc_feature            1..1719
                        note = Synthetic Construct
source                  1..1719
                        mol_type = other DNA
```

```
                         organism = synthetic construct
SEQUENCE: 83
gaggtgcagc tggtggaaag cggcggagga ctggtgcagc ccggcagaag cctgagactg  60
agctgcgccg ccagcggctt caccttcgac gactacgcca tgcactgggt ccgacaggcc  120
cctggcaagg gcctggaatg ggtgtccgcc atcacctgga acagcggcca catcgactac  180
gccgacagcg tggaaggccg gttcaccatc agccgggaca acgccaagaa cagcctgtac  240
ctgcagatga acagcctgcg ggccgaggac accgccgtgt actactgcgc caaggtgtcc  300
tacctgagca ccgccagcag cctggactac tggggccagg gcaccctggt caccgtgtcc  360
agtcaggtcc agctgcagca gagcggccct gagctggtca agcctggcgc cagcgtgaag  420
atcagctgca aggccagcgg ctacagcttc accagctact ggatccactg gatcaagcag  480
cggcctggcc agggcctcga gtggatcggc atgatcgacc ccagcgacgg cgagacacgg  540
ctgaaccaga gattccaggg cagagccacc ctgaccgtgg acgagagcac cagcaccgcc  600
tacatgcagc tgcggagccc caccagcgag gatagcgccg tgtattattg cacccggctg  660
aaagagtacg gcaactacga cagcttctac ttcgacgtgt ggggagccgg caccctcgtg  720
acagtgtcct ccgcttccac caagggcccc agcgtgttcc ctctggcccc tagcagcaag  780
agcacatctg gcggaacagc cgccctgggc tgcctggtca aggactactt tcccgagccc  840
gtgaccgtgt cctggaactc tggtgccctg acaagcggag tgcatacctt ccctgccgtg  900
ctgcagagca gcggcctgta ctctctgagc agcgtggtca ccgtgccaag cagcagcctg  960
ggcacccaga cctacatctg caacgtgaac cacaagccct ccaacaccaa ggtggacaag  1020
aaggtggaac ccaagagctg cgacaagacc cacacctgtc ctccctgtcc tgcccctgaa  1080
ctgctgggcg gaccctccgt gttcctgttc cctccaaagc ccaaggatac cctgatgatc  1140
agccggaccc ctgaagtgac ctgcgtggtg gtggacgtgt cccacgagga tcccgaagtg  1200
aagttcaatt ggtacgtgga cggcgtggaa gtgcataacg ccaagaccaa gcccagagag  1260
gaacagtaca acagcaccta ccgggtggtg tccgtgctga cagtgctgca ccaggactgg  1320
ctgaacggca aagagtacaa gtgcaaggtg tccaacaagg ccctgccagc ccctatcgag  1380
aaaaccatca gcaaggccaa gggccagccc cgcgagcctc aggtgtacac actgcctcca  1440
tgccgggacg agctgaccaa gaaccaggtg tccctgtggt gcctcgtgaa gggcttctac  1500
ccctccgata tcgccgtgga atgggagagc aacggccagc ccgagaacaa ctacaagacc  1560
acccctcccg tgctggacag cgacggctca ttcttcctgt acagcaagct gaccgtggac  1620
aagtcccggt ggcagcaggg caacgtgttc agctgctctg tgatgcacga ggccctgcac  1680
aaccggttca cccagaagtc cctgagcctg agccctggc                        1719

SEQ ID NO: 84            moltype = DNA  length = 1023
FEATURE                  Location/Qualifiers
misc_feature             1..1023
                         note = Synthetic Construct
source                   1..1023
                         mol_type = other DNA
                         organism = synthetic construct
SEQUENCE: 84
gacatccaga tgacccagag ccccgccagc ctgagcgtgt ccgtgggcga taccatcacc  60
ctgacctgcc acgccagcca gaacatcgac gtgtggctga gctggttcca gcagaagccc  120
ggcaacatcc ccaagctgct gatctacaag gccagcaacc tgcacaccgg cgtgcccagc  180
agattcagcg gctctggcag cggcaccggc tttaccctga ccatcagcag cctgcagccc  240
gaggatatcg ccacctacta ctgccagcag gcccacagct acccccttcac cttcggcgga  300
ggcaccaagc tggaaatcaa gggcggcagc ggcagctccg gcagcggcgg agacattcag  360
atgacacagt cccccagcag cctgtccgcc agcgtgggcg acagagtgac catcacctgt  420
cgggccagcc agggcatccg gaactacctg gcctggtatc agcagaaacc tggcaaggcc  480
cctaaactgc tcatctacgc cgccagcaca ctgcagtctg gcgtgccctc cagattctcc  540
ggaagcggct ccggcaccga tttcaccctg acaatctcat ctctgcagcc tgaggacgtg  600
gccacatatt actgccagag atacaacaga gccccctaca cctttggcca gggcaccaag  660
gtcgagatta agggcggatc cggctccagc ggcagcggag gacgtacggt ggccgctcct  720
tccgtgttca tcttccctcc ctccgacgag cagctgaagt ccggcaccgc ctccgtggtg  780
tgtctgctga acaacttcta ccctcgggag gccaaggtgc agtggaaggt ggacaacgcc  840
ctgcagtccg gcaactccca ggagtccgtc accgagcagg actccaagga cagcacctac  900
tccctgtcct ccaccctgac cctgtccaag gccgactacg agaagcacaa ggtgtacgcc  960
tgtgaggtga cccaccaggg cctgtccagc cctgtgacca agtccttcaa ccggggcgag  1020
tgc                                                               1023

SEQ ID NO: 85            moltype = AA  length = 452
FEATURE                  Location/Qualifiers
REGION                   1..452
                         note = Synthetic Construct
source                   1..452
                         mol_type = protein
                         organism = synthetic construct
SEQUENCE: 85
QVQLQQSGPE LVKPGASVKI SCKASGYSFT SYWIHWIKQR PGQGLEWIGM IDPSDGETRL  60
NQRFQGRATL TVDESTSTAY MQLRSPTSED SAVYYCTRLK EYGNYDSFYF DVWGAGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVCTLPPS  360
RDELTKNQVS LSCAVKGFYP SDIAVEWESN GQPENNYKTT PPVLDSDGSF FLVSKLTVDK  420
SRWQQGNVFS CSVMHEALHN HYTQKSLSLS PG                               452

SEQ ID NO: 86            moltype = AA  length = 213
FEATURE                  Location/Qualifiers
REGION                   1..213
```

-continued

```
                         note = Synthetic Construct
source                   1..213
                         mol_type = protein
                         organism = synthetic construct
SEQUENCE: 86
DIQMTQSPAS LSVSVGDTIT LTCHASQNID VWLSWFQQKP GNIPKLLIYK ASNLHTGVPS  60
RFSGSGSGTG FTLTISSLQP EDIATYYCQQ AHSYPFTFGG GTKLEIKGQP KAAPSVTLFP  120
PSSEELQANK ATLVCLISDF YPGAVTVAWK ADSSPVKAGV ETTTPSKQSN NKYAASSYLS  180
LTPEQWKSHR SYSCQVTHEG STVEKTVAPT ECS                               213

SEQ ID NO: 87            moltype = AA  length = 568
FEATURE                  Location/Qualifiers
REGION                   1..568
                         note = Synthetic Construct
source                   1..568
                         mol_type = protein
                         organism = synthetic construct
SEQUENCE: 87
EVQLKESGPG LVAPGGSLSI TCTVSGFSLT DSSINWVRQP PGKGLEWLGM IWGDGRIDYA  60
DALKSRLSIS KDSSKSQVFL EMTSLRTDDT ATYYCARDGY FPYAMDFWGQ GTSVTVSSEV  120
QLVESGGGLV QPGRSLRLSC AASGFTFDDY AMHWVRQAPG KGLEWVSAIT WNSGHIDYAD  180
SVEGRFTISR DNAKNSLYLQ MNSLRAEDTA VYYCAKVSYL STASSLDYWG QGTLVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPCRDEL  480
TKNQVSLWCL VKGFYPSDIA VEWESNGQPE NNYKTTPPVL DSDGSFFLYS KLTVDKSRWQ  540
QGNVFSCSVM HEALHNRFTQ KSLSLSPG                                     568

SEQ ID NO: 88            moltype = AA  length = 344
FEATURE                  Location/Qualifiers
REGION                   1..344
                         note = Synthetic Construct
source                   1..344
                         mol_type = protein
                         organism = synthetic construct
SEQUENCE: 88
IQMTQSPSSL SASVGDRVTI TCRASQGIRN YLAWYQQKPG KAPKLLIYAA STLQSGVPSR  60
FSGSGSGTDF TLTISSLQPE DVATYYCQRY NRAPYTFGQG TKVEIKGGSG SSGSGGDIVL  120
TQSPASLAVS LGQRATISCR ASESVDSYGQ SYMHWYQQKA GQPPKLLIYL ASNLESGVPA  180
RFSGSGSRTD FTLTIDPVQA EDAATYYCQQ NAEDSRTFGG GTKLEIKGGS GSSGSGGRTV  240
AAPSVFIFPP SDEQLKSGTA SVVCLLNNFY PREAKVQWKV DNALQSGNSQ ESVTEQDSKD  300
STYSLSSTLT LSKADYEKHK VYACEVTHQG LSSPVTKSFN RGEC                   344

SEQ ID NO: 89            moltype = DNA  length = 1356
FEATURE                  Location/Qualifiers
misc_feature             1..1356
                         note = Synthetic Construct
source                   1..1356
                         mol_type = other DNA
                         organism = synthetic construct
SEQUENCE: 89
caggtgcagc tgcagcagag cggccccgag ctggtgaagc ccggcgccag cgtgaagatc  60
agctgcaagg ccagcggcta cagcttcacc agctactgga ttcactggat caagcagcgc  120
cccggccagg gcctggagtg gatcggcatg atcgacccca gcgacggcga gacccgcctg  180
aaccagcgct tccagggccg cgccaccctg accgtggacg agagcaccag caccgcctac  240
atgcagctgc gcagccccac cagcgaggac agcgccgtgt actactgcac ccgcctgaag  300
gagtacggca actacgacag cttctacttc gacgtgtggg gcgccggcac cctggtgacc  360
gtgagcagcg ccagcaccaa gggccccagc gtgttccccc tggcccctag cagcaagagc  420
acatctggcg gcacagccgc cctgggctgc ctggtcaagg actacttccc cgagcccgtg  480
acagtgtcct ggaactctgg cgccctgacc agcggagtgc ataccttccc tgccgtgctg  540
cagtccagcg gcctgtacag cctgagcagc gtggtcacag tgcccagcag cagcctgggc  600
acccagacct acatctgcaa cgtgaaccac aagcccagca acaccaaggt ggacaagaag  660
gtggaaccca agagctgcga caagacccac acctgtcccc cctgccctgc ccctgaactg  720
ctgggcggac cctccgtgtt cctgttcccc ccaaagccca aggacaccct gatgatcagc  780
cggacccccg aagtgacctg cgtggtggtg gacgtgtccc acgaggaccc tgaagtgaag  840
ttcaattggt acgtggacgg cgtggaagtg cataacgcca agaccaagcc cagagaggaa  900
cagtacaaca gcacctaccg ggtggtgtcc gtgctgaccg tgctgcacca ggactggctg  960
aacggcaaag agtacaagtg caaggtgtcc aacaaggccc tgcctgcccc catcgagaaa  1020
accatcagca aggccaaggg ccagcctaga gagccccaag tctgcaccct gccccccagc  1080
agagatgagc tgaccaagaa ccaggtgtcc ctgagctgcg ccgtgaaggg cttctacccc  1140
agcgatatcg ccgtggaatg ggagagcaac ggccagcccg agaacaacta caagaccacc  1200
ccccctgtgc tggacagcga cggctcattc ttcctggtgt ccaagctgac agtggacaag  1260
agccggtggc agcagggcaa cgtgttcagc tgcagcgtga tgcacgaggc cctgcacaac  1320
cattacaccc agaagtccct gagcctgagc cccggc                            1356

SEQ ID NO: 90            moltype = DNA  length = 639
FEATURE                  Location/Qualifiers
misc_feature             1..639
```

-continued

```
                         note = Synthetic Construct
source                   1..639
                         mol_type = other DNA
                         organism = synthetic construct
SEQUENCE: 90
gacatccaga tgacccagag ccccgccagc ctgagcgtgt ccgtgggcga taccatcacc  60
ctgacctgcc acgccagcca gaacatcgac gtgtggctga gctggttcca gcagaagccc  120
ggcaacatcc ccaagctgct gatctacaag gccagcaacc tgcacaccgg cgtgcccagc  180
agattcagcg gctctggcag cggcaccggc tttaccctga ccatcagcag cctgcagccc  240
gaggatatcg ccacctacta ctgccagcag gcccacagct acccccttcac cttcggcgga  300
ggcaccaagc tggaaatcaa gggacagccc aaggctgccc cctcggtcac cctgttcccc  360
ccaagctctg aggaactgca ggccaacaag gccaccctcg tgtgcctgat cagcgacttc  420
taccctggcg ccgtgaccgt ggcctggaag gccgatagct ctcccgtgaa ggccggcgtg  480
gaaaccacca cccccagcaa gcagagcaac aacaaatacg ccgccagcag ctacctgagc  540
ctgaccccccg agcagtggaa gtcccaccgg tcctacagct gccaggtcac acacgagggc  600
agcaccgtgg aaaagaccgt ggcccccacc gagtgcagc                          639

SEQ ID NO: 91            moltype = DNA  length = 1704
FEATURE                  Location/Qualifiers
misc_feature             1..1704
                         note = Synthetic Construct
source                   1..1704
                         mol_type = other DNA
                         organism = synthetic construct
SEQUENCE: 91
gaggtgcagc tgaaagagtc cggccctgga ctggtggccc ctggcggcag cctgagcatc  60
acctgtaccg tgtccggctt cagcctgacc gacagcagca tcaactgggt ccgacagccc  120
cctggcaagg gcctggaatg gctgggcatg atctggggcg acggccggat cgactacgcc  180
gacgccctga agtcccggct gagcatcagc aaggacagca gcaagagcca ggtgttcctg  240
gaaatgacca gcctgcggac cgacgacacc gccacctact actgcgccag ggacggctac  300
ttcccctacg ccatggattt ctggggccag ggcaccagcg tgaccgtgtc ctccgaagtg  360
cagctggtgg aaagcggcgg aggcctggtg cagcccggca gaagcctgag actgagctgc  420
gccgccagcg gcttcacctt cgacgactac gccatgcact gggtccgcca ggctcccgga  480
aagggactcg agtgggtgtc cgccatcacc tggaacagcg gccacatcga ttacgccgat  540
agcgtggaag gccggttcac catcagccgg gacaacgcca agaacagcct gtacctgcag  600
atgaacagcc tgagagccga ggataccgcc gtgtactact gtgccaaggt gtcctacctg  660
agcaccgcca gcagcctgga ctactgggga cagggaaccc tggtcaccgt gtccagcgct  720
tccaccaagg gccccagcgt gttccctctg gcccctagca gcaagagcac atctggcgga  780
acagccgccc tgggctgcct ggtcaaggac tactttcccg agcccgtgac cgtgtcctgg  840
aactctggtg ccctgacaag cggagtgcat accttccctg ccgtgctgca gagcagcggc  900
ctgtactctc tgagcagcgt ggtcaccgtg ccaagcagca gcctgggcac ccagacctac  960
atctgcaacg tgaaccacaa gccctccaac accaaggtgg acaagaaggt ggaacccaag  1020
agctgcgaca agacccacac ctgtcctccc tgtcctgccc ctgaactgct gggcggaccc  1080
tccgtgttcc tgttccctcc aaagcccaag gataccctga tgatcagccg gacccctgaa  1140
gtgacctgcg tggtggtgga cgtgtcccac gaggatcccg aagtgaagtt caattggtac  1200
gtggacggcg tggaagtgca taacgccaag accaagccca gagaggaaca gtacaacagc  1260
acctaccggg tggtgtccgt gctgacagtg ctgcaccagg actggctgaa cggcaaagag  1320
tacaagtgca aggtgtccaa caaggccctg ccagcccccta tcgagaaaac catcagcaag  1380
gccaagggcc agccccgcga gcctcaggtg tacacactgc ctccatgccg ggacgagctg  1440
accaagaacc aggtgtccct gtggtgcctc gtgaagggct tctacccctc cgatatcgcc  1500
gtggaatggg agagcaacgg ccagcccgag aacaactaca agaccacccc tcccgtgctg  1560
gacagcgacg gctcattctt cctgtacagc aagctgaccg tggacaagtc ccggtggcag  1620
cagggcaacg tgttcagctg ctctgtgatg cacgaggccc tgcacaaccg gttcacccag  1680
aagtccctga gcctgagccc tggc                                          1704

SEQ ID NO: 92            moltype = DNA  length = 1035
FEATURE                  Location/Qualifiers
misc_feature             1..1035
                         note = Synthetic Construct
source                   1..1035
                         mol_type = other DNA
                         organism = synthetic construct
SEQUENCE: 92
gacatccaga tgacccagag ccccagcagc ctgagcgcca gcgtgggcga cagagtgacc  60
atcacctgtc gggccagcca gggcatccgg aactacctgg cctggtatca gcagaagccc  120
ggcaaggccc ccaagctgct gatctacgcc gccagcacac tgcagagcgg cgtgcccagc  180
agattcagcg gcagcggctc cggcaccgac ttcaccctga ccatcagcag cctgcagccc  240
gaggacgtgg ccacctacta ctgccagcgg tacaacagag ccccctacac cttcggccag  300
ggcaccaagg tggaaatcaa gggcggctct ggcagctccg gctctggcgg cgatatcgtg  360
ctgacccagt ctcccgccag cctggccgtg tctctgggcc agagagccac catcagctgc  420
agagccagcg agagcgtgga cagctacggc cagagctaca tgcattggta tcagcagaaa  480
gccggccagc ctcctaaact gctcatctac ctggccagca acctggaatc cggcgtgccc  540
gccaggtttt ccggcagcgg cagcagaacc gatttcacac tgacaatcga ccccgtgcag  600
gccgaggatg ccgccacata ttactgtcag cagaacgccg aggacagccg gaccttcggc  660
ggaggcacca agctcgagat taagggcgga agcggctcca gcggcagtgg cggacgtacg  720
gtggccgctc cttccgtgtt catcttccct ccctccgacg agcagctgaa gtccggcacc  780
gcctccgtgg tgtgtctgct gaacaacttc taccctcggg aggccaaggt gcagtggaag  840
gtggacaacg ccctgcagtc cggcaactcc caggagtccg tcaccgagca ggactccaag  900
gacagcacct actccctgtc ctccaccctg accctgtcca aggccgacta cgagaagcac  960
```

-continued

```
aaggtgtacg cctgtgaggt gacccaccag ggcctgtcca gccctgtgac caagtccttc  1020
aaccggggcg agtgc                                                   1035

SEQ ID NO: 93          moltype = AA  length = 568
FEATURE                Location/Qualifiers
REGION                 1..568
                       note = Synthetic Construct
source                 1..568
                       mol_type = protein
                       organism = synthetic construct
SEQUENCE: 93
EVQLVESGGG LVQPGRSLRL SCAASGFTFD DYAMHWVRQA PGKGLEWVSA ITWNSGHIDY  60
ADSVEGRFTI SRDNAKNSLY LQMNSLRAED TAVYYCAKVS YLSTASSLDY WGQGTLVTVS  120
SEVQLKESGP GLVAPGGSLS ITCTVSGFSL TDSSINWVRQ PPGKGLEWLG MIWGDGRIDY  180
ADALKSRLSI SKDSSKSQVF LEMTSLRTDD TATYYCARDG YFPYAMDFWG QGTSVTVSSA  240
STKGPSVFPL APSSKSTSGG TAALGCLVKD YFPEPVTVSW NSGALTSGVH TFPAVLQSSG  300
LYSLSSVVTV PSSSLGTQTY ICNVNHKPSN TKVDKKVEPK SCDKTHTCPP CPAPELLGGP  360
SVFLFPPKPK DTLMISRTPE VTCVVVDVSH EDPEVKFNWY VDGVEVHNAK TKPREEQYNS  420
TYRVVSVLTV LHQDWLNGKE YKCKVSNKAL PAPIEKTISK AKGQPREPQV YTLPPCRDEL  480
TKNQVSLWCL VKGFYPSDIA VEWESNGQPE NNYKTTPPVL DSDGSFFLYS KLTVDKSRWQ  540
QGNVFSCSVM HEALHNRFTQ KSLSLSPG                                     568

SEQ ID NO: 94          moltype = AA  length = 345
FEATURE                Location/Qualifiers
REGION                 1..345
                       note = Synthetic Construct
source                 1..345
                       mol_type = protein
                       organism = synthetic construct
SEQUENCE: 94
DIVLTQSPAS LAVSLGQRAT ISCRASESVD SYGQSYMHWY QQKAGQPPKL LIYLASNLES  60
GVPARFSGSG SRTDFTLTID PVQAEDAATY YCQQNAEDSR TFGGGTKLEI KGGSGSSGSG  120
GDIQMTQSPS SLSASVGDRV TITCRASQGI RNYLAWYQQK PGKAPKLLIY AASTLQSGVP  180
SRFSGSGSGT DFTLTISSLQ PEDVATYYCQ RYNRAPYTFG QGTKVEIKGG SGSSGSGGRT  240
VAAPSVFIFP PSDEQLKSGT ASVVCLLNNF YPREAKVQWK VDNALQSGNS QESVTEQDSK  300
DSTYSLSSTL TLSKADYEKH KVYACEVTHQ GLSSPVTKSF NRGEC                  345

SEQ ID NO: 95          moltype = DNA  length = 1704
FEATURE                Location/Qualifiers
misc_feature           1..1704
                       note = Synthetic Construct
source                 1..1704
                       mol_type = other DNA
                       organism = synthetic construct
SEQUENCE: 95
gaggtgcagc tggtggaaag cggcggagga ctggtgcagc ccggcagaag cctgagactg  60
agctgcgccg ccagcggctt caccttcgac gactacgcca tgcactgggt ccgacaggcc  120
cctggcaagg gcctggaatg ggtgtccgcc atcacctgga acagcggcca catcgactac  180
gccgacagcg tggaaggccg gttcaccatc agccgggaca acgccaagaa cagcctgtac  240
ctgcagatga acagcctgcg ggccgaggac accgccgtgt actactgcgc caaggtgtcc  300
tacctgagca ccgccagcag cctggactac tggggccagg gcaccctggt caccgtgtcc  360
tccgaagtgc agctgaaaga gtccggccct ggcctggtgg cccctggcgg cagcctgagc  420
atcacctgta ccgtgtccgg cttcagcctg accgacagca gcatcaactg ggtccgccag  480
cctcccggaa agggactcga gtggctgggc atgatctggg gcgacggccg gatcgattac  540
gccgatgccc tgaagtcccg gctgagcatc agcaaggaca gcagcaagag ccaggtgttc  600
ctggaaatga ccagcctgag aaccgacgac accgccacct actactgtgc ccgggacggc  660
tacttcccct acgccatgga tttctgggga cagggaacca gcgtgaccgt gtccagcgct  720
tccaccaagg gccccagcgt gttccctctg gcccctagca gcaagagcac atctggcgga  780
acagccgccc tgggctgcct ggtcaaggac tactttcccg agcccgtgac cgtgtcctgg  840
aactctggtg ccctgacaag cggagtgcat accttccctg ccgtgctgca gagcagcggc  900
ctgtactctc tgagcagcgt ggtcaccgtg ccaagcagca gcctgggcac ccagacctac  960
atctgcaacg tgaaccacaa gccctccaac accaaggtgg acaagaaggt ggaacccaag  1020
agctgcgaca agacccacac ctgtcctccc tgtcctgccc ctgaactgct gggcggaccc  1080
tccgtgttcc tgttccctcc aaagcccaag gataccctga tgatcagccg gacccctgaa  1140
gtgacctgcg tggtggtgga cgtgtcccac gaggatcccg aagtgaagtt caattggtac  1200
gtggacggcg tggaagtgca taacgccaag accaagccca gagaggaaca gtacaacagc  1260
acctaccggg tggtgtccgt gctgacagtg ctgcaccagg actggctgaa cggcaaagag  1320
tacaagtgca aggtgtccaa caaggccctg ccagcccccta tcgagaaaac catcagcaag  1380
gccaagggcc agccccgcga gcctcaggtg tacacactgc ctccatgccg ggacgagctg  1440
accaagaacc aggtgtccct gtggtgcctc gtgaagggct tctacccctc cgatatcgcc  1500
gtggaatggg agagcaacgg ccagcccgag aacaactaca agaccacccc tcccgtgctg  1560
gacagcgacg gctcattctt cctgtacagc aagctgaccg tggacaagtc ccggtggcag  1620
cagggcaacg tgttcagctg ctctgtgatg cacgaggccc tgcacaaccg gttcacccag  1680
aagtccctga gcctgagccc tggc                                         1704

SEQ ID NO: 96          moltype = DNA  length = 1035
FEATURE                Location/Qualifiers
misc_feature           1..1035
                       note = Synthetic Construct
```

```
source                  1..1035
                        mol_type = other DNA
                        organism = synthetic construct
SEQUENCE: 96
gacatcgtgc tgacccagag ccctgccagc ctggccgtgt ctctgggcca gagagccacc  60
atcagctgcc gggccagcga gagcgtggac agctacggcc agagctacat gcactggtat  120
cagcagaagg ccggccagcc ccccaagctg ctgatctacc tggccagcaa cctggaaagc  180
ggcgtgcccg ccagattcag cggcagcggc agcagaaccg acttcaccct gaccatcgac  240
cccgtgcagg ccgaggacgc cgccacctac tactgccagc agaacgccga ggacagccgg  300
accttcggcg gaggcaccaa gctggaaatc aagggcggct ccggcagcag cggctctggc  360
ggcgatatcc agatgaccca gtcccccagc agcctgagcg ccagcgtggg cgacagagtg  420
accatcacct gtagagccag ccagggcatc cggaactacc tggcttggta tcagcagaaa  480
cccggaaagg cccctaaact gctcatctac gccgccagca ccctgcagtc cggcgtgcca  540
agcagattct ccggctctgg cagcggcacc gatttcacac tgacaatcag cagcctgcag  600
cccgaggatg tggccaccta ttattgccag agatacaaca gagcccccta caccttcggc  660
cagggcacca aggtcgagat taagggcgga agcggcagct ccggctccgg cggacgtacg  720
gtggccgctc cttccgtgtt catcttccct ccctccgacg agcagctgaa gtccggcacc  780
gcctccgtgg tgtgtctgct gaacaacttc taccctcggg aggccaaggt gcagtggaag  840
gtggacaacg ccctgcagtc cggcaactcc caggagtccg tcaccgagca ggactccaag  900
gacagcacct actccctgtc ctccaccctg accctgtcca aggccgacta cgagaagcac  960
aaggtgtacg cctgtgaggt gacccaccag ggcctgtcca gccctgtgac caagtccttc  1020
aaccggggcg agtgc                                                   1035

SEQ ID NO: 97           moltype = DNA  length = 1710
FEATURE                 Location/Qualifiers
misc_feature            1..1710
                        note = Synthetic Construct
source                  1..1710
                        mol_type = other DNA
                        organism = synthetic construct
SEQUENCE: 97
gaggtgcagc tgaaagagtc cggccctgga ctggtggccc ctggcggcag cctgagcatc  60
acctgtaccg tgtccggctt cagcctgacc gacagcagca tcaactgggt ccgacagccc  120
cctggcaagg gcctggaatg gctgggcatg atctggggcg acggccggat cgactacgcc  180
gacgccctga agtcccggct gagcatcagc aaggacagca gcaagagcca ggtgttcctg  240
gaaatgacca gcctgcggac cgacgacacc gccacctact actgcgccag ggacggctac  300
ttcccctacg ccatggattt ctggggccag ggcaccagcg tgaccgtgtc cagtcaggtc  360
cagctgcagc agagcggccc tgagctggtc aagcctggcg ccagcgtgaa gatcagctgc  420
aaggccagcg gctacagctt caccagctac tggatccact ggatcaagca gcggcctggc  480
cagggcctcg agtggatcgg aatgatcgac cccagcgacg gcgagacacg gctgaaccag  540
agattccagg gcagagccac cctgaccgtg gacgagagca ccagcaccgc ctacatgcag  600
ctgcggagcc ccaccagcga ggacagcgcc gtgtactact gcacccggct gaaagaatac  660
ggcaactacg acagcttcta cttcgacgtg tggggagccg gcaccctggt caccgtgtct  720
agcgcttcca ccaagggccc cagcgtgttc cctctggccc ctagcagcaa gagcacatct  780
ggcggaacag ccgccctggg ctgcctggtc aaggactact tcccgagcc cgtgaccgtg  840
tcctggaact ctggtgccct gacaagcgga gtgcatacct tccctgccgt gctgcagagc  900
agcggcctgt actctctgag cagcgtggtc accgtgccaa gcagcagcct gggcacccag  960
acctacatct gcaacgtgaa ccacaagccc tccaacacca aggtggacaa gaaggtggaa  1020
cccaagagct gcgacaagac ccacacctgt cctccctgtc ctgcccctga actgctgggc  1080
ggaccctccg tgttcctgtt ccctccaaag cccaaggata ccctgatgat cagccggacc  1140
cctgaagtga cctgcgtggt ggtggacgtg tcccacgagg atcccgaagt gaagttcaat  1200
tggtacgtgg acggcgtgga agtgcataac gccaagacca agcccagaga ggaacagtac  1260
aacagcacct accgggtggt gtccgtgctg acagtgctgc accaggactg gctgaacggc  1320
aaagagtaca agtgcaaggt gtccaacaag gccctgccag cccctatcga gaaaaccatc  1380
agcaaggcca agggccagcc ccgcgagcct caggtgtaca cactgcctcc atgccgggac  1440
gagctgacca agaaccaggt gtccctgtgg tgcctcgtga agggcttcta cccctccgat  1500
atcgccgtgg aatgggagag caacggccag cccgagaaca actacaagac cacccctccc  1560
gtgctggaca gcgacggctc attcttcctg tacagcaagc tgaccgtgga caagtcccgg  1620
tggcagcagg gcaacgtgtt cagctgctct gtgatgcacg aggccctgca caaccggttc  1680
acccagaagt ccctgagcct gagccctggc                                   1710

SEQ ID NO: 98           moltype = AA  length = 4
FEATURE                 Location/Qualifiers
REGION                  1..4
                        note = Synthetic Construct
source                  1..4
                        mol_type = protein
                        organism = synthetic construct
SEQUENCE: 98
GGGG                                                               4

SEQ ID NO: 99           moltype = AA  length = 5
FEATURE                 Location/Qualifiers
REGION                  1..5
                        note = Synthetic Construct
source                  1..5
                        mol_type = protein
                        organism = synthetic construct
SEQUENCE: 99
```

```
GGGGG                                                         5

SEQ ID NO: 100          moltype = AA  length = 6
FEATURE                 Location/Qualifiers
REGION                  1..6
                        note = Synthetic Construct
source                  1..6
                        mol_type = protein
                        organism = synthetic construct
SEQUENCE: 100
GGGGGG                                                        6

SEQ ID NO: 101          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 101
GGGGGGG                                                       7

SEQ ID NO: 102          moltype = AA  length = 8
FEATURE                 Location/Qualifiers
REGION                  1..8
                        note = Synthetic Construct
source                  1..8
                        mol_type = protein
                        organism = synthetic construct
SEQUENCE: 102
GGGGGGGG                                                      8

SEQ ID NO: 103          moltype = AA  length = 5
FEATURE                 Location/Qualifiers
REGION                  1..5
                        note = Synthetic Construct
source                  1..5
                        mol_type = protein
                        organism = synthetic construct
SEQUENCE: 103
GGGGS                                                         5

SEQ ID NO: 104          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 104
GGGGSGGGGS                                                    10

SEQ ID NO: 105          moltype = AA  length = 15
FEATURE                 Location/Qualifiers
REGION                  1..15
                        note = Synthetic Construct
source                  1..15
                        mol_type = protein
                        organism = synthetic construct
SEQUENCE: 105
GGGGSGGGGS GGGGS                                              15

SEQ ID NO: 106          moltype = AA  length = 5
FEATURE                 Location/Qualifiers
REGION                  1..5
                        note = Synthetic Construct
source                  1..5
                        mol_type = protein
                        organism = synthetic construct
SEQUENCE: 106
TKGPS                                                         5

SEQ ID NO: 107          moltype = AA  length = 5
FEATURE                 Location/Qualifiers
REGION                  1..5
                        note = Synthetic Construct
source                  1..5
                        mol_type = protein
                        organism = synthetic construct
```

-continued

```
SEQUENCE: 107
TVAAP                                                        5

SEQ ID NO: 108          moltype = AA  length = 5
FEATURE                 Location/Qualifiers
REGION                  1..5
                        note = Synthetic Construct
source                  1..5
                        mol_type = protein
                        organism = synthetic construct
SEQUENCE: 108
QPKAA                                                        5

SEQ ID NO: 109          moltype = AA  length = 5
FEATURE                 Location/Qualifiers
REGION                  1..5
                        note = Synthetic Construct
source                  1..5
                        mol_type = protein
                        organism = synthetic construct
SEQUENCE: 109
QRIEG                                                        5

SEQ ID NO: 110          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 110
ASTKGPS                                                      7

SEQ ID NO: 111          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 111
RTVAAPS                                                      7

SEQ ID NO: 112          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 112
GQPKAAP                                                      7

SEQ ID NO: 113          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 113
HIDSPNK                                                      7

SEQ ID NO: 114          moltype = AA  length = 448
FEATURE                 Location/Qualifiers
REGION                  1..448
                        note = Synthetic Construct
source                  1..448
                        mol_type = protein
                        organism = synthetic construct
SEQUENCE: 114
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
AASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPCQEEMT  360
KNQVSLWCLV KGFYPSDIAV EWESNGQPEN NYKTTPPVLD SDGSFFLYSK LTVDKSRWQE  420
GNVFSCSVMH EALHNHYTQK SLSLSLGK                                  448
```

```
SEQ ID NO: 115         moltype = AA  length = 213
FEATURE                Location/Qualifiers
REGION                 1..213
                       note = Synthetic Construct
source                 1..213
                       mol_type = protein
                       organism = synthetic construct
SEQUENCE: 115
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 116         moltype = DNA  length = 1344
FEATURE                Location/Qualifiers
misc_feature           1..1344
                       note = Synthetic Construct
source                 1..1344
                       mol_type = other DNA
                       organism = synthetic construct
SEQUENCE: 116
caggtgcagc tgcagcagcc tggcgccgaa ctcgtgaaac ctggcgcctc cgtgaagatg  60
agctgcaagg ccagcggcta caccttcacc agctacaaca tgcactgggt caagcagacc  120
cccggcagag gcctggaatg gatcggcgcc atctaccccg gcaacggcga cacctcctac  180
aaccagaagt tcaagggcaa ggccaccctg accgccgaca agagcagcag cacagcctac  240
atgcagctgt ccagcctgac cagcgaggac agcgccgtgt actactgcgc cagaagcacc  300
tactacggcg gcgactggta cttcaacgtg tggggagccg gcaccaccgt gacagtgtct  360
gctgcttcga ccaagggccc atcggtgttc cctctggccc cttgcagcag aagcaccagc  420
gaatctacag ccgccctggg ctgcctcgtg aaggactact tccccgagcc cgtgaccgtg  480
tcctggaact ctggcgctct gacaagcggc gtgcacacct tccagccgt gctccagagc  540
agcggcctgt actctctgag cagcgtcgtg acagtgccca gcagcagcct gggcaccaag  600
acctacacct gtaacgtgga ccacaagccc agcaacacca aggtggacaa gcgggtggaa  660
tctaagtacg gccctccctg ccctccttgc ccagcccctg aatttctggg cggaccctcc  720
gtgttcctgt tcccccaaa gcccaaggac accctgatga tcagccggac ccccgaagtg  780
acctgcgtgg tggtggatgt gtcccaggaa gatcccgagg tgcagttcaa ttggtacgtg  840
gacggcgtgg aagtgcacaa cgccaagacc aagcccagag aggaacagtt caacagcacc  900
taccgggtgg tgtccgtgct gaccgtgctg caccaggact ggctgaacgg caaagagtac  960
aagtgcaagg tgtccaacaa gggcctgccc agctccatcg agaaaaccat cagcaaggcc  1020
aagggccagc cccgcgagcc tcaagtgtat accctgcccc cttgccagga agagatgacc  1080
aagaaccagg tgtccctgtg gtgtctcgtg aaaggcttct accccagcga cattgccgtg  1140
gaatgggaga gcaacggcca gcccgagaac aactacaaga ccaccccccc tgtgctggac  1200
agcgacggct cattcttcct gtactccaag ctgaccgtgg acaagagccg gtggcaggaa  1260
ggcaacgtgt tcagctgctc cgtgatgcac gaggccctgc acaaccacta cacccagaag  1320
tccctgtctc tgtccctggg caag                                        1344

SEQ ID NO: 117         moltype = DNA  length = 639
FEATURE                Location/Qualifiers
misc_feature           1..639
                       note = Synthetic Construct
source                 1..639
                       mol_type = other DNA
                       organism = synthetic construct
SEQUENCE: 117
cagatcgtgc tgagccagag ccctgccatc ctgagcgctt ccccaggcga gaaagtgacc  60
atgacctgca gagccagcag cagcgtgtcc tacatccact ggttccagca gaagcccggc  120
agcagcccca agccttggat ctacgccacc agcaatctgg ccagcggagt gcctgtgcgg  180
tttagcggct ctggcagcgg cacaagctac agcctgacca tcagccgggt ggaagccgaa  240
gatgccgcca cctactactg ccagcagtgg accagcaacc cccccacatt tggcggaggc  300
accaagctgg aaatcaagcg tacggtggcc gctcccagcg tgttcatctt cccacctagc  360
gacgagcagc tgaagtccgg cacagcctct gtcgtgtgcc tgctgaacaa cttctacccc  420
cgcgaggcca aagtgcagtg gaaggtggac aacgccctgc agagcggcaa cagccaggaa  480
agcgtgaccg agcaggacag caaggactcc acctacagcc tgagcagcac cctgacactg  540
agcaaggccg actacgagaa gcacaaggtg tacgcctgcg aagtgaccca ccagggcctg  600
tctagccccg tgaccaagag cttcaaccgg ggcgagtgt                        639

SEQ ID NO: 118         moltype = DNA  length = 1713
FEATURE                Location/Qualifiers
misc_feature           1..1713
                       note = Synthetic Construct
source                 1..1713
                       mol_type = other DNA
                       organism = synthetic construct
SEQUENCE: 118
caggtgcagc tgcaggaatc tggccctggc ctcgtgaagc ctagccagac cctgagcctg  60
acctgtaccg tgtccggctt cagcctgagc gactacggcg tgcactgggt gcgccagcca  120
cctggaaaag gcctggaatg gctgggcgtg atctgggctg gcggaggcac caactacaac  180
cccagcctga agtccagaaa gaccatcagc aaggacacca gcaagaacca ggtgtccctg  240
aagctgagca gcgtgacagc cgccgatacc gccgtgtact actgcgccag agacaagggc  300
```

```
tacagctact actacagcat ggactactgg ggccagggca ccaccgtgac cgtgtcatcc  360
tctcaggtgc agctggtgga atctggcggc ggagtggtgc agcctggcag aagcctgaga  420
ctgagctgtg ccgccagcgg cttcaccttc accaaggcct ggatgcactg ggtgcgccag  480
gcccctggaa agcagctgga atgggtggcc cagatcaagg acaagagcaa cagctacgcc  540
acctactacg ccgacagcgt gaagggccgg ttcaccatca gccgggacga cagcaagaac  600
accctgtacc tgcagatgaa cagcctgcgg gccgaggaca ccgccgtgta ctactgtcgg  660
ggcgtgtact atgccctgag ccccttcgat tactggggcc agggaaccct cgtgaccgtg  720
tctagtcgga ccgcttcgac caagggccca tcggtgttcc ctctggcccc ttgcagcaga  780
agcaccagcg aatctacagc cgccctgggc tgcctcgtga aggactactt tcccgagccc  840
gtgaccgtgt cctggaactc tggcgctctg acaagcggcg tgcacacctt tccagccgtg  900
ctccagagca gcggcctgta ctctctgagc agcgtcgtga cagtgcccag cagcagcctg  960
ggcaccaaga cctacacctg taacgtggac cacaagccca gcaacaccaa ggtggacaag  1020
cgggtggaat ctaagtacgg ccctccctgc cctccttgcc cagcccctga atttctgggc  1080
ggaccctccg tgttcctgtt cccccaaag cccaaggaca ccctgatgat cagccggacc  1140
cccgaagtga cctgcgtggt ggtggatgtg tcccaggaag atcccgaggt gcagttcaat  1200
tggtacgtgg acggcgtgga agtgcacaac gccaagacca agcccagaga ggaacagttc  1260
aacagcacct accgggtggt gtccgtgctg accgtgctgc accaggactg gctgaacggc  1320
aaagagtaca agtgcaaggt gtccaacaag ggcctgccca gctccatcga gaaaaccatc  1380
agcaaggcca agggccagcc ccgcgagcct caagtgtgta ccctgccccc tagccaggaa  1440
gagatgacca agaaccaggt gtccctgagc tgtgccgtga aaggcttcta ccccagcgac  1500
attgccgtgg aatgggagag caacggccag cccgagaaca actacaagac cacccccct  1560
gtgctggaca gcgacggctc attcttcctg gtgtccaagc tgaccgtgga caagagccgg  1620
tggcaggaag gcaacgtgtt cagctgctcc gtgatgcacg aggccctgca caaccactac  1680
acccagaagt ccctgtctct gtccctgggc aag                               1713

SEQ ID NO: 119         moltype = DNA  length = 1026
FEATURE                Location/Qualifiers
misc_feature           1..1026
                       note = Synthetic Construct
source                 1..1026
                       mol_type = other DNA
                       organism = synthetic construct
SEQUENCE: 119
gacatcgtga tgacccagac ccccctgagc ctgagcgtga cacctggaca gcctgccagc  60
atcagctgca agagcagcca gagcctggtg cacaacaacg ccaacaccta cctgagctgg  120
tatctgcaga agcccggcca gagcccccag tccctgatct acaaggtgtc caacagattc  180
agcggcgtgc ccgacagatt ctccggcagc ggctctggca ccgacttcac cctgaagatc  240
agccgggtgg aagccgagga cgtgggcgtg tactattgtg gccagggcac ccagtacccc  300
ttcacctttg gcagcggcac caaggtggaa atcaagggcc agcccaaggc cgccccccgac  360
atcgtgctga cacagagccc tgctagcctg gccgtgtctc ctggacagag ggccaccatc  420
acctgtagag ccagcgagag cgtggaatat tacgtgacca gcctgatgca gtggtatcag  480
cagaagcccg gccagccccc caagctgctg attttcgccg ccagcaacgt ggaaagcggc  540
gtgccagcca gattttccgg cagcggctct ggcaccgact tcaccctgac catcaacccc  600
gtggaagcca acgacgtggc caactactac tgccagcaga gccggaaggt gccctacacc  660
tttggccagg gcaccaagct ggaaatcaag accaagggcc ccagcccgtac ggtggccgct  720
cccagcgtgt tcatcttccc acctagcgac gagcagctga agtccggcac agcctctgtc  780
gtgtgcctgc tgaacaactt ctacccccgc gaggccaaag tgcagtggaa ggtggacaac  840
gccctgcaga gcggcaacag ccaggaaagc gtgaccgagc aggacagcaa ggactccacc  900
tacagcctga gcagcaccct gacactgagc aaggccgact acgagaagca caaggtgtac  960
gcctgcgaag tgacccacca gggcctgtct agccccgtga ccaagagctt caaccggggc  1020
gagtgt                                                             1026

SEQ ID NO: 120         moltype = AA  length = 8
FEATURE                Location/Qualifiers
REGION                 1..8
                       note = Synthetic Construct
source                 1..8
                       mol_type = protein
                       organism = synthetic construct
SEQUENCE: 120
GYTFTSYN                                                           8

SEQ ID NO: 121         moltype = AA  length = 8
FEATURE                Location/Qualifiers
REGION                 1..8
                       note = Synthetic Construct
source                 1..8
                       mol_type = protein
                       organism = synthetic construct
SEQUENCE: 121
IYPGNGDT                                                           8

SEQ ID NO: 122         moltype = AA  length = 14
FEATURE                Location/Qualifiers
REGION                 1..14
                       note = Synthetic Construct
source                 1..14
                       mol_type = protein
                       organism = synthetic construct
```

```
SEQUENCE: 122
ARSTYYGGDW YFNV                                                     14

SEQ ID NO: 123          moltype = AA  length = 5
FEATURE                 Location/Qualifiers
REGION                  1..5
                        note = Synthetic Construct
source                  1..5
                        mol_type = protein
                        organism = synthetic construct
SEQUENCE: 123
SSVSY                                                               5

SEQ ID NO: 124          moltype =   length =
SEQUENCE: 124
000

SEQ ID NO: 125          moltype = AA  length = 7
FEATURE                 Location/Qualifiers
REGION                  1..7
                        note = Synthetic Construct
source                  1..7
                        mol_type = protein
                        organism = synthetic construct
SEQUENCE: 125
QQWTSNP                                                             7

SEQ ID NO: 126          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 126
GYIFTNYNIH                                                          10

SEQ ID NO: 127          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 127
AIYPGNGDAP                                                          10

SEQ ID NO: 128          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 128
ANWDVAFAY                                                           9

SEQ ID NO: 129          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 129
GFTFDDYAMH                                                          10

SEQ ID NO: 130          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 130
AITWNSGHID                                                          10

SEQ ID NO: 131          moltype = AA  length = 12
FEATURE                 Location/Qualifiers
```

```
REGION                  1..12
                        note = Synthetic Construct
source                  1..12
                        mol_type = protein
                        organism = synthetic construct
SEQUENCE: 131
VSYLSTASSL DY                                                    12

SEQ ID NO: 132          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 132
GYSFTSYWIH                                                       10

SEQ ID NO: 133          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 133
MIDPSDGET                                                        9

SEQ ID NO: 134          moltype = AA  length = 14
FEATURE                 Location/Qualifiers
REGION                  1..14
                        note = Synthetic Construct
source                  1..14
                        mol_type = protein
                        organism = synthetic construct
SEQUENCE: 134
LKEYGNYDSF YFDV                                                  14

SEQ ID NO: 135          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 135
GFSLTDSSIN                                                       10

SEQ ID NO: 136          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 136
MIWGDGRID                                                        9

SEQ ID NO: 137          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 137
DGYFPYAMDF                                                       10

SEQ ID NO: 138          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 138
KASQDIDRYM A                                                     11

SEQ ID NO: 139          moltype = AA  length = 7
```

```
FEATURE                Location/Qualifiers
REGION                 1..7
                       note = Synthetic Construct
source                 1..7
                       mol_type = protein
                       organism = synthetic construct
SEQUENCE: 139
DTSTLQS                                                        7

SEQ ID NO: 140         moltype = AA  length = 8
FEATURE                Location/Qualifiers
REGION                 1..8
                       note = Synthetic Construct
source                 1..8
                       mol_type = protein
                       organism = synthetic construct
SEQUENCE: 140
LQYDNLWT                                                       8

SEQ ID NO: 141         moltype = AA  length = 11
FEATURE                Location/Qualifiers
REGION                 1..11
                       note = Synthetic Construct
source                 1..11
                       mol_type = protein
                       organism = synthetic construct
SEQUENCE: 141
RASQGIRNYL A                                                   11

SEQ ID NO: 142         moltype = AA  length = 9
FEATURE                Location/Qualifiers
REGION                 1..9
                       note = Synthetic Construct
source                 1..9
                       mol_type = protein
                       organism = synthetic construct
SEQUENCE: 142
QRYNRAPYT                                                      9

SEQ ID NO: 143         moltype = AA  length = 11
FEATURE                Location/Qualifiers
REGION                 1..11
                       note = Synthetic Construct
source                 1..11
                       mol_type = protein
                       organism = synthetic construct
SEQUENCE: 143
HASQNIDVWL S                                                   11

SEQ ID NO: 144         moltype = AA  length = 9
FEATURE                Location/Qualifiers
REGION                 1..9
                       note = Synthetic Construct
source                 1..9
                       mol_type = protein
                       organism = synthetic construct
SEQUENCE: 144
QQAHSYPFT                                                      9

SEQ ID NO: 145         moltype = AA  length = 15
FEATURE                Location/Qualifiers
REGION                 1..15
                       note = Synthetic Construct
source                 1..15
                       mol_type = protein
                       organism = synthetic construct
SEQUENCE: 145
RASESVDSYG QSYMH                                               15

SEQ ID NO: 146         moltype = AA  length = 7
FEATURE                Location/Qualifiers
REGION                 1..7
                       note = Synthetic Construct
source                 1..7
                       mol_type = protein
                       organism = synthetic construct
SEQUENCE: 146
LASNLES                                                        7
```

```
SEQ ID NO: 147          moltype = AA  length = 9
FEATURE                 Location/Qualifiers
REGION                  1..9
                        note = Synthetic Construct
source                  1..9
                        mol_type = protein
                        organism = synthetic construct
SEQUENCE: 147
QQNAEDSRT                                                          9

SEQ ID NO: 148          moltype = AA  length = 10
FEATURE                 Location/Qualifiers
REGION                  1..10
                        note = Synthetic Construct
source                  1..10
                        mol_type = protein
                        organism = synthetic construct
SEQUENCE: 148
GGSGSSGSGG                                                         10

SEQ ID NO: 149          moltype = AA  length = 11
FEATURE                 Location/Qualifiers
REGION                  1..11
                        note = Synthetic Construct
source                  1..11
                        mol_type = protein
                        organism = synthetic construct
SEQUENCE: 149
QSLVHNNGNT Y                                                       11

SEQ ID NO: 150          moltype = AA  length = 120
FEATURE                 Location/Qualifiers
REGION                  1..120
                        note = Synthetic Construct
source                  1..120
                        mol_type = protein
                        organism = synthetic construct
SEQUENCE: 150
EVQLVESGGG LVQPGGSLRL SCAASGFNIK DTYIHWVRQA PGKGLEWVAR IYPTNGYTRY  60
ADSVKGRFTI SADTSKNTAY LQMNSLRAED TAVYYCSRWG GDGFYAMDYW GQGTLVTVSS  120

SEQ ID NO: 151          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 151
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIK                107

SEQ ID NO: 152          moltype = AA  length = 121
FEATURE                 Location/Qualifiers
REGION                  1..121
                        note = Synthetic Construct
source                  1..121
                        mol_type = protein
                        organism = synthetic construct
SEQUENCE: 152
QVQLVESGGG VVQPGRSLRL SCAASGFTFT KAWMHWVRQA PGKQLEWVAQ IKDKSNSYAT  60
YYADSVKGRF TISRDDSKNT LYLQMNSLRA EDTAVYYCRG VYYALSPFDY WGQGTLVTVS  120
S                                                                  121

SEQ ID NO: 153          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 153
DIVMTQTPLS LSVTPGQPAS ISCKSSQSLV HNNANTYLSW YLQKPGQSPQ SLIYKVSNRF  60
SGVPDRFSGS GSGTDFTLKI SRVEAEDVGV YYCGQGTQYP FTFGSGTKVE IK          112

SEQ ID NO: 154          moltype = AA  length = 121
FEATURE                 Location/Qualifiers
REGION                  1..121
                        note = Synthetic Construct
```

```
source                  1..121
                        mol_type = protein
                        organism = synthetic construct
SEQUENCE: 154
QVQLVESGGG VVQPGRSLRL SCAASGFTFT KAWMHWVRQA PGKGLEWVAQ IKDKSNSYAT  60
YYADSVKGRF TISRDNSKNT LYLQMNSLRA EDTAVYYCRG VYYALSPFDY WGQGTLVTVS  120
S                                                                  121

SEQ ID NO: 155          moltype = AA  length = 112
FEATURE                 Location/Qualifiers
REGION                  1..112
                        note = Synthetic Construct
source                  1..112
                        mol_type = protein
                        organism = synthetic construct
SEQUENCE: 155
DIVMTQTPLS LSVTPGQPAS ISCKSSQSLV HNNGNTYLSW YLQKPGQSPQ LLIYKVSNRF  60
SGVPDRFSGS GSGTDFTLKI SRVEAEDVGV YYCGQGTQYP FTFGGGTKVE IK          112

SEQ ID NO: 156          moltype = AA  length = 124
FEATURE                 Location/Qualifiers
REGION                  1..124
                        note = Synthetic Construct
source                  1..124
                        mol_type = protein
                        organism = synthetic construct
SEQUENCE: 156
QVQLVQSGAE VKKPGSSVKV SCKASGYAFS SYWMNWVRQA PGQGLEWIGQ IWPGDGDTNY  60
NQKFKGRATL TADESTSTAY MELSSLRSED TAVYYCARRE TTTVGRYYYA MDYWGQGTTV  120
TVSS                                                               124

SEQ ID NO: 157          moltype = AA  length = 111
FEATURE                 Location/Qualifiers
REGION                  1..111
                        note = Synthetic Construct
source                  1..111
                        mol_type = protein
                        organism = synthetic construct
SEQUENCE: 157
DLVLTQSPAS LAVSPGQRAT ITCKASQSVD YDGDSYLNWY QQKPGQPPKL LIYDASNLVS  60
GVPARFSGSG SGTDFTLTIN PVEANDTANY YCQQSTEDPW TFGQGTKLEI K           111

SEQ ID NO: 158          moltype = AA  length = 121
FEATURE                 Location/Qualifiers
REGION                  1..121
                        note = Synthetic Construct
source                  1..121
                        mol_type = protein
                        organism = synthetic construct
SEQUENCE: 158
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
A                                                                  121

SEQ ID NO: 159          moltype = AA  length = 106
FEATURE                 Location/Qualifiers
REGION                  1..106
                        note = Synthetic Construct
source                  1..106
                        mol_type = protein
                        organism = synthetic construct
SEQUENCE: 159
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIK                 106

SEQ ID NO: 160          moltype = AA  length = 120
FEATURE                 Location/Qualifiers
REGION                  1..120
                        note = Synthetic Construct
source                  1..120
                        mol_type = protein
                        organism = synthetic construct
SEQUENCE: 160
QVQLVQSGAE VVKPGASVKV SCKASGYTFT SYYIHWVRQA PGQGLEWIGS IYPGNVNTNY  60
AQKFQGRATL TVDTSISTAY MELSRLRSDD TAVYYCTRSH YGLDWNFDVW GKGTTVTVSS  120

SEQ ID NO: 161          moltype = AA  length = 107
FEATURE                 Location/Qualifiers
REGION                  1..107
```

```
                        note = Synthetic Construct
source                  1..107
                        mol_type = protein
                        organism = synthetic construct
SEQUENCE: 161
DIQMTQSPSS LSASVGDRVT ITCQASQNIY VWLNWYQQKP GKAPKLLIYK ASNLHTGVPS  60
RFSGSGSGTD FTLTISSLQP EDIATYYCQQ GQTYPYTFGQ GTKLEIK               107

SEQ ID NO: 162          moltype = AA  length = 120
FEATURE                 Location/Qualifiers
REGION                  1..120
                        note = Synthetic Construct
source                  1..120
                        mol_type = protein
                        organism = synthetic construct
SEQUENCE: 162
QVQLQESGPG LVKPSQTLSL TCTVSGFSLS DYGVHWVRQP PGKGLEWLGV IWAGGGTNYN  60
PSLKSRKTIS KDTSKNQVSL KLSSVTAADT AVYYCARDKG YSYYYSMDYW GQGTTVTVSS  120

SEQ ID NO: 163          moltype = AA  length = 111
FEATURE                 Location/Qualifiers
REGION                  1..111
                        note = Synthetic Construct
source                  1..111
                        mol_type = protein
                        organism = synthetic construct
SEQUENCE: 163
DIVLTQSPAS LAVSPGQRAT ITCRASESVE YYVTSLMQWY QQKPGQPPKL LIFAASNVES  60
GVPARFSGSG SGTDFTLTIN PVEANDVANY YCQQSRKVPY TFGQGTKLEI K          111

SEQ ID NO: 164          moltype = AA  length = 120
FEATURE                 Location/Qualifiers
REGION                  1..120
                        note = Synthetic Construct
source                  1..120
                        mol_type = protein
                        organism = synthetic construct
SEQUENCE: 164
QVQLVQSGAE VAKPGTSVKL SCKASGYTFT DYWMQWVKQR PGQGLEWIGT IYPGDGDTGY  60
AQKFQGKATL TADKSSKTVY MHLSSLASED SAVYYCARGD YYGSNSLDYW GQGTSVTVSS  120

SEQ ID NO: 165          moltype = AA  length = 107
FEATURE                 Location/Qualifiers
REGION                  1..107
                        note = Synthetic Construct
source                  1..107
                        mol_type = protein
                        organism = synthetic construct
SEQUENCE: 165
DIVMTQSHLS MSTSLGDPVS ITCKASQDVS TVVAWYQQKP GQSPRRLIYS ASYRYIGVPD  60
RFTGSGAGTD FTFTISSVQA EDLAVYYCQQ HYSPPYTFGG GTKLEIK               107

SEQ ID NO: 166          moltype = AA  length = 118
FEATURE                 Location/Qualifiers
REGION                  1..118
                        note = Synthetic Construct
source                  1..118
                        mol_type = protein
                        organism = synthetic construct
SEQUENCE: 166
QVQLVQSGAE VKKPGSSVKV SCKASGYIFT NYNIHWVKKS PGQGLEWIGA IYPGNGDAPY  60
SQKFQGKATL TADTSTSTTY MELSSLRSED TAVYYCVRAN WDVAFAYWGQ GTLVTVSS    118

SEQ ID NO: 167          moltype = AA  length = 106
FEATURE                 Location/Qualifiers
REGION                  1..106
                        note = Synthetic Construct
source                  1..106
                        mol_type = protein
                        organism = synthetic construct
SEQUENCE: 167
DIQMTQSPSS LSASVGDRVT ITCKASQDID RYMAWYQDKP GKAPRLLIHD TSTLQSGVPS  60
RFSGSGSGRD YTLTISNLEP EDFATYYCLQ YDNLWTFGGG TKVEIK                106

SEQ ID NO: 168          moltype = AA  length = 121
FEATURE                 Location/Qualifiers
REGION                  1..121
                        note = Synthetic Construct
source                  1..121
```

```
                         mol_type = protein
                         organism = synthetic construct
SEQUENCE: 168
EVQLVESGGG LVQPGRSLRL SCAASGFTFD DYAMHWVRQA PGKGLEWVSA ITWNSGHIDY  60
ADSVEGRFTI SRDNAKNSLY LQMNSLRAED TAVYYCAKVS YLSTASSLDY WGQGTLVTVS  120
S                                                                 121

SEQ ID NO: 169           moltype = AA  length = 107
FEATURE                  Location/Qualifiers
REGION                   1..107
                         note = Synthetic Construct
source                   1..107
                         mol_type = protein
                         organism = synthetic construct
SEQUENCE: 169
DIQMTQSPSS LSASVGDRVT ITCRASQGIR NYLAWYQQKP GKAPKLLIYA ASTLQSGVPS  60
RFSGSGSGTD FTLTISSLQP EDVATYYCQR YNRAPYTFGQ GTKVEIK               107

SEQ ID NO: 170           moltype = AA  length = 123
FEATURE                  Location/Qualifiers
REGION                   1..123
                         note = Synthetic Construct
source                   1..123
                         mol_type = protein
                         organism = synthetic construct
SEQUENCE: 170
QVQLQQSGPE LVKPGASVKI SCKASGYSFT SYWIHWIKQR PGQGLEWIGM IDPSDGETRL  60
NQRFQGRATL TVDESTSTAY MQLRSPTSED SAVYYCTRLK EYGNYDSFYF DVWGAGTLVT  120
VSS                                                               123

SEQ ID NO: 171           moltype = AA  length = 107
FEATURE                  Location/Qualifiers
REGION                   1..107
                         note = Synthetic Construct
source                   1..107
                         mol_type = protein
                         organism = synthetic construct
SEQUENCE: 171
DIQMTQSPAS LSVSVGDTIT LTCHASQNID VWLSWFQQKP GNIPKLLIYK ASNLHTGVPS  60
RFSGSGSGTG FTLTISSLQP EDIATYYCQQ AHSYPFTFGG GTKLEIK               107

SEQ ID NO: 172           moltype = AA  length = 118
FEATURE                  Location/Qualifiers
REGION                   1..118
                         note = Synthetic Construct
source                   1..118
                         mol_type = protein
                         organism = synthetic construct
SEQUENCE: 172
EVQLKESGPG LVAPGGSLSI TCTVSGFSLT DSSINWVRQP PGKGLEWLGM IWGDGRIDYA  60
DALKSRLSIS KDSSKSQVFL EMTSLRTDDT ATYYCARDGY FPYAMDFWGQ GTSVTVSS    118

SEQ ID NO: 173           moltype = AA  length = 111
FEATURE                  Location/Qualifiers
REGION                   1..111
                         note = Synthetic Construct
source                   1..111
                         mol_type = protein
                         organism = synthetic construct
SEQUENCE: 173
DIVLTQSPAS LAVSLGQRAT ISCRASESVD SYGQSYMHWY QQKAGQPPKL LIYLASNLES  60
GVPARFSGSG SRTDFTLTID PVQAEDAATY YCQQNAEDSR TFGGGTKLEI K           111

SEQ ID NO: 174           moltype = AA  length = 5
FEATURE                  Location/Qualifiers
REGION                   1..5
                         note = Synthetic Construct
VARIANT                  1..5
                         note = Can be absent or present, or present in repeats of
                          up to 5 times
source                   1..5
                         mol_type = protein
                         organism = synthetic construct
SEQUENCE: 174
GGGGS                                                             5

SEQ ID NO: 175           moltype = AA  length = 7
FEATURE                  Location/Qualifiers
REGION                   1..7
```

-continued

```
                         note = Synthetic Construct
source                   1..7
                         mol_type = protein
                         organism = synthetic construct
SEQUENCE: 175
GQPKAAP                                                                   7

SEQ ID NO: 176           moltype = AA  length = 5
FEATURE                  Location/Qualifiers
REGION                   1..5
                         note = Synthetic Construct
source                   1..5
                         mol_type = protein
                         organism = synthetic construct
SEQUENCE: 176
DKTHT                                                                     5

SEQ ID NO: 177           moltype = AA  length = 6
FEATURE                  Location/Qualifiers
REGION                   1..6
                         note = Synthetic Construct
source                   1..6
                         mol_type = protein
                         organism = synthetic construct
SEQUENCE: 177
TKGPSR                                                                    6

SEQ ID NO: 178           moltype = AA  length = 7
FEATURE                  Location/Qualifiers
REGION                   1..7
                         note = Synthetic Construct
source                   1..7
                         mol_type = protein
                         organism = synthetic construct
SEQUENCE: 178
AASTLQS                                                                   7

SEQ ID NO: 179           moltype = AA  length = 7
FEATURE                  Location/Qualifiers
REGION                   1..7
                         note = Synthetic Construct
source                   1..7
                         mol_type = protein
                         organism = synthetic construct
SEQUENCE: 179
KASNLHT                                                                   7
```

What is claimed is:

1. A trivalent and/or trispecific binding protein comprising four polypeptide chains that form three antigen binding sites that specifically bind one or more target proteins, wherein a first polypeptide chain of the binding protein comprises a structure represented by the formula:

$$V_{L2}\text{—}L_1\text{—}V_{L1}\text{—}L_2\text{—}C_L \quad [I]$$

and a second polypeptide chain of the binding protein comprises a structure represented by the formula:

$$V_{H1}\text{—}L_3\text{—}V_{H2}\text{—}L_4\text{—}C_{H1}\text{—hinge—}C_{H2}\text{—}C_{H3} \quad [II]$$

and a third polypeptide chain of the binding protein comprises a structure represented by the formula:

$$V_{H3}\text{—}C_{H1}\text{—hinge—}C_{H2}\text{—}C_{H3} \quad [III]$$

and a fourth polypeptide chain of the binding protein comprises a structure represented by the formula:

$$V_{L3}\text{—}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are each independently amino acid linkers or zero amino acids in length;

wherein the polypeptide of formula I and the polypeptide of formula II form a cross-over light chain-heavy chain pair of the binding protein;

wherein $V_{H1}$ and $V_{L1}$ form a binding pair and a first antigen binding site, $V_{H2}$ and $V_{L2}$ form a binding pair and a second antigen binding site, and $V_{H3}$ and $V_{L3}$ form a binding pair and a third antigen binding site; and wherein the first antigen binding site specifically binds human IL4 or IL13, and the second antigen binding site specifically binds human IL4 or IL13, the first and second antigen binding sites being different.

2. An isolated nucleic acid molecule comprising a nucleotide sequence encoding the binding protein of claim 1.

3. An expression vector comprising the nucleic acid molecule of claim 2.

4. An isolated host cell comprising the nucleic acid molecule of claim 2.

5. An isolated host cell comprising the expression vector of claim 3.

6. A pharmaceutical composition comprising the binding protein of claim 1 and a pharmaceutically acceptable carrier.

7. A method of treating cancer in a patient comprising administering to the patient a therapeutically effective amount of the pharmaceutical composition of claim 6, wherein the binding protein comprises one antigen binding site that specifically binds a T-cell surface protein and another antigen binding site that specifically binds a target protein.

8. The method of claim 7, wherein the patient is a human.

9. A method of treating an inflammatory disease or disorder in a patient comprising administering to the patient a therapeutically effective amount of the pharmaceutical composition of claim 6, wherein the binding protein comprises three antigen binding sites that each specifically bind a cytokine target protein.

10. The method of claim 9, wherein the patient is a human.

* * * * *